United States Patent
Shalek et al.

(10) Patent No.: US 12,105,089 B2
(45) Date of Patent: Oct. 1, 2024

(54) CELL ATLAS OF THE HEALTHY AND ULCERATIVE COLITIS HUMAN COLON

(71) Applicants: The Broad Institute, Inc., Cambridge, MA (US); Massachusetts Institute of Technology, Cambridge, MA (US); The General Hospital Corporation, Boston, MA (US)

(72) Inventors: Alexander K. Shalek, Cambridge, MA (US); Christopher Smillie, Cambridge, MA (US); Rebecca H. Herbst, Cambridge, MA (US); Moshe Biton, Cambridge, MA (US); Aviv Regev, Cambridge, MA (US); Jose Ordovas-Montanes, Cambridge, MA (US); Ramnik Xavier, Cambridge, MA (US)

(73) Assignees: The Broad Institute, Inc., Cambridge, MA (US); Massachusetts Institution of Technology, Cambridge, MA (US); The General Hospital Corporation, Boston, MA (US)

( * ) Notice: Subject to any disclaimer, the term of this patent is extended or adjusted under 35 U.S.C. 154(b) by 871 days.

(21) Appl. No.: 16/632,018

(22) PCT Filed: Jul. 17, 2018

(86) PCT No.: PCT/US2018/042554
§ 371 (c)(1),
(2) Date: Jan. 17, 2020

(87) PCT Pub. No.: WO2019/018844
PCT Pub. Date: Jan. 24, 2019

(65) Prior Publication Data
US 2021/0325387 A1    Oct. 21, 2021

Related U.S. Application Data

(60) Provisional application No. 62/533,638, filed on Jul. 17, 2017, provisional application No. 62/581,424, filed on Nov. 3, 2017, provisional application No. 62/692,541, filed on Jun. 29, 2018.

(51) Int. Cl.
G01N 33/569     (2006.01)
C12Q 1/6883     (2018.01)
G01N 33/68      (2006.01)

(52) U.S. Cl.
CPC ..... *G01N 33/56966* (2013.01); *C12Q 1/6883* (2013.01); *G01N 33/6893* (2013.01); *C12Q 2600/106* (2013.01); *C12Q 2600/158* (2013.01); *G01N 2800/065* (2013.01); *G01N 2800/52* (2013.01)

(58) Field of Classification Search
CPC .................. G01N 33/56966; G01N 33/6893
See application file for complete search history.

(56) References Cited

U.S. PATENT DOCUMENTS

| | | |
|---|---|---|
| 4,816,567 A | 3/1989 | Cabilly et al. |
| 5,030,015 A | 7/1991 | Baker et al. |
| 5,270,163 A | 12/1993 | Gold et al. |
| 5,811,097 A | 9/1998 | Allison et al. |
| 5,869,326 A | 2/1999 | Hofmann |
| 6,479,626 B1 | 11/2002 | Kim et al. |
| 6,534,261 B1 | 3/2003 | Cox et al. |
| 6,607,882 B1 | 8/2003 | Cox et al. |
| 6,746,838 B1 | 6/2004 | Choo et al. |
| 6,794,136 B1 | 9/2004 | Eisenberg et al. |
| 6,824,978 B1 | 11/2004 | Cox et al. |
| 6,866,997 B1 | 3/2005 | Choo et al. |
| 6,903,185 B2 | 6/2005 | Kim et al. |
| 6,933,113 B2 | 8/2005 | Case et al. |
| 6,979,539 B2 | 12/2005 | Cox et al. |
| 7,013,219 B2 | 3/2006 | Case et al. |
| 7,030,215 B2 | 4/2006 | Liu et al. |
| 7,220,719 B2 | 5/2007 | Case et al. |
| 7,241,573 B2 | 7/2007 | Choo et al. |

(Continued)

FOREIGN PATENT DOCUMENTS

| | | |
|---|---|---|
| EP | 2 764 103 A2 | 8/2014 |
| EP | 2 771 468 A1 | 9/2014 |

(Continued)

OTHER PUBLICATIONS

The Broad Institute, In., "International Preliminary Report on Patentability issued in International Application No. PCT/US2018/042554", mailed on Jan. 30, 2020, 11 pages.

Huang, et al., "Fine-Mapping Inflammatory Bowel Disease Loci to Single-Variant Resolution", Nature, vol. 547, No. 7662, Jul. 13, 2017, 36 pages.

(Continued)

*Primary Examiner* — Kevin E Weddington
(74) *Attorney, Agent, or Firm* — F. Brent Nix, Esq.; Johnson, Marcou, Isaacs & Nix, LLC; Christopher D. Southgate, Esq.

(57) ABSTRACT

The present invention provides for a human cell atlas of the colon from healthy and diseased subjects. The atlas was obtained by single sequencing of about 117,000 cells. The present invention discloses novel markers for cell types. Moreover, genes associated with disease are identified in the colon and colon specific cell types. The invention provides for diagnostic assays based on gene markers and cell composition, as well as target cell types that express genes associated with disease. Finally, disclosed are novel cell types and methods of quantitating, detecting and isolating the cell types.

20 Claims, 70 Drawing Sheets

Specification includes a Sequence Listing.

(56) References Cited

U.S. PATENT DOCUMENTS

| | | |
|---|---|---|
| 7,241,574 B2 | 7/2007 | Choo et al. |
| 7,585,849 B2 | 9/2009 | Liu et al. |
| 7,595,376 B2 | 9/2009 | Kim et al. |
| 8,021,867 B2 | 9/2011 | Smith et al. |
| 8,119,361 B2 | 2/2012 | Smith et al. |
| 8,119,381 B2 | 2/2012 | Smith et al. |
| 8,124,369 B2 | 2/2012 | Smith et al. |
| 8,129,134 B2 | 3/2012 | Smith et al. |
| 8,133,697 B2 | 3/2012 | Smith et al. |
| 8,163,514 B2 | 4/2012 | Smith et al. |
| 8,440,431 B2 | 5/2013 | Voytas et al. |
| 8,440,432 B2 | 5/2013 | Voytas et al. |
| 8,450,471 B2 | 5/2013 | Voytas et al. |
| 8,697,359 B1 | 4/2014 | Zhang |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 2004/0171156 A1 | 9/2004 | Hartley et al. |
| 2006/0233797 A1 | 10/2006 | Gujrathi |
| 2011/0082188 A1 | 4/2011 | Chakravarti |
| 2011/0265198 A1 | 10/2011 | Gregory et al. |
| 2012/0017290 A1 | 1/2012 | Cui et al. |
| 2013/0236946 A1 | 9/2013 | Gouble |
| 2013/0303391 A1 | 11/2013 | Li et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0310830 A1 | 10/2014 | Zhang et al. |
| 2015/0184139 A1 | 7/2015 | Zhang et al. |
| 2015/0232883 A1 | 8/2015 | Dahlman et al. |
| 2015/0258124 A1 | 9/2015 | Katajisto et al. |
| 2016/0194604 A1 | 7/2016 | Karp et al. |
| 2016/0208243 A1 | 7/2016 | Zhang et al. |
| 2017/0211142 A1 | 7/2017 | Smargon et al. |

FOREIGN PATENT DOCUMENTS

| | | | |
|---|---|---|---|
| EP | 2 784 162 A1 | 10/2014 | |
| EP | 3 009 511 A2 | 4/2016 | |
| WO | 96/40281 A2 | 12/1996 | |
| WO | 97/49450 A1 | 12/1997 | |
| WO | 98/52609 A1 | 11/1998 | |
| WO | 2014/018423 A2 | 1/2014 | |
| WO | 2014/093595 A1 | 6/2014 | |
| WO | 2014/093622 A2 | 6/2014 | |
| WO | 2014/093635 A1 | 6/2014 | |
| WO | 2014/093655 A2 | 6/2014 | |
| WO | 2014/093661 A2 | 6/2014 | |
| WO | 2014/093694 A1 | 6/2014 | |
| WO | 2014/093701 A1 | 6/2014 | |
| WO | 2014/093709 A1 | 6/2014 | |
| WO | 2014/093712 A1 | 6/2014 | |
| WO | 2014/093718 A1 | 6/2014 | |
| WO | WO-2014186728 A2 * | 11/2014 | ........... C07K 16/244 |
| WO | 2014/204723 A1 | 12/2014 | |
| WO | 2014/204724 A1 | 12/2014 | |
| WO | 2014/204725 A1 | 12/2014 | |
| WO | 2014/204726 A1 | 12/2014 | |
| WO | 2014/204727 A1 | 12/2014 | |
| WO | 2014/204728 A1 | 12/2014 | |
| WO | 2014/204729 A1 | 12/2014 | |
| WO | 2014/210353 A2 | 12/2014 | |
| WO | 2015/058052 A1 | 4/2015 | |
| WO | 2015/070083 A1 | 5/2015 | |
| WO | 2015067913 A1 | 5/2015 | |
| WO | 2015/089351 A1 | 6/2015 | |
| WO | 2015/089354 A1 | 6/2015 | |
| WO | 2015/089364 A1 | 6/2015 | |
| WO | 2015/089419 A2 | 6/2015 | |
| WO | 2015/089427 A1 | 6/2015 | |
| WO | 2015/089462 A1 | 6/2015 | |
| WO | 2015/089465 A1 | 6/2015 | |
| WO | 2015/089473 A1 | 6/2015 | |
| WO | 2015/089486 A2 | 6/2015 | |
| WO | 2016/028682 A1 | 2/2016 | |
| WO | 2016/040476 A1 | 3/2016 | |
| WO | 2016/049163 A2 | 3/2016 | |
| WO | 2016/049258 A2 | 3/2016 | |
| WO | 2016/069591 A2 | 5/2016 | |
| WO | 2016/094867 A1 | 6/2016 | |
| WO | 2016/094874 A1 | 6/2016 | |
| WO | 2016/094880 A1 | 6/2016 | |
| WO | 2016/106244 A1 | 6/2016 | |
| WO | 2016/094872 A9 | 8/2016 | |
| WO | 2016138488 A2 | 9/2016 | |
| WO | 2016/161516 A1 | 10/2016 | |
| WO | 2016/168584 A1 | 10/2016 | |
| WO | 2016/205749 A1 | 12/2016 | |
| WO | 2016/205759 A1 | 12/2016 | |
| WO | 2017/070605 A1 | 4/2017 | |
| WO | 2017/106290 A1 | 6/2017 | |
| WO | WO-2017093750 A1 * | 6/2017 | ........... C12Q 1/6883 |
| WO | 2017/164936 A1 | 9/2017 | |
| WO | 2017/219027 A1 | 12/2017 | |
| WO | 2018/035250 A1 | 2/2018 | |
| WO | 2018/170333 A1 | 9/2018 | |
| WO | 2019/005866 A1 | 1/2019 | |
| WO | 2019/010384 A1 | 1/2019 | |
| WO | 2019/018440 A1 | 1/2019 | |
| WO | 2019/089803 A1 | 5/2019 | |
| WO | 2019/113506 A1 | 6/2019 | |

OTHER PUBLICATIONS

The Broad Institute, Inc., "Notification of Transmittal of the International Search Report and the Written Opinion of the International Searching Authority, or the Declaration for PCT/US18/42554", Dec. 27, 2018, 17 pages.

Cupi, et al., "Plasma Cells in the Mucosa of Patients with Inflammatory Bowel Disease Produce Granzyme B and Possess Cytotoxic Activities", J. Immunol., 192, 2014, pp. 6083-6091.

Hosomi, et al., "Increased numbers of immature plasma cells in peripheral blood specifically overexpress chemokine receptor CXCR3 and CXCR4 in patients with ulcerative colitis", Clinical and Experimental Immunology, 163, 2010, pp. 215-224.

Østvik, et al., "Expression of Toll-like receptor-3 is enhanced in active inflammatory bowel disease and mediates the excessive release of lipocalin 2", Clinical and Experimental Immunology, 173, 2013, pp. 502-511.

Scaldaferri, et al., "Mucosal biomarkers in inflammatory bowel disease: Key pathogenic players or disease predictors?", World J Gastroenterol, 16(21), Jun. 2010, pp. 2616-2625.

Timmermans, et al., "B-Cell Dysregulation in Crohn's Disease Is Partially Restored with Infliximab Therapy", PLOS One, vol. 11, No. 7, Jul. 28, 2016, 15 pages.

(56) References Cited

OTHER PUBLICATIONS

The Broad Institute, Inc., "Communication pursuant to Rule 164(1) EPC for EP 18835095.3", Apr. 21, 2021, 28 pages.

\* cited by examiner

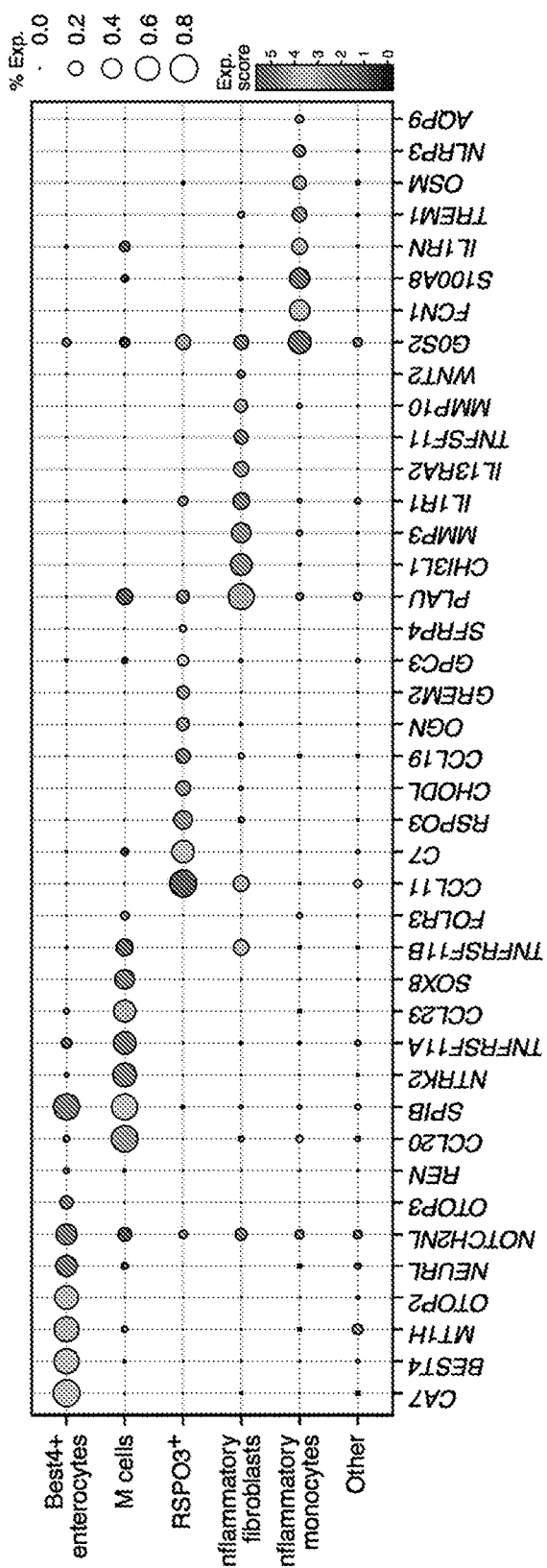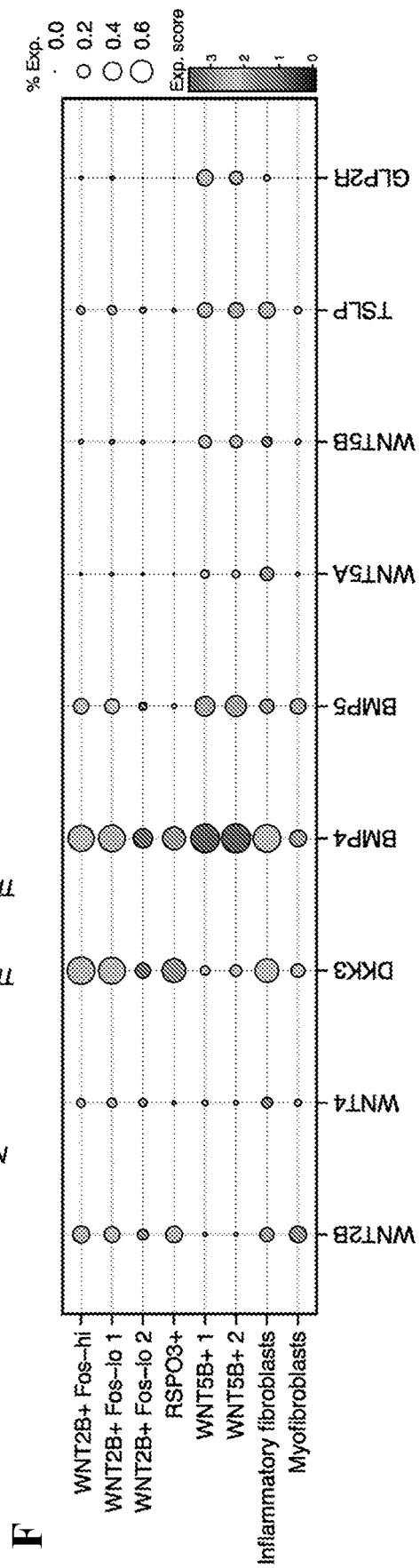
FIG. 26E-F

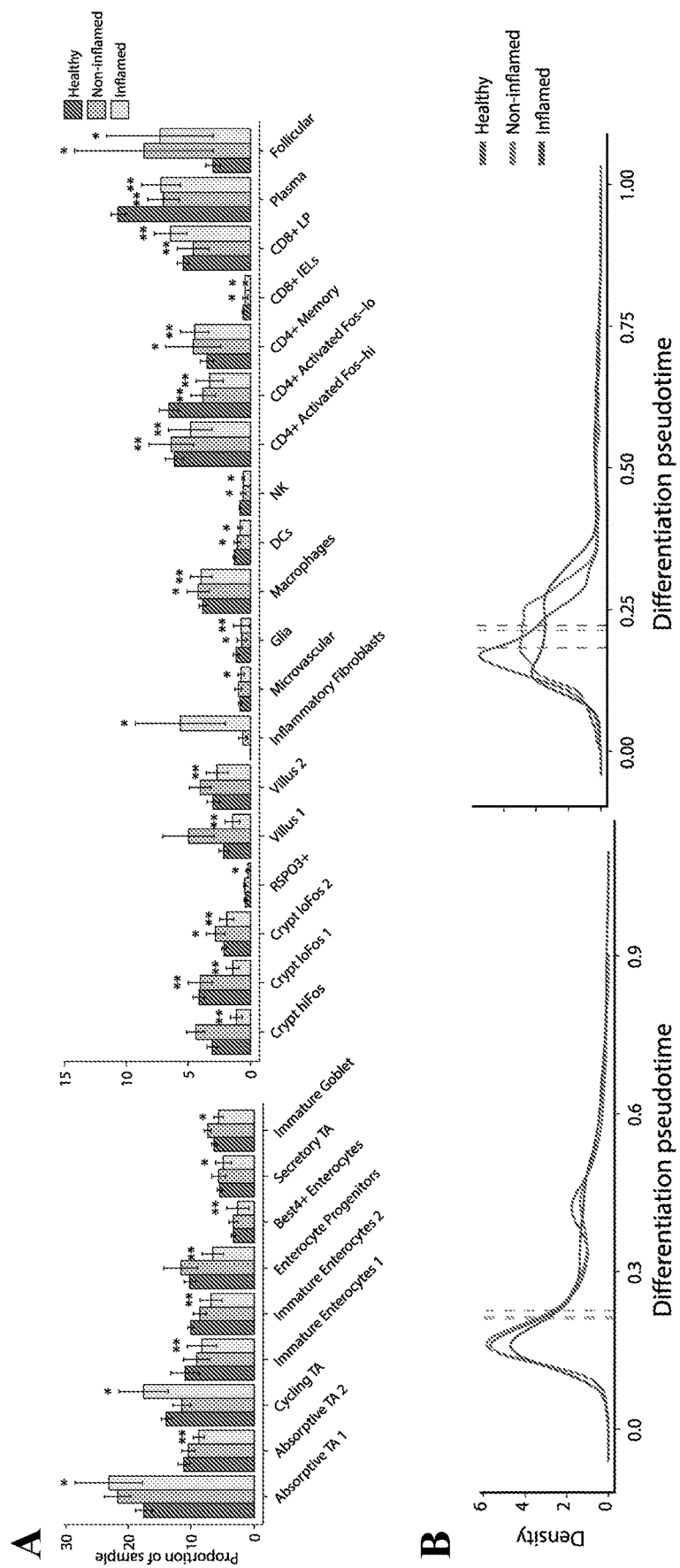
FIG. 27A-B

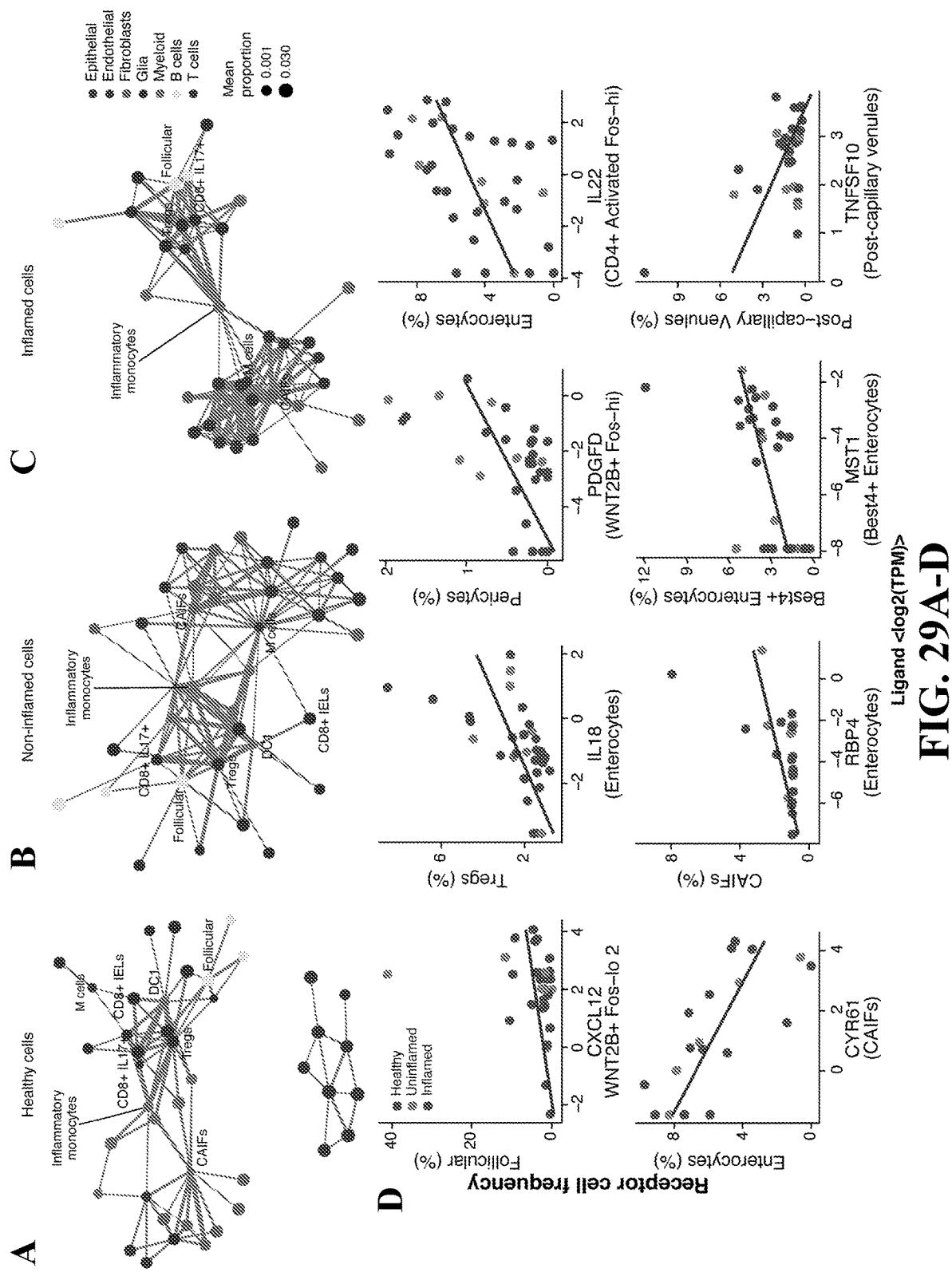
FIG. 29A-D

SEQUENCE LISTING

<160> NUMBER OF SEQ ID NOS: 2

<210> SEQ ID NO 1
<211> LENGTH: 288
<212> TYPE: PRT
<213> ORGANISM: Artificial Sequence
<220> FEATURE:
<223> OTHER INFORMATION: Synthetic N-terminal capping region

<400> SEQUENCE: 1

```
Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
                20                  25                  30

Ser Pro Pro Ala Gly Gly Pro Leu Asp Gly Leu Pro Ala Arg Arg Thr
            35                  40                  45

Met Ser Arg Thr Arg Leu Pro Ser Pro Ala Pro Ser Pro Ala Phe
    50                  55                  60

Ser Ala Asp Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
                100                 105                 110

Ala Ala Asp Ala Pro Pro Pro Thr Met Arg Val Ala Val Thr Ala Ala
                115                 120                 125

Arg Pro Pro Arg Ala Lys Pro Ala Pro Arg Arg Ala Ala Gln Pro
    130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175

Ala Gln His His Glu Ala Leu Val Gly His Gly Phe Thr His Ala His
                180                 185                 190

Ile Val Ala Leu Ser Gln His Pro Ala Ala Leu Gly Thr Val Ala Val
            195                 200                 205

Lys Tyr Gln Asp Met Ile Ala Ala Leu Pro Glu Ala Thr His Glu Ala
    210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
                245                 250                 255

Thr Gly Gln Leu Leu Lys Ile Ala Lys Arg Gly Gly Val Thr Ala Val
                260                 265                 270

Glu Ala Val His Ala Trp Arg Asn Ala Leu Thr Gly Ala Pro Leu Asn
                275                 280                 285
```

<210> SEQ ID NO 2
<211> LENGTH: 183
<212> TYPE: PRT
<213> ORGANISM: Artificial Sequence
<220> FEATURE:
<223> OTHER INFORMATION: Synthetic C-terminal capping region

<400> SEQUENCE: 2

```
Arg Pro Ala Leu Glu Ser Ile Val Ala Gln Leu Ser Arg Pro Asp Pro
1               5                   10                  15
```

-continued

```
Ala Leu Ala Ala Leu Thr Asn Asp His Leu Val Ala Leu Ala Cys Leu
            20                  25                  30

Gly Gly Arg Pro Ala Leu Asp Ala Val Lys Lys Gly Leu Pro His Ala
        35                  40                  45

Pro Ala Leu Ile Lys Arg Thr Asn Arg Arg Ile Pro Glu Arg Thr Ser
    50                  55                  60

His Arg Val Ala Asp His Ala Gln Val Val Arg Val Leu Gly Phe Phe
65                      70                  75                  80

Gln Cys His Ser His Pro Ala Gln Ala Phe Asp Asp Ala Met Thr Gln
                85                  90                  95

Phe Gly Met Ser Arg His Gly Leu Leu Gln Leu Phe Arg Arg Val Gly
            100                 105                 110

Val Thr Glu Leu Glu Ala Arg Ser Gly Thr Leu Pro Pro Ala Ser Gln
        115                 120                 125

Arg Trp Asp Arg Ile Leu Gln Ala Ser Gly Met Lys Arg Ala Lys Pro
    130                 135                 140

Ser Pro Thr Ser Thr Gln Thr Pro Asp Gln Ala Ser Leu His Ala Phe
145                 150                 155                 160

Ala Asp Ser Leu Glu Arg Asp Leu Asp Ala Pro Ser Pro Met His Glu
            165                 170                 175

Gly Asp Gln Thr Arg Ala Ser
            180
```

CELL ATLAS OF THE HEALTHY AND ULCERATIVE COLITIS HUMAN COLON

CROSS-REFERENCE TO RELATED APPLICATIONS

This application claims the benefit of U.S. Provisional Application Nos. 62/533,638, filed Jul. 17, 2017, 62/581,424, filed Nov. 3, 2017 and 62/692,541, filed Jun. 29, 2018. The entire contents of the above-identified applications are hereby fully incorporated herein by reference.

STATEMENT REGARDING FEDERALLY SPONSORED RESEARCH

This invention was made with government support under Grant Nos. OD020839, AI089992, CA217377, AI039671, AI118672, HG006193 and CA202820 awarded by the National Institutes of Health. The government has certain rights in the invention.

REFERENCE TO AN ELECTRONIC SEQUENCE LISTING

The contents of the electronic sequence listing ("BROD-2203US_ST25.txt"; Size is 4,929 bytes and it was created on Nov. 23, 2020) is herein incorporated by reference in its entirety.

TECHNICAL FIELD

The subject matter disclosed herein is generally directed to a cell atlas of the human colon in healthy and disease states. The subject matter further relates to novel cell specific and disease specific markers.

BACKGROUND

Tissues function through the coordinated actions of diverse parenchymal, immune, and stromal cell types responding to local and distal cues. Breakdown in any cellular compartment can lead to disease, due to intrinsic cell dysfunction or through compensations by other cells to restore tissue homeostasis. This intricate interplay among cells makes it difficult to determine the causal cellular mechanisms that initiate or promote disease. In the past, measuring the contribution of each cellular compartment was hampered by the need to average bulk measurements across the entire tissue or to assess known cell subsets or selected genes a priori.

The small intestinal mucosa is a complex system. The mucosa comprises multiple cell types involved in absorption, defense, secretion and more. These cell types are rapidly renewed from intestinal stem cells. The types of cells, their differentiation, and signals controlling differentiation and activation are poorly understood. The small intestinal mucosa also possesses a large and active immune system, poised to detect antigens and bacteria at the mucosal surface and to drive appropriate responses of tolerance or an active immune response. Finally, there is complex luminal milieu which comprises a combination of diverse microbial species and their products as well as derivative products of the diet. It is increasingly clear that a functional balance between the epithelium and the constituents within the lumen plays a central role in both maintaining the normal mucosa and the pathophysiology of many gastrointestinal disorders. Many disorders, such as irritable bowel disease, Crohn's disease, and food allergies, have proven difficult to treat. Inflammatory bowel disease (IBD) is a group of inflammatory conditions of the colon and small intestine, principally including Crohn's disease and ulcerative colitis, with other forms of IBD representing far fewer cases (e.g., collagenous colitis, lymphocytic colitis, diversion colitis, Behçet's disease and indeterminate colitis). Pathologically, Crohn's disease affects the full thickness of the bowel wall (e.g., transmural lesions) and can affect any part of the gastrointestinal tract, while ulcerative colitis is restricted to the mucosa (epithelial lining) of the colon and rectum. Some of the genetic factors predisposing one to IBD are known, as explored in Daniel B. Graham and Ramnik J. Xavier "From Genetics of Inflammatory Bowel Disease Towards Mechanistic Insights" Trends Immunol. 2013 August; 34(8): 371-378 (incorporated herein). The manner in which these multiple factors interact remains unclear.

A case in point is ulcerative colitis (UC), a major subtype of Inflammatory Bowel Disease (IBD), where inflammation begins in the rectum and extends proximally in a contiguous fashion. Left-sided disease is characterized by a sharp demarcation between inflamed and non-inflamed segments. Explaining the geographical restriction of UC remains a challenge. While endoscopic examination followed by histological analysis are the current standard of care, they fail to capture key aspects of the disease, including immune cell activation states, cell-specific cytokine profiles, and disease-related features of stromal cells, and do not distinguish the pathways associated with chronic inflammation from attempts at disease restitution. Furthermore, several genes mapped by genome-wide association studies (GWAS) as associated with disease risk suggests a critical role for the intestinal barrier in preventing IBD, with defects in autophagy, ER stress, oxidative stress, cell death, IL23R/Th17 biology, immune tolerance, solute transport and perturbed innate and adaptive immune signaling [REF]. However, the cellular compartments and cell-cell interactions in which these GWAS genes and pathways act are often unknown.

Single-cell RNA-Seq (scRNA-Seq) can help advance our understanding of complex disease by comprehensively mapping the cell types and states in the tissue, distinguishing changes in cell-intrinsic expression programs from cell-extrinsic changes in cell frequencies, and predicting how these connect through cell-cell interactions. When comparing healthy and disease tissue, this may help determine with precision: which cell populations are disrupted in disease? Which cell-intrinsic programs are changed? What cell-cell interactions affect cell recruitment during inflammation and disease resolution? What are the cells-of-action of disease risk genes? and, What are the effects of current therapies and how might therapeutic resistance arise? Unlike bulk profiling, which averages across cell types, scRNA-Seq can readily distinguish between cell-intrinsic changes in expression program and cell-extrinsic changes in cell frequencies and cell-cell interactions. Unlike most in situ methods, which require prior knowledge of the genes and proteins of interest, scRNA-Seq can in principle do so systematically across all cells and programs in the tissue ecosystem, including those that may not yet be known to present in the tissue. This approach has been demonstrated for tumors (see, e.g., Tirosh, et al., Dissecting the multicellular ecosystem of metastatic melanoma by single-cell RNA-seq. Science 2016, 352, 189-196), but not yet for other complex immune mediated diseases, such as UC, where the window for disease onset, activity and resolution is measurable with endoscopic biopsies.

For example, Inflammatory bowel disease (IBD) is a chronic and debilitating disorder that affects millions of people worldwide. IBD is heterogeneous, comprising two main subtypes, Crohn's disease (CD) and ulcerative colitis (UC), which have different risk factors and clinical presentations. CD patients typically have discontinuous inflammation that extends deep into the mucosa throughout the gastrointestinal tract, while UC patients have continuous inflammation that is largely restricted to the mucosa of the large intestine. IBD is thought to arise from a maladaptive immune response to the gut Here, Applicants used intestinal biopsies microbiota in a genetically susceptible host. Genome-wide association studies (GWAS) have pinpointed hundreds of IBD-associated loci that explain ~10% of disease susceptibility. While linkage disequilibrium has precluded mapping most loci to single variants, fine-mapping studies have directly implicated several genes, including NOD2, IL23R, ATG16L1, and PTPN22. Functional analysis of these genes suggests a critical role for the intestinal barrier in preventing IBD, with defects in autophagy, immune signaling, and epithelial barrier function leading to elevated disease risk. However, the functional roles for most such genes are unknown and the ability of GWAS to detect causal variants exceeds our ability to generate functional insights into the disease.

SUMMARY

In certain example embodiments, the present invention provides for a human cell atlas of the colon for healthy and disease states and methods of use. This disclosure provides a rationale for modulating intestinal cell balance, function, differentiation and/or activity for the treatment of both IBD and other disorders.

In certain embodiments, the IBD is Crohn's disease or ulcerative colitis. In certain embodiments, the IBD is collagenous colitis, lymphocytic colitis, diversion colitis, Behçet's disease, or indeterminate colitis.

In one aspect, the present invention provides for a method of detecting inflammatory bowel disease (IBD) comprising measuring in a biological sample obtained from the gastrointestinal tract of a subject the frequency of one or more cell types selected from the group consisting of B cells, T cells, endothelial cells, epithelial cells, fibroblasts and myeloid cells compared to the total of all cell types in the sample, wherein IBD is detected when the frequency of one or more cell types is altered as compared to a healthy frequency. The one or more cell types may be selected from the group consisting of colitis-associated inflammatory fibroblasts (CAIFs), absorptive transit amplifying (TA) 1 cells, absorptive TA 2 cells, class switching B cells, crypt fibroblasts (loFos), glial cells, goblet 1 cells, neutrophils, plasma B cells, post-capillary venules and tolerogenic DCs.

In certain embodiments, the cell type may be detected by measuring one or markers for each cell type selected from Table 1 A-D, Table 9, Table 11 or Table 12. The top 250 markers for each cell type are listed in ranked order.

In another aspect, the present invention provides for a method of detecting IBD comprising measuring in a biological sample obtained from the gastrointestinal tract of a subject the expression of a gene or polypeptide selected from the group consisting of: MTRNR2L1, HLA-B, CHI3L1, EIF5A, RPL3, S100P, TIMP1, REG1A, C8orf4, HMGCS2, DMBT1, AC005540.3, OLFM4, IL13RA2, MMP3, REG4, IGJ, DEFA5, TNFRSF12A, BGN, SELENBP1, TPM4, IFITM2, TNFRSF11B, PKM, PHLDA1, MT1G, LGALS4, IGFBP5, URAD, ANXA2, HLA-DRA, PLA2G2A, PDPN, S100A11, SELL, SOD2, LDHA, SMDT1, CCL8, FCGRT, RPL9, CYR61, NNMT, LMNA, HIF1A, CD82, LINC00152, TAGLN2, IFITM3, EMP1, AKR1C1, CD63, FKBP1A, PTMA, COL6A3, REG3A, BACE2, C10orf99, CNN3, CEBPB, RPL13A, LCN2, HSPA1B, CKB, PHGR1, CD59, C11orf96, ANXA5, RPL18A, COL4A1, CTHRC1, PCOLCE, COL1A1, FTL, EMP3, GEM, COL4A2, PRSS23, S100A6, S100A3, CA1, REG1B, TNC, CCR7, MEOX1, FGF7, MMP1, RPS3A, THY1, RPS26, PKIB, CHP2, SERPINE1, TXNIP, COL6A1, RPS4Y1, PSME2, CAV1, ANGPTL2, TAGLN, TFF1, HGF, PDIA3, CDH13, ACADS, KDELR2, NOP10, SELM, HAPLN3, FABP4, PTGES, DSTN, CCL5, VAMP8, MT-ND1, SERPINH1, HYI, POLR2L, PPIB, HLA-DMA, TST, AQP1, SPARC, CA2, CCL13, MT-CYB, HLA-DPB1, SPINK1, AQP8, ATOX1, RPL37A, IER3, ENO1, MT1H, HSPA5, HSPA1A, ITM2C, SDC2, ID1, AMN, FABP6, PIGZ, COL8A1, DUOXA2, TPM2, CRIP2, HYAL2, CPXM1, NCOA7, RPS29, TMEM258, CLDN7, PHLDA2, TMSB10, F2R, PXMP2, SRM, CFB, NDUFA4L2, CBX3, NXPE4, ACAA2, NDRG2, KANSL1-AS1, KLF2, LAPTM4A, ITGA5, DHRS4, CDX2, PRKCDBP, RPL6, SOCS3, GPR160, PPDPF, SEPP1, TMEM141, ELP5, NRG1, SPON2, CXCL1, ID3, PTRF, CALR, TMEM165, HSP90B1, CLEC9A, INHBA, SPHK1, FABP1, LGALS2, PDLIM4, TMEM158, CKMT1A, TRMT112, CCDC3, HOXB13, MRGPRF, CALU, ACSF2, MMP10, VSIG2, RAMP1, MT1M, APOA4, TFPI2, FXYD3, MORF4L1, PEBP1, STAP2, NFKBIA, MT-CO3, DHRS11, SPINT2, PRRX2, RCN3, EIF4A1, TUBB, TSHZ2, KRT8, ACTN1, VAMP5, RPL10, IL11, AGT, SERPINA1, SLC26A2, CLU, APOBEC3B, DNAJB1, THBS2, UBD, PIM3, PRKAR1A, IL32, IGFBP7, UGT2A3, HLA-DRB5, PPA1, CHCHD10, COL6A2, CD55, RNASET2, CTGF, MT-CO1, CTSK, C19orf10, SERPINE2, HSD17B12 and SAA1; or MTRNR2L1, HLA-B, RPL3, TIMP1, IGJ, IFITM2, CCR7, CCL5 and IGFBP7; or MTRNR2L1, HLA-B, RPL3, TIMP1, IGJ, IFITM2, CCR7, CCL5 and IGFBP7; or genes in Table 4, 6, 8, 13, 14 or 15, wherein the genes or polypeptides are differentially expressed in IBD as compared to a healthy gastrointestinal tract reference level. The expression of MTRNR2L1, HLA-B, TIMP1, CCR7, IFITM2, and IGFBP7 may be upregulated as compared to a healthy reference level and the expression of RPL3, IGJ and CCL5 may be downregulated as compared to a healthy reference level.

In another aspect, the present invention provides for a method of detecting IBD comprising measuring in B cells obtained from the gastrointestinal tract of a subject the expression of a gene or polypeptide specific for the indicated cell type in brackets selected from the group consisting of: [Plasma_B_cells] G0S2, FABP1, TNFRSF18, PHGR1, AGR2, GAS6, RPL3, LMNA, TIMP1, SMOC1, HIST1H1C, HSP90AA1, TNFRSF4, HSPA1A, HSPA1B, CYP20A1, KRT19, CXCR4, DNAJB1, XBP1, GOLGA2 and CADM1; or [Class_switching_B_cells] TIMP1, RPL3, HSP90AA1, LMNA, ILVBL, CD69, CTHRC1, TNFRSF4, G0S2, PABPC4, ITM2C, AGR2, RPS3A, RNASE6, LGALS4, HLA-DMA, FXYD3, PTMA, TNFRSF18, RP11-16E12.2, H3F3B, KLF6, QPRT, TPM4 and SMOC1; or [Follicular_B_cells] C12orf75, METAP2, CCND3, HLA-DQB1, HLA-DRB5, RPS4Y1, TUBB2A, LCK, RMI2, SMARCB1, HLA-DPB1, TCEA1, MME, RPL9, SLBP, CD63, UBE2D3, A4GALT, PLD4, SIT1, PPP1CC, PAIP2, CCDC109B, DCAF12, SRSF3, HLA-DQA1, HLA-C, ISG20, HMGN1, HMCES, HNRNPC, HLA-DPA1, TUBB2B, HNRNPA3, CD27, EIF1AY, ITGAE, TPD52, ECHS1, RAPiB, HLA-DQA2, GGA2, CHCHD10, ACTR3, HLA-DRA, SGPP1, PGAM1, DCK, TSG101, HNRNPM, LTB, CLIC4, LSM10, GDI2, RGS16, CAPG, SRSF2, ZFAND2A, RPL36, CBX3, AGR2, MRPL47, TRA2A, FBL, SELT, SUMO2, HADHB, DEF8, FGD2, LIMD2, PSIP1, RBBP7, BZW1, TSTD1, MTF2, IKZF1, RUVBL1, BACH2, PIM1, CHRAC1, EZR, MCM5, IGJ, COX6B1, PRPSAP2, TK1 and CCR7.

In another aspect, the present invention provides for a method of detecting IBD comprising measuring in endothelial cells obtained from the gastrointestinal tract of a subject the expression of a gene or polypeptide specific for the indicated cell type in brackets selected from the group consisting of: [Microvascular_cells] PLAT, AQP1, CD9, HLA-A, HLA-DRA, EGLN3, LDHB, HLA-C, RBP5, CD99, PASK, S100A10, SERPINE1, CXCL12, JUN, ANXA2, TESC, IGJ, FOSB, LIMS1, HSPA1A, CALU, RCN3, S100A6, CST3, PRSS23, SEPP1, HSPA1B, WWTR1, RAMP1, GPX4, PSMB9, PSME2, CTGF, CD82, LGALS4, SNED1, TNFRSF4, IER3, VAMP8, ALDOA, HLA-B, TAP1, CD36, F2RL3, KDR, COL15A1 and PLAU; or [Post-capillary_venules] PTGS1, RAMP1, PDLIM1, HLA-A, OLFML3, PLAT, STXBP6, UBD, LY6E, TNFSF10, CD9, MGP, CPE, PSMB8, PHLDA1, EIF4A2, GIMAP7, TMEM100, CST3, HLA-C, RPL9, RPL10, LPCAT4, AQP1, GIMAP1, SRPX, MALAT1, RPL3, AGR2, PRSS23, COL4A3BP, EFEMP1, SNHG7, TUBA1B, PTGES, NFKBIZ, B2M, FTH1, C19orf66, CDKN3, RNF181, EEF1B2, MDK, CLIC1, TPTEP1, TFF3, S100A10, JUN, CRIP1 and MED24; or [Vitamin_metabolizing]PLAT, CXCL12, ENPP2, TXNIP, IGFBP4, CD36, ANXA2, OAZ2, CD320, AQP1, CTGF, RGS5, TGFBR2, RAMP1, CD9, C16orf80, CXCR4, CLDN5, STC1, GJA1, FAM213A, PLAU, HLA-E, PRKCDBP, RBP5, RPL9, SAT1, TNFSF10, S100A4, TSPAN7, AKRIC3, C8orf4, HLA-DPB1, SRP14, TNFRSF4, TIMP1, ANXA1, C1orf54, RND1, ANGPT2, EGR1, STAT3, SH3BP5, RPL29, CTNNBIP1, LSMD1, HLA-C, RBM17, GYPC, NDUFA7, IER2, COTL1, RPLP0, SDPR, IDI1, SLC6A6, RPL10A, MYL6, AQP3, NKX2-3, COASY and SOD2; or [Endothelial_pericytes] FAM222B, RP11-490M8.1, TWF2, ZNF205 and HYI.

In another aspect, the present invention provides for a method of detecting IBD comprising measuring in epithelial cells obtained from the gastrointestinal tract of a subject the expression of a gene or polypeptide specific for the indicated cell type in brackets selected from the group consisting of: [Enterocytes] SPINK1, PLA2G2A, IL18, ATP1B3, MTRNR2L1, GSTP1, GPX2, CYBA, TAX1BP3, S100A14, NQO1, TSPAN3, NAALADL1, CTSA, RARRES3, OAS1, LGALS1, HMGCS2, PCK1, PRDX5, MUC1, TMEM37, KRTCAP3, MT2A, MX1 and S100A11; or [Tuft_cells] PTGS1, ESYT2, SHC1, HPGDS, HOOK1, BCKDK and RALGAPA1; or [Goblet_2] SPINK4, NUPR1, S100A14, BAIAP2L1, BDKRB1, MT-ND2, FAM3B, MUC13, TFF1, ANO9 and TUBB2A; or [Absorptive_TA_1] REG1A, CD74, RPL3, HLA-DRB1, MT2A, RPS3A, ARHGDIB, TIMP1, LIN7C, MTRNR2L1, KCNK6, RPL18A, TNFRSF12A and SEC11C; or [Secretory_TA] HLA-DRA, HLA-DRB1, RARRES2, ID3, HLA-DMA, UGT2B17, CD74, HLA-DRB5, REG1A, HLA-DPB1, HLA-DPA1 and GLBIL2; or [Absorptive_TA_2] AGR2, HLA-DRA, CD74, S100A11, HSPB1, SPINK1, HLA-DRB1, TIMP1, RARRES3, SELENBP1, GPX2, MUC12, ID3, ARHGDIB, REG1A, PLA2G2A, CEACAM5, IDH2, IGJ, RNASET2, BSG, PSMB9, ADIRF, LEFTY1, RARRES1, LYZ, MTRNR2L1, TFF1, RPS4Y1, SRSF6, CNPY2, GSTP1 and ATP1B3; or [Cycling_TA] RARRES2, ARHGDIB, IGJ, BST2, PKIG, PITX1, ETS2, HLA-DRA, TIMP1, MTRNR2L1, HRCT1, ZNF90, MUC12, AKR1B1, HLA-DPA1, VAMP7, S100P, NQO1, DEK, ABRACL, REG1A, ACAT1, DNAJB1, HLA-DRB1 and IGFBP4; or [Goblet_1] SPINK4, ITLN1, IGJ, AGR2, SDF2L1, TIMP1, PDLIM1, MUC2, LYZ, SELK, HMGCS2, SEC11C, SSR4, DNAJA1, FKBP11, REG4, EZR, SELM, CISD1, SYTL1, PHLDA2 and CHPF.

In another aspect, the present invention provides for a method of detecting IBD comprising measuring in fibroblasts obtained from the gastrointestinal tract of a subject the expression of a gene or polypeptide specific for the indicated cell type in brackets selected from the group consisting of: [Inflammatory_fibroblasts] COL1A2, GBP1, IFI27, DYNLT1, PKM, PHLDA1, DUSP1, CNOT4, CCL8, LAP3, ACP5, GSTT1, GALNT11, PSMB9, TNIP2, PSMB8, HAPLN3 and PERP; or [Fibroblast_pericytes] NET1; or [Myofibroblasts] PDLIM7, NBL1, C12orf75, PHLDA2, IGFBP5, PRSS23, TM4SF1, SQRDL, MRGPRF, RERG, MXRA8, RPS4Y1, EGR1, HOXD9, TDO2, DUSP1, LMNA, CYB5R3, DDAH2 and TFPI2; or [Villus_fibroblasts] MMP2, SRPX2, TNC, MMP1, S100A4, NSG1, EDNRB, AGT, TRPA1, CPE, VSTM2A, RBP4, TSHZ2, IL32, VASN, CRIP1, NR4A2, PCTP, PRSS23, MCL1, NDUFA4L2, ANXA1, TMSB4X, PDLIM1, IGFBP3, CEBPD, FOXF1, ACP1, CIS, FRZB, ECM1, DMKN, ID4, PDGFRA, GADD45B and SPARCL1; or [Crypt_fibroblasts_(hiFos)] TM4SF1, VASN, GSN, FGF7, PLAT, CLEC14A, IQGAP2, 11D3, FN1, SEPP1, TNXB, CCL13, TPBG, HSD17B2, STMN2, GPX3, VIM and TNFSF10; or [Crypt_fibroblasts_(loFos)] GPX3, NR4A1, CIS, TM4SF1, DUSP1, ID1, LGALS3BP, COL15A1, SERPINGI, TNFAIP6, CFD, ADAMDEC1, MZT2B, MIF, EGR1, DKK3, NBEAL1, GSN, GGT5, FOXF1, RPL9 and CD74.

In another aspect, the present invention provides for a method of detecting IBD comprising measuring in macrophages obtained from the gastrointestinal tract of a subject the expression of a gene or polypeptide specific for the indicated cell type in brackets selected from the group consisting of LGMN, RNASEI, AKR1B1, LGALS2, A2M, C15orf48, VMO1, SERPINF1, SPINT1, ACP5, TFF3, RNASET2, ENPP2, LGALS1, MMP9, CORO1A, CSTB, SELK, MT2A, FBP1, PLSCR1, FXYD5, NR1H3, UCHL3, SEPP1 and AGR2.

In another aspect, the present invention provides for a method of detecting IBD comprising measuring in T cells obtained from the gastrointestinal tract of a subject the expression of a gene or polypeptide specific for the indicated cell type in brackets selected from the group consisting of: [T_cells] NUB1, CAV1, EIF2S1, COL6A1, POSTN, ALAS1 and RGCC; or [Activated_CD4_cells_loFos] S100A4, RPS29, TIMP1, RPL9, CFL1, VIM, ANXA1, PHLDA1, S100A11 and HLA-A; or [Activated_CD4_cells_hiFos] IGJ and ADSS; or [CD8_IELs] CCL3, CCL4, RPL10, RPL6, CD3E, MTRNR2L1, ARHGDIB, CD3G, RPL3, ITGB2, KLRB1, IFNG, RPL22, RPL18A and PTMA; or [CD8_LP_cells] RPL9, EMP3 and ARFRPI; or [Tregs] CD7, CD2, TIA1 and GRSF1; or [Memory_T_cells] RPL9, PFN1, IL32, ANXA1, S100A4, ARPCIB, KLRB1, RPL30, ANAPC5, GAPDH, B2M, RPS28, PSME2, AK5, SERF2, RILPL2, RPS29, TAGLN2, FXYD5, S100A11, ANXA5, S100A6, PNRC1, ARPC2 and ZFP36; or [Cycling_CD8_cells] ENTPD1, CD2, EIF5A, LCK, HAVCR2, ATP5L, KLRB1, CALR, MTPN, CENPA and MIF.

In another aspect, the present invention provides for a method of detecting IBD comprising measuring in cells obtained from the gastrointestinal tract of a subject the expression of a gene or polypeptide specific for the indicated cell type in brackets selected from the group consisting of: [Stem_cells] AQP1, RPL3, RPS4Y1, LYZ, LCN2, ID3, HLA-DRA, HLA-DRB1, HLA-DMA, HLA-DPA1, C2, NQO1, B2M, ARHGDIB, DNAJB1, RARRES2, MTRNR2L1, HLA-C, CD74, C19orf70, GSTT1, TESC, IFI27, PSME1, HMGCS2, HLA-DRB5, RPL6, UGT2B17, HLA-DPB1, PSMB9 and SCARB2; or [Enteroendocrine] RARRES2, HLA-DRA, SEC11C, MT2A, NIPSNAP1, OLFM4, DDC, MDK and CD82; or [Glial_cells] ALDH1A1, CLU, ANXA1, SPP1, IL32, CAPS, FIBIN, RPL3, RPL9, HLA-G, MRPS6, LINC00152, HOXC6, CDKN2A, TUBA1A, HLA-DQA2, SOCS3, SEPP1, IGJ, HLA-DRB5, KLC1, HLA-DRB1, NDUFB4, ENTPD2, SRGN, PMEPA1, HSPA1B, FKBPIA, GLIPR2, UBR4, UBB, COX7A1, LSM3, PRDX2 and NUPR1; or [Dendritic_cells] CST3, MARCKSL1, CD52, PPA1, IGJ, SERPINB1, TYMP, STMN1, FCER1A, DNAJB1 and PRELID1; or [Mast_cells], NFKBIZ, EGR3, ILIRL1, HLA-B, CAPG, EGR2, HLA-C, RPS4Y1, CTSW, EIF4G2 and ZEB2; or [Cycling_monocytes] TFF3, ATP2A3, GSDMD, EMP3, IL12RB1, PSMD11, ENPP2, ALOX5AP and AK1; or [Tolerogenic_DCs] TXN; or [Neutrophils] GBP1, FCGR2B, GSTO1, RPL30, TMEM176B, EMG1 and GDI2; or [NK_cells] ILF3, CALCOCO2 and CD47.

In certain embodiments, the cell type according to any embodiment herein may be obtained by sorting cells based on expression of one or markers for each cell type selected from Table 1 A-D, Table 9, Table 11 or Table 12. The sorting may be performed by deconvolution of bulk expression data in silico. Not being bound by a theory, the quantity of cells may be determined by cell specific markers and gene expression assigned to each cell. The biological sample according to any embodiment herein may be obtained by colonoscopy.

In another aspect, the present invention provides for a method of treating IBD comprising modulating the activity of one or more gastrointestinal tract cell types selected from the group consisting plasma B cells, class switching B cells, follicular B cells, microvascular cells, post-capillary venules, vitamin metabolizing, endothelial pericytes, enterocytes, tuft cells, goblet 2, absorptive TA 1, secretory TA, absorptive TA 2, cycling TA, goblet 1, stem cells, enteroendocrine, glial cells, inflammatory fibroblasts, fibroblast pericytes, myofibroblasts, villus fibroblasts, crypt fibroblasts (hiFos), crypt fibroblasts (loFos), T cells, macrophages, dendritic cells, mast cells, cycling monocytes, tolerogenic DCs, neutrophils, activated CD4 cells loFos, activated CD4 cells hiFos, CD8 IELs, CD8 LP cells, Tregs, memory T cells, NK cells and cycling CD8 cells. The one or more cell types may express one or more IBD GWAS genes selected from the group consisting of: IL32, MHCII, RNF186 and SLC39A8; or LMAN2, ATF4, TRIB1, HSPA6, RABEP2, CAMP, TSPAN14, STRN4, MOB2, HYAL1, DOCK9, CTSA, TST, PLEKHG6, RHPN2, C2CD2L, D2HGDH, REG4, DDC, HCK, MED16, GRB7, SPRED2, COG5, ADK, RIT1, SLC15A3, PLAU, ING5, NF2, PDLIM7, ZP1, PLA2G4A, CCL13, TTYH3, NFKBIZ, VPS 11, CARD9, TNNI2, RIPK2, GPBAR1, SLC11A1, IFNG, CD28, EIF3G, CUL1, FASLG, MXD3, TCF19, DPAGT1, PHTF1, HOXA5, COX15 and LIF; or [GPCR] CCR10, GPRC5D, GPR18, CXCR5, CALCRL, F2RL3, FZD4, SiPR1, GPR4, APLNR, FZD6, LPAR6, GPR146, AVPR2, HRH1, GPRC5B, TBXA2R, GPRC5A, FZD5, GPR39, LGR5, VIPR1, F2RL1, LGR4, OPN3, FFAR4, GPR153, GPR37L1, FZD3, LPAR1, GPR137, SMOX, ADORA2B, BDKRB1, PGF, ADRA2A, PTGIR, EDNRA, MRGPRF, F2R, EDNRB, GLP2R, PTGFR, ACKR3, FZD1, ADORA1, ADORA3, CMKLR1, FPR3, P2RY13, ADRB2, LPAR5, P2RY14, GPR34, PTAFR, CCRL2, GPBAR1, FFAR2, C5AR1, C3AR1, CCR1, FPR1, GPR82, CXCR6, CCR7, DHX15, CCR6, GPR68, PTGDR and LTB4R; or [cell-cell interaction] TNFRSF17, SEMA4A, EBI3, RAMP3, ROBO4, F2RL3, APLN, NRP2, CCL21, ICAM2, PLXND1, HRH1, EPHA2, CGN, CELA3B, CFTR, RGMB, SCT, AZGP1, TSPAN1, IL22RA1, ILIR2, RSPO3, NRXN1, NCAM1, ANGPTL2, TNC, MMP1, COL18A1, CIQTNF1, COL5A3, NEO1, NTN1, BMP2, TSLP, SEMA3A, PROS1, ANGPTL1, CCL19, CD4, LY96, IL5RA, SIRPA, IL23A, IL1B, OSM, OLR1, KLRC2, CXCR6, IL17RA, KLRC1, ADAM10 and TNF; or [epithelial cells] CTSA, TNIP1, SEPHS2, AGPAT2, MIDN, FAM132A, SLC26A3, CHP2, SULT1A2, TMEM171, SULT1A1, C1orf106, HNF4A, PLEKHG6, FUT2, CEBPA, GSDMB, EDN3, PTK6, PSORS1C1, RHPN2, VDR, SLC26A6, AGPAT3, MST1R, NGEF, EFNA2, C2CD2L, ITPKA, SLC22A5, SLC35D1, AGXT, NXPE4, SLC39A8, TMEM258, F12, D2HGDH, BCL2L15, CFTR, GOT1, PLK1, ERGIC1, ITLN1, REG4, SULT2B1, CCDC60, CACNA2D2, SLC19A3, AGFG2, PLXNB1, DDC, C2orf54, LFNG, SNAPC4, MEX3A, GCG, GPBAR1, RXFP4, UCKL1, HCK, CAMP, BLM, SOX4, IFT172, RNF186, SMURF1, RNF123, TREH, HOXA11-AS, NOS2, C2CD4D, CEBPG, IL10RB, PRKCD, MED16, SEC16A, PPP1R12C, FOXO1, EPS8L1, TRIM31, CDH1, APOBR, SCNN1A, GRB7, SLC22A23, FRYL, ACHE, SMAD3, MAGI3, SPRED2, SMPD3, FAM83E, IL1R2, USP12, PWP2, ABCA7, SYT7 and COG5. Thus, cells may be targeted that express GWAS genes.

In another aspect, the present invention provides for an isolated gastrointestinal tract cell characterized by expression of one or markers for a cell type selected from Table 1 A-D, Table 9, Table 11 or Table 12.

In another aspect, the present invention provides for a method for detecting or quantifying gastrointestinal tract cells in a biological sample of a subject, the method comprising detecting or quantifying in the biological sample gastrointestinal tract cells as defined in any embodiment herein. The gastrointestinal tract cell may be detected or quantified using one or more markers for a cell type selected from Table 1 A-D, Table 9, Table 11 or Table 12.

In another aspect, the present invention provides for a method of isolating a gastrointestinal tract cell from a biological sample of a subject, the method comprising isolating from the biological sample gastrointestinal tract cells as defined as defined in any embodiment herein. The gastrointestinal tract cell may be isolated using one or more surface markers for a cell type selected from Table 1 A-D, Table 9, Table 11 or Table 12.

In certain embodiments, the gastrointestinal tract cells may be isolated, detected or quantified using a technique selected from the group consisting of RT-PCR, RNA-seq, single cell RNA-seq, western blot, ELISA, flow cytometry, mass cytometry, fluorescence activated cell sorting, fluorescence microscopy, affinity separation, magnetic cell separation, microfluidic separation, and combinations thereof.

In another aspect, the present invention provides for a method of modulating the gastrointestinal tract cell composition comprising treating a subject with an agent capable of targeting intestinal stem cells to differentiate. The intestinal stem cells may be targeted to differentiate into absorptive transit amplifying (TA) 1 cells, absorptive TA 2 cells or class switching B cells.

In another aspect, the present invention provides for a method of modulating the gastrointestinal tract cell composition or activity comprising treating a subject with an agent capable of targeting a receptor-ligand interaction. The receptor-ligand interaction may comprise: CCR7 and one or more of CCL19 and CCL21; TNFB and LTBR; LGR5 and RSPO3; IL15 and IL15RA; FGF23 and FGFR1; CCL8 and CCR1; CXCL2 and XCR1; or XCL2 and XCR1.

In certain embodiments, IBD comprises Crohn's disease or ulcerative colitis (UC).

In another aspect, the present invention provides for a method of detecting drug resistance in inflammatory bowel disease (IBD) comprising measuring in a biological sample obtained from the gastrointestinal tract of a subject the frequency of colitis-associated inflammatory fibroblasts (CAIFs) compared to the total of all cell types in the sample, wherein drug resistance is detected when the frequency of CAIFs is altered as compared to a healthy frequency. The drug resistance may be resistance to anti-TNF therapy. The cell type may be detected by measuring one or markers selected from the group consisting of MMP3, MMP10, PLAU, IL1R1, IL13RA2, CXCL6, CCL11, TNFSF11 and TNFRSF11B.

These and other aspects, objects, features, and advantages of the example embodiments will become apparent to those having ordinary skill in the art upon consideration of the following detailed description of illustrated example embodiments.

DETAILED DESCRIPTION OF THE EXAMPLE EMBODIMENTS

General Definitions

Figure 1:
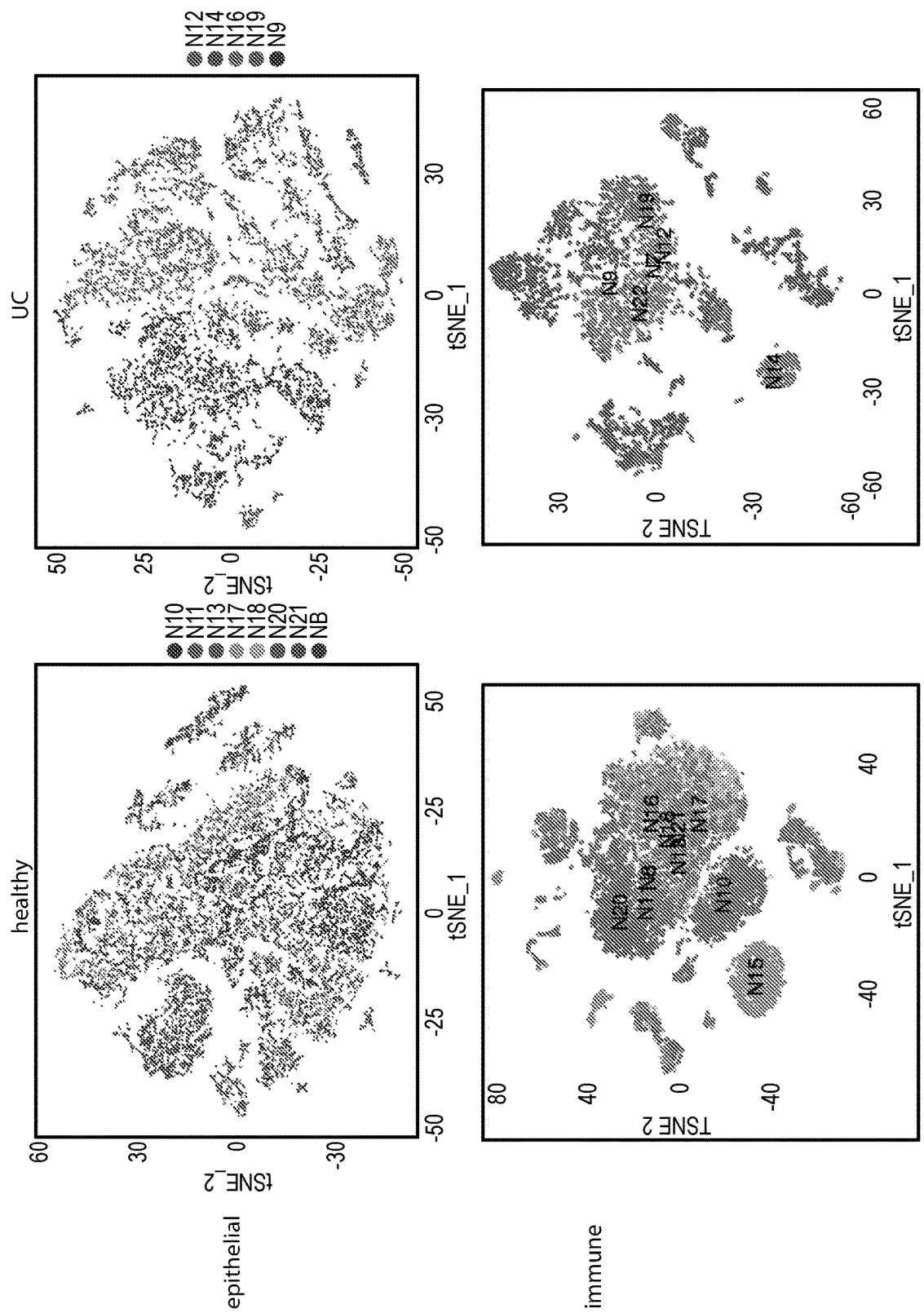
FIG. 1—illustrates that epithelial cells in UC patients partition by patient and healthy cells by cell type in tSNE plots.

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited in this application are indicative of the level of skill in the art(s) to which the application pertains. All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide for a human cell atlas of the colon from healthy and diseased subjects. Applicants identified additional phenotypic markers for these cells in the lamina propria and addressed the role of these location-specific regulatory cells in the prevention and the resolution of intestinal inflammation in human UC. The atlas was obtained by single sequencing of about 117,819 cells. By sequencing single cells from biopsies that are routinely collected during the treatment of IBD, Applicants were able to generate complete molecular profiles of the disease within each patient at single cell resolution. This single cell census of the human colon during health and disease revealed nearly all disease-relevant cell types, with the notable exception of neutrophils, and will serve as a foundational resource for the scientific community. Surprisingly, the analysis revealed new cell types and states in the colon, including a subset of chemosensory epithelial cells that may detect pH and contribute to sour taste perception in the colon, and several disease-specific cell subsets whose contributions to IBD were largely unknown, including M cells, CAIFs, inflammatory monocytes, and $CD8^+IL-17^+$ T cells. The analysis provides a framework for using sc-RNA-Seq to understand complex diseases: first, mapping cell types and cell states within healthy and diseased tissue, identifying changes in cell proportions with disease, and partitioning changes in gene expression into those that are shared by cell lineages or unique to cell subsets; then, integrating these analyses to understand how changes in gene expression propagate into changes in cell-cell interactions, identifying the "cell-of-action" for GWAS genes, and understanding the complex genetic risk factors for the disease.

The present invention discloses novel markers for cell types. Moreover, genes associated with disease are identified in the colon and colon specific cell types. The invention provides for diagnostic assays based on gene markers and cell composition, as well as target cell types that express genes associated with disease. The invention provides for modulating cell types and cell-cell interactions in the gut (e.g., for treating IBD). Finally, disclosed are novel cell types and methods of quantitating, detecting and isolating the cell types Biomarkers and Signatures The invention further relates to various biomarkers for quantitating, detecting or isolating gut cell subpopulations. The populations may be detected by detecting one or more biomarkers in a sample.

The term "biomarker" is widespread in the art and commonly broadly denotes a biological molecule, more particularly an endogenous biological molecule, and/or a detectable portion thereof, whose qualitative and/or quantitative evaluation in a tested object (e.g., in or on a cell, cell population, tissue, organ, or organism, e.g., in a biological sample of a subject) is predictive or informative with respect to one or more aspects of the tested object's phenotype and/or genotype. The terms "marker" and "biomarker" may be used interchangeably throughout this specification. Biomarkers as intended herein may be nucleic acid-based or peptide-, polypeptide- and/or protein-based. For example, a marker may be comprised of peptide(s), polypeptide(s) and/or protein(s) encoded by a given gene, or of detectable portions thereof. Further, whereas the term "nucleic acid" generally encompasses DNA, RNA and DNA/RNA hybrid molecules, in the context of markers the term may typically refer to heterogeneous nuclear RNA (hnRNA), pre-mRNA, messenger RNA (mRNA), or complementary DNA (cDNA), or detectable portions thereof. Such nucleic acid species are particularly useful as markers, since they contain qualitative and/or quantitative information about the expression of the gene. Particularly preferably, a nucleic acid-based marker may encompass mRNA of a given gene, or cDNA made of the mRNA, or detectable portions thereof. Any such nucleic acid(s), peptide(s), polypeptide(s) and/or protein(s) encoded by or produced from a given gene are encompassed by the term "gene product(s)".

Preferably, markers as intended herein may be extracellular or cell surface markers, as methods to measure extracellular or cell surface marker(s) need not disturb the integrity of the cell membrane and may not require fixation/permeabilization of the cells.

Unless otherwise apparent from the context, reference herein to any marker, such as a peptide, polypeptide, protein, or nucleic acid, may generally also encompass modified forms of said marker, such as bearing post-expression modifications including, for example, phosphorylation, glycosylation, lipidation, methylation, cysteinylation, sulphonation, glutathionylation, acetylation, oxidation of methionine to methionine sulphoxide or methionine sulphone, and the like.

The term "peptide" as used throughout this specification preferably refers to a polypeptide as used herein consisting essentially of 50 amino acids or less, e.g., 45 amino acids or less, preferably 40 amino acids or less, e.g., 35 amino acids or less, more preferably 30 amino acids or less, e.g., 25 or less, 20 or less, 15 or less, 10 or less or 5 or less amino acids.

The term "polypeptide" as used throughout this specification generally encompasses polymeric chains of amino acid residues linked by peptide bonds. Hence, insofar a protein is only composed of a single polypeptide chain, the terms "protein" and "polypeptide" may be used interchangeably herein to denote such a protein. The term is not limited to any minimum length of the polypeptide chain. The term may encompass naturally, recombinantly, semi-synthetically or synthetically produced polypeptides. The term also encompasses polypeptides that carry one or more co- or post-expression-type modifications of the polypeptide chain, such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes polypeptide variants or mutants which carry amino acid sequence variations vis-à-vis a corresponding native polypeptide, such as, e.g., amino acid deletions, additions and/or substitutions. The term contemplates both full-length polypeptides and polypeptide parts or fragments, e.g., naturally-occurring polypeptide parts that ensue from processing of such full-length polypeptides.

The term "protein" as used throughout this specification generally encompasses macromolecules comprising one or more polypeptide chains, i.e., polymeric chains of amino acid residues linked by peptide bonds. The term may encompass naturally, recombinantly, semi-synthetically or synthetically produced proteins. The term also encompasses proteins that carry one or more co- or post-expression-type modifications of the polypeptide chain(s), such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes protein variants or mutants which carry amino acid sequence variations vis-à-vis a corresponding native protein, such as, e.g., amino acid deletions, additions and/or substitutions. The term contemplates both full-length proteins and protein parts or fragments, e.g., naturally-occurring protein parts that ensue from processing of such full-length proteins.

The reference to any marker, including any peptide, polypeptide, protein, or nucleic acid, corresponds to the marker commonly known under the respective designations in the art. The terms encompass such markers of any organism where found, and particularly of animals, preferably warm-blooded animals, more preferably vertebrates, yet more preferably mammals, including humans and non-human mammals, still more preferably of humans.

The terms particularly encompass such markers, including any peptides, polypeptides, proteins, or nucleic acids, with a native sequence, i.e., ones of which the primary sequence is the same as that of the markers found in or derived from nature. A skilled person understands that native sequences may differ between different species due to genetic divergence between such species. Moreover, native sequences may differ between or within different individuals of the same species due to normal genetic diversity (variation) within a given species. Also, native sequences may differ between or even within different individuals of the same species due to somatic mutations, or post-transcriptional or post-translational modifications. Any such variants or isoforms of markers are intended herein. Accordingly, all sequences of markers found in or derived from nature are considered "native". The terms encompass the markers when forming a part of a living organism, organ, tissue or cell, when forming a part of a biological sample, as well as when at least partly isolated from such sources. The terms also encompass markers when produced by recombinant or synthetic means.

In certain embodiments, markers, including any peptides, polypeptides, proteins, or nucleic acids, may be human, i.e., their primary sequence may be the same as a corresponding primary sequence of or present in a naturally occurring human markers. Hence, the qualifier "human" in this connection relates to the primary sequence of the respective markers, rather than to their origin or source. For example, such markers may be present in or isolated from samples of human subjects or may be obtained by other means (e.g., by recombinant expression, cell-free transcription or translation, or non-biological nucleic acid or peptide synthesis).

The reference herein to any marker, including any peptide, polypeptide, protein, or nucleic acid, also encompasses fragments thereof. Hence, the reference herein to measuring (or measuring the quantity of) any one marker may encompass measuring the marker and/or measuring one or more fragments thereof.

For example, any marker and/or one or more fragments thereof may be measured collectively, such that the measured quantity corresponds to the sum amounts of the collectively measured species. In another example, any marker and/or one or more fragments thereof may be measured each individually. The terms encompass fragments arising by any mechanism, in vivo and/or in vitro, such as, without limitation, by alternative transcription or translation, exo- and/or endo-proteolysis, exo- and/or endo-nucleolysis, or degradation of the peptide, polypeptide, protein, or nucleic acid, such as, for example, by physical, chemical and/or enzymatic proteolysis or nucleolysis.

The term "fragment" as used throughout this specification with reference to a peptide, polypeptide, or protein generally denotes a portion of the peptide, polypeptide, or protein, such as typically an N- and/or C-terminally truncated form of the peptide, polypeptide, or protein. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the amino acid sequence length of said peptide, polypeptide, or protein. For example, insofar not exceeding the length of the full-length peptide, polypeptide, or protein, a fragment may include a sequence of ≥5 consecutive amino acids, or ≥10 consecutive amino acids, or ≥20 consecutive amino acids, or ≥30 consecutive amino acids, e.g., ≥40 consecutive amino acids, such as for example ≥50 consecutive amino acids, e.g., ≥60, ≥70, ≥80, ≥90, ≥100, ≥200, ≥300, ≥400, ≥500 or ≥600 consecutive amino acids of the corresponding full-length peptide, polypeptide, or protein.

The term "fragment" as used throughout this specification with reference to a nucleic acid (polynucleotide) generally denotes a 5'- and/or 3'-truncated form of a nucleic acid. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the nucleic acid sequence length of said nucleic acid. For example, insofar not exceeding the length of the full-length nucleic acid, a fragment may include a sequence of ≥5 consecutive nucleotides, or ≥10 consecutive nucleotides, or ≥20 consecutive nucleotides, or ≥30 consecutive nucleotides, e.g., ≥40 consecutive nucleotides, such as for example ≥50 consecutive nucleotides, e.g., ≥60, ≥70, ≥80, ≥90, ≥100, ≥200, ≥300, ≥400, ≥500 or ≥600 consecutive nucleotides of the corresponding full-length nucleic acid.

Cells such as immune cells as disclosed herein may in the context of the present specification be said to "comprise the expression" or conversely to "not express" one or more markers, such as one or more genes or gene products; or be described as "positive" or conversely as "negative" for one or more markers, such as one or more genes or gene products; or be said to "comprise" a defined "gene or gene product signature".

Such terms are commonplace and well-understood by the skilled person when characterizing cell phenotypes. By means of additional guidance, when a cell is said to be positive for or to express or comprise expression of a given marker, such as a given gene or gene product, a skilled person would conclude the presence or evidence of a distinct signal for the marker when carrying out a measurement capable of detecting or quantifying the marker in or on the cell. Suitably, the presence or evidence of the distinct signal for the marker would be concluded based on a comparison of the measurement result obtained for the cell to a result of the same measurement carried out for a negative control (for example, a cell known to not express the marker) and/or a positive control (for example, a cell known to express the marker). Where the measurement method allows for a quantitative assessment of the marker, a positive cell may generate a signal for the marker that is at least 1.5-fold higher than a signal generated for the marker by a negative control cell or than an average signal generated for the marker by a population of negative control cells, e.g., at least 2-fold, at least 4-fold, at least 10-fold, at least 20-fold, at least 30-fold, at least 40-fold, at least 50-fold higher or even higher. Further, a positive cell may generate a signal for the marker that is 3.0 or more standard deviations, e.g., 3.5 or more, 4.0 or more, 4.5 or more, or 5.0 or more standard deviations, higher than an average signal generated for the marker by a population of negative control cells.

The present invention is also directed to signatures and uses thereof. As used herein a "signature" may encompass any gene or genes, protein or proteins, or epigenetic element(s) whose expression profile or whose occurrence is associated with a specific cell type, subtype, or cell state of a specific cell type or subtype within a population of cells (e.g., tumor infiltrating lymphocytes). In certain embodiments, the expression of the CD8$^+$ TIL signatures are dependent on epigenetic modification of the genes or regulatory elements associated with the genes. Thus, in certain embodiments, use of signature genes includes epigenetic modifications that may be detected or modulated. For ease of discussion, when discussing gene expression, any gene or genes, protein or proteins, or epigenetic element(s) may be substituted. Reference to a gene name throughout the specification encompasses the human gene, mouse gene and all other orthologues as known in the art in other organisms. As used herein, the terms "signature", "expression profile", or "expression program" may be used interchangeably. It is to be understood that also when referring to proteins (e.g. differentially expressed proteins), such may fall within the definition of "gene" signature. Levels of expression or activity or prevalence may be compared between different cells in order to characterize or identify for instance signatures specific for cell (sub)populations. Increased or decreased expression or activity of signature genes may be compared between different cells in order to characterize or identify for instance specific cell (sub)populations. The detection of a signature in single cells may be used to identify and quantitate for instance specific cell (sub)populations. A signature may include a gene or genes, protein or proteins, or epigenetic element(s) whose expression or occurrence is specific to a cell (sub)population, such that expression or occurrence is exclusive to the cell (sub)population. A gene signature as used herein, may thus refer to any set of up- and down-regulated genes that are representative of a cell type or subtype. A gene signature as used herein, may also refer to any set of up- and down-regulated genes between different cells or cell (sub)populations derived from a gene-expression profile. For example, a gene signature may comprise a list of genes differentially expressed in a distinction of interest.

The signature as defined herein (being it a gene signature, protein signature or other genetic or epigenetic signature) can be used to indicate the presence of a cell type, a subtype of the cell type, the state of the microenvironment of a population of cells, a particular cell type population or subpopulation, and/or the overall status of the entire cell (sub)population. Furthermore, the signature may be indicative of cells within a population of cells in vivo. The signature may also be used to suggest for instance particular therapies, or to follow up treatment, or to suggest ways to modulate immune systems. The signatures of the present invention may be discovered by analysis of expression profiles of single-cells within a population of cells from isolated samples (e.g. tumor samples), thus allowing the discovery of novel cell subtypes or cell states that were previously invisible or unrecognized. The presence of subtypes or cell states may be determined by subtype specific or cell state specific signatures. The presence of these specific cell (sub)types or cell states may be determined by applying the signature genes to bulk sequencing data in a sample. Not being bound by a theory the signatures of the present invention may be microenvironment specific, such as their expression in a particular spatio-temporal context. Not being bound by a theory, signatures as discussed herein are specific to a particular pathological context. Not being bound by a theory, a combination of cell subtypes having a particular signature may indicate an outcome. Not being bound by a theory, the signatures can be used to deconvolute the network of cells present in a particular pathological condition. Not being bound by a theory the presence of specific cells and cell subtypes are indicative of a particular response to treatment, such as including increased or decreased susceptibility to treatment. The signature may indicate the presence of one particular cell type.

The signature according to certain embodiments of the present invention may comprise or consist of one or more genes, proteins and/or epigenetic elements, such as for instance 1, 2, 3, 4, 5, 6, 7, 8, 9, 10 or more. In certain embodiments, the signature may comprise or consist of two or more genes, proteins and/or epigenetic elements, such as for instance 2, 3, 4, 5, 6, 7, 8, 9, 10 or more. In certain embodiments, the signature may comprise or consist of three or more genes, proteins and/or epigenetic elements, such as for instance 3, 4, 5, 6, 7, 8, 9, 10 or more. In certain embodiments, the signature may comprise or consist of four or more genes, proteins and/or epigenetic elements, such as for instance 4, 5, 6, 7, 8, 9, 10 or more. In certain embodiments, the signature may comprise or consist of five or more genes, proteins and/or epigenetic elements, such as for instance 5, 6, 7, 8, 9, 10 or more. In certain embodiments, the signature may comprise or consist of six or more genes, proteins and/or epigenetic elements, such as for instance 6, 7, 8, 9, 10 or more. In certain embodiments, the signature may comprise or consist of seven or more genes, proteins and/or epigenetic elements, such as for instance 7, 8, 9, 10 or more. In certain embodiments, the signature may comprise or consist of eight or more genes, proteins and/or epigenetic elements, such as for instance 8, 9, 10 or more. In certain embodiments, the signature may comprise or consist of nine or more genes, proteins and/or epigenetic elements, such as for instance 9, 10 or more. In certain embodiments, the signature may comprise or consist of ten or more genes, proteins and/or epigenetic elements, such as for instance 10, 11, 12, 13, 14, 15, or more. It is to be understood that a signature according to the invention may for instance also include genes or proteins as well as epigenetic elements combined.

In certain embodiments, a signature is characterized as being specific for a particular cell or cell (sub)population state if it is upregulated or only present, detected or detectable in that particular cell or cell (sub)population state (e.g., disease or healthy), or alternatively is downregulated or only absent, or undetectable in that particular cell or cell (sub)population state. In this context, a signature consists of one or more differentially expressed genes/proteins or differential epigenetic elements when comparing different cells or cell (sub)populations, including comparing different gut cell or gut cell (sub)populations, as well as comparing gut cell or gut cell (sub)populations with healthy or disease (sub)populations. It is to be understood that "differentially expressed" genes/proteins include genes/proteins which are up- or down-regulated as well as genes/proteins which are turned on or off. When referring to up- or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art.

As discussed herein, differentially expressed genes/proteins, or differential epigenetic elements may be differentially expressed on a single cell level, or may be differentially expressed on a cell population level. Preferably, the differentially expressed genes/proteins or epigenetic elements as discussed herein, such as constituting the gene signatures as discussed herein, when as to the cell population or subpopulation level, refer to genes that are differentially expressed in all or substantially all cells of the population or subpopulation (such as at least 80%, preferably at least 90%, such as at least 95% of the individual cells). This allows one to define a particular subpopulation of immune cells. As referred to herein, a "subpopulation" of cells preferably refers to a particular subset of cells of a particular cell type which can be distinguished or are uniquely identifiable and set apart from other cells of this cell type. The cell subpopulation may be phenotypically characterized, and is preferably characterized by the signature as discussed herein. A cell (sub)population as referred to herein may constitute of a (sub)population of cells of a particular cell type characterized by a specific cell state.

When referring to induction, or alternatively suppression of a particular signature, preferable is meant induction or alternatively suppression (or upregulation or downregulation) of at least one gene/protein and/or epigenetic element of the signature, such as for instance at least two, at least three, at least four, at least five, at least six, or all genes/proteins and/or epigenetic elements of the signature.

Various aspects and embodiments of the invention may involve analyzing gene signatures, protein signature, and/or other genetic or epigenetic signature based on single cell analyses (e.g. single cell RNA sequencing) or alternatively based on cell population analyses, as is defined herein elsewhere.

In certain example embodiments, the signature genes may be used to deconvolute the network of cells present in a tumor based on comparing them to data from bulk analysis of a tumor sample. In certain example embodiments, the presence of specific immune cells and immune cell subtypes may be indicative of tumor growth, invasiveness and/or resistance to treatment. In one example embodiment, detection of one or more signature genes may indicate the presence of a particular cell type or cell types. In certain example embodiments, the presence of immune cell types within a tumor may indicate that the tumor will be sensitive to a treatment (e.g., checkpoint blockade therapy). In one embodiment, the signature genes of the present invention are applied to bulk sequencing data from a tumor sample obtained from a subject, such that information relating to disease outcome and personalized treatments is determined.

Detection of Gut Cell Sub-Populations

In one embodiment, the method comprises detecting or quantifying gut cells in a biological sample obtained from the gastrointestinal tract (e.g., colon, intestine). A marker, for example a gene or gene product, for example a peptide, polypeptide, protein, or nucleic acid, or a group of two or more markers, is "detected" or "measured" in a tested object (e.g., in or on a cell, cell population, tissue, organ, or organism, e.g., in a biological sample of a subject) when the presence or absence and/or quantity of said marker or said group of markers is detected or determined in the tested object, preferably substantially to the exclusion of other molecules and analytes, e.g., other genes or gene products.

The terms "increased" or "increase" or "upregulated" or "upregulate" as used herein generally mean an increase by a statically significant amount. For avoidance of doubt, "increased" means a statistically significant increase of at least 10% as compared to a reference level, including an increase of at least 20%, at least 30%, at least 40%, at least 50%, at least 60%, at least 70%, at least 80%, at least 90%, at least 100% or more, including, for example at least 2-fold, at least 3-fold, at least 4-fold, at least 5-fold, at least 10-fold increase or greater as compared to a reference level, as that term is defined herein.

The term "reduced" or "reduce" or "decrease" or "decreased" or "downregulate" or "downregulated" as used herein generally means a decrease by a statistically significant amount relative to a reference. For avoidance of doubt, "reduced" means statistically significant decrease of at least 10% as compared to a reference level, for example a decrease by at least 20%, at least 30%, at least 40%, at least 50%, or at least 60%, or at least 70%, or at least 80%, at least 90% or more, up to and including a 100% decrease (i.e., absent level as compared to a reference sample), or any decrease between 10-100% as compared to a reference level, as that.

The terms "sample" or "biological sample" as used throughout this specification include any biological specimen obtained from a subject. Particularly useful samples are those known to comprise, or expected or predicted to comprise gut cells as taught herein. Preferably, a sample may be readily obtainable by minimally invasive methods, such as blood collection or tissue biopsy, allowing the removal/isolation/provision of the sample from the subject (e.g., colonoscopy).

The terms "quantity", "amount" and "level" are synonymous and generally well-understood in the art. The terms as used throughout this specification may particularly refer to an absolute quantification of a marker in a tested object (e.g., in or on a cell, cell population, tissue, organ, or organism, e.g., in a biological sample of a subject), or to a relative quantification of a marker in a tested object, i.e., relative to another value such as relative to a reference value, or to a range of values indicating a base-line of the marker. Such values or ranges may be obtained as conventionally known.

An absolute quantity of a marker may be advantageously expressed as weight or as molar amount, or more commonly as a concentration, e.g., weight per volume or mol per volume. A relative quantity of a marker may be advantageously expressed as an increase or decrease or as a fold-increase or fold-decrease relative to said another value, such as relative to a reference value. Performing a relative comparison between first and second variables (e.g., first and second quantities) may but need not require determining first the absolute values of said first and second variables. For example, a measurement method may produce quantifiable readouts (such as, e.g., signal intensities) for said first and second variables, wherein said readouts are a function of the value of said variables, and wherein said readouts may be directly compared to produce a relative value for the first variable vs. the second variable, without the actual need to first convert the readouts to absolute values of the respective variables.

Reference values may be established according to known procedures previously employed for other cell populations, biomarkers and gene or gene product signatures. For example, a reference value may be established in an individual or a population of individuals characterized by a particular diagnosis, prediction and/or prognosis of said disease or condition (i.e., for whom said diagnosis, prediction and/or prognosis of the disease or condition holds true). Such population may comprise without limitation 2 or more, 10 or more, 100 or more, or even several hundred or more individuals.

A "deviation" of a first value from a second value may generally encompass any direction (e.g., increase: first value>second value; or decrease: first value<second value) and any extent of alteration.

For example, a deviation may encompass a decrease in a first value by, without limitation, at least about 10% (about 0.9-fold or less), or by at least about 20% (about 0.8-fold or less), or by at least about 30% (about 0.7-fold or less), or by at least about 40% (about 0.6-fold or less), or by at least about 50% (about 0.5-fold or less), or by at least about 60% (about 0.4-fold or less), or by at least about 70% (about 0.3-fold or less), or by at least about 80% (about 0.2-fold or less), or by at least about 90% (about 0.1-fold or less), relative to a second value with which a comparison is being made.

For example, a deviation may encompass an increase of a first value by, without limitation, at least about 10% (about 1.1-fold or more), or by at least about 20% (about 1.2-fold or more), or by at least about 30% (about 1.3-fold or more), or by at least about 40% (about 1.4-fold or more), or by at least about 50% (about 1.5-fold or more), or by at least about 60% (about 1.6-fold or more), or by at least about 70% (about 1.7-fold or more), or by at least about 80% (about 1.8-fold or more), or by at least about 90% (about 1.9-fold or more), or by at least about 100% (about 2-fold or more), or by at least about 150% (about 2.5-fold or more), or by at least about 200% (about 3-fold or more), or by at least about 500% (about 6-fold or more), or by at least about 700% (about 8-fold or more), or like, relative to a second value with which a comparison is being made.

Preferably, a deviation may refer to a statistically significant observed alteration. For example, a deviation may refer to an observed alteration which falls outside of error margins of reference values in a given population (as expressed, for example, by standard deviation or standard error, or by a predetermined multiple thereof, e.g., ±1×SD or ±2×SD or ±3×SD, or ±1×SE or ±2×SE or ±3×SE). Deviation may also refer to a value falling outside of a reference range defined by values in a given population (for example, outside of a range which comprises ≥40%, ≥50%, ≥60%, ≥70%, ≥75% or 80% or ≥85% or 90% or ≥95% or even 100% of values in said population).

In a further embodiment, a deviation may be concluded if an observed alteration is beyond a given threshold or cut-off. Such threshold or cut-off may be selected as generally known in the art to provide for a chosen sensitivity and/or specificity of the prediction methods, e.g., sensitivity and/or specificity of at least 50%, or at least 60%, or at least 70%, or at least 80%, or at least 85%, or at least 90%, or at least 95%.

For example, receiver-operating characteristic (ROC) curve analysis can be used to select an optimal cut-off value of the quantity of a given immune cell population, biomarker or gene or gene product signatures, for clinical use of the present diagnostic tests, based on acceptable sensitivity and specificity, or related performance measures which are well-known per se, such as positive predictive value (PPV), negative predictive value (NPV), positive likelihood ratio (LR+), negative likelihood ratio (LR−), Youden index, or similar.

The terms "diagnosis" and "monitoring" are commonplace and well-understood in medical practice. By means of further explanation and without limitation the term "diagnosis" generally refers to the process or act of recognizing, deciding on or concluding on a disease or condition in a subject on the basis of symptoms and signs and/or from results of various diagnostic procedures (such as, for example, from knowing the presence, absence and/or quantity of one or more biomarkers characteristic of the diagnosed disease or condition).

The term "monitoring" generally refers to the follow-up of a disease or a condition in a subject for any changes which may occur over time.

The terms "prognosing" or "prognosis" generally refer to an anticipation on the progression of a disease or condition and the prospect (e.g., the probability, duration, and/or extent) of recovery. A good prognosis of the diseases or conditions taught herein may generally encompass anticipation of a satisfactory partial or complete recovery from the diseases or conditions, preferably within an acceptable time period. A good prognosis of such may more commonly encompass anticipation of not further worsening or aggravating of such, preferably within a given time period. A poor prognosis of the diseases or conditions as taught herein may generally encompass anticipation of a substandard recovery and/or unsatisfactorily slow recovery, or to substantially no recovery or even further worsening of such.

The terms also encompass prediction of a disease. The terms "predicting" or "prediction" generally refer to an advance declaration, indication or foretelling of a disease or condition in a subject not (yet) having said disease or condition. For example, a prediction of a disease or condition in a subject may indicate a probability, chance or risk that the subject will develop said disease or condition, for example within a certain time period or by a certain age. Said probability, chance or risk may be indicated inter alia as an absolute value, range or statistics, or may be indicated relative to a suitable control subject or subject population (such as, e.g., relative to a general, normal or healthy subject or subject population). Hence, the probability, chance or risk that a subject will develop a disease or condition may be advantageously indicated as increased or decreased, or as fold-increased or fold-decreased relative to a suitable control subject or subject population. As used herein, the term "prediction" of the conditions or diseases as taught herein in a subject may also particularly mean that the subject has a 'positive' prediction of such, i.e., that the subject is at risk of having such (e.g., the risk is significantly increased vis-à-vis a control subject or subject population). The term "prediction of no" diseases or conditions as taught herein as described herein in a subject may particularly mean that the subject has a 'negative' prediction of such, i.e., that the subject's risk of having such is not significantly increased vis-à-vis a control subject or subject population.

Methods of Detection and Isolation of Cell Types Using Biomarkers

In certain embodiments, the gut cell types may be detected, quantified or isolated using a technique selected from the group consisting of flow cytometry, mass cytometry, fluorescence activated cell sorting (FACS), fluorescence microscopy, affinity separation, magnetic cell separation, microfluidic separation, RNA-seq (e.g., bulk or single cell), quantitative PCR, MERFISH (multiplex (in situ) RNA FISH) and combinations thereof. The technique may employ one or more agents capable of specifically binding to one or more gene products expressed or not expressed by the gut cells, preferably on the cell surface of the gut cells. The one or more agents may be one or more antibodies. Other methods including absorbance assays and colorimetric assays are known in the art and may be used herein.

Depending on factors that can be evaluated and decided on by a skilled person, such as, inter alia, the type of a marker (e.g., peptide, polypeptide, protein, or nucleic acid), the type of the tested object (e.g., a cell, cell population, tissue, organ, or organism, e.g., the type of biological sample of a subject, e.g., whole blood, plasma, serum, tissue biopsy), the expected abundance of the marker in the tested object, the type, robustness, sensitivity and/or specificity of the detection method used to detect the marker, etc., the marker may be measured directly in the tested object, or the tested object may be subjected to one or more processing steps aimed at achieving an adequate measurement of the marker.

In other example embodiments, detection of a marker may include immunological assay methods, wherein the ability of an assay to separate, detect and/or quantify a marker (such as, preferably, peptide, polypeptide, or protein) is conferred by specific binding between a separable, detectable and/or quantifiable immunological binding agent (antibody) and the marker. Immunological assay methods include without limitation immunohistochemistry, immunocytochemistry, flow cytometry, mass cytometry, fluorescence activated cell sorting (FACS), fluorescence microscopy, fluorescence based cell sorting using microfluidic systems, immunoaffinity adsorption based techniques such as affinity chromatography, magnetic particle separation, magnetic activated cell sorting or bead based cell sorting using microfluidic systems, enzyme-linked immunosorbent assay (ELISA) and ELISPOT based techniques, radioimmunoassay (RIA), Western blot, etc.

In certain example embodiments, detection of a marker or signature may include biochemical assay methods, including inter alia assays of enzymatic activity, membrane channel activity, substance-binding activity, gene regulatory activity, or cell signaling activity of a marker, e.g., peptide, polypeptide, protein, or nucleic acid.

In other example embodiments, detection of a marker may include mass spectrometry analysis methods. Generally, any mass spectrometric (MS) techniques that are capable of obtaining precise information on the mass of peptides, and preferably also on fragmentation and/or (partial) amino acid sequence of selected peptides (e.g., in tandem mass spectrometry, MS/MS; or in post source decay, TOF MS), may be useful herein for separation, detection and/or quantification of markers (such as, preferably, peptides, polypeptides, or proteins). Suitable peptide MS and MS/MS techniques and systems are well-known per se (see, e.g., Methods in Molecular Biology, vol. 146: "Mass Spectrometry of Proteins and Peptides", by Chapman, ed., Humana Press 2000, ISBN 089603609x; Biemann 1990. Methods Enzymol 193: 455-79; or Methods in Enzymology, vol. 402: "Biological Mass Spectrometry", by Burlingame, ed., Academic Press 2005, ISBN 9780121828073) and may be used herein. MS arrangements, instruments and systems suitable for biomarker peptide analysis may include, without limitation, matrix-assisted laser desorption/ionisation time-of-flight (MALDI-TOF) MS; MALDI-TOF post-source-decay (PSD); MALDI-TOF/TOF; surface-enhanced laser desorption/ionization time-of-flight mass spectrometry (SELDI-TOF) MS; electrospray ionization mass spectrometry (ESI-MS); ESI-MS/MS; ESI-MS/(MS)n (n is an integer greater than zero); ESI 3D or linear (2D) ion trap MS; ESI triple quadrupole MS; ESI quadrupole orthogonal TOF (Q-TOF); ESI Fourier transform MS systems; desorption/ionization on silicon (DIOS); secondary ion mass spectrometry (SIMS); atmospheric pressure chemical ionization mass spectrometry (APCI-MS); APCI-MS/MS; APCI-(MS)n; atmospheric pressure photoionization mass spectrometry (APPI-MS); APPI-MS/MS; and APPI-(MS)n. Peptide ion fragmentation in tandem MS (MS/MS) arrangements may be achieved using manners established in the art, such as, e.g., collision induced dissociation (CID). Detection and quantification of markers by mass spectrometry may involve multiple reaction monitoring (MRM), such as described among others by Kuhn et al. 2004 (Proteomics 4: 1175-86). MS peptide analysis methods may be advantageously combined with upstream peptide or protein separation or fractionation methods, such as for example with the chromatographic and other methods.

In other example embodiments, detection of a marker may include chromatography methods. In a one example embodiment, chromatography refers to a process in which a mixture of substances (analytes) carried by a moving stream of liquid or gas ("mobile phase") is separated into components as a result of differential distribution of the analytes, as they flow around or over a stationary liquid or solid phase ("stationary phase"), between said mobile phase and said stationary phase. The stationary phase may be usually a finely divided solid, a sheet of filter material, or a thin film of a liquid on the surface of a solid, or the like. Chromatography may be columnar. While particulars of chromatography are well known in the art, for further guidance see, e.g., Meyer M., 1998, ISBN: 047198373X, and "Practical HPLC Methodology and Applications", Bidlingmeyer, B. A., John Wiley & Sons Inc., 1993. Exemplary types of chromatography include, without limitation, high-performance liquid chromatography (HPLC), normal phase HPLC (NP-HPLC), reversed phase HPLC (RP-HPLC), ion exchange chromatography (IEC), such as cation or anion exchange chromatography, hydrophilic interaction chromatography (HILIC), hydrophobic interaction chromatography (HIC), size exclusion chromatography (SEC) including gel filtration chromatography or gel permeation chromatography, chromatofocusing, affinity chromatography such as immunoaffinity, immobilised metal affinity chromatography, and the like.

In certain embodiments, further techniques for separating, detecting and/or quantifying markers may be used in conjunction with any of the above described detection methods. Such methods include, without limitation, chemical extraction partitioning, isoelectric focusing (IEF) including capillary isoelectric focusing (CIEF), capillary isotachophoresis (CITP), capillary electrochromatography (CEC), and the like, one-dimensional polyacrylamide gel electrophoresis (PAGE), two-dimensional polyacrylamide gel electrophoresis (2D-PAGE), capillary gel electrophoresis (CGE), capillary zone electrophoresis (CZE), micellar electrokinetic chromatography (MEKC), free flow electrophoresis (FFE), etc.

In certain examples, such methods may include separating, detecting and/or quantifying markers at the nucleic acid level, more particularly RNA level, e.g., at the level of hnRNA, pre-mRNA, mRNA, or cDNA. Standard quantitative RNA or cDNA measurement tools known in the art may be used. Non-limiting examples include hybridization-based analysis, microarray expression analysis, digital gene-expression profiling (DGE), RNA-in-situ hybridization (RISH), Northern-blot analysis and the like; PCR, RT-PCR, RT-qPCR, end-point PCR, digital PCR or the like; supported oligonucleotide detection, pyrosequencing, polony cyclic sequencing by synthesis, simultaneous bi-directional sequencing, single-molecule sequencing, single molecule real time sequencing, true single molecule sequencing, hybridization-assisted nanopore sequencing, sequencing by synthesis, single-cell RNA sequencing (sc-RNA seq), or the like. By means of an example, methods to profile the RNA content of large numbers of individual cells have been recently developed.

In certain embodiments, the invention involves plate based single cell RNA sequencing (see, e.g., Picelli, S. et al., 2014, "Full-length RNA-seq from single cells using Smartseq2" Nature protocols 9, 171-181, doi:10.1038/nprot.2014.006).

In certain embodiments, special microfluidic devices have been developed to encapsulate each cell in an individual drop, associate the RNA of each cell with a 'cell barcode' unique to that cell/drop, measure the expression level of each RNA with sequencing, and then use the cell barcodes to determine which cell each RNA molecule came from. In certain embodiments, single cells are segregated. In these regards, reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. January; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Vitak, et al., "Sequencing thousands of single-cell genomes with combinatorial indexing" Nature Methods, 14(3):302-308, 2017; Cao, et al., Comprehensive single-cell transcriptional profiling of a multicellular organism. Science, 357(6352): 661-667, 2017; and Gierahn et al., "Seq-Well: portable, low-cost RNA sequencing of single cells at high throughput" Nature Methods 14, 395-398 (2017), all the contents and disclosure of each of which are herein incorporated by reference in their entirety.

In certain embodiments, the invention involves single nucleus RNA sequencing. In this regard reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October; 14(10):955-958; and International patent application number PCT/US2016/059239, published as WO2017164936 on Sep. 28, 2017, which are herein incorporated by reference in their entirety.

The terms "isolating" or "purifying" as used throughout this specification with reference to a particular component of a composition or mixture (e.g., the tested object such as the biological sample) encompass processes or techniques whereby such component is separated from one or more or (substantially) all other components of the composition or mixture (e.g., the tested object such as the biological sample). The terms do not require absolute purity. Instead, isolating or purifying the component will produce a discrete environment in which the abundance of the component relative to one or more or all other components is greater than in the starting composition or mixture (e.g., the tested object such as the biological sample). A discrete environment may denote a single medium, such as for example a single solution, dispersion, gel, precipitate, etc. Isolating or purifying the specified cells from the tested object such as the biological sample may increase the abundance of the specified cells relative to all other cells comprised in the tested object such as the biological sample, or relative to other cells of a select subset of the cells comprised in the tested object such as the biological sample, e.g., relative to other white blood cells, peripheral blood mononuclear cells, immune cells, antigen presenting cells, or dendritic cells comprised in the tested object such as the biological sample.

By means of example, isolating or purifying the specified cells from the tested object such as the biological sample may yield a cell population, in which the specified cells constitute at least 40% (by number) of all cells of said cell population, for example, at least 45%, preferably at least 50%, at least 55%, more preferably at least 60%, at least 65%, still more preferably at least 70%, at least 75%, even more preferably at least 80%, at least 85%, and yet more preferably at least 90%, at least 95%, at least 96%, at least 97%, at least 98%, at least 99%, or even 100% of all cells of said cell population.

The method may allow to detect or conclude the presence or absence of the specified cells in a tested object (e.g., in a cell population, tissue, organ, organism, or in a biological sample of a subject). The method may also allow to quantify the specified cells in a tested object (e.g., in a cell population, tissue, organ, organism, or in a biological sample of a subject). The quantity of the specified cells in the tested object such as the biological sample may be suitably expressed for example as the number (count) of the specified immune cells per standard unit of volume (e.g., ml, µl or nl) or weight (e.g., g or mg or ng) of the tested object such as the biological sample. The quantity of the specified cells in the tested object such as the biological sample may also be suitably expressed as a percentage or fraction (by number) of all cells comprised in the tested object such as the biological sample, or as a percentage or fraction (by number) of a select subset of the cells comprised in the tested object such as the biological sample, e.g., as a percentage or fraction (by number) of white blood cells, peripheral blood mononuclear cells, immune cells, antigen presenting cells, or dendritic cells comprised in the tested object such as the biological sample. The quantity of the specified cells in the tested object such as the biological sample may also be suitably represented by an absolute or relative quantity of a suitable surrogate analyte, such as a peptide, polypeptide, protein, or nucleic acid expressed or comprised by the specified cells.

Where a marker is detected in or on a cell, the cell may be conventionally denoted as positive ($^+$) or negative ($-$) for the marker. Semi-quantitative denotations of marker expression in cells are also commonplace in the art, such as particularly in flow cytometry quantifications, for example, "dim" vs. "bright", or "low" vs. "medium"/"intermediate" vs. "high", or "$-$" vs. "$^+$" vs. "$^{++}$", commonly controlled in flow cytometry quantifications by setting of the gates. Where a marker is quantified in or on a cell, absolute quantity of the marker may also be expressed for example as the number of molecules of the marker comprised by the cell.

Where a marker is detected and/or quantified on a single cell level in a cell population, the quantity of the marker may also be expressed as a percentage or fraction (by number) of cells comprised in said population that are positive for said marker, or as percentages or fractions (by number) of cells comprised in said population that are "dim" or "bright", or that are "low" or "medium"/"intermediate" or "high", or that are "$-$" or "$^+$" or "$^{++}$". By means of an example, a sizeable proportion of the tested cells of the cell population may be positive for the marker, e.g., at least about 20%, at least about 40%, at least about 50%, at least about 60%, at least about 70%, at least about 80%, at least about 90%, at least about 95%, or up to 100%.

Use of Specific Binding Agents

In certain embodiments, the aforementioned methods and techniques may employ agent(s) capable of specifically binding to one or more gene products, e.g., peptides, polypeptides, proteins, or nucleic acids, expressed or not expressed by the immune cells as taught herein. In certain preferred embodiments, such one or more gene products, e.g., peptides, polypeptides, or proteins, may be expressed on the cell surface of the immune cells (i.e., cell surface markers, e.g., transmembrane peptides, polypeptides or proteins, or secreted peptides, polypeptides or proteins which remain associated with the cell surface). Hence, further disclosed are binding agents capable of specifically binding to markers, such as genes or gene products, e.g., peptides, polypeptides, proteins, or nucleic acids as taught herein. Binding agents as intended throughout this specification may include inter alia antibodies, aptamers, spiegelmers (L-aptamers), photoaptamers, protein, peptides, peptidomimetics, nucleic acids such as oligonucleotides (e.g., hybridization probes or amplification or sequencing primers and primer pairs), small molecules, or combinations thereof.

The term "aptamer" refers to single-stranded or double-stranded oligo-DNA, oligo-RNA or oligo-DNA/RNA or any analogue thereof that specifically binds to a target molecule such as a peptide. Advantageously, aptamers display fairly high specificity and affinity (e.g., KA in the order $1\times10^9$ M-1) for their targets. Aptamer production is described inter alia in U.S. Pat. No. 5,270,163; Ellington & Szostak 1990 (Nature 346: 818-822); Tuerk & Gold 1990 (Science 249: 505-510); or "Me Aptamer Handbook: Functional Oligonucleotides and Their Applications", by Klussmann, ed., Wiley-VCH 2006, ISBN 3527310592, incorporated by reference herein. The term "photoaptamer" refers to an aptamer that contains one or more photoreactive functional groups that can covalently bind to or crosslink with a target molecule. The term "spiegelmer" refers to an aptamer which includes L-DNA, L-RNA, or other left-handed nucleotide derivatives or nucleotide-like molecules. Aptamers containing left-handed nucleotides are resistant to degradation by naturally occurring enzymes, which normally act on substrates containing right-handed nucleotides. The term "peptidomimetic" refers to a non-peptide agent that is a topological analogue of a corresponding peptide. Methods of rationally designing peptidomimetics of peptides are known in the art. For example, the rational design of three peptidomimetics based on the sulphated 8-mer peptide CCK26-33, and of two peptidomimetics based on the 11-mer peptide Substance P, and related peptidomimetic design principles, are described in Horwell 1995 (Trends Biotechnol 13: 132-134).

Binding agents may be in various forms, e.g., lyophilised, free in solution, or immobilised on a solid phase. They may be, e.g., provided in a multi-well plate or as an array or microarray, or they may be packaged separately, individually, or in combination.

The term "specifically bind" as used throughout this specification means that an agent (denoted herein also as "specific-binding agent") binds to one or more desired molecules or analytes (e.g., peptides, polypeptides, proteins, or nucleic acids) substantially to the exclusion of other molecules which are random or unrelated, and optionally substantially to the exclusion of other molecules that are structurally related. The term "specifically bind" does not necessarily require that an agent binds exclusively to its intended target(s). For example, an agent may be said to specifically bind to target(s) of interest if its affinity for such intended target(s) under the conditions of binding is at least about 2-fold greater, preferably at least about 5-fold greater, more preferably at least about 10-fold greater, yet more preferably at least about 25-fold greater, still more preferably at least about 50-fold greater, and even more preferably at least about 100-fold, or at least about 1000-fold, or at least about 104-fold, or at least about 105-fold, or at least about 106-fold or more greater, than its affinity for a non-target molecule, such as for a suitable control molecule (e.g., bovine serum albumin, casein).

Preferably, the specific binding agent may bind to its intended target(s) with affinity constant (KA) of such binding $KA \geq 1\times10^6$ M-1, more preferably $KA \geq 1\times10^7$ M-1, yet more preferably $KA \geq 1\times10^8$ M-1, even more preferably $KA \geq 1\times10^9$ M-1, and still more preferably $KA \geq 1\times10^{10}$ M-1 or $KA \geq 1\times10^{11}$ M-1 or $KA \geq 1\times10^{12}$ M-1, wherein KA=[SBA_T]/[SBA][T], SBA denotes the specific-binding agent, T denotes the intended target. Determination of KA can be carried out by methods known in the art, such as for example, using equilibrium dialysis and Scatchard plot analysis.

In certain embodiments, the one or more binding agents may be one or more antibodies. As used herein, the term "antibody" is used in its broadest sense and generally refers to any immunologic binding agent. The term specifically encompasses intact monoclonal antibodies, polyclonal antibodies, multivalent (e.g., 2-, 3- or more-valent) and/or multi-specific antibodies (e.g., bi- or more-specific antibodies) formed from at least two intact antibodies, and antibody fragments insofar they exhibit the desired biological activity (particularly, ability to specifically bind an antigen of interest, i.e., antigen-binding fragments), as well as multivalent and/or multi-specific composites of such fragments. The term "antibody" is not only inclusive of antibodies generated by methods comprising immunization, but also includes any polypeptide, e.g., a recombinantly expressed polypeptide, which is made to encompass at least one complementarity-determining region (CDR) capable of specifically binding to an epitope on an antigen of interest. Hence, the term applies to such molecules regardless whether they are produced in vitro or in vivo. Antibodies also encompasses chimeric, humanized and fully humanized antibodies.

An antibody may be any of IgA, IgD, IgE, IgG and IgM classes, and preferably IgG class antibody. An antibody may be a polyclonal antibody, e.g., an antiserum or immunoglobulins purified there from (e.g., affinity-purified). An antibody may be a monoclonal antibody or a mixture of monoclonal antibodies. Monoclonal antibodies can target a particular antigen or a particular epitope within an antigen with greater selectivity and reproducibility. By means of example and not limitation, monoclonal antibodies may be made by the hybridoma method first described by Kohler et al. 1975 (Nature 256: 495), or may be made by recombinant DNA methods (e.g., as in U.S. Pat. No. 4,816,567). Monoclonal antibodies may also be isolated from phage antibody libraries using techniques as described by Clackson et al. 1991 (Nature 352: 624-628) and Marks et al. 1991 (J Mol Biol 222: 581-597), for example.

Antibody binding agents may be antibody fragments. "Antibody fragments" comprise a portion of an intact antibody, comprising the antigen-binding or variable region thereof. Examples of antibody fragments include Fab, Fab', F(ab')2, Fv and scFv fragments, single domain (sd) Fv, such as VH domains, VL domains and VHH domains; diabodies; linear antibodies; single-chain antibody molecules, in particular heavy-chain antibodies; and multivalent and/or multispecific antibodies formed from antibody fragment(s), e.g., dibodies, tribodies, and multibodies. The above designations Fab, Fab', F(ab')2, Fv, scFv etc. are intended to have their art-established meaning.

The term antibody includes antibodies originating from or comprising one or more portions derived from any animal species, preferably vertebrate species, including, e.g., birds and mammals. Without limitation, the antibodies may be chicken, turkey, goose, duck, guinea fowl, quail or pheasant. Also without limitation, the antibodies may be human, murine (e.g., mouse, rat, etc.), donkey, rabbit, goat, sheep, guinea pig, camel (e.g., *Camelus bactrianus* and *Camelus dromedarius*), llama (e.g., *Lama pacos, Lama glama* or *Lama vicugna*) or horse.

A skilled person will understand that an antibody can include one or more amino acid deletions, additions and/or substitutions (e.g., conservative substitutions), insofar such alterations preserve its binding of the respective antigen. An antibody may also include one or more native or artificial modifications of its constituent amino acid residues (e.g., glycosylation, etc.).

Methods of producing polyclonal and monoclonal antibodies as well as fragments thereof are well known in the art, as are methods to produce recombinant antibodies or fragments thereof (see for example, Harlow and Lane, "Antibodies: A Laboratory Manual", Cold Spring Harbour Laboratory, New York, 1988; Harlow and Lane, "Using Antibodies: A Laboratory Manual", Cold Spring Harbour Laboratory, New York, 1999, ISBN 0879695447; "Monoclonal Antibodies: A Manual of Techniques", by Zola, ed., CRC Press 1987, ISBN 0849364760; "Monoclonal Antibodies: A Practical Approach", by Dean & Shepherd, eds., Oxford University Press 2000, ISBN 0199637229; Methods in Molecular Biology, vol. 248: "Antibody Engineering: Methods and Protocols", Lo, ed., Humana Press 2004, ISBN 1588290921).

As used herein, a "blocking" antibody or an antibody "antagonist" is one which inhibits or reduces biological activity of the antigen(s) it binds. In certain embodiments, the blocking antibodies or antagonist antibodies or portions thereof described herein completely inhibit the biological activity of the antigen(s).

Antibodies may act as agonists or antagonists of the recognized polypeptides. For example, the present invention includes antibodies which disrupt receptor/ligand interactions either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or of one of its down-stream substrates by immunoprecipitation followed by western blot analysis. In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex. Likewise, encompassed by the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides disclosed herein. The antibody agonists and antagonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16): 3668-3678 (1998); Harrop et al., J. Immunol. 161(4):1786-1794 (1998); Zhu et al., Cancer Res. 58(15):3209-3214 (1998); Yoon et al., J. Immunol. 160(7):3170-3179 (1998); Prat et al., J. Cell. Sci. III (Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4): 755-762 (1995); Muller et al., Structure 6(9):1153-1167 (1998); Bartunek et al., Cytokine 8(1):14-20 (1996).

The antibodies as defined for the present invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Simple binding assays can be used to screen for or detect agents that bind to a target protein, or disrupt the interaction between proteins (e.g., a receptor and a ligand). Because certain targets of the present invention are transmembrane proteins, assays that use the soluble forms of these proteins rather than full-length protein can be used, in some embodiments. Soluble forms include, for example, those lacking the transmembrane domain and/or those comprising the IgV domain or fragments thereof which retain their ability to bind their cognate binding partners. Further, agents that inhibit or enhance protein interactions for use in the compositions and methods described herein, can include recombinant peptido-mimetics.

Detection methods useful in screening assays include antibody-based methods, detection of a reporter moiety, detection of cytokines as described herein, and detection of a gene signature as described herein.

Another variation of assays to determine binding of a receptor protein to a ligand protein is through the use of affinity biosensor methods. Such methods may be based on the piezoelectric effect, electrochemistry, or optical methods, such as ellipsometry, optical wave guidance, and surface plasmon resonance (SPR).

The term "antibody-like protein scaffolds" or "engineered protein scaffolds" broadly encompasses proteinaceous non-immunoglobulin specific-binding agents, typically obtained by combinatorial engineering (such as site-directed random mutagenesis in combination with phage display or other molecular selection techniques). Usually, such scaffolds are derived from robust and small soluble monomeric proteins (such as Kunitz inhibitors or lipocalins) or from a stably folded extra-membrane domain of a cell surface receptor (such as protein A, fibronectin or the ankyrin repeat).

Such scaffolds have been extensively reviewed in Binz et al. (Engineering novel binding proteins from nonimmunoglobulin domains. Nat Biotechnol 2005, 23:1257-1268), Gebauer and Skerra (Engineered protein scaffolds as next-generation antibody therapeutics. Curr Opin Chem Biol. 2009, 13:245-55), Gill and Damle (Biopharmaceutical drug discovery using novel protein scaffolds. Curr Opin Biotechnol 2006, 17:653-658), Skerra (Engineered protein scaffolds for molecular recognition. J Mol Recognit 2000, 13:167-187), and Skerra (Alternative non-antibody scaffolds for molecular recognition. Curr Opin Biotechnol 2007, 18:295-304), and include without limitation affibodies, based on the Z-domain of staphylococcal protein A, a three-helix bundle of 58 residues providing an interface on two of its alpha-helices (Nygren, Alternative binding proteins: Affibody binding proteins developed from a small three-helix bundle scaffold. FEBS J 2008, 275:2668-2676); engineered Kunitz domains based on a small (ca. 58 residues) and robust, disulphide-crosslinked serine protease inhibitor, typically of human origin (e.g. LACI-D1), which can be engineered for different protease specificities (Nixon and Wood, Engineered protein inhibitors of proteases. Curr Opin Drug Discov Dev 2006, 9:261-268); monobodies or adnectins based on the 10th extracellular domain of human fibronectin III (10Fn3), which adopts an Ig-like beta-sandwich fold (94 residues) with 2-3 exposed loops, but lacks the central disulphide bridge (Koide and Koide, Monobodies: antibody mimics based on the scaffold of the fibronectin type III domain. Methods Mol Biol 2007, 352:95-109); anticalins derived from the lipocalins, a diverse family of eight-stranded beta-barrel proteins (ca. 180 residues) that naturally form binding sites for small ligands by means of four structurally variable loops at the open end, which are abundant in humans, insects, and many other organisms (Skerra, Alternative binding proteins: Anticalins-harnessing the structural plasticity of the lipocalin ligand pocket to engineer novel binding activities. FEBS J 2008, 275:2677-2683); DARPins, designed ankyrin repeat domains (166 residues), which provide a rigid interface arising from typically three repeated beta-turns (Stumpp et al., DARPins: a new generation of protein therapeutics. Drug Discov Today 2008, 13:695-701); avimers (multimerized LDLR-A module) (Silverman et al., Multivalent avimer proteins evolved by exon shuffling of a family of human receptor domains. Nat Biotechnol 2005, 23:1556-1561); and cysteine-rich knottin peptides (Kolmar, Alternative binding proteins: biological activity and therapeutic potential of cystine-knot miniproteins. FEBS J 2008, 275:2684-2690).

Nucleic acid binding agents, such as oligonucleotide binding agents, are typically at least partly antisense to a target nucleic acid of interest. The term "antisense" generally refers to an agent (e.g., an oligonucleotide) configured to specifically anneal with (hybridise to) a given sequence in a target nucleic acid, such as for example in a target DNA, hnRNA, pre-mRNA or mRNA, and typically comprises, consist essentially of or consist of a nucleic acid sequence that is complementary or substantially complementary to said target nucleic acid sequence. Antisense agents suitable for use herein, such as hybridisation probes or amplification or sequencing primers and primer pairs may typically be capable of annealing with (hybridizing to) the respective target nucleic acid sequences at high stringency conditions, and capable of hybridising specifically to the target under physiological conditions. The terms "complementary" or "complementarity" as used throughout this specification with reference to nucleic acids, refer to the normal binding of single-stranded nucleic acids under permissive salt (ionic strength) and temperature conditions by base pairing, preferably Watson-Crick base pairing. By means of example, complementary Watson-Crick base pairing occurs between the bases A and T, A and U or G and C. For example, the sequence 5'-A-G-U-3' is complementary to sequence 5'-A-C-U-3'.

The reference to oligonucleotides may in particular but without limitation include hybridization probes and/or amplification primers and/or sequencing primers, etc., as commonly used in nucleic acid detection technologies.

Binding agents as discussed herein may suitably comprise a detectable label. The term "label" refers to any atom, molecule, moiety or biomolecule that may be used to provide a detectable and preferably quantifiable read-out or property, and that may be attached to or made part of an entity of interest, such as a binding agent. Labels may be suitably detectable by for example mass spectrometric, spectroscopic, optical, colourimetric, magnetic, photochemical, biochemical, immunochemical or chemical means. Labels include without limitation dyes; radiolabels such as $^{32}P$, $^{33}P$, $^{35}S$, $^{125}I$, $^{131}I$; electron-dense reagents; enzymes (e.g., horse-radish peroxidase or alkaline phosphatase as commonly used in immunoassays); binding moieties such as biotin-streptavidin; haptens such as digoxigenin; luminogenic, phosphorescent or fluorogenic moieties; mass tags; and fluorescent dyes alone or in combination with moieties that may suppress or shift emission spectra by fluorescence resonance energy transfer (FRET).

In some embodiments, binding agents may be provided with a tag that permits detection with another agent (e.g., with a probe binding partner). Such tags may be, for example, biotin, streptavidin, his-tag, myc tag, maltose, maltose binding protein or any other kind of tag known in the art that has a binding partner. Example of associations which may be utilised in the probe:binding partner arrangement may be any, and includes, for example biotin:streptavidin, his-tag:metal ion (e.g., $Ni2^+$), maltose:maltose binding protein, etc.

The marker-binding agent conjugate may be associated with or attached to a detection agent to facilitate detection. Examples of detection agents include, but are not limited to, luminescent labels; colourimetric labels, such as dyes; fluorescent labels; or chemical labels, such as electroactive agents (e.g., ferrocyanide); enzymes; radioactive labels; or radiofrequency labels. The detection agent may be a particle. Examples of such particles include, but are not limited to, colloidal gold particles; colloidal sulphur particles; colloidal selenium particles; colloidal barium sulfate particles; colloidal iron sulfate particles; metal iodate particles; silver halide particles; silica particles; colloidal metal (hydrous) oxide particles; colloidal metal sulfide particles; colloidal lead selenide particles; colloidal cadmium selenide particles; colloidal metal phosphate particles; colloidal metal ferrite particles; any of the above-mentioned colloidal particles coated with organic or inorganic layers; protein or peptide molecules; liposomes; or organic polymer latex particles, such as polystyrene latex beads. Preferable particles may be colloidal gold particles.

In certain embodiments, the one or more binding agents are configured for use in a technique selected from the group consisting of flow cytometry, fluorescence activated cell sorting, mass cytometry, fluorescence microscopy, affinity separation, magnetic cell separation, microfluidic separation, and combinations thereof.

Identifying Modulators

A further aspect of the invention relates to a method for identifying an agent capable of modulating one or more phenotypic aspects of a gut cell or gut cell population as disclosed herein, comprising: a) applying a candidate agent to the cell or cell population; b) detecting modulation of one or more phenotypic aspects of the cell or cell population by the candidate agent, thereby identifying the agent.

The term "modulate" broadly denotes a qualitative and/or quantitative alteration, change or variation in that which is being modulated. Where modulation can be assessed quantitatively—for example, where modulation comprises or consists of a change in a quantifiable variable such as a quantifiable property of a cell or where a quantifiable variable provides a suitable surrogate for the modulation—modulation specifically encompasses both increase (e.g., activation) or decrease (e.g., inhibition) in the measured variable. The term encompasses any extent of such modulation, e.g., any extent of such increase or decrease, and may more particularly refer to statistically significant increase or decrease in the measured variable. By means of example, modulation may encompass an increase in the value of the measured variable by at least about 10%, e.g., by at least about 20%, preferably by at least about 30%, e.g., by at least about 40%, more preferably by at least about 50%, e.g., by at least about 75%, even more preferably by at least about 100%, e.g., by at least about 150%, 200%, 250%, 300%, 400% or by at least about 500%, compared to a reference situation without said modulation; or modulation may encompass a decrease or reduction in the value of the measured variable by at least about 10%, e.g., by at least about 20%, by at least about 30%, e.g., by at least about 40%, by at least about 50%, e.g., by at least about 60%, by at least about 70%, e.g., by at least about 80%, by at least about 90%, e.g., by at least about 95%, such as by at least about 96%, 97%, 98%, 99% or even by 100%, compared to a reference situation without said modulation. Preferably, modulation may be specific or selective, hence, one or more desired phenotypic aspects of a gut cell or gut cell population may be modulated without substantially altering other (unintended, undesired) phenotypic aspect(s).

The term "agent" broadly encompasses any condition, substance or agent capable of modulating one or more phenotypic aspects of an gut cell or gut cell population as disclosed herein. Such conditions, substances or agents may be of physical, chemical, biochemical and/or biological nature. The term "candidate agent" refers to any condition, substance or agent that is being examined for the ability to modulate one or more phenotypic aspects of an gut cell or gut cell population as disclosed herein in a method comprising applying the candidate agent to the gut cell or gut cell population (e.g., exposing the gut cell or gut cell population to the candidate agent or contacting the gut cell or gut cell population with the candidate agent) and observing whether the desired modulation takes place.

Agents may include any potential class of biologically active conditions, substances or agents, such as for instance antibodies, proteins, peptides, nucleic acids, oligonucleotides, small molecules, or combinations thereof.

By means of example but without limitation, agents can include low molecular weight compounds, but may also be larger compounds, or any organic or inorganic molecule effective in the given situation, including modified and unmodified nucleic acids such as antisense nucleic acids, RNAi, such as siRNA or shRNA, CRISPR/Cas systems, peptides, peptidomimetics, receptors, ligands, and antibodies, aptamers, polypeptides, nucleic acid analogues or variants thereof. Examples include an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof. Agents can be selected from a group comprising: chemicals; small molecules; nucleic acid sequences; nucleic acid analogues; proteins; peptides; aptamers; antibodies; or fragments thereof. A nucleic acid sequence can be RNA or DNA, and can be single or double stranded, and can be selected from a group comprising; nucleic acid encoding a protein of interest, oligonucleotides, nucleic acid analogues, for example peptide-nucleic acid (PNA), pseudo-complementary PNA (pc-PNA), locked nucleic acid (LNA), modified RNA (mod-RNA), single guide RNA etc. Such nucleic acid sequences include, for example, but are not limited to, nucleic acid sequence encoding proteins, for example that act as transcriptional repressors, antisense molecules, ribozymes, small inhibitory nucleic acid sequences, for example but are not limited to RNAi, shRNAi, siRNA, micro RNAi (mRNAi), antisense oligonucleotides, CRISPR guide RNA, for example that target a CRISPR enzyme to a specific DNA target sequence etc. A protein and/or peptide or fragment thereof can be any protein of interest, for example, but are not limited to: mutated proteins; therapeutic proteins and truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, minibodies, triabodies, humanized proteins, humanized antibodies, chimeric antibodies, modified proteins and fragments thereof. Alternatively, the agent can be intracellular within the cell as a result of introduction of a nucleic acid sequence into the cell and its transcription resulting in the production of the nucleic acid and/or protein modulator of a gene within the cell. In some embodiments, the agent is any chemical, entity or moiety, including without limitation synthetic and naturally-occurring non-proteinaceous entities. In certain embodiments, the agent is a small molecule having a chemical moiety. Agents can be known to have a desired activity and/or property, or can be selected from a library of diverse compounds.

In certain embodiments, an agent may be a hormone, a cytokine, a lymphokine, a growth factor, a chemokine, a cell surface receptor ligand such as a cell surface receptor agonist or antagonist, or a mitogen.

Non-limiting examples of hormones include growth hormone (GH), adrenocorticotropic hormone (ACTH), dehydroepiandrosterone (DHEA), cortisol, epinephrine, thyroid hormone, estrogen, progesterone, testosterone, or combinations thereof.

Non-limiting examples of cytokines include lymphokines (e.g., interferon-γ, IL-2, IL-3, IL-4, IL-6, granulocyte-macrophage colony-stimulating factor (GM-CSF), interferon-γ, leukocyte migration inhibitory factors (T-LIF, B-LIF), lymphotoxin-alpha, macrophage-activating factor (MAF), macrophage migration-inhibitory factor (MIF), neuroleukin, immunologic suppressor factors, transfer factors, or combinations thereof), monokines (e.g., IL-1, TNF-alpha, interferon-α, interferon-β, colony stimulating factors, e.g., CSF2, CSF3, macrophage CSF or GM-CSF, or combinations thereof), chemokines (e.g., beta-thromboglobulin, C chemokines, CC chemokines, CXC chemokines, CX3C chemokines, macrophage inflammatory protein (MIP), or combinations thereof), interleukins (e.g., IL-1, IL-2, IL-3, IL-4, IL-5, IL-6, IL-7, IL-8, IL-9, IL-10, IL-11, IL-12, IL-13, IL-14, IL-15, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, or combinations thereof), and several related signalling molecules, such as tumour necrosis factor (TNF) and interferons (e.g., interferon-α, interferon-β, interferon-γ, interferon-k, or combinations thereof).

Non-limiting examples of growth factors include those of fibroblast growth factor (FGF) family, bone morphogenic protein (BMP) family, platelet derived growth factor (PDGF) family, transforming growth factor beta (TGFbeta) family, nerve growth factor (NGF) family, epidermal growth factor (EGF) family, insulin related growth factor (IGF) family, hepatocyte growth factor (HGF) family, hematopoietic growth factors (HeGFs), platelet-derived endothelial cell growth factor (PD-ECGF), angiopoietin, vascular endothelial growth factor (VEGF) family, glucocorticoids, or combinations thereof.

Non-limiting examples of mitogens include phytohaemagglutinin (PHA), concanavalin A (conA), lipopolysaccharide (LPS), pokeweed mitogen (PWM), phorbol ester such as phorbol myristate acetate (PMA) with or without ionomycin, or combinations thereof.

Non-limiting examples of cell surface receptors the ligands of which may act as agents include Toll-like receptors (TLRs) (e.g., TLR1, TLR2, TLR3, TLR4, TLR5, TLR6, TLR7, TLR8, TLR9, TLR10, TLR11, TLR12 or TLR13), CD80, CD86, CD40, CCR7, or C-type lectin receptors.

In certain embodiments, the present invention provides for gene signature screening. The concept of signature screening was introduced by Stegmaier et al. (Gene expression-based high-throughput screening (GE-HTS) and application to leukemia differentiation. Nature Genet. 36, 257-263 (2004)), who realized that if a gene-expression signature was the proxy for a phenotype of interest, it could be used to find small molecules that effect that phenotype without knowledge of a validated drug target. The signatures of the present invention may be used to screen for drugs that induce or reduce the signature in epithelial, stromal, glia, or immune cells as described herein. The signature may be used for GE-HTS. In certain embodiments, pharmacological screens may be used to identify drugs that selectively activate gut cells. Not being bound by a theory, activation or inactivation of gut cells may have a therapeutic effect. Not being bound by a theory modulating a signature associated with disease may provide a therapeutic effect.

The Connectivity Map (cmap) is a collection of genome-wide transcriptional expression data from cultured human cells treated with bioactive small molecules and simple pattern-matching algorithms that together enable the discovery of functional connections between drugs, genes and diseases through the transitory feature of common gene-expression changes (see, Lamb et al., The Connectivity Map: Using Gene-Expression Signatures to Connect Small Molecules, Genes, and Disease. Science 29 Sep. 2006: Vol. 313, Issue 5795, pp. 1929-1935, DOI: 10.1126/science.1132939; and Lamb, J., The Connectivity Map: a new tool for biomedical research. Nature Reviews Cancer January 2007: Vol. 7, pp. 54-60). In certain embodiments, Cmap can be used to screen for small molecules capable of modulating a signature of the present invention in silico.

Particular screening applications of this invention relate to the testing of pharmaceutical compounds in drug research. The reader is referred generally to the standard textbook In vitro Methods in Pharmaceutical Research, Academic Press, 1997, and U.S. Pat. No. 5,030,015. In certain aspects of this invention, the culture of the invention is used to grow and differentiate a cachectic target cell to play the role of test cells for standard drug screening and toxicity assays. Assessment of the activity of candidate pharmaceutical compounds generally involves combining the target cell (e.g., a myocyte, an adipocyte, a cardiomyocyte or a hepatocyte) with the candidate compound, determining any change in the morphology, marker phenotype, or metabolic activity of the cells that is attributable to the candidate compound (compared with untreated cells or cells treated with an inert compound, such as vehicle), and then correlating the effect of the candidate compound with the observed change. The screening may be done because the candidate compound is designed to have a pharmacological effect on the target cell, or because a candidate compound may have unintended side effects on the target cell. Alternatively, libraries can be screened without any predetermined expectations in hopes of identifying compounds with desired effects.

Cytotoxicity can be determined in the first instance by the effect on cell viability and morphology. In certain embodiments, toxicity may be assessed by observation of vital staining techniques, ELISA assays, immunohistochemistry, and the like or by analyzing the cellular content of the culture, e.g., by total cell counts, and differential cell counts or by metabolic markers such as MTT and XTT.

Additional further uses of the culture of the invention include, but are not limited to, its use in research e.g., to elucidate mechanisms leading to the identification of novel targets for therapies, and to generate genotype-specific cells for disease modeling, including the generation of new therapies customized to different genotypes. Such customization can reduce adverse drug effects and help identify therapies appropriate to the patient's genotype.

In certain embodiments, the present invention provides method for high-throughput screening. "High-throughput screening" (HTS) refers to a process that uses a combination of modern robotics, data processing and control software, liquid handling devices, and/or sensitive detectors, to efficiently process a large amount of (e.g., thousands, hundreds of thousands, or millions of) samples in biochemical, genetic or pharmacological experiments, either in parallel or in sequence, within a reasonably short period of time (e.g., days). Preferably, the process is amenable to automation, such as robotic simultaneous handling of 96 samples, 384 samples, 1536 samples or more. A typical HTS robot tests up to 100,000 to a few hundred thousand compounds per day. The samples are often in small volumes, such as no more than 1 mL, 500 µl, 200 µl, 100 µl, 50 µl or less. Through this process, one can rapidly identify active compounds, small molecules, antibodies, proteins or polynucleotides which modulate a particular biomolecular/genetic pathway. The results of these experiments provide starting points for further drug design and for understanding the interaction or role of a particular biochemical process in biology. Thus "high-throughput screening" as used herein does not include handling large quantities of radioactive materials, slow and complicated operator-dependent screening steps, and/or prohibitively expensive reagent costs, etc.

Genetic Modifying Agents

In certain embodiments, the one or more modulating agents may be a genetic modifying agent. The genetic modifying agent may comprise a CRISPR system, a zinc finger nuclease system, a TALEN, or a meganuclease.

In general, a CRISPR-Cas or CRISPR system as used in herein and in documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA)(chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g, Shmakov et al. (2015) "Discovery and Functional Characterization of Diverse Class 2 CRISPR-Cas Systems", Molecular Cell, DOI: dx.doi.org/10.1016/j.molcel.2015.10.008.

In certain embodiments, a protospacer adjacent motif (PAM) or PAM-like motif directs binding of the effector protein complex as disclosed herein to the target locus of interest. In some embodiments, the PAM may be a 5' PAM (i.e., located upstream of the 5' end of the protospacer). In other embodiments, the PAM may be a 3' PAM (i.e., located downstream of the 5' end of the protospacer). The term "PAM" may be used interchangeably with the term "PFS" or "protospacer flanking site" or "protospacer flanking sequence".

In a preferred embodiment, the CRISPR effector protein may recognize a 3' PAM. In certain embodiments, the CRISPR effector protein may recognize a 3' PAM which is 5'H, wherein H is A, C or U.

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to a RNA polynucleotide being or comprising the target sequence. In other words, the target RNA may be a RNA polynucleotide or a part of a RNA polynucleotide to which a part of the gRNA, i.e. the guide sequence, is designed to have complementarity and to which the effector function mediated by the complex comprising CRISPR effector protein and a gRNA is to be directed. In some embodiments, a target sequence is located in the nucleus or cytoplasm of a cell.

In certain example embodiments, the CRISPR effector protein may be delivered using a nucleic acid molecule encoding the CRISPR effector protein. The nucleic acid molecule encoding a CRISPR effector protein, may advantageously be a codon optimized CRISPR effector protein. An example of a codon optimized sequence, is in this instance a sequence optimized for expression in eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a CRISPR effector protein is a codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at kazusa.or.jp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

In certain embodiments, the methods as described herein may comprise providing a Cas transgenic cell in which one or more nucleic acids encoding one or more guide RNAs are provided or introduced operably connected in the cell with a regulatory element comprising a promoter of one or more gene of interest. As used herein, the term "Cas transgenic cell" refers to a cell, such as a eukaryotic cell, in which a Cas gene has been genomically integrated. The nature, type, or origin of the cell are not particularly limiting according to the present invention. Also the way the Cas transgene is introduced in the cell may vary and can be any method as is known in the art. In certain embodiments, the Cas transgenic cell is obtained by introducing the Cas transgene in an isolated cell. In certain other embodiments, the Cas transgenic cell is obtained by isolating cells from a Cas transgenic organism. By means of example, and without limitation, the Cas transgenic cell as referred to herein may be derived from a Cas transgenic eukaryote, such as a Cas knock-in eukaryote. Reference is made to WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR Cas system of the present invention. Methods of US Patent Publication No. 20130236946 assigned to Cellectis directed to targeting the Rosa locus may also be modified to utilize the CRISPR Cas system of the present invention. By means of further example reference is made to Platt et. al. (Cell; 159(2):440-455 (2014)), describing a Cas9 knock-in mouse, which is incorporated herein by reference. The Cas transgene can further comprise a Lox-Stop-polyA-Lox(LSL) cassette thereby rendering Cas expression inducible by Cre recombinase. Alternatively, the Cas transgenic cell may be obtained by introducing the Cas transgene in an isolated cell. Delivery systems for transgenes are well known in the art. By means of example, the Cas transgene may be delivered in for instance eukaryotic cell by means of vector (e.g., AAV, adenovirus, lentivirus) and/or particle and/or nanoparticle delivery, as also described herein elsewhere.

It will be understood by the skilled person that the cell, such as the Cas transgenic cell, as referred to herein may comprise further genomic alterations besides having an integrated Cas gene or the mutations arising from the sequence specific action of Cas when complexed with RNA capable of guiding Cas to a target locus.

In certain aspects the invention involves vectors, e.g. for delivering or introducing in a cell Cas and/or RNA capable of guiding Cas to a target locus (i.e. guide RNA), but also for propagating these components (e.g. in prokaryotic cells). A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety. Thus, the embodiments disclosed herein may also comprise transgenic cells comprising the CRISPR effector system. In certain example embodiments, the transgenic cell may function as an individual discrete volume. In other words samples comprising a masking construct may be delivered to a cell, for example in a suitable delivery vesicle and if the target is present in the delivery vesicle the CRISPR effector is activated and a detectable signal generated.

The vector(s) can include the regulatory element(s), e.g., promoter(s). The vector(s) can comprise Cas encoding sequences, and/or a single, but possibly also can comprise at least 3 or 8 or 16 or 32 or 48 or 50 guide RNA(s) (e.g., sgRNAs) encoding sequences, such as 1-2, 1-3, 1-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s); and, when a single vector provides for more than 16 RNA(s), one or more promoter(s) can drive expression of more than one of the RNA(s), e.g., when there are 32 RNA(s), each promoter can drive expression of two RNA(s), and when there are 48 RNA(s), each promoter can drive expression of three RNA(s). By simple arithmetic and well established cloning protocols and the teachings in this disclosure one skilled in the art can readily practice the invention as to the RNA(s) for a suitable exemplary vector such as AAV, and a suitable promoter such as the U6 promoter. For example, the packaging limit of AAV is ~4.7 kb. The length of a single U6-gRNA (plus restriction sites for cloning) is 361 bp. Therefore, the skilled person can readily fit about 12-16, e.g., 13 U6-gRNA cassettes in a single vector. This can be assembled by any suitable means, such as a golden gate strategy used for TALE assembly (genome-engineering.org/taleffectors/). The skilled person can also use a tandem guide strategy to increase the number of U6-gRNAs by approximately 1.5 times, e.g., to increase from 12-16, e.g., 13 to approximately 18-24, e.g., about 19 U6-gRNAs. Therefore, one skilled in the art can readily reach approximately 18-24, e.g., about 19 promoter-RNAs, e.g., U6-gRNAs in a single vector, e.g., an AAV vector. A further means for increasing the number of promoters and RNAs in a vector is to use a single promoter (e.g., U6) to express an array of RNAs separated by cleavable sequences. And an even further means for increasing the number of promoter-RNAs in a vector, is to express an array of promoter-RNAs separated by cleavable sequences in the intron of a coding sequence or gene; and, in this instance it is advantageous to use a polymerase II promoter, which can have increased expression and enable the transcription of long RNA in a tissue specific manner. (see, e.g., nar.oxfordjournals.org/content/34/7/e53.short and nature.com/mt/journal/v16/n9/abs/mt2008144a.html). In an advantageous embodiment, AAV may package U6 tandem gRNA targeting up to about 50 genes. Accordingly, from the knowledge in the art and the teachings in this disclosure the skilled person can readily make and use vector(s), e.g., a single vector, expressing multiple RNAs or guides under the control or operatively or functionally linked to one or more promoters-especially as to the numbers of RNAs or guides discussed herein, without any undue experimentation.

The guide RNA(s) encoding sequences and/or Cas encoding sequences, can be functionally or operatively linked to regulatory element(s) and hence the regulatory element(s) drive expression. The promoter(s) can be constitutive promoter(s) and/or conditional promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the β-actin promoter, the phosphoglycerol kinase (PGK) promoter, and the EF1α promoter. An advantageous promoter is the promoter is U6.

Additional effectors for use according to the invention can be identified by their proximity to cas1 genes, for example, though not limited to, within the region 20 kb from the start of the cas1 gene and 20 kb from the end of the cas1 gene. In certain embodiments, the effector protein comprises at least one HEPN domain and at least 500 amino acids, and wherein the C2c2 effector protein is naturally present in a prokaryotic genome within 20 kb upstream or downstream of a Cas gene or a CRISPR array. Non-limiting examples of Cas proteins include Cas1, CasiB, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In certain example embodiments, the C2c2 effector protein is naturally present in a prokaryotic genome within 20 kb upstream or downstream of a Cas 1 gene. The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related, or are only partially structurally related. An "orthologue" of a protein as used herein is a protein of a different species which performs the same or a similar function as the protein it is an orthologue of. Orthologous proteins may but need not be structurally related, or are only partially structurally related.

Guide Molecules

The methods described herein may be used to screen inhibition of CRISPR systems employing different types of guide molecules. As used herein, the term "guide sequence" and "guide molecule" in the context of a CRISPR-Cas system, comprises any polynucleotide sequence having sufficient complementarity with a target nucleic acid sequence to hybridize with the target nucleic acid sequence and direct sequence-specific binding of a nucleic acid-targeting complex to the target nucleic acid sequence. The guide sequences made using the methods disclosed herein may be a full-length guide sequence, a truncated guide sequence, a full-length sgRNA sequence, a truncated sgRNA sequence, or an E+F sgRNA sequence. In some embodiments, the degree of complementarity of the guide sequence to a given target sequence, when optimally aligned using a suitable alignment algorithm, is about or more than about 50%, 60%, 75%, 80%, 85%, 90%, 95%, 97.5%, 99%, or more. In certain example embodiments, the guide molecule comprises a guide sequence that may be designed to have at least one mismatch with the target sequence, such that a RNA duplex formed between the guide sequence and the target sequence. Accordingly, the degree of complementarity is preferably less than 99%. For instance, where the guide sequence consists of 24 nucleotides, the degree of complementarity is more particularly about 96% or less. In particular embodiments, the guide sequence is designed to have a stretch of two or more adjacent mismatching nucleotides, such that the degree of complementarity over the entire guide sequence is further reduced. For instance, where the guide sequence consists of 24 nucleotides, the degree of complementarity is more particularly about 96% or less, more particularly, about 92% or less, more particularly about 88% or less, more particularly about 84% or less, more particularly about 80% or less, more particularly about 76% or less, more particularly about 72% or less, depending on whether the stretch of two or more mismatching nucleotides encompasses 2, 3, 4, 5, 6 or 7 nucleotides, etc. In some embodiments, aside from the stretch of one or more mismatching nucleotides, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence (or a sequence in the vicinity thereof) may be evaluated in a test tube by providing the target nucleic acid sequence, components of a nucleic acid-targeting complex, including the guide sequence to be tested and a control guide sequence different from the test guide sequence, and comparing binding or rate of cleavage at or in the vicinity of the target sequence between the test and control guide sequence reactions. Other assays are possible, and will occur to those skilled in the art. A guide sequence, and hence a nucleic acid-targeting guide RNA may be selected to target any target nucleic acid sequence.

In certain embodiments, the guide sequence or spacer length of the guide molecules is from 15 to 50 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer. In certain example embodiment, the guide sequence is 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nt.

In some embodiments, the guide sequence is an RNA sequence of between 10 to 50 nt in length, but more particularly of about 20-30 nt advantageously about 20 nt, 23-25 nt or 24 nt. The guide sequence is selected so as to ensure that it hybridizes to the target sequence. This is described more in detail below. Selection can encompass further steps which increase efficacy and specificity.

In some embodiments, the guide sequence has a canonical length (e.g., about 15-30 nt) is used to hybridize with the target RNA or DNA. In some embodiments, a guide molecule is longer than the canonical length (e.g., >30 nt) is used to hybridize with the target RNA or DNA, such that a region of the guide sequence hybridizes with a region of the RNA or DNA strand outside of the Cas-guide target complex. This can be of interest where additional modifications, such deamination of nucleotides is of interest. In alternative embodiments, it is of interest to maintain the limitation of the canonical guide sequence length.

In some embodiments, the sequence of the guide molecule (direct repeat and/or spacer) is selected to reduce the degree secondary structure within the guide molecule. In some embodiments, about or less than about 75%, 50%, 40%, 30%, 25%, 20%, 15%, 10%, 5%, 1%, or fewer of the nucleotides of the nucleic acid-targeting guide RNA participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and PA Carr and GM Church, 2009, Nature Biotechnology 27(12): 1151-62).

In some embodiments, it is of interest to reduce the susceptibility of the guide molecule to RNA cleavage, such as to cleavage by Cas13. Accordingly, in particular embodiments, the guide molecule is adjusted to avoid cleavage by Cas13 or other RNA-cleaving enzymes.

In certain embodiments, the guide molecule comprises non-naturally occurring nucleic acids and/or non-naturally occurring nucleotides and/or nucleotide analogs, and/or chemically modifications. Preferably, these non-naturally occurring nucleic acids and non-naturally occurring nucleotides are located outside the guide sequence. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, a locked nucleic acid (LNA) nucleotides comprising a methylene bridge between the 2' and 4' carbons of the ribose ring, or bridged nucleic acids (BNA). Other examples of modified nucleotides include 2'-O-methyl analogs, 2'-deoxy analogs, or 2'-fluoro analogs. Further examples of modified bases include, but are not limited to, 2-aminopurine, 5-bromouridine, pseudouridine, inosine, 7-methylguanosine. Examples of guide RNA chemical modifications include, without limitation, incorporation of 2'-O-methyl (M), 2'-O-methyl 3'phosphorothioate (MS), S-constrained ethyl(cEt), or 2'-O-methyl 3'thioPACE (MSP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33(9):985-9, doi: 10.1038/nbt.3290, published online 29 Jun. 2015 Ragdarm et al., 0215, PNAS, E7110-E7111; Allerson et al., J. Med. Chem. 2005, 48:901-904; Bramsen et al., Front. Genet., 2012, 3:154; Deng et al., PNAS, 2015, 112:11870-11875; Sharma et al., MedChemComm., 2014, 5:1454-1471; Hendel et al., Nat. Biotechnol. (2015) 33(9): 985-989; Li et al., Nature Biomedical Engineering, 2017, 1, 0066 DOI:10.1038/s41551-017-0066). In some embodiments, the 5' and/or 3' end of a guide RNA is modified by a variety of functional moieties including fluorescent dyes, polyethylene glycol, cholesterol, proteins, or detection tags. (See Kelly et al., 2016, J. Biotech. 233:74-83). In certain embodiments, a guide comprises ribonucleotides in a region that binds to a target RNA and one or more deoxyribonucleotides and/or nucleotide analogs in a region that binds to Cas13. In an embodiment of the invention, deoxyribonucleotides and/or nucleotide analogs are incorporated in engineered guide structures, such as, without limitation, stem-loop regions, and the seed region. For Cas13 guide, in certain embodiments, the modification is not in the 5'-handle of the stem-loop regions. Chemical modification in the 5'-handle of the stem-loop region of a guide may abolish its function (see Li, et al., Nature Biomedical Engineering, 2017, 1:0066). In certain embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or 75 nucleotides of a guide is chemically modified. In some embodiments, 3-5 nucleotides at either the 3' or the 5' end of a guide is chemically modified. In some embodiments, only minor modifications are introduced in the seed region, such as 2'-F modifications. In some embodiments, 2'-F modification is introduced at the 3' end of a guide. In certain embodiments, three to five nucleotides at the 5' and/or the 3' end of the guide are chemically modified with 2'-O-methyl (M), 2'-O-methyl 3' phosphorothioate (MS), S-constrained ethyl(cEt), or 2'-O-methyl 3' thioPACE (MSP). Such modification can enhance genome editing efficiency (see Hendel et al., Nat. Biotechnol. (2015) 33(9): 985-989). In certain embodiments, all of the phosphodiester bonds of a guide are substituted with phosphorothioates (PS) for enhancing levels of gene disruption. In certain embodiments, more than five nucleotides at the 5' and/or the 3' end of the guide are chemically modified with 2'-O-Me, 2'-F or S constrained ethyl(cEt). Such chemically modified guide can mediate enhanced levels of gene disruption (see Ragdarm et al., 0215, PNAS, E7110-E7111). In an embodiment of the invention, a guide is modified to comprise a chemical moiety at its 3' and/or 5' end. Such moieties include, but are not limited to amine, azide, alkyne, thio, dibenzocyclooctyne (DBCO), or Rhodamine. In certain embodiment, the chemical moiety is conjugated to the guide by a linker, such as an alkyl chain. In certain embodiments, the chemical moiety of the modified guide can be used to attach the guide to another molecule, such as DNA, RNA, protein, or nanoparticles. Such chemically modified guide can be used to identify or enrich cells generically edited by a CRISPR system (see Lee et al., eLife, 2017, 6:e25312, DOI:10.7554).

In some embodiments, the modification to the guide is a chemical modification, an insertion, a deletion or a split. In some embodiments, the chemical modification includes, but is not limited to, incorporation of 2'-O-methyl (M) analogs, 2'-deoxy analogs, 2-thiouridine analogs, N6-methyladenosine analogs, 2'-fluoro analogs, 2-aminopurine, 5-bromo-uridine, pseudouridine (Ψ), N1-methylpseudouridine (me1Ψ), 5-methoxyuridine(5moU), inosine, 7-methylguanosine, 2'-O-methyl 3'phosphorothioate (MS), S-constrained ethyl(cEt), phosphorothioate (PS), or 2'-O-methyl 3'thioPACE (MSP). In some embodiments, the guide comprises one or more of phosphorothioate modifications. In certain embodiments, at least 1, 2, 3, 4, 5, 6, 7, 8, 9, 10, 11, 12, 13, 14, 15, 16, 17, 18, 19, 20, or 25 nucleotides of the guide are chemically modified. In certain embodiments, one or more nucleotides in the seed region are chemically modified. In certain embodiments, one or more nucleotides in the 3'-terminus are chemically modified. In certain embodiments, none of the nucleotides in the 5'-handle is chemically modified. In some embodiments, the chemical modification in the seed region is a minor modification, such as incorporation of a 2'-fluoro analog. In a specific embodiment, one nucleotide of the seed region is replaced with a 2'-fluoro analog. In some embodiments, 5 to 10 nucleotides in the 3'-terminus are chemically modified. Such chemical modifications at the 3'-terminus of the Cas13 CrRNA may improve Cas13 activity. In a specific embodiment, 1, 2, 3, 4, 5, 6, 7, 8, 9 or 10 nucleotides in the 3'-terminus are replaced with 2'-fluoro analogues. In a specific embodiment, 1, 2, 3, 4, 5, 6, 7, 8, 9 or 10 nucleotides in the 3'-terminus are replaced with 2'-O-methyl (M) analogs.

In some embodiments, the loop of the 5'-handle of the guide is modified. In some embodiments, the loop of the 5'-handle of the guide is modified to have a deletion, an insertion, a split, or chemical modifications. In certain embodiments, the modified loop comprises 3, 4, or 5 nucleotides. In certain embodiments, the loop comprises the sequence of UCUU, UUUU, UAUU, or UGUU.

In some embodiments, the guide molecule forms a stem-loop with a separate non-covalently linked sequence, which can be DNA or RNA. In particular embodiments, the sequences forming the guide are first synthesized using the standard phosphoramidite synthetic protocol (Herdewijn, P., ed., Methods in Molecular Biology Col 288, Oligonucleotide Synthesis: Methods and Applications, Humana Press, New Jersey (2012)). In some embodiments, these sequences can be functionalized to contain an appropriate functional group for ligation using the standard protocol known in the art (Hermanson, G. T., Bioconjugate Techniques, Academic Press (2013)). Examples of functional groups include, but are not limited to, hydroxyl, amine, carboxylic acid, carboxylic acid halide, carboxylic acid active ester, aldehyde, carbonyl, chlorocarbonyl, imidazolylcarbonyl, hydrozide, semicarbazide, thio semicarbazide, thiol, maleimide, haloalkyl, sulfonyl, ally, propargyl, diene, alkyne, and azide. Once this sequence is functionalized, a covalent chemical bond or linkage can be formed between this sequence and the direct repeat sequence. Examples of chemical bonds include, but are not limited to, those based on carbamates, ethers, esters, amides, imines, amidines, aminotrizines, hydrozone, disulfides, thioethers, thioesters, phosphorothioates, phosphorodithioates, sulfonamides, sulfonates, fulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, these stem-loop forming sequences can be chemically synthesized. In some embodiments, the chemical synthesis uses automated, solid-phase oligonucleotide synthesis machines with 2'-acetoxyethyl orthoester (2'-ACE) (Scaringe et al., J. Am. Chem. Soc. (1998) 120: 11820-11821; Scaringe, Methods Enzymol. (2000) 317: 3-18) or 2'-thionocarbamate (2'-TC) chemistry (Dellinger et al., J. Am. Chem. Soc. (2011) 133: 11540-11546; Hendel et al., Nat. Biotechnol. (2015) 33:985-989).

In certain embodiments, the guide molecule comprises (1) a guide sequence capable of hybridizing to a target locus and (2) a tracr mate or direct repeat sequence whereby the direct repeat sequence is located upstream (i.e., 5') from the guide sequence. In a particular embodiment the seed sequence (i.e. the sequence essential critical for recognition and/or hybridization to the sequence at the target locus) of the guide sequence is approximately within the first 10 nucleotides of the guide sequence.

In a particular embodiment the guide molecule comprises a guide sequence linked to a direct repeat sequence, wherein the direct repeat sequence comprises one or more stem loops or optimized secondary structures. In particular embodiments, the direct repeat has a minimum length of 16 nts and a single stem loop. In further embodiments the direct repeat has a length longer than 16 nts, preferably more than 17 nts, and has more than one stem loops or optimized secondary structures. In particular embodiments the guide molecule comprises or consists of the guide sequence linked to all or part of the natural direct repeat sequence. A typical Type V or Type VI CRISPR-cas guide molecule comprises (in 3' to 5' direction or in 5' to 3' direction): a guide sequence a first complimentary stretch (the "repeat"), a loop (which is typically 4 or 5 nucleotides long), a second complimentary stretch (the "anti-repeat" being complimentary to the repeat), and a poly A (often poly U in RNA) tail (terminator). In certain embodiments, the direct repeat sequence retains its natural architecture and forms a single stem loop. In particular embodiments, certain aspects of the guide architecture can be modified, for example by addition, subtraction, or substitution of features, whereas certain other aspects of guide architecture are maintained. Preferred locations for engineered guide molecule modifications, including but not limited to insertions, deletions, and substitutions include guide termini and regions of the guide molecule that are exposed when complexed with the CRISPR-Cas protein and/or target, for example the stemloop of the direct repeat sequence.

In particular embodiments, the stem comprises at least about 4 bp comprising complementary X and Y sequences, although stems of more, e.g., 5, 6, 7, 8, 9, 10, 11 or 12 or fewer, e.g., 3, 2, base pairs are also contemplated. Thus, for example X2-10 and Y2-10 (wherein X and Y represent any complementary set of nucleotides) may be contemplated. In one aspect, the stem made of the X and Y nucleotides, together with the loop will form a complete hairpin in the overall secondary structure; and, this may be advantageous and the amount of base pairs can be any amount that forms a complete hairpin. In one aspect, any complementary X:Y basepairing sequence (e.g., as to length) is tolerated, so long as the secondary structure of the entire guide molecule is preserved. In one aspect, the loop that connects the stem made of X:Y basepairs can be any sequence of the same length (e.g., 4 or 5 nucleotides) or longer that does not interrupt the overall secondary structure of the guide molecule. In one aspect, the stemloop can further comprise, e.g. an MS2 aptamer. In one aspect, the stem comprises about 5-7 bp comprising complementary X and Y sequences, although stems of more or fewer basepairs are also contemplated. In one aspect, non-Watson Crick basepairing is contemplated, where such pairing otherwise generally preserves the architecture of the stemloop at that position.

In particular embodiments the natural hairpin or stemloop structure of the guide molecule is extended or replaced by an extended stemloop. It has been demonstrated that extension of the stem can enhance the assembly of the guide molecule with the CRISPR-Cas protein (Chen et al. Cell. (2013);

155(7): 1479-1491). In particular embodiments the stem of the stemloop is extended by at least 1, 2, 3, 4, 5 or more complementary basepairs (i.e. corresponding to the addition of 2, 4, 6, 8, 10 or more nucleotides in the guide molecule). In particular embodiments these are located at the end of the stem, adjacent to the loop of the stemloop.

In particular embodiments, the susceptibility of the guide molecule to RNAses or to decreased expression can be reduced by slight modifications of the sequence of the guide molecule which do not affect its function. For instance, in particular embodiments, premature termination of transcription, such as premature transcription of U6 Pol-III, can be removed by modifying a putative Pol-III terminator (4 consecutive U's) in the guide molecules sequence. Where such sequence modification is required in the stemloop of the guide molecule, it is preferably ensured by a basepair flip.

In a particular embodiment, the direct repeat may be modified to comprise one or more protein-binding RNA aptamers. In a particular embodiment, one or more aptamers may be included such as part of optimized secondary structure. Such aptamers may be capable of binding a bacteriophage coat protein as detailed further herein.

In some embodiments, the guide molecule forms a duplex with a target RNA comprising at least one target cytosine residue to be edited. Upon hybridization of the guide RNA molecule to the target RNA, the cytidine deaminase binds to the single strand RNA in the duplex made accessible by the mismatch in the guide sequence and catalyzes deamination of one or more target cytosine residues comprised within the stretch of mismatching nucleotides.

A guide sequence, and hence a nucleic acid-targeting guide RNA may be selected to target any target nucleic acid sequence. The target sequence may be mRNA.

In certain embodiments, the target sequence should be associated with a PAM (protospacer adjacent motif) or PFS (protospacer flanking sequence or site); that is, a short sequence recognized by the CRISPR complex. Depending on the nature of the CRISPR-Cas protein, the target sequence should be selected such that its complementary sequence in the DNA duplex (also referred to herein as the non-target sequence) is upstream or downstream of the PAM. In the embodiments of the present invention where the CRISPR-Cas protein is a Cas13 protein, the complementary sequence of the target sequence is downstream or 3' of the PAM or upstream or 5' of the PAM. The precise sequence and length requirements for the PAM differ depending on the Cas13 protein used, but PAMs are typically 2-5 base pair sequences adjacent the protospacer (that is, the target sequence). Examples of the natural PAM sequences for different Cas13 orthologues are provided herein below and the skilled person will be able to identify further PAM sequences for use with a given Cas13 protein.

Further, engineering of the PAM Interacting (PI) domain may allow programing of PAM specificity, improve target site recognition fidelity, and increase the versatility of the CRISPR-Cas protein, for example as described for Cas9 in Kleinstiver B P et al. Engineered CRISPR-Cas9 nucleases with altered PAM specificities. Nature. 2015 Jul. 23; 523 (7561):481-5. doi: 10.1038/nature14592. As further detailed herein, the skilled person will understand that Cas13 proteins may be modified analogously.

In particular embodiment, the guide is an escorted guide. By "escorted" is meant that the CRISPR-Cas system or complex or guide is delivered to a selected time or place within a cell, so that activity of the CRISPR-Cas system or complex or guide is spatially or temporally controlled. For example, the activity and destination of the 3 CRISPR-Cas system or complex or guide may be controlled by an escort RNA aptamer sequence that has binding affinity for an aptamer ligand, such as a cell surface protein or other localized cellular component. Alternatively, the escort aptamer may for example be responsive to an aptamer effector on or in the cell, such as a transient effector, such as an external energy source that is applied to the cell at a particular time.

The escorted CRISPR-Cas systems or complexes have a guide molecule with a functional structure designed to improve guide molecule structure, architecture, stability, genetic expression, or any combination thereof. Such a structure can include an aptamer.

Aptamers are biomolecules that can be designed or selected to bind tightly to other ligands, for example using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can for example be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in biotechnology 26.8 (2008): 442-449; and, Hicke B J, Stephens A W. "Escort aptamers: a delivery service for diagnosis and therapy." J Clin Invest 2000, 106:923-928). Aptamers may also be constructed that function as molecular switches, responding to a que by changing properties, such as RNA aptamers that bind fluorophores to mimic the activity of green fluorescent protein (Paige, Jeremy S., Karen Y. Wu, and Samie R. Jaffrey. "RNA mimics of green fluorescent protein." Science 333.6042 (2011): 642-646). It has also been suggested that aptamers may be used as components of targeted siRNA therapeutic delivery systems, for example targeting cell surface proteins (Zhou, Jiehua, and John J. Rossi. "Aptamer-targeted cell-specific RNA interference." Silence 1.1 (2010): 4).

Accordingly, in particular embodiments, the guide molecule is modified, e.g., by one or more aptamer(s) designed to improve guide molecule delivery, including delivery across the cellular membrane, to intracellular compartments, or into the nucleus. Such a structure can include, either in addition to the one or more aptamer(s) or without such one or more aptamer(s), moiety(ies) so as to render the guide molecule deliverable, inducible or responsive to a selected effector. The invention accordingly comprehends an guide molecule that responds to normal or pathological physiological conditions, including without limitation pH, hypoxia, $O_2$ concentration, temperature, protein concentration, enzymatic concentration, lipid structure, light exposure, mechanical disruption (e.g. ultrasound waves), magnetic fields, electric fields, or electromagnetic radiation.

Light responsiveness of an inducible system may be achieved via the activation and binding of cryptochrome-2 and CIB1. Blue light stimulation induces an activating conformational change in cryptochrome-2, resulting in recruitment of its binding partner CIB1. This binding is fast and reversible, achieving saturation in <15 sec following pulsed stimulation and returning to baseline <15 min after the end of stimulation. These rapid binding kinetics result in a system temporally bound only by the speed of transcription/translation and transcript/protein degradation, rather than uptake and clearance of inducing agents. Crytochrome-2 activation is also highly sensitive, allowing for the use of low light intensity stimulation and mitigating the risks of phototoxicity. Further, in a context such as the intact mammalian brain, variable light intensity may be used to control the size of a stimulated region, allowing for greater precision than vector delivery alone may offer.

The invention contemplates energy sources such as electromagnetic radiation, sound energy or thermal energy to induce the guide. Advantageously, the electromagnetic radiation is a component of visible light. In a preferred embodiment, the light is a blue light with a wavelength of about 450 to about 495 nm. In an especially preferred embodiment, the wavelength is about 488 nm. In another preferred embodiment, the light stimulation is via pulses. The light power may range from about 0-9 mW/cm². In a preferred embodiment, a stimulation paradigm of as low as 0.25 sec every 15 sec should result in maximal activation.

The chemical or energy sensitive guide may undergo a conformational change upon induction by the binding of a chemical source or by the energy allowing it act as a guide and have the Cas13 CRISPR-Cas system or complex function. The invention can involve applying the chemical source or energy so as to have the guide function and the Cas13 CRISPR-Cas system or complex function; and optionally further determining that the expression of the genomic locus is altered.

There are several different designs of this chemical inducible system: 1. ABI-PYL based system inducible by Abscisic Acid (ABA) (see, e.g., stke.sciencemag.org/cgi/content/abstract/sigtrans;4/164/rs2), 2. FKBP-FRB based system inducible by rapamycin (or related chemicals based on rapamycin) (see, e.g., www.nature.com/nmeth/journal/v2/n6/full/nmeth763.html), 3. GID1-GAI based system inducible by Gibberellin (GA) (see, e.g., www.nature.com/nchembio/journal/v8/n5/full/nchembio.922.html).

A chemical inducible system can be an estrogen receptor (ER) based system inducible by 4-hydroxytamoxifen (4OHT) (see, e.g., www.pnas.org/content/104/3/1027.abstract). A mutated ligand-binding domain of the estrogen receptor called ERT2 translocates into the nucleus of cells upon binding of 4-hydroxytamoxifen. In further embodiments of the invention any naturally occurring or engineered derivative of any nuclear receptor, thyroid hormone receptor, retinoic acid receptor, estrogen receptor, estrogen-related receptor, glucocorticoid receptor, progesterone receptor, androgen receptor may be used in inducible systems analogous to the ER based inducible system.

Another inducible system is based on the design using Transient receptor potential (TRP) ion channel based system inducible by energy, heat or radio-wave (see, e.g., www.sciencemag.org/content/336/6081/604). These TRP family proteins respond to different stimuli, including light and heat. When this protein is activated by light or heat, the ion channel will open and allow the entering of ions such as calcium into the plasma membrane. This influx of ions will bind to intracellular ion interacting partners linked to a polypeptide including the guide and the other components of the Cas13 CRISPR-Cas complex or system, and the binding will induce the change of sub-cellular localization of the polypeptide, leading to the entire polypeptide entering the nucleus of cells. Once inside the nucleus, the guide protein and the other components of the Cas13 CRISPR-Cas complex will be active and modulating target gene expression in cells.

While light activation may be an advantageous embodiment, sometimes it may be disadvantageous especially for in vivo applications in which the light may not penetrate the skin or other organs. In this instance, other methods of energy activation are contemplated, in particular, electric field energy and/or ultrasound which have a similar effect.

Electric field energy is preferably administered substantially as described in the art, using one or more electric pulses of from about 1 Volt/cm to about 10 kVolts/cm under in vivo conditions. Instead of or in addition to the pulses, the electric field may be delivered in a continuous manner. The electric pulse may be applied for between 1 μs and 500 milliseconds, preferably between 1 μs and 100 milliseconds. The electric field may be applied continuously or in a pulsed manner for 5 about minutes.

As used herein, "electric field energy" is the electrical energy to which a cell is exposed. Preferably the electric field has a strength of from about 1 Volt/cm to about 10 kVolts/cm or more under in vivo conditions (see WO97/49450).

As used herein, the term "electric field" includes one or more pulses at variable capacitance and voltage and including exponential and/or square wave and/or modulated wave and/or modulated square wave forms. References to electric fields and electricity should be taken to include reference the presence of an electric potential difference in the environment of a cell. Such an environment may be set up by way of static electricity, alternating current (AC), direct current (DC), etc, as known in the art. The electric field may be uniform, non-uniform or otherwise, and may vary in strength and/or direction in a time dependent manner.

Single or multiple applications of electric field, as well as single or multiple applications of ultrasound are also possible, in any order and in any combination. The ultrasound and/or the electric field may be delivered as single or multiple continuous applications, or as pulses (pulsatile delivery).

Electroporation has been used in both in vitro and in vivo procedures to introduce foreign material into living cells. With in vitro applications, a sample of live cells is first mixed with the agent of interest and placed between electrodes such as parallel plates. Then, the electrodes apply an electrical field to the cell/implant mixture. Examples of systems that perform in vitro electroporation include the Electro Cell Manipulator ECM600 product, and the Electro Square Porator T820, both made by the BTX Division of Genetronics, Inc (see U.S. Pat. No. 5,869,326).

The known electroporation techniques (both in vitro and in vivo) function by applying a brief high voltage pulse to electrodes positioned around the treatment region. The electric field generated between the electrodes causes the cell membranes to temporarily become porous, whereupon molecules of the agent of interest enter the cells. In known electroporation applications, this electric field comprises a single square wave pulse on the order of 1000 V/cm, of about 100 .mu.s duration. Such a pulse may be generated, for example, in known applications of the Electro Square Porator T820.

Preferably, the electric field has a strength of from about 1 V/cm to about 10 kV/cm under in vitro conditions. Thus, the electric field may have a strength of 1 V/cm, 2 V/cm, 3 V/cm, 4 V/cm, 5 V/cm, 6 V/cm, 7 V/cm, 8 V/cm, 9 V/cm, 10 V/cm, 20 V/cm, 50 V/cm, 100 V/cm, 200 V/cm, 300 V/cm, 400 V/cm, 500 V/cm, 600 V/cm, 700 V/cm, 800

V/cm, 900 V/cm, 1 kV/cm, 2 kV/cm, 5 kV/cm, 10 kV/cm, 20 kV/cm, 50 kV/cm or more. More preferably from about 0.5 kV/cm to about 4.0 kV/cm under in vitro conditions. Preferably the electric field has a strength of from about 1 V/cm to about 10 kV/cm under in vivo conditions. However, the electric field strengths may be lowered where the number of pulses delivered to the target site are increased. Thus, pulsatile delivery of electric fields at lower field strengths is envisaged.

Preferably the application of the electric field is in the form of multiple pulses such as double pulses of the same strength and capacitance or sequential pulses of varying strength and/or capacitance. As used herein, the term "pulse" includes one or more electric pulses at variable capacitance and voltage and including exponential and/or square wave and/or modulated wave/square wave forms.

Preferably the electric pulse is delivered as a waveform selected from an exponential wave form, a square wave form, a modulated wave form and a modulated square wave form.

A preferred embodiment employs direct current at low voltage. Thus, Applicants disclose the use of an electric field which is applied to the cell, tissue or tissue mass at a field strength of between IV/cm and 20V/cm, for a period of 100 milliseconds or more, preferably 15 minutes or more.

Ultrasound is advantageously administered at a power level of from about 0.05 W/cm2 to about 100 W/cm2. Diagnostic or therapeutic ultrasound may be used, or combinations thereof.

As used herein, the term "ultrasound" refers to a form of energy which consists of mechanical vibrations the frequencies of which are so high they are above the range of human hearing. Lower frequency limit of the ultrasonic spectrum may generally be taken as about 20 kHz. Most diagnostic applications of ultrasound employ frequencies in the range 1 and 15 MHz' (From Ultrasonics in Clinical Diagnosis, P. N. T. Wells, ed., 2nd. Edition, Publ. Churchill Livingstone [Edinburgh, London & NY, 1977]).

Ultrasound has been used in both diagnostic and therapeutic applications. When used as a diagnostic tool ("diagnostic ultrasound"), ultrasound is typically used in an energy density range of up to about 100 mW/cm2 (FDA recommendation), although energy densities of up to 750 mW/cm2 have been used. In physiotherapy, ultrasound is typically used as an energy source in a range up to about 3 to 4 W/cm2 (WHO recommendation). In other therapeutic applications, higher intensities of ultrasound may be employed, for example, HIFU at 100 W/cm up to 1 kW/cm2 (or even higher) for short periods of time. The term "ultrasound" as used in this specification is intended to encompass diagnostic, therapeutic and focused ultrasound.

Focused ultrasound (FUS) allows thermal energy to be delivered without an invasive probe (see Morocz et al 1998 Journal of Magnetic Resonance Imaging Vol. 8, No. 1, pp. 136-142. Another form of focused ultrasound is high intensity focused ultrasound (HIFU) which is reviewed by Moussatov et al in Ultrasonics (1998) Vol. 36, No. 8, pp. 893-900 and TranHuuHue et al in Acustica (1997) Vol. 83, No. 6, pp. 1103-1106.

Preferably, a combination of diagnostic ultrasound and a therapeutic ultrasound is employed. This combination is not intended to be limiting, however, and the skilled reader will appreciate that any variety of combinations of ultrasound may be used. Additionally, the energy density, frequency of ultrasound, and period of exposure may be varied.

Preferably the exposure to an ultrasound energy source is at a power density of from about 0.05 to about 100 Wcm−2.

Even more preferably, the exposure to an ultrasound energy source is at a power density of from about 1 to about 15 Wcm−2.

Preferably the exposure to an ultrasound energy source is at a frequency of from about 0.015 to about 10.0 MHz. More preferably the exposure to an ultrasound energy source is at a frequency of from about 0.02 to about 5.0 MHz or about 6.0 MHz. Most preferably, the ultrasound is applied at a frequency of 3 MHz.

Preferably the exposure is for periods of from about 10 milliseconds to about 60 minutes. Preferably the exposure is for periods of from about 1 second to about 5 minutes. More preferably, the ultrasound is applied for about 2 minutes. Depending on the particular target cell to be disrupted, however, the exposure may be for a longer duration, for example, for 15 minutes.

Advantageously, the target tissue is exposed to an ultrasound energy source at an acoustic power density of from about 0.05 Wcm−2 to about 10 Wcm−2 with a frequency ranging from about 0.015 to about 10 MHz (see WO 98/52609). However, alternatives are also possible, for example, exposure to an ultrasound energy source at an acoustic power density of above 100 Wcm−2, but for reduced periods of time, for example, 1000 Wcm−2 for periods in the millisecond range or less.

Preferably the application of the ultrasound is in the form of multiple pulses; thus, both continuous wave and pulsed wave (pulsatile delivery of ultrasound) may be employed in any combination. For example, continuous wave ultrasound may be applied, followed by pulsed wave ultrasound, or vice versa. This may be repeated any number of times, in any order and combination. The pulsed wave ultrasound may be applied against a background of continuous wave ultrasound, and any number of pulses may be used in any number of groups.

Preferably, the ultrasound may comprise pulsed wave ultrasound. In a highly preferred embodiment, the ultrasound is applied at a power density of 0.7 Wcm−2 or 1.25 Wcm−2 as a continuous wave. Higher power densities may be employed if pulsed wave ultrasound is used.

Use of ultrasound is advantageous as, like light, it may be focused accurately on a target. Moreover, ultrasound is advantageous as it may be focused more deeply into tissues unlike light. It is therefore better suited to whole-tissue penetration (such as but not limited to a lobe of the liver) or whole organ (such as but not limited to the entire liver or an entire muscle, such as the heart) therapy. Another important advantage is that ultrasound is a non-invasive stimulus which is used in a wide variety of diagnostic and therapeutic applications. By way of example, ultrasound is well known in medical imaging techniques and, additionally, in orthopedic therapy. Furthermore, instruments suitable for the application of ultrasound to a subject vertebrate are widely available and their use is well known in the art.

In particular embodiments, the guide molecule is modified by a secondary structure to increase the specificity of the CRISPR-Cas system and the secondary structure can protect against exonuclease activity and allow for 5' additions to the guide sequence also referred to herein as a protected guide molecule.

In one aspect, the invention provides for hybridizing a "protector RNA" to a sequence of the guide molecule, wherein the "protector RNA" is an RNA strand complementary to the 3' end of the guide molecule to thereby generate a partially double-stranded guide RNA. In an embodiment of the invention, protecting mismatched bases (i.e. the bases of the guide molecule which do not form part of the guide sequence) with a perfectly complementary protector sequence decreases the likelihood of target RNA binding to the mismatched basepairs at the 3' end. In particular embodiments of the invention, additional sequences comprising an extended length may also be present within the guide molecule such that the guide comprises a protector sequence within the guide molecule. This "protector sequence" ensures that the guide molecule comprises a "protected sequence" in addition to an "exposed sequence" (comprising the part of the guide sequence hybridizing to the target sequence). In particular embodiments, the guide molecule is modified by the presence of the protector guide to comprise a secondary structure such as a hairpin. Advantageously there are three or four to thirty or more, e.g., about 10 or more, contiguous base pairs having complementarity to the protected sequence, the guide sequence or both. It is advantageous that the protected portion does not impede thermodynamics of the CRISPR-Cas system interacting with its target. By providing such an extension including a partially double stranded guide molecule, the guide molecule is considered protected and results in improved specific binding of the CRISPR-Cas complex, while maintaining specific activity.

In particular embodiments, use is made of a truncated guide (tru-guide), i.e. a guide molecule which comprises a guide sequence which is truncated in length with respect to the canonical guide sequence length. As described by Nowak et al. (Nucleic Acids Res (2016) 44 (20): 9555-9564), such guides may allow catalytically active CRISPR-Cas enzyme to bind its target without cleaving the target RNA. In particular embodiments, a truncated guide is used which allows the binding of the target but retains only nickase activity of the CRISPR-Cas enzyme.

CRISPR RNA-Targeting Effector Proteins

In one example embodiment, the CRISPR system effector protein is an RNA-targeting effector protein. In certain embodiments, the CRISPR system effector protein is a Type VI CRISPR system targeting RNA (e.g., Cas13a, Cas13b, Cas13c or Cas13d). Example RNA-targeting effector proteins include Cas13b and C2c2 (now known as Cas13a). It will be understood that the term "C2c2" herein is used interchangeably with "Cas13a". "C2c2" is now referred to as "Cas13a", and the terms are used interchangeably herein unless indicated otherwise. As used herein, the term "Cas13" refers to any Type VI CRISPR system targeting RNA (e.g., Cas13a, Cas13b, Cas13c or Cas13d). When the CRISPR protein is a C2c2 protein, a tracrRNA is not required. C2c2 has been described in Abudayyeh et al. (2016) "C2c2 is a single-component programmable RNA-guided RNA-targeting CRISPR effector"; Science; DOI: 10.1126/science.aaf5573; and Shmakov et al. (2015) "Discovery and Functional Characterization of Diverse Class 2 CRISPR-Cas Systems", Molecular Cell, DOI: dx.doi.org/10.1016/j.molcel.2015.10.008; which are incorporated herein in their entirety by reference. Cas13b has been described in Smargon et al. (2017) "Cas13b Is a Type VI-B CRISPR-Associated RNA-Guided RNases Differentially Regulated by Accessory Proteins Csx27 and Csx28," Molecular Cell. 65, 1-13; dx.doi.org/10.1016/j.molcel.2016.12.023., which is incorporated herein in its entirety by reference.

In some embodiments, one or more elements of a nucleic acid-targeting system is derived from a particular organism comprising an endogenous CRISPR RNA-targeting system. In certain example embodiments, the effector protein CRISPR RNA-targeting system comprises at least one HEPN domain, including but not limited to the HEPN domains described herein, HEPN domains known in the art, and domains recognized to be HEPN domains by comparison to consensus sequence motifs. Several such domains are provided herein. In one non-limiting example, a consensus sequence can be derived from the sequences of C2c2 or Cas13b orthologs provided herein. In certain example embodiments, the effector protein comprises a single HEPN domain. In certain other example embodiments, the effector protein comprises two HEPN domains.

In one example embodiment, the effector protein comprise one or more HEPN domains comprising a RxxxxH motif sequence. The RxxxxH motif sequence can be, without limitation, from a HEPN domain described herein or a HEPN domain known in the art. RxxxxH motif sequences further include motif sequences created by combining portions of two or more HEPN domains. As noted, consensus sequences can be derived from the sequences of the orthologs disclosed in U.S. Provisional Patent Application 62/432,240 entitled "Novel CRISPR Enzymes and Systems," U.S. Provisional Patent Application 62/471,710 entitled "Novel Type VI CRISPR Orthologs and Systems" filed on Mar. 15, 2017, and U.S. Provisional Patent Application 62/484,786 entitled "Novel Type VI CRISPR Orthologs and Systems," filed on Apr. 12, 2017.

In certain other example embodiments, the CRISPR system effector protein is a C2c2 nuclease. The activity of C2c2 may depend on the presence of two HEPN domains. These have been shown to be RNase domains, i.e. nuclease (in particular an endonuclease) cutting RNA. C2c2 HEPN may also target DNA, or potentially DNA and/or RNA. On the basis that the HEPN domains of C2c2 are at least capable of binding to and, in their wild-type form, cutting RNA, then it is preferred that the C2c2 effector protein has RNase function. Regarding C2c2 CRISPR systems, reference is made to U.S. Provisional 62/351,662 filed on Jun. 17, 2016 and U.S. Provisional 62/376,377 filed on Aug. 17, 2016. Reference is also made to U.S. Provisional 62/351,803 filed on Jun. 17, 2016. Reference is also made to U.S. Provisional 62/432,240, entitled "Novel Crispr Enzymes and Systems" filed Dec. 9, 2016 bearing Broad Institute No. 10035.PA4. Reference is further made to East-Seletsky et al. "Two distinct RNase activities of CRISPR-C2c2 enable guide-RNA processing and RNA detection" Nature doi:10/1038/nature19802 and Abudayyeh et al. "C2c2 is a single-component programmable RNA-guided RNA targeting CRISPR effector" bioRxiv doi:10.1101/054742.

In certain embodiments, the C2c2 effector protein is from an organism of a genus selected from the group consisting of: *Leptotrichia, Listeria, Corynebacterium, Sutterella, Legionella, Treponema, Filifactor, Eubacterium, Streptococcus, Lactobacillus, Mycoplasma, Bacteroides, Fluviicola, Flavobacterium, Sphaerochaeta, Azospirillum, Gluconacetobacter, Neisseria, Roseburia, Parvibaculum, Staphylococcus, Nitratifractor, Mycoplasma, Campylobacter*, and *Lachnospira*, or the C2c2 effector protein is an organism selected from the group consisting of: *Leptotrichia shahii, Leptotrichia. wadei, Listeria seeligeri, Clostridium aminophilum, Camobacterium gallinarum, Paludibacter propionicigenes, Listeria* weihenstephanensis, or the C2c2 effector protein is a *L. wadei* F0279 or *L. wadei* F0279 (Lw2) C2C2 effector protein. In another embodiment, the one or more guide RNAs are designed to detect a single nucleotide polymorphism, splice variant of a transcript, or a frameshift mutation in a target RNA or DNA.

In certain example embodiments, the RNA-targeting effector protein is a Type VI-B effector protein, such as Cas13b and Group 29 or Group 30 proteins. In certain example embodiments, the RNA-targeting effector protein comprises one or more HEPN domains. In certain example embodiments, the RNA-targeting effector protein comprises a C-terminal HEPN domain, a N-terminal HEPN domain, or both. Regarding example Type VI-B effector proteins that may be used in the context of this invention, reference is made to U.S. application Ser. No. 15/331,792 entitled "Novel CRISPR Enzymes and Systems" and filed Oct. 21, 2016, International Patent Application No. PCT/US2016/058302 entitled "Novel CRISPR Enzymes and Systems", and filed Oct. 21, 2016, and Smargon et al. "Cas13b is a Type VI-B CRISPR-associated RNA-Guided RNase differentially regulated by accessory proteins Csx27 and Csx28" Molecular Cell, 65, 1-13 (2017); dx.doi.org/10.1016/j.molcel.2016.12.023, and U.S. Provisional Application No. to be assigned, entitled "Novel Cas13b Orthologues CRISPR Enzymes and System" filed Mar. 15, 2017. In particular embodiments, the Cas13b enzyme is derived from *Bergeyella zoohelcum*.

In certain example embodiments, the RNA-targeting effector protein is a Cas13c effector protein as disclosed in U.S. Provisional Patent Application No. 62/525,165 filed Jun. 26, 2017, and PCT Application No. US 2017/047193 filed Aug. 16, 2017.

In some embodiments, one or more elements of a nucleic acid-targeting system is derived from a particular organism comprising an endogenous CRISPR RNA-targeting system. In certain embodiments, the CRISPR RNA-targeting system is found in *Eubacterium* and Ruminococcus. In certain embodiments, the effector protein comprises targeted and collateral ssRNA cleavage activity. In certain embodiments, the effector protein comprises dual HEPN domains. In certain embodiments, the effector protein lacks a counterpart to the Helical-1 domain of Cas13a. In certain embodiments, the effector protein is smaller than previously characterized class 2 CRISPR effectors, with a median size of 928 aa. This median size is 190 aa (17%) less than that of Cas13c, more than 200 aa (18%) less than that of Cas13b, and more than 300 aa (26%) less than that of Cas13a. In certain embodiments, the effector protein has no requirement for a flanking sequence (e.g., PFS, PAM).

In certain embodiments, the effector protein locus structures include a WYL domain containing accessory protein (so denoted after three amino acids that were conserved in the originally identified group of these domains; see, e.g., WYL domain IPR026881). In certain embodiments, the WYL domain accessory protein comprises at least one helix-turn-helix (HTH) or ribbon-helix-helix (RHH) DNA-binding domain. In certain embodiments, the WYL domain containing accessory protein increases both the targeted and the collateral ssRNA cleavage activity of the RNA-targeting effector protein. In certain embodiments, the WYL domain containing accessory protein comprises an N-terminal RHH domain, as well as a pattern of primarily hydrophobic conserved residues, including an invariant tyrosine-leucine doublet corresponding to the original WYL motif. In certain embodiments, the WYL domain containing accessory protein is WYL1. WYL1 is a single WYL-domain protein associated primarily with Ruminococcus.

In other example embodiments, the Type VI RNA-targeting Cas enzyme is Cas13d. In certain embodiments, Cas13d is *Eubacterium siraeum* DSM 15702 (EsCas13d) or Ruminococcus sp. N15.MGS-57 (RspCas13d) (see, e.g., Yan et al., Cas13d Is a Compact RNA-Targeting Type VI CRISPR Effector Positively Modulated by a WYL-Domain-Containing Accessory Protein, Molecular Cell (2018), doi.org/10.1016/j.molcel.2018.02.028). RspCas13d and EsCas13d have no flanking sequence requirements (e.g., PFS, PAM).

Cas13 RNA Editing

In one aspect, the invention provides a method of modifying or editing a target transcript in a eukaryotic cell. In some embodiments, the method comprises allowing a CRISPR-Cas effector module complex to bind to the target polynucleotide to effect RNA base editing, wherein the CRISPR-Cas effector module complex comprises a Cas effector module complexed with a guide sequence hybridized to a target sequence within said target polynucleotide, wherein said guide sequence is linked to a direct repeat sequence. In some embodiments, the Cas effector module comprises a catalytically inactive CRISPR-Cas protein. In some embodiments, the guide sequence is designed to introduce one or more mismatches to the RNA/RNA duplex formed between the target sequence and the guide sequence. In particular embodiments, the mismatch is an A-C mismatch. In some embodiments, the Cas effector may associate with one or more functional domains (e.g. via fusion protein or suitable linkers). In some embodiments, the effector domain comprises one or more cytidine or adenosine deaminases that mediate endogenous editing of via hydrolytic deamination. In particular embodiments, the effector domain comprises the adenosine deaminase acting on RNA (ADAR) family of enzymes. In particular embodiments, the adenosine deaminase protein or catalytic domain thereof capable of deaminating adenosine or cytidine in RNA or is an RNA specific adenosine deaminase and/or is a bacterial, human, cephalopod, or *Drosophila* adenosine deaminase protein or catalytic domain thereof, preferably TadA, more preferably ADAR, optionally huADAR, optionally (hu)ADAR1 or (hu)ADAR2, preferably huADAR2 or catalytic domain thereof.

The present application relates to modifying a target RNA sequence of interest (see, e.g, Cox et al., Science. 2017 Nov. 24; 358(6366):1019-1027). Using RNA-targeting rather than DNA targeting offers several advantages relevant for therapeutic development. First, there are substantial safety benefits to targeting RNA: there will be fewer off-target events because the available sequence space in the transcriptome is significantly smaller than the genome, and if an off-target event does occur, it will be transient and less likely to induce negative side effects. Second, RNA-targeting therapeutics will be more efficient because they are cell-type independent and not have to enter the nucleus, making them easier to deliver.

A further aspect of the invention relates to the method and composition as envisaged herein for use in prophylactic or therapeutic treatment, preferably wherein said target locus of interest is within a human or animal and to methods of modifying an Adenine or Cytidine in a target RNA sequence of interest, comprising delivering to said target RNA, the composition as described herein. In particular embodiments, the CRISPR system and the adenosine deaminase, or catalytic domain thereof, are delivered as one or more polynucleotide molecules, as a ribonucleoprotein complex, optionally via particles, vesicles, or one or more viral vectors. In particular embodiments, the invention thus comprises compositions for use in therapy. This implies that the methods can be performed in vivo, ex vivo or in vitro. In particular embodiments, when the target is a human or animal target, the method is carried out ex vivo or in vitro.

A further aspect of the invention relates to the method as envisaged herein for use in prophylactic or therapeutic treatment, preferably wherein said target of interest is within a human or animal and to methods of modifying an Adenine or Cytidine in a target RNA sequence of interest, comprising delivering to said target RNA, the composition as described herein. In particular embodiments, the CRISPR system and the adenosine deaminase, or catalytic domain thereof, are delivered as one or more polynucleotide molecules, as a ribonucleoprotein complex, optionally via particles, vesicles, or one or more viral vectors.

In one aspect, the invention provides a method of generating a eukaryotic cell comprising a modified or edited gene. In some embodiments, the method comprises (a) introducing one or more vectors into a eukaryotic cell, wherein the one or more vectors drive expression of one or more of: Cas effector module, and a guide sequence linked to a direct repeat sequence, wherein the Cas effector module associate one or more effector domains that mediate base editing, and (b) allowing a CRISPR-Cas effector module complex to bind to a target polynucleotide to effect base editing of the target polynucleotide within said disease gene, wherein the CRISPR-Cas effector module complex comprises a Cas effector module complexed with the guide sequence that is hybridized to the target sequence within the target polynucleotide, wherein the guide sequence may be designed to introduce one or more mismatches between the RNA/RNA duplex formed between the guide sequence and the target sequence. In particular embodiments, the mismatch is an A-C mismatch. In some embodiments, the Cas effector may associate with one or more functional domains (e.g. via fusion protein or suitable linkers). In some embodiments, the effector domain comprises one or more cytidine or adenosine deaminases that mediate endogenous editing of via hydrolytic deamination. In particular embodiments, the effector domain comprises the adenosine deaminase acting on RNA (ADAR) family of enzymes. In particular embodiments, the adenosine deaminase protein or catalytic domain thereof capable of deaminating adenosine or cytidine in RNA or is an RNA specific adenosine deaminase and/or is a bacterial, human, cephalopod, or *Drosophila* adenosine deaminase protein or catalytic domain thereof, preferably TadA, more preferably ADAR, optionally huADAR, optionally (hu)ADAR1 or (hu)ADAR2, preferably huADAR2 or catalytic domain thereof.

A further aspect relates to an isolated cell obtained or obtainable from the methods described herein comprising the composition described herein or progeny of said modified cell, preferably wherein said cell comprises a hypoxanthine or a guanine in replace of said Adenine in said target RNA of interest compared to a corresponding cell not subjected to the method. In particular embodiments, the cell is a eukaryotic cell, preferably a human or non-human animal cell, optionally a therapeutic T cell or an antibody-producing B-cell.

In some embodiments, the modified cell is a therapeutic T cell, such as a T cell suitable for adoptive cell transfer therapies (e.g., CAR-T therapies). The modification may result in one or more desirable traits in the therapeutic T cell, as described further herein.

The invention further relates to a method for cell therapy, comprising administering to a patient in need thereof the modified cell described herein, wherein the presence of the modified cell remedies a disease in the patient. In one embodiment, the modified cell for cell therapy is a epithelial cell (e.g., tuft cell).

The present invention may be further illustrated and extended based on aspects of CRISPR-Cas development and use as set forth in the following articles and particularly as relates to delivery of a CRISPR protein complex and uses of an RNA guided endonuclease in cells and organisms:

Multiplex genome engineering using CRISPR-Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR-Cas-Mediated Genome Engineering. Wang H., Yang H., Shivalila C S., Dawlaty M M., Cheng A W., Zhang F., Jaenisch R. Cell May 9; 153(4): 910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463): 472-6. doi: 10.1038/Nature12466. Epub 2013 Aug. 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013);

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014 (2014);

Development and Applications of CRISPR-Cas9 for Genome Engineering, Hsu P D, Lander E S, Zhang F., Cell. June 5; 157(6):1262-78 (2014).

Genetic screens in human cells using the CRISPR-Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh 00, Barcena C, Hsu P D, Habib N, Gootenberg J S, Nishimasu H, Nureki O, Zhang F., Nature. January 29; 517(7536):583-8 (2015).

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520(7546):186-91(2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., "CRISPR-Cas9 cleavage of viral DNA efficiently suppresses hepatitis B virus," Scientific Reports 5:10833. doi: 10.1038/srep10833 (Jun. 2, 2015).

Nishimasu et al., "Crystal Structure of *Staphylococcus aureus* Cas9," Cell 162, 1113-1126 (Aug. 27, 2015).

BCL11A enhancer dissection by Cas9-mediated in situ saturating mutagenesis, Canver et al., Nature 527(7577): 192-7 (Nov. 12, 2015) doi: 10.1038/nature15521. Epub 2015 Sep. 16.

*Cpf1 Is a Single RNA-Guided Endonuclease of a Class 2 CRISPR-Cas System*, Zetsche et al., Cell 163, 759-71 (Sep. 25, 2015).

*Discovery and Functional Characterization of Diverse Class 2 CRISPR-Cas Systems*, Shmakov et al., Molecular Cell, 60(3), 385-397 doi: 10.1016/j.molcel.2015.10.008 Epub Oct. 22, 2015.

*Rationally engineered Cas9 nucleases with improved specifcity*, Slaymaker et al., Science 2016 Jan. 1 351 (6268): 84-88 doi: 10.1126/science.aad5227. Epub 2015 Dec. 1.

Gao et al, "Engineered Cpf1 Enzymes with Altered PAM Specificities," bioRxiv 091611; doi: http://dx.doi.org/10.1101/091611 (Dec. 4, 2016).

Cox et al., "RNA editing with CRISPR-Cas13," Science. 2017 Nov. 24; 358(6366):1019-1027. Doi: 10.1126/science.aaq0180. Epub 2017 Oct. 25.

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR-Cas system for the one-step generation of mice carrying mutations in multiple genes which were traditionally generated in multiple steps by sequential recombination in embryonic stem cells and/or time-consuming intercrossing of mice with a single mutation. The CRISPR-Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors.

Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and guide RNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knock-out approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR-Cas9 knockout and nucleotide preference at the cleavage site. The authors also found that the sequence preference for CRISPRi/a is substantially different from that for CRISPR-Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Canver et al. (2015) demonstrated a CRISPR-Cas9-based functional investigation of non-coding genomic elements. The authors developed pooled CRISPR-Cas9 guide RNA libraries to perform in situ saturating mutagenesis of the human and mouse BCL11A enhancers which revealed critical features of the enhancers.

Zetsche et al. (2015) reported characterization of Cpf1, a class 2 CRISPR nuclease from *Francisella novicida* U112 having features distinct from Cas9. Cpf1 is a single RNA-guided endonuclease lacking tracrRNA, utilizes a T-rich protospacer-adjacent motif, and cleaves DNA via a staggered DNA double-stranded break.

Shmakov et al. (2015) reported three distinct Class 2 CRISPR-Cas systems. Two system CRISPR enzymes (C2c1 and C2c3) contain RuvC-like endonuclease domains distantly related to Cpf1. Unlike Cpf1, C2c1 depends on both crRNA and tracrRNA for DNA cleavage. The third enzyme (C2c2) contains two predicted HEPN RNase domains and is tracrRNA independent.

Slaymaker et al (2016) reported the use of structure-guided protein engineering to improve the specificity of *Streptococcus pyogenes* Cas9 (SpCas9). The authors developed "enhanced specificity" SpCas9 (eSpCas9) variants which maintained robust on-target cleavage with reduced off-target effects.

Cox et al., (2017) reported the use of catalytically inactive Cas13 (dCas13) to direct adenosine-to-inosine deaminase activity by ADAR2 (adenosine deaminase acting on RNA type 2) to transcripts in mammalian cells. The system, referred to as RNA Editing for Programmable A to I Replacement (REPAIR), has no strict sequence constraints and can be used to edit full-length transcripts. The authors further engineered the system to create a high-specificity variant and minimized the system to facilitate viral delivery.

The methods and tools provided herein are may be designed for use with or Cas13, a type II nuclease that does not make use of tracrRNA. Orthologs of Cas13 have been identified in different bacterial species as described herein. Further type II nucleases with similar properties can be identified using methods described in the art (Shmakov et al. 2015, 60:385-397; Abudayeh et al. 2016, Science, 5; 353 (6299)). In particular embodiments, such methods for identifying novel CRISPR effector proteins may comprise the steps of selecting sequences from the database encoding a seed which identifies the presence of a CRISPR Cas locus, identifying loci located within 10 kb of the seed comprising Open Reading Frames (ORFs) in the selected sequences, selecting therefrom loci comprising ORFs of which only a single ORF encodes a novel CRISPR effector having greater than 700 amino acids and no more than 90% homology to a known CRISPR effector. In particular embodiments, the seed is a protein that is common to the CRISPR-Cas system, such as Cas1. In further embodiments, the CRISPR array is used as a seed to identify new effector proteins.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

With respect to general information on CRISPR/Cas Systems, components thereof, and delivery of such components, including methods, materials, delivery vehicles, vectors, particles, and making and using thereof, including as to amounts and formulations, as well as CRISPR-Cas-expressing eukaryotic cells, CRISPR-Cas expressing eukaryotes, such as a mouse, reference is made to: U.S. Pat. Nos. 8,999,641, 8,993,233, 8,697,359, 8,771,945, 8,795,965, 8,865,406, 8,871,445, 8,889,356, 8,889,418, 8,895,308, 8,906,616, 8,932,814, and 8,945,839; US Patent Publications US 2014-0310830 (U.S. application Ser. No. 14/105, 031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256, 912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); US 2015-0184139 (U.S. application Ser. No. 14/324,960); Ser. No. 14/054,414 European Patent Applications EP 2 771 468 (EP13818570.7), EP 2 764 103 (EP13824232.6), and EP 2 784 162

(EP14170383.5); and PCT Patent Publications WO2014/093661 (PCT/US2013/074743), WO2014/093694 (PCT/US2013/074790), WO2014/093595 (PCT/US2013/074611), WO2014/093718 (PCT/US2013/074825), WO2014/093709 (PCT/US2013/074812), WO2014/093622 (PCT/US2013/074667), WO2014/093635 (PCT/US2013/074691), WO2014/093655 (PCT/US2013/074736), WO2014/093712 (PCT/US2013/074819), WO2014/093701 (PCT/US2013/074800), WO2014/018423 (PCT/US2013/051418), WO2014/204723 (PCT/US2014/041790), WO2014/204724 (PCT/US2014/041800), WO2014/204725 (PCT/US2014/041803), WO2014/204726 (PCT/US2014/041804), WO2014/204727 (PCT/US2014/041806), WO2014/204728 (PCT/US2014/041808), WO2014/204729 (PCT/US2014/041809), WO2015/089351 (PCT/US2014/069897), WO2015/089354 (PCT/US2014/069902), WO2015/089364 (PCT/US2014/069925), WO2015/089427 (PCT/US2014/070068), WO2015/089462 (PCT/US2014/070127), WO2015/089419 (PCT/US2014/070057), WO2015/089465 (PCT/US2014/070135), WO2015/089486 (PCT/US2014/070175), WO2015/058052 (PCT/US2014/061077), WO2015/070083 (PCT/US2014/064663), WO2015/089354 (PCT/US2014/069902), WO2015/089351 (PCT/US2014/069897), WO2015/089364 (PCT/US2014/069925), WO2015/089427 (PCT/US2014/070068), WO2015/089473 (PCT/US2014/070152), WO2015/089486 (PCT/US2014/070175), WO2016/049258 (PCT/US2015/051830), WO2016/094867 (PCT/US2015/065385), WO2016/094872 (PCT/US2015/065393), WO2016/094874 (PCT/US2015/065396), WO2016/106244 (PCT/US2015/067177).

Mention is also made of U.S. application 62/180,709, 17 Jun. 2015, PROTECTED GUIDE RNAS (PGRNAS); U.S. application 62/091,455, filed, 12 Dec. 2014, PROTECTED GUIDE RNAS (PGRNAS); U.S. application 62/096,708, 24 Dec. 2014, PROTECTED GUIDE RNAS (PGRNAS); U.S. application 62/091,462, 12 Dec. 2014, 62/096,324, 23 Dec. 2014, 62/180,681, 17 Jun. 2015, and 62/237,496, 5 Oct. 2015, DEAD GUIDES FOR CRISPR TRANSCRIPTION FACTORS; U.S. application 62/091,456, 12 Dec. 2014 and 62/180,692, 17 Jun. 2015, ESCORTED AND FUNCTIONALIZED GUIDES FOR CRISPR-CAS SYSTEMS; U.S. application 62/091,461, 12 Dec. 2014, DELIVERY, USE AND THERAPEUTIC APPLICATIONS OF THE CRISPR-CAS SYSTEMS AND COMPOSITIONS FOR GENOME EDITING AS TO HEMATOPOETIC STEM CELLS (HSCs); U.S. application 62/094,903, 19 Dec. 2014, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 2014, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 2014, 62/181,641, 18 Jun. 2015, and 62/181,667, 18 Jun. 2015, RNA-TARGETING SYSTEM; U.S. application 62/096,656, 24 Dec. 2014 and 62/181,151, 17 Jun. 2015, CRISPR HAVING OR ASSOCIATED WITH DESTABILIZATION DOMAINS; U.S. application 62/096,697, 24 Dec. 2014, CRISPR HAVING OR ASSOCIATED WITH AAV; U.S. application 62/098,158, 30 Dec. 2014, ENGINEERED CRISPR COMPLEX INSERTIONAL TARGETING SYSTEMS; U.S. application 62/151,052, 22 Apr. 2015, CELLULAR TARGETING FOR EXTRACELLULAR EXOSOMAL REPORTING; U.S. application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 61/939,154, 12 feb. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/054,675, 24 Sep. 2014 and 62/181,002, 17 Jun. 2015, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 2014 and 62/181,690, 18 Jun. 2015, FUNCTIONAL SCREENING WITH OPTIMIZED FUNCTIONAL CRISPR-CAS SYSTEMS; U.S. application 62/055,487, 25 Sep. 2014, FUNCTIONAL SCREENING WITH OPTIMIZED FUNCTIONAL CRISPR-CAS SYSTEMS; U.S. application 62/087,546, 4 Dec. 2014 and 62/181,687, 18 Jun. 2015, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 2014, CRISPR MEDIATED IN VIVO MODELING AND GENETIC SCREENING OF TUMOR GROWTH AND METASTASIS.

Mention is made of U.S. application 62/181,659, 18 Jun. 2015 and 62/207,318, 19 Aug. 2015, ENGINEERING AND OPTIMIZATION OF SYSTEMS, METHODS, ENZYME AND GUIDE SCAFFOLDS OF CAS9 ORTHOLOGS AND VARIANTS FOR SEQUENCE MANIPULATION. Mention is made of U.S. application 62/181,663, 18 Jun. 2015 and 62/245,264, 22 Oct. 2015, NOVEL CRISPR ENZYMES AND SYSTEMS, U.S. application 62/181,675, 18 Jun. 2015, 62/285,349, 22 Oct. 2015, 62/296,522, 17 Feb. 2016, and 62/320,231, 8 Apr. 2016, NOVEL CRISPR ENZYMES AND SYSTEMS, U.S. application 62/232,067, 24 Sep. 2015, U.S. application Ser. No. 14/975,085, 18 Dec. 2015, European application No. 16150428.7, U.S. application 62/205,733, 16 Aug. 2015, U.S. application 62/201,542, 5 Aug. 2015, U.S. application 62/193,507, 16 Jul. 2015, and U.S. application 62/181,739, 18 Jun. 2015, each entitled NOVEL CRISPR ENZYMES AND SYSTEMS and of U.S. application 62/245,270, 22 Oct. 2015, NOVEL CRISPR ENZYMES AND SYSTEMS. Mention is also made of U.S. application 61/939,256, 12 Feb. 2014, and WO 2015/089473 (PCT/US2014/070152), 12 Dec. 2014, each entitled ENGINEERING OF SYSTEMS, METHODS AND OPTIMIZED GUIDE COMPOSITIONS WITH NEW ARCHITECTURES FOR SEQUENCE MANIPULATION. Mention is also made of PCT/US2015/045504, 15 Aug. 2015, U.S. application 62/180,699, 17 Jun. 2015, and U.S. application 62/038,358, 17 Aug. 2014, each entitled GENOME EDITING USING CAS9 NICKASES.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

In particular embodiments, pre-complexed guide RNA and CRISPR effector protein, (optionally, adenosine deaminase fused to a CRISPR protein or an adaptor) are delivered as a ribonucleoprotein (RNP). RNPs have the advantage that they lead to rapid editing effects even more so than the RNA method because this process avoids the need for transcription. An important advantage is that both RNP delivery is transient, reducing off-target effects and toxicity issues. Efficient genome editing in different cell types has been observed by Kim et al. (2014, Genome Res. 24(6):1012-9), Paix et al. (2015, Genetics 204(1):47-54), Chu et al. (2016, BMC Biotechnol. 16:4), and Wang et al. (2013, Cell. 9; 153(4):910-8).

In particular embodiments, the ribonucleoprotein is delivered by way of a polypeptide-based shuttle agent as described in WO2016161516. WO2016161516 describes efficient transduction of polypeptide cargos using synthetic peptides comprising an endosome leakage domain (ELD) operably linked to a cell penetrating domain (CPD), to a histidine-rich domain and a CPD. Similarly these polypeptides can be used for the delivery of CRISPR-effector based RNPs in eukaryotic cells.

Tale Systems

As disclosed herein editing can be made by way of the transcription activator-like effector nucleases (TALENs) system. Transcription activator-like effectors (TALEs) can be engineered to bind practically any desired DNA sequence. Exemplary methods of genome editing using the TALEN system can be found for example in Cermak T. Doyle E L. Christian M. Wang L. Zhang Y. Schmidt C, et al. Efficient design and assembly of custom TALEN and other TAL effector-based constructs for DNA targeting. Nucleic Acids Res. 2011; 39:e82; Zhang F. Cong L. Lodato S. Kosuri S. Church G M. Arlotta P Efficient construction of sequence-specific TAL effectors for modulating mammalian transcription. Nat Biotechnol. 2011; 29:149-153 and U.S. Pat. Nos. 8,450,471, 8,440,431 and 8,440,432, all of which are specifically incorporated by reference.

In advantageous embodiments of the invention, the methods provided herein use isolated, non-naturally occurring, recombinant or engineered DNA binding proteins that comprise TALE monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", or "TALE monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is $X_{1-11}$-($X_{12}X_{13}$)-$X_{14-33 \text{ or } 34 \text{ or } 35}$, where the subscript indicates the amino acid position and X represents any amino acid. $X_{12}X_{13}$ indicate the RVDs. In some polypeptide monomers, the variable amino acid at position 13 is missing or absent and in such polypeptide monomers, the RVD consists of a single amino acid. In such cases the RVD may be alternatively represented as X*, where X represents $X_{12}$ and (*) indicates that $X_{13}$ is absent. The DNA binding domain comprises several repeats of TALE monomers and this may be represented as ($X_{1-11}$-($X_{12}X_{13}$)-$X_{14-33 \text{ or } 34 \text{ or } 35}$)$_z$, where in an advantageous embodiment, z is at least 5 to 40. In a further advantageous embodiment, z is at least 10 to 26.

The TALE monomers have a nucleotide binding affinity that is determined by the identity of the amino acids in its RVD. For example, polypeptide monomers with an RVD of NI preferentially bind to adenine (A), polypeptide monomers with an RVD of NG preferentially bind to thymine (T), polypeptide monomers with an RVD of HD preferentially bind to cytosine (C) and polypeptide monomers with an RVD of NN preferentially bind to both adenine (A) and guanine (G). In yet another embodiment of the invention, polypeptide monomers with an RVD of IG preferentially bind to T. Thus, the number and order of the polypeptide monomer repeats in the nucleic acid binding domain of a TALE determines its nucleic acid target specificity. In still further embodiments of the invention, polypeptide monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated by reference in its entirety.

The TALE polypeptides used in methods of the invention are isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In a preferred embodiment of the invention, polypeptide monomers having RVDs RN, NN, NK, SN, NH, KN, HN, NQ, HH, RG, KH, RH and SS preferentially bind to guanine. In a much more advantageous embodiment of the invention, polypeptide monomers having RVDs RN, NK, NQ, HH, KH, RH, SS and SN preferentially bind to guanine and thereby allow the generation of TALE polypeptides with high binding specificity for guanine containing target nucleic acid sequences. In an even more advantageous embodiment of the invention, polypeptide monomers having RVDs HH, KH, NH, NK, NQ, RH, RN and SS preferentially bind to guanine and thereby allow the generation of TALE polypeptides with high binding specificity for guanine containing target nucleic acid sequences. In a further advantageous embodiment, the RVDs that have high binding specificity for guanine are RN, NH RH and KH. Furthermore, polypeptide monomers having an RVD of NV preferentially bind to adenine and guanine. In more preferred embodiments of the invention, polypeptide monomers having RVDs of H*, HA, KA, N*, NA, NC, NS, RA, and S* bind to adenine, guanine, cytosine and thymine with comparable affinity.

The predetermined N-terminal to C-terminal order of the one or more polypeptide monomers of the nucleic acid or DNA binding domain determines the corresponding predetermined target nucleic acid sequence to which the TALE polypeptides will bind. As used herein the polypeptide monomers and at least one or more half polypeptide monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases this region may be referred to as repeat 0. In animal genomes, TALE binding sites do not necessarily have to begin with a thymine (T) and TALE polypeptides may target DNA sequences that begin with T, A, G or C. The tandem repeat of TALE monomers always ends with a half-length repeat or a stretch of sequence that may share identity with only the first 20 amino acids of a repetitive full length TALE monomer and this half repeat may be referred to as a half-monomer (FIG. 8), which is included in the term "TALE monomer". Therefore, it follows that the length of the nucleic acid or DNA being targeted is equal to the number of full polypeptide monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region.

An exemplary amino acid sequence of a N-terminal capping region is:

```
                                          (SEQ ID NO: 1)
M D P I R S R T P S P A R E L L S G P Q P D G V Q

P T A D R G V S P P A G G P L D G L P A R R T M S

R T R L P S P P A P S P A F S A D S F S D L L R Q

F D P S L F N T S L F D S L P P F G A H H T E A A

T G E W D E V Q S G L R A A D A P P P T M R V A V

T A A R P P R A K P A P R R R A A Q P S D A S P A
```

-continued
```
A Q V D L R T L G Y S Q Q Q Q E K I K P K V R S T

V A Q H H E A L V G H G F T H A H I V A L S Q H P

A A L G T V A V K Y Q D M I A A L P E A T H E A I

V G V G K Q W S G A R A L E A L L T V A G E L R G

P P L Q L D T G Q L L K I A K R G G V T A V E A V

H A W R N A L T G A P L N
```

An exemplary amino acid sequence of a C-terminal capping region is:

```
                                          (SEQ ID NO: 2)
R P A L E S I V A Q L S R P D P A L A A L T N D H

L V A L A C L G G R P A L D A V K K G L P H A P A

L I K R T N R R I P E R T S H R V A D H A Q V V R

V L G F F Q C H S H P A Q A F D D A M T Q F G M S

R H G L L Q L F R R V G V T E L E A R S G T L P P

A S Q R W D R I L Q A S G M K R A K P S P T S T Q

T P D Q A S L H A F A D S L E R D L D A P S P M H

E G D Q T R A S
```

As used herein the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full length capping region, while fragments that include the C-terminal 20 amino acids retain greater than 50% of the efficacy of the full length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies may be generated by any of a number of computer programs known in the art, which include but are not limited to BLAST or FASTA. Suitable computer program for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In advantageous embodiments described herein, the TALE polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the TALE polypeptides described herein, the activity mediated by the effector domain is a biological activity. For example, in some embodiments the effector domain is a transcriptional inhibitor (i.e., a repressor domain), such as an mSin interaction domain (SID). SID4X domain or a Krüppel-associated box (KRAB) or fragments of the KRAB domain. In some embodiments the effector domain is an enhancer of transcription (i.e. an activation domain), such as the VP16, VP64 or p65 activation domain. In some embodiments, the nucleic acid binding is linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination the activities described herein.

ZN-Finger Nucleases

Other preferred tools for genome editing for use in the context of this invention include zinc finger systems and TALE systems. One type of programmable DNA-binding domain is provided by artificial zinc-finger (ZF) technology, which involves arrays of ZF modules to target new DNA-binding sites in the genome. Each finger module in a ZF array targets three DNA bases. A customized array of individual zinc finger domains is assembled into a ZF protein (ZFP).

ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to FokI cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms. Exemplary methods of genome editing using ZFNs can be found for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference.

Meganucleases

As disclosed herein editing can be made by way of meganucleases, which are endodeoxyribonucleases characterized by a large recognition site (double-stranded DNA sequences of 12 to 40 base pairs). Exemplary method for using meganucleases can be found in U.S. Pat. Nos. 8,163,514; 8,133,697; 8,021,867; 8,119,361; 8,119,381; 8,124,369; and 8,129,134, which are specifically incorporated by reference.

Pharmaceuticals

Another aspect of the invention provides a composition, pharmaceutical composition or vaccine comprising the intestinal epithelial cells, intestinal epithelial stem cells, or intestinal immune cells (preferably intestinal epithelial cells) or populations thereof as taught herein.

A "pharmaceutical composition" refers to a composition that usually contains an excipient, such as a pharmaceutically acceptable carrier that is conventional in the art and that is suitable for administration to cells or to a subject.

The term "pharmaceutically acceptable" as used throughout this specification is consistent with the art and means compatible with the other ingredients of a pharmaceutical composition and not deleterious to the recipient thereof.

As used herein, "carrier" or "excipient" includes any and all solvents, diluents, buffers (such as, e.g., neutral buffered saline or phosphate buffered saline), solubilisers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavourings, aromatisers, thickeners, agents for achieving a depot effect, coatings, antifungal agents, preservatives, stabilisers, antioxidants, tonicity controlling agents, absorption delaying agents, and the like. The use of such media and agents for pharmaceutical active components is well known in the art. Such materials should be non-toxic and should not interfere with the activity of the cells or active components.

The precise nature of the carrier or excipient or other material will depend on the route of administration. For example, the composition may be in the form of a parenterally acceptable aqueous solution, which is pyrogen-free and has suitable pH, isotonicity and stability. For general principles in medicinal formulation, the reader is referred to Cell Therapy: Stem Cell Transplantation, Gene Therapy, and Cellular Immunotherapy, by G. Morstyn & W. Sheridan eds., Cambridge University Press, 1996; and Hematopoietic Stem Cell Therapy, E. D. Ball, J. Lister & P. Law, Churchill Livingstone, 2000.

The pharmaceutical composition can be applied parenterally, rectally, orally or topically. Preferably, the pharmaceutical composition may be used for intravenous, intramuscular, subcutaneous, peritoneal, peridural, rectal, nasal, pulmonary, mucosal, or oral application. In a preferred embodiment, the pharmaceutical composition according to the invention is intended to be used as an infuse. The skilled person will understand that compositions which are to be administered orally or topically will usually not comprise cells, although it may be envisioned for oral compositions to also comprise cells, for example when gastro-intestinal tract indications are treated. Each of the cells or active components (e.g., modulants, immunomodulants, antigens) as discussed herein may be administered by the same route or may be administered by a different route. By means of example, and without limitation, cells may be administered parenterally and other active components may be administered orally.

Liquid pharmaceutical compositions may generally include a liquid carrier such as water or a pharmaceutically acceptable aqueous solution. For example, physiological saline solution, tissue or cell culture media, dextrose or other saccharide solution or glycols such as ethylene glycol, propylene glycol or polyethylene glycol may be included.

The composition may include one or more cell protective molecules, cell regenerative molecules, growth factors, anti-apoptotic factors or factors that regulate gene expression in the cells. Such substances may render the cells independent of their environment.

Such pharmaceutical compositions may contain further components ensuring the viability of the cells therein. For example, the compositions may comprise a suitable buffer system (e.g., phosphate or carbonate buffer system) to achieve desirable pH, more usually near neutral pH, and may comprise sufficient salt to ensure isoosmotic conditions for the cells to prevent osmotic stress. For example, suitable solution for these purposes may be phosphate-buffered saline (PBS), sodium chloride solution, Ringer's Injection or Lactated Ringer's Injection, as known in the art. Further, the composition may comprise a carrier protein, e.g., albumin (e.g., bovine or human albumin), which may increase the viability of the cells.

Further suitably pharmaceutically acceptable carriers or additives are well known to those skilled in the art and for instance may be selected from proteins such as collagen or gelatine, carbohydrates such as starch, polysaccharides, sugars (dextrose, glucose and sucrose), cellulose derivatives like sodium or calcium carboxymethylcellulose, hydroxypropyl cellulose or hydroxypropylmethyl cellulose, pregelatinized starches, pectin agar, carrageenan, clays, hydrophilic gums (acacia gum, guar gum, arabic gum and xanthan gum), alginic acid, alginates, hyaluronic acid, polyglycolic and polylactic acid, dextran, pectins, synthetic polymers such as water-soluble acrylic polymer or polyvinylpyrrolidone, proteoglycans, calcium phosphate and the like.

If desired, cell preparation can be administered on a support, scaffold, matrix or material to provide improved tissue regeneration. For example, the material can be a granular ceramic, or a biopolymer such as gelatine, collagen, or fibrinogen. Porous matrices can be synthesized according to standard techniques (e.g., Mikos et al., Biomaterials 14: 323, 1993; Mikos et al., Polymer 35:1068, 1994; Cook et al., J. Biomed. Mater. Res. 35:513, 1997). Such support, scaffold, matrix or material may be biodegradable or non-biodegradable. Hence, the cells may be transferred to and/or cultured on suitable substrate, such as porous or non-porous substrate, to provide for implants.

For example, cells that have proliferated, or that are being differentiated in culture dishes, can be transferred onto three-dimensional solid supports in order to cause them to multiply and/or continue the differentiation process by incubating the solid support in a liquid nutrient medium of the invention, if necessary. Cells can be transferred onto a three-dimensional solid support, e.g. by impregnating the support with a liquid suspension containing the cells. The impregnated supports obtained in this way can be implanted in a human subject. Such impregnated supports can also be re-cultured by immersing them in a liquid culture medium, prior to being finally implanted. The three-dimensional solid support needs to be biocompatible so as to enable it to be implanted in a human. It may be biodegradable or non-biodegradable.

The cells or cell populations can be administered in a manner that permits them to survive, grow, propagate and/or differentiate towards desired cell types (e.g. differentiation) or cell states. The cells or cell populations may be grafted to or may migrate to and engraft within the intended organ.

In certain embodiments, a pharmaceutical cell preparation as taught herein may be administered in a form of liquid composition. In embodiments, the cells or pharmaceutical composition comprising such can be administered systemically, topically, within an organ or at a site of organ dysfunction or lesion.

Preferably, the pharmaceutical compositions may comprise a therapeutically effective amount of the specified intestinal epithelial cells, intestinal epithelial stem cells, or intestinal immune cells (preferably intestinal epithelial cells) and/or other active components. The term "therapeutically effective amount" refers to an amount which can elicit a biological or medicinal response in a tissue, system, animal or human that is being sought by a researcher, veterinarian, medical doctor or other clinician, and in particular can prevent or alleviate one or more of the local or systemic symptoms or features of a disease or condition being treated.

A further aspect of the invention provides a population of the intestinal epithelial cells, intestinal epithelial stem cells, or intestinal immune cells (preferably intestinal epithelial cells) as taught herein. The terms "cell population" or "population" denote a set of cells having characteristics in common. The characteristics may include in particular the one or more marker(s) or gene or gene product signature(s) as taught herein. The intestinal epithelial cells, intestinal epithelial stem cells, or intestinal immune cells (preferably intestinal epithelial cells) cells as taught herein may be comprised in a cell population. By means of example, the specified cells may constitute at least 40% (by number) of all cells of the cell population, for example, at least 45%, preferably at least 50%, at least 55%, more preferably at least 60%, at least 65%, still more preferably at least 70%, at least 75%, even more preferably at least 80%, at least 85%, and yet more preferably at least 90%, at least 95%, at least 96%, at least 97%, at least 98%, at least 99%, or even 100% of all cells of the cell population.

The isolated intestinal epithelial cells, intestinal epithelial stem cells, or intestinal immune cells (preferably intestinal epithelial cells) of populations thereof as disclosed throughout this specification may be suitably cultured or cultivated in vitro. The term "in vitro" generally denotes outside, or external to, a body, e.g., an animal or human body. The term encompasses "ex vivo". The terms "culturing" or "cell culture" are common in the art and broadly refer to maintenance of cells and potentially expansion (proliferation, propagation) of cells in vitro. Typically, animal cells, such as mammalian cells, such as human cells, are cultured by exposing them to (i.e., contacting them with) a suitable cell culture medium in a vessel or container adequate for the purpose (e.g., a 96-, 24-, or 6-well plate, a T-25, T-75, T-150 or T-225 flask, or a cell factory), at art-known conditions conducive to in vitro cell culture, such as temperature of 37° C., 5% v/v $CO_2$ and >95% humidity.

The term "medium" as used herein broadly encompasses any cell culture medium conducive to maintenance of cells, preferably conducive to proliferation of cells. Typically, the medium will be a liquid culture medium, which facilitates easy manipulation (e.g., decantation, pipetting, centrifugation, filtration, and such) thereof.

Differentiation

A relatively more specialised cell may differ from an unspecialised or relatively less specialised cell in one or more demonstrable phenotypic characteristics, such as, for example, the presence, absence or level of expression of particular cellular components or products, e.g., RNA, proteins or other substances, activity of certain biochemical pathways, morphological appearance, proliferation capacity and/or kinetics, differentiation potential and/or response to differentiation signals, electrophysiological behaviour, etc., wherein such characteristics signify the progression of the relatively more specialised cell further along the developmental pathway. Non-limiting examples of differentiation may include, e.g., the change of a pluripotent stem cell into a given type of multipotent progenitor or stem cell, the change of a multipotent progenitor or stem cell into a given type of unipotent progenitor or stem cell, or the change of a unipotent progenitor or stem cell to more specialised cell types or to terminally specialised cells within a given cell lineage.

The terms "diagnosis" and "monitoring" are commonplace and well-understood in medical practice. By means of further explanation and without limitation the term "diagnosis" generally refers to the process or act of recognising, deciding on or concluding on a disease or condition in a subject on the basis of symptoms and signs and/or from results of various diagnostic procedures (such as, for example, from knowing the presence, absence and/or quantity of one or more biomarkers characteristic of the diagnosed disease or condition).

The term "monitoring" generally refers to the follow-up of a disease or a condition in a subject for any changes which may occur over time.

The terms "prognosing" or "prognosis" generally refer to an anticipation on the progression of a disease or condition and the prospect (e.g., the probability, duration, and/or extent) of recovery. A good prognosis of the diseases or conditions taught herein may generally encompass anticipation of a satisfactory partial or complete recovery from the diseases or conditions, preferably within an acceptable time period. A good prognosis of such may more commonly encompass anticipation of not further worsening or aggravating of such, preferably within a given time period. A poor prognosis of the diseases or conditions as taught herein may generally encompass anticipation of a substandard recovery and/or unsatisfactorily slow recovery, or to substantially no recovery or even further worsening of such.

The terms also encompass prediction of a disease. the terms "predicting" or "prediction" generally refer to an advance declaration, indication or foretelling of a disease or condition in a subject not (yet) having the disease or condition. For example, a prediction of a disease or condition in a subject may indicate a probability, chance or risk that the subject will develop the disease or condition, for example within a certain time period or by a certain age. The probability, chance or risk may be indicated inter alia as an absolute value, range or statistics, or may be indicated relative to a suitable control subject or subject population (such as, e.g., relative to a general, normal or healthy subject or subject population). Hence, the probability, chance or risk that a subject will develop a disease or condition may be advantageously indicated as increased or decreased, or as fold-increased or fold-decreased relative to a suitable control subject or subject population. As used herein, the term "prediction" of the conditions or diseases as taught herein in a subject may also particularly mean that the subject has a 'positive' prediction of such, i.e., that the subject is at risk of having such (e.g., the risk is significantly increased vis-à-vis a control subject or subject population). The term "prediction of no" diseases or conditions as taught herein as described herein in a subject may particularly mean that the subject has a 'negative' prediction of such, i.e., that the subject's risk of having such is not significantly increased vis-à-vis a control subject or subject population.

As used throughout this specification, the terms "treat", "treating" and "treatment" refer to the alleviation or measurable lessening of one or more symptoms or measurable markers of a pathological condition such as a disease or disorder. Measurable lessening includes any statistically significant decline in a measurable marker or symptom. Generally, the terms encompass both curative treatments and treatments directed to reduce symptoms and/or slow progression of the disease. The terms encompass both the therapeutic treatment of an already developed pathological condition, as well as prophylactic or preventative measures, wherein the aim is to prevent or lessen the chances of incidence of a pathological condition. In certain embodiments, the terms may relate to therapeutic treatments. In certain other embodiments, the terms may relate to preventative treatments. Treatment of a chronic pathological condition during the period of remission may also be deemed to constitute a therapeutic treatment. The term may encompass ex vivo or in vivo treatments as appropriate in the context of the present invention.

As used throughout this specification, the terms "prevent", "preventing" and "prevention" refer to the avoidance or delay in manifestation of one or more symptoms or measurable markers of a pathological condition, such as a disease or disorder. A delay in the manifestation of a symptom or marker is a delay relative to the time at which such symptom or marker manifests in a control or untreated subject with a similar likelihood or susceptibility of developing the pathological condition. The terms "prevent", "preventing" and "prevention" include not only the avoidance or prevention of a symptom or marker of the pathological condition, but also a reduced severity or degree of any one of the symptoms or markers of the pathological condition, relative to those symptoms or markers in a control or non-treated individual with a similar likelihood or susceptibility of developing the pathological condition, or relative to symptoms or markers likely to arise based on historical or statistical measures of populations affected by the disease or disorder. By "reduced severity" is meant at least a 10% reduction in the severity or degree of a symptom or measurable marker relative to a control or reference, e.g., at least 15%, 20%, 30%, 40%, 50%, 60%, 70%, 80%, 90%, 95%, 99% or even 100% (i.e., no symptoms or measurable markers).

The terms "disease" or "disorder" are used interchangeably throughout this specification, and refer to any alternation in state of the body or of some of the organs, interrupting or disturbing the performance of the functions and/or causing symptoms such as discomfort, dysfunction, distress, or even death to the person afflicted or those in contact with a person. A disease or disorder can also be related to a distemper, ailing, ailment, malady, disorder, sickness, illness, complaint, indisposition, or affliction.

In certain embodiments, the pathological condition may be an infection, inflammation, proliferative disease, autoimmune disease, or allergy.

The term "infection" as used herein refers to presence of an infective agent, such as a pathogen, e.g., a microorganism, in or on a subject, which, if its presence or growth were inhibited, would result in a benefit to the subject. Hence, the term refers to the state produced by the establishment, more particularly invasion and multiplication, of an infective agent, such as a pathogen, e.g., a microorganism, in or on a suitable host. An infection may produce tissue injury and progress to overt disease through a variety of cellular and toxic mechanisms.

The term "inflammation" generally refers to a response in vasculated tissues to cellular or tissue injury usually caused by physical, chemical and/or biological agents, that is marked in the acute form by the classical sequences of pain, heat, redness, swelling, and loss of function, and serves as a mechanism initiating the elimination, dilution or walling-off of noxious agents and/or of damaged tissue. Inflammation histologically involves a complex series of events, including dilation of the arterioles, capillaries, and venules with increased permeability and blood flow, exudation of fluids including plasma proteins, and leukocyte migration into the inflammatory focus.

Further, the term encompasses inflammation caused by extraneous physical or chemical injury or by biological agents, e.g., viruses, bacteria, fungi, protozoan or metazoan parasite infections, as well as inflammation which is seemingly unprovoked, e.g., which occurs in the absence of demonstrable injury or infection, inflammation responses to self-antigens (auto-immune inflammation), inflammation responses to engrafted xenogeneic or allogeneic cells, tissues or organs, inflammation responses to allergens, etc. The term covers both acute inflammation and chronic inflammation. Also, the term includes both local or localised inflammation, as well as systemic inflammation, i.e., where one or more inflammatory processes are not confined to a particular tissue but occur generally in the endothelium and/or other organ systems.

Systemic inflammatory conditions may particularly encompass systemic inflammatory response syndrome (SIRS) or sepsis. "SIRS" is a systemic inflammatory response syndrome with no signs of infection. It can be characterised by the presence of at least two of the four following clinical criteria: fever or hypothermia (temperature of 38.0° C.) or more, or temperature of 36.0° C. or less; tachycardia (at least 90 beats per minute); tachypnea (at least 20 breaths per minute or $PaCO_2$ less than 4.3 kPa (32.0 mm Hg) or the need for mechanical ventilation); and an altered white blood cell (WBC) count of $12 \times 10^6$ cells/mL or more, or an altered WBC count of $4 \times 10^6$ cells/mL or less, or the presence of more than 10% band forms. "Sepsis" can generally be defined as SIRS with a documented infection, such as for example a bacterial infection. Infection can be diagnosed by standard textbook criteria or, in case of uncertainty, by an infectious disease specialist. Bacteraemia is defined as sepsis where bacteria can be cultured from blood. Sepsis may be characterised or staged as mild sepsis, severe sepsis (sepsis with acute organ dysfunction), septic shock (sepsis with refractory arterial hypotension), organ failure, multiple organ dysfunction syndrome and death.

The term "proliferative disease" generally refers to any disease or disorder characterised by neoplastic cell growth and proliferation, whether benign, pre-malignant, or malignant. The term proliferative disease generally includes all transformed cells and tissues and all cancerous cells and tissues. Proliferative diseases or disorders include, but are not limited to abnormal cell growth, benign tumours, pre-malignant or precancerous lesions, malignant tumors, and cancer.

The terms "tumor" or "tumor tissue" refer to an abnormal mass of tissue resulting from excessive cell division. A tumor or tumor tissue comprises "tumor cells" which are neoplastic cells with abnormal growth properties and no useful bodily function. Tumors, tumor tissue and tumor cells may be benign, pre-malignant or malignant, or may represent a lesion without any cancerous potential. A tumor or tumor tissue may also comprise "tumor-associated non-tumor cells", e.g., vascular cells which form blood vessels to supply the tumor or tumor tissue. Non-tumor cells may be induced to replicate and develop by tumor cells, for example, the induction of angiogenesis in a tumor or tumor tissue.

The term "cancer" refers to a malignant neoplasm characterised by deregulated or unregulated cell growth. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor. The term "metastatic" or "metastasis" generally refers to the spread of a cancer from one organ or tissue to another non-adjacent organ or tissue. The occurrence of the proliferative disease in the other non-adjacent organ or tissue is referred to as metastasis.

As used throughout the present specification, the terms "autoimmune disease" or "autoimmune disorder" used interchangeably refer to a diseases or disorders caused by an immune response against a self-tissue or tissue component (self-antigen) and include a self-antibody response and/or cell-mediated response. The terms encompass organ-specific autoimmune diseases, in which an autoimmune response is directed against a single tissue, as well as non-organ specific autoimmune diseases, in which an autoimmune response is directed against a component present in two or more, several or many organs throughout the body.

Non-limiting examples of autoimmune diseases include but are not limited to acute disseminated encephalomyelitis (ADEM); Addison's disease; ankylosing spondylitis; antiphospholipid antibody syndrome (APS); aplastic anemia; autoimmune gastritis; autoimmune hepatitis; autoimmune thrombocytopenia; Behçet's disease; coeliac disease; dermatomyositis; diabetes mellitus type I; Goodpasture's syndrome; Graves' disease; Guillain-Barre syndrome (GBS); Hashimoto's disease; idiopathic thrombocytopenic purpura; inflammatory bowel disease (IBD) including Crohn's disease and ulcerative colitis; mixed connective tissue disease; multiple sclerosis (MS); myasthenia gravis; opsoclonus myoclonus syndrome (OMS); optic neuritis; Ord's thyroiditis; pemphigus; pernicious anaemia; polyarteritis nodosa; polymyositis; primary biliary cirrhosis; primary myxedema; psoriasis; rheumatic fever; rheumatoid arthritis; Reiter's syndrome; scleroderma; Sjögren's syndrome; systemic lupus erythematosus; Takayasu's arteritis; temporal arteritis; vitiligo; warm autoimmune hemolytic anemia; or Wegener's granulomatosis.

"Activation" generally refers to the state of a cell, such as preferably T cell, following sufficient cell surface moiety ligation (e.g., interaction between the T cell receptor on the surface of a T cell (such as naturally-occurring TCR or genetically engineered TCR, e.g., chimeric antigen receptor, CAR) and MHC-bound antigen peptide presented on the surface of the immune cell as taught herein) to induce a noticeable biochemical or morphological change of the cell, such as preferably T cell. In particular, "activation" may refer to the state of a T cell that has been sufficiently stimulated to induce detectable cellular proliferation of the T cell. Activation can also encompass induced cytokine production, and detectable T cell effector functions, e.g., regulatory or cytolytic effector functions. The T cells and immune cells may be may be suitably contacted by admixing the T cells and immune cells in an aqueous composition, e.g., in a culture medium, in sufficient numbers and for a sufficient duration of time to produce the desired T cell activation.

The terms "increased" or "increase" or "upregulated" or "upregulate" as used herein generally mean an increase by a statically significant amount. For avoidance of doubt, "increased" means a statistically significant increase of at least 10% as compared to a reference level, including an increase of at least 20%, at least 30%, at least 40%, at least 50%, at least 60%, at least 70%, at least 80%, at least 90%, at least 100% or more, including, for example at least 2-fold, at least 3-fold, at least 4-fold, at least 5-fold, at least 10-fold increase or greater as compared to a reference level, as that term is defined herein.

The term "reduced" or "reduce" or "decrease" or "decreased" or "downregulate" or "downregulated" as used herein generally means a decrease by a statistically significant amount relative to a reference. For avoidance of doubt, "reduced" means statistically significant decrease of at least 10% as compared to a reference level, for example a decrease by at least 20%, at least 30%, at least 40%, at least 50%, or least 60%, or least 70%, or least 80%, at least 90% or more, up to and including a 100% decrease (i.e., absent level as compared to a reference sample), or any decrease between 10-100% as compared to a reference level, as that term is defined herein. The term "abolish" or "abolished" may in particular refer to a decrease by 100/6, i.e., absent level as compared to a reference sample.

Any one or more of the several successive molecular mechanisms involved in the expression of a given gene or polypeptide may be targeted by the intestinal epithelial cells, intestinal epithelial stem cells, or intestinal immune cells (preferably intestinal epithelial cells) cell modification as intended herein. Without limitation, these may include targeting the gene sequence (e.g., targeting the polypeptide-encoding, non-coding and/or regulatory portions of the gene sequence), the transcription of the gene into RNA, the polyadenylation and where applicable splicing and/or other post-transcriptional modifications of the RNA into mRNA, the localization of the mRNA into cell cytoplasm, where applicable other post-transcriptional modifications of the mRNA, the translation of the mRNA into a polypeptide chain, where applicable post-translational modifications of the polypeptide, and/or folding of the polypeptide chain into the mature conformation of the polypeptide. For compartmentalized polypeptides, such as secreted polypeptides and transmembrane polypeptides, this may further include targeting trafficking of the polypeptides, i.e., the cellular mechanism by which polypeptides are transported to the appropriate sub-cellular compartment or organelle, membrane, e.g. the plasma membrane, or outside the cell. Functional genomics can be used to modify cells for therapeutic purposes, and identify networks and pathways. For example, Graham et al ("Functional genomics identifies negative regulatory nodes controlling phagocyte oxidative burst," *Nature Communications* 6, Article number: 7838 (2015)) describes functional genetic screens to identify the phagocytic oxidative burst. With the rapid advancement of genomic technology, it is now possible to associate genetic variation with phenotypes of intestinal epithelial cells, intestinal epithelial stem cells, or intestinal immune cells (preferably intestinal epithelial cells) at the population level. In particular, genome-wide association studies (GWAS) have implicated genetic loci associated with risk for IBD and allowed for inference of new biological processes that contribute to disease. These studies highlight innate defense mechanisms such as antibacterial autophagy, superoxide generation during oxidative burst and reactive nitrogen species produced by iNOS. However, GWAS requires functional analysis to unlock new insights. For example, many risk loci are densely populated with coding genes, which complicates identification of causal genes. Even when fine mapping clearly identifies key genes, a majority have poorly defined functions in host immunity. Moreover, any given gene may have multiple functions depending on the cell type in which it is expressed as well as environmental cues. Such context-specific functions of regulatory genes are largely unexplored. Thus, human genetics offers an opportunity to leverage insight from large amounts of genetic variation within healthy and patient populations to interrogate mechanisms of immunity. Irrespective of their putative roles in IBD pathology, genes within risk loci are likely to be highly enriched for genes controlling signaling pathways.

The invention is further described in the following examples, which do not limit the scope of the invention described in the claims.

EXAMPLES

Example 1—Map of the Cellular and Molecular Composition in the Healthy and Inflamed Gut Applicants have generated a foundational resource in the healthy and inflamed gut for: (1) Cell composition (i.e., changes in proportions of different cell types/states), (2) Cell intrinsic states (i.e., changes in gene expression within a cell type), (3) Cell-cell interactions (i.e., changes in cell-cell interaction mechanisms), and (4) the relevant cell types for each gene (e.g., GWAS genes).

GWAS gene→cell type→cell state→cell interaction→disease

Applicants used single cell RNA-seq of colonoscopy samples from healthy individuals and UC patients to generate the cell atlas. The samples were obtained from 10 healthy individuals (37,435 non-inflamed cells were initially analyzed), 10 UC patients (17,400 cells (10,688 uninflamed; 6,712 inflamed) were initially analyzed). Three additional samples were analyzed. In total 117,819 cells were analyzed (49,765 epithelial, 11,556 stromal, 56,498 immune). The samples were small biopsies containing about <80,000 cells. The biopsies were fresh and dislocation and processing were performed by applicants. A subset of greater than 50,000 cells are presented on some plots herein.

Figure 2:
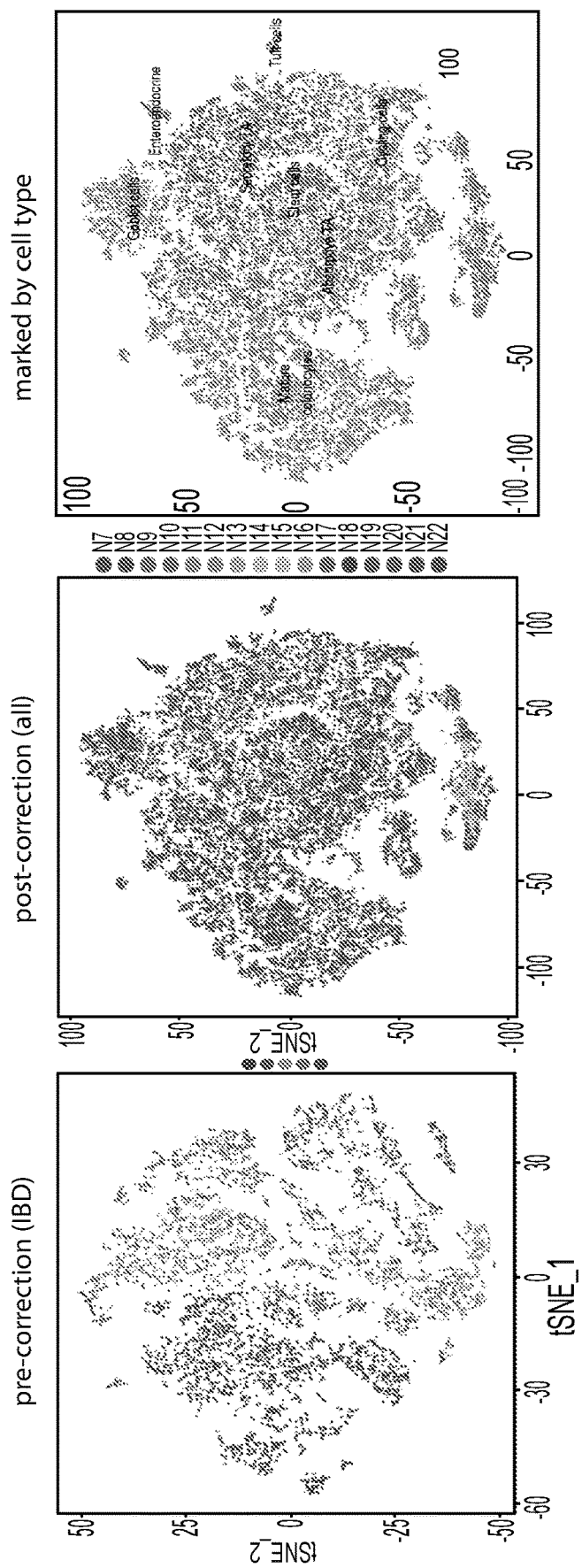
FIG. 2—illustrates that computational modeling can address batch effects in tSNE plots.

FIG. 1 shows that initial clustering analysis partitioned cells by patient in the UC samples and by cell type in the healthy samples. This result was similar as in Tirosh, et al. (Dissecting the multicellular ecosystem of metastatic melanoma by single-cell RNA-seq. Science 2016, 352, 189-196) where malignant cells partitioned by patient and non-malignant cells partitioned by cell type. Applicants used computational modeling to address the batch effects and partition the cells by cell type (FIG. 2).

Figure 3:
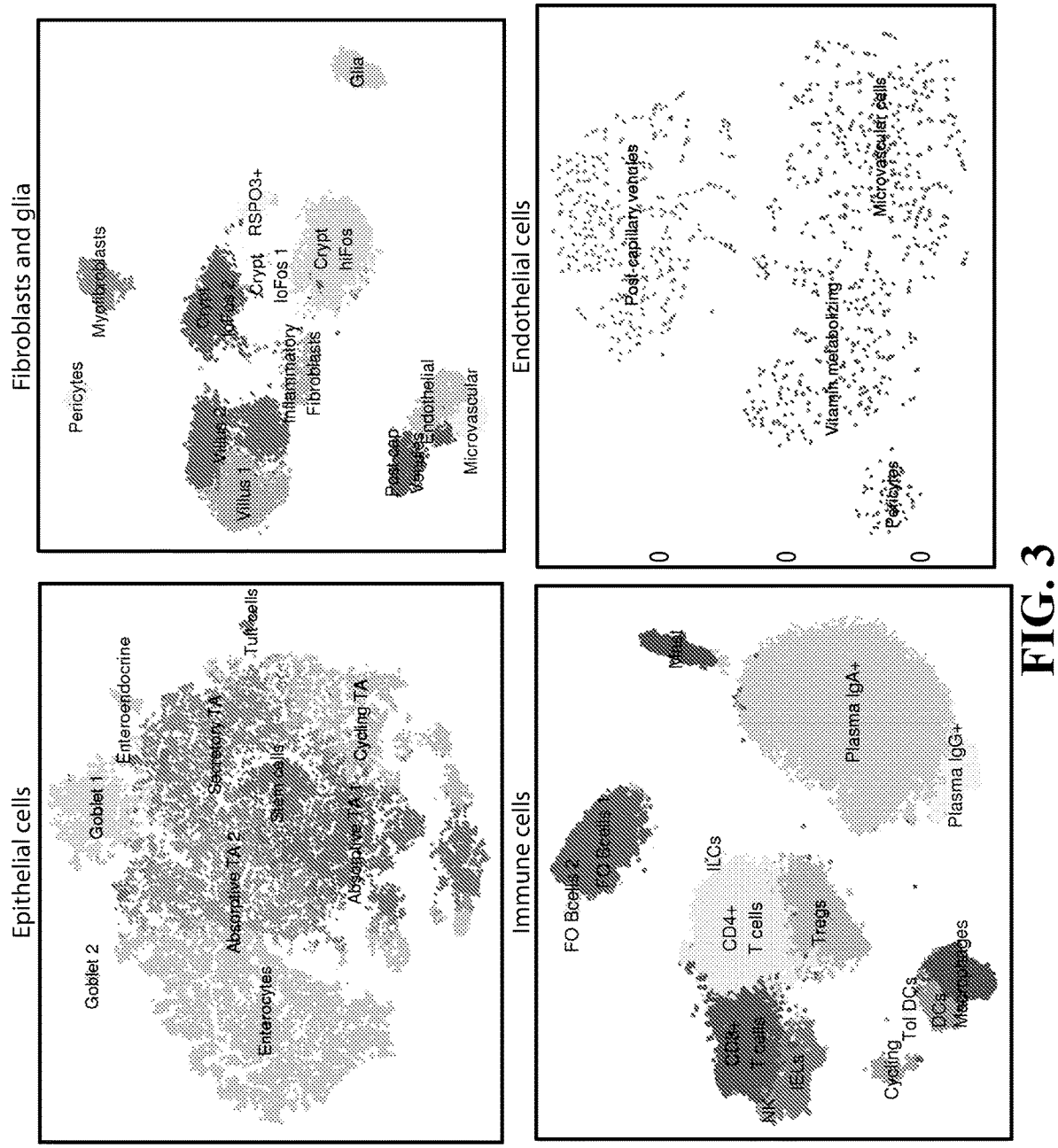
FIG. 3—illustrates that the atlas uncovers almost all cell types and subtypes in the colon.
Figure 4:
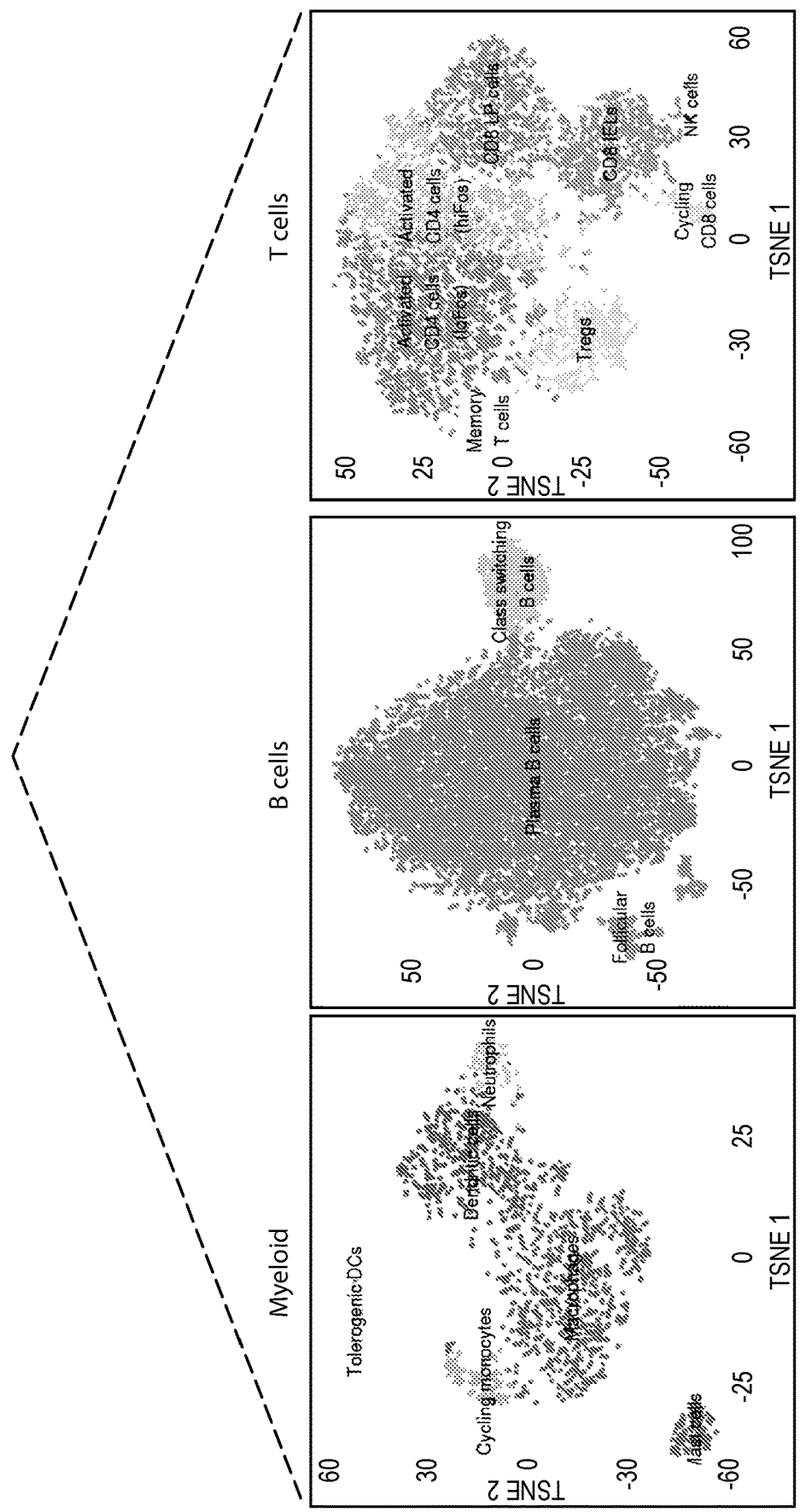
FIG. 4—illustrates that the atlas uncovers almost all immune cell types and subtypes in the colon.

FIGS. 3 and 4 show that the atlas uncovers almost all cell types and subtypes in the colon. Applicants identified the following cell types and subtypes in the colon: Plasma B cells, Class switching B cells, Follicular B cells, T cells, Macrophages, Dendritic cells, Mast cells, Cycling monocytes, Tolerogenic DCs, Neutrophils, Activated CD4 cells loFos, Activated CD4 cells hiFos, CD8 IELs, CD8 LP cells, Tregs, Memory T cells, NK cells, Cycling CD8 cells, Microvascular cells, Post-capillary venules, Vitamin metabolizing, Endothelial pericytes, Enterocytes, Tuft cells, Goblet 2, Absorptive TA 1, Secretory TA, Absorptive TA 2, Cycling TA, Goblet 1, Stem cells, Enteroendocrine, Glial cells, Inflammatory fibroblasts, Fibroblast pericytes, Myofibroblasts, Villus fibroblasts, Crypt fibroblasts (hiFos) and Crypt fibroblasts (loFos). Applicants identified markers specific for each cell type. Table 1 A-D shows the top 250 genes expressed in each cell type.

TABLE 1A

| Plasma_B_cells | Class_switching_B_cells | Follicular_B_cells | Microvascular_cells | Post-capillary_venules |
|---|---|---|---|---|
| HERPUD1 | IGLL5 | CD79A | PRSS23 | DARC |
| IGJ | IGJ | MS4A1 | RGCC | NPC2 |
| SSR4 | TMSB10 | CD79B | PLVAP | CLDN5 |
| SEC11C | CFL1 | VPREB3 | VWA1 | CPE |
| XBP1 | TMSB4X | TCL1A | PASK | MADCAM1 |
| MZB1 | PFN1 | FCRLA | GNG11 | CLU |
| FKBP11 | MYL6 | CD37 | CA4 | DUSP23 |
| DERL3 | FTH1 | CD19 | CD36 | JAM2 |
| SPCS2 | GAPDH | SMIM14 | CD320 | PLVAP |
| TNFRSF17 | ACTB | CST3 | VWF | LY6E |
| CD79A | IGLL1 | CD63 | ENG | ECSCR |
| SSR3 | TNFRSF17 | LTB | RAMP2 | SDCBP |
| UBE2J1 | CD79A | LIMD2 | SLC9A3R2 | TSPAN7 |
| SPCS1 | DERL3 | CD22 | ESAM | EGFL7 |
| DNAJB9 | MT-CO1 | BLK | CRIP2 | VWF |
| EAF2 | MZB1 | LGALS3 | GSN | GNG11 |
| FKBP2 | SERF2 | PTPRCAP | SPARCL1 | RAMP2 |
| MANF | AL928768.3 | AL928768.3 | FKBP1A | APLNR |
| PRDX4 | ACTG1 | HLA-DQA1 | TMEM204 | RAMP3 |
| SDF2L1 | RPL28 | CD53 | ITM2B | ITM2B |
| SERP1 | RPS24 | BANK1 | RBP5 | CTNNAL1 |
| AL928768.3 | MT-CO3 | RHOH | TM4SF18 | IGFBP4 |
| SPCS3 | ATP5E | S100A6 | RAMP3 | NNMT |
| CYBA | COX4I1 | GPR18 | EGFL7 | HLA-E |
| WT1-AS | HLA-A | CORO1A | HSPG2 | GIMAP7 |
| CRELD2 | PPAPDC1B | BCAS4 | CCDC85B | GPR126 |
| VIMP | GNG7 | CXCR5 | ECSCR | ICAM1 |
| SEC61B | UBA52 | CD74 | TMEM88 | HHEX |
| PDIA6 | ICAM3 | SERPINA9 | SDPR | GIMAP4 |
| HSP90B1 | UQCR11 | LRMP | VAMP5 | TNFSF10 |
| GNG7 | RPS12 | FCGRT | BCAM | LINC01013 |
| PPAPDC1B | SSR4 | EAF2 | CAV1 | AC011526.1 |
| CD27 | S100A6 | RGS13 | MGP | CLEC14A |
| FAM46C | PPDPF | CXCR4 | EMCN | IGFBP7 |
| PDIA4 | RPL31 | POU2AF1 | ELTD1 | NPDC1 |
| ISG20 | CHCHD2 | SMARCB1 | PLAT | NCOA7 |
| PABPC4 | BTF3 | CD52 | KDR | CAV1 |
| TRAM1 | SRP14 | SPIB | CLEC14A | LMO2 |
| ANKRD37 | CD27 | MGST3 | HLA-E | SNCG |
| RPL36AL | TOMM7 | BLNK | IGFBP7 | CTGF |
| C19orf10 | PFDN5 | HLA-DRA | FLT1 | TM4SF1 |
| CCR10 | MYL12B | CD72 | PODXL | FAM213A |
| IGLL5 | YBX1 | POU2F2 | SEPW1 | SPARCL1 |
| HSPA5 | EAF2 | ACTR3 | IGFBP4 | CRIP2 |
| ACTB | UBE2J1 | FCRL2 | HTRA1 | ITM2A |
| LMAN2 | SRGN | HMGN1 | SPARC | FAM167B |
| MEI1 | RPL30 | CD40 | CAV2 | FKBP1A |
| DUSP5 | EIF3K | ARPC2 | SLC14A1 | ESAM |
| SELK | NDUFA11 | GGA2 | AC011526.1 | IFITM3 |
| UBC | CYTIP | EZR | SH3BP5 | TMEM100 |

TABLE 1A-continued

| | | | | |
|---|---|---|---|---|
| FCRL5 | RPL23 | HERPUD1 | FAM167B | CCL14 |
| CST3 | TRAM1 | NCF1 | FAM213A | BCAM |
| TXNDC11 | ATP5G2 | IRF8 | SNCG | GIMAP1 |
| UAP1 | FAM46C | HLA-DPA1 | GIMAP7 | CD34 |
| PIM2 | TCEB2 | HLA-DQB1 | CDC37 | IFI27 |
| CFL1 | PTMA | HLA-DPB1 | IFITM3 | TGFBR2 |
| SPAG4 | ERLEC1 | LAPTM5 | RP11-536O18.2 | CYBA |
| YPEL5 | SH3BGRL3 | UBE2J1 | PPAP2A | RBP5 |
| PFN1 | EDF1 | HLA-DOB | TSC22D1 | CYYR1 |
| S100A6 | HM13 | FCER2 | IFITM2 | ZNF385D |
| TPD52 | RPS7 | C12orf75 | ICAM2 | NRN1 |
| CHPF | KDELR1 | SWAP70 | PTRF | HLA-DRA |
| RP11-90F5.1 | ARHGDIB | HMCES | EHD4 | ADIRF |
| HSPA1B | FKBP11 | BTG1 | NQO1 | CD320 |
| POU2AF1 | PABPC4 | P2RX5 | CLDN5 | CD59 |
| JUN | SPCS3 | LY86 | CD59 | SRPX |
| BTG2 | RPL38 | CYTIP | COL4A1 | ENG |
| TXNDC15 | COX6B1 | METAP2 | PPAP2B | CFI |
| TSC22D3 | ALDOA | CD180 | HLA-C | HLA-A |
| TMEM258 | RPS11 | AICDA | CXorf36 | HSPB1 |
| TMED10 | CLIC1 | CD9 | NPDC1 | HLA-DPB1 |
| MCL1 | TPI1 | LY9 | ARHGAP29 | PIM3 |
| TMSB10 | TXNDC15 | HLA-DRB1 | ANGPT2 | HLA-DRB5 |
| TPST2 | RPL10A | ANXA2 | HSPB1 | SEPW1 |
| ACTG1 | CHST12 | ISG20 | CD34 | SDPR |
| NR4A1 | NDUFA13 | SEPW1 | TM4SF1 | ENPP2 |
| S100A10 | TRMT112 | ARHGDIB | APP | NOSTRIN |
| TNFRSF18 | DPP7 | HMGA1 | BAALC | DNAJA1 |
| ERLEC1 | IFNAR2 | TCEA1 | C16orf80 | PTRF |
| NUCB2 | RPL11 | POLD4 | EFNA1 | KCTD12 |
| TMSB4X | MYL12A | CD83 | ACVRL1 | IFITM2 |
| RPN2 | RPSA | BASP1 | LXN | HLA-DRB1 |
| SUB1 | RPL26 | STAG3 | IGFBP3 | MYCT1 |
| PNOC | ISG20 | S100A11 | CYYR1 | GIMAP5 |
| SELM | ATP6V1G1 | SNX29P2 | MYL12A | CCDC85B |
| SLAMF7 | RPL27 | TPD52 | MGLL | CNN3 |
| IFNAR2 | POU2AF1 | IFI27 | HLA-A | LMCD1 |
| DDOST | ALG5 | ARPC3 | HLA-DRA | KANK3 |
| MYL12B | PSMA7 | HTR3A | STOM | CD74 |
| TNFRSF13B | RPL24 | GCSAM | EGLN3 | HLA-DPA1 |
| FGF23 | SLC25A3 | PNOC | ROBO4 | HLA-C |
| LMAN1 | SEC62 | E2F5 | SPTBN1 | CDH5 |
| ANKRD28 | CNPY2 | CD27 | ABI3 | ADM5 |
| CD38 | BST2 | RAC2 | HLX | NFKBIA |
| ICAM3 | TMEM230 | AC023590.1 | RASIP1 | SPARC |
| GAPDH | RPL37 | STX7 | HLA-B | PALMD |
| DNAJB11 | CD63 | LYL1 | TGFBR2 | CHCHD10 |
| ARF4 | SLAMF7 | TMSB10 | S100A13 | LPCAT4 |
| AC104699.1 | LGALS1 | UCP2 | MMRN2 | ERG |
| CDK2AP2 | GYPC | IL32 | IVNS1ABP | SH3BP5 |
| TMEM59 | RPS9 | HLA-DMA | CTGF | STXBP6 |
| ALG5 | NDUFA4 | SELT | F2RL3 | BST2 |
| C16orf74 | COX5B | LAT2 | ENPP2 | CAV2 |
| SRPRB | DUSP5 | IFITM3 | WWTR1 | SMAD1 |
| CIRBP | RPS13 | BFSP2 | EXOC3L2 | CLIC2 |
| FTH1 | HNRNPDL | GDI2 | B2M | IFIT1 |
| TMED2 | LRPAP1 | HLA-DMB | NOTCH4 | TPD52L1 |
| RGS2 | PARK7 | HHEX | GABARAPL2 | SOCS3 |
| IGFBP7 | MEI1 | LGALS4 | IFI27 | GALNT15 |
| RABAC1 | RPL19 | EPCAM | S100A16 | HLA-DQA1 |
| CD74 | RHEB | MZB1 | HES1 | CYP1B1 |
| SSR2 | VIM | SIT1 | GMFG | ICAM2 |
| ARHGDIB | RPL32 | PLEKHF2 | IL3RA | HSPA1A |
| DNAJB1 | COX7C | TNFRSF13B | GAS6 | IRF1 |
| CYTIP | COX6A1 | RHOC | IDO1 | FBLN2 |
| ZBP1 | PTPRCAP | OAZ1 | COL4A2 | HYAL2 |
| HM13 | SMARCB1 | KRT18 | MSN | EIF1 |
| AMPD1 | COMMD3 | LCP1 | FSCN1 | SELP |
| MYL12A | LSP1 | HVCN1 | HHEX | LIFR |
| RHOC | PSENEN | C15orf48 | MYCT1 | S100A16 |
| GSN | RPS25 | KRT8 | ACE | TCF4 |
| IFI27 | ARL6IP4 | ITM2B | TSPAN7 | MPZL2 |
| REEP5 | EMC4 | MBD4 | EPAS1 | YBX3 |
| TMEM208 | ARPC3 | BIK | FAM110D | EGR1 |
| SDC1 | ATP5O | TXN | C9orf3 | ARL2 |
| GLA | MT-ND4 | CCND3 | CALCRL | MTUS1 |
| TUBA1A | GMFG | DEF8 | HLA-DRB1 | B2M |
| EEF1D | SRPRB | RASGRP2 | SOX18 | SNHG7 |
| KDELR2 | ATP5B | MARCKSL1 | FABP5 | FAM110D |
| B4GALT3 | NDUFA1 | NEIL1 | GALNT18 | CALCRL |

TABLE 1A-continued

| | | | | |
|---|---|---|---|---|
| PDE4B | RPL37A | SUGCT | ITM2A | ELTD1 |
| RGCC | RAC1 | RP11-64H13.1 | A2M | PIR |
| LGALS1 | EIF3F | RFTN1 | IFITM1 | JUNB |
| RGS1 | DNAJB11 | ITM2C | IGFBP6 | IL3RA |
| LGALS3 | ATP5J | MT2A | NOSTRIN | RNASE1 |
| PDK1 | MT-ATP6 | TNFAIP8 | JAM2 | IL33 |
| TMEM176B | RPS20 | ZCCHC7 | RNASE1 | VGLL4 |
| SH3BGRL3 | MGAT1 | LINC00926 | MYL12B | IFIT3 |
| IFITM3 | CRELD2 | AIM2 | SLCO2A1 | EFEMP1 |
| KIAA0125 | UBL5 | STK17A | CALM1 | AC116035.1 |
| MYL6 | MT-CYB | CISD3 | NES | KLF4 |
| SRGN | SELM | CYB561A3 | KANK3 | TESC |
| RP11-92E3.2 | VAMP2 | SLBP | ARHGAP18 | EPCAM |
| TRIB1 | OSTC | TMEM156 | RND1 | STOM |
| CITED2 | ICAM2 | BACH2 | FTH1 | CD55 |
| ID2 | EMP3 | LMNA | CLIC2 | RND1 |
| EVI2B | NACA | ATP1A1 | LDB2 | CDC42EP3 |
| KRTCAP2 | CALM2 | GYPC | MPZL2 | TIMP1 |
| BEX5 | RPS3 | RMI2 | PEA15 | HES1 |
| CISD2 | NDUFS8 | PPP1CC | MCAM | TSPAN4 |
| SEPW1 | COX7A2 | UBE2N | DLL4 | PLK2 |
| ANXA1 | PLP2 | AGR2 | MFNG | ATP5G3 |
| RPN1 | CCR10 | PARP1 | C8orf4 | TXNIP |
| EIF1 | TPD52 | MME | HLA-DPB1 | HLA-DMA |
| FOSB | SELT | HCLS1 | BST2 | BAG3 |
| HAX1 | ZNF706 | PABPC1 | PTPRB | PDLIM4 |
| IL32 | PIM2 | IGLL5 | TSPAN4 | MGP |
| IFITM2 | HINT1 | RGS16 | ACTN4 | ID3 |
| TMED4 | UAP1 | CD1C | IPO11 | PHGR1 |
| SEMA4A | SNRPD2 | RGS19 | DUSP6 | TIE1 |
| RAB30 | S100A10 | PAX5 | TEK | AGR2 |
| SLC17A9 | SLC35B1 | ETHE1 | GUK1 | SEMA6A |
| SLC38A5 | REEP5 | HLA-DQA2 | ID3 | HLA-B |
| CAPZB | TMEM66 | DCK | CDH5 | TAGLN2 |
| PTPRCAP | ATRAID | ITSN2 | IMP3 | KRT222 |
| H3F3B | SOD1 | SH2B2 | TBCD | TMEM176A |
| COPE | RPS23 | SUSD3 | CABP1 | SORBS2 |
| WNT10A | GUK1 | SRSF3 | GIMAP1 | ST8SIA4 |
| TMED9 | TMED4 | LYN | JUP | IFI16 |
| CUTA | RPS21 | SYPL1 | TNFRSF4 | LGALS4 |
| E2F5 | DNAJC1 | ARPC1B | ARHGDIB | GIMAP8 |
| HSPA1A | NDUFB2 | CTSD | PRX | KRT8 |
| SELT | MT-ND5 | IL16 | GRB10 | BAALC |
| HES1 | NUCB2 | ZFAND6 | PCDH12 | FAM107A |
| EZR | PABPC1 | PRPSAP2 | NRP1 | JUN |
| DUSP1 | RPL12 | MAP3K7CL | SRGN | S100A13 |
| RNU12 | ATF4 | S100A10 | ERG | ZFP36 |
| PAIP2B | DNAJB9 | PXK | NKX2-3 | A2M |
| SPINK2 | B4GALT3 | RP11-960L18.1 | CLIC4 | DTL |
| SLC35B1 | HNRNPA1 | CCR7 | TUBA1B | EID1 |
| SMARCB1 | NEDD8 | LSM10 | SLC25A6 | PKP4 |
| SEPP1 | CISD2 | LYPLA1 | LAYN | CCL21 |
| DNAJC1 | KRTCAP2 | DCAF12 | TMEM255B | HLA-DQB1 |
| SEL1L | ERGIC2 | CTSH | GIMAP4 | LIMCH1 |
| HSP90AA1 | UQCRQ | TMEM243 | LIMCH1 | GADD45B |
| AC093818.1 | CNBP | TFEB | THBD | CD9 |
| HLA-A | LAMTOR4 | AC079767.4 | CD74 | CXorf36 |
| ICAM2 | COX6C | UBE2G1 | HLA-DPA1 | HAPLN3 |
| TPI1 | CD44 | WIPF1 | TSPAN12 | VIM |
| EMB | LMAN1 | KIAA0125 | CDC42EP1 | ADCY4 |
| QPCT | TMBIM4 | HNRNPC | COX7A1 | WARS |
| SPATS2 | CST3 | FXYD3 | SCARF1 | PLAT |
| RHOH | C4orf3 | ID2 | TXNIP | ACVRL1 |
| APOE | EIF4A2 | CBX3 | SEMA3F | MEOX1 |
| MANEA | FXYD5 | SNAP23 | RHOA | CYB5A |
| IRF4 | NDUFB8 | MOB1A | LDHB | INPP1 |
| ANXA2 | AUP1 | DBNL | SORBS2 | LDB2 |
| IFITM1 | DDOST | DOK3 | TACC1 | IL1R1 |
| JSRP1 | GSTK1 | PLCG2 | ITGA6 | TMEM176B |
| COMMD3 | C19orf43 | KRT19 | KIFC3 | ARL4A |
| SRM | PRDX2 | IGJ | LGALS4 | CTHRC1 |
| CXCL14 | SKP1 | SQRDL | TIE1 | PRCP |
| SMDT1 | A1BG | FCRL3 | HLA-DRB5 | IFIT2 |
| MT-CO3 | SAP18 | RRAS2 | PRDX1 | TMEM173 |
| RPS5 | TMA7 | CERS4 | PELO | FAM198B |
| IL2RG | UBE2D3 | OSER1 | TP53I11 | FABP1 |
| SRPR | DHRS7 | LMO2 | SERPINI1 | GPR146 |
| ERGIC2 | RPS15 | TAGAP | PPA1 | MLEC |
| PTMS | LGALS3 | FTL | FAM101B | MMP28 |
| PLP2 | PSMB6 | BTK | S100A6 | SQSTM1 |

TABLE 1A-continued

| | | | | |
|---|---|---|---|---|
| OSTC | SDF2L1 | ATP5I | PPFIBP1 | KRT18 |
| CNPY2 | CHID1 | ANP32B | RPL12 | SERTAD1 |
| S100A4 | ATP5G3 | PTPRC | TMEM173 | IFITM1 |
| SRP14 | RBM39 | RCSD1 | ANKRD65 | LPAR6 |
| PPIB | LAMP2 | TUBB4B | PLXNA2 | RASIP1 |
| SIL1 | ATP6V0E1 | RPS4Y1 | APLN | ALDH1A1 |
| GLRX | ITM2B | MLEC | CD93 | MX1 |
| CD69 | EVI2B | GSTP1 | ITGA1 | PTPRB |
| RPL28 | EIF3H | CCNI | C10orf54 | NKX2-3 |
| SLC25A4 | SEC11C | HLA-A | VAT1 | PPP1R15A |
| TMBIM6 | UFM1 | RP11-138I18.2 | KLHDC8B | NEAT1 |
| S100A11 | OS9 | NPM1 | PHGR1 | IGJ |
| TNFRSF4 | C11orf31 | SGPP1 | TINAGL1 | MEIS2 |
| LGALS4 | ANXA7 | HSH2D | CYBA | GIMAP6 |
| JTB | CALM1 | BLVRB | ME3 | SRGN |
| RPL8 | PSMB3 | ORAI2 | TNFSF10 | CLDN7 |
| THAP2 | TPT1 | TNFRSF17 | SERPINE1 | LAPTM4A |
| COTL1 | TAPBP | ALOX5 | RHOC | PLA1A |
| TIFA | CHPF | PTPN6 | EPHX1 | EPAS1 |
| TXNIP | ERGIC3 | ACTG1 | NDUFA12 | SLC41A3 |
| FCRLA | DERL2 | GPSM3 | PTMA | LAYN |
| ENO1 | HIGD2A | MTMR14 | CCND1 | ASRGL1 |
| CD151 | 15-Sep | FAM65B | GIMAP5 | FOS |
| BRSK1 | ARPC2 | TFF3 | RPLP1 | IFI6 |
| ARPC1B | NDUFB4 | KLHL5 | GPX1 | CSF2RB |
| A2M | RPLP2 | GRB2 | RBP7 | CSRP2 |
| AC104024.1 | ST13 | GNG7 | KRT8 | C10orf128 |
| LMTK3 | JTB | CCDC69 | SEC14L1 | DDX5 |
| SSR1 | ATP5D | CR2 | CHCHD10 | GBP2 |
| RNASET2 | NUDT22 | TMEM141 | PRIG | IFI44L |
| COX5B | GNL3 | DDX39A | PSMB5 | TIMP3 |
| SEC61A1 | NDUFB11 | SRGN | ARHGEF15 | EIF4A2 |
| HSH2D | NHP2L1 | MEF2C | SCARB1 | EVA1C |
| ATP5E | ARF1 | HLA-DRB5 | PRKCH | IDH2 |
| DCN | SEC61A1 | LAMTOR4 | MCF2L | RAB13 |
| CHID1 | CHMP2A | REL | GPR116 | NEDD9 |
| MT-CO1 | RPL14 | KIAA0226L | DYNLL1 | DNAJB4 |
| RP11-16E12.2 | NPM1 | PRDX5 | HEG1 | NR2F2 |
| ERGIC3 | ARMCX3 | CCDC109B | OSBPL1A | CAPG |
| TXNDC5 | SRPR | PPDPF | ARL2 | IPO11 |

| Vitamin_metabolizing | Endothelial_pericytes | Enterocytes | Tuft_cells | Goblet_2 |
|---|---|---|---|---|
| CD320 | RGS5 | RPL15 | AZGP1 | MUC2 |
| RAMP2 | HIGD1B | RPS2 | LRMP | TFF1 |
| CLDN5 | CD320 | RPL13 | SH2D6 | RPL13 |
| PLVAP | PLVAP | RPS6 | MARCKSL1 | ZG16 |
| SLC9A3R2 | CLDN5 | GUCA2A | AVIL | RPL10 |
| GNG11 | CRIP2 | RPL10 | BIK | RPL15 |
| IGFBP4 | RAMP2 | AQP8 | SH2D7 | RPS4X |
| TXNIP | CAV1 | RPL32 | HCK | RPS2 |
| ENPP2 | ESAM | RPS4X | ANXA4 | RPS18 |
| CLEC14A | GNG11 | RPS19 | PTGS1 | RPS19 |
| TMEM88 | CD36 | SLC26A3 | ALOX5 | RPL32 |
| ESAM | COX4I2 | RPLP1 | ANXA13 | FCGBP |
| CRIP2 | NDUFA4L2 | RPS18 | KRT18 | RPL19 |
| SPARCL1 | IGFBP4 | PLAC8 | IL17RB | S100P |
| HLA-E | MGP | CEACAM7 | TPM1 | CEACAM5 |
| RAMP3 | EGFL7 | FXYD3 | TRPM5 | TSPAN1 |
| CD59 | TMEM88 | KRT20 | EIF1B | RPL11 |
| CAV1 | SPARCL1 | FABP1 | BMX | RPS9 |
| VAMP5 | RBP7 | PRAP1 | HPGDS | RPS14 |
| IFI27 | IGFBP7 | TSPAN1 | POU2F3 | FXYD3 |
| JAM2 | MYL9 | CEACAM5 | GNG13 | RPL10A |
| ECSCR | SLC9A3R2 | SDCBP2 | HTR3E | RPL35 |
| SEPW1 | TINAGL1 | SRI | PSTPIP2 | LYPD8 |
| EGFL7 | NOTCH3 | MS4A12 | SPIB | RPL12 |
| BCAM | CLEC14A | PHGR1 | PLCG2 | RPS5 |
| GIMAP7 | TXNIP | C19orf33 | ELF3 | MUC1 |
| CD36 | ENPP2 | RPS8 | MATK | ENTPD8 |
| NPDC1 | JAM2 | RPS9 | KRT8 | RPLP1 |
| RBP7 | SDPR | RPL10A | C11orf53 | RPS8 |
| GSN | GIMAP7 | CTD-2228K2.5 | TFF3 | RPL35A |
| CYYR1 | RAMP3 | RPL35 | EPCAM | RPL26 |
| SDPR | TM4SF1 | MISP | RASSF6 | CLDN4 |
| EFNA1 | ECSCR | GUCA2B | RGS13 | RPS13 |
| ICAM2 | HLA-E | RPS5 | FYB | TFF3 |
| TM4SF1 | CYYR1 | TMEM54 | CRYM | REP15 |
| EMCN | IFITM3 | RPS7 | PRSS3 | FAM3D |
| IFITM3 | SPARC | SLC51B | IGJ | RPS27A |

TABLE 1A-continued

| | | | | |
|---|---|---|---|---|
| MGP | A2M | RPL19 | TREH | RPS3 |
| TSPAN7 | GSN | RPL11 | SPINT2 | GNB2L1 |
| FKBP1A | CALD1 | CDHR5 | IL13RA1 | RPS7 |
| IL3RA | HSPA1A | RPL5 | NMU | RPS16 |
| IFITM1 | CAV2 | RPL35A | SOX4 | CLDN7 |
| PODXL | CCDC85B | RPS13 | DPYSL3 | RPL6 |
| IFITM2 | VWF | CLDN7 | ASCL2 | RPLP2 |
| TGFBR2 | VAMP5 | RPL12 | LGALS4 | RPS15 |
| STOM | ZFP36 | RPS23 | HEPACAM2 | RPS15A |
| PPA1 | HLA-C | CEACAM1 | LGALS1 | MUC13 |
| ENG | HSPB1 | CA2 | HOTAIRM1 | RPLP0 |
| HES1 | HLA-DRA | ANPEP | PLEKHB1 | SDCBP2 |
| CD34 | EGR1 | LYPD8 | CLDN4 | RPL8 |
| VWF | TM4SF18 | KRT8 | PPAP2C | ELF3 |
| HLA-C | IFI27 | LINC01133 | PPDPF | GDPD3 |
| RBP5 | CSRP2 | RPS3 | PTPN18 | NACA |
| CAV2 | JUNB | RPS12 | OGDHL | RPS12 |
| SLC14A1 | NOSTRIN | RPLP0 | MDK | RPL23A |
| PRSS23 | FOS | RPL26 | FXYD3 | RPL5 |
| PLAT | CDH5 | GNB2L1 | OCIAD2 | CLDN3 |
| CDC37 | RNASE1 | SFN | RP11-39B14.5 | PHGR1 |
| A2M | GADD45B | RPS15A | CLDN3 | RPS23 |
| CCDC85B | IFITM2 | RPL14 | ESPL1 | C19orf33 |
| TNFSF10 | FRZB | RPS14 | FABP1 | GUCA2B |
| EPAS1 | IER2 | PRSS3 | ALOX5AP | PLAC8 |
| RNASE1 | ENG | LGALS3 | ANXA3 | RPL4 |
| OAZ2 | CTGF | RPL6 | CD74 | BCAS1 |
| SRP14 | JUN | RPL4 | FURIN | RPS6 |
| CTGF | ICAM2 | RPS16 | PPP1R1B | RPL13A |
| HLA-DRB1 | BGN | RPS15 | MT-CO3 | TBX10 |
| GIMAP4 | TPPP3 | RPL23A | ANKS4B | TUBB2A |
| HLA-DRA | FOSB | PTMA | HSPB1 | TM4SF5 |
| ELTD1 | RBP5 | PKIB | NCMAP | SMIM6 |
| ITM2B | HLA-DPB1 | RPS27A | DEFB1 | VSIG2 |
| FAM107A | HES1 | AMN | ZFP36 | SERPINA1 |
| AC011526.1 | HLA-DRB1 | RPL27A | CC2D1A | IFI27 |
| APP | HLA-DRB5 | GPA33 | COX5A | LGALS9B |
| MPZL2 | MGLL | GCNT3 | MT-CO1 | KRT8 |
| IGFBP7 | SLC14A1 | PRDX6 | EHF | ZG16B |
| TMEM204 | SEPW1 | AGPAT2 | CALM2 | MT-CO1 |
| GPR146 | EPAS1 | AOC1 | SOX9 | PTMA |
| CD74 | FKBP1A | SULT1A2 | IFT172 | SERINC2 |
| FLT1 | ITM2B | MEP1A | 7SK | RPL14 |
| C16orf80 | SNCG | RPL8 | ITM2C | TRIM31 |
| ACVRL1 | C8orf4 | RPL31 | CASP6 | RPL24 |
| FAM167B | SOCS3 | SMIM22 | EMP3 | AMN |
| MMRN2 | LDB2 | TMIGD1 | COX6C | TPSG1 |
| MGLL | ELTD1 | KRT19 | ATP1A1 | FFAR4 |
| HLA-DPB1 | PLAT | CA4 | PHGR1 | KLK1 |
| NOSTRIN | EMCN | CLDN3 | CCDC115 | TMEM54 |
| GIMAP1 | ID3 | SERINC2 | GFI1B | RPL27A |
| BST2 | GIMAP4 | RPL13A | HSPA1A | RPS20 |
| HYAL2 | PRSS23 | PIGR | S100A11 | CDHR5 |
| TIMP3 | BST2 | NEAT1 | KIAA1324 | CLTB |
| TM4SF18 | CD59 | RPL29 | EPS8L3 | RPL29 |
| HHEX | FAM167B | FTH1 | NREP | CREB3L1 |
| GIMAP5 | TSC22D1 | TST | HLA-DPB1 | RPL3 |
| RPLP1 | HSPA1B | CLCA4 | HLA-DRA | EPCAM |
| SLCO2A1 | RGS16 | RPL7A | HLA-DRB1 | FOXA3 |
| SNCG | PDGFRB | PPP1R14D | MYO1B | RPL31 |
| FAM213A | ADIRF | MUC12 | B2M | CAPN8 |
| HLA-DPA1 | GJA4 | MUC13 | GADD45B | GPA33 |
| HEY1 | TGFBR2 | TMEM171 | KLK11 | CFDP1 |
| SOX17 | KLF2 | HIST1H1C | CLRN3 | TMSB10 |
| PTRF | MFGE8 | CLDN4 | ATP2A3 | RPS25 |
| EMP2 | APP | C2orf88 | NDUFB4 | RPS24 |
| RPL12 | PODXL | TRIM31 | COX7A2 | AQP8 |
| NKX2-3 | TIMP3 | MYO15B | S100A14 | KRT18 |
| SYNPO | HLA-A | ETHE1 | EIF5 | RPL30 |
| SOCS3 | BCAM | RPL18 | PRDX2 | FAM177B |
| NRN1 | SLC2A3 | RPS25 | CYB5A | RPL18 |
| RPLP0 | DNAJA1 | S100A6 | C15orf48 | LGALS4 |
| IFIT3 | MCAM | RETSAT | CLDN7 | RPL7A |
| CDH5 | SERPING1 | RPS20 | CHPT1 | SPATS2L |
| HLA-A | CD74 | CES2 | CKB | KRT8 |
| IER2 | SYNPO | CA1 | COX7C | PRR15L |
| TSC22D1 | ISYNA1 | RPL24 | SLC25A6 | PRSS3 |
| RND1 | COX7A1 | RPL3 | MAP7 | DHRS9 |
| KANK3 | LHFP | RPL28 | VSNL1 | PIGR |
| THBD | SRGN | C11orf86 | MT-ND4 | NEAT1 |

TABLE 1A-continued

| | | | | |
|---|---|---|---|---|
| NQO1 | THBD | SPINT2 | BUB3 | PLA2G10 |
| C8orf4 | EFNA1 | RPL30 | KRT19 | EEF1D |
| LDB2 | MMRN2 | RPLP2 | CCDC28B | RPL27 |
| ARHGAP29 | HLA-DPA1 | CYSTM1 | SRI | SCNN1A |
| C10orf10 | FAM107A | SLC26A2 | SMIM22 | FABP1 |
| EHD4 | IRF1 | MT-CO1 | FBP1 | RPL28 |
| HSPB1 | CLIC2 | RPSA | H1F0 | SMIM22 |
| HLA-DRB5 | PTRF | COL17A1 | ALDH2 | FAM101A |
| GABARAPL2 | CYGB | S100A10 | PAFAH1B3 | FTL |
| NOTCH4 | RPLP0 | LINC00035 | MAOB | FAU |
| GPR116 | PPA1 | MYH14 | HLA-DRB5 | HIST1H1C |
| HEG1 | MYCT1 | EPCAM | HLA-DMA | PARM1 |
| CLIC2 | H3F3B | RPS24 | ACTG1 | CEACAM6 |
| SRGN | B2M | C15orf48 | MIEN1 | CEACAM7 |
| FABP5 | SPINT2 | NACA | MT-CYB | GSN |
| NFIB | GPX3 | HSD17B2 | HOXB6 | ARL14 |
| AIF1L | TSPAN7 | SLC17A4 | TIMP1 | MISP |
| ADAM15 | COL18A1 | TMSB10 | GPX2 | CA2 |
| NOV | FLT1 | RPL36 | ZFHX3 | GUCA2A |
| C9orf3 | SOD3 | EEF1D | CD9 | MLPH |
| S100A16 | EIF1 | SLC44A4 | MALAT1 | CEACAM1 |
| SH3BP5 | COL1A2 | CDKN2B-S1 | RPL37A | SPINT2 |
| HLA-B | PPAP2B | LGALS4 | NCK2 | YBX1 |
| B2M | TCF4 | IFI27 | TAS1R3 | RPL36 |
| PIK3R3 | SERTAD1 | PPDPF | PIK3CG | SCGB2A1 |
| PLLP | STOM | BTNL3 | RBM38 | C15orf48 |
| C10orf54 | C16orf80 | NPM1 | LDHA | NAAA |
| SPARC | HLA-DMA | BTNL8 | COX5B | MT-ND2 |
| CFI | APOLD1 | ELF3 | ESPN | RPSA |
| GAS6 | NRN1 | HN1 | ESYT2 | CLDN8 |
| PPAP2A | HES4 | POLD4 | PSMD9 | ASS1 |
| LY6E | SOX17 | ST14 | ANXA2 | S100A6 |
| SERTAD1 | LGALS1 | SLC6A8 | MT-ND1 | POLD4 |
| TIE1 | ZFP36L1 | CLTB | TXN | MXD1 |
| MYCT1 | REM1 | LAMB3 | STMN1 | PFDN5 |
| TMEM109 | ID1 | SLC51A | DEGS2 | SLC25A6 |
| CD93 | NPDC1 | CLDN23 | PMM1 | MYO15B |
| RPS2 | AC011526.1 | CDHR2 | HOXA11-AS | MLLT3 |
| GIMAP6 | CFI | TMEM45B | IP6K2 | TP53INP2 |
| ID1 | CYB5R3 | TMEM37 | TMEM176B | RPL18A |
| TAGLN2 | EFHD1 | CHP2 | ZNHIT3 | UBA52 |
| ZFP36 | OAZ2 | GPRC5A | ATP5B | MT-CO2 |
| S100A13 | CD34 | HPGD | IFITM2 | ST3GAL4 |
| CYBA | NES | CKB | RPL36 | ITM2C |
| TACC1 | SRP14 | FCGBP | HMX2 | ATP5G2 |
| LAP3 | HHEX | AK1 | TSC22D3 | LMO7 |
| CFLAR | TMEM204 | ASS1 | ACADSB | RPL34 |
| HSPA1A | C1QTNF1 | PRR15 | S100A4 | AGR2 |
| LMCD1 | GABARAPL2 | ITM2C | RHEB | AC009133.21 |
| TINAGL1 | COL3A1 | TMPRSS2 | SPINT1 | SYTL2 |
| DLL4 | MYH9 | YBX1 | IMP4 | RAB27A |
| TNFRSF4 | DNAJB1 | S100A11 | LSMD1 | RPL37 |
| PTP4A3 | PHGR1 | PRR13 | ATPIF1 | CKB |
| KDR | LGALS4 | KRT18 | ADH5 | VILL |
| SPTBN1 | ITGA7 | DHRS11 | H2AFJ | CA4 |
| HLX | HEY1 | HNRNPA1 | IGFBP2 | LINC01133 |
| ROBO4 | FAM222B | GNA11 | RAB4A | RP11-94O2.2 |
| PTPRB | HSPG2 | NDRG1 | SPATS2L | S100A14 |
| IFI6 | GPR116 | CCL15 | AFAP1L2 | MEP1A |
| FAM110D | TACC1 | RPL27 | WFDC2 | CYBA |
| ATOH8 | BBX | SPINT1 | DNAJB1 | MT-CO3 |
| APLNR | SH3BP5 | DEFB1 | SKAP2 | PKIB |
| LPAR6 | C10orf10 | CFDP1 | HLA-DQB1 | KCNK1 |
| PRMT1 | EHD2 | DHRS9 | ANXA5 | MAST2 |
| PALMD | TNS1 | PFDN5 | RPL31 | EIF4A1 |
| COL15A1 | FAM213A | PTPRH | PBXIP1 | CLDN23 |
| SEMA3G | LCN6 | FLNB | COL27A1 | HPGD |
| NDUFA12 | PPP1R14A | ACAA2 | MT-ND5 | SMIM5 |
| RGS3 | FAM110D | PRSS8 | RAB25 | MALAT1 |
| TMEM255B | RPLP1 | RPS11 | FRAT2 | SPINT1 |
| CHCHD10 | SDCBP | RPL37 | AOC1 | MT-ATP6 |
| COX4I1 | SOX7 | C10orf99 | GSTP1 | PRSS8 |
| CD151 | GEM | RHOC | MT-CO2 | CLCA4 |
| ARL2 | EMP2 | RPL34 | RTN4 | MT-ND4 |
| SLC25A6 | LMO2 | EIF4A1 | TUBA1A | RPS3A |
| ID3 | NEAT1 | CDA | RPS27L | EEF2 |
| SCARF1 | TIE1 | BLOC1S1 | CCDC14 | ST14 |
| GALNT18 | IGFBP6 | HHLA2 | FUT3 | MUC12 |
| LIFR | COL4A1 | AHCYL2 | TP53I3 | HIST1H2AC |
| SWAP70 | APLNR | LDHB | MCL1 | RHOC |

TABLE 1A-continued

|  |  |  |  |  |
|---|---|---|---|---|
| RPL29 | SEPP1 | GDPD3 | TSPO | RP11-665N17.4 |
| SEC14L1 | PLK2 | HRCT1 | ZFP36L1 | RPL37A |
| RPS19 | HYAL2 | MT-CO2 | CMTM8 | MT-ND1 |
| RPL10A | RPS29 | FAM3D | PRDX5 | TSPAN3 |
| HLA-DMA | RNASET2 | ATP5G2 | HES6 | IGJ |
| RRAS | TAGLN2 | FAM132A | PTMA | RPS11 |
| LCN6 | SLCO2A1 | SLC9A3R1 | NDUFB11 | EIF1 |
| WARS | PRIG | PKP3 | CHN2 | KRT19 |
| EPHX1 | KRT8 | STAP2 | TMEM63A | HSP90AB1 |
| DUSP6 | RPS2 | SLC22A18 | RASSF7 | BEST2 |
| JUNB | CXorf36 | ESPN | VIL1 | RASEF |
| PRKCDBP | LRRC32 | MT-CO3 | MT-ATP6 | AOC1 |
| RPL18 | RHOA | VIM | CERS6 | SPDEF |
| RALB | GIMAP1 | TJP3 | ID3 | LGALS9C |
| SORBS2 | LIFR | PCK1 | CDH17 | NPM1 |
| EIF1 | HDAC7 | CTSA | TMSB10 | PCK1 |
| ALPL | TSPAN4 | BSG | ARPC1B | PABPC1 |
| FOS | C10orf54 | ARL14 | IFI6 | NLN |
| RPS5 | CYBA | TSPAN8 | FAM200B | SEPP1 |
| TMEM173 | IFIT3 | ENTPD8 | CDX2 | VIPR1 |
| CALM1 | HEG1 | CDH17 | HOXB9 | HNRNPA1 |
| KLF2 | GIMAP5 | MT-ND5 | COX6A1 | GPRIN2 |
| VWA1 | NQO1 | CDKN2B | AP1M2 | BTNL3 |
| ADCY4 | IL3RA | PEX26 | RNF186 | QSOX1 |
| NES | PTPRB | SLC25A6 | RPS21 | SMIM14 |
| ETS2 | KANK3 | SLC25A5 | SHC1 | BTNL8 |
| MGAT1 | IFITM1 | GGT6 | CD14 | ITLN1 |
| SERPING1 | NKX2-3 | LSR | DPP7 | NEDD4L |
| SNX3 | TMEM176B | NLN | LYZ | GPR153 |
| COX7A1 | GPRC5B | RPL18A | SEPP1 | TDP2 |
| ACTN4 | TCF21 | APOBEC3B | PERP | CYSTM1 |
| CARHSP1 | NDUFA12 | PABPC1 | RNF24 | SH3BGRL3 |
| ERG | ARID5B | EIF1 | TBC1D2B | CDHR2 |
| RPS4X | RAC1 | IL32 | MACROD1 | PTPRF |
| RAC1 | TNFSF10 | SULT1A1 | MYO10 | ISG20 |
| CYB5R3 | EPHX1 | LMO7 | RPS11 | LSR |
| LRRC32 | PRKCDBP | CGN | IFITM3 | FBXO32 |
| IMP3 | ITGA1 | RPL37A | EPHB3 | OASL |
| RNASET2 | PLAU | S100A14 | ASMTL | RPL23 |
| BTNL9 | FAM162B | LLGL2 | YPEL5 | CYP3A5 |
| RPL13 | DUSP1 | IFITM3 | H2AFY2 | SLC26A3 |
| YBX3 | ACTN4 | MVP | STK38 | PRAP1 |
| HPCAL1 | APOL3 | CLCN2 | JUNB | MT-ND5 |
| RPS18 | COL6A2 | TPRN | PPAP2A | SLC44A4 |
| ELK3 | ROBO4 | ACOX1 | LACTB2 | KCNK5 |
| KLF4 | UBC | AKR1B10 | TAGLN2 | RASSF7 |
| PVRL2 | IGJ | CA12 | SMARCC1 | H2AFJ |
| RHOC | WNT6 | MT-ATP6 | GAPDH | CA1 |
| SNHG7 | TMEM255B | MPST | AC005355.2 | STARD10 |
| CTNNBIP1 | COL15A1 | TSPAN3 | TMPRSS2 | CDH1 |
| RPL28 | ADAMTS1 | FAU | C7orf55 | STAP2 |
| RASIP1 | RPL10 | PARK7 | TSPAN13 | STX19 |
| HYAL1 | PTMA | C1orf106 | SNX3 | PLAUR |

TABLE 1B

| Absorptive_TA_1 | Secretory_TA | Absorptive_TA_2 | Cycling_A | Goblet_1 |
|---|---|---|---|---|
| TXN | MT-ND1 | FABP1 | EPCAM | TFF3 |
| GPX2 | B2M | SELENBP1 | LGALS4 | KLK1 |
| MGST1 | TFF3 | CA2 | MGST1 | ITLN1 |
| EPCAM | MT-ATP6 | LGALS4 | AGR2 | FCGBP |
| AGR2 | PRDX5 | C15orf48 | C15orf48 | AGR2 |
| C15orf48 | MUC2 | S100A14 | GPX2 | CLCA1 |
| PPP1R1B | FCGBP | PHGR1 | KRT8 | LRRC26 |
| LGALS4 | KLK1 | KRT19 | CLDN7 | RETNLB |
| HMGCS2 | RPL36 | ETHE1 | CLDN3 | MUC2 |
| TSPAN8 | AGR2 | FXYD3 | PIGR | WFDC2 |
| C10orf99 | PIGR | LGALS3 | HLA-DPA1 | SPINK1 |
| UGT2B17 | ITLN1 | UQCRQ | PHGR1 | SPINK4 |
| ATP5B | GPX2 | PIGR | FXYD3 | KRT18 |
| CLDN7 | ATP5G1 | COX5B | TXN | REP15 |
| S100A14 | MT-ND4 | MT-ND1 | ARHGDIB | ZG16 |
| PHGR1 | EPCAM | MT-CO2 | VIM | SERPINA1 |
| ELF3 | LGALS4 | COX4I1 | ELF3 | TPSG1 |
| PIGR | ZG16 | C10orf99 | HLA-DPB1 | LGALS4 |
| CDX1 | MT1G | MT-CO3 | BST2 | ST6GALNAC1 |

TABLE 1B-continued

| | | | | |
|---|---|---|---|---|
| MT1G | CLDN3 | MT-ND4 | TUBB4B | FAM3D |
| CLDN3 | FABP1 | MT-ATP6 | CD74 | KRT8 |
| FABP1 | PHGR1 | MT1G | KRT18 | EPCAM |
| FXYD3 | KRT8 | TST | S100A14 | STARD10 |
| KRT8 | CLCA1 | ATP5G3 | MT1G | PHGR1 |
| COX5A | COX4I1 | KRT8 | ARPC1B | SMIM22 |
| ATP5G3 | CLDN7 | CA1 | ATP5G1 | FXYD3 |
| KRT18 | H3F3B | TMEM54 | HMGCS2 | GMDS |
| PRDX5 | FXYD3 | CHCHD10 | KRTCAP3 | HEPACAM2 |
| CYC1 | MT-ND2 | ATP5G1 | CD9 | RNASE1 |
| RPLP0 | RPS14 | SLC26A2 | HLA-DRB1 | KRT19 |
| ATP5G1 | MALAT1 | TXN | PPP1R1B | MT-ND1 |
| MT1E | IGJ | B2M | CLDN4 | CLDN3 |
| SLC25A5 | KRT18 | CLDN7 | TSPAN8 | VSIG2 |
| TIMP1 | CLDN4 | CES2 | HLA-DRA | C15orf48 |
| LEFTY1 | RPL37A | COX7A2 | SUCLG1 | PIGR |
| FAM3D | RPS29 | UQCR10 | CDX1 | CLDN7 |
| UQCRH | MT-CO2 | COX6C | NUPR1 | ANXA13 |
| KLF5 | RPS18 | COX6B1 | FAM3D | SPDEF |
| CHCHD10 | C15orf48 | HMGCS2 | CYC1 | MT-CO3 |
| CLDN4 | MT-CO3 | AKR1C3 | FABP1 | TMEM141 |
| LGALS3 | TSPAN8 | CKB | PRDX5 | ANG |
| SUCLG2 | EIF1 | EPCAM | SMIM22 | COX6C |
| CD9 | SPINK1 | HSD11B2 | LGALS1 | ELF3 |
| TSPO | RPL35 | AGR2 | TMEM141 | S100A14 |
| KRT19 | SMIM22 | SMIM22 | TMEM54 | HMGCS2 |
| SMIM22 | SPINK4 | MT-ND5 | CKB | BEST2 |
| C19orf33 | STARD10 | AMN | CST3 | MB |
| NXPE4 | FAM3D | MGST1 | NDUFAB1 | FABP1 |
| B2M | MT-CYB | MT-CYB | C10orf99 | CREB3L1 |
| SUCLG1 | MT-ND3 | COX8A | ITM2C | RPL36 |
| ATP5A1 | RPS21 | C19orf33 | TMSB4X | GPX2 |
| ATP5F1 | CD74 | TMEM141 | ARPC2 | CLDN4 |
| GAPDH | HLA-DPA1 | COX6A1 | HLA-DRB5 | S100A6 |
| COX4I1 | HLA-C | AKR7A3 | SPINK1 | RP11-234B24.2 |
| COX5B | WFDC2 | MT1E | PLP2 | URAD |
| RP11-519G16.5 | ATP5I | GOLM1 | SPINT2 | TCEA3 |
| TMEM54 | TMEM141 | AKR1B10 | HLA-DMA | TSPAN8 |
| ETHE1 | ELF3 | PRSS3 | HLA-DMB | MT1G |
| UQCRC2 | RETNLB | CLDN3 | MT1E | TSPAN1 |
| CA2 | TIMP1 | CISD3 | COX5A | TMEM61 |
| TMEM141 | HMGCS2 | ATP5D | ATP5B | RAP1GAP |
| HLA-E | RPS3 | MT-CO1 | ECH1 | C10orf99 |
| CDX2 | PPP1R1B | MT-ND2 | TUBA1A | REG4 |
| COX6C | RPS15 | CHP2 | IGJ | PRDX5 |
| C1QBP | TMEM54 | H3F3B | FXYD5 | MT-ND4 |
| RPSA | KRT19 | KRT18 | SELENBP1 | CCL15 |
| KRTCAP3 | MT1E | NDUFA1 | ETFB | UQCRH |
| OLFM4 | ZFP36 | VSIG2 | HLA-DQB1 | H3F3B |
| UQCRFS1 | RPL12 | TIMP1 | SRI | NANS |
| S100A10 | KRTCAP3 | COX7C | KRT19 | NPDC1 |
| ATP5C1 | COX5B | FAM3D | KLF5 | MT-ATP6 |
| H3F3B | IGLL5 | PDE4C | IGLL5 | MT-CYB |
| GSN | RPS9 | EIF1 | LGALS3 | MT-CO2 |
| MRPL12 | MGST1 | COX5A | HADH | IGJ |
| CD74 | C10orf99 | LGALS1 | CDX2 | MT-ND2 |
| CKMT1B | RPL8 | CD74 | UQCRC1 | IGFBP2 |
| SLC25A6 | ITM2B | TSPAN1 | SMAGP | SPINT2 |
| ARHGDIB | RPLP2 | CLDN4 | TIMP1 | EIF1 |
| RPS2 | CHCHD10 | TSPAN8 | ACTB | C2orf82 |
| MPC2 | UBC | SLC22A18AS | LY6E | COX5A |
| SELENBP1 | HLA-DRB1 | CYC1 | COA3 | IFI27 |
| RPS24 | COX6B1 | MT-ND3 | COTL1 | HES6 |
| RPS18 | ATP5D | ATPIF1 | IGFBP2 | COX5B |
| MAOA | NDUFB11 | UQCR11 | ACADS | TIMP1 |
| RPL8 | C19orf33 | ELF3 | PLA2G2A | CDC42EP5 |
| CKB | S100A14 | SDCBP2 | STARD10 | FOXA3 |
| MPST | HLA-DRA | ATP5I | CES2 | S100A4 |
| IGJ | RPS5 | IGJ | TST | PPDPF |
| TRABD2A | COX5A | CDX1 | LEFTY1 | ZG16B |
| ATP5O | RPS12 | TSPO | CKMT1B | MT-CO1 |
| RPS6 | RPL13 | SRI | ATP5G3 | IL1R2 |
| HINT1 | ARHGDIB | UQCRC1 | CISD3 | TMEM176B |
| SPINK1 | C2orf82 | MGST3 | ISG15 | HSD11B2 |
| HLA-DPA1 | RPS8 | S100A6 | RARRES2 | CD9 |
| ECH1 | RPS2 | MRPL41 | MPC2 | BTG1 |
| PHB | TCEA3 | TCEA3 | HLA-E | UQCR10 |
| CES2 | HLA-DPB1 | NDUFB9 | ECHS1 | IFT172 |
| AKR1C3 | LEFTY1 | COX7B | CKMT1A | COX6B1 |
| CKMT1A | ACTB | ZFP36 | UQCRQ | TPM1 |

TABLE 1B-continued

| | | | | |
|---|---|---|---|---|
| PLA2G2A | LRRC26 | ATP5J | GGH | ZFP36 |
| RPL5 | MUC5B | ATP5B | TSPO | SERF2 |
| UQCR10 | NUPR1 | SLC39A5 | MPST | TSTA3 |
| IGFBP2 | MT-ND5 | KRTCAP3 | ATP5F1 | MGST1 |
| COX7C | CKB | NXPE4 | COX4I1 | TSPAN13 |
| COX6B1 | UQCR10 | GPT | ATPIF1 | C19orf33 |
| LCN2 | SELENBP1 | MS4A12 | CYCS | MT-ND3 |
| RPL7A | RPL27A | ANXA5 | UQCRH | ATP5G3 |
| ZFP36 | MT-CO1 | ACADS | ZFP36 | FAM195A |
| RPS8 | UQCRQ | SLPI | MACROD1 | ITM2B |
| CMBL | STRA13 | PXMP2 | COX5B | RAB25 |
| FAM84A | RPL7A | NDUFB2 | STAP2 | FTL |
| PEBP1 | RPL32 | FAM162A | RPLP0 | CDX1 |
| S100A4 | RPS19 | DBI | RP11-519G16.5 | STAP2 |
| STARD10 | CISD3 | ARHGDIB | COX6C | DNAJA1 |
| HLA-C | TPSG1 | PPP1R14D | RGS10 | TMEM54 |
| IGFBP7 | AMN | GPX2 | SLC44A4 | FABP2 |
| PPP1R14D | URAD | UQCRH | NANS | ATP5I |
| HLA-DPB1 | MT2A | TMEM45B | NDUFV1 | CHCHD10 |
| PDE4C | RPLP1 | CYSTM1 | RPS18 | ARPC1B |
| RPS3A | TSPO | MYO1A | B2M | TSTD1 |
| PCK1 | COX6C | CDHR5 | NBL1 | UBC |
| GSTA1 | RPL18 | SLC44A4 | ALDH2 | PPP1R1B |
| RPL26 | DUSP1 | DHRS11 | GNAI2 | DDX5 |
| STAP2 | HERPUD1 | ADIRF | C1QBP | ACTB |
| RPS3 | RPS6 | PPP1R1B | S100A4 | MLPH |
| RPL10A | TMSB10 | CKMT1B | MLEC | ETHE1 |
| SEPP1 | RPSA | MT1M | SUCLG2 | SH3BGRL3 |
| ATP5I | ARPC1B | HLA-C | MINOS1 | KIAA1324 |
| FAM162A | DDX5 | ITM2B | S100A10 | KRT20 |
| UQCRC1 | ATP5G3 | PKIB | OAZ1 | HSPA1A |
| TCEA3 | UQCRH | USMG5 | PSAP | STRA13 |
| CHP2 | NDUFA1 | FAM195A | ATP5I | IFITM2 |
| RPL31 | ANXA5 | FCGBP | TIMM13 | CKB |
| ATP5D | TIMM13 | IFITM3 | SEPP1 | AC011523.2 |
| RPL37A | HLA-B | MPC2 | HSPD1 | HLA-C |
| SRI | COX8A | S100A10 | RPL36 | UGT2B17 |
| HLA-DRB1 | CDX1 | MISP | UQCRFS1 | ENTPD8 |
| SELK | HLA-E | STAP2 | ATP5A1 | COX4I1 |
| TSPAN1 | SEPP1 | MGAT4B | ANXA5 | CST3 |
| RPS23 | CDC42EP5 | SULT1A1 | HLA-C | RGCC |
| SOCS3 | SNX3 | PYCARD | S100A6 | B2M |
| RAB25 | CYC1 | ATP1A1 | SFN | RAB15 |
| MT1X | HLA-DRB5 | DNAJA1 | ATP5O | CD74 |
| COX6A1 | MRPL12 | ZG16 | AP1M2 | NDUFA1 |
| NACA | HLA-DMA | ASL | MT2A | MT1E |
| RPS29 | IFITM2 | NPM1 | RAC2 | ERI3 |
| GMDS | RPL28 | MPST | RGCC | TST |
| COA3 | RPL38 | MUC4 | GSN | ERN2 |
| UBC | RPS11 | UBC | STRA13 | TNNC2 |
| RPL36 | DNAJA1 | SLC26A3 | ATP5J2 | NEURL1 |
| SPINT2 | HLA-A | SLC51B | CA2 | GSN |
| ITM2C | RPL37 | URAD | PEBP1 | LGALS3 |
| IFITM3 | COX7C | HLA-B | TYMP | CAMK2N1 |
| RPL13A | ETHE1 | S100A4 | PRDX2 | SMAGP |
| DNPH1 | HLA-DQB1 | HLA-E | H3F3B | IFITM3 |
| ISG15 | MZT2B | CDH17 | SQRDL | TSPO |
| SLC25A3 | LITAF | CKMT1A | GJB1 | CAPN9 |
| UGT2A3 | ISG15 | ANPEP | PBK | MALAT1 |
| SLC39A5 | TRABD2A | SLC25A5 | RPL37A | CDX2 |
| RPL12 | MZT2A | ABCC3 | UCP2 | TMEM176A |
| RPL29 | TSC22D3 | UQCRFS1 | TPM4 | IGLL5 |
| FAM195A | TSTD1 | IGLL5 | CHCHD10 | SLC44A4 |
| URAD | ARPC2 | DUSP1 | TMEM98 | TTC39A |
| NDUFA10 | ECI1 | TRMT112 | ADIRF | COX7B |
| SQRDL | ETFB | IFITM2 | DDT | OAZ1 |
| HSPD1 | MPC2 | SHD | AKR1B10 | COX8A |
| DDT | IGFBP2 | JUNB | S100A16 | JUNB |
| IFITM2 | PLA2G2A | TSC22D3 | PLEKHJ1 | UQCRQ |
| NUPR1 | TST | ATP5E | LGALS3BP | MARCKSL1 |
| TPI1 | GSTP1 | TMSB10 | ARPC3 | SCNN1A |
| NOX1 | HIST1H4C | TXNDC17 | NOX1 | LYPD8 |
| ACADS | SDCBP | HLA-DRA | EEF1B2 | COX7A2 |
| ATPIF1 | DNPH1 | SQRDL | FAM162A | CTD-2547H18.1 |
| TSC22D3 | RPL31 | CIRBP | RPS14 | RASD1 |
| TMSB10 | SOCS3 | SERINC2 | GGCT | CIRBP |
| RPS27A | S100A4 | DDT | RPS8 | KRTCAP3 |
| ANXA5 | PRDX2 | LDHB | TCEA3 | H1F0 |
| PRSS3 | RP11-357H14.17 | NDUFB7 | GMDS | NXPE4 |
| TFF3 | COX7B | CMBL | RPS6 | RPS24 |

TABLE 1B-continued

| | | | | |
|---|---|---|---|---|
| GOLM1 | HSPA1A | IFI27 | ETHE1 | RPL37A |
| RPS15A | RARRES2 | AOC1 | LAMTOR4 | PCBD1 |
| HLA-B | CLUH | RAB25 | MT-ND1 | YPEL5 |
| MACROD1 | RPLP0 | KLF5 | RPL8 | HLA-E |
| PXMP2 | MPST | PCK1 | SH3BGRL3 | MUC1 |
| TST | SPINT2 | SPINT2 | HLA-B | ITM2C |
| COX7A2 | TXN | TCEB2 | IMPDH2 | ATP5G1 |
| AP1M2 | GSN | NDUFA2 | TUFM | KCNMA1 |
| TUBB | UQCRC1 | C2orf82 | PXMP2 | PRR15L |
| IGLL5 | CES2 | HERPUD1 | NDUFA10 | RPL26 |
| GJB1 | RPL29 | S100A16 | LYZ | HLA-DRB1 |
| EIF1 | ATPIF1 | GSN | PHB | CYC1 |
| ARPC1B | ST6GALNAC1 | HNRNPA1 | VIL1 | AGR3 |
| CISD3 | MGAT4B | BCL2L15 | NDUFA1 | FFAR4 |
| PKIB | MLEC | LAPTM4A | ACTR3 | AMN |
| GPR160 | REP15 | UGT2B17 | HINT1 | RPS29 |
| MRPS33 | IFI27 | STARD10 | RAB25 | SCGB2A1 |
| DCTPP1 | FBL | EID1 | IRF8 | KLF5 |
| AKR1B1 | DNAJB1 | NDUFB3 | CHP2 | DUSP1 |
| CDH17 | UQCR11 | MRPL12 | AKR1B1 | DNAJC12 |
| AKR7A3 | RNASE1 | ESRRA | FCGRT | MUC4 |
| HSPA1A | NDUFS5 | MT2A | RPS3 | ATP5J2 |
| RPS14 | IMPA2 | PNRC1 | RPL26 | RAB27A |
| PLP2 | DDT | NDUFV1 | RPL10A | COX7C |
| RGS10 | MYL12A | GJB1 | HOXB7 | IL32 |
| MT-CYB | RHOA | MYO1D | MAOA | PSAP |
| TKT | RPL11 | NAP1L1 | AMN | RP11-357H14.17 |
| MDH2 | RPL10A | VIL1 | TSPAN1 | HLA-DRA |
| ITM2B | NDUFB7 | DDX5 | MT1M | HSPA8 |
| HLA-DRA | RAB25 | TMC4 | MRPL12 | MUC5B |
| EEF1B2 | SUCLG1 | NDUFS7 | ITM2B | PLA2G10 |
| DUSP1 | FAM195A | SOCS3 | NPC2 | MPC2 |
| PSMB9 | MUC4 | MAOA | NXPE4 | DUSP2 |
| AMN | SFN | KRT20 | UQCRC2 | TRABD2A |
| AKR1B10 | MT1X | PLCD3 | SDC1 | DYRK4 |
| FBL | GCHFR | SFN | ACAT1 | KLK15 |
| NDUFAB1 | MUC1 | ROMO1 | IFITM2 | LXN |
| DBI | FKBP1A | SSR2 | RPS21 | NDUFB4 |
| MTCH2 | RAB7A | EEF1D | HERPUDI | C12orf57 |
| RPL14 | GMDS | ITM2C | RPL13 | SLC12A2 |
| RPL3 | TMEM176B | PADI2 | TPM1 | DCTPP1 |
| RPL11 | FOS | NDUFB1 | SH3YL1 | TMSB10 |
| RPS9 | TRPM4 | DPP7 | HSD17B11 | GADD45B |

| Stem_cells | Enteroendocrine | Glial_cells | Inflammatory_fibroblasts | Fibroblast_pericytes |
|---|---|---|---|---|
| B2M | PCSK1N | CRYAB | VCAM1 | RGS5 |
| LEFTY1 | CRYBA2 | ALDH1A1 | NNMT | BGN |
| TMSB4X | SCGN | GPM6B | LUM | CSRP2 |
| ASCL2 | CHGA | PLP1 | SOD2 | NDUFA4L2 |
| MT-ND4 | PYY | SPP1 | CCL2 | MYL9 |
| LGALS4 | SCG5 | S100B | TDO2 | MFGE8 |
| SMOC2 | GCG | FXYD1 | COL3A1 | TINAGL1 |
| PRDX5 | FEV | PRNP | C1S | TSC22D1 |
| RGMB | MS4A8 | PMP22 | MFAP4 | COX4I2 |
| MT-CYB | TTR | CLU | C1R | FRZB |
| FXYD3 | CACNA1A | TUBA1A | MMP2 | ADIRF |
| GPX2 | PRDX5 | CD9 | CTSK | TPPP3 |
| CDCA7 | HLA-C | MPZ | PDPN | HIGD1B |
| MT-CO3 | HOXB9 | SPARC | FBLN1 | COL18A1 |
| TSPAN8 | FXYD3 | NRXN1 | DCN | GPX3 |
| PHGR1 | STARD10 | DKK3 | CTSC | SOD3 |
| MT-ND2 | RAB26 | CYR61 | RARRES2 | IGFBP7 |
| MT-ND1 | B2M | LGI4 | GPX3 | NET1 |
| EPCAM | LGALS4 | MATN2 | APOE | CALD1 |
| ELF3 | PHGR1 | TUBB2B | SELM | 4-Sep |
| PIGR | RAB3B | ANXA2 | CALD1 | TPM2 |
| HLA-C | KRT18 | PMEPA1 | IFITM3 | SERPINI1 |
| MT-ATP6 | MARCKSL1 | PCSK2 | TMEM176A | NOTCH3 |
| MT-ND3 | MDK | PEBP1 | CYGB | PGF |
| KRT8 | SLC29A4 | GFRA3 | DYNLT1 | HES4 |
| MT-CO1 | KRT8 | CAPS | COL1A2 | ACTA2 |
| PPP1R1B | EPCAM | CALM2 | ADAMDEC1 | MGP |
| EPHB3 | ELF3 | MYOT | WARS | ISYNA1 |
| SMIM22 | SST | L1CAM | TMEM176B | PDGFRB |
| KRT18 | HLA-B | S100A1 | COL6A2 | SPARC |
| HSPB1 | TMSB4X | COMT | CFD | FAM162B |
| CLDN7 | ARX | CD59 | GGT5 | HSPB1 |
| CLDN4 | VIM | PLEKHB1 | NDN | H2AFJ |

TABLE 1B-continued

| | | | | |
|---|---|---|---|---|
| RPS18 | CLDN3 | TIMP3 | FOXF1 | BCAM |
| C15orf48 | HLA-DPA1 | CDH19 | NINJ1 | PLXDC1 |
| HMGCS2 | C15orf48 | SMIM5 | PLAU | CD36 |
| HLA-B | FABP1 | TSPAN11 | LAP3 | CAV1 |
| RPS24 | RPL37A | NTM | EMILIN1 | DSTN |
| RPS21 | MLXIPL | C8orf4 | IGFBP7 | PRSS23 |
| CLDN3 | COX6C | CNN3 | STMN2 | REM1 |
| RPL36 | C19orf77 | MAL | CXCL14 | LHFP |
| SPINK1 | HLA-DRA | FIBIN | EPSTI1 | COL4A2 |
| RPL37 | NEUROD1 | FBLN2 | HAPLN3 | RGS16 |
| MT-CO2 | CPE | CCL2 | CD63 | LURAP1L |
| RPS6 | SMIM22 | CBR1 | GBP1 | TPM1 |
| SLC12A2 | TSPAN1 | FGFBP2 | SPARC | TAGLN |
| RPL37A | HLA-DRB1 | ARHGAP15 | COL1A1 | EGR1 |
| S100A14 | TFF3 | LGALS1 | PKIG | IFITM3 |
| RPL31 | IGJ | JUN | LGALS1 | HLA-C |
| RPL12 | HLA-DPB1 | PRKCDBP | SERPING1 | EHD2 |
| MT1G | CLDN4 | SNCA | CFH | MEST |
| BST2 | ITM2B | RPS6 | DMKN | PKIG |
| ACTB | SEPP1 | IGFBP7 | SERPINF1 | LGALS1 |
| MARCKSL1 | IFITM3 | NDRG2 | PAQR5 | STOM |
| PDZK1IP1 | RTN1 | COL9A3 | THY1 | A2M |
| MGST1 | SPINK1 | ST6GALNAC2 | SOD3 | STEAP4 |
| RNF186 | LDHA | TTR | COL6A1 | PTGIR |
| GNB2L1 | VWA5B2 | TMEM176B | CNOT4 | RPLP2 |
| RPS3 | CD74 | RPS2 | LINC01082 | PTK2 |
| RPLP0 | RPL36 | FOS | TNFRSF1A | RBPMS |
| ETS2 | SOX4 | AP1S2 | PMP22 | EPS8 |
| HLA-A | SCT | WISP2 | GSTT1 | PPP1R14A |
| CD63 | BEX2 | HES1 | SGCE | SRGN |
| CST3 | ISL1 | VIM | TPM2 | COL3A1 |
| ARHGDIB | ANXA5 | RGS16 | A2M | GEM |
| FAM3D | GSN | FEZ1 | TFPI | CRIP2 |
| MT-ND5 | RPS29 | SORBS2 | CLEC11A | ZFP36L1 |
| CKB | S100A14 | FCGR2B | FTH1 | ARID5A |
| RPS4X | HOXB8 | IFITM3 | MFGE8 | ARVCF |
| GSN | CHGB | RP4-792G4.2 | SPON2 | EPHX1 |
| C10orf99 | GUCY2C | RHOB | GBP4 | HLA-A |
| FABP1 | FXYD5 | TMEM176A | C2 | ADAMTS1 |
| ALDH1B1 | CLDN7 | ART3 | SFTA1P | PRKCDBP |
| MT1E | HLA-DMA | EGR1 | LAPTM4A | MAP3K7CL |
| TRABD2A | HLA-DRB5 | RPL8 | TIMP1 | NDUFAF4 |
| KLK1 | KRT19 | TUBB2A | CDH11 | C1R |
| SELENBP1 | PRDX2 | PDLIM4 | LY6E | CALM2 |
| STARD10 | SPINT2 | IL11RA | PLAT | C8orf4 |
| AGR2 | EIF1 | RPS19 | CEBPB | SDC2 |
| RPL26 | ETV1 | ANXA5 | APOL1 | TCF21 |
| SPINT2 | HLA-E | SOCS3 | PROCR | ESAM |
| ARPC1B | QPCT | RPS18 | TMEM205 | HEYL |
| KRT19 | KIF12 | PHLDA3 | GADD45G | KNOP1 |
| RPS5 | DDC | NRN1 | EVA1A | EFHD1 |
| RPS2 | LITAF | TSPAN15 | ICAM1 | SERPING1 |
| RPL13 | TMEM141 | MIA | FHL2 | RCAN2 |
| TFF3 | TMEM61 | COL18A1 | KLF6 | C1QTNF1 |
| S100A11 | MT-ND3 | RPLP1 | LGALS3BP | RBPMS2 |
| MYL6 | COX5A | SPARCL1 | RCN1 | SERPINH1 |
| AQP1 | IGLL5 | TPT1 | BST2 | NDRG2 |
| FERMT1 | LY6E | C1orf198 | CCL8 | FXYD6 |
| MT-ND4L | MPC2 | SCCPDH | GALNT11 | COL6A1 |
| RABAC1 | IFITM2 | S100A10 | IGFBP3 | GPRC5C |
| HLA-DPA1 | UCP2 | S100A4 | ECM1 | MAP1LC3A |
| RPL29 | NDUFB11 | RPL11 | CYR61 | RERG |
| LY6E | COX6B1 | RASSF4 | F3 | GUCY1B3 |
| HLA-E | HEPACAM2 | TNFAIP6 | HSD11B1 | ASPN |
| SLC25A6 | HLA-A | SGCE | CEBPD | EPAS1 |
| TIMP1 | COX4I1 | COL1A2 | IGFBP6 | CTSF |
| RPL8 | CXXC4 | NNMT | EFEMP2 | UBA2 |
| CD74 | KIAA1324 | CADM4 | SEPP1 | GUCY1A3 |
| RPL35A | TPH1 | TAX1BP3 | PRR24 | RPS14 |
| RPL10A | VAMP5 | RPL19 | COL18A1 | LRRC32 |
| KRTCAP3 | ATP5G1 | RPS3 | NAB2 | MSC |
| UBB | RPS9 | TFAP2A | SCARA5 | NR2F2 |
| RPS12 | MT-ND4 | RCAN1 | TNFAIP6 | LGALS3BP |
| KLF5 | SLC25A6 | IER2 | TNIP2 | ANGPT2 |
| NOS2 | MT-ND1 | MYL9 | TCF21 | CD151 |
| RPL5 | ERI3 | RPS14 | PRR16 | SORBS3 |
| OLFM4 | ZFP36 | GPNMB | IFI35 | MCAM |
| SOX4 | S100A11 | TUBA1B | PTGIR | COL1A2 |
| RPL32 | RPS14 | GPX3 | BRCC3 | GNG11 |
| RPS23 | NPC2 | FAM210B | EID1 | PTMS |

TABLE 1B-continued

| | | | | |
|---|---|---|---|---|
| SEPP1 | PCBD1 | ID3 | POSTN | MYH11 |
| GUK1 | RPS21 | CADM2 | PSMA2 | RNASET2 |
| COX5A | CKB | GATM | APOC1 | RPLP1 |
| RPS8 | ATP5G2 | HSPB2 | CXCL1 | THY1 |
| MLXIP | GPBAR1 | RHOC | S100A13 | TGFBI |
| CEACAM5 | SELENBP1 | RPLP2 | CD302 | COL6A2 |
| RPS19 | NDUFA3 | RPL18 | RBP1 | ASAH1 |
| QTRT1 | SMIM6 | NGFR | EMP3 | PLOD2 |
| IFITM3 | RPS11 | HSPA2 | BSG | RARRES2 |
| STXBP6 | KLK1 | ASPA | SPG20 | EFEMP1 |
| RPL14 | BAIAP3 | FST | TNFRSF11B | SOCS3 |
| CDX1 | RPS2 | MARCKS | UBE2L6 | RPS18 |
| RPL30 | RPS18 | KCNMB4 | IL7 | RPS19 |
| RPS9 | RPL12 | SBSPON | PSME2 | LBH |
| RHOC | MYL12A | PSAP | SCT | SELM |
| RPL7A | TM4SF5 | OLFML2A | IL11 | NEXN |
| CDX2 | CADPS | RPL10 | SRGN | CDS2 |
| HLA-DRB1 | C21orf58 | SEPP1 | IGJ | GADD45B |
| IFI27 | DNAJC12 | C1S | ARID5B | COX7A1 |
| RPS14 | CTSC | RPL13A | EDEM2 | FKBP7 |
| IFITM2 | PPT1 | CXXC5 | PSMA4 | HLA-B |
| TXN | RARRES1 | S100A6 | TAP2 | CD248 |
| RPL34 | RPS3 | EMP2 | IFI6 | PTRF |
| ISG15 | DNAJA1 | RPL13 | FBLIM1 | F2R |
| HLA-DPB1 | SNX3 | MXRA8 | COL5A2 | MRVI1 |
| IGJ | NGFRAP1 | SERPING1 | FOSB | NFASC |
| PFN1 | ISG15 | RPS4X | ATP5E | PPIL4 |
| AP003774.1 | CDX1 | RPL31 | PCOLCE | STK16 |
| GPR160 | RPL38 | RPL28 | COL14A1 | SMDT1 |
| H3F3B | C12orf75 | SRGN | ETHE1 | NF2 |
| CD9 | TAX1BP3 | FGL2 | CDK2AP2 | ATF3 |
| CDHR1 | RPS8 | TBCB | IFITM2 | APOE |
| HLA-DRB5 | PPP1R1B | ENTPD2 | ANXA5 | FLNA |
| HLA-DMA | LYZ | SELM | TRIM47 | TUBA1A |
| S100A4 | HMGCS2 | PHLDA1 | TSPAN4 | RRAD |
| NUPR1 | PAM | EID1 | PDGFRA | TRIB2 |
| RPL18 | PLA2G12A | NGFRAP1 | ISG15 | OAZ2 |
| RPL27A | ACTB | ANGPTL7 | CD276 | RPL19 |
| RPS15 | SPINK4 | RPS8 | ADM | HRC |
| HLA-DRA | IFITM1 | RPL26 | APH1A | HCFC1R1 |
| RPS15A | COX8A | JUNB | IL34 | HEY2 |
| ANXA5 | IGFBP2 | SLITRK6 | FILIP1L | C11orf96 |
| RPL38 | TSTD1 | RPS12 | MAD2L2 | LAPTM4A |
| TMEM54 | LYPD8 | RPL15 | ADD3 | RPL27A |
| FXYD5 | RPSA | RPL12 | TAGLN2 | RPL11 |
| RPL24 | C4orf48 | SLC22A17 | PHGR1 | ARHGEF17 |
| RPS29 | HLA-DQB1 | RERG | SQSTM1 | CACNA1H |
| PSMB9 | GPX2 | PCBP4 | PLAC9 | TGFB1I1 |
| ARSE | MLXIP | CADM1 | MESDC2 | COTL1 |
| RPSA | LAP3 | RPS23 | NR2F1 | PLEKHA4 |
| RPL11 | ATP5E | ATF3 | SERPINH1 | RPS13 |
| CTSC | HSPA1A | RPS27A | NUBP2 | GULP1 |
| EEF1B2 | AGR2 | ITPR1 | LAMA4 | PARM1 |
| ARPC2 | TNNC1 | LGALS3BP | CYB5R1 | OLFM2 |
| CAPZB | TPPP3 | FSTL3 | TSPAN9 | RPS5 |
| ZKSCAN1 | SOCS3 | RPS5 | SEC63 | RASL12 |
| TYMP | MT-ATP6 | FAU | DKK3 | S100A10 |
| KIAA1324 | QTRT1 | RPL32 | F10 | RPS6 |
| LRIG1 | HERPUD1 | ZFP36L1 | AGT | ITGA7 |
| IMPDH2 | ETFB | SOD1 | COX5B | DOCK7 |
| GLTSCR2 | MRPL41 | SERTAD1 | BBIP1 | ANGPT1 |
| RNF43 | CD55 | RPS16 | TNIP1 | CD74 |
| RPS27A | PEMT | PCMT1 | COTL1 | CLMN |
| ATP1A1 | PRSS3 | RARRES2 | IFIT1 | ENTPD3 |
| PSME2 | C10orf54 | ITGB1BP1 | IFITM1 | RPL36 |
| RPL23 | CKMT1A | RPLP0 | PTGDS | MAB21L2 |
| RPS7 | TCEA3 | CTNNAL1 | CD40 | ILK |
| DYNLL1 | TYMP | RPS20 | ALDH1A3 | COASY |
| RPLP2 | S100A4 | HSPA1A | ACP5 | RPL28 |
| LGR5 | PSMB9 | YWHAE | NUPR1 | MSRB3 |
| OAZ1 | RPL18 | CST3 | GSN | CYGB |
| SOCS3 | RPS15 | RPS9 | OS9 | PDE1A |
| EIF3D | MT1G | SLC15A3 | MRFAP1 | FHL2 |
| SUCLG1 | RPL32 | CLIC4 | CLEC2B | CCL2 |
| HSPA1A | PIGR | DYNLL1 | ARHGDIB | ZNF580 |
| URAD | MT-CO3 | RPS15A | GNG11 | CASC3 |
| PTGDR | CUTA | RPSA | NUMA1 | SH3BGRL3 |
| CHDH | KIAA1456 | MT2A | PPAP2B | HLA-F |
| KCNN4 | CTSD | S100A16 | LGALS4 | TMEM98 |
| PSMA7 | RAC1 | WDR86 | SYPL1 | RRAGA |

TABLE 1B-continued

| | | | | |
|---|---|---|---|---|
| TAGLN2 | QDPR | DLX2 | FBN1 | LINC00152 |
| C19orf33 | C19orf45 | GSN | FABP1 | LGI4 |
| EPHB2 | RPL13 | LAMP1 | TMEM119 | MXRA8 |
| ETHE1 | WFDC2 | ID4 | MMP3 | GPI |
| PABPC1 | HSPB1 | POLR2F | ATPIF1 | 10-Sep |
| SELM | RPL31 | RXRG | S100A3 | MYLK |
| ITM2B | CD59 | SECISBP2L | C1RL | CCDC146 |
| IGLL5 | OCIAD2 | RPS7 | AKR1B1 | PTP4A3 |
| MPST | KIAA1377 | TMOD2 | HTRA3 | NNT-AS1 |
| UQCRH | CENPV | RPL6 | NBL1 | ARHGAP29 |
| UBC | EMC10 | SH3BGRL3 | SLC9A3R2 | FILIP1 |
| TDGF1 | PLAUR | DEPDC7 | TYMP | SCN4B |
| PPAP2C | DNAJB9 | ERBB3 | PUS3 | FOS |
| NQO1 | RPL37 | PON2 | EZR | RPS15 |
| RARRES2 | EPHB3 | STARD13 | PRKCDBP | MOCS1 |
| S100A6 | GADD45B | RPL23A | ANG | PPP1R15A |
| HLA-DQB1 | HIST1H4C | SCD | OLFML3 | EPC1 |
| TSC22D3 | SERINC2 | GRAMD3 | CXCL6 | FXYD5 |
| CDKN1A | CTSS | AHNAK | GPX8 | VIM |
| TGIF1 | URAD | CDC42EP1 | CPQ | SERTAD3 |
| AP000344.3 | RGS2 | IFIT3 | CCL13 | RPL8 |
| C10orf54 | NDUFA11 | RPL27A | TNFRSF12A | ID3 |
| SH3BGRL3 | ATP6AP2 | RPL5 | PGRMC1 | HN1 |
| WNK2 | NUDT16L1 | C1R | PSMB9 | EFEMP2 |
| RPS2O | SAT1 | CMTM5 | TPST1 | EBF1 |
| RHOA | ANXA2 | TNFRSF12A | PAPPA | TIMP1 |
| MYL12A | TIMM13 | RPL29 | FAM105A | LPL |
| COPE | UQCR10 | RPS29 | COPA | GNAI1 |
| VAMP8 | PRR15L | ARHGAP12 | EHD2 | RSBN1L |

TABLE 1C

| Myofibroblasts | Villus_fibroblasts | Crypt_fibroblasts_(hiFos) | Crypt_fibroblasts_(loFos) | T_cells |
|---|---|---|---|---|
| ACTA2 | NSG1 | ADAMDEC1 | CFD | DCN |
| TAGLN | F3 | CFD | DCN | LUM |
| MYL9 | FRZB | DCN | ADAMDEC1 | CFD |
| TPM2 | CXCL14 | C1S | FBLN1 | ADAMDEC1 |
| PDLIM3 | DMKN | LUM | LUM | C1R |
| ACTG2 | VSTM2A | FBLN1 | MFAP4 | C1S |
| HHIP | POSTN | HAPLN1 | C1R | FBLN1 |
| SOSTDC1 | BMP4 | CCL8 | APOE | TCF21 |
| MYLK | ENHO | C1R | C1S | APOE |
| FHL1 | PLAT | MFAP4 | SOD3 | COL3A1 |
| HSD17B6 | MMP2 | APOE | TCF21 | CXCL12 |
| MYL6 | EDNRB | CTSC | COL1A2 | MFAP4 |
| TPM1 | HSD17B2 | CCL2 | ABCA8 | GPX3 |
| MYH11 | COL6A1 | COL1A2 | COL3A1 | HAPLN1 |
| DSTN | COL6A2 | TCF21 | CTSC | CFH |
| CNN1 | SDC2 | COL3A1 | CYGB | SERPINF1 |
| NDUFA4 | AGT | CYGB | CXCL12 | COL1A2 |
| TGFB1I1 | TMEM176B | ABCA8 | CXCL14 | CCL2 |
| NPNT | IGFBP3 | SOD3 | CTSK | PPAP2B |
| DCN | NBL1 | STMN2 | TMEM176B | PLAC9 |
| PDLIM7 | CYGB | CXCL14 | GPX3 | PTN |
| PRKCDBP | FENDRR | PROCR | RBP1 | PTGDS |
| WFDC1 | RARRES2 | GPX3 | PROCR | IGFBP7 |
| CXCL14 | FOXF1 | CXCL12 | COL6A2 | PROCR |
| COL3A1 | MFGE8 | A2M | PLAC9 | COL6A2 |
| COL1A2 | CAV1 | RBP1 | CCL8 | CTSC |
| SMTN | ECM1 | COL1A1 | PTN | CXCL14 |
| FLNA | TPM2 | SERPINF1 | IGFBP7 | SOD3 |
| HHIP-AS1 | MFAP4 | PTN | LINC01082 | CYGB |
| C1S | PDGFRA | CCL13 | CALD1 | CCL13 |
| SELM | COL3A1 | TMEM176B | A2M | CCL8 |
| PPIC | COL1A2 | CTSK | TMEM176A | IFITM3 |
| LUM | GPX3 | LINC01082 | COL1A1 | PMP22 |
| PPP1R14A | C1S | PPAP2B | SERPINF1 | CCL11 |
| ADAMDEC1 | LGALS1 | GSN | IFITM3 | RARRES2 |
| COL1A1 | CALD1 | CFH | CFH | GSN |
| TM4SF1 | TMEM119 | IGFBP7 | ADH1B | CD2 |
| COL6A2 | FAM150B | CCL11 | SERPING1 | COL14A1 |
| NBL1 | WFDC1 | CLEC11A | CCL2 | ADH1B |
| NEXN | APLP2 | ADH1B | CLEC11A | SCARA5 |
| LGALS1 | COL1A1 | GGT5 | HAPLN1 | A2M |
| C1R | BMP5 | PLAC9 | GGT5 | COL1A1 |
| ILK | PDLIM1 | SCARA5 | RARRES2 | FXYD1 |

TABLE 1C-continued

| | | | | |
|---|---|---|---|---|
| KCNMB1 | TMSB4X | VCAM1 | SCARA5 | DKK3 |
| SPARC | SCPEP1 | DKK3 | CCL13 | CALD1 |
| CSRP1 | PDGFD | COL6A2 | LGALS3BP | CD3D |
| MFAP4 | MMP11 | PMP22 | GSN | PPAP2A |
| CALD1 | MMP1 | TMEM176A | MMP2 | ADAM28 |
| IGFBP7 | SPARC | SEPP1 | DKK3 | TMEM176B |
| LINC01082 | TMEM176A | MATN2 | CCL11 | CLEC11A |
| HSPB1 | IGFBP7 | PPAP2A | PMP22 | CTSK |
| APOE | PROCR | CYR61 | PPAP2B | EFEMP1 |
| POSTN | LGALS3BP | CALD1 | HAAO | PCOLCE |
| APOC1 | PPP1R14A | ADAM28 | ADAM28 | CD69 |
| FBLN1 | PKIG | RARRES2 | CD63 | EMILIN1 |
| TMEM176B | IGFBP6 | MMP2 | PCOLCE | STMN2 |
| SPARCL1 | TRPA1 | BMP4 | BMP4 | MMP2 |
| CAV1 | TIMP1 | SERPING1 | COL6A1 | GGT5 |
| LMOD1 | MYL9 | VIM | SEPP1 | HAAO |
| AOC3 | MRPS6 | SGCE | SPON2 | NDN |
| CFD | PCOLCE | EFEMP1 | SPARC | SPON2 |
| RBPMS | SLITRK6 | PCOLCE | PPP1R14A | RBP1 |
| TCEAL4 | C1R | IFITM3 | PPAP2A | CD52 |
| IFITM3 | IFITM3 | ECM1 | FHL2 | THY1 |
| TUBB6 | TCF21 | LTBP4 | LGALS1 | BMP4 |
| MMP2 | SERPINF1 | PTGDS | PTGDS | VCAN |
| MXRA8 | TGFBI | LAPTM4A | MFGE8 | GNG11 |
| CD151 | REEP2 | SPARC | EMILIN1 | SCT |
| TCF21 | SOX6 | CD63 | VIM | PPP1R14A |
| ACTN1 | TSLP | COL6A1 | PRKCDBP | ABCA8 |
| PDIA5 | CLEC11A | PPP1R14A | THY1 | LAPTM4A |
| PMP22 | INSC | SPON2 | SELM | TMEM176A |
| EFEMP2 | CTC-276P9.1 | HAAO | GNG11 | LGALS1 |
| LGALS3BP | SRGN | FOS | LAPTM4A | LTB |
| CD9 | RBP4 | SNAI2 | LTBP4 | LINC01082 |
| EMILIN1 | LTBP4 | NNMT | TIMP1 | PAMR1 |
| TUBA1A | PITX1 | FHL2 | STMN2 | PLTP |
| GSN | LAPTM4A | GNG11 | EFEMP2 | IGFBP6 |
| MRGPRF | EMILIN1 | MEG3 | SNAI2 | NDUFA4L2 |
| MFGE8 | MAGED2 | TM4SF1 | ECM1 | VIM |
| COL6A1 | GLP2R | FABP4 | SGCE | SELM |
| UBE2E3 | LAMA4 | EMILIN1 | VCAM1 | CIRBP |
| C9orf3 | A2M | LGALS3BP | IL34 | FABP4 |
| PTMS | PROM1 | EFEMP2 | IGFBP6 | S100A4 |
| SERPINF1 | RGS10 | CXCL1 | SPARCL1 | QSOX1 |
| JUNB | LHFP | LGALS1 | NOVA1 | RGCC |
| RCN1 | BAMBI | PLAT | FBLN5 | FBLN5 |
| FXYD1 | RBPMS | IGFBP6 | NGFRAP1 | PLAT |
| CES1 | ANXA5 | SOCS3 | PLTP | MEG3 |
| NUPR1 | AKR1B1 | TPM2 | MATN2 | SRGN |
| RARRES2 | BSG | SMPDL3A | FXYD1 | TIMP1 |
| SRGN | PRR16 | NDN | EDIL3 | GSTT1 |
| FN1 | MAP1B | SELM | TPM2 | EMIDI |
| SDC2 | GADD45G | FXYD1 | SFTA1P | SERPING1 |
| FOXF1 | TSPAN4 | C2 | TSPAN4 | CD3E |
| PCOLCE | S100A13 | PLTP | MEG3 | ANXA1 |
| SERPING1 | GLT8D2 | VCAN | EPHX1 | LTBP4 |
| SCPEP1 | HSPB1 | NGFRAP1 | QSOX1 | CCL5 |
| AC131025.8 | C11orf96 | QSOX1 | MYL9 | SPARCL1 |
| SGCE | EFEMP2 | SDC2 | SRGN | MXRA8 |
| MIR145 | FGF9 | EPHX1 | TM4SF1 | IFI27L2 |
| CRYAB | EID1 | GSTM3 | EFEMP1 | FN1 |
| LTBP1 | PTMS | SPARCL1 | PLAT | GSTM3 |
| CRIP2 | COL5A1 | TIMP1 | OLFML3 | MYL9 |
| DUSP1 | MXRA8 | FHL1 | GSTM3 | PHGR1 |
| CERCAM | FKBP10 | SRGN | CCDC80 | CD63 |
| TPPP3 | PTGDR2 | COLEC11 | DPT | SEPP1 |
| SH3BGRL | CPE | EDIL3 | RAB13 | TPM2 |
| VIM | SGCE | IL34 | ITIH5 | GATA3 |
| CKB | TNC | PRKCDBP | NNMT | TFPI |
| NGFRAP1 | TAGLN | C11orf96 | SDC2 | LEPROT |
| PTCH1 | DCN | ARHGDIB | FSTL1 | C16orf89 |
| SOD3 | TXNL1 | FBLN5 | LOXL1 | SGCE |
| COL4A2 | EMID1 | SFTA1P | FABP4 | LGALS3BP |
| LRRC17 | CRISPLD2 | EID1 | S100A13 | LCK |
| GNG11 | SRPX2 | FXYD6 | COL14A1 | DPT |
| CYBA | C1orf21 | MYL9 | NDN | SNAI2 |
| RBP1 | NDN | THY1 | MXRA8 | ZFP36L1 |
| IER2 | ISCU | LINC01116 | UBE2E3 | IL32 |
| CPQ | CD9 | TFPI | FHL1 | TSC22D3 |
| MAP1LC3A | ACP1 | LOXL1 | TAC3 | LAMB1 |
| BMP5 | PALLD | MXRA8 | IFITM2 | MATN2 |
| OSR1 | F2R | IRF1 | EID1 | C6orf48 |

TABLE 1C-continued

| | | | | |
|---|---|---|---|---|
| AKR7A2 | BST2 | PITX1 | PITX1 | SPARC |
| NDN | CPM | MFGE8 | C2 | CNBP |
| PKIG | SELM | UBE2E3 | LRP1 | NANS |
| S100A13 | PTN | FGF7 | NUPR1 | FSTL1 |
| HMG20B | WNT5B | SERPINH1 | VKORC1 | EEF1D |
| RP11-332H18.4 | SERPING1 | OLFML3 | APOC1 | AEBP1 |
| CFH | RBP1 | ARID5B | FKBP10 | SERPINH1 |
| GAS6 | FBLN1 | PPIC | FXYD6 | NNMT |
| FOSB | NDUFA4L2 | RAB13 | LAMA4 | WNT2B |
| LPP | PCDH18 | CFL1 | PPIC | C11orf96 |
| PALLD | APOD | JUNB | DMKN | PDPN |
| TTLL7 | KREMEN1 | KCNS3 | EMID1 | GZMK |
| IGFBP5 | TUBA1A | S100A13 | NDUFA4L2 | ELANE |
| LAPTM4A | ID1 | CEBPD | PLAU | TRIM22 |
| WLS | ADM | TSPAN4 | FOXF1 | CLEC14A |
| EDNRB | PRKCDBP | APOC1 | FN1 | PITX1 |
| FAM127A | IFITM1 | LAMA4 | GLT8D2 | SLC25A5 |
| ARHGDIB | CXCL12 | C6orf48 | COL5A1 | CXCL1 |
| CSRP2 | TSHZ2 | ZFP36L1 | CTC-276P9.1 | COL6A3 |
| TIMP2 | LRRN4CL | GLT8D2 | COLEC11 | IDH2 |
| MAMDC2 | PTCHI | NDUFA4L2 | CFL1 | COLEC11 |
| P2RY14 | LAMB1 | EMID1 | EHD2 | COX5A |
| S100A4 | HHIP | CCL7 | RBPMS | MXRA5 |
| TRIP6 | VIM | SRPX | COL18A1 | EDIL3 |
| SH3BGRL3 | NNMT | TIMP3 | SCPEP1 | EFEMP2 |
| CBR1 | CIRBP | ANGPTL4 | SMPDL3A | PPIC |
| MMP14 | CAPZB | SCPEP1 | WFDC1 | TDO2 |
| SEPW1 | CD63 | DPT | DUSP1 | C4orf3 |
| MFAP5 | TGFB1I1 | ADM | COX5A | VPS25 |
| FENDRR | IL32 | GADD45B | FOSB | FNDC1 |
| CALU | PLK2 | NUPR1 | C6orf48 | CYP7B1 |
| TMEM176A | TBX2 | LRP1 | SERPINE2 | SPRY1 |
| CTSK | ANGPTL4 | CYBA | FAM127A | PCDH7 |
| C1QTNF2 | PCSK6 | RAB34 | TMEM119 | ZFP36L2 |
| SNAI2 | TSPAN2 | PRNP | GSTM5 | DMKN |
| COL4A1 | WLS | EGR1 | CPQ | ALDOA |
| CD63 | AEBP1 | ZFP36 | RAB34 | COL6A1 |
| COX7A1 | SCUBE2 | PROS1 | AKR1B1 | HTRA3 |
| LOXL2 | LANCL2 | ITIH5 | CD81 | PRKCDBP |
| CYB5R3 | LOXL2 | CD81 | SLC9A3R2 | CXCR4 |
| FOS | FIP1L1 | CIRBP | TNFAIP6 | KRT8 |
| IL32 | RTN4 | FOXF1 | FILIP1L | KLRB1 |
| RPL28 | ADH5 | CCDC80 | VCAN | PHLDA1 |
| CFL2 | TM4SF1 | NEGR1 | TGFB1I1 | FGF7 |
| LTBP4 | C7orf50 | COX5A | COL15A1 | LAMA4 |
| EHD2 | IL1R1 | NOVA1 | ATRAID | TAC3 |
| ITM2C | EMP3 | FN1 | TFPI | COL18A1 |
| STMN2 | CYBA | CPQ | WNT2B | SPINT2 |
| BSG | CAV2 | ID3 | SERPINH1 | THNSL2 |
| VCAN | TMEM100 | FKBP10 | PRNP | NEXN |
| LAMB1 | MAP1LC3A | BST2 | CTSF | RNASE1 |
| MAP1B | IFI27 | WFDC1 | MDK | FXYD6 |
| VCL | SEMA4D | TDO2 | ACTA2 | LOXL1 |
| P2RX1 | PXDN | DMKN | CST3 | CD81 |
| WNT2B | HAAO | COL5A2 | KLF6 | TMEM66 |
| PARVA | NPY | COL14A1 | TGFBI | CRIP2 |
| S100A6 | RGCC | PGRMC1 | TIMP3 | TIMP3 |
| ECM1 | SGCB | PHGR1 | ABCA6 | H3F3B |
| TCEAL1 | FHL1 | SH3BGRL3 | FGF7 | IRF1 |
| LAMA4 | TPBG | ANXA5 | CYBRD1 | ECM1 |
| VKORC1 | NUPR1 | EHD2 | MMP23B | IFI27 |
| NME4 | TBX3 | TAC3 | EVA1A | DDR2 |
| TMEM98 | RGS1 | VASN | PTMS | SLC9A3R2 |
| RPLP2 | LEPROT | SLC25A5 | TNFRSF1A | SGCA |
| TIMP1 | GNAI1 | AEBP1 | C7 | CD74 |
| CD74 | MSC | RBPMS | RP11-14N7.2 | COL15A1 |
| PPP1CC | PTX3 | CCNI | RGCC | SFTA1P |
| A2M | ACTA2 | CNBP | CDH11 | CDK2AP2 |
| CTSS | CD74 | SPRY1 | FGFR4 | PTGER2 |
| PTS | LRP1 | SEC11C | BST2 | FABP1 |
| PPAP2A | TMEM98 | PLAU | IGFBP5 | TNFAIP3 |
| TTC3 | PLBD1 | IFITM2 | CXCL1 | FGFR2 |
| ADH5 | CPQ | 4-Sep | CP | FHL1 |
| MCL1 | VASN | GSTM5 | C16orf89 | KRT18 |
| FAM105A | AMPD3 | ABCA6 | LINC01116 | RND3 |
| MAGED2 | IGFBP5 | FILIP1L | CIRBP | SCPEP1 |
| NKX2-3 | MXRA5 | MT-ND2 | SAMD11 | MAPK10 |
| RAB34 | PHGR1 | LEPROT | SAT1 | LY6E |
| SGCA | STMN2 | FSTL1 | SH3BGRL3 | CLEC2B |
| CCDC107 | GULP1 | MT-CO2 | MIR497HG | FTH1 |

TABLE 1C-continued

| | | | | |
|---|---|---|---|---|
| SERPINH1 | CCDC68 | TUBA1A | PHGR1 | NUPR1 |
| FILIP1L | SPON2 | HES1 | HTRA3 | CD5 |
| MINOS1 | CH25H | CSF1 | AEBP1 | IL34 |
| AEBP1 | PLAU | CDK2AP2 | TMEM9 | EMP3 |
| NEO1 | MRVI1 | CDH11 | S100A4 | NUDT16L1 |
| EID1 | CD151 | PFN1 | SCT | CCDC80 |
| PDGFC | CNTFR | HTRA3 | MXRA5 | IL1R1 |
| DCTN2 | COL6A3 | RND3 | CNBP | EVL |
| CBR3 | PDLIM4 | HSPA1A | IFITM1 | RP11-14N7.2 |
| RCAN2 | CYTL1 | JUN | PDLIM3 | CSF1 |
| RERG | COL4A5 | MT-ND4 | KCNS3 | GNAO1 |
| CLEC11A | HMGB1 | CST3 | ISLR | LRP1 |
| FSTL1 | ST5 | HINT1 | HSPA8 | ITIH5 |
| C2 | GADD45B | TNFAIP6 | PFN1 | MFGE8 |
| FHL3 | ID3 | CHL1 | BDH2 | DUSP2 |
| TGM2 | CYR61 | ADAMTS1 | ELANE | FHL2 |
| MORF4L2 | CTSF | ACTA2 | HINT1 | TRAT1 |
| TMEM47 | CTSK | SERPINE2 | WARS | FARP1 |
| ISG20 | ENPP6 | C16orf89 | COX7A1 | MRPL23 |
| ACTB | LUM | MYL12A | PAMR1 | TM4SF1 |
| CD99 | HOXA10 | RCN1 | LY6E | LAMA2 |
| EFEMP1 | SERPINH1 | IGJ | CRYAB | GZMA |
| ZYX | FILIP1L | TMEM98 | MYL12A | PAM |
| SAMD11 | SEC62 | ELANE | SPRY1 | RNASET2 |
| SSPN | GPC1 | MAMDC2 | IL6ST | GPC6 |
| RBBP7 | ARPC1B | CTC-276P9.1 | ANGPTL1 | IL7R |
| CPED1 | PDPN | CD302 | GAS6 | IFITM2 |
| RGS10 | TUSC3 | PCDH18 | NENF | FBN1 |
| CREB3 | RP11-332H18.4 | FAM92A1 | RUNX1T1 | ACTA2 |
| DDAH2 | C12orf57 | GRK5 | CYBA | RARRES3 |
| SEPP1 | NOVA1 | WNT2B | ANXA1 | ADM |
| MIR143HG | WFS1 | MDK | NEGR1 | FKBP10 |
| NENF | NGFRAP1 | POSTN | CYCS | COL5A1 |
| PITX1 | CDH11 | ISLR | COL6A3 | CCDC127 |
| COL6A3 | OLFML3 | EPHA7 | SLC25A5 | GAPDH |
| KANK2 | ZFP36L1 | ANGPTL1 | PAM | MGST1 |
| NUDT4 | PDE1A | PHLDA1 | IL32 | VKORC1 |
| ARHGEF25 | ECHDC2 | HSD11B1 | CRIP2 | HSD11B1 |
| MMP23B | BRK1 | FTH1 | TDO2 | DUSP23 |
| THYN1 | HLA-A | RGCC | COL4A2 | CHCHD10 |
| RGS1 | TCF4 | IL6ST | RGS1 | SSBP3 |
| ARPC1B | SEC11C | SMIM10 | PCDH18 | NGFRAP1 |
| RCN3 | COL4A6 | TMEM150C | P4HA2 | ARHGAP24 |
| SQRDL | RCAN2 | CTSF | CYB5R3 | EID1 |
| APCDD1 | SCARB2 | ATP6AP2 | TSTD1 | ID4 |
| RP11-532F6.3 | MMP14 | AKR1B1 | EEF1D | C11orf58 |
| NDUFB9 | SH3BGRL3 | SVEP1 | MT-CO2 | CREG1 |

| | Macrophages | Dendritic_cells | Mast_cells | Cycling_monocytes | Tolerogenic_DCs |
|---|---|---|---|---|---|
| | FTL | CST3 | TPSAB1 | FTL | SNX3 |
| | C1QB | CLEC10A | VWA5A | PSAP | CPVL |
| | C1QC | HLA-DPB1 | LTC4S | MS4A6A | IDO1 |
| | PSAP | HLA-DPA1 | C1orfl86 | GPX1 | CST3 |
| | C1QA | HLA-DQB1 | CPA3 | AIF1 | CLEC9A |
| | CTSB | FCER1A | SLC18A2 | C1QA | LGALS2 |
| | CD68 | HLA-DQA1 | HPGDS | C1QC | C1orf54 |
| | CTSD | HLA-DRA | MAOB | C1QB | HLA-DPB1 |
| | TYROBP | HLA-DRB1 | HDC | CST3 | DNASE1L3 |
| | SAT1 | CD74 | CLU | TYROBP | IRF8 |
| | LGMN | AIF1 | NFKBIZ | IGSF6 | HLA-DPA1 |
| | FCER1G | LST1 | RP11-354E11.2 | CD68 | CD74 |
| | MS4A7 | IL1B | SAMSN1 | CTSB | HLA-DQB1 |
| | MS4A6A | LYZ | GATA2 | DNASE1L3 | LSP1 |
| | AIF1 | CPVL | ANXA1 | FCER1G | COTL1 |
| | ACP5 | AMICA1 | GLUL | MS4A7 | HLA-DQA1 |
| | MS4A4A | HLA-DMA | FCER1A | MS4A4A | HLA-DRA |
| | DNASE1L3 | TYROBP | KRT1 | NPC2 | AIF1 |
| | GPX1 | FCER1G | CAPG | LYZ | HLA-DQB2 |
| | IGSF6 | SPI1 | CTSG | IL1B | HLA-DRB1 |
| | FUCA1 | MS4A6A | PPP1R15A | VSIG4 | SPI1 |
| | FCGRT | HLA-DQB2 | SLC45A3 | LST1 | LYZ |
| | SEPP1 | HLA-DMB | HPGD | SDS | HLA-DOB |
| | HLA-DMB | CFP | HS3ST1 | CTSD | HLA-DRB5 |
| | NPC2 | HLA-DRB5 | GMPR | GRN | HLA-DQA2 |
| | HLA-DPA1 | IGSF6 | KIT | CPVL | ACTB |
| | STAB1 | LGALS2 | RGS13 | FGL2 | LST1 |
| | HLA-DQA1 | PLAUR | CD9 | SPI1 | RGS10 |
| | HLA-DPB1 | CD83 | FCER1G | HLA-DPB1 | BATF3 |
| | RNASET2 | IFI30 | NFKBIA | SAT1 | CADM1 |

TABLE 1C-continued

| | | | | |
|---|---|---|---|---|
| LST1 | PLD4 | BTK | CD74 | MPEG1 |
| LYZ | CD1C | HSP90AB1 | HLA-DRB1 | ASB2 |
| HLA-DRA | MNDA | CD44 | HLA-DQA1 | C1orf162 |
| CD14 | COTL1 | MITF | HLA-DPA1 | PPT1 |
| HLA-DMA | GPX1 | SERPINB1 | RNASE6 | FGL2 |
| GPNMB | HLA-DQA2 | LMNA | FAM26F | S100A6 |
| HLA-DRB1 | ITGB2 | ADRB2 | PLAUR | HLA-DMB |
| PLA2G7 | SGK1 | VIM | CTSZ | BASP1 |
| APOC1 | GPR183 | TYROBP | HLA-DRA | CD83 |
| CD74 | FGL2 | SRGN | HLA-DRB5 | KIAA0226L |
| SDS | C1orf162 | IL1RL1 | RNASET2 | HLA-DMA |
| CTSS | SRGN | SDPR | PLA2G7 | SGK1 |
| LAPTM5 | FAM26F | FAM46A | SEPP1 | TMSB4X |
| CD163L1 | LY86 | BTG2 | CD14 | RGCC |
| RNASE6 | RNASE6 | ALOX5 | HLA-DQB1 | PLEK |
| VSIG4 | RGS2 | NSMCE1 | STAB1 | S100B |
| HLA-DQB1 | DNASE1L3 | CTNNBL1 | HLA-DMA | SERPINF2 |
| GRN | CTSH | MIR24-2 | LAPTM5 | ARPC2 |
| ADORA3 | CD1E | LEO1 | CLEC10A | SMCO4 |
| CTSZ | FCGR2B | SDCBP | ACP5 | ITGB2 |
| S100A11 | MS4A7 | PTGS1 | HLA-DMB | HCK |
| SPI1 | LAPTM5 | LAT2 | AP2S1 | CST7 |
| PLD3 | SAT1 | ALOX5AP | NCF4 | UCP2 |
| TREM2 | CD1D | FTH1 | S100A11 | WDFY4 |
| FOLR2 | C1QA | DDX5 | IGF1 | CPNE3 |
| CYBA | CXCL16 | AC020571.3 | A2M | TNNI2 |
| CST3 | ACTB | DNAJA1 | CCL3 | GLIPR1 |
| RNASE1 | RNASET2 | BACE2 | ITGB2 | DUSP2 |
| ATP6V1F | HCK | CD69 | SLC7A7 | PTPRE |
| CCL3 | CACNA2D3 | DUSP6 | CD300A | RNASET2 |
| SLC40A1 | CORO1A | MLPH | LGMN | ARPC1B |
| LIPA | MPEG1 | JUN | SLC40A1 | LY86 |
| GLUL | ARPC1B | IL1RAPL1 | TYMP | SLAMF8 |
| CSTB | VSIG4 | SIGLEC8 | C1orf162 | SLAMF7 |
| CPVL | BID | RAB27B | GLUL | C20orf27 |
| ASAH1 | STX11 | LAT | RGS10 | LIMD2 |
| VAMP8 | CTSS | UBB | VAMP8 | FLT3 |
| ATP6V0D2 | FTL | ACOT7 | SRGN | FAM49B |
| RENBP | SAMHD1 | STMN1 | P2RY6 | PARVG |
| CREG1 | GLIPR1 | FXYD5 | C1orf54 | CORO1A |
| CLEC10A | CSF2RA | EGR2 | MNDA | BID |
| FCGR2A | CD68 | ALDH1A1 | AMICA1 | GCSAM |
| FAM26F | LSP1 | NCOA4 | IFI30 | RAB32 |
| RGS10 | INSIG1 | GCSAML | CTSH | FAM26F |
| TMSB4X | IL8 | CD33 | FCGRT | CD9 |
| CTSL | NR4A3 | STX3 | CSF1R | LCP1 |
| NCF4 | ARPC3 | SVOPL | FCGR2A | ARHGDIB |
| AP2S1 | DUSP2 | ATP6V0A2 | TGFBI | CKS2 |
| LY86 | FAM110A | LAPTM4A | LGALS1 | SUSD3 |
| IGF1 | CD33 | HSP90AA1 | MPEG1 | PABPC1 |
| HLA-DRB5 | TMSB4X | CD63 | GPR183 | FKBP1B |
| FGL2 | C1QC | ANKRD28 | SERPINF1 | GSTP1 |
| AKR1B1 | CD86 | LAPTM5 | TBXAS1 | PPDPF |
| MALAT1 | RGS10 | EGR1 | IL8 | P2RY6 |
| AMICA1 | PHACTR1 | ARL5B | CTSS | FCER1G |
| APOE | PPDPF | CATSPER1 | APOC1 | NAP1L1 |
| IFI30 | AOAH | HSPH1 | RNF130 | CD48 |
| CD163 | PYCARD | KLRG1 | HCK | TYMP |
| ITGB2 | PTPRE | CLIC1 | ALOX5AP | LAPTM5 |
| HLA-DQB2 | ARHGDIB | TSC22D1 | CD36 | MT-ND2 |
| S100A9 | RNF130 | S100A4 | ADORA3 | ID2 |
| CD300A | PLEK | ATP6V1F | SIRPA | AMICA1 |
| UCP2 | TYMP | CTD-3203P2.2 | CYBA | AIM2 |
| CSF1R | GRN | SGK1 | PLD3 | CLNK |
| OAZ1 | NCF4 | RENBP | PDLIM1 | LGALS3 |
| GM2A | TBXAS1 | PLIN2 | RGS1 | IFI27 |
| PLAUR | C1QB | PTPN6 | GPNMB | CSF2RA |
| NPL | ARRB2 | ANXA2 | CD4 | VMO1 |
| HCK | IFI27 | FAM212A | RGS2 | DUSP4 |
| LILRB4 | UCP2 | FOSB | TIMP1 | ID3 |
| C1orf54 | ARL5B | ASAH1 | APOE | SAT1 |
| C5AR1 | DUSP1 | HSPA8 | OAZ1 | TLR10 |
| LGALS1 | CD48 | ASRGL1 | VIM | TYROBP |
| RNF130 | RHOG | LYL1 | ATP6V0B | MIR142 |
| CD209 | RGS1 | EIF4G2 | CORO1A | GPR183 |
| TTYH3 | NR4A2 | STXBP6 | HLA-DQA2 | TSPO |
| PRDX1 | NCF2 | TNFSF10 | CREG1 | MNDA |
| RAB42 | HCLS1 | GRAP2 | HLA-DQB2 | PFN1 |
| IL1B | ARPC2 | NFKBID | S100A9 | LGALS1 |
| FABP3 | PILRA | CSF2RB | PPT1 | GPX1 |

TABLE 1C-continued

| | | | | |
|---|---|---|---|---|
| MPEG1 | CD53 | RAC2 | LY86 | HSPA1A |
| CD36 | P2RY13 | NR4A1 | TXN | ACTG1 |
| SLC7A7 | CLEC4A | HSPA1B | EPCAM | CCND1 |
| NINJ1 | PPT1 | H3F3B | LILRB4 | CNN2 |
| C3AR1 | CHMP1B | SMYD3 | FUCA1 | LTB |
| CHMP1B | GPSM3 | MPP1 | FXYD5 | SAMHD1 |
| CAPG | ZNF385A | FAR2 | GNAI2 | NAAA |
| ADAP2 | ATF3 | LMO4 | ADAP2 | ITM2C |
| OTOA | LITAF | SRSF5 | CSF2RA | HCLS1 |
| CFD | ZNF331 | ARHGDIB | LGALS4 | TACSTD2 |
| HSD17B14 | PARVG | EIF3D | NINJ1 | PSMB9 |
| CD83 | MIR142 | EGR3 | ATP5G1 | XCR1 |
| LILRB5 | NAMPT | CD82 | FCGR1A | PLCD1 |
| P2RY6 | P2RY6 | MYADM | EMP3 | SERPINB9 |
| CMKLR1 | FAM49B | TESPA1 | KRT18 | TMEM176B |
| SERPINF1 | FTH1 | RASSF5 | CAMK1 | GMFG |
| CTSC | GAPT | CALB2 | PHGR1 | COX7A2 |
| BLVRA | NPC2 | BIRC3 | CD163L1 | CD99 |
| TYMP | ITGB2-AS1 | HINT1 | KRT8 | PPM1J |
| TBXAS1 | HLA-DOA | CD22 | C3AR1 | H2AFY |
| RGS1 | CYBA | IL18 | IFI27 | PYCARD |
| CXCL16 | OAZ1 | HSPD1 | S100A4 | RGS1 |
| CD86 | P1D1 | STXBP2 | RAB31 | TMEM59 |
| CD4 | CCL3 | MBOAT7 | DAB2 | SRGN |
| A2M | RILPL2 | RGCC | ANXA1 | ZYX |
| IL8 | CXCR4 | IER2 | ATP6V1F | CLEC7A |
| C1orf162 | CSF1R | MSRA | TUBB4B | NABP1 |
| NAGK | ARL4C | JUNB | CD209 | ZFP36L2 |
| ATP6VOB | PDLIM1 | BHLHE40 | TFF3 | ABI3 |
| HLA-DQA2 | IGJ | ARHGEF6 | LSP1 | MT-ND1 |
| FTH1 | NCF1 | CST3 | ARHGDIB | CD37 |
| CAMK1 | G0S2 | DUSP10 | UCP2 | FNBP1 |
| GPR34 | HSPA1A | SCYL1 | CXCL16 | EVI2A |
| SLAMF8 | VAMP8 | RGS10 | HBEGF | HAVCR2 |
| S100A6 | TNFSF13B | PRDX6 | ZNF331 | ARPC3 |
| IL18BP | H2AFY | ACTG1 | FCGR2B | CD63 |
| CTSH | OLR1 | CHST2 | CTSC | HES1 |
| ARHGDIB | HCST | CD37 | RBI | KIAA1598 |
| PLTP | MT-CYB | DDX3X | SRI | VAC14 |
| COTL1 | TMEM59 | ESYT1 | YWHAH | IGFBP7 |
| ARL4C | CXorf21 | CRBN | RENBP | TAP1 |
| FPR3 | CNPY3 | SYTL2 | SGK1 | LDLRAD4 |
| SRGN | EIF4A1 | CTSD | CD163 | ELOVL5 |
| HMOX1 | THEMIS2 | HNRNPM | C5AR1 | IL16 |
| TNFSF13B | C20orf27 | P2RY14 | LILRB2 | RGS19 |
| CYBB | CD300A | CD83 | COTL1 | DUSP10 |
| LAIR1 | S100A11 | SLC2A6 | CLEC4A | PDLIM7 |
| GLIPR1 | YBX1 | CKS2 | TMSB4X | TWF2 |
| ITM2B | LGALS1 | ARHGAP18 | LAIR1 | CTSZ |
| YWHAH | IGFBP7 | TIMP3 | ASAH1 | IFITM3 |
| TGFBI | ANXA1 | TMEM154 | EEF2 | CXCR4 |
| HLA-DOA | PTPRC | CMA1 | PLD4 | COX5B |
| CCL4 | AGPAT9 | MALAT1 | MAFB | VIM |
| DAB2 | FCGR2A | RGS1 | RPL24 | SELPLG |
| EBI3 | CTSZ | DNAJB1 | FCER1A | CFL1 |
| GATM | PPIF | FCGRT | PLTP | ATG3 |
| ATOX1 | DOK2 | PFN1 | TUBA1B | C12orf5 |
| FCGR3A | MT-ND2 | EXD3 | RPS27A | PNMA1 |
| ARPC3 | GNA15 | LIF | GMFG | APOL3 |
| TNFAIP8L2 | KRT18 | GBE1 | AXL | RAB31 |
| ABI3 | HERPUD1 | CHORDC1 | CLEC7A | MT-CYB |
| RHOG | HBEGF | GAPT | PRDX5 | MYCL |
| RGS2 | SCIMP | HSPE1 | CD83 | IFNGR1 |
| CCL18 | LCP1 | ITM2B | HCST | GYPC |
| HN1 | PTGS2 | UBXN10 | GNPDA1 | GPSM3 |
| RAC1 | LIMD2 | CNIH1 | IGJ | PLEKHO1 |
| TMEM176B | PMAIP1 | SLC16A3 | TUBB | LSM6 |
| KRT8 | PABPC1 | GNPTAB | RPL31 | MSL3 |
| PYCARD | KDM6B | TSPO | DUSP1 | UQCR10 |
| PILRA | IL32 | RPL28 | RPL35A | LGALS4 |
| LGALS4 | FPR3 | MAML1 | P2RY13 | CXCR3 |
| SLCO2B1 | PFN1 | TUBA1B | CD9 | CIITA |
| SMS | BSG | UBE3A | BLVRA | BCL2A1 |
| CORO1A | GMFG | NFE2L2 | GLIPR1 | ROGDI |
| ZNF331 | SLC31A2 | SH3BGRL3 | TNFSF13B | TGFBI |
| ARRB2 | SNX10 | ELF1 | GATM | MIR4435-1HG |
| IFI27 | SEPW1 | PRKAR1A | OSM | CKLF |
| SIGLEC7 | ZFP36 | ENPP3 | CLDN7 | IGJ |
| GPR183 | FOSB | GALNT6 | NCF1 | BST2 |
| DOK2 | KYNU | CCL2 | CTSL | DGAT2 |

TABLE 1C-continued

| | | | | |
|---|---|---|---|---|
| CLEC4A | RGS19 | ACTR3 | GM2A | NDUFB9 |
| CECR1 | PHGR1 | TMEM66 | LRRC25 | COX6C |
| TMEM37 | SDS | NCF4 | C15orf48 | MT-ND5 |
| RHOC | AKIRIN2 | BEX4 | AKR1B1 | KLF6 |
| ANXA1 | DSTN | BLVRA | RAB42 | KRT18 |
| PHGR1 | VIM | SERP2 | GSN | 1-Mar |
| AP1B1 | S100A4 | TM6SF1 | TREM2 | EVI2B |
| NCF1 | RB1 | ITM2A | RPL34 | CPPED1 |
| GRB2 | ARPC5 | DHRS7 | SLCO2B1 | FERMT3 |
| GAL3ST4 | H3F3B | IFI27 | ADAMDEC1 | ST8SIA4 |
| ID1 | PAK1 | 2-Sep | TSPO | PTPRC |
| NINJ2 | RAB32 | CD84 | TRPM2 | GNAI2 |
| SDSL | CSF3R | HSPA9 | RPL18 | ATP5J |
| CD63 | GSN | FECH | RPL5 | GPR137B |
| ABHD12 | RAB31 | PRDX5 | H2AFZ | HSPA1B |
| GNPDA1 | ID3 | IFITM10 | SDSL | RNASE6 |
| CD81 | TNFAIP8L2 | HSPA1A | MT1E | AKIRIN2 |
| LRRC25 | SOD2 | DLC1 | FABP1 | LITAF |
| YBX1 | SLAMF8 | HIF1A | ENG | TOMM34 |
| GPSM3 | CCL3L1 | LYN | TNFAIP8L2 | PTPRCAP |
| TFPT | LILRB2 | DDX3Y | LIPA | AP1S2 |
| MKNK1 | PRDX5 | ZEB2 | NCF2 | BSG |
| SLC15A3 | ANXA5 | RHOG | ARL4C | MT-ND4 |
| BRI3 | RABAC1 | RBMX | MGST1 | MCL1 |
| ADAMDEC1 | S100A6 | CDK5 | GPSM3 | ACTR3 |
| IL2RA | FCGRT | DDX39A | RAC1 | CD40 |
| IGJ | COX6C | TMSB10 | CECR1 | MT-ATP6 |
| RBI | CD52 | EIF1 | ARPC1B | PPA1 |
| MPP1 | NGFRAP1 | NEK6 | PARVB | KCNMB1 |
| SLC7A8 | PLEKHO1 | CSF2 | CYBB | MAP4K1 |
| TNFAIP2 | RAB20 | CSF1 | VMO1 | EPCAM |
| SCIMP | ITM2C | CXCL14 | SLC16A3 | MYADM |
| TFF3 | CEBPD | PIK3R6 | DOK2 | CAP1 |
| NCKAP1L | CD9 | GPR65 | TNFAIP2 | SIGLEC10 |
| FXYD3 | CD151 | RPS4Y1 | ARRB2 | CECR1 |
| ARPC1B | NUDT1 | VAV1 | ATPIF1 | ACTN1 |
| SIGLEC1 | CCDC88A | IL4R | COX5B | RAB7L1 |
| TUBA1B | MAT2A | SELM | ITGB7 | FAM110A |
| BSG | PRMT10 | EVL | NAGK | LINC00152 |
| EEF2 | GCA | HNRNPA2B1 | ATF3 | INPP5D |
| BST2 | LINC00936 | BCL2A1 | IL1RN | PHGR1 |
| HCST | COX5B | RALB | SUCLG1 | GRN |
| LGALS3 | MCL1 | CORO1A | HSD17B14 | AC093673.5 |
| MNDA | CARD9 | RAB32 | CD86 | C12orf57 |
| RAB20 | REL | WDR45B | KRT19 | PHACTR1 |
| FCGR1A | BCL2A1 | LINC00863 | TTYH3 | CD86 |
| PTAFR | TUBA1B | ABCB8 | ANXA5 | S100A4 |
| CD53 | FGR | EIF2AK1 | SOD2 | DAPP1 |
| HCLS1 | ABI3 | SAR1B | BST2 | RHOG |
| LSP1 | SOCS3 | RHBDD2 | CAPG | CYB5R3 |
| AGR2 | IFNGR1 | DHRS9 | FOLR2 | C10orf128 |
| C12orf57 | JUNB | SEMA7A | PRDX2 | RHOF |
| AOAH | GHRL | CCDC28A | STX11 | KRT8 |
| STMN1 | MT-ND5 | TRAPPC2P1 | SNCA | ANXA6 |
| GMFG | NAGK | IGFBP7 | PTGS2 | ITM2B |
| IRF8 | CIITA | GPR35 | CMKLR1 | SCNM1 |
| AXL | CPPED1 | PAK1 | ATP5B | PRDX5 |
| MMP14 | LGALS3BP | PARVB | RPL37A | CAT |
| C15orf48 | KLF4 | RARRES1 | RASSF4 | PTRHD1 |
| TRPM2 | WAS | IL5RA | S100A6 | CD72 |

TABLE 1D

| Neutrophils | Activated_CD4_cells_loFos | Activated_CD4_cells_hiFos | CD8_IELs | CD8_LP_cells |
|---|---|---|---|---|
| S100A9 | RPLP1 | IL32 | CCL5 | CCL5 |
| SOD2 | RPS3 | ANXA1 | CD7 | IL32 |
| IL1B | IL32 | KLF6 | GZMA | NKG7 |
| PLAUR | RPL10A | S100A4 | NKG7 | CCL4 |
| LST1 | RPS25 | CD69 | HOPX | GZMA |
| AIF1 | RPSA | DNAJA1 | IL32 | DUSP2 |
| SPI1 | RPL32 | HSPA8 | CKLF | CD8A |
| G0S2 | ANXA1 | CD3D | KLRC2 | SH3BGRL3 |
| LYZ | RPLP2 | RPLP1 | CD160 | CST7 |
| SAT1 | RPL19 | LTB | GZMB | CD8B |
| FPR1 | RPS19 | CCL5 | PTPRCAP | CD52 |
| TYROBP | TPT1 | CD52 | TMIGD2 | GZMK |

TABLE 1D-continued

| | | | | |
|---|---|---|---|---|
| FCER1G | RPS15A | ID2 | HCST | ZFP36L2 |
| SERPINA1 | RPLP0 | SH3BGRL3 | EVL | HCST |
| FTH1 | RPL13 | BTG1 | CD52 | HOPX |
| FCGR1A | RPL11 | TNFAIP3 | CD3D | PFN1 |
| S100A8 | RPL28 | TNFRSF25 | GNLY | TMSB4X |
| IGSF6 | RPS12 | CALM1 | CD3E | BTG1 |
| CFP | RPL13A | TSC22D3 | SH3BGRL3 | GZMB |
| IL1RN | RPL30 | EIF1 | RAC2 | CD3D |
| HLA-DRA | RPS27A | TMEM66 | CTSW | CD3E |
| CTSS | RPL4 | CD2 | PHGR1 | GZMH |
| TYMP | RPS14 | ZFP36L2 | IGJ | CKLF |
| FAM26F | RPS6 | RPS3 | TMSB4X | MYL12A |
| HLA-DQB1 | RPL23A | RPSA | GAPDH | CXCR4 |
| FGL2 | RPS2 | CD3E | CORO1A | CFL1 |
| CPVL | CD52 | TMSB4X | ABI3 | NR4A2 |
| STX11 | RPS18 | RPS19 | PRF1 | B2M |
| HLA-DRB1 | RPL6 | SRSF7 | ACTB | ARHGDIB |
| CD14 | LTB | HSP90AA1 | CD3G | LYAR |
| FTL | RPL27A | DUSP1 | ARHGDIB | ANXA1 |
| HLA-DPB1 | S100A4 | MYL12A | SIRPG | RPL28 |
| HLA-DQA1 | RPL10A | ARHGDIB | LCK | CTSW |
| COTL1 | RPL3 | ACTB | ACTG1 | TMEM66 |
| NCF2 | RPS16 | RPL28 | RARRES3 | C9orf142 |
| HLA-DRB5 | RPS5 | CORO1A | PFN1 | PSMB9 |
| LILRB2 | IL7R | RPLP2 | CD247 | RPLP2 |
| APOBEC3A | RPL31 | PFN1 | STK17A | RPS3 |
| EREG | RPL14 | ABRACL | CAPG | PTPRCAP |
| C1orf162 | UBA52 | IL7R | TBC1D10C | LAG3 |
| S100A11 | RPS15 | LEPROTL1 | XCL2 | CORO1A |
| CDC42EP2 | RPL18 | RAC2 | FABP1 | HLA-B |
| PLEK | SH3BGRL3 | B2M | ARPC2 | GZMM |
| MS4A7 | RPS20 | CD47 | CD96 | IFNG |
| LY86 | RPS13 | IFITM3 | C9orf142 | TUBA4A |
| HLA-DPA1 | RPL27 | APRT | LGALS4 | ID2 |
| IFI30 | RPS8 | HLA-DRA | FTH1 | S100A4 |
| HLA-DMB | EEF1B2 | RPLP0 | XCL1 | RPS19 |
| LGALS2 | RPS23 | IL2RG | CD8A | CD69 |
| ITGB2 | RPS4X | TPT1 | 1-Sep | CD7 |
| C5AR1 | RPL12 | RPL10 | CST3 | ACTB |
| SRGN | ARHGDIB | CD53 | AC092580.4 | HLA-A |
| CYBA | RPS3A | DNAJB1 | CFL1 | CD2 |
| TIMP1 | RPL35A | PTGER4 | CST7 | PSME1 |
| CD74 | RPL5 | ID3 | CLIC1 | ALOX5AP |
| CST3 | RPL15 | PPP2R5C | PPP1CA | RPL27A |
| CD36 | RPL37 | CD40LG | IL2RB | HSPA8 |
| TNFSF13B | RPL8 | HLA-DPB1 | ALOX5AP | LEPROTL1 |
| MS4A6A | TMEM66 | CKLF | TIGIT | SRGN |
| BID | RPL34 | RPS12 | RPS19 | HSPB1 |
| GBP1 | CD3D | RPS27A | IGLL5 | SRRT |
| GLRX | RPL29 | PHLDA1 | PLEKHF1 | RPS27A |
| NFKBIA | IGFBP7 | RPL19 | ACAP1 | RPL30 |
| MNDA | PTGER4 | FTL | PTPN6 | CXCR3 |
| CXCL10 | RPL35 | DRAP1 | P2RY11 | CALM1 |
| ACTB | CD3E | CD63 | ID2 | KLF6 |
| FCN1 | RPS7 | DEDD2 | MYL12A | RPL13A |
| IL8 | TOMM7 | GPSM3 | FASLG | CREM |
| ARPC1B | CXCR4 | DDX5 | CYTIP | BIN1 |
| HLA-DQA2 | MYL12A | 1-Sep | KLRD1 | RPL23A |
| PILRA | RPL18A | UBE2D3 | DRAP1 | APRT |
| LILRB1 | BTG1 | CFL1 | CD8B | RPS20 |
| FGR | RPL9 | GRN | CLIC3 | HLA-C |
| NINJ1 | RPL7A | PSMB9 | IFITM3 | CYBA |
| CD86 | TMSB4X | TPM3 | CXCR3 | ABRACL |
| LINC00877 | CD63 | CD48 | PPP1R18 | TC2N |
| OAZ1 | CORO1A | RPL14 | RPS4Y1 | 1-Sep |
| TREM1 | FAU | PDCL3 | ACTR3 | CD99 |
| ASGR1 | CD2 | SAMSN1 | GRN | EVL |
| HLA-DMA | TNFAIP3 | PSME2 | RGL4 | ICAM3 |
| TNFAIP2 | RPL36 | RPS6 | TPI1 | IFITM3 |
| ARPC3 | CCL5 | SRGN | COTL1 | LCK |
| CAMK1 | EEF1D | RPL32 | TRAPPC1 | C12orf75 |
| S100A4 | GPSM3 | ALOX5AP | KLRC1 | ARPC2 |
| CPPED1 | LDHB | RPS20 | HSPA1A | FYN |
| RAB20 | RPS9 | ARHGDIA | CIB1 | XCL1 |
| RIPK2 | LEPROTL1 | SOCS1 | PSMB10 | PRF1 |
| CXCL9 | PFN1 | DDIT4 | ITGA1 | PSAP |
| LAP3 | KLF6 | MIR24-2 | LAT2 | ATP5E |
| ATP6V0B | CALM1 | HLA-B | CD244 | YPEL5 |
| HCK | CD69 | HLA-DRB1 | ITGAE | DRAP1 |
| GCA | APRT | PGK1 | ENO1 | MCL1 |

TABLE 1D-continued

| | | | | | |
|---|---|---|---|---|---|
| RP11-290F20.3 | GLTSCR2 | LAPTM4A | BCAS4 | CRTAM | |
| LILRB4 | GPR183 | FDX1 | CDK2AP2 | PPP1CA | |
| CD37 | RPL26 | RPL27A | NFKBIA | RPLP1 | |
| PRELID1 | RPL36AL | RPS4X | PTMA | RPS15A | |
| RNASET2 | GIMAP7 | CITED2 | GIMAP7 | GSTK1 | |
| GCH1 | HSPB1 | PSME1 | RPLP2 | TIMP1 | |
| CYBB | ABRACL | RAN | NPC2 | CLIC1 | |
| NCF4 | PSAP | MALAT1 | ARPC1B | ID3 | |
| IL23A | HLA-DPB1 | H3F3B | VASP | TMA7 | |
| RP11-701P16.5 | RPL24 | RPS15A | LSP1 | PTPRC | |
| SERPINB9 | HLA-DRB1 | FOSB | HERPUD1 | PPP2R5C | |
| MPEG1 | PTPRCAP | CXCR4 | RGCC | RGCC | |
| CCL3 | KLRB1 | BCAS2 | PTPN22 | RNF167 | |
| CFD | IFITM3 | ALG13 | CISH | MYL12B | |
| UBE2D1 | HLA-DPA1 | LCK | MATK | PSME2 | |
| THEMIS2 | FTL | RPL11 | HSPA1B | HMOX2 | |
| STXBP2 | EVL | CDC42SE2 | SOCS3 | RPL13 | |
| ARRB2 | APOE | RPL13 | RPS3 | CD59 | |
| GPX1 | FXYD5 | CACYBP | RPL13A | SAMSN1 | |
| TIFAB | CD74 | IDS | PSME1 | RARRES3 | |
| CORO1A | HLA-DRA | GALM | PTPN7 | TRAPPC1 | |
| DUSP2 | DDX5 | CD6 | CD2 | TAPBP | |
| TESC | RPS4Y1 | CCL20 | ASB2 | SH3KBP1 | |
| CD68 | RGCC | RPS2 | OSTF1 | APOBEC3G | |
| SPHK1 | TC2N | RPL31 | DOK2 | GLIPR2 | |
| KYNU | HSPA1A | UBE2D2 | ITGB7 | PSMB10 | |
| BCL2A1 | CMPK1 | IL4I1 | MT-CO1 | DHRS7 | |
| GLUL | CD6 | SLAMF1 | CD59 | RPL19 | |
| BLVRA | IL2RG | FOS | TNFRSF18 | TSC22D3 | |
| KDM6B | SRGN | MGAT4A | RPLP1 | MALAT1 | |
| NAMPT | NPM1 | TRMT112 | FCER1G | STK17A | |
| SLC31A2 | TSC22D3 | FAM96B | LAG3 | DENND2D | |
| NUP214 | PDCL3 | IL12RB1 | HSPB1 | RPL31 | |
| ABI3 | ZFP36L2 | SVIP | ARL6IP5 | ITM2A | |
| SELK | CD59 | CCR6 | WAS | CDK2AP2 | |
| PSAP | CFL1 | RPL36AL | BUB3 | MZT2A | |
| SAMSN1 | SOCS1 | PLP2 | RGS1 | RGS1 | |
| PPIF | NACA | CYCS | CD69 | SOCS1 | |
| ATF5 | RPL38 | TTC39C | SLC16A3 | GUK1 | |
| AMICA1 | CKLF | HLA-DPA1 | HLA-DRA | GRAP2 | |
| IGJ | CD37 | NOP58 | RPS3A | C19orf60 | |
| ITM2C | SH2D2A | ENO1 | PTTG1 | TNFAIP3 | |
| YBX1 | GNB2L1 | MYADM | LDLRAD4 | IL2RG | |
| ACSL1 | IGJ | RPS25 | CD53 | DDX5 | |
| RNASE6 | BTF3 | HNRNPA0 | PSAP | EEF1D | |
| ZFAND5 | NPC2 | JUN | PTGER2 | RPS12 | |
| GRN | CXCL14 | YPEL5 | SH3BP1 | ARPC1B | |
| WAS | CCDC109B | PPP1R15A | CHMP4A | PTGER4 | |
| TNFAIP8 | LGALS1 | SERP1 | IDH2 | ZNF331 | |
| JUN | HSPA8 | RPS14 | RPS27A | BUB3 | |
| ASGR2 | CRIP1 | EVL | LSM2 | RBM8A | |
| CXCL2 | HSPA1B | PSAP | EEF1A1 | CAP1 | |
| FCGR1B | CCR6 | FAU | HCLS1 | RPS18 | |
| LIMD2 | RPS29 | RPL13A | MYL12B | 7-Sep | |
| DOK2 | PFDN5 | PTPRCAP | CRIP1 | C19orf24 | |
| PFN1 | TTC39C | TAGAP | PABPC1 | HLA-DRB1 | |
| LILRA2 | RPS21 | DHRS7 | LYAR | FAM177A1 | |
| PYCARD | C9orf142 | H2AFZ | FYN | CRIP1 | |
| ISG15 | RPL37A | AMD1 | BIN1 | ABT1 | |
| KMO | RPL17 | CD74 | RGS19 | CXCL14 | |
| IL10 | PABPC1 | ODF2L | DEF6 | RPS25 | |
| CTSH | EIF1 | SND1 | RPL18A | SNRPB | |
| CD48 | GSTK1 | OSTF1 | IFI27 | RPS2 | |
| RTN1 | ARL4A | ERP29 | LCP1 | EIF1 | |
| IKZF1 | YPEL5 | PNP | HENMT1 | CTSB | |
| SH3BGRL3 | CD7 | ARL4A | CXCR6 | BAX | |
| C19orf38 | HCST | RPL30 | RPL9 | MFSD10 | |
| RIN3 | LAPTM5 | MRPL11 | FCGRT | RPL36AL | |
| PSME2 | ITM2C | AATF | RPS10 | RORA | |
| HCLS1 | ID2 | RPL4 | CCL4 | SRSF7 | |
| CD83 | FYB | MCL1 | RPS27 | HNRNPUL1 | |
| AP1S2 | TUBA4A | JUNB | APOBEC3G | COPE | |
| LCP1 | 1-Sep | BAZ1A | CD99 | FTL | |
| ITGAX | RPL22 | EIF4A3 | TPM3 | C9orf78 | |
| PKM | RORA | CREM | RPL17 | PDCL3 | |
| CFL1 | LAPTM4A | SRSF2 | GYPC | TAGAP | |
| VAMP8 | PLD3 | RPS5 | GSTK1 | UBE2D3 | |
| IFNGR2 | SNRPD2 | MRPL34 | IL2RG | C14orf1 | |
| NPC2 | METTL9 | SNHG8 | ATP5E | PLP2 | |
| RILPL2 | B2M | C9orf142 | GYG1 | GPSM3 | |

TABLE 1D-continued

| | | | | |
|---|---|---|---|---|
| GPBAR1 | CACYBP | MTFP1 | FOSB | UBE2L3 |
| CSF1R | SAMSN1 | RPS8 | SASH3 | GPR65 |
| OSM | HIGD2A | PRR5 | C19orf53 | ATP6V0E1 |
| CCRL2 | ARPC1B | ACTG1 | 7-Sep | RAC2 |
| CLEC10A | 9-Sep | CHCHD7 | FXYD3 | KLRD1 |
| IL4I1 | GPR171 | RPS13 | TSEN54 | HLA-DRA |
| CD52 | AES | PTGER2 | COMMD8 | EBP |
| SYK | LAT | HSPE1 | CYBA | RPSA |
| CHMP1B | ACTB | TC2N | PSME2 | TMUB1 |
| NLRP3 | NKG7 | SAP18 | EGR1 | RNF149 |
| HBEGF | DYNLT3 | RORA | CD74 | HLA-DQA1 |
| CCL3L1 | TRAT1 | CCDC109B | GZMM | GAPDH |
| IFI27 | EIF3E | CDK2AP2 | CAPN12 | STUB1 |
| IL27 | RARRES3 | UBE2S | SPINT2 | SNRPD2 |
| ATP6V1F | OXNAD1 | LAT | C9orf78 | CSNK1D |
| ARHGDIB | SERPINB6 | CD97 | POLR3GL | HSPA1A |
| TMSB10 | SPINT2 | GSTK1 | PDLIM1 | RPL14 |
| VSIG4 | COMMD6 | PSENEN | C9orf16 | RALY |
| ANXA2 | HNRNPA1 | LDHA | GUK1 | RPL22L1 |
| VASP | ACP5 | EIF4A1 | CCND2 | FAM96B |
| PPDPF | RAP1A | FUS | GPR68 | TOMM7 |
| ARL5B | RPSAP58 | HNRNPUL1 | TNFSF14 | SNRPB2 |
| MT-CYB | EEF1A1 | C14orf166 | RHOC | METTL5 |
| GBP5 | CREM | SPINT2 | IL16 | RPL32 |
| PSTPIP2 | RCAN3 | SURF4 | SLC9A3R1 | PNN |
| GPR183 | CD48 | MZT2A | MIF | MBP |
| HCAR2 | SPOCK2 | CXXC1 | MT-CYB | CLDND1 |
| SAMHD1 | TNFSF13B | PCBP1 | TTC1 | GTF3A |
| HAPLN3 | EIF3H | RPS18 | SAT1 | ATF6B |
| CAPG | SAT2 | ANXA5 | TSC22D4 | CDC42SE2 |
| EPSTI1 | LYAR | HMGN1 | LAPTM4A | ALG13 |
| RNF130 | PLP2 | HCST | SCML4 | RPS16 |
| ID3 | MZT2A | PSMA7 | PTPN4 | RBCK1 |
| CREM | MGAT4A | LAPTM5 | COMMD6 | CD9 |
| LITAF | SMDT1 | TIMP1 | HLA-DRB5 | CD74 |
| CXCL3 | ANXA5 | EML4 | RP11-47L3.1 | PHGR1 |
| PLA2G7 | ENO1 | AMICA1 | SSNA1 | EPSTI1 |
| UBE2E2 | TMEM14B | ICAM3 | CASP4 | CD53 |
| H2AFY | PSME1 | IL17A | CTSB | OAZ1 |
| UBXN11 | CYCS | EIF1AX | ARPC3 | PPP1R18 |
| RGS2 | ATP5L | DYNLT3 | APRT | RPS14 |
| RHOG | RBM3 | IFITM2 | RPL7 | CSRNP1 |
| CASP1 | ICAM3 | PRKCQ-AS1 | VAMP8 | BLVRB |
| CD274 | ALOX5AP | RBL2 | RPL4 | RPL27 |
| HCAR3 | C19orf24 | HSP90B1 | HLA-DQB1 | RPL3 |
| LINC00936 | GMFG | SNRPB | FAM173A | OXNAD1 |
| TUBA1B | NEAT1 | FERMT3 | SLA2 | NEDD8 |
| IL18BP | EGR1 | GHITM | GPR171 | C11orf31 |
| C12orf57 | PTPRC | SELT | SAMSN1 | HSPA9 |
| EMG1 | CD97 | NFKBIA | PSMB9 | TPM3 |
| PTGS2 | UBE2D2 | RPS16 | CD37 | CHMP4A |
| MYO1F | TXNIP | RPL22L1 | ANAPC16 | PSENEN |
| NADK | GTF3A | ISG20 | RPL21 | MLX |
| RABAC1 | RPS11 | SNRPD2 | RPSA | RPL34 |
| A2M | PPP2R5C | IFI35 | HMOX2 | CIB1 |
| GDI2 | SNRPG | CASP1 | LSM10 | OCIAD2 |
| GLIPR1 | TMA7 | NPC2 | PSMD13 | SLC38A1 |
| HSPB1 | RPL22L1 | SLC1A5 | PGK1 | TADA3 |
| DSTN | IFITM2 | TRAPPC1 | TYROBP | IDH2 |
| NMI | DUSP2 | TUBA4A | HLA-DRB1 | GHITM |
| CD9 | RPL23 | MAX | C11orf48 | NHP2L1 |
| DUSP1 | SCML4 | UXT | RPL28 | ATP5D |
| MCL1 | C19orf53 | HSPB1 | GGA1 | ACADVL |
| BSG | GGA1 | RBM3 | EEF1D | ATP8A1 |
| MT-ND3 | MZB1 | RAB8A | LAPTM5 | GATA3 |
| RNF19B | ARHGEF1 | TAPBP | GPR34 | NAA50 |
| GLIPR2 | HERPUD1 | RPL23A | TSTA3 | AKR1A1 |
| PSMB9 | JUN | EMP3 | BANF1 | CD97 |
| GAPT | PHLDA1 | UBA52 | CDIP1 | MZB1 |
| NAGK | PRKCQ-AS1 | CRIP1 | C11orf31 | MEA1 |
| C10orf54 | ZFAS1 | NR4A2 | STXBP2 | PSMB8 |
| CTSB | EEF2 | TAP1 | RPL22 | MYEOV2 |
| CD53 | COTL1 | SS18L2 | CALM1 | UBE2I |
| CSF3R | TRAPPC6A | FLT3LG | RPL36A | ZFP36 |
| SCIMP | CTSD | GPR183 | NUDT14 | FIBP |

TABLE 1D-continued

| MT-ND4 | NDUFS5 | IRF1 | IRF2 | C14orf166 |
|---|---|---|---|---|
| PSMA4 | CLIC1 | CXCR3 | MRPL46 | SIGIRR |
| HCST | RPS24 | PPP6C | YPEL5 | RPL10 |

| Tregs | Memory_T_cells | NK_cells | Cycling_CD8_cells | Inflammatory_CD2_DCs |
|---|---|---|---|---|
| IL32 | LDHB | NKG7 | CD3D | LST1 |
| CORO1B | RPL11 | TYROBP | CD3E | IL4I1 |
| BATF | CCR7 | FCER1G | NKG7 | KRT86 |
| TIGIT | RPS12 | XCL2 | CD2 | LTB |
| PFN1 | RPL32 | CTSW | CCL5 | FXYD5 |
| BTG1 | RPS3 | XCL1 | CD7 | ALDOC |
| CD3D | RPL19 | CLIC3 | IL32 | KRT81 |
| ARHGDIB | RPLP2 | IL2RB | GZMA | ID2 |
| CREM | RPL13 | GZMB | CST3 | LTA4H |
| ICA1 | RPS15A | CCL4 | ITM2A | NFKBIA |
| C9orf16 | RPS14 | GSTP1 | TUBB4B | ZFP36L1 |
| DNPH1 | RPL23A | KLRC1 | CTSW | CASP3 |
| TNFRSF4 | RPL31 | MATK | PTPRCAP | TNFRSF25 |
| CARD16 | RPSA | APOBEC3G | GZMB | HSPA8 |
| RAP1A | RPS4X | CST7 | VIM | MIR24-2 |
| LTB | RPL18 | GZMA | CD8A | LIF |
| ARPC1B | RPS6 | GNLY | CD8B | TYROBP |
| CTLA4 | RPS13 | GZMK | B2M | DUSP1 |
| NDUFV2 | RPL28 | CD7 | CD96 | NXT1 |
| FOXP3 | RPL27A | KLRD1 | AC092580.4 | HNRNPA0 |
| PMVK | RPS2 | HCST | SH3BGRL3 | MPG |
| PBXIP1 | RPS25 | EIF3G | CD3G | HMGN3 |
| LCK | LTB | PFN1 | RGL4 | CXCR4 |
| CD63 | RPS18 | PRF1 | LGALS1 | NR4A1 |
| BIRC3 | RPL30 | FGR | FCGRT | CSF2 |
| PTPRCAP | RPL4 | KRT81 | HCST | PRMT10 |
| ITM2C | RPS9 | HOPX | PLA2G16 | CD83 |
| UCP2 | RPL35A | CAPG | TMIGD2 | DNAJA1 |
| IL2RG | RPS27A | CCL3 | IFNG | H2AFY |
| AC017002.1 | RPS8 | KLRF1 | RAC2 | SRSF2 |
| SRGN | RPL10A | MAP3K8 | GYPC | TMIGD2 |
| LGALS1 | GNB2L1 | SRGN | SPINT2 | OTUD5 |
| CD44 | CD63 | IFITM2 | LGALS4 | CD300LF |
| CALM3 | RPS23 | CD3D | HLA-DRA | SPINK2 |
| DUSP4 | RPS20 | STK17A | CD69 | TPT1 |
| RGS1 | RPL14 | FAM177A1 | LY6E | TLE1 |
| TNFRSF1B | RPL36 | PTP4A1 | LDHA | DLL1 |
| MIR4435-1HG | RPL37 | ITGB2 | ARHGDIB | PTGDR |
| LAIR2 | RPL13A | CCL5 | GIMAP7 | NCOA7 |
| ICOS | IL32 | BTG1 | SRGN | CD52 |
| TNFRSF18 | RPL27 | NR4A2 | TBC1D10C | AMICA1 |
| HLA-A | PABPC1 | APMAP | CD52 | MAFF |
| ACTB | RPL26 | DUSP2 | RPL8 | BIRC3 |
| SPOCK2 | RPL8 | PTGDR | EPCAM | JUNB |
| ANKRD12 | SELL | GZMH | RARRES3 | TOX2 |
| EIF3H | RPS21 | CORO1A | CD9 | DRAP1 |
| GSTP1 | RPL5 | KRT86 | H2AFZ | CD69 |
| B2M | RPS15 | CD160 | ATPIF1 | IL23R |
| CORO1A | RPL10 | LAT2 | MSN | ARL4A |
| CD27 | LGALS1 | ID2 | APOBEC3G | TCIRG1 |
| CCL5 | RPS16 | MIB2 | GZMM | UBB |
| LAT | BTG1 | ALOX5AP | SLC9A3R1 | IER2 |
| PKM | RPL34 | BCO2 | CDKN2A | CAT |
| PPP1R18 | RPL29 | NCR3 | COX5B | EIF1 |
| ANXA1 | RPL12 | ARPC5L | C15orf48 | AREG |
| EEF1D | TMEM66 | MYL12A | ICAM3 | FOSB |
| HINT1 | FXYD5 | FTL | TXN | ZFP36 |
| IL10 | ARHGDIB | CD97 | CD37 | TCP1 |
| RAC2 | RPS5 | PPP1R2 | SKAP1 | CD164 |
| ASB2 | RPLP1 | CD247 | PIM1 | DDX3X |
| LAG3 | RPS7 | GLIPR2 | SLA2 | METTL9 |
| FOS | EEF1B2 | CLIC1 | TRAT1 | ZNF75A |
| ATP5L | RPS19 | SLC35E1 | CXCR3 | C16orf91 |
| TBC1D4 | CD52 | 7-Sep | TCEA2 | NR4A2 |
| COTL1 | FAU | CHST12 | PRKCH | TNFRSF18 |
| RPL28 | RPL7A | CDC42SE1 | ATP5B | MAP3K8 |
| RHOH | GLTSCR2 | C20orf24 | EMP3 | TEX30 |
| NINJ2 | NOSIP | LSP1 | MARCKSL1 | BZW1 |
| RHOG | NPM1 | SAMD3 | HLA-DRB1 | H3F3B |
| GMFG | LEF1 | PTPRCAP | HLA-B | DDX18 |
| CST3 | RPL6 | HSPB1 | PEBP1 | MRPL18 |
| CD52 | ZFP36L2 | ABHD17A | TRAF3IP3 | PRPF6 |
| PPP1R2 | RPL15 | RGCC | ATP5G1 | PRAM1 |
| UBE2D2 | EIF3E | CD44 | RPL37A | SLC43A2 |

TABLE 1D-continued

| | | | | |
|---|---|---|---|---|
| FYB | TCF7 | MAPK1 | HLA-DPB1 | RAN |
| TNFRSF9 | HINT1 | LDLRAD4 | PRF1 | FCER1G |
| PTTG1 | RPS29 | ACTB | HOPX | MGAT4A |
| CD2 | RPLP0 | EVL | GSTP1 | SLC25A39 |
| TRAF3IP3 | UBA52 | TMIGD2 | PDLIM7 | NFKBIZ |
| NTMT1 | LEPROTL1 | MRPL3 | CST7 | BLVRA |
| RPS15A | RPL22 | GZMM | GRN | FOS |
| ADTRP | RPL38 | ZFP36L2 | HLA-DPA1 | RNASET2 |
| CACYBP | ITM2C | NUDT14 | IFITM2 | IL2RG |
| S100A4 | HSPA1A | TESC | LCK | EIF4A1 |
| GPR183 | RPL3 | SH2D1B | EVL | LINC00299 |
| JUN | TRAT1 | CHD2 | GZMK | EMP3 |
| ENO1 | EEF1D | FAM49B | SIRPG | DNAJB1 |
| UBC | EEF2 | VDAC1 | LGALS3 | IL7R |
| TNIP2 | BTF3 | BIN2 | NANS | BST2 |
| 1-Sep | LGALS3 | ARHGDIA | CD74 | CREM |
| EVL | SMDT1 | CDHR1 | CYC1 | SLC16A3 |
| CXCR6 | PFDN5 | SIGIRR | AGR2 | KIAA1324 |
| HSPA8 | TOMM7 | VPS37B | HLA-C | UNC93B1 |
| TAPSAR1 | HNRNPA1 | TNFRSF18 | SH2D1A | ENO1 |
| GNB2L1 | EIF3F | GRK6 | LAPTM5 | SKIL |
| XRCC6 | CCDC109B | DUSP1 | SLC25A5 | RNF139 |
| CYTIP | PTPRCAP | ZFP36 | CORO1A | HSP90AA1 |
| CD37 | CD3D | SELM | HLA-A | BEX2 |
| RPL13A | CD37 | IDS | HSPD1 | TMEM243 |
| NSA2 | RPL23 | PRDX1 | RPL36 | DDIT4 |
| CD3E | RPS3A | RHOF | IL2RB | RBM39 |
| HMGN1 | PSAP | LGALS3 | LSP1 | SIK1 |
| TRAPPC4 | GIMAP7 | CFL1 | TSPAN5 | PSMD13 |
| TRAPPC1 | RPL24 | CMC1 | GCHFR | RASD1 |
| SH2D1A | LIMD2 | RNF113A | ATP5G3 | AQP3 |
| TIMP1 | RPL37A | IL2RG | HIST1H4C | MED30 |
| ARID5B | RPL9 | TIMM8B | GPX2 | HHEX |
| SKAP1 | RPS11 | FASLG | RPL38 | ZNF331 |
| DOK2 | TRAF3IP3 | TMSB4X | SAMSN1 | BTG2 |
| SNRPB | RPS24 | SRSF5 | COX5A | RPL22L1 |
| ISG20 | PASK | LAMTOR5 | HN1 | NCR3 |
| TNFRSF14 | TPT1 | AKNA | HLA-DQA1 | MYADM |
| FXYD5 | NACA | USF2 | ATP5O | LPXN |
| CDKN2A | CORO1A | RAC2 | UQCR10 | RBPJ |
| RPL36AL | COX7C | NDUFB8 | UBE2C | UBE2S |
| PCBP1 | IFITM3 | SDHC | GMFG | DPAGT1 |
| LAPTM5 | EIF3H | RANGRF | GNG2 | NHP2 |
| PTPN2 | CXCR4 | KLRB1 | FYN | CYCS |
| UXS1 | ANAPC5 | PSMB2 | HES1 | PRR5 |
| PMAIP1 | RPL18A | SLC16A3 | GNLY | CCT4 |
| UGP2 | CD7 | RIN3 | ID2 | HMGN1 |
| 9-Sep | DENND2D | RBM38 | UQCRQ | BCAS2 |
| ARF6 | MZT2A | IDI1 | XCL1 | BTG1 |
| CMC2 | RPL35 | UBXN2B | HLA-DMA | MAP2K1 |
| LIMD2 | FAIM3 | LINC00667 | RPS29 | CXXC5 |
| PSME1 | OCIAD2 | CST3 | ANXA1 | ATG4B |
| LEPROTL1 | GPSM3 | PPP5C | RGCC | SFPQ |
| TMSB4X | C6orf48 | ID3 | CCNB1 | SRGN |
| IGBP1 | UBB | DRAP1 | BST2 | NPC2 |
| PYHIN1 | RNF138 | NFKBIA | ATP5A1 | TUBA4A |
| BCAS2 | CYTH1 | CCNL1 | CLEC2D | CALM1 |
| PHLDA1 | SERPINB6 | NXT1 | ECHS1 | TXK |
| PRR13 | CCL5 | ARID5A | CCNB2 | SPTLC2 |
| ZNHIT1 | FAM177A1 | AGTRAP | ATP5J2 | ANP32A |
| SOD1 | DCXR | ARHGDIB | TNFRSF18 | CCR6 |
| MAPK1IP1L | NUCB1 | CBX3 | CKS2 | PROSC |
| OSER1 | DAP3 | TCEB2 | NCAPH | TXNL1 |
| CASP4 | P4HB | RPS3 | RPL5 | TRAF4 |
| RGCC | FYB | ZNF814 | RAC1 | HSP90AB1 |
| NAMPT | HLA-DPA1 | LINC00996 | ARPC1B | SRSF5 |
| 6-Sep | FOSB | PSMA7 | ABI3 | SLA |
| IDI1 | 6-Sep | CD69 | GPX1 | RNF19B |
| GBP2 | CHI3L2 | YPEL3 | MT1G | COL9A2 |
| SSU72 | ID3 | APRT | CYTIP | NFKB1 |
| COPE | CST3 | HMGN1 | SURF4 | PPP2CA |
| YWHAZ | ARPC1B | CPNE1 | CTSH | NAP1L1 |
| COMMD3 | JUNB | IGFBP7 | FXYD5 | SRP9 |
| GLRX | RARRES3 | PPP1CA | PFKP | BEX4 |
| RBBP4 | BEX2 | YWHAZ | CRIP1 | TMEM123 |
| PTPRC | ICOS | EBP | ZAP70 | TUBB4B |
| HIGD2A | HLA-DRB1 | MIR24-2 | ICOS | LGALS3BP |
| SMS | IFITM1 | ZNF331 | MT1E | TNF |
| CCL20 | PFN1 | GCHFR | RPL12 | HSPD1 |
| ANP32A | CD3E | TRAPPC1 | RORA | SAMD10 |

TABLE 1D-continued

| | | | | |
|---|---|---|---|---|
| NPM1 | TBC1D10C | DDIT4 | IL2RG | CSTB |
| NAPA | RNASET2 | GRB2 | IFI16 | CRIP1 |
| APOE | EIF2S3 | OCIAD2 | ETFB | CD47 |
| RPL15 | CASP8 | MPG | UPP1 | EMC10 |
| HSPB11 | FXN | RALA | ATP5J | SACM1L |
| ACTR3 | CYLD | C19orf25 | S100A4 | ANXA5 |
| CDC42SE2 | SC5D | SNRPA1 | PSMB9 | IFI44L |
| TMEM66 | LMNA | BUB3 | STK17A | CAPG |
| SNX5 | MAL | PLAC8 | RPS14 | FAM213B |
| CHCHD10 | AIM1 | PDCD4 | KRT19 | EIF3D |
| ICAM3 | TMSB4X | SLC25A39 | TIMM13 | EIF4G2 |
| JUNB | MRPL16 | RPL7L1 | CD247 | ERBB2IP |
| LIMSI | COTL1 | NSMCE1 | RPS4Y1 | ARF1 |
| EPSTI1 | CRLF3 | BUD31 | RPL7A | PARL |
| C19orf43 | H2AFV | PAPOLA | TMSB4X | HSPA5 |
| PIM2 | AAK1 | CALM1 | RPS18 | ZFAS1 |
| LINC00152 | SLC2A3 | MRPS11 | GZMH | GSN |
| GTF3C6 | CTSD | C1orf162 | SRI | WDR45B |
| SOCS1 | AC013264.2 | PSME2 | PIGR | TPM3 |
| RPL11 | TMSB10 | LDHB | KRT18 | SERTAD2 |
| UFC1 | 1-Sep | CD59 | COX4I1 | CA13 |
| TSC22D1 | IGBP1 | RBCK1 | CCL4 | AKAP17A |
| ARPC4 | RPS4Y1 | GRN | CENPW | CUTA |
| NUDT1 | ZFP36 | BCAP31 | STOM | CDC42SE1 |
| ANAPC16 | COMMD6 | AIM1 | CREM | PRKAR1A |
| TPRKB | DNMT1 | TGFB1 | PTTG1 | EPS8L2 |
| PHGR1 | GIMAP4 | TIPARP | RPL35A | H2AFX |
| WDR1 | CXCL14 | MYO1F | FKBP11 | CXCL2 |
| RPS2 | YPEL5 | SF3B2 | PHB | ALG13 |
| CD58 | WHSC1L1 | NDUFS8 | PTGER2 | SNRPB |
| DDX5 | ZNF331 | RTN3 | SUCLG1 | B3GALT5 |
| RPS27A | CD27 | NDUFA3 | ACAP1 | NRBP1 |
| SMCO4 | GSTK1 | PPP1R14B | AIP | AUP1 |
| EEF2 | SSU72 | PTMA | PLEKHF1 | GPATCH3 |
| LDHB | HLA-DPB1 | SH2D1A | UQCR11 | TRIAP1 |
| CUTA | SPOCK2 | PIGX | HSPE1 | SF1 |
| TNIP1 | TIMP1 | PTPN4 | TPM1 | GPR65 |
| SKP1 | SLC25A6 | JAK1 | HINT1 | VEZT |
| ITM2A | C1orf228 | IRF8 | DBI | PCBP1 |
| HCLS1 | LCK | TADA3 | CCND3 | NR1H2 |
| HLA-G | NAA38 | HSPE1 | ITK | FKBP3 |
| GYPC | DCK | GGA1 | RPS6 | TNFRSF4 |
| RPS3 | GPR18 | RTCA | CLDN7 | CD3E |
| SH3BGRL3 | CTSC | TLN1 | CD53 | GPR68 |
| RPS27L | HERPUD1 | TRMT2A | EEF2 | TNFSF4 |
| GPX1 | TPI1 | PSTPIP1 | SH2D2A | H2AFZ |
| SNRPB2 | RGCC | GGNBP2 | COX6B1 | PSME1 |
| AKIRIN2 | LINC00861 | NHP2 | HMGA1 | JMY |
| PSMD8 | CD59 | PSD4 | RNF187 | NUP54 |
| COX17 | EVL | RTFDC1 | NDUFA11 | XCL1 |
| UBE2I | CORO1B | PSMD6 | HMGN1 | GNA15 |
| SELT | CYCS | DCXR | STMN1 | LTC4S |
| IL2RA | ZNHIT3 | TSPAN32 | UQCRC2 | TXNDC17 |
| FAIM3 | TOMM20 | CUTC | LAT | GATA3 |
| GK | TUBA4A | ATP6V1G1 | HLA-DQB1 | N4BP2L2 |
| NAA38 | 9-Sep | IFITM1 | AK2 | CTSH |
| PSMA2 | DGUOK | C19orf66 | WDR54 | SLC39A4 |
| SNRPD2 | LYRM4 | PPP1R18 | RPS24 | PER1 |
| RPL24 | FTL | TMEM14C | TSC22D3 | AC022182.3 |
| PIK3IP1 | JUN | ALKBH2 | MTPN | HCST |
| ID3 | LAT | POLR2L | MYO1G | PCDH9 |
| SLAMF1 | PIK3IP1 | METRNL | KLRG1 | TPI1 |
| RPL18 | OAZ2 | SERBP1 | NRM | RP11-425D10.10 |
| UBXN1 | FOS | C9orf16 | FOSL2 | SERTAD1 |
| FTL | HSPB1 | BHLHE40 | 1-Sep | KIT |
| H2AFV | AES | TSC22D4 | PRDX5 | ERGIC3 |
| CMTM7 | COX4I1 | S100A6 | SSBP4 | ZNF814 |
| LINC00649 | LRRFIP1 | RBM39 | RPS13 | FOSL2 |
| RPL34 | RAB1A | RNF125 | GIMAP1 | LYPLA2 |
| HSD17B10 | MALAT1 | MAFF | MPC2 | SIVA1 |
| BAX | RILPL2 | SLC9A3R1 | COX7C | JTB |
| CLPP | HLA-DRA | STXBP2 | GMNN | ANP32E |
| HSPA1B | GTF3A | CLDND1 | GNB2L1 | RNFT1 |
| CD7 | ABHD14B | AP2M1 | PABPC1 | EIF5 |
| RPS25 | ACP5 | PSMD8 | HLA-DRB5 | BAD |
| HLA-DRA | CHCHD7 | VAPA | FAM162A | PNP |
| ZNF706 | RAN | SOCS1 | OASL | HNRNPK |
| RPL12 | CD74 | HNRNPA2B1 | OSTF1 | MGMT |
| DCXR | VAMP2 | DHRS7 | DOK2 | TCTN3 |
| CUL9 | APRT | AKIRIN2 | C1QBP | C6orf57 |

TABLE 1D-continued

| | | | | |
|---|---|---|---|---|
| RNF213 | C19orf43 | COA5 | LIMD2 | PCNP |
| ZC2HC1A | TSC22D4 | COMMD6 | CD160 | TP53I13 |
| ALDOA | BRMS1 | ATG12 | TUBB | C3orf17 |
| G3BP2 | RASAL3 | ARPC2 | RPL24 | MRPS15 |
| HCST | NDUFS6 | KLHDC4 | DDT | GPX7 |
| CIB1 | NPC2 | LRRFIP1 | GTPBP1 | CASP6 |
| PDCL3 | LSM14A | APOBR | ATP2B4 | HLA-B |
| SSBP1 | CCDC104 | ETF1 | NDUFC1 | CRTC2 |
| CCT7 | WDR82 | CASP4 | RAB27A | MBOAT7 |
| HPRT1 | MEA1 | CASP3 | PRDX3 | TNFAIP3 |
| PTGES3 | GADD45B | CD53 | CXCR6 | DCAF11 |
| MRPS35 | ANXA2 | U2AF1 | RPL23 | SRSF7 |
| SRP19 | CD28 | TSEN15 | CDC20 | PPP1R11 |
| HSP90B1 | FCGRT | AOAH | NASP | ZNF207 |
| BUB3 | LINC00649 | HLA-DPA1 | RHOF | FURIN |
| BTG3 | PHGR1 | OBFC1 | CDKN3 | WDR83OS |

Figure 5:
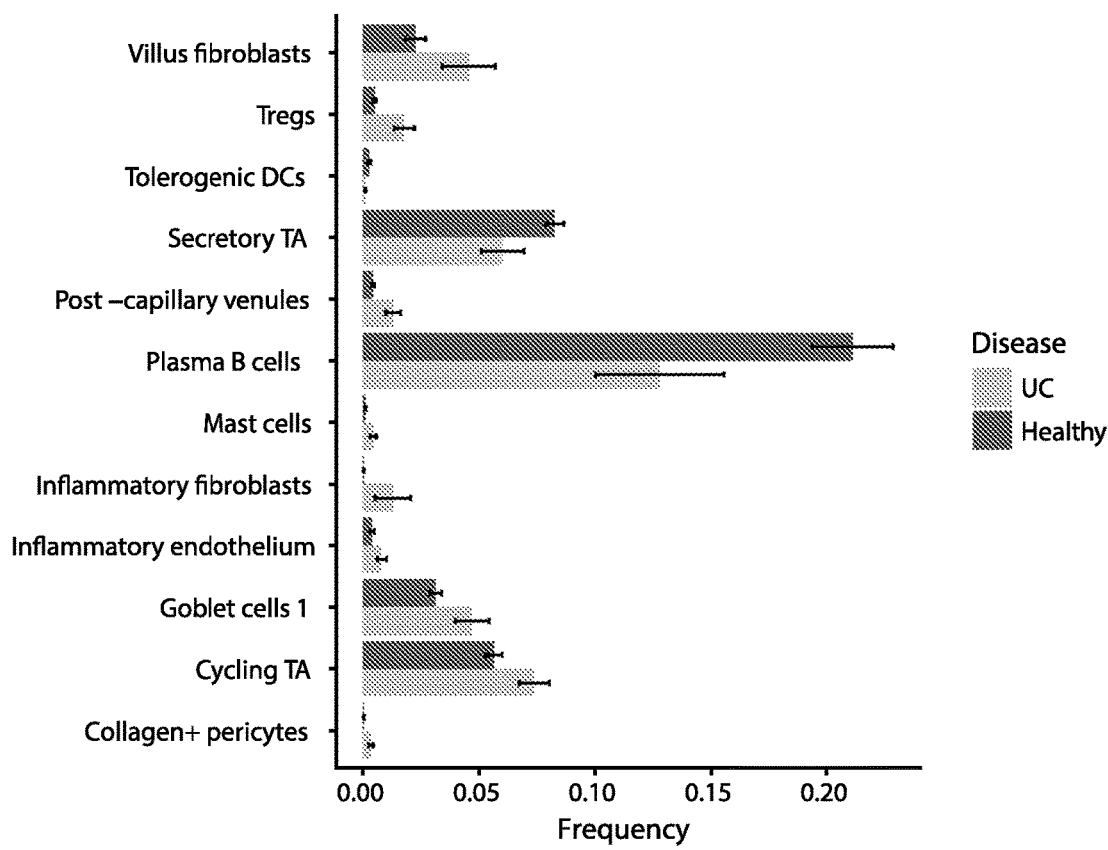
FIG. 5—illustrates the changes in cellular composition in UC.
Figure 6:
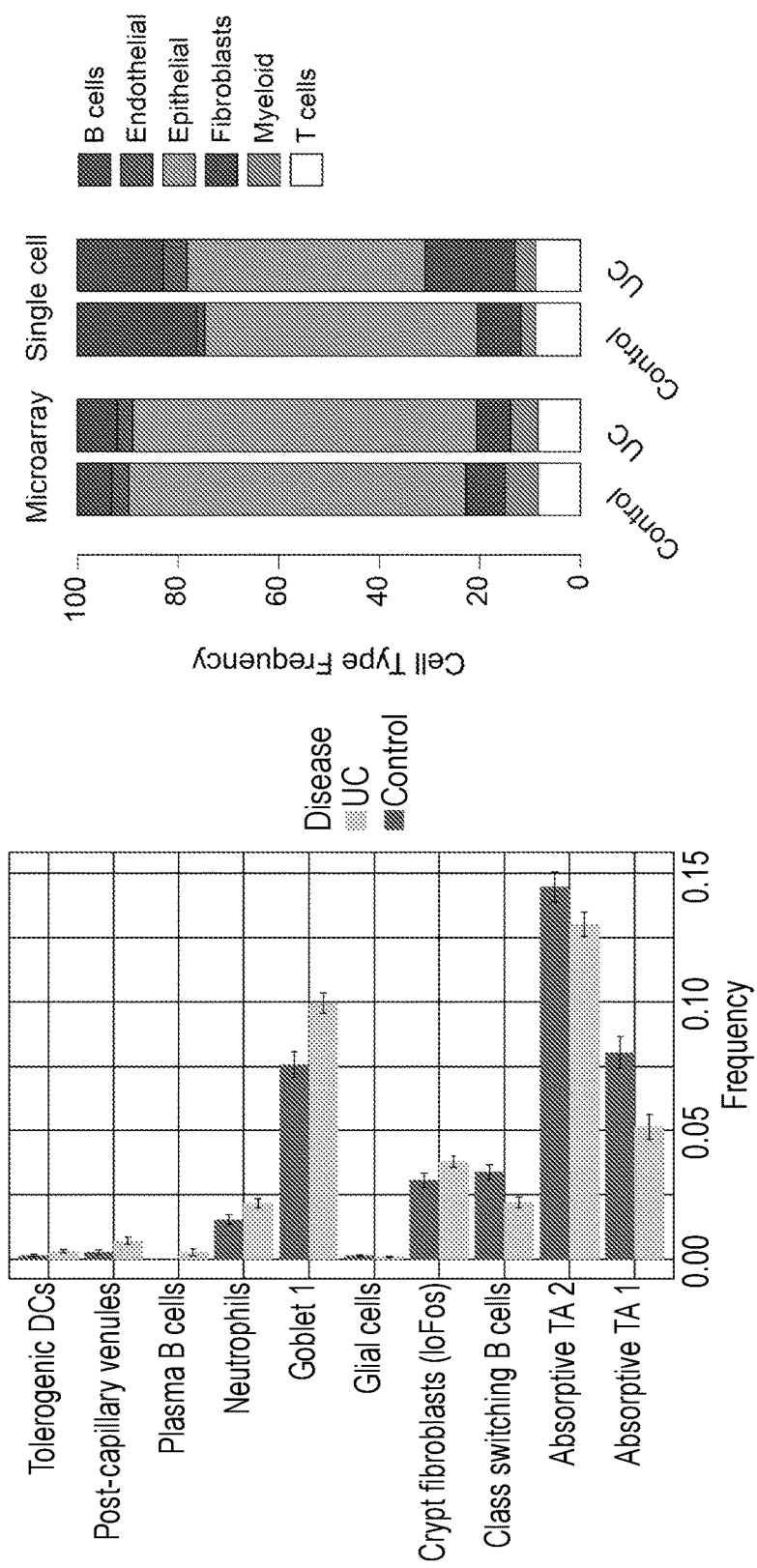
FIG. 6—illustrates that the atlas can be used to analyze compositional changes by deconvolution of bulk profiles.

FIGS. 5 and 6 show that the cell composition changes between UC and healthy controls. Applicants can use the expression profiles to deconvolute bulk expression data. Thus, Applicants can determine the cell composition of a colonoscopy sample obtained from a subject and analyzed by RNA-seq.

Figure 7:
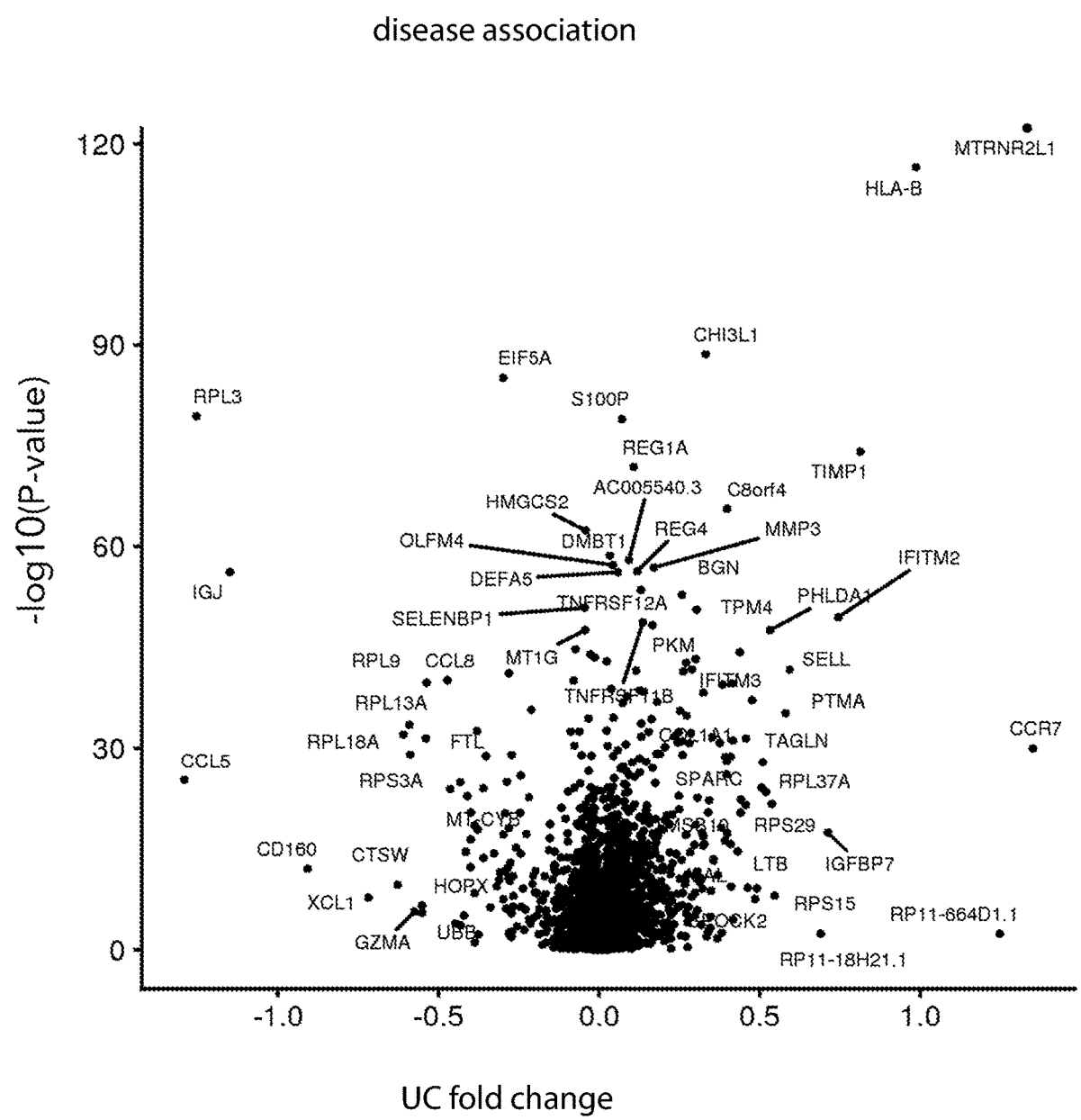
FIG. 7—illustrates genes differentially expressed in UC.
Figure 8:
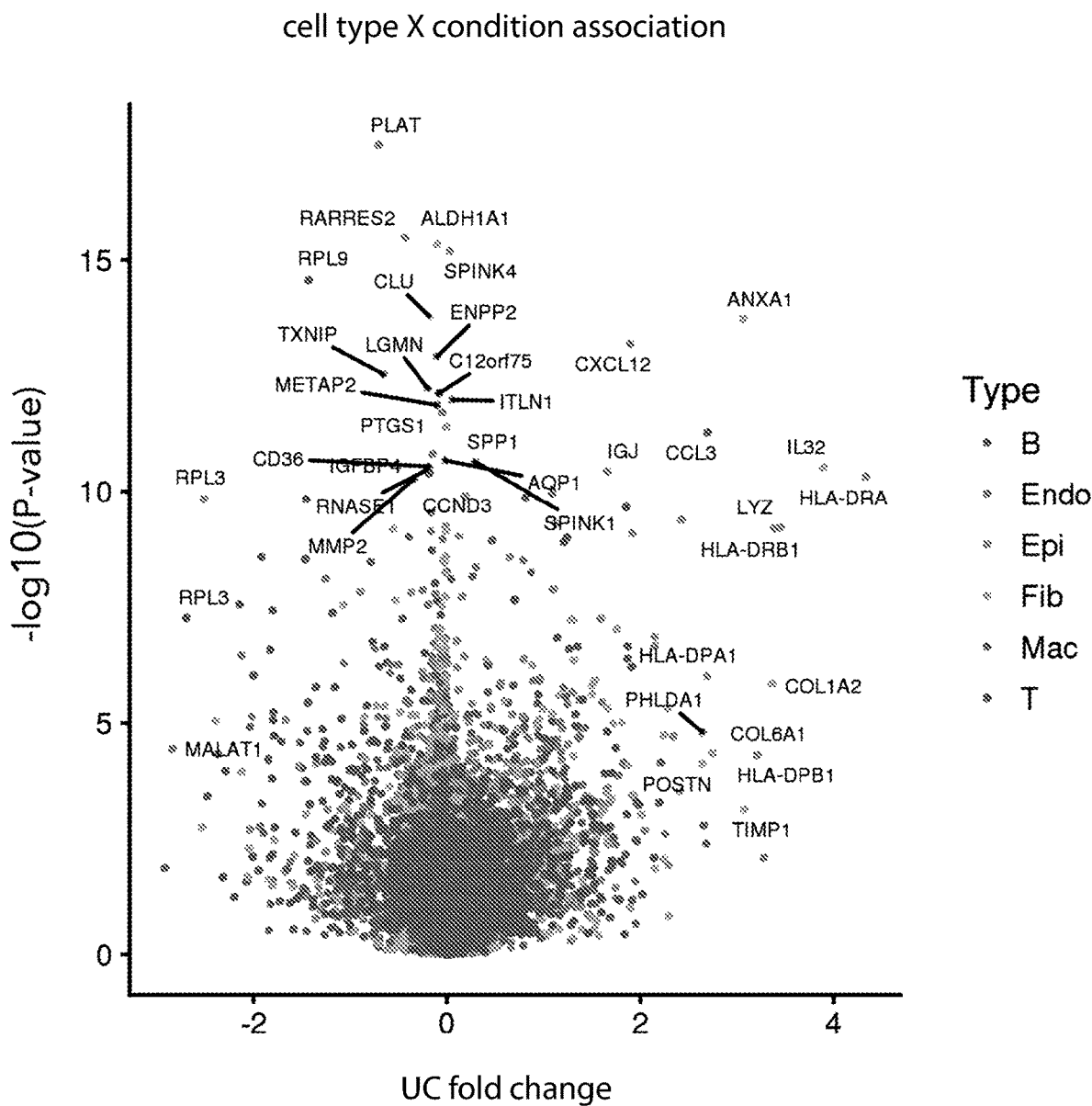
FIG. 8—illustrates cell type specific differential expression of genes in UC.
Figure 9:
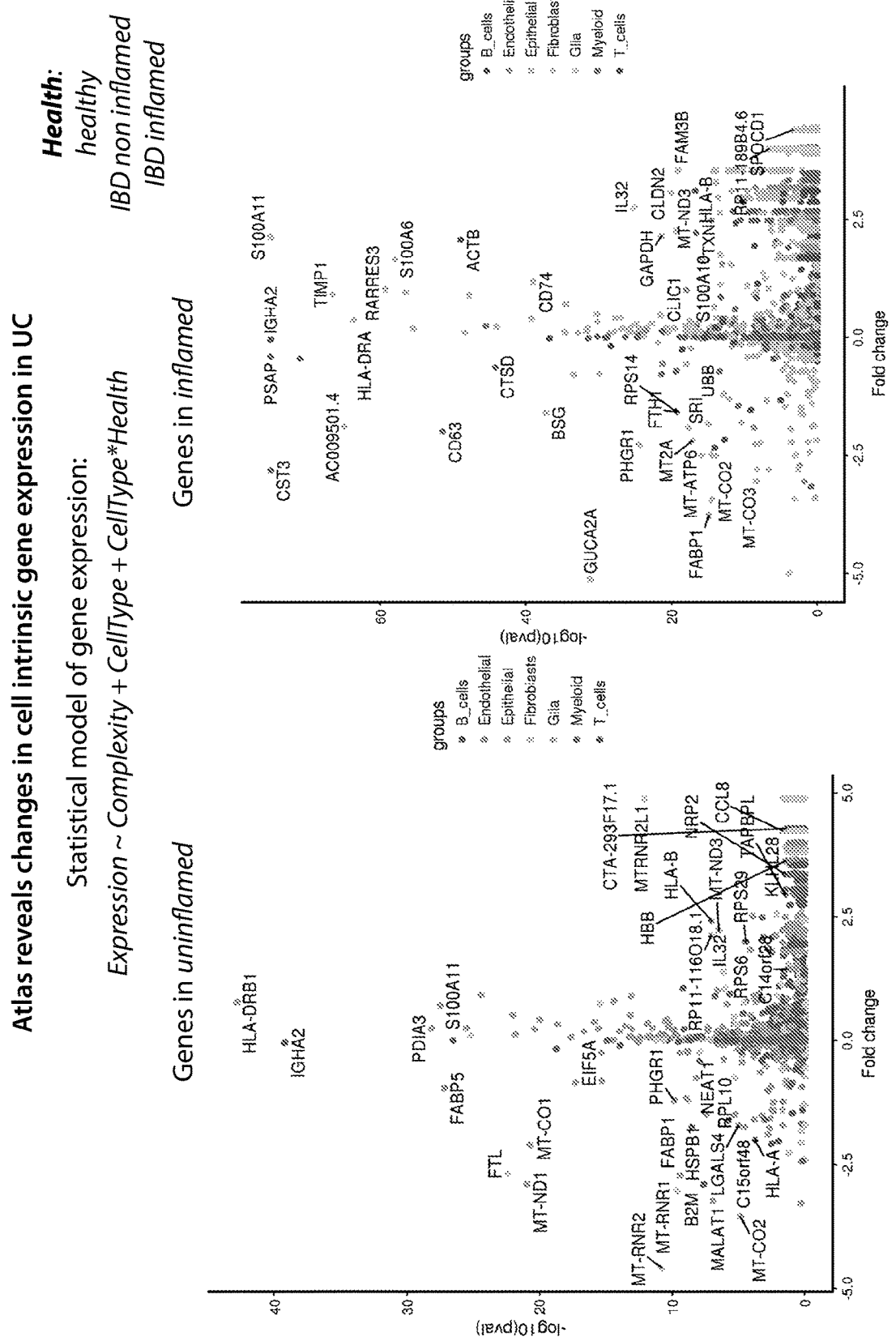
FIG. 9—illustrates genes differentially expressed in uninflamed tissue and in inflamed tissue.

Applicants also determined genes that were associated with disease. FIG. 7 shows genes differentially expressed across the entire colon and FIG. 8 shows genes differentially expressed in specific cell types. FIG. 9 shows differential gene expression in UC cell types for uninflamed and inflamed tissue. IL-32 and MHC-II are two of the strongest signals and are also genes identified by GWAS. Genes differentially expressed in each cell type during disease is shown in Table 2 A-E.

TABLE 2A

| NA 1-50 | NA 51-100 | NA 101-150 | NA 151-200 | NA 201-250 | Plasma_B_cells | Class_switching_B_cells |
|---|---|---|---|---|---|---|
| MTRNR2L1 | EMP1 | TAGLN | RPS29 | MMP10 | G0S2 | TIMP1 |
| HLA-B | AKR1C1 | TFF1 | TMEM258 | VSIG2 | FABP1 | RPL3 |
| CHI3L1 | CD63 | HGF | CLDN7 | RAMP1 | TNFRSF18 | HSP90AA1 |
| EIF5A | FKBP1A | PDIA3 | PHLDA2 | MT1M | PHGR1 | LMNA |
| RPL3 | PTMA | CDH13 | TMSB10 | APOA4 | AGR2 | ILVBL |
| S100P | COL6A3 | ACADS | F2R | TFPI2 | GAS6 | CD69 |
| TIMP1 | REG3A | KDELR2 | PXMP2 | FXYD3 | RPL3 | CTHRC1 |
| REG1A | BACE2 | NOP10 | SRM | MORF4L1 | LMNA | TNFRSF4 |
| C8orf4 | C10orf99 | SELM | CFB | PEBP1 | TIMP1 | G0S2 |
| HMGCS2 | CNN3 | HAPLN3 | NDUFA4L2 | STAP2 | SMOC1 | PABPC4 |
| DMBT1 | CEBPB | FABP4 | CBX3 | NFKBIA | HIST1H1C | ITM2C |
| AC005540.3 | RPL13A | PTGES | NXPE4 | MT-CO3 | HSP90AA1 | AGR2 |
| OLFM4 | LCN2 | DSTN | ACAA2 | DHRS11 | TNFRSF4 | RPS3A |
| IL13RA2 | HSPA1B | CCL5 | NDRG2 | SPINT2 | HSPA1A | RNASE6 |
| MMP3 | CKB | VAMP8 | KANSL1-AS1 | PRRX2 | HSPA1B | LGALS4 |
| REG4 | PHGR1 | MT-ND1 | KLF2 | RCN3 | CYP20A1 | HLA-DMA |
| IGJ | CD59 | SERPINH1 | LAPTM4A | EIF4A1 | KRT19 | FXYD3 |
| DEFA5 | C11orf96 | HYI | ITGA5 | TUBB | CXCR4 | PTMA |
| TNFRSF12A | ANXA5 | POLR2L | DHRS4 | TSHZ2 | DNAJB1 | TNFRSF18 |
| BGN | RPL18A | PPIB | CDX2 | KRT8 | XBP1 | RP11-16E12.2 |
| SELENBP1 | COL4A1 | HLA-DMA | PRKCDBP | ACTN1 | GOLGA2 | H3F3B |
| TPM4 | CTHRC1 | TST | RPL6 | VAMP5 | CADM1 | KLF6 |
| IFITM2 | PCOLCE | AQP1 | SOCS3 | RPL10 | NA | QPRT |
| TNFRSF11B | COL1A1 | SPARC | GPR160 | IL11 | NA | TPM4 |
| PKM | FTL | CA2 | PPDPF | AGT | NA | SMOC1 |
| PHLDA1 | EMP3 | CCL13 | SEPP1 | SERPINA1 | NA | NA |
| MT1G | GEM | MT-CYB | TMEM141 | SLC26A2 | NA | NA |
| LGALS4 | COL4A2 | HLA-DPB1 | ELP5 | CLU | NA | NA |
| IGFBP5 | PRSS23 | SPINK1 | NRG1 | APOBEC3B | NA | NA |
| URAD | S100A6 | AQP8 | SPON2 | DNAJB1 | NA | NA |
| ANXA2 | S100A3 | ATOX1 | CXCL1 | THBS2 | NA | NA |
| HLA-DRA | CA1 | RPL37A | ID3 | UBD | NA | NA |
| PLA2G2A | REG1B | IER3 | PTRF | PIM3 | NA | NA |
| PDPN | TNC | ENO1 | CALR | PRKAR1A | NA | NA |
| S100A11 | CCR7 | MT1H | TMEM165 | IL32 | NA | NA |
| SELL | MEOX1 | HSPA5 | HSP90B1 | IGFBP7 | NA | NA |
| SOD2 | FGF7 | HSPA1A | CLEC9A | UGT2A3 | NA | NA |
| LDHA | MMP1 | ITM2C | INHBA | HLA-DRB5 | NA | NA |
| SMDT1 | RPS3A | SDC2 | SPHK1 | PPA1 | NA | NA |
| CCL8 | THY1 | ID1 | FABP1 | CHCHD10 | NA | NA |
| FCGRT | RPS26 | AMN | LGALS2 | COL6A2 | NA | NA |
| RPL9 | PKIB | FABP6 | PDLIM4 | CD55 | NA | NA |
| CYR61 | CHP2 | PIGZ | TMEM158 | RNASET2 | NA | NA |
| NNMT | SERPINE1 | COL8A1 | CKMT1A | CTGF | NA | NA |
| LMNA | TXNIP | DUOXA2 | TRMT112 | MT-CO1 | NA | NA |
| HIF1A | COL6A1 | TPM2 | CCDC3 | CTSK | NA | NA |

TABLE 2A-continued

| | | | | | | |
|---|---|---|---|---|---|---|
| CD82 | RPS4Y1 | CRIP2 | HOXB13 | C19orf10 | NA | NA |
| LINC00152 | PSME2 | HYAL2 | MRGPRF | SERPINE2 | NA | NA |
| TAGLN2 | CAV1 | CPXM1 | CALU | HSD17B12 | NA | NA |
| IFITM3 | ANGPTL2 | NCOA7 | ACSF2 | SAA1 | NA | NA |

| Follicular_B_cells 1-50 | Follicular_B_cells 51-87 | Microvascular_cells |
|---|---|---|
| C12orf75 | LTB | PLAT |
| METAP2 | CLIC4 | AQP1 |
| CCND3 | LSM10 | CD9 |
| HLA-DQB1 | GDI2 | HLA-A |
| HLA-DRB5 | RGS16 | HLA-DRA |
| RPS4Y1 | CAPG | EGLN3 |
| TUBB2A | SRSF2 | LDHB |
| LCK | ZFAND2A | HLA-C |
| RMI2 | RPL36 | RBP5 |
| SMARCB1 | CBX3 | CD99 |
| HLA-DPB1 | AGR2 | PASK |
| TCEA1 | MRPL47 | S100A10 |
| MME | TRA2A | SERPINE1 |
| RPL9 | FBL | CXCL12 |
| SLBP | SELT | JUN |
| CD63 | SUMO2 | ANXA2 |
| UBE2D3 | HADHB | TESC |
| A4GALT | DEF8 | IGJ |
| PLD4 | FGD2 | FOSB |
| SIT1 | LIMD2 | LIMS1 |
| PPP1CC | PSIP1 | HSPA1A |
| PAIP2 | RBBP7 | CALU |
| CCDC109B | BZW1 | RCN3 |
| DCAF12 | TSTD1 | S100A6 |
| SRSF3 | MTF2 | CST3 |
| HLA-DQA1 | IKZF1 | PRSS23 |
| HLA-C | RUVBL1 | SEPP1 |
| ISG20 | BACH2 | HSPA1B |
| HMGN1 | PIM1 | WWTR1 |
| HMCES | CHRAC1 | RAMP1 |
| HNRNPC | EZR | GPX4 |
| HLA-DPA1 | MCM5 | PSMB9 |
| TUBB2B | IGJ | PSME2 |
| HNRNPA3 | COX6B1 | CTGF |
| CD27 | PRPSAP2 | CD82 |
| EIF1AY | TK1 | LGALS4 |
| ITGAE | CCR7 | SNED1 |
| TPD52 | | TNFRSF4 |
| ECHS1 | | IER3 |
| RAP1B | | VAMP8 |
| HLA-DQA2 | | ALDOA |
| GGA2 | | HLA-B |
| CHCHD10 | | TAP1 |
| ACTR3 | | CD36 |
| HLA-DRA | | F2RL3 |
| SGPP1 | | KDR |
| PGAM1 | | COL15A1 |
| DCK | | PLAU |
| TSG101 | | NA |
| HNRNPM | | NA |

TABLE 2B

| Post-capillary_venules | Vitamin_metabolizing | Endothelial_pericytes | Enterocytes | Tuft_cells |
|---|---|---|---|---|
| PTGS1 | PLAT | FAM222B | SPINK1 | PTGS1 |
| RAMP1 | CXCL12 | RP11-490M8.1 | PLA2G2A | ESYT2 |
| PDLIM1 | ENPP2 | TWF2 | IL18 | SHC1 |
| HLA-A | TXNIP | ZNF205 | ATP1B3 | HPGDS |
| OLFML3 | IGFBP4 | HYI | MTRNR2L1 | HOOK1 |
| PLAT | CD36 | NA | GSTP1 | BCKDK |
| STXBP6 | ANXA2 | NA | GPX2 | RALGAPA1 |
| UBD | OAZ2 | NA | CYBA | NA |
| LY6E | CD320 | NA | TAX1BP3 | NA |
| TNFSF10 | AQP1 | NA | S100A14 | NA |
| CD9 | CTGF | NA | NQO1 | NA |
| MGP | RGS5 | NA | TSPAN3 | NA |
| CPE | TGFBR2 | NA | NAALADL1 | NA |
| PSMB8 | RAMP1 | NA | CTSA | NA |
| PHLDA1 | CD9 | NA | RARRES3 | NA |

TABLE 2B-continued

| | | | | |
|---|---|---|---|---|
| EIF4A2 | C16orf80 | NA | OAS1 | NA |
| GIMAP7 | CXCR4 | NA | LGALS1 | NA |
| TMEM100 | CLDN5 | NA | HMGCS2 | NA |
| CST3 | STC1 | NA | PCK1 | NA |
| HLA-C | GJA1 | NA | PRDX5 | NA |
| RPL9 | FAM213A | NA | MUC1 | NA |
| RPL10 | PLAU | NA | TMEM37 | NA |
| LPCAT4 | HLA-E | NA | KRTCAP3 | NA |
| AQP1 | PRKCDBP | NA | MT2A | NA |
| GIMAP1 | RBP5 | NA | MX1 | NA |
| SRPX | RPL9 | NA | S100A11 | NA |
| MALAT1 | SAT1 | NA | NA | NA |
| RPL3 | TNFSF10 | NA | NA | NA |
| AGR2 | S100A4 | NA | NA | NA |
| PRSS23 | TSPAN7 | NA | NA | NA |
| COL4A3BP | AKR1C3 | NA | NA | NA |
| EFEMP1 | C8orf4 | NA | NA | NA |
| SNHG7 | HLA-DPB1 | NA | NA | NA |
| TUBA1B | SRP14 | NA | NA | NA |
| PTGES | TNFRSF4 | NA | NA | NA |
| NFKBIZ | TIMP1 | NA | NA | NA |
| B2M | ANXA1 | NA | NA | NA |
| FTH1 | C1orf54 | NA | NA | NA |
| C19orf66 | RND1 | NA | NA | NA |
| CDKN3 | ANGPT2 | NA | NA | NA |
| RNF181 | EGR1 | NA | NA | NA |
| EEF1B2 | STAT3 | NA | NA | NA |
| MDK | SH3BP5 | NA | NA | NA |
| CLIC1 | RPL29 | NA | NA | NA |
| TPTEP1 | CTNNBIP1 | NA | NA | NA |
| TFF3 | LSMD1 | NA | NA | NA |
| S100A10 | HLA-C | NA | NA | NA |
| JUN | RBM17 | NA | NA | NA |
| CRIP1 | GYPC | NA | NA | NA |
| MED24 | NDUFA7 | NA | NA | NA |
| NA | IER2 | NA | NA | NA |
| NA | COTL1 | NA | NA | NA |
| NA | RPLP0 | NA | NA | NA |
| NA | SDPR | NA | NA | NA |
| NA | IDI1 | NA | NA | NA |
| NA | SLC6A6 | NA | NA | NA |
| NA | RPL10A | NA | NA | NA |
| NA | MYL6 | NA | NA | NA |
| NA | AQP3 | NA | NA | NA |
| NA | NKX2-3 | NA | NA | NA |
| NA | COASY | NA | NA | NA |
| NA | SOD2 | NA | NA | NA |

| Goblet_2 | Absorptive_TA_1 | Secretory_TA | Absorptive_TA_2 | Cycling_TA |
|---|---|---|---|---|
| SPINK4 | REG1A | HLA-DRA | AGR2 | RARRES2 |
| NUPR1 | CD74 | HLA-DRB1 | HLA-DRA | ARHGDIB |
| S100A14 | RPL3 | RARRES2 | CD74 | IGJ |
| BAIAP2L1 | HLA-DRB1 | ID3 | S100A11 | BST2 |
| BDKRB1 | MT2A | HLA-DMA | HSPB1 | PKIG |
| MT-ND2 | RPS3A | UGT2B17 | SPINK1 | PITX1 |
| FAM3B | ARHGDIB | CD74 | HLA-DRB1 | ETS2 |
| MUC13 | TIMP1 | HLA-DRB5 | TIMP1 | HLA-DRA |
| TFF1 | LIN7C | REG1A | RARRES3 | TIMP1 |
| ANO9 | MTRNR2L1 | HLA-DPB1 | SELENBP1 | MTRNR2L1 |
| TUBB2A | KCNK6 | HLA-DPA1 | GPX2 | HRCT1 |
| NA | RPL18A | GLB1L2 | MUC12 | ZNF90 |
| NA | TNFRSF12A | NA | ID3 | MUC12 |
| NA | SEC11C | NA | ARHGDIB | AKR1B1 |
| NA | NA | NA | REG1A | HLA-DPA1 |
| NA | NA | NA | PLA2G2A | VAMP7 |
| NA | NA | NA | CEACAM5 | S100P |
| NA | NA | NA | IDH2 | NQO1 |
| NA | NA | NA | IGJ | DEK |
| NA | NA | NA | RNASET2 | ABRACL |
| NA | NA | NA | BSG | REG1A |
| NA | NA | NA | PSMB9 | ACAT1 |
| NA | NA | NA | ADIRF | DNAJB1 |
| NA | NA | NA | LEFTY1 | HLA-DRB1 |
| NA | NA | NA | RARRES1 | IGFBP4 |
| NA | NA | NA | LYZ | NA |
| NA | NA | NA | MTRNR2L1 | NA |
| NA | NA | NA | TFF1 | NA |
| NA | NA | NA | RPS4Y1 | NA |
| NA | NA | NA | SRSF6 | NA |

TABLE 2B-continued

| | | | | |
|---|---|---|---|---|
| NA | NA | NA | CNPY2 | NA |
| NA | NA | NA | GSTP1 | NA |
| NA | NA | NA | ATP1B3 | NA |
| NA | NA | NA | NA | NA |
| NA | NA | NA | NA | NA |
| NA | NA | NA | NA | NA |
| NA | NA | NA | NA | NA |
| NA | NA | NA | NA | NA |
| NA | NA | NA | NA | NA |
| NA | NA | NA | NA | NA |
| NA | NA | NA | NA | NA |
| NA | NA | NA | NA | NA |
| NA | NA | NA | NA | NA |
| NA | NA | NA | NA | NA |
| NA | NA | NA | NA | NA |
| NA | NA | NA | NA | NA |
| NA | NA | NA | NA | NA |
| NA | NA | NA | NA | NA |
| NA | NA | NA | NA | NA |
| NA | NA | NA | NA | NA |
| NA | NA | NA | NA | NA |
| NA | NA | NA | NA | NA |
| NA | NA | NA | NA | NA |
| NA | NA | NA | NA | NA |
| NA | NA | NA | NA | NA |
| NA | NA | NA | NA | NA |
| NA | NA | NA | NA | NA |
| NA | NA | NA | NA | NA |
| NA | NA | NA | NA | NA |
| NA | NA | NA | NA | NA |
| NA | NA | NA | NA | NA |
| NA | NA | NA | NA | NA |
| NA | NA | NA | NA | NA |
| NA | NA | NA | NA | NA |
| NA | NA | NA | NA | NA |
| NA | NA | NA | NA | NA |
| NA | NA | NA | NA | NA |

TABLE 2C

| Goblet_1 | Stem_cells | Enteroendocrine | Glial-cells | Inflammatory-fibroblasts | Fibroblast_pericytes |
|---|---|---|---|---|---|
| SPINK4 | AQP1 | RARRES2 | ALDH1A1 | COL1A2 | NET1 |
| ITLN1 | RPL3 | HLA-DRA | CLU | GBP1 | NA |
| IGJ | RPS4Y1 | SEC11C | ANXA1 | IFI27 | NA |
| AGR2 | LYZ | MT2A | SPP1 | DYNLT1 | NA |
| SDF2L1 | LCN2 | NIPSNAP1 | IL32 | PKM | NA |
| TIMP1 | ID3 | OLFM4 | CAPS | PHLDA1 | NA |
| PDLIM1 | HLA-DRA | DDC | FIBIN | DUSP1 | NA |
| MUC2 | HLA-DRB1 | MDK | RPL3 | CNOT4 | NA |
| LYZ | HLA-DMA | CD82 | RPL9 | CCL8 | NA |
| SELK | HLA-DPA1 | NA | HLA-G | LAP3 | NA |
| HMGCS2 | C2 | NA | MRPS6 | ACP5 | NA |
| SEC11C | NQO1 | NA | LINC00152 | GSTT1 | NA |
| SSR4 | B2M | NA | HOXC6 | GALNT11 | NA |
| DNAJA1 | ARHGDIB | NA | CDKN2A | PSMB9 | NA |
| FKBP11 | DNAJB1 | NA | TUBA1A | TNIP2 | NA |
| REG4 | RARRES2 | NA | HLA-DQA2 | PSMB8 | NA |
| EZR | MTRNR2L1 | NA | SOCS3 | HAPLN3 | NA |
| SELM | HLA-C | NA | SEPP1 | PERP | NA |
| CISD1 | CD74 | NA | IGJ | NA | NA |
| SYTL1 | C19orf70 | NA | HLA-DRB5 | NA | NA |
| PHLDA2 | GSTT1 | NA | KLC1 | NA | NA |
| CHPF | TESC | NA | HLA-DRB1 | NA | NA |
| NA | IFI27 | NA | NDUFB4 | NA | NA |
| NA | PSME1 | NA | ENTPD2 | NA | NA |
| NA | HMGCS2 | NA | SRGN | NA | NA |
| NA | HLA-DRB5 | NA | PMEPA1 | NA | NA |
| NA | RPL6 | NA | HSPA1B | NA | NA |
| NA | UGT2B17 | NA | FKBP1A | NA | NA |
| NA | HLA-DPB1 | NA | GLIPR2 | NA | NA |
| NA | PSMB9 | NA | UBR4 | NA | NA |
| NA | SCARB2 | NA | UBB | NA | NA |
| NA | NA | NA | COX7A1 | NA | NA |
| NA | NA | NA | LSM3 | NA | NA |

TABLE 2C-continued

| | | | | | |
|---|---|---|---|---|---|
| NA | NA | NA | PRDX2 | NA | NA |
| NA | NA | NA | NUPR1 | NA | NA |
| NA | NA | NA | NA | NA | NA |

| Myofibroblasts | Villus_fibroblasts | Crypt_fibroblasts_(hiFos) | Crypt_fibroblasts_(loFos) |
|---|---|---|---|
| PDLIM7 | MMP2 | TM4SF1 | GPX3 |
| NBL1 | SRPX2 | VASN | NR4A1 |
| C12orf75 | TNC | GSN | C1S |
| PHLDA2 | MMP1 | FGF7 | TM4SF1 |
| IGFBP5 | S100A4 | PLAT | DUSP1 |
| PRSS23 | NSG1 | CLEC14A | ID1 |
| TM4SF1 | EDNRB | IQGAP2 | LGALS3BP |
| SQRDL | AGT | ID3 | COL15A1 |
| MRGPRF | TRPA1 | FN1 | SERPING1 |
| RERG | CPE | SEPP1 | TNFAIP6 |
| MXRA8 | VSTM2A | TNXB | CFD |
| RPS4Y1 | RBP4 | CCL13 | ADAMDEC1 |
| EGR1 | TSHZ2 | TPBG | MZT2B |
| HOXD9 | IL32 | HSD17B2 | MIF |
| TDO2 | VASN | STMN2 | EGR1 |
| DUSP1 | CRIP1 | GPX3 | DKK3 |
| LMNA | NR4A2 | VIM | NBEAL1 |
| CYB5R3 | PCTP | TNFSF10 | GSN |
| DDAH2 | PRSS23 | NA | GGT5 |
| TFPI2 | MCL1 | NA | FOXF1 |
| NA | NDUFA4L2 | NA | RPL9 |
| NA | ANXA1 | NA | CD74 |
| NA | TMSB4X | NA | NA |
| NA | PDLIM1 | NA | NA |
| NA | IGFBP3 | NA | NA |
| NA | CEBPD | NA | NA |
| NA | FOXF1 | NA | NA |
| NA | ACP1 | NA | NA |
| NA | C1S | NA | NA |
| NA | FRZB | NA | NA |
| NA | ECM1 | NA | NA |
| NA | DMKN | NA | NA |
| NA | ID4 | NA | NA |
| NA | PDGFRA | NA | NA |
| NA | GADD45B | NA | NA |
| NA | SPARCL1 | NA | NA |

TABLE 2D

| T_cells | Macrophages | Dendritic_cells | Mast_cells | Cyding_monocytes | Tolerogenic_DCs |
|---|---|---|---|---|---|
| NUB1 | LGMN | CST3 | NFKBIZ | TFF3 | TXN |
| CAV1 | RNASE1 | MARCKSL1 | EGR3 | ATP2A3 | NA |
| EIF2S1 | AKR1B1 | CD52 | IL1RL1 | GSDMD | NA |
| COL6A1 | LGALS2 | PPA1 | HLA-B | EMP3 | NA |
| POSTN | A2M | IGJ | CAPG | IL12RB1 | NA |
| ALAS1 | C15orf48 | SERPINB1 | EGR2 | PSMD11 | NA |
| RGCC | VMO1 | TYMP | HLA-C | ENPP2 | NA |
| NA | SERPINF1 | STMN1 | RPS4Y1 | ALOX5AP | NA |
| NA | SPINT1 | FCER1A | CTSW | AK1 | NA |
| NA | ACP5 | DNAJB1 | EIF4G2 | NA | NA |
| NA | TFF3 | PRELID1 | ZEB2 | NA | NA |
| NA | RNASET2 | NA | NA | NA | NA |
| NA | ENPP2 | NA | NA | NA | NA |
| NA | LGALS1 | NA | NA | NA | NA |
| NA | MMP9 | NA | NA | NA | NA |
| NA | CORO1A | NA | NA | NA | NA |
| NA | CSTB | NA | NA | NA | NA |
| NA | SELK | NA | NA | NA | NA |
| NA | MT2A | NA | NA | NA | NA |
| NA | FBP1 | NA | NA | NA | NA |
| NA | PLSCR1 | NA | NA | NA | NA |
| NA | FXYD5 | NA | NA | NA | NA |
| NA | NR1H3 | NA | NA | NA | NA |
| NA | UCHL3 | NA | NA | NA | NA |

TABLE 2D-continued

| | | | | | |
|---|---|---|---|---|---|
| NA | SEPP1 | NA | NA | NA | NA |
| NA | AGR2 | NA | NA | NA | NA |

| Neutrophils | Activated_CD4_cells_loFos | Activated_CD4_cells_hiFos | CD8_IELs |
|---|---|---|---|
| GBP1 | S100A4 | IGJ | CCL3 |
| FCGR2B | RPS29 | ADSS | CCL4 |
| GSTO1 | TIMP1 | NA | RPL10 |
| RPL30 | RPL9 | NA | RPL6 |
| TMEM176B | CFL1 | NA | CD3E |
| EMG1 | VIM | NA | MTRNR2L1 |
| GDI2 | ANXA1 | NA | ARHGDIB |
| NA | PHLDA1 | NA | CD3G |
| NA | S100A11 | NA | RPL3 |
| NA | HLA-A | NA | ITGB2 |
| NA | NA | NA | KLRB1 |
| NA | NA | NA | IFNG |
| NA | NA | NA | RPL22 |
| NA | NA | NA | RPL18A |
| NA | NA | NA | PTMA |
| NA | NA | NA | NA |
| NA | NA | NA | NA |
| NA | NA | NA | NA |
| NA | NA | NA | NA |
| NA | NA | NA | NA |
| NA | NA | NA | NA |
| NA | NA | NA | NA |
| NA | NA | NA | NA |
| NA | NA | NA | NA |
| NA | NA | NA | NA |

TABLE 2E

| CD8_LP_cells | Tregs | Memory_T_cells | NK_cells | Cycling_CD8_cells |
|---|---|---|---|---|
| RPL9 | CD7 | RPL9 | ILF3 | ENTPD1 |
| EMP3 | CD2 | PFN1 | CALCOCO2 | CD2 |
| ARFRP1 | TIA1 | IL32 | CD47 | EIF5A |
| NA | GRSF1 | ANXA1 | NA | LCK |
| NA | NA | S100A4 | NA | HAVCR2 |
| NA | NA | ARPC1B | NA | ATP5L |
| NA | NA | KLRB1 | NA | KLRB1 |
| NA | NA | RPL30 | NA | CALR |
| NA | NA | ANAPC5 | NA | MTPN |
| NA | NA | GAPDH | NA | CENPA |
| NA | NA | B2M | NA | MIF |
| NA | NA | RPS28 | NA | NA |
| NA | NA | PSME2 | NA | NA |
| NA | NA | AK5 | NA | NA |
| NA | NA | SERF2 | NA | NA |
| NA | NA | RILPL2 | NA | NA |
| NA | NA | RPS29 | NA | NA |
| NA | NA | TAGLN2 | NA | NA |
| NA | NA | FXYD5 | NA | NA |
| NA | NA | S100A11 | NA | NA |
| NA | NA | ANXA5 | NA | NA |
| NA | NA | S100A6 | NA | NA |
| NA | NA | PNRC1 | NA | NA |
| NA | NA | ARPC2 | NA | NA |
| NA | NA | ZFP36 | NA | NA |

Figure 10:
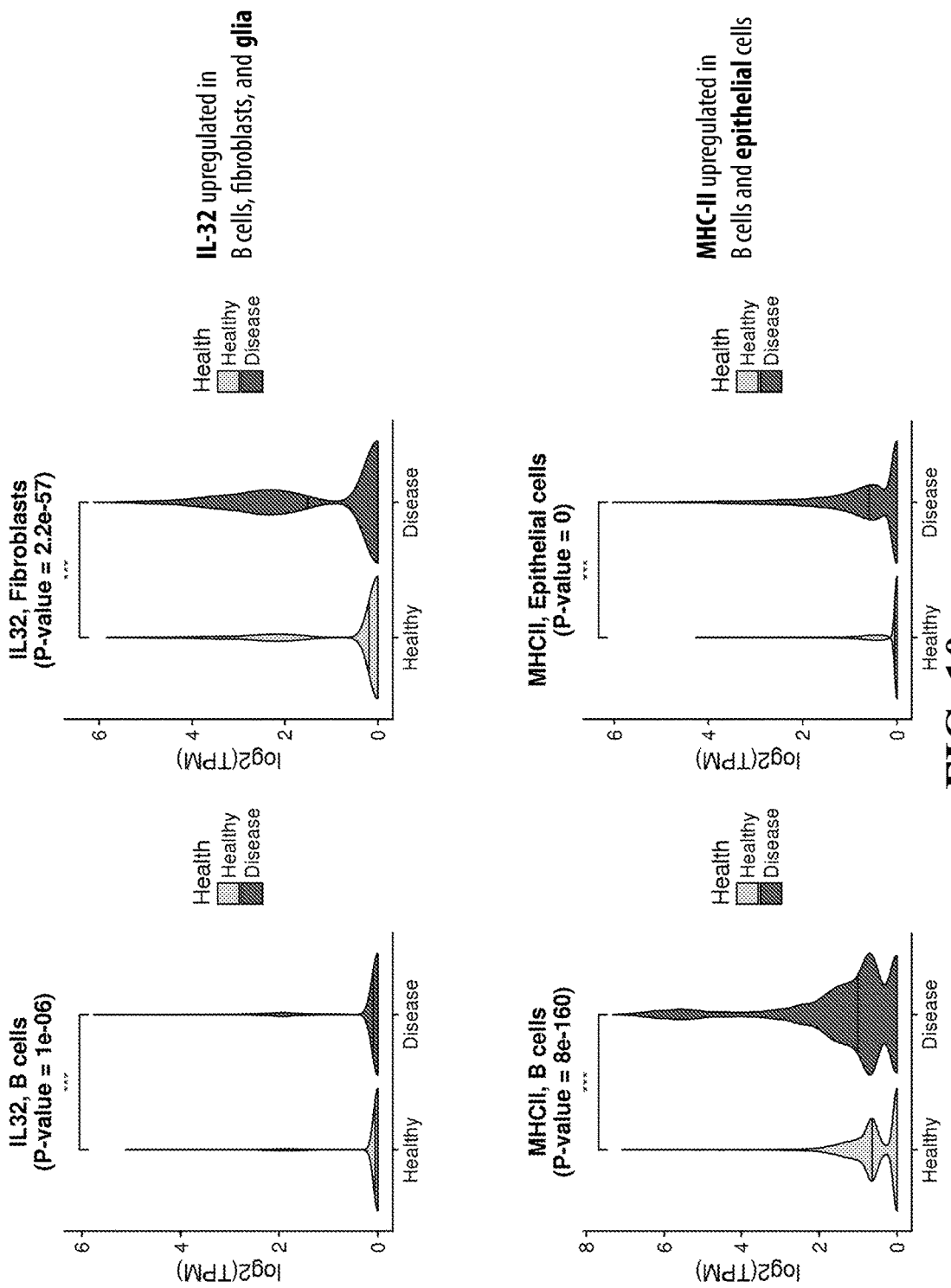
FIG. 10—illustrates violin plots for key IBD GWAS in specific cell types present in healthy and disease colon.
Figure 11:
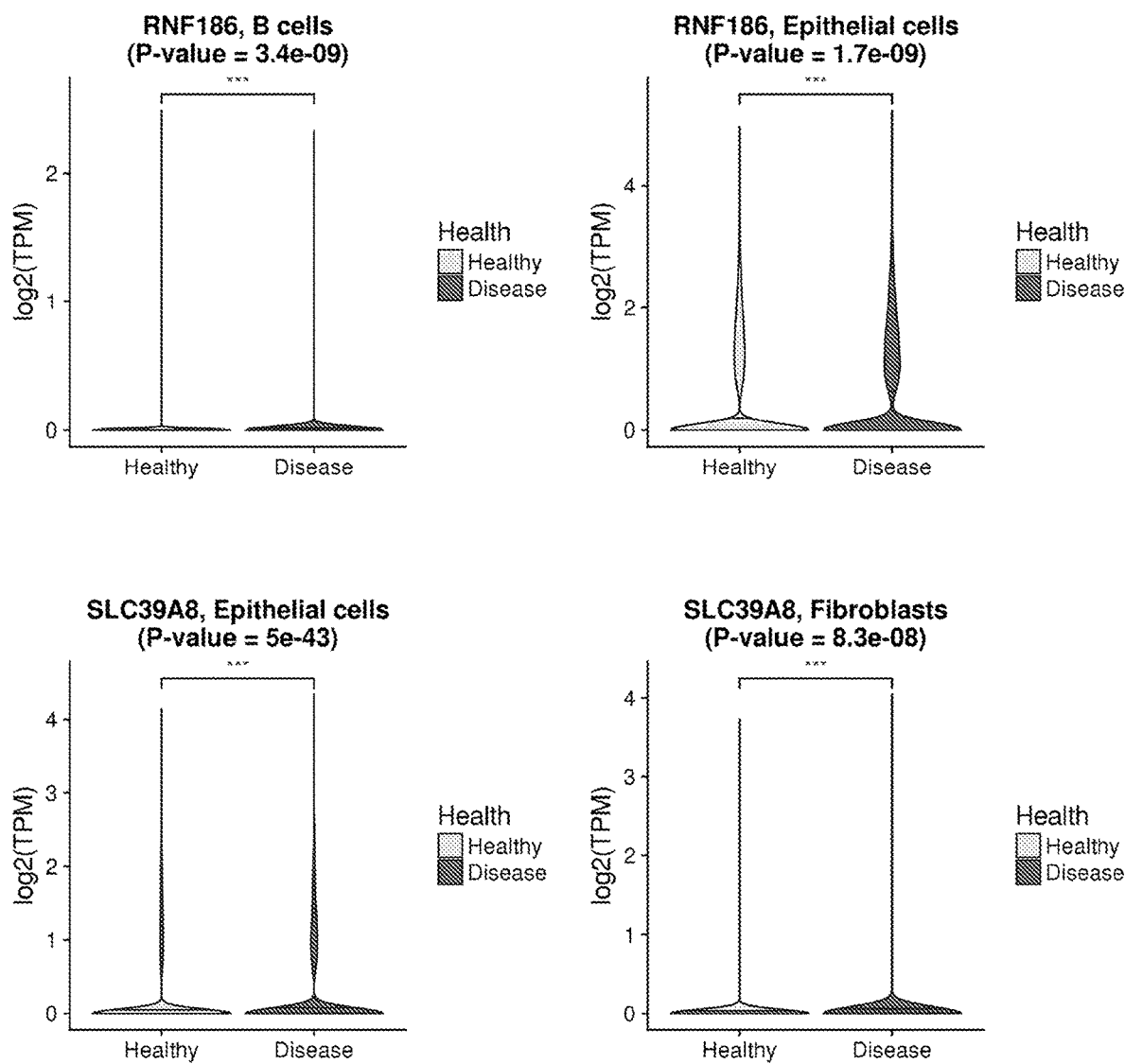
FIG. 11—illustrates violin plots for key IBD GWAS in specific cell types present in healthy and disease colon.
Figure 12:
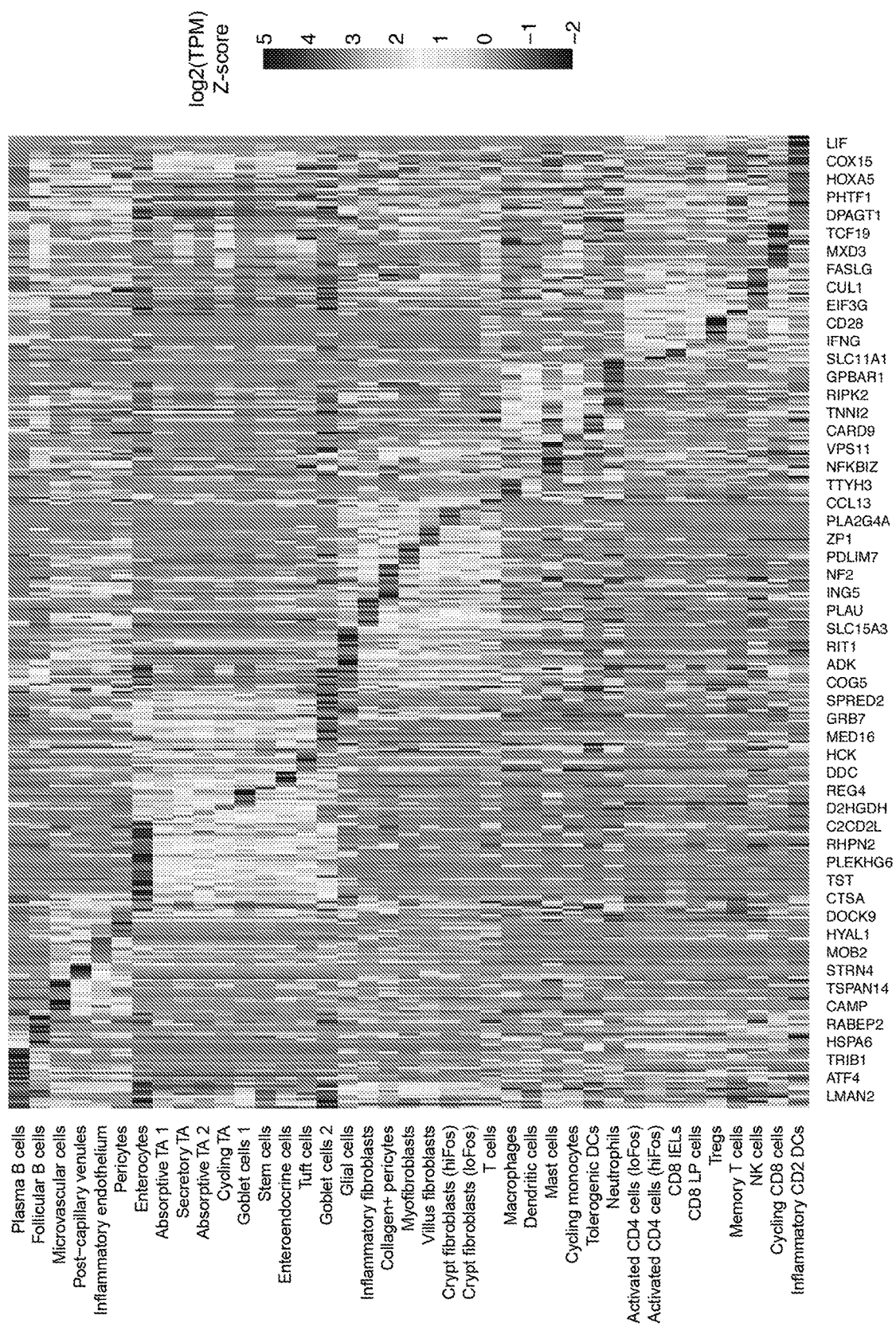
FIG. 12—illustrates the cell-of-origin for key IBD GWAS genes.
Figure 13:
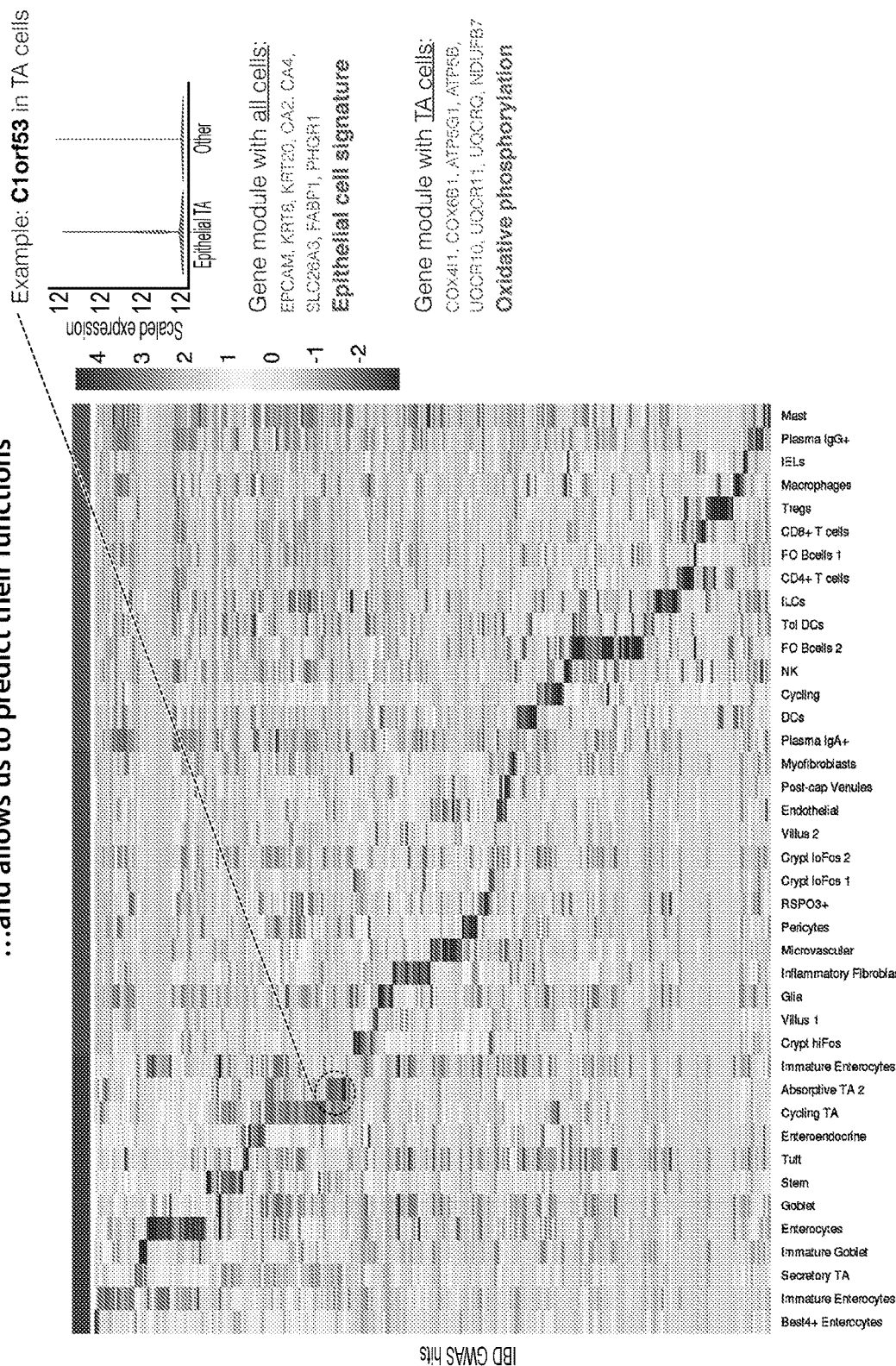
FIG. 13—illustrates the cell-of-origin for key IBD GWAS genes. Gene modules for all cells and TA cells are specific for an epithelial cell signature and oxidative phosphorylation signature.
Figure 14:
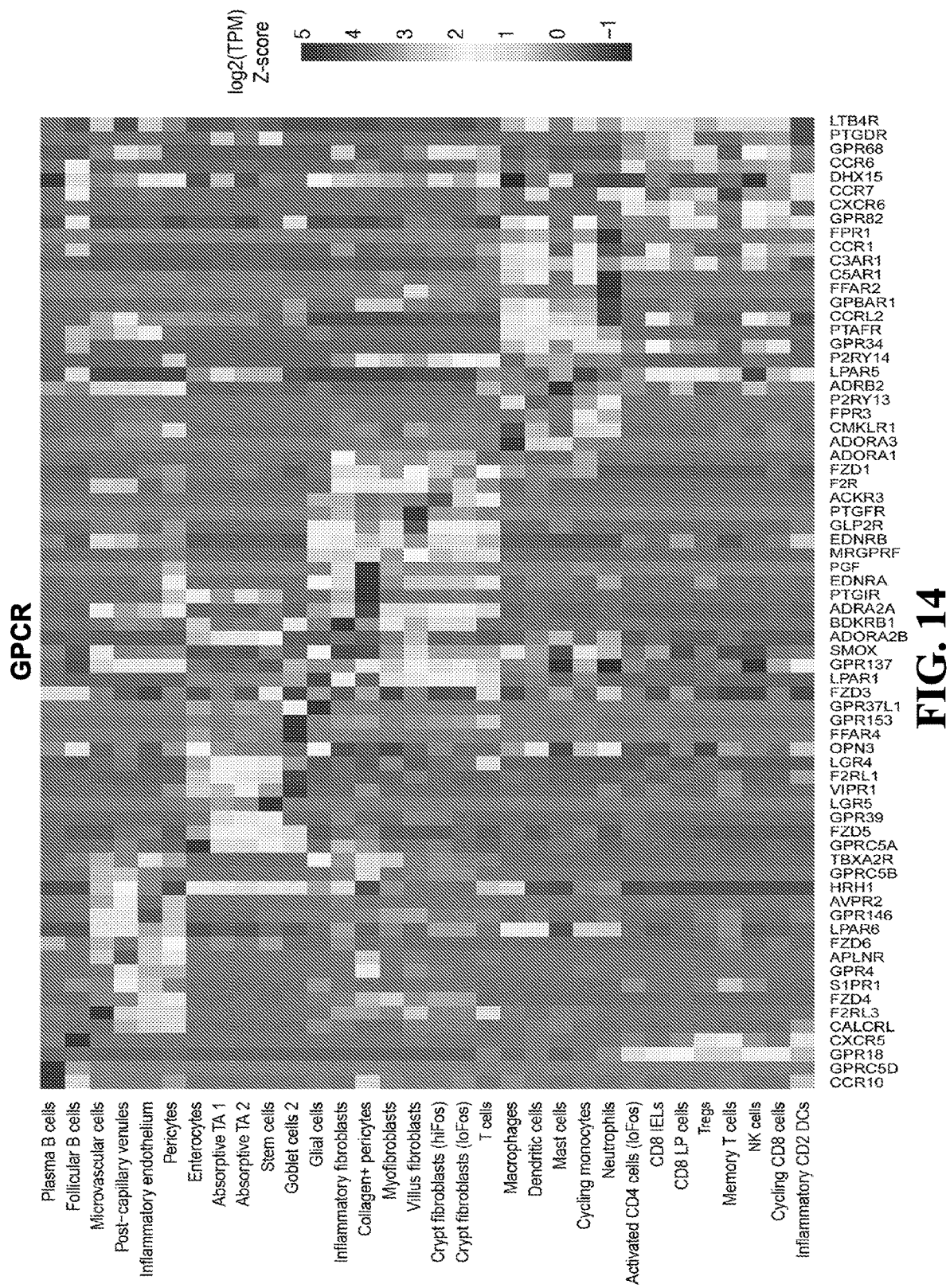
FIG. 14—illustrates the cell-of-origin for key IBD GWAS G-protein coupled receptor (GPCR) genes.
Figure 15:
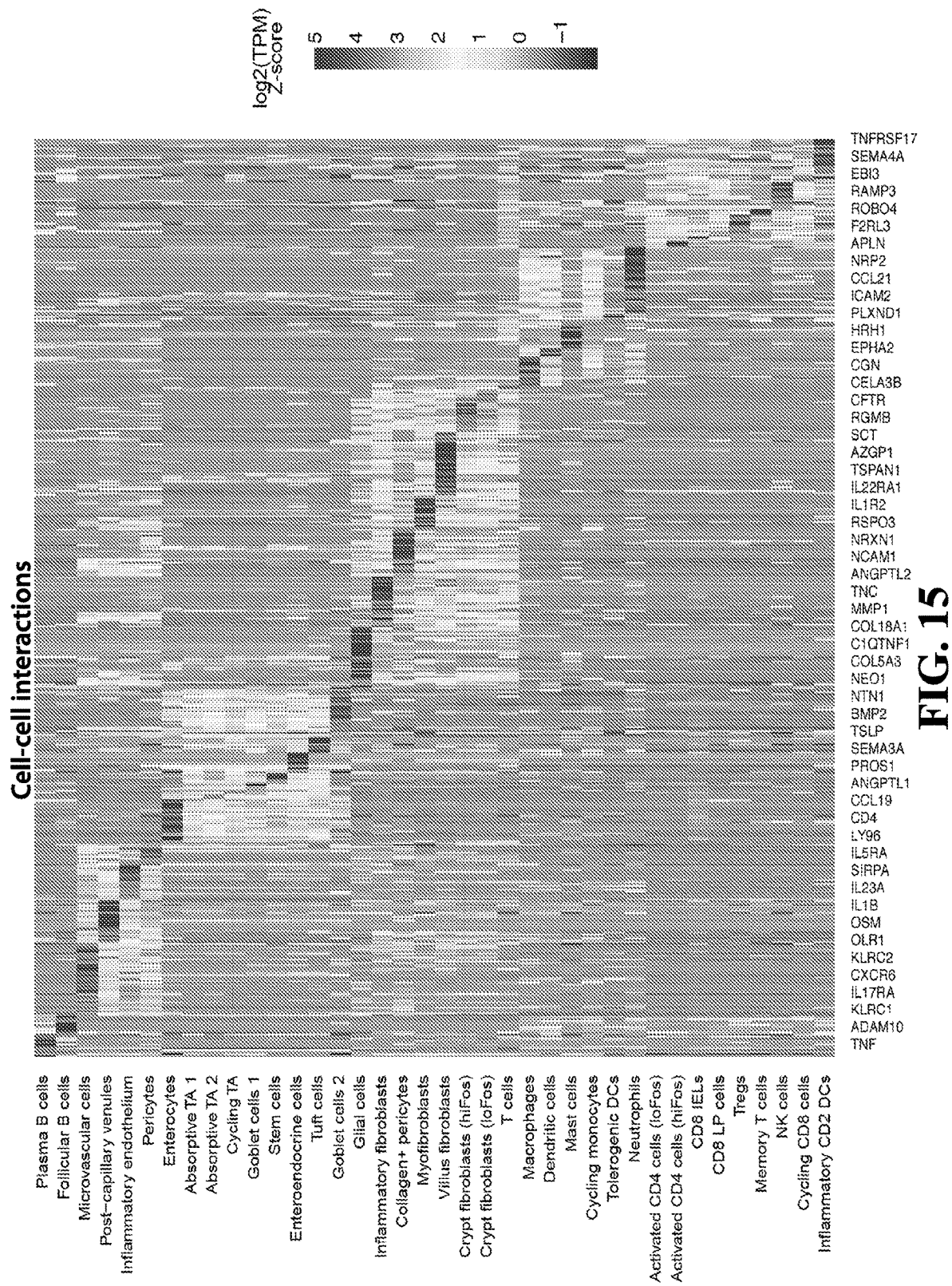
FIG. 15—illustrates the cell-of-origin for key IBD GWAS cell-cell interaction or cell-cell communication genes.
Figure 16:
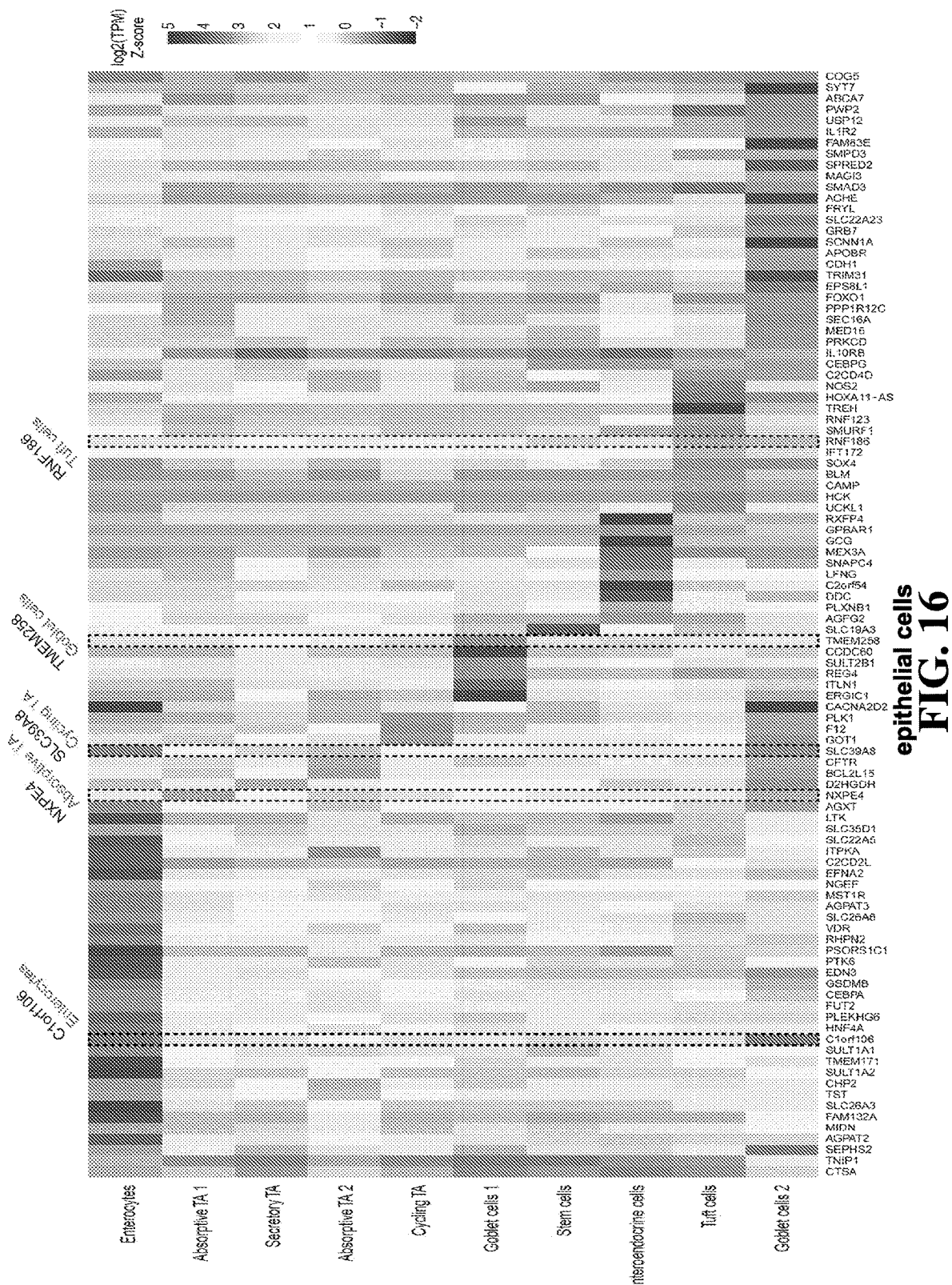
FIG. 16—illustrates the cell-of-origin for key IBD GWAS genes expressed in epithelial cells.
Figure 17:
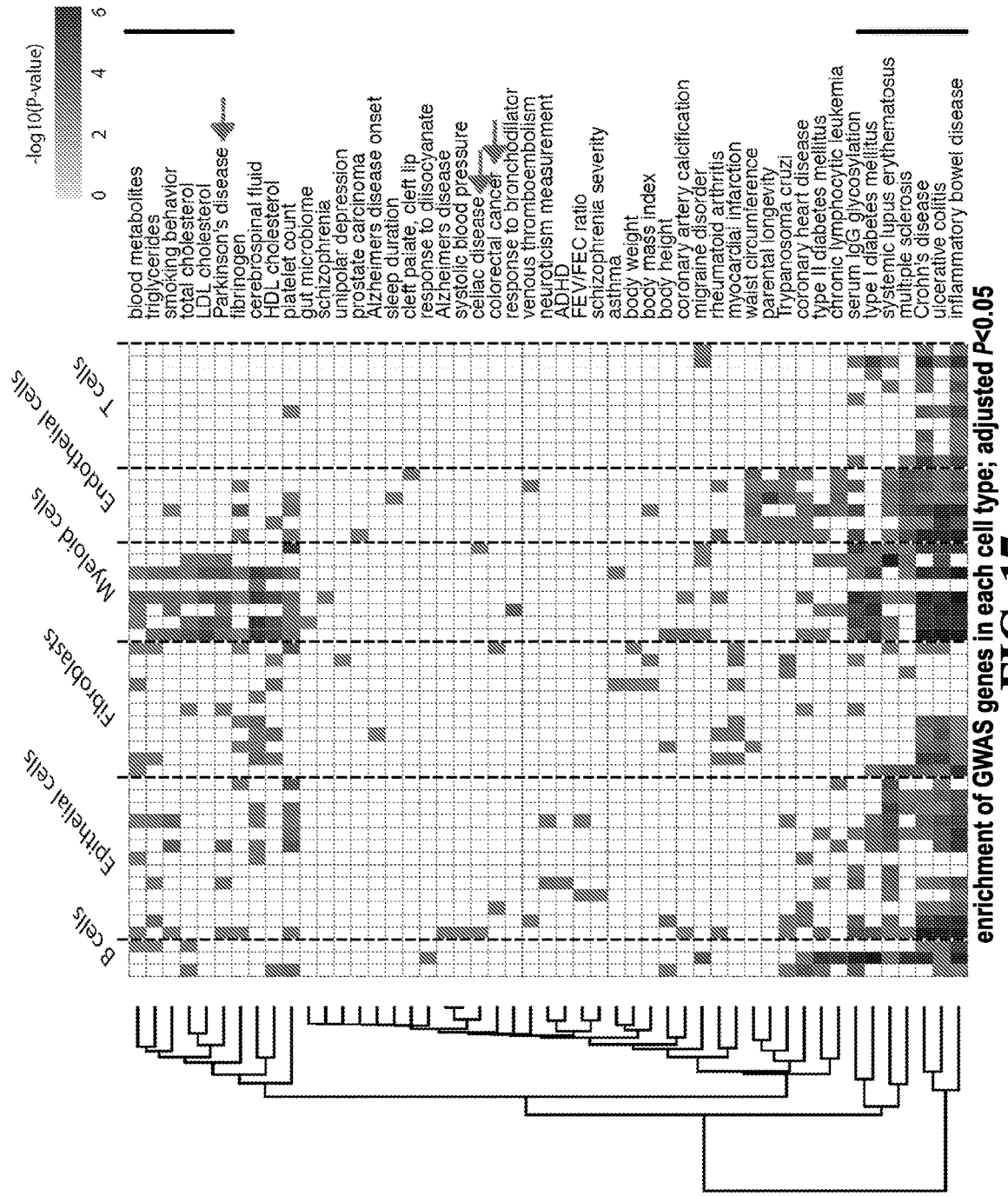
FIG. 17—illustrates that the atlas can be used to determine the cell-of-origin for GWAS genes for other indications.

Applicants were able to determine the cell of origin for genes associated with disease by genome wide association (GWAS) (e.g., IBD). Previous studies have shown 94 IBD loci fine mapped in 67,852 individuals (Hung et al., Nature 2017). FIGS. 10 and 11 show violin plots for key IBD genes in healthy and disease samples. Applicants also show heatmaps for GWAS genes expressed in each cell type (FIGS. 12 and 13). Applicants show a heatmap for G-protein coupled receptors (GPCR), genes involved in cell-cell interactions, and in epithelial cells in the gut cell types. (FIGS. 14, 15 and 16). Key genes are highlighted in FIG. 16. FIG. 17 shows that genes associated with other disease indications can be localized to specific cell types in the atlas.

Figure 18:
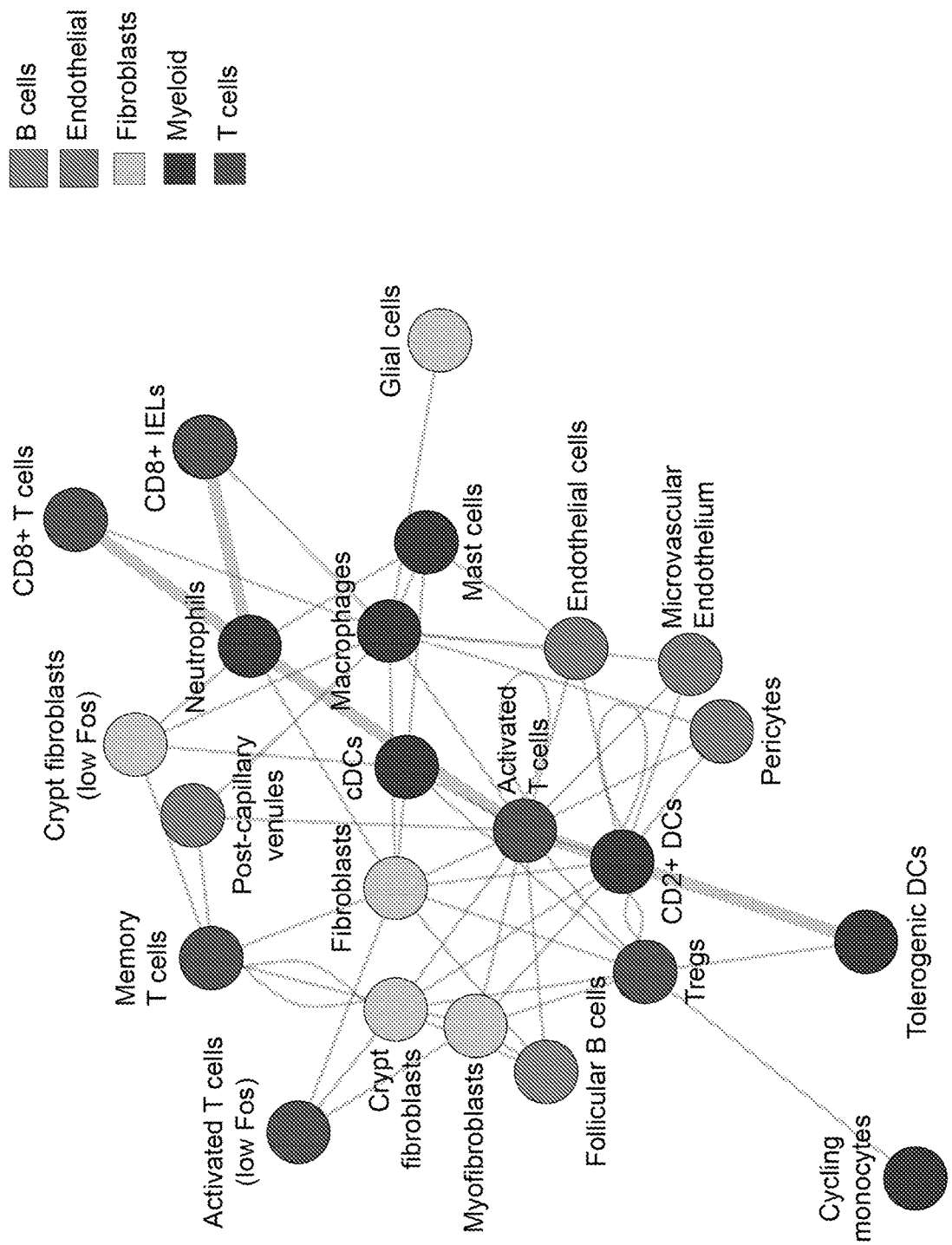
FIG. 18—illustrates that the atlas can be used to determine cell-cell interaction mechanisms.
Figure 19:
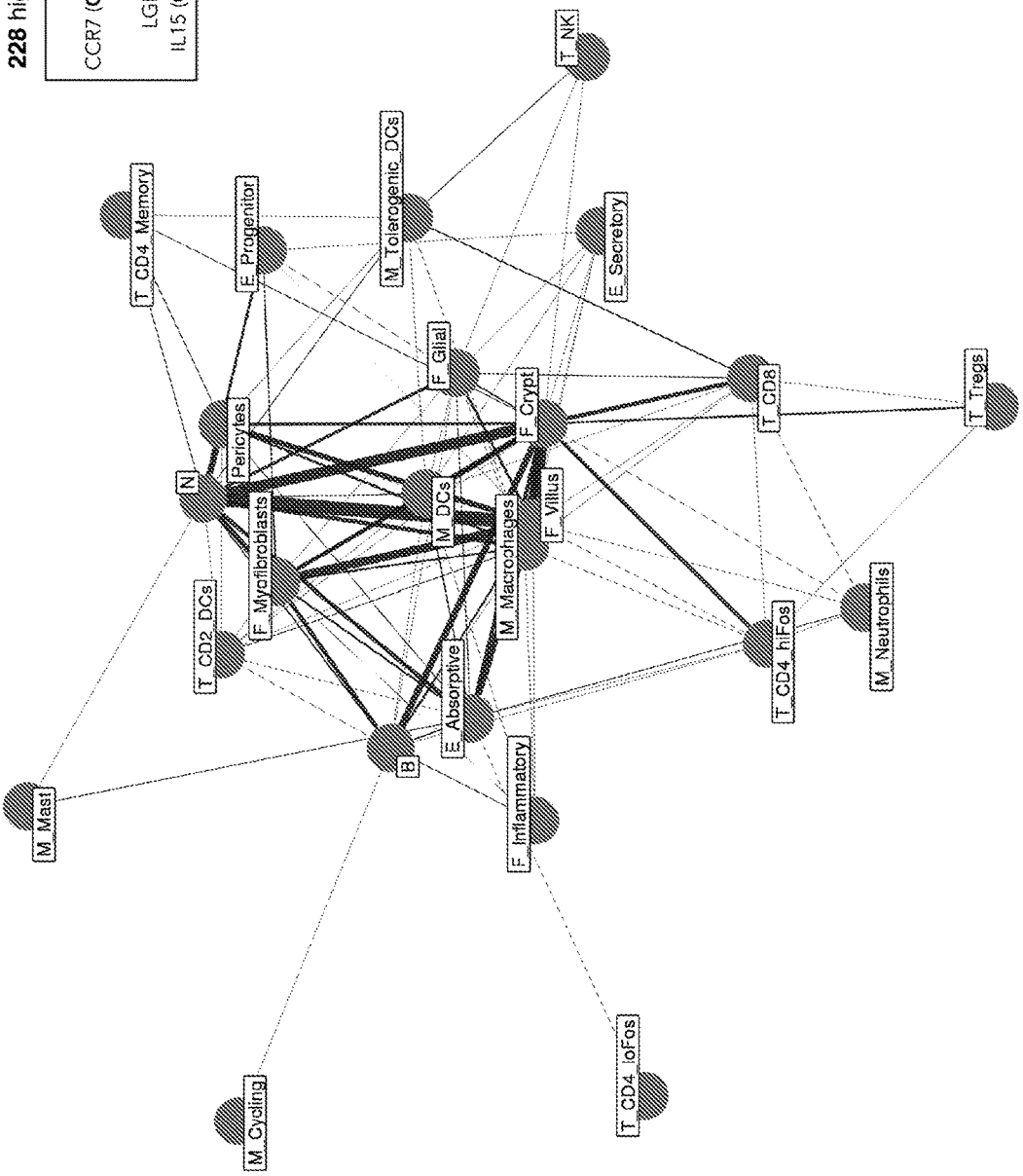
FIG. 19—illustrates cell-cell interactions in the healthy gut.
Figure 20:
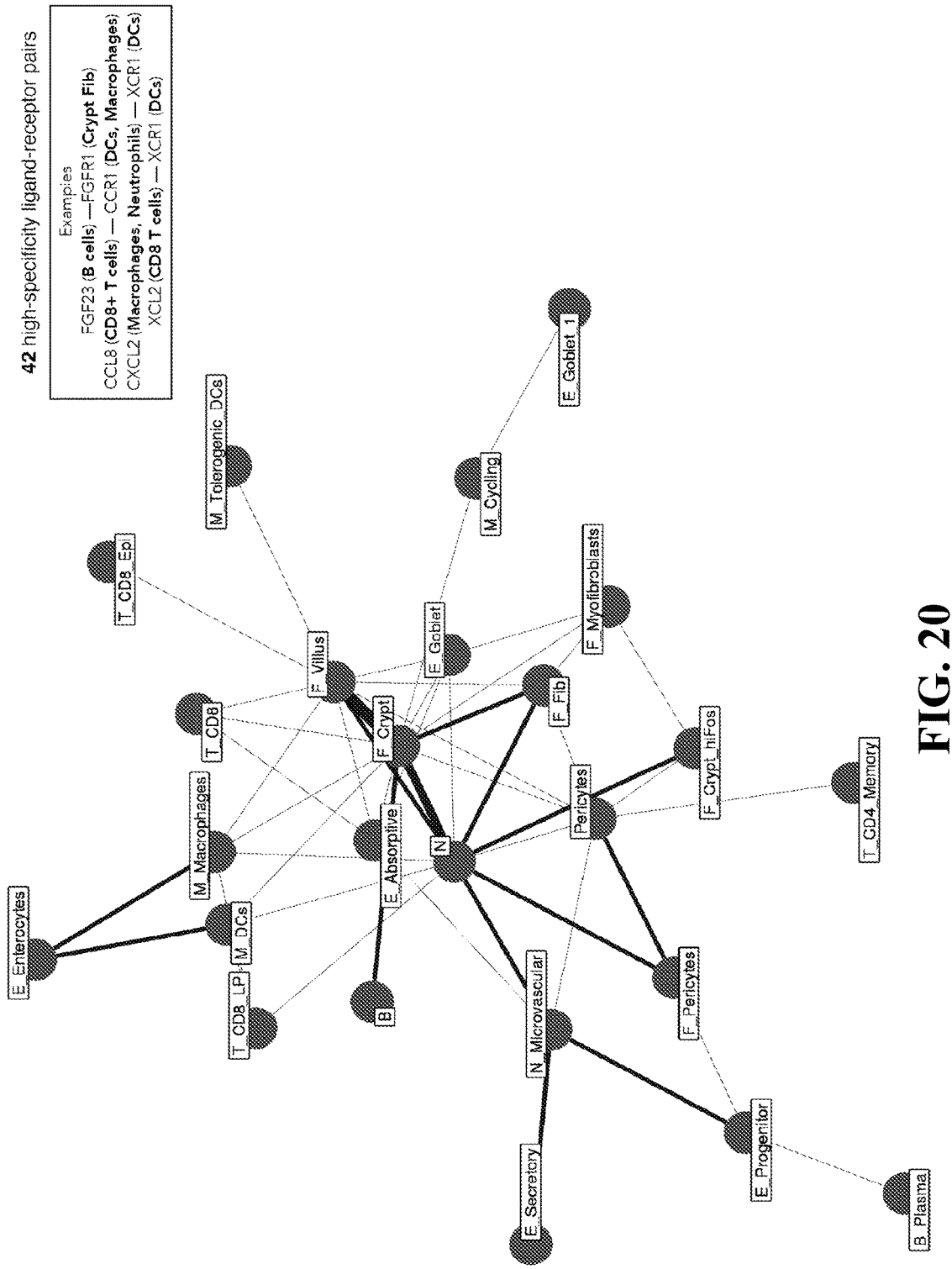
FIG. 20—illustrates cell-cell interactions in the diseased gut.
Figure 21:
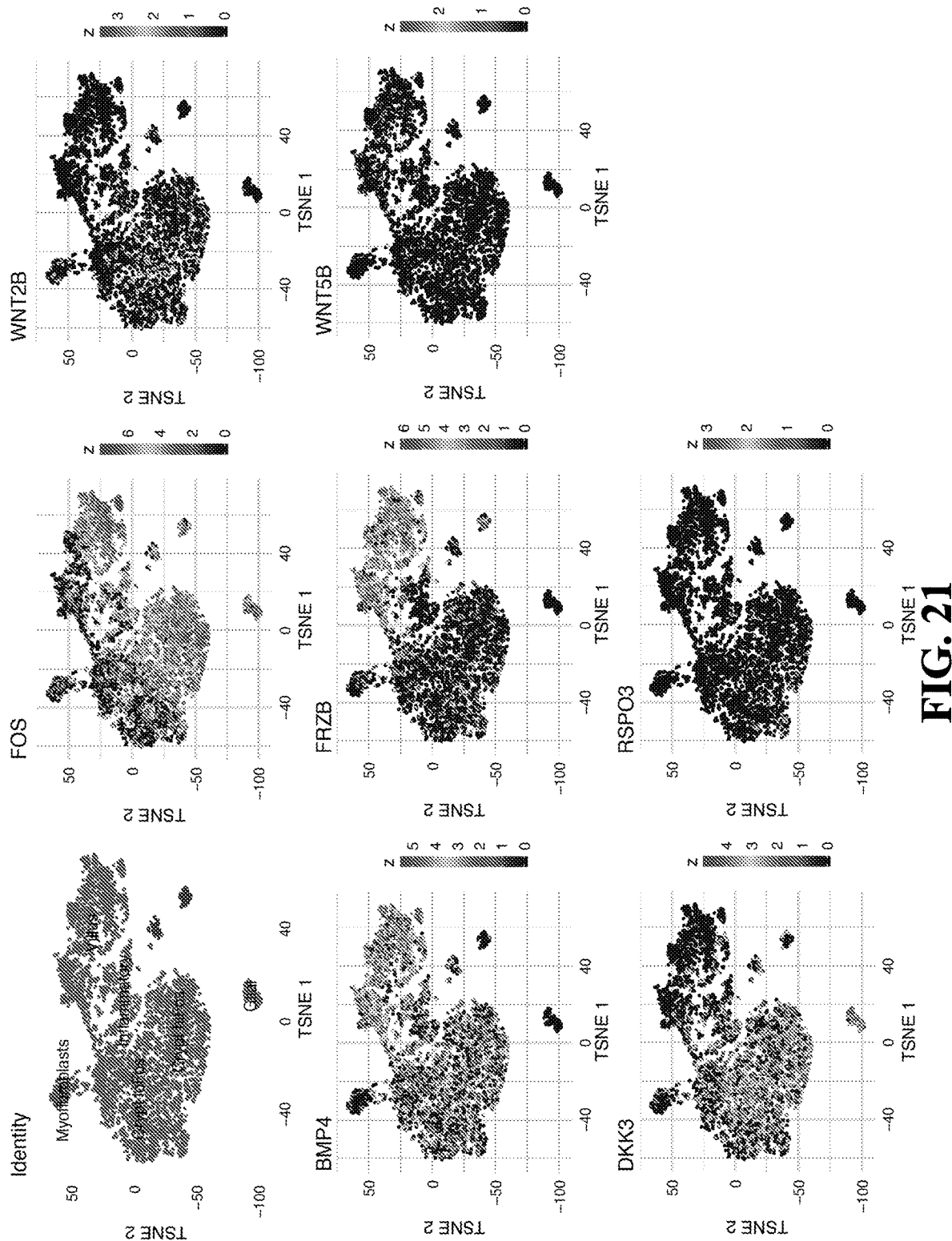
FIG. 21—illustrates that the atlas can be used to determine fibroblasts that support the stem cell niche.

Applicants also show that the atlas may be used to determine cell-cell interaction mechanisms within the gut (FIG. 18). FIG. 19 shows cell-cell interactions in healthy tissue and FIG. 20 shows cell-cell interactions in diseased tissue. Applicants identified for the first time cell types that interact in healthy and disease gut tissue and have determined high specificity ligand receptor pairs that allow the cells to interact. Not being bound by a theory, modulating these interactions can allow modulation of the gut to prevent and treat disease (e.g., IBD). Not being bound by a theory the interactions may be disrupted using small molecules, antibodies and/or soluble proteins.

Figure 22:
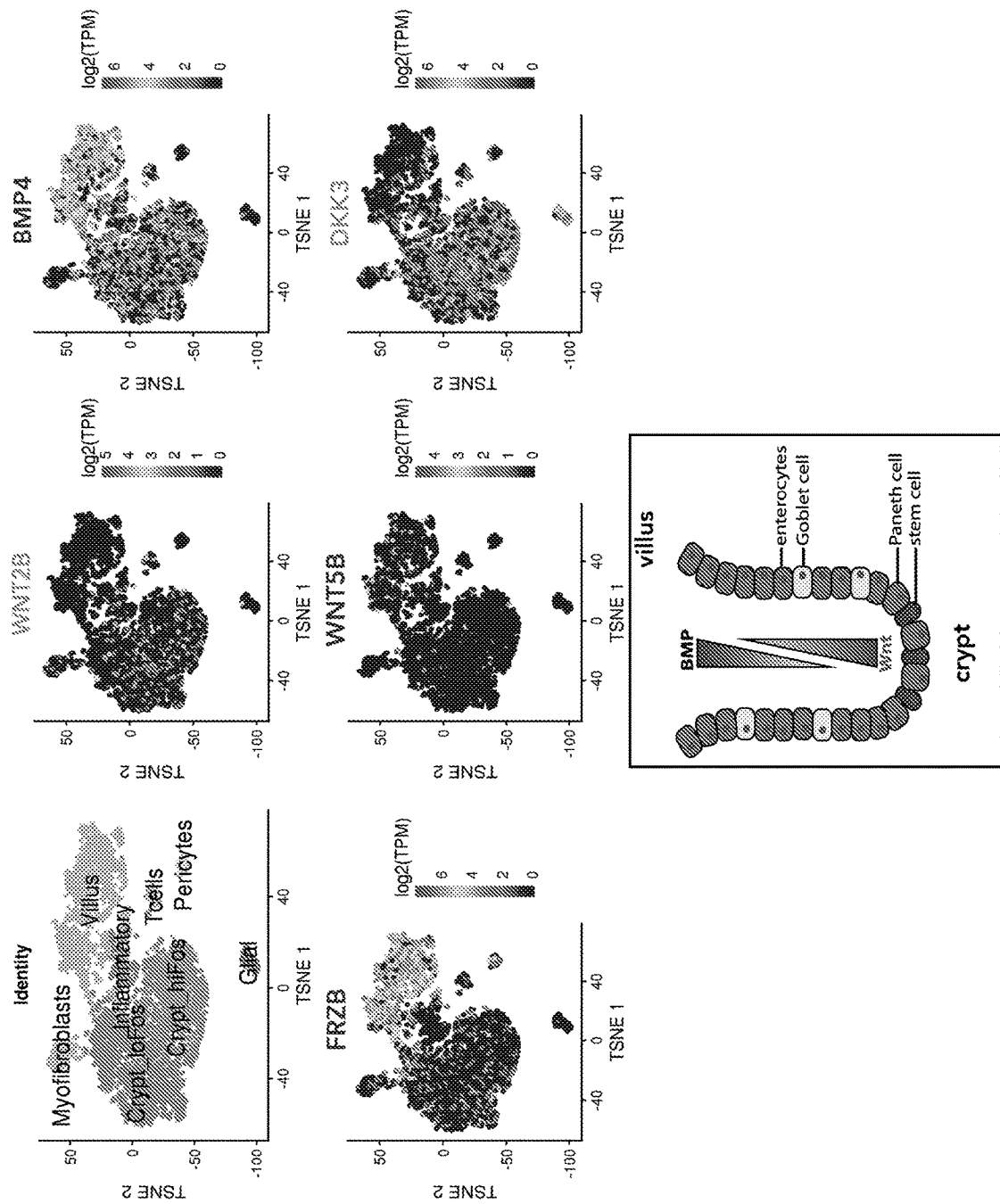
FIG. 22—illustrates fibroblasts genes that support the stem cell niche (right) BMP expression and Wnt expression in the villus and crypt.
Figure 23:
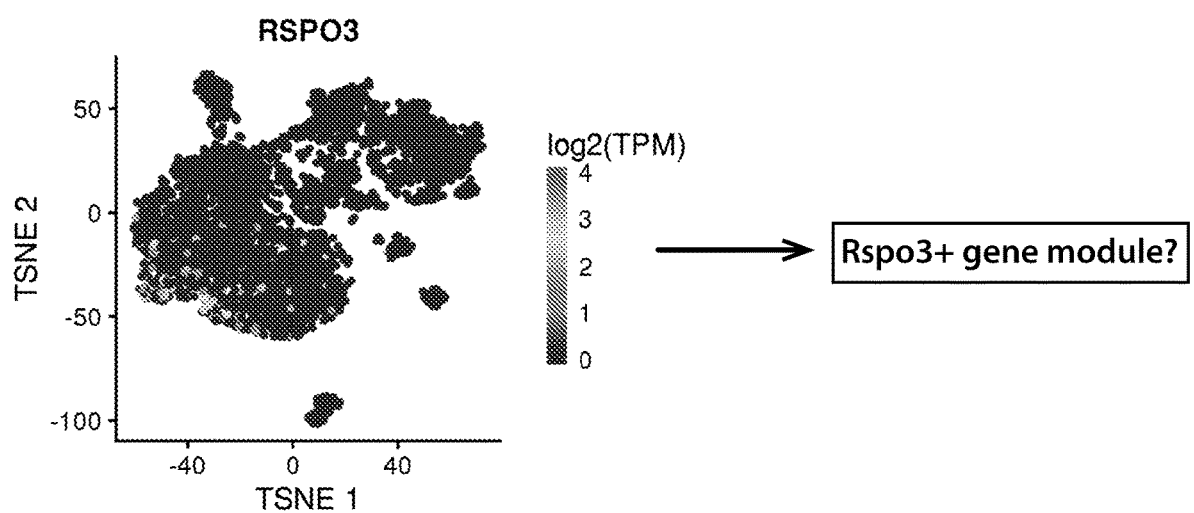
FIG. 23—illustrates Rspo3 gene expression in the tSNE plot of FIG. 22.
Figure 24:
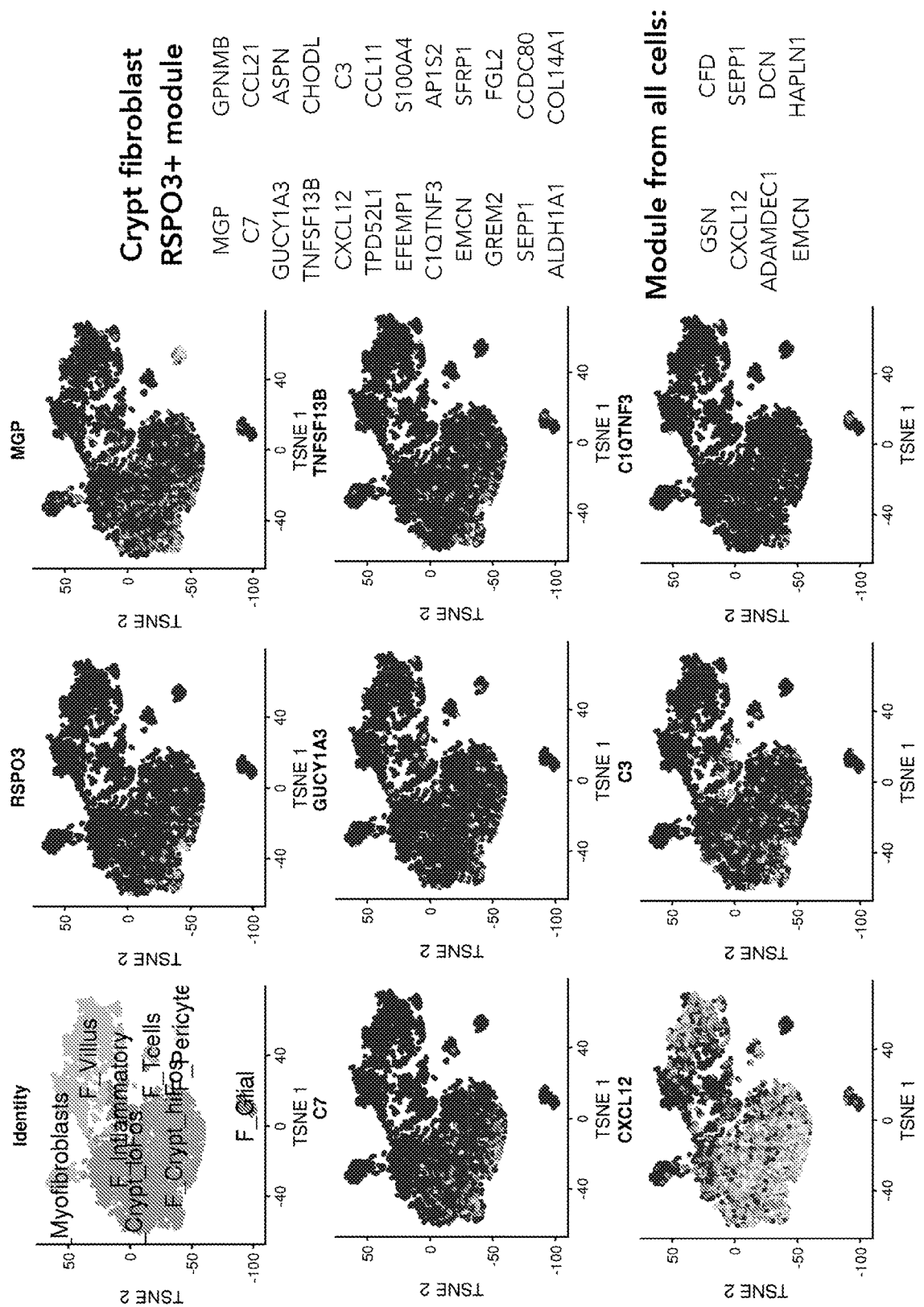
FIG. 24—illustrates a Rspo3 gene-expression module and a module from all cells in the tSNE plot.

Finally, Applicants show that fibroblasts that support the stem cell niche can be identified using the atlas (FIGS. 21-24). FIG. 22 shows genes expressed in the villus (e.g., BMP) and genes expressed in the crypt (e.g., Wnt). Genes associated with either locus can be identified by examining gene expression the tSNE plot. For example, FIGS. 23 and 24 show RSPO3 expression in the tSNE plot and an RSPO3 module may be identified by co-expression in the plot (e.g., MGP, C7, GUCY1A3, TNFSF13B, CXCL12, C3, and C1QTNF3).

The genes and cell types identified in this study can also be used to perform in situ validation, functional tests (e.g., organoids), GWAS covariation studies (e.g., to relate changes in cell types through molecular connections).

Figure 25:
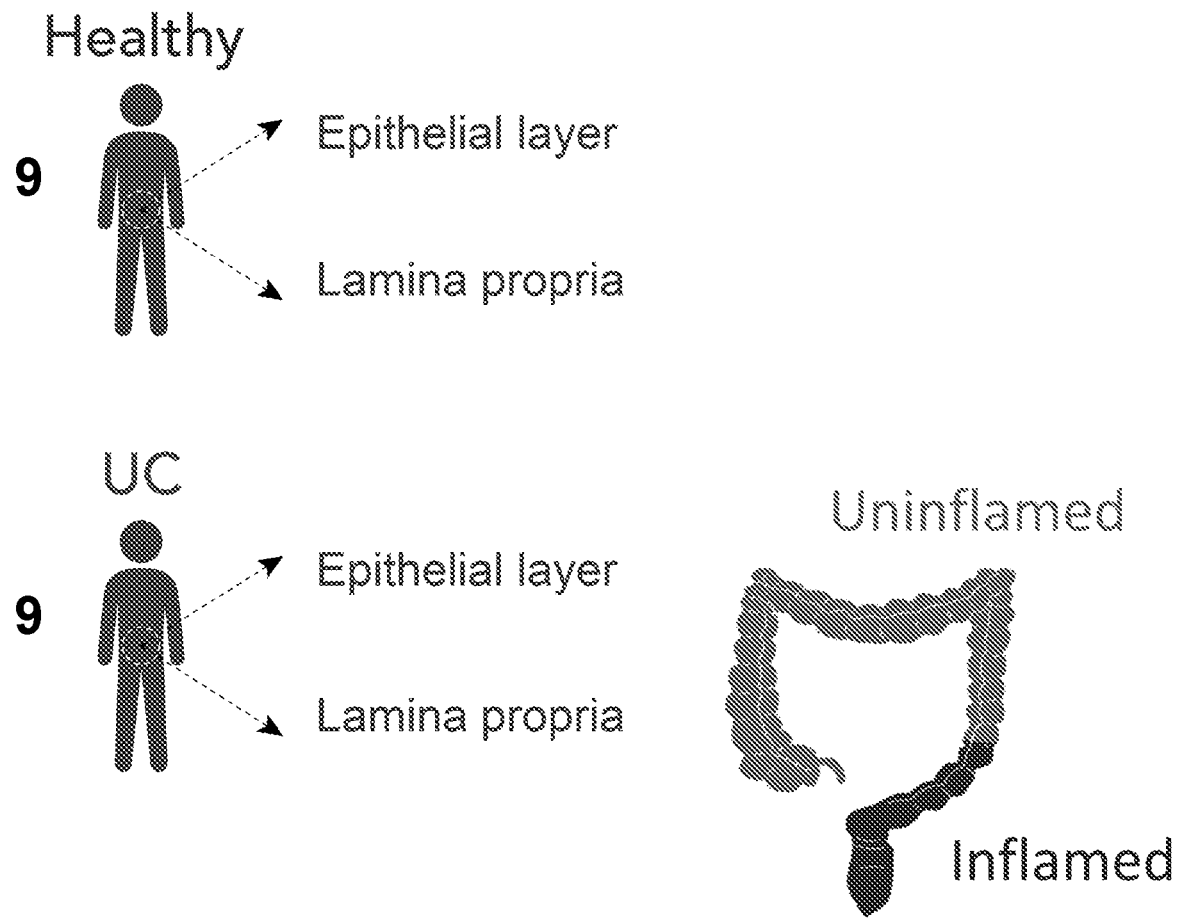
FIG. 25—illustrates a diagram of the study design and sample collection.
Figure 31:
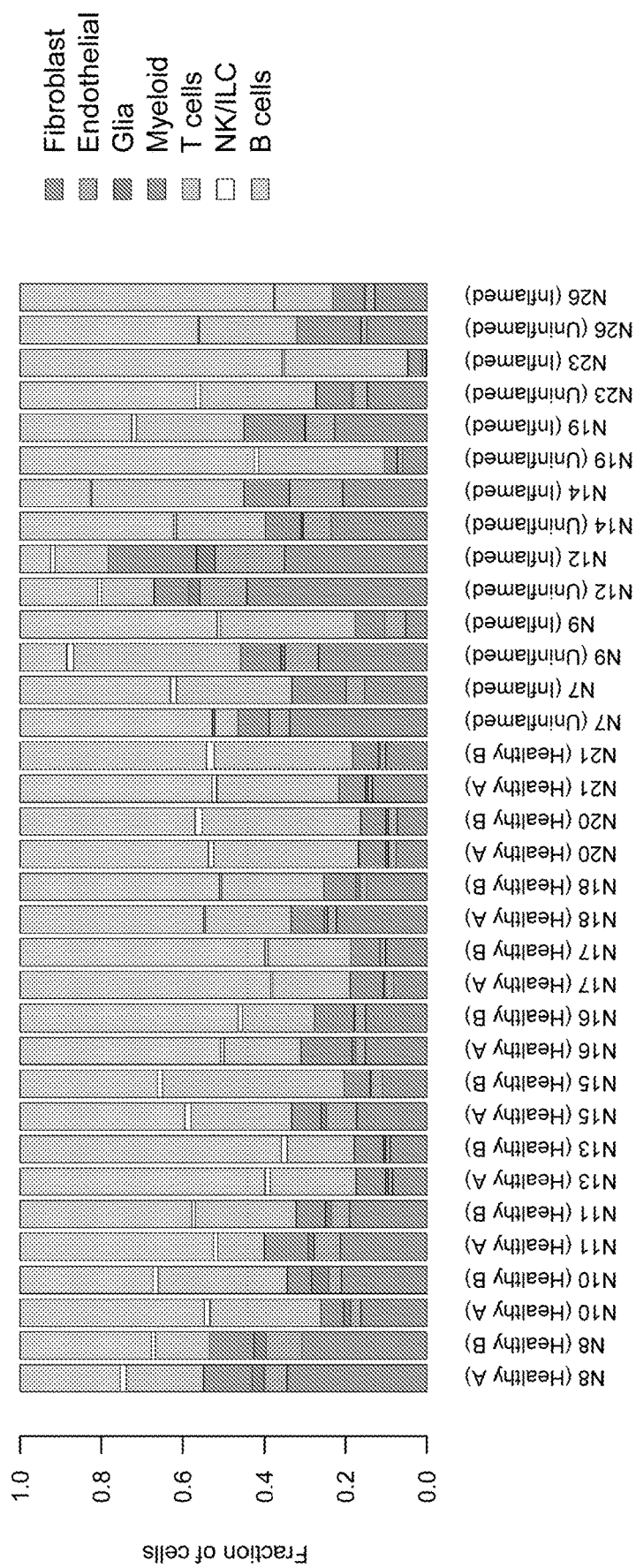
FIG. 31—Barplots showing the fraction of cells in the samples.
Figure 32:
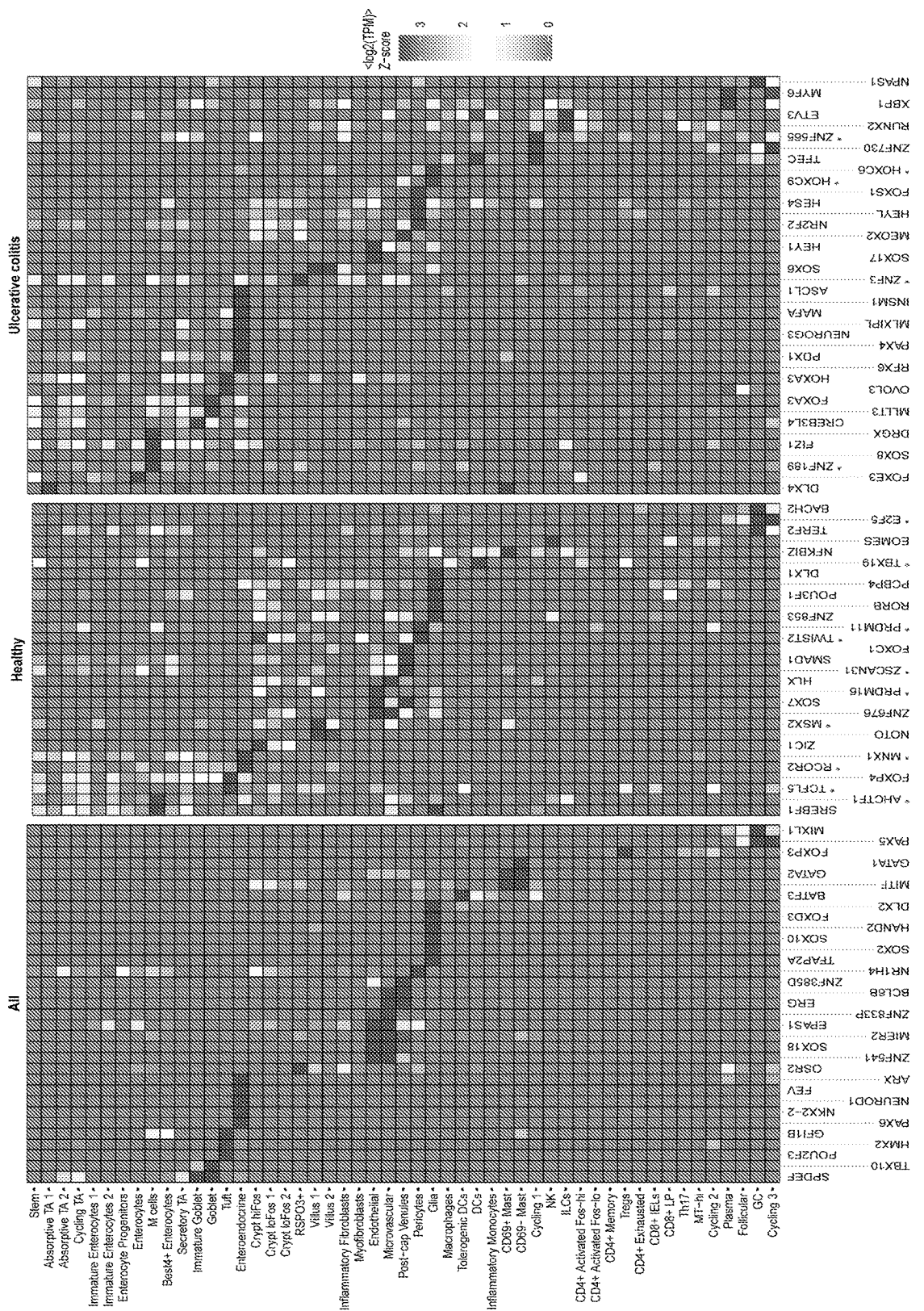
FIG. 32—Heatmap showing expression of transcription factors across all cells, healthy cells and UC cells.

Example 2—scRNA-Seq Atlas of Colon Biopsies from Healthy Individuals and Ulcerative Colitis (UC) Patients To understand the cellular and molecular changes associated with UC, Applicants obtained 115,517 high-quality single cell transcriptomes from 34 colon biopsies (each<2.4 mm$^2$) that were collected from 7 patients with left-sided colitis and 10 healthy individuals who underwent colonoscopic examination (FIG. 25, STAR Methods). To investigate the transitions between healthy mucosa and chronic inflammation, while mitigating patient-specific variability, paired samples were collected from each subject during a single procedure. For UC patients, these were assessed as adjacent inflamed and non-inflamed tissue (FIG. 25, STAR Methods); non-inflamed biopsies may be either "non-colitis" (i.e. no history of inflammation) or "post-colitis" (i.e. resolved inflammation). From healthy subjects, these were two location-matched adjacent samples to estimate transcriptional and compositional variability. Immediately after collection, Applicants separated tissue samples into "epithelial" (EPI) and "lamina propria" (LP) fractions (allowing recovery of sufficient LP cells), dissociated them into single cell suspensions, and profiled the cells using scRNA-seq (FIG. 25 and FIG. 31, STAR Methods). As expected, EPI samples mostly consisted of epithelial cells (89%±15% epithelial cells on average) with some tissue-resident immune cells, such as intraepithelial lymphocytes and mast cells (FIG. 26D), whereas LP samples primarily contained immune and stromal cells (84%±18% immune and stromal cells on average).

Example 3—a Comprehensive Census of 51 Cell Subsets and their Molecular Signatures To construct a cell atlas of the human colon in health and disease, Applicants used the expression levels of known markers to divide the cells into three groups: i) epithelial cells, ii) immune cells, including myeloid and lymphoid lineages, and iii) stromal cells, including fibroblasts, glia, and endothelial cells.

The single cell profiles partitioned into 51 subsets by unsupervised clustering (FIG. 26B,H, after correction for technical and biological variation, STAR Methods), which Applicants annotated post-hoc known markers (FIG. 26C) to reveal 15 epithelial, 23 immune (lymphoid and myeloid) and 13 stromal (fibroblasts, glia, and endothelial cells) subsets. The "cell subsets" almost invariably had representation from all specimens, and were proportionally distributed across samples of the same type (FIGS. 26D and 31), indicating that the clustering is driven by shared programs across samples, rather than by inter-sample differences.

Even though the cells were isolated from miniscule biopsies (~2.4 mm$^2$), the 51 subsets recapitulate nearly all of the known cellular diversity within the colonic mucosa (FIG. 26B) and highlight new subsets (below). This includes 15 subsets of epithelial cells, pseudo=temporally ordered along the differentiation trajectory (FIG. 26H), from LGR5$^+$ intestinal stem cell to mature absorptive and secretory cell fates and including M cells (below); 8 subsets of fibroblasts partitioned defined by WNT and BMP signaling, including novel inflammation-associated fibroblasts, discussed below (also, including three subsets of WNT2B+ fibroblasts, two subsets of BMP4+ fibroblasts, as well as RSPO3+ fibroblasts, myofibroblasts, and inflammation-associated fibroblasts); four subsets of endothelial cells partitioned; one glia subset; seven myeloid cells (including inflammatory monocytes; below), four B cell subsets, ten T cell subsets across CD4$^+$ Tconv, CD4$^+$ Tregs and CD8$^+$ cells, including CD8$^+$ IL-17$^+$ T cells, and CD4$^+$PD-1$^+$ T cells, innate lymphoid cells (a mix of ILC2s and 3s), and NK cells (NKs) (FIG. 26B,H). To Applicants knowledge, known subsets missing from the census include submucosal enteric neurons, which require a distinct isolation approach (e.g., single nucleus RNA-Seq Habib et al., 2017), plasmacytoid dendritic cells (pDCs; possibly due to either low frequencies or uneven spatial distribution), and neutrophils, which express degradative enzymes that may damage their RNA or membranes. As expected, Applicants do not capture submucosal cells, such as myocytes and adipocytes, which require colon resection material.

Figure 33:
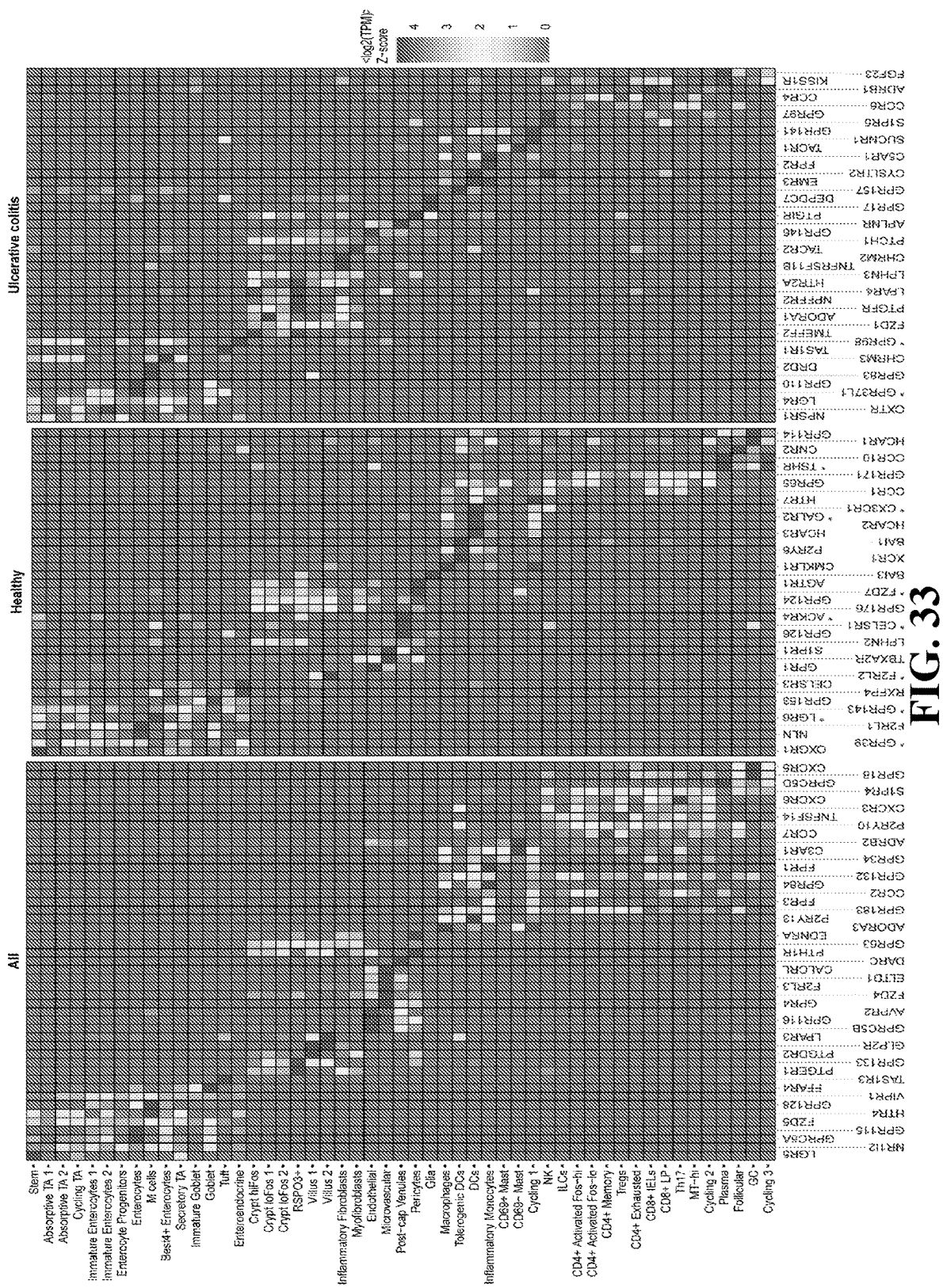
FIG. 33—Heatmap showing expression of G protein-coupled receptors (GPRC) across all cells, healthy cells and UC cells.
Figure 34:
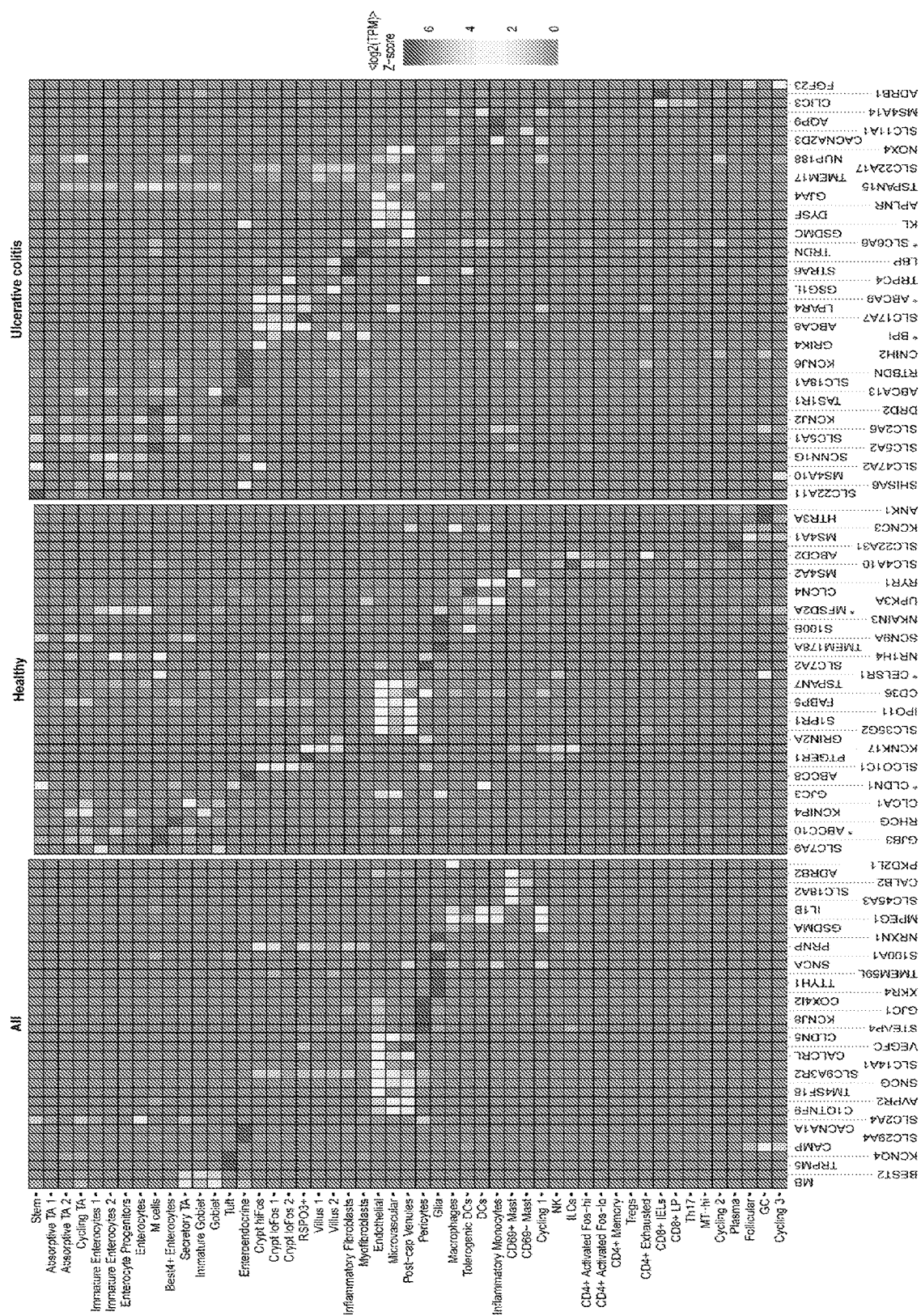
FIG. 34—Heatmap showing expression of transporters across all cells, healthy cells and UC cells.
Figure 35:
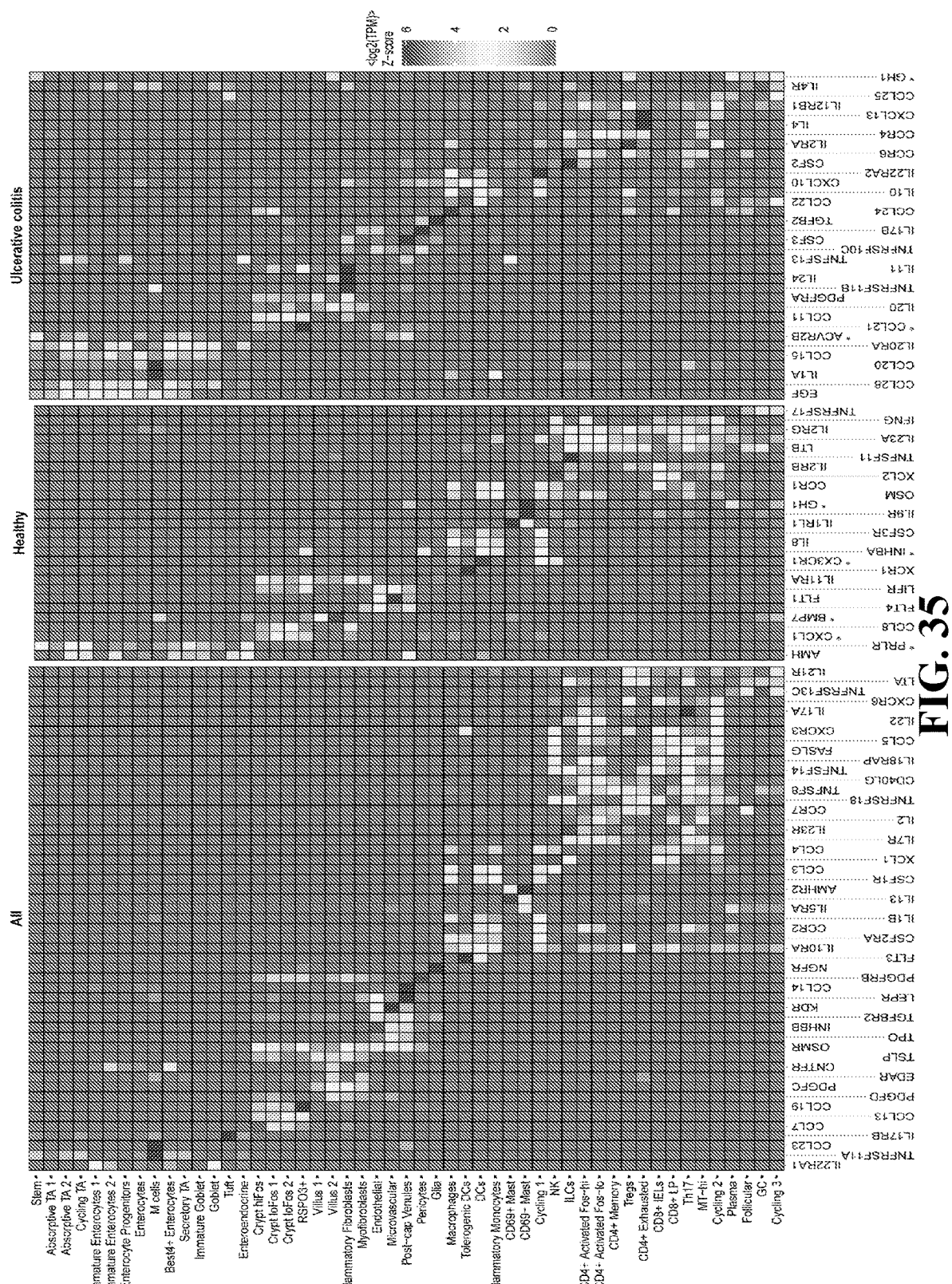
FIG. 35—Heatmap showing expression of cytokines across all cells, healthy cells and UC cells.
Figure 36:
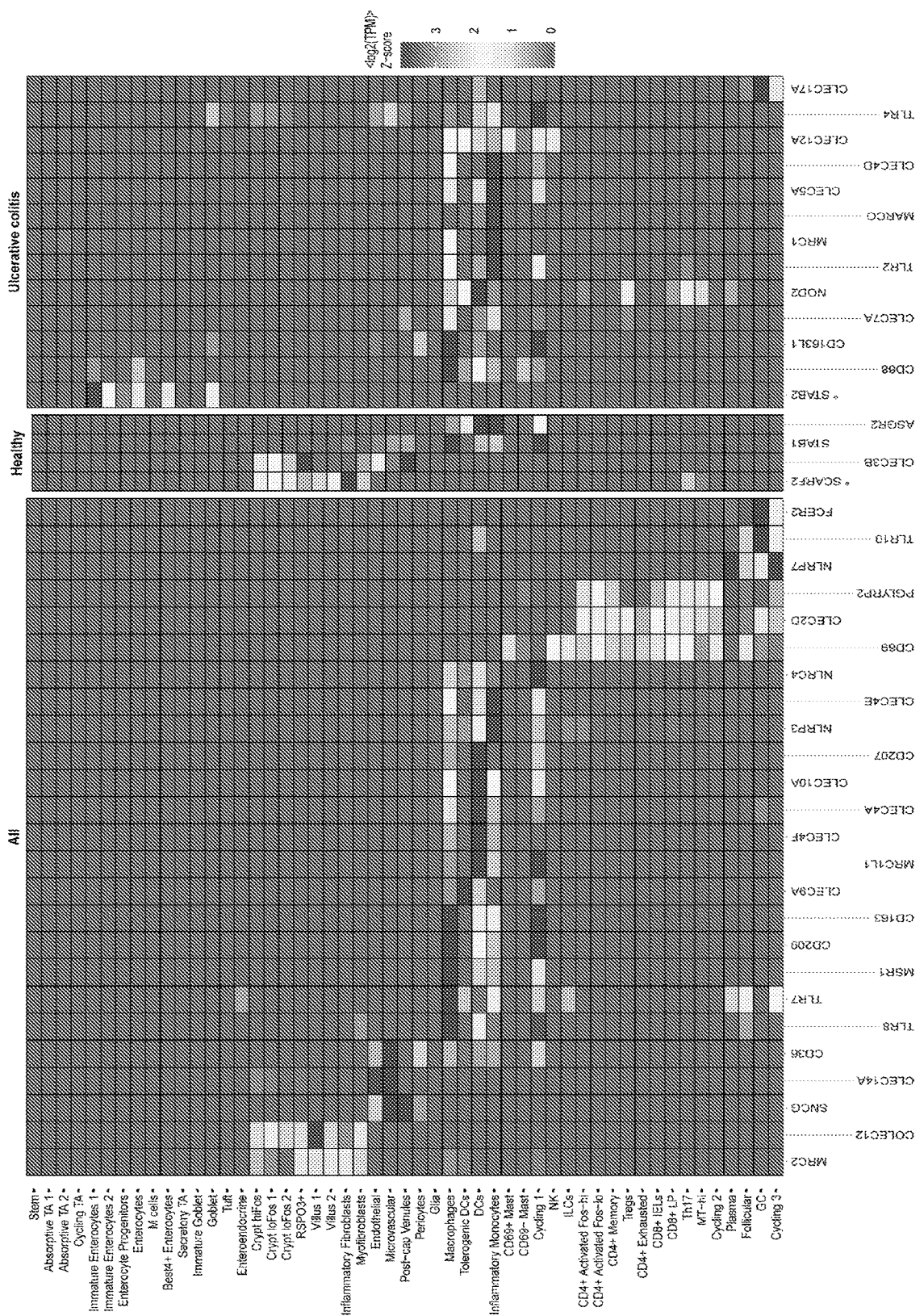
FIG. 36—Heatmap showing expression of pattern recognition receptors (PRR) across all cells, healthy cells and UC cells.

Each cell subset is supported by a distinct expression profile, including known and new markers of known subsets and signatures of new subsets (FIG. 26H), with cell type-specific transcription factors (TFs), G protein-coupled receptors (GPCRs), transporters, cytokines, and pattern recognition receptors (FIGS. 32-36). For example, the CD4$^+$ FOXP3$^+$IL10$^+$ T$_{regs}$ expressed BATF, a critical TF for the differentiation of tissue-resident T$_{regs}$ (FIG. 32); inflammatory monocytes, thought to underlie chronic immune activation in many diseases, but not previously profiled in UC patients, express Oncostatin M (OSM), a cytokine associated with resistance to anti-tumor necrosis factor (TNF) therapy in IBD patients (FIG. 35). Surprisingly, compared to other cell types, plasma cells and cycling B cells expressed relatively high levels of the NOD-like receptor, NLRP7, a gene associated with IBD through GWAS, which recognizes microbial lipopeptides and is not known to be expressed by B cells (FIG. 33).

Figure 26A:
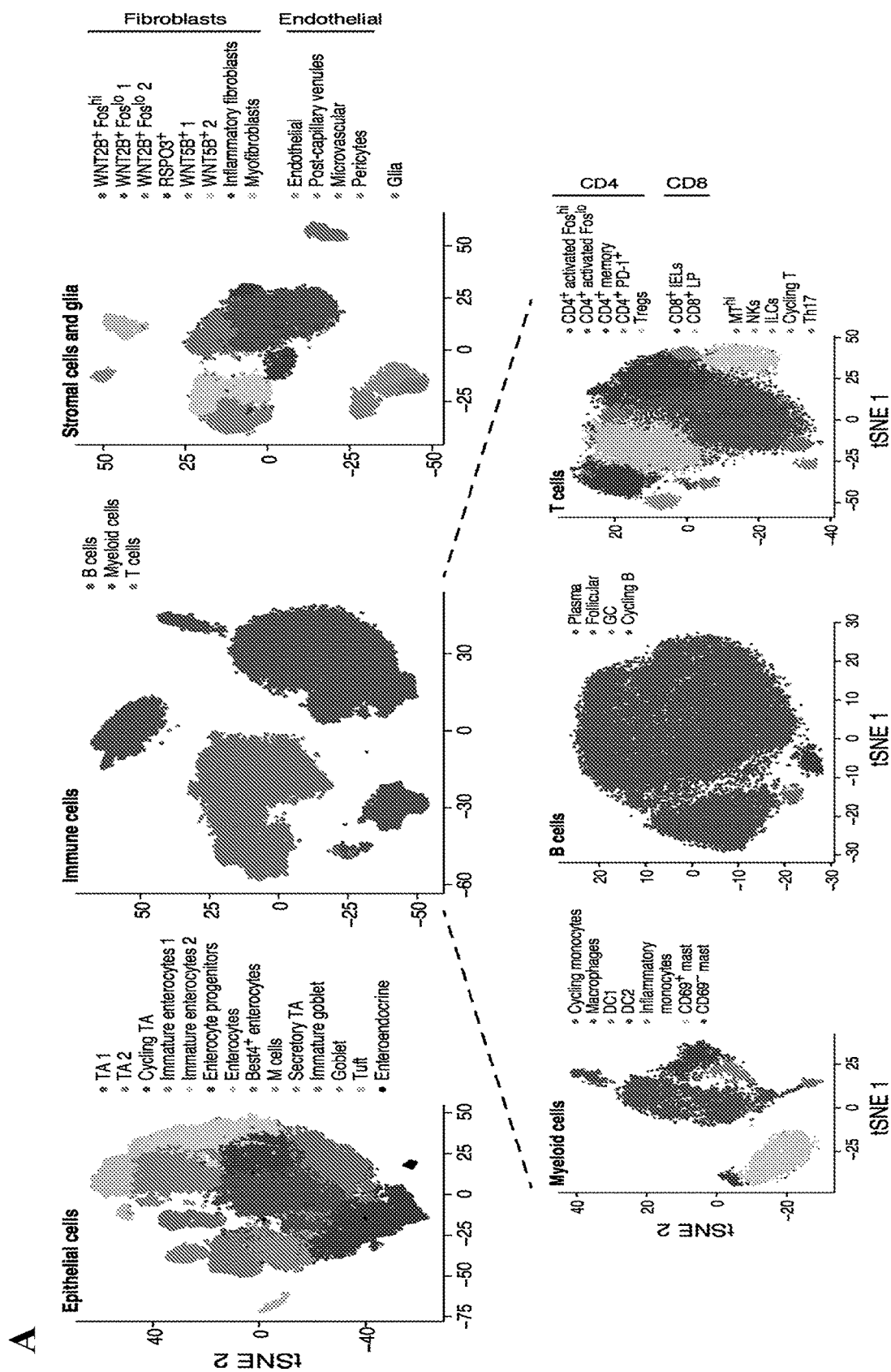
FIG. 26—Cell atlas of the human colon in health and disease. a. tSNE clustering by cell type. b. Heatmap showing expression of cell type specific markers. c. Barplot showing proportions of cell subsets across samples of the same type (health, uninflamed, inflamed). d. Plot showing distribution of cell types. e. Expression of novel markers in cell subsets. f. Expression of specific markers in cell subsets. g. Pathway showing that angiotensinogen is produced by WNT5B+ fibroblasts, renin by BEST4+ enterocytes, Angiotensin Converting Enzyme (ACE) by epithelial and endothelial cells, and the angiotensin receptor AGTR1 by WNT2B+ fibroblasts and pericytes. h. Heatmap showing expression of cell type specific markers.
Figure 26B:
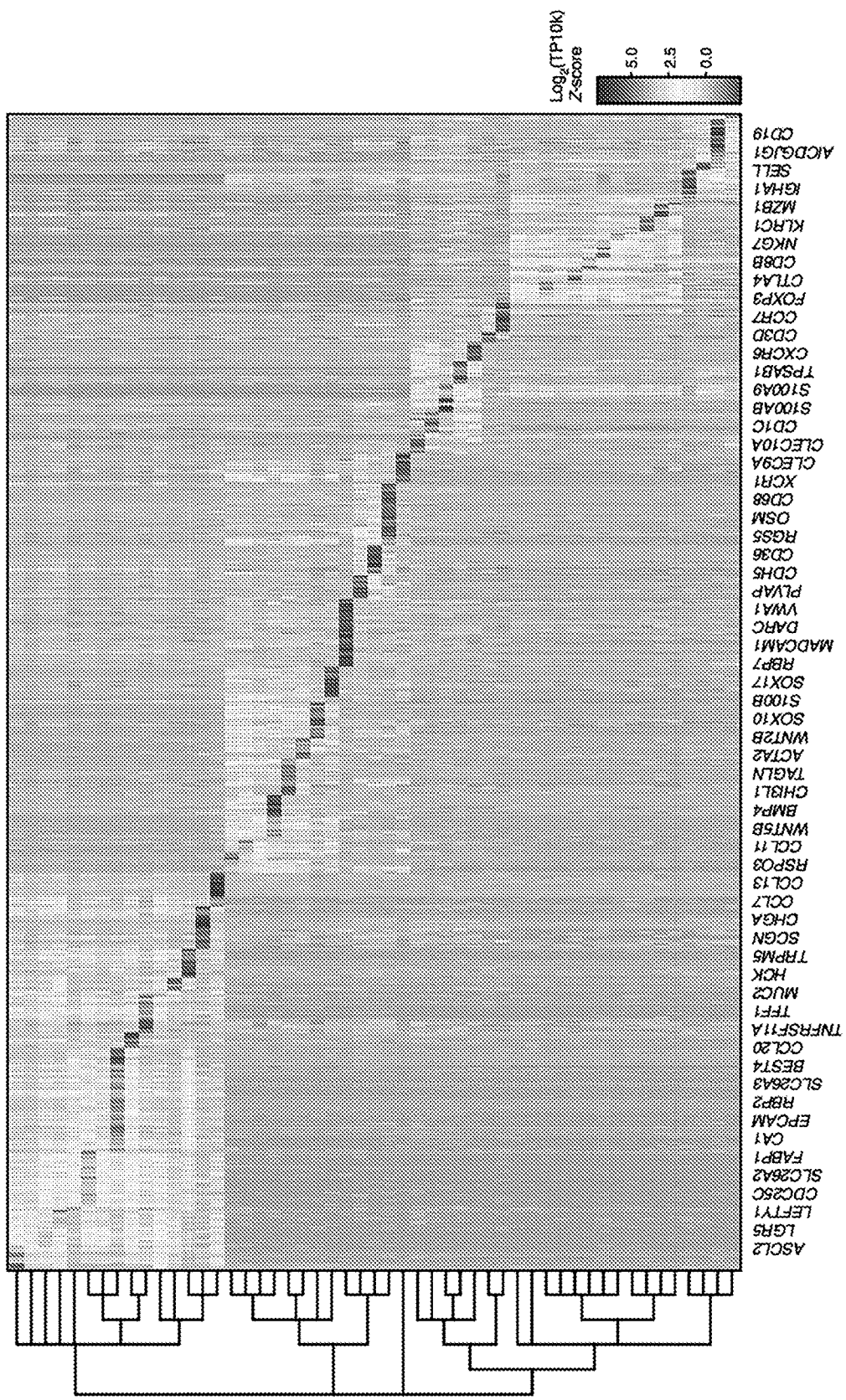
Figure 26C:
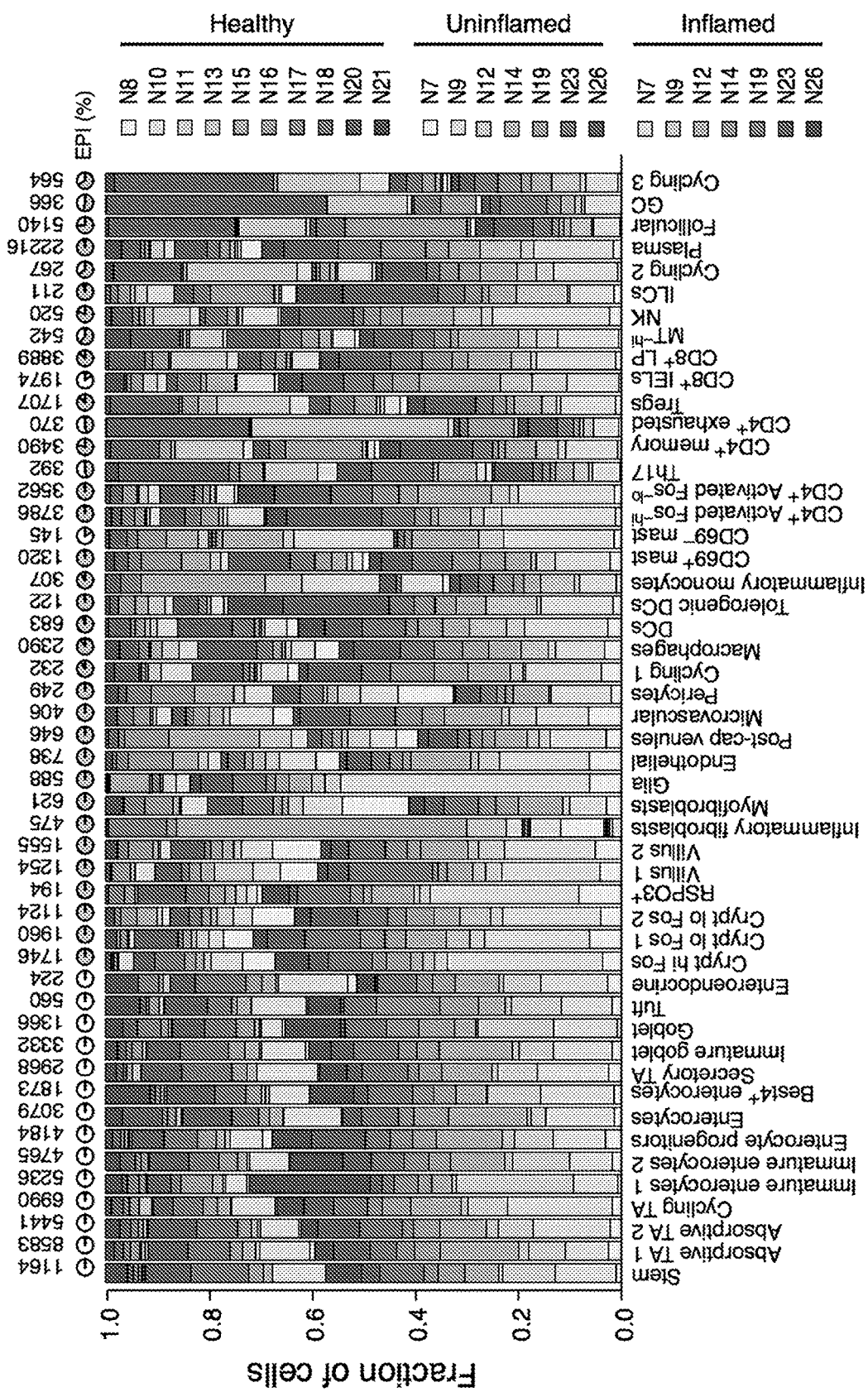
Figure 26D:
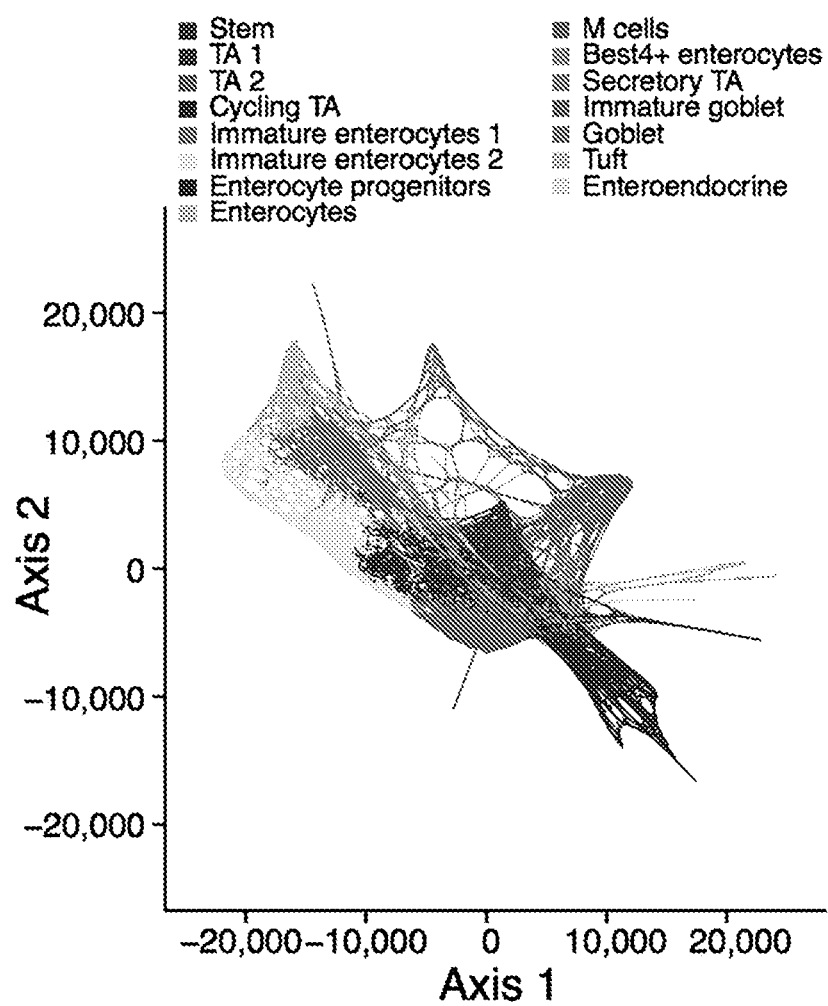
Figure 26G:
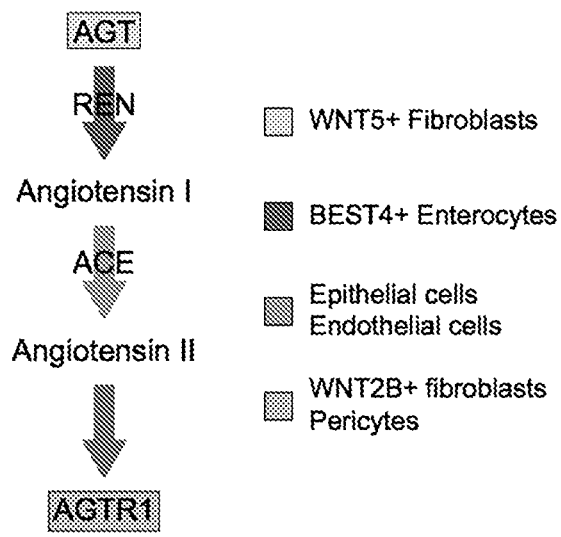
Figure 26H:
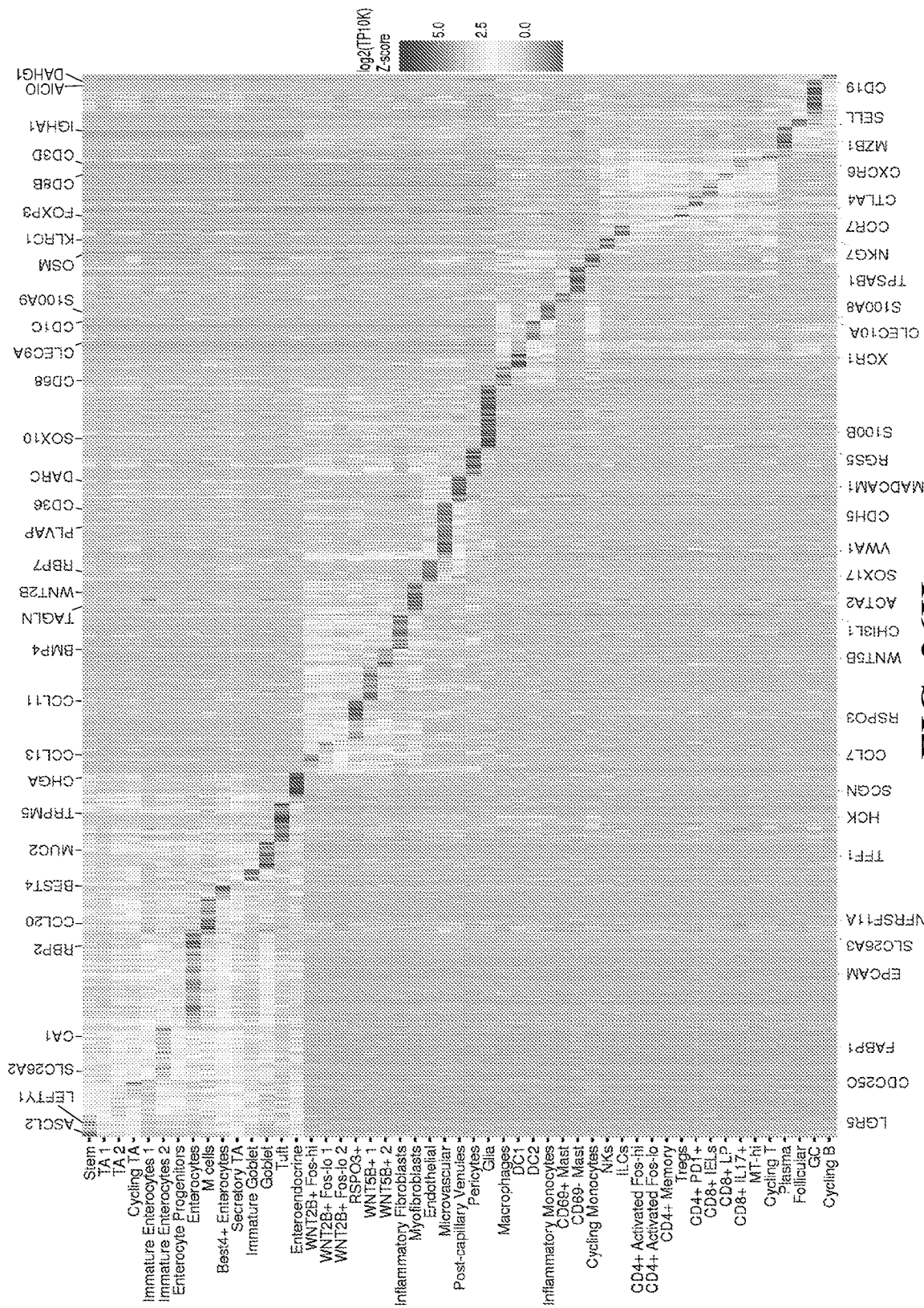

Example 4—New BEST4$^+$ Epithelial Cells and Fibroblast Subsets in the Healthy Colon The census reveled a new subset of chemosensory BEST4$^+$ enterocytes that express genes related to acid and electrolyte sensing (e.g., pH (acid sensing) and electrolyte balance) (FIG. 26E), including BEST4, OTOP2, CA7, and Renin (REN), to likely complete a local renin-angiotensin system (RAS) in the colon (FIG. 26E,G). In particular, the otopetrin family encodes proton-selective ion channels, including OTOP1, which is enriched in taste receptor cells and contributes to sour taste perception through the detection of acids. Within the intestine, tuft cells are thought to transduce bitter, sweet, and umami tastes through the calcium channel TRPM5, but distinct pathways are required for sour and salty tastes. BEST4$^+$ enterocytes may therefore be responsible for pH sensing and sour taste perception within the colon. These cells also express SPIB, a TF also expressed by tuft and microfold cells, suggesting they may be developmentally related. Based on the data (FIG. 26G), angiotensinogen is produced by WNT5B$^+$ fibroblasts, renin by BEST4$^+$ enterocytes (e.g., in response to local electrolyte levels), Angiotensin Converting Enzyme (ACE) by epithelial and endothelial cells, and the angiotensin receptor AGTR1 by WNT2B$^+$ fibroblasts and pericytes, suggesting this pathway may be involved in local colon vasoconstriction.

Multiple fibroblast subsets differed by the expression of WNT and BMP signaling genes, reflecting distinct positions along the intestinal crypt-villus axis. One subset is transcriptionally similar to subepithelial telocytes, a rare population of mesenchymal cells that supports the epithelium that were recently profiled in mice. Some express higher levels of WNT2B, WNT4, and DKK3, and thus may reside near the intestinal crypt, whereas others highly express BMP4, BMP5, and WNT5, and thus may reside away from the crypt (FIG. 26F). All subsets express low levels of FOXL1, the defining marker of subepithelial telocytes in mice, a rare population of mesenchymal cells that supports the epithelium, and share additional marker genes with subepithelial telocytes, but the data show that these genes have distinct expression patterns in humans (FIG. 26F). WNT5B$^+$ subsets (but not Tuft cells) are major sources of expression of thymic stromal lymphopoietin (TSLP), a cytokine that is crucial for the activation of ILC2s and Th2-inducing DCs in the colon, and of the receptor for glucagon-like peptide 2 (GLP2R), a peptide hormone produced by enteroendocrine cells to regulate gut metabolism and physiology (FIG. 26F).

One subset of WNT2B fibroblasts expresses R-spondin-3 (RSPO3) (FIG. 26E,F), the ligand for LGR5, a hallmark receptor of ISCs This subset expresses several other genes related to WNT/BMP signaling, including Gremlin 2 (a BMP inhibitor), glypican, and secreted frizzled-related protein, along with the immune recruiting chemokines CCL11, CCL19, CCL21, and CXCL12 (also expressed by secondary lymphoid organs), supporting a role of an inflammatory microenvironment to maintain the ISC niche.

Example 5—the Colon Cellular Composition in Dramatically Remodeled in UC

Figure 29E:
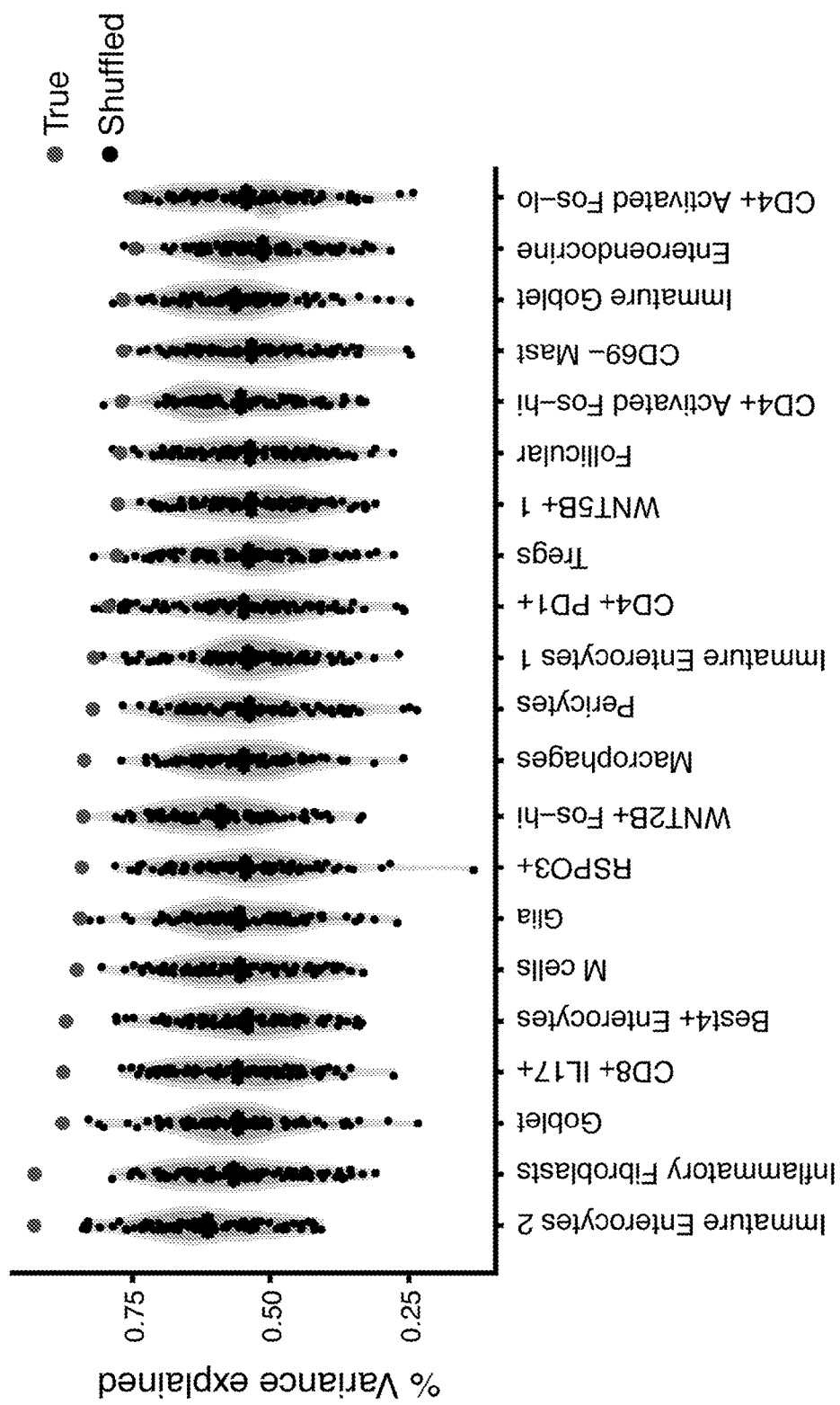
FIG. 29—Cell-Cell Network Rewiring and GWAS. a. Healthy cell-cell network. b. Non-inflamed cell-cell network c. Inflamed cell-cell network. d. shows ligand expression correlated with the frequency of the cells expressing its cognate receptor. e. LASSO regression analysis to predict the frequency of each cell subset using the expression levels of all cognate ligands of its receptors in other cells.

Changes in the composition of cell types that monitor luminal contents and titrate the immune response may affect the functional integrity of the mucosa in UC. To identify such changes, Applicants searched for cell subsets whose proportion changes in the colon between healthy, non-inflamed, and inflamed specimens. Prior work has examined changes in specific cell types, such as infiltration of neutrophils, mast cells, and IL-17$^+$ T cells into the LP, but typically focused on specific cell types. Conversely, the census captures an extensive range of cells simultaneously, but, by definition, as the frequency of one cell subset increases, the frequencies of others decline. Thus, Applicants tested for changes in each subset proportions with a conservative statistical model that accounts for these dependencies (STAR Methods). (To identify changes that may be statistically dependent but physiologically important, Applicants also performed univariate analysis; FIG. 29E).

The analysis highlighted a dramatic remodeling of the colon's cell type composition, spanning 9 epithelial subsets, 10 immune subsets and 9 stromal subsets. often with gradual changes from healthy to uninflamed to inflamed tissue. Applicants correctly captured many changes in cell proportions in UC patients that were previously reported, such as the increase in non-inflamed and inflamed samples in proportions of gut resident mast cells, CD8$^+$ IL-17$^+$ T cells, T$_{regs}$, and endothelial cell subsets in non-inflamed and inflamed samples (FIG. 27A). The magnitudes of these changes increased progressively from healthy to non-inflamed to inflamed samples, suggesting that even nominally "healthy" tissue from UC patients is altered and may represent a transitional state along the course of disease (pre-inflammation or post-resolution).

Figure 38:
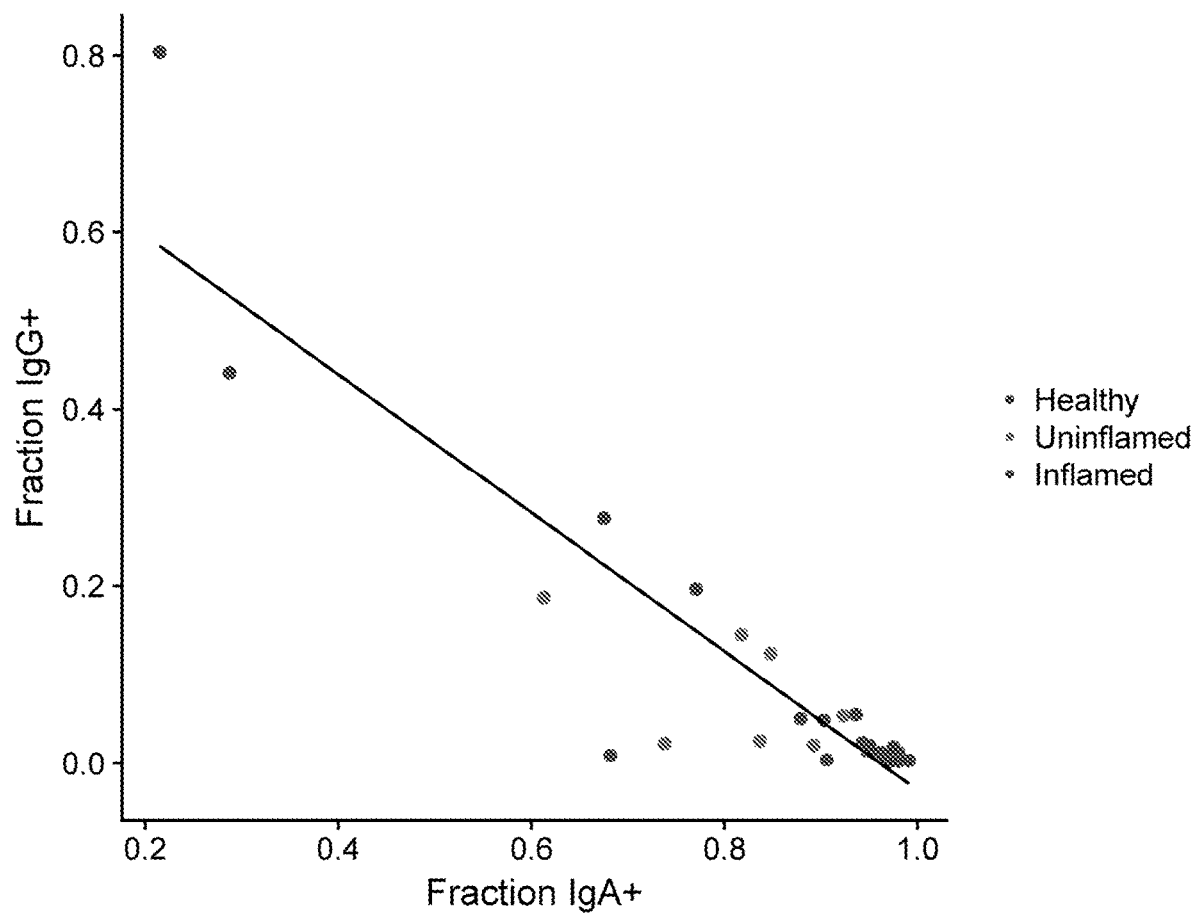
FIG. 38—illustrates IgG class switching in healthy and inflamed tissues.
Figure 39A:
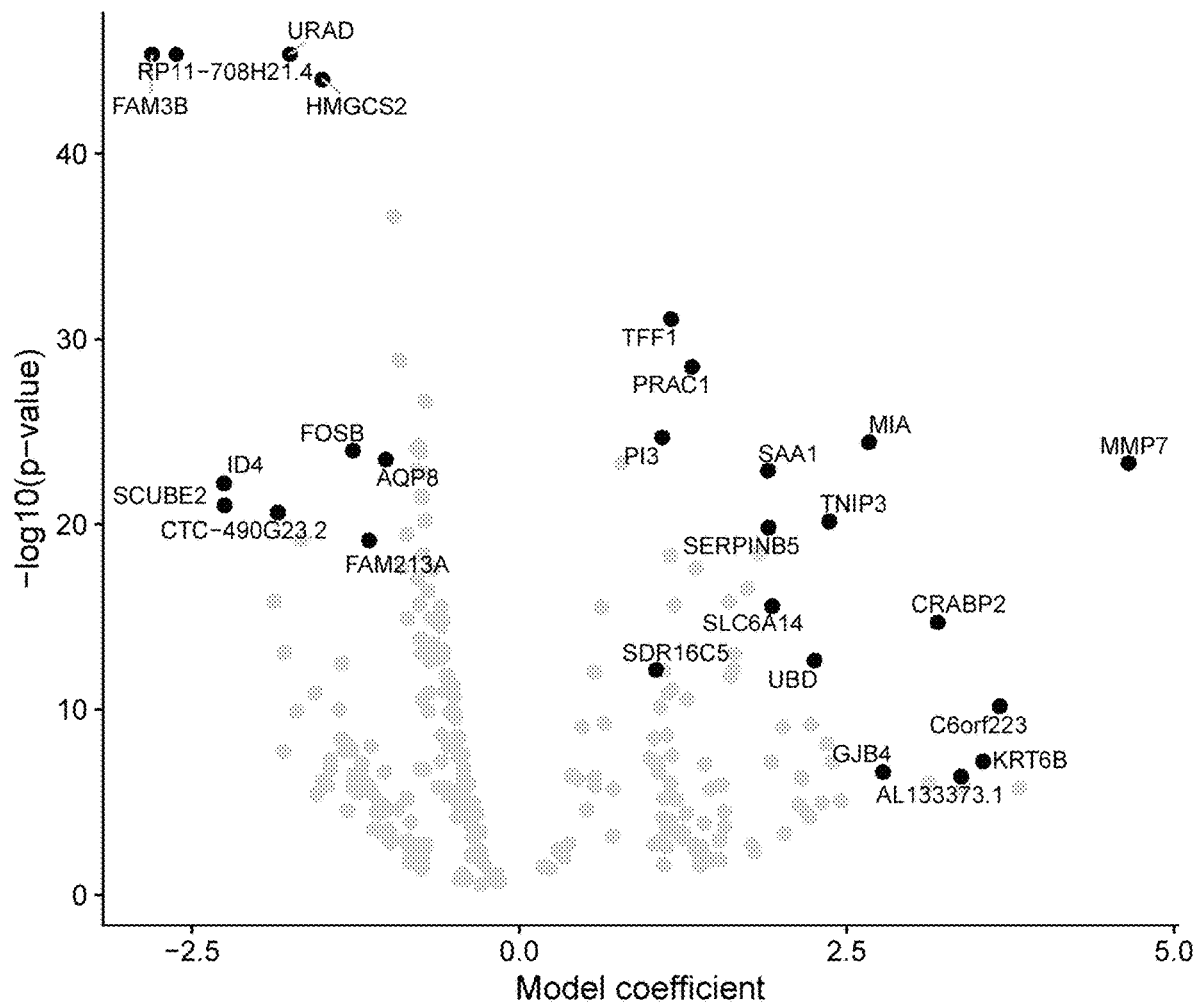
FIG. 39—a. Volcano plot showing general epithelial markers for uninflamed cells. b. Volcano plot showing general fibroblast markers for uninflamed cells. c. Volcano plot showing general immune markers for uninflamed cells. d. Volcano plot showing cell specific epithelial markers for uninflamed cells. e. Volcano plot showing cell specific fibroblast markers for uninflamed cells. f. Volcano plot showing cell specific immune markers for uninflamed cells.
Figure 39B:
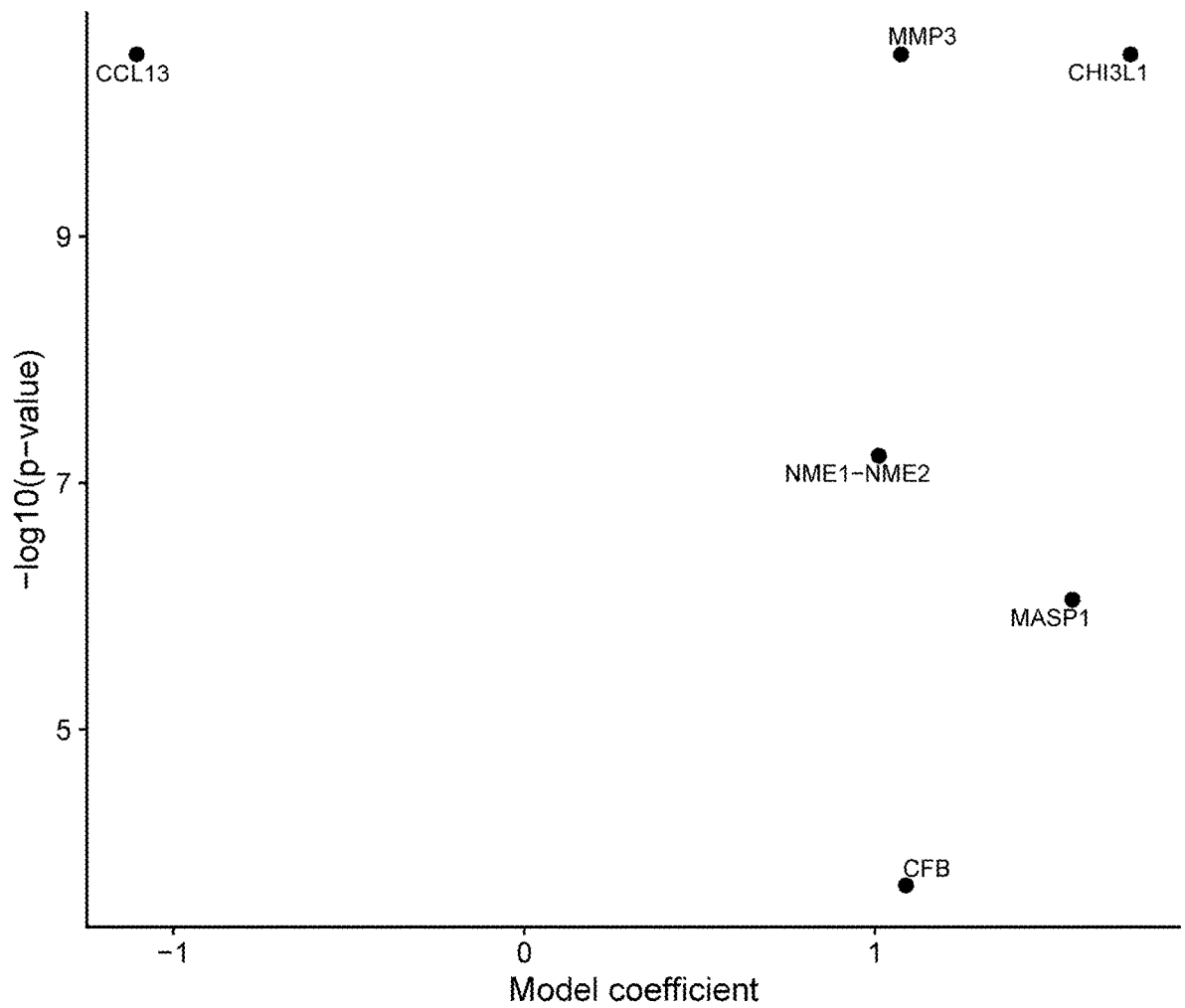
Figure 39C:
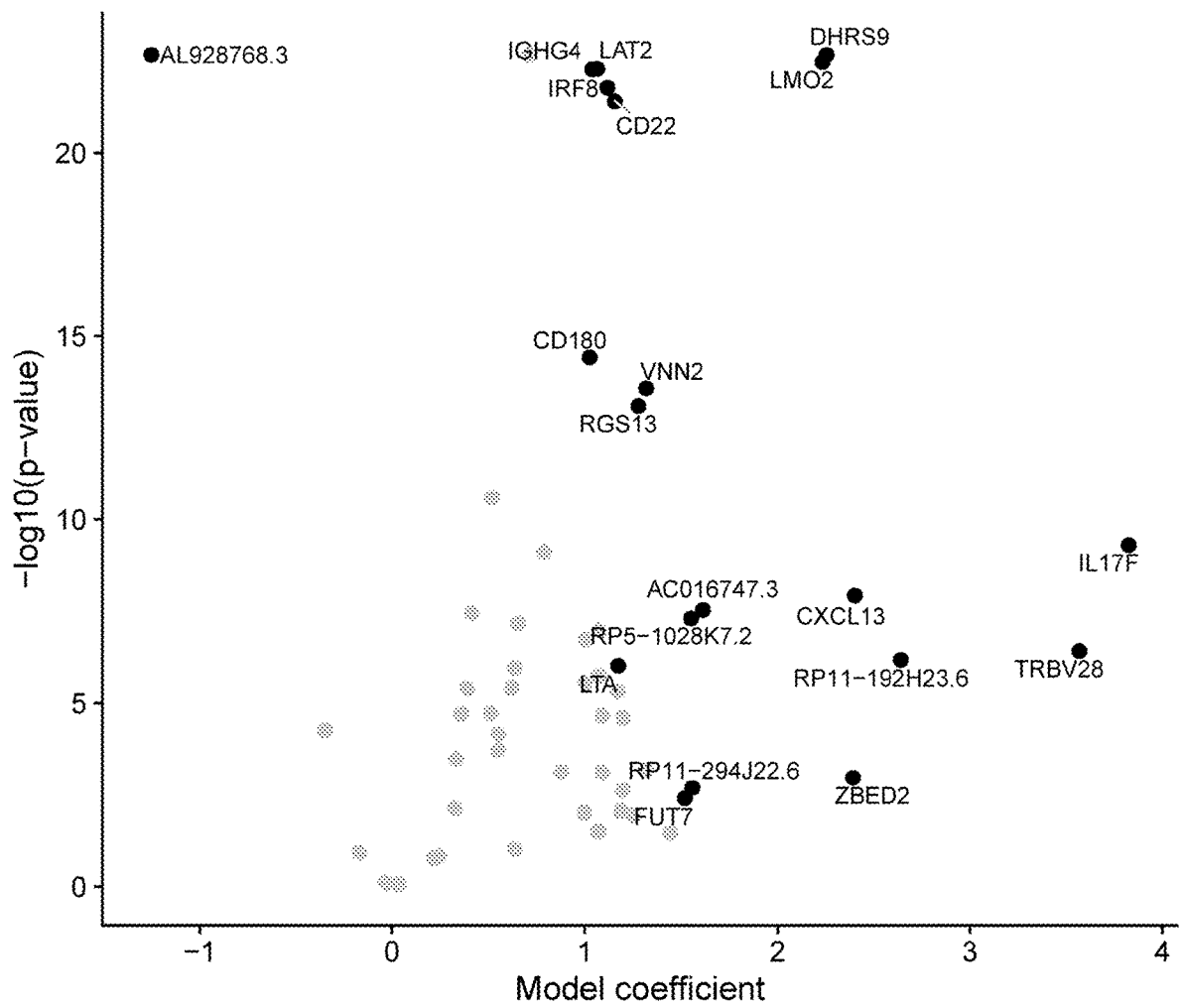
Figure 39D:
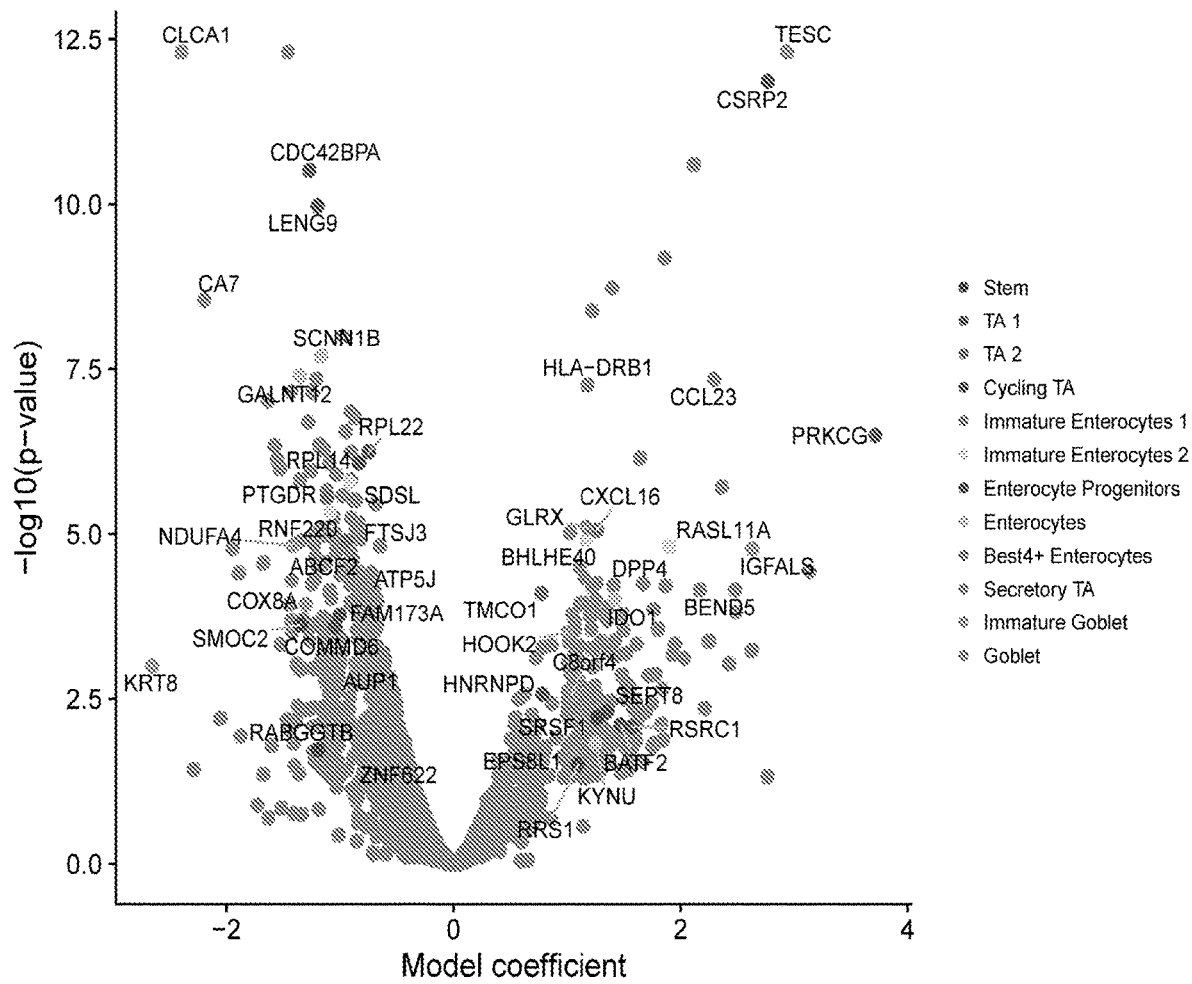
Figure 39E:
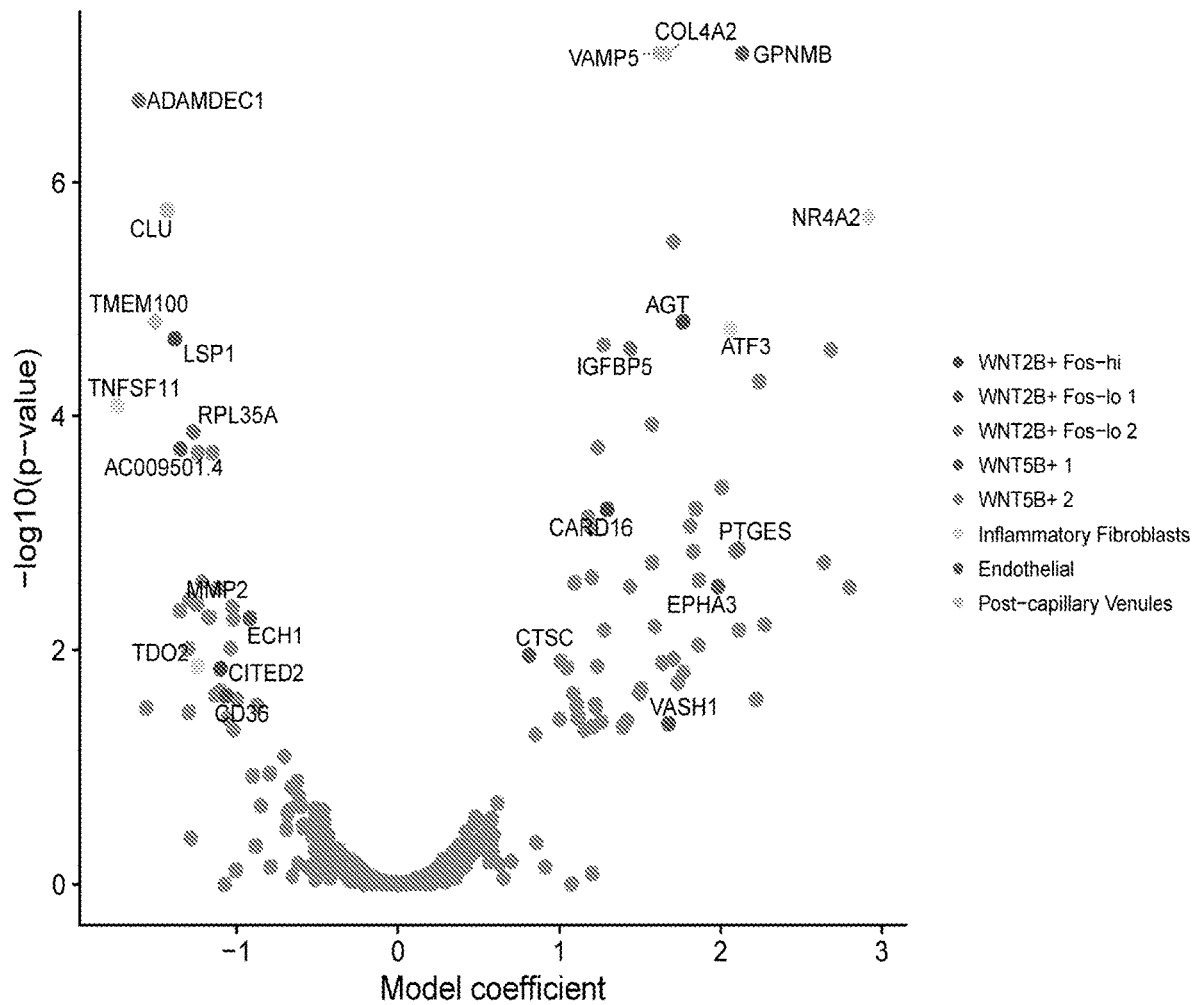
Figure 39F:
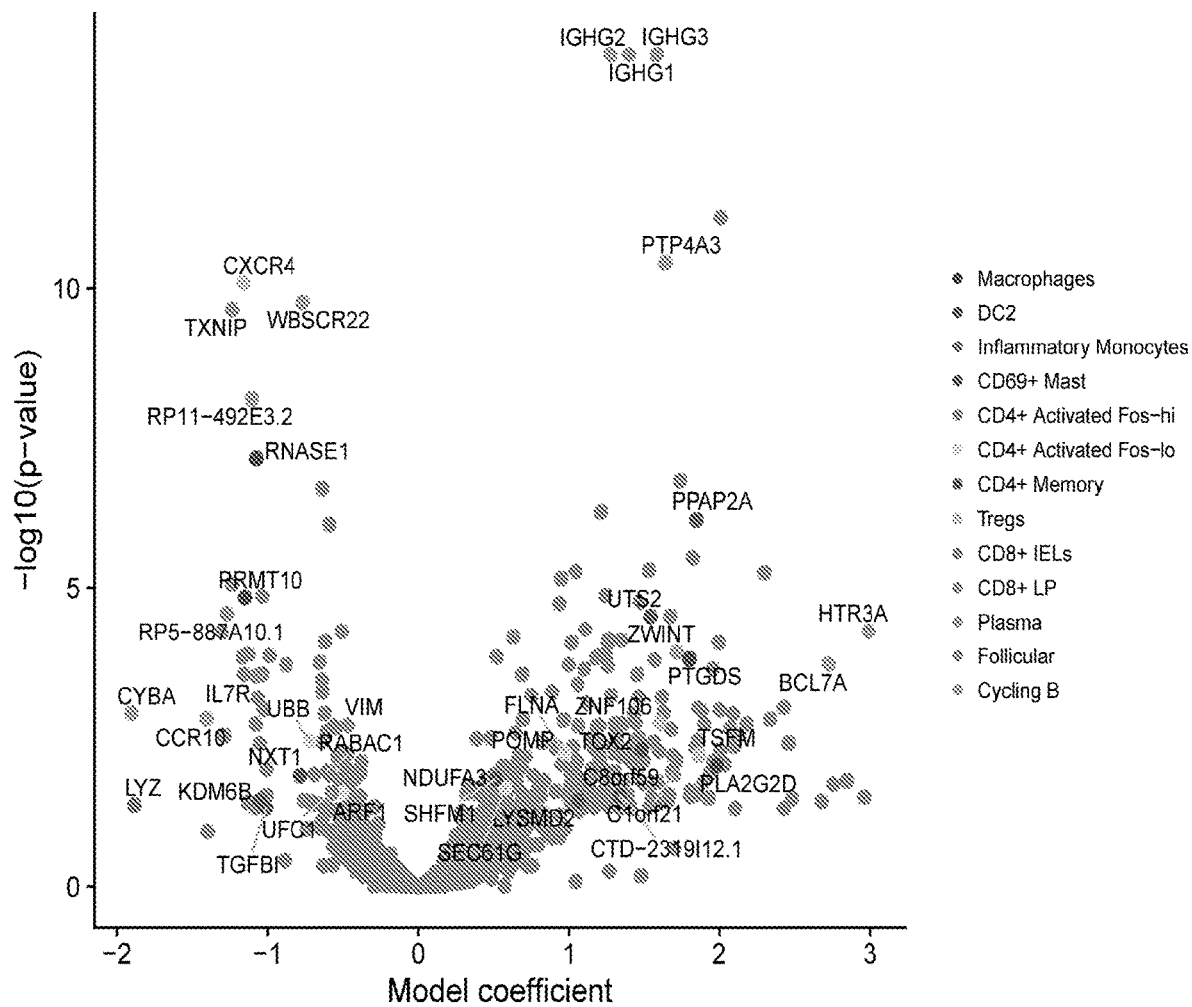
Figure 40A:
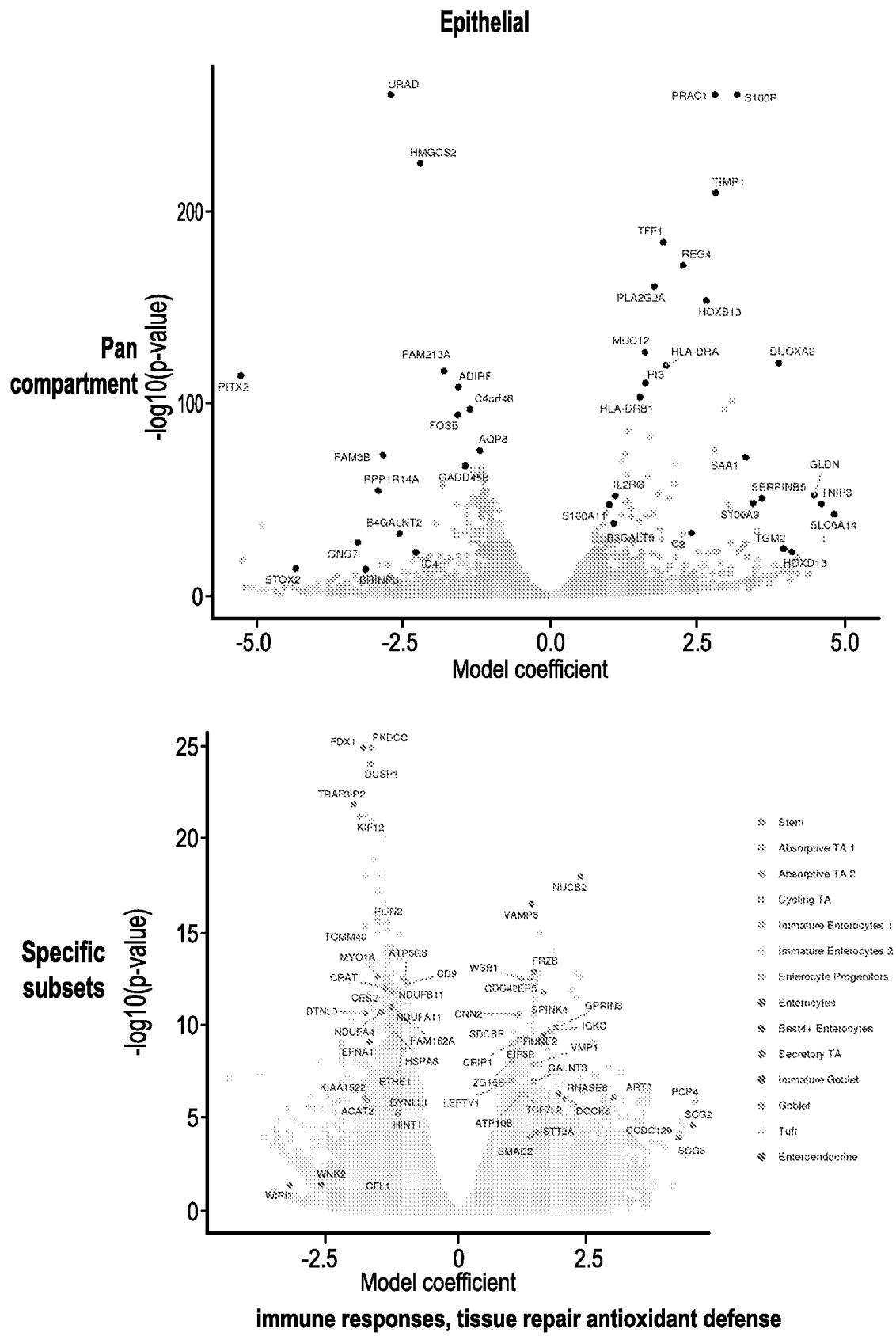
FIG. 40—Most cell intrinsic expression changes in UC are shared between inflamed and uninflamed regions. a. general pan compartment and subset specific epithelial markers for inflamed and uninflamed cells. b. general pan compartment and subset specific stroma markers for inflamed and uninflamed cells. c. general pan compartment and subset specific immune markers for inflamed and uninflamed cells.
Figure 40B:
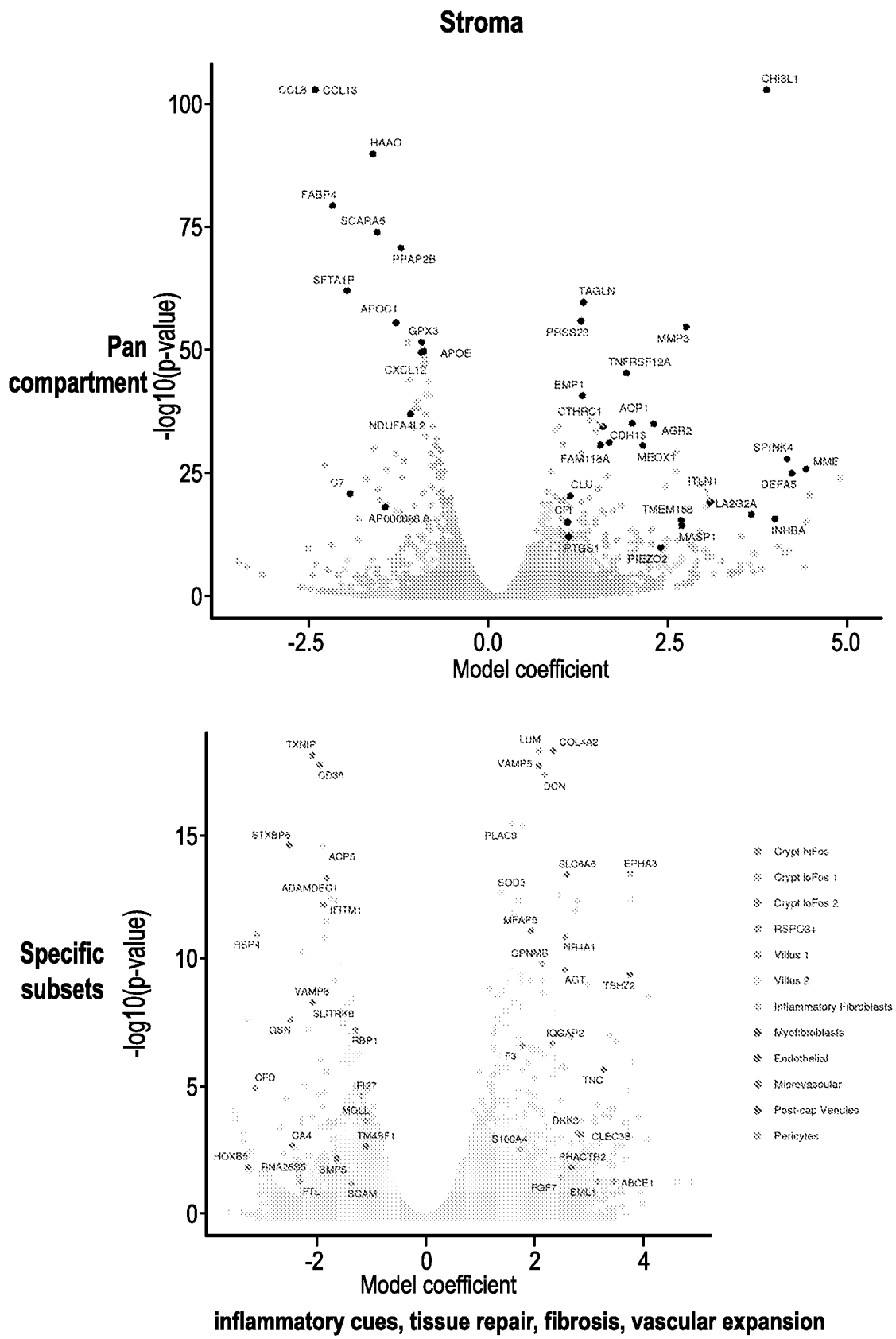
Figure 40C:
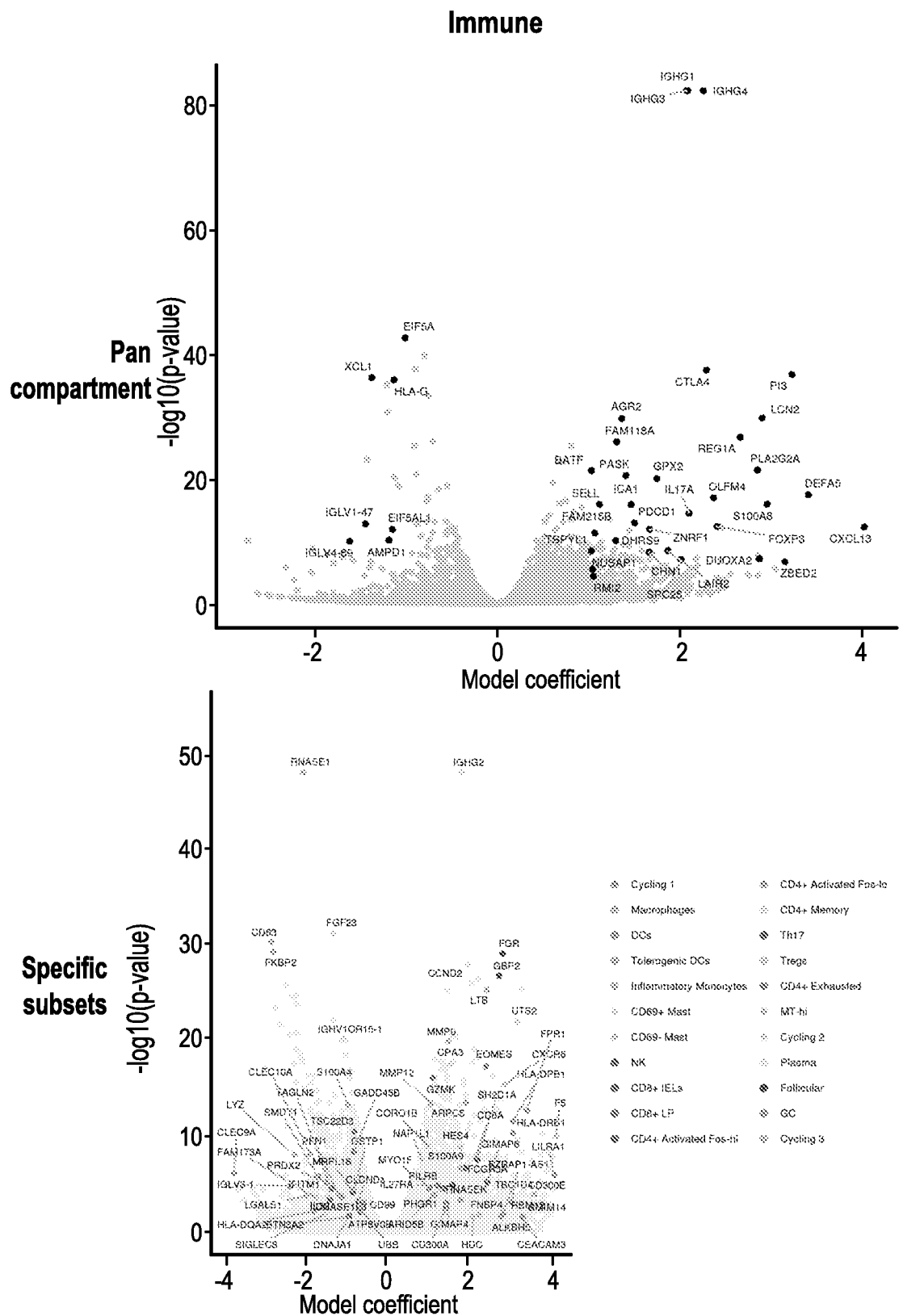
Figure 41A:
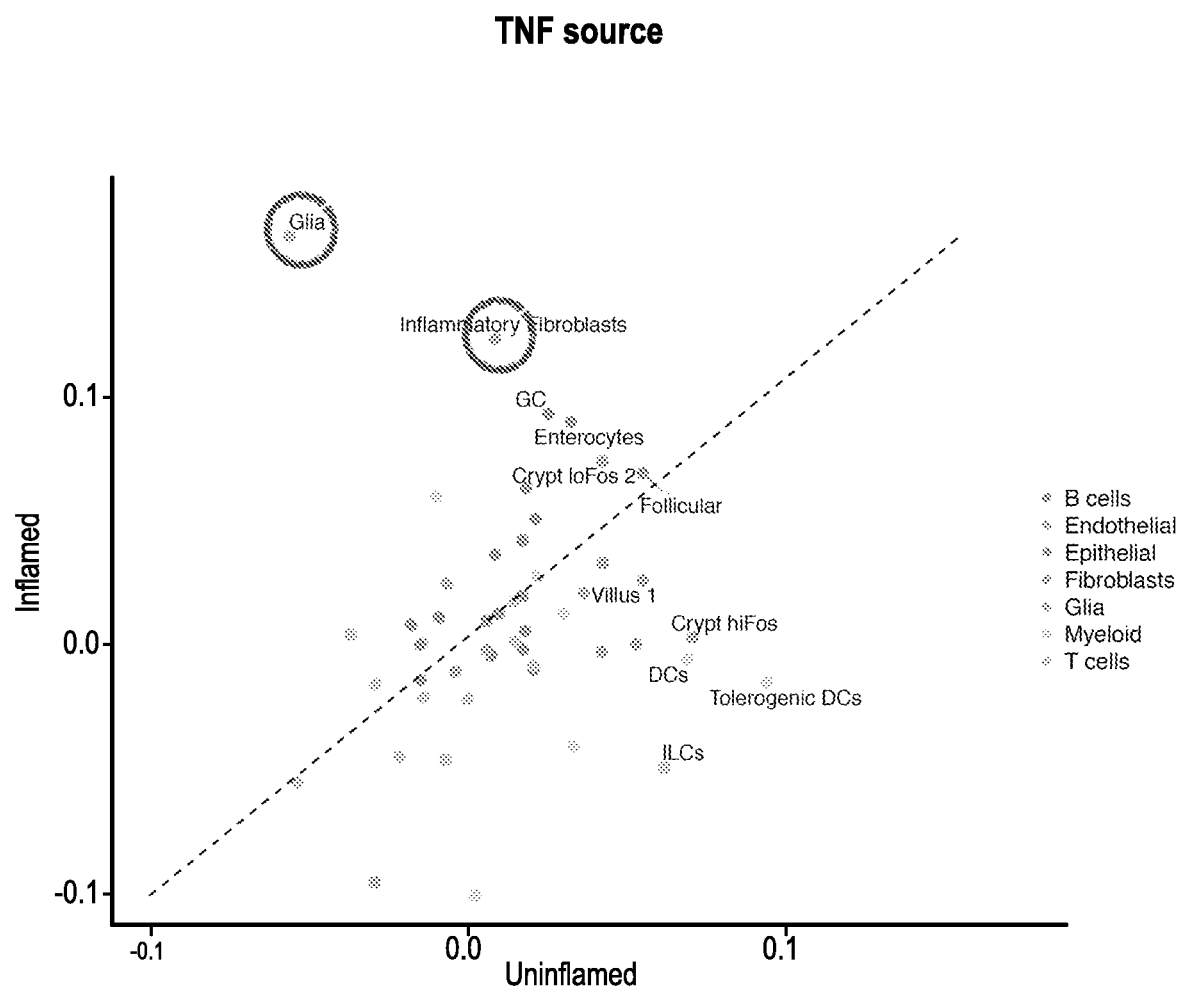
FIG. 41—A shift in TNF source to CAIF may underlie resistance to anti-TNF therapy. a. Plot showing fold change of TNF signaling. b. anti-TNF violin plots.
Figure 41B:
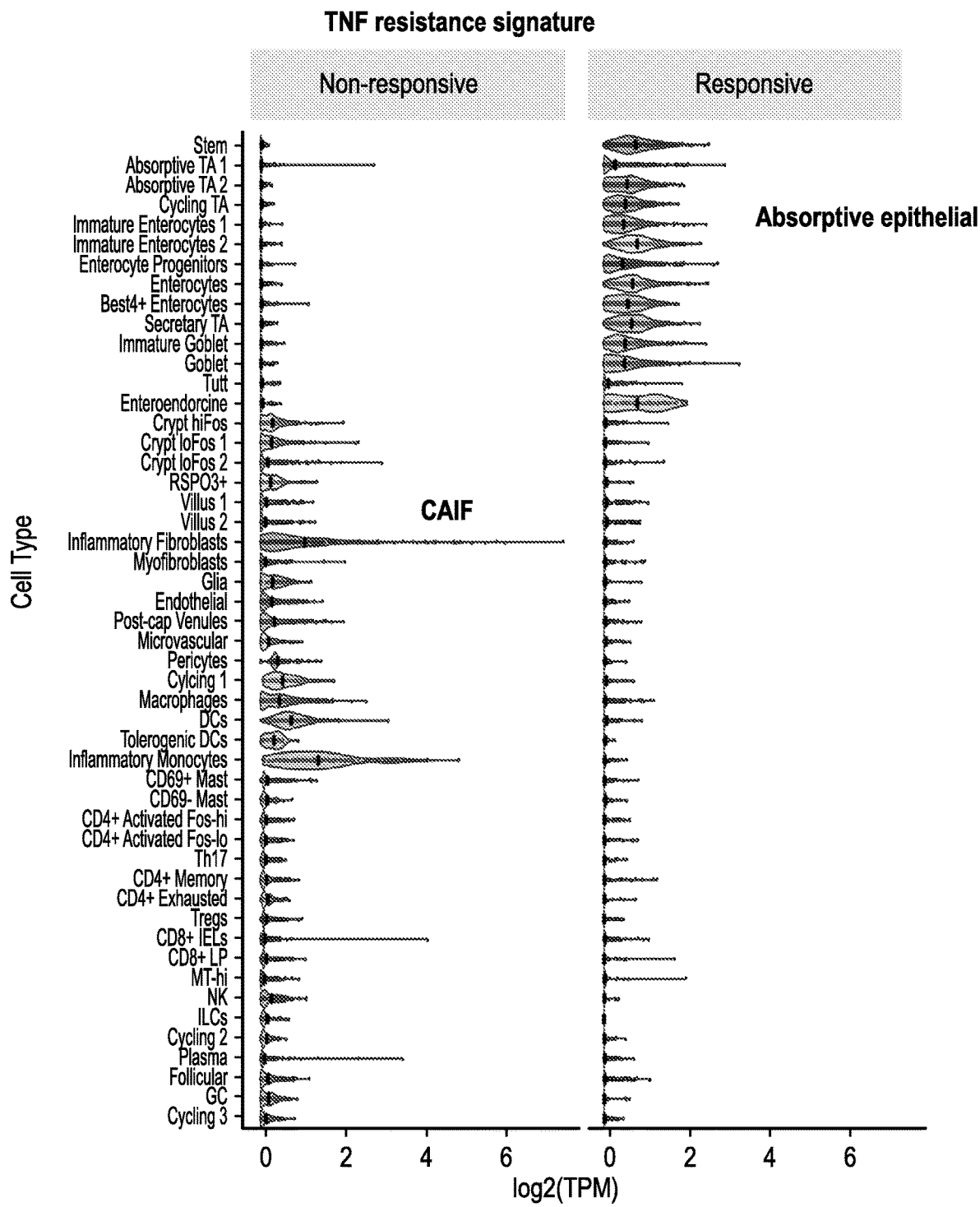

Although the total number of immune cells increased with the disease, within the immune compartment, colitis was associated with substantial reductions in plasma B cells and proportional increases in FO B cells (FIG. 27A). Within plasma cells, the frequency of IgA$^+$ cells decreased and that of IgG$^+$ cells concomitantly increased in both non-inflamed and inflamed tissue (Spearman's $\rho=-0.80$; $P=1.4\times10^{-7}$; FIG. 38), suggesting that immunoglobulin class-switching is occurring in the cells and may promote tissue inflammation and the generation of auto-antibodies.

Consistent with studies of inflammation in mice, microfold cells (M cells), specialized follicle associated epithelium (FAE) cells that deliver luminal antigens to immune cells situated in their basolateral pockets, were rarely found in healthy patients, but expanded significantly with UC (FIG. 27A). M cells play major roles in recognizing the gut microbiota and initiating mucosal immune responses. They highly express chemokines such as CCL20 and CCL23 suggesting that increased antigen sampling from the lumen is coupled to immune cell recruitment at the site of inflammation. Their expansion outside of lymphoid follicles with UC is unexpected, although congruent with studies of inflammation in mice, and suggests that M cells may have previously unappreciated roles in the disease.

Example 6—a New Inflammation-Associated Fibroblast Subset Unique to the UC Colon Although most fibroblast subsets are present in both healthy subjects and UC patients, Applicants discovered a new subset of fibroblasts found almost exclusively within biopsies from UC patients, particularly in inflamed samples (FIGS. 26D and 27A), which Applicants termed colitis-associated inflammatory fibroblasts (CAIFs). CAIFs are enriched for the expression of fibrinolytic enzymes (e.g., MMP3, MMP10, PLAU) and immune signaling molecules (e.g., IL1R1, IL13RA2, CXCL6, CCL11, TNFSF11, TNFRSF11B) (FIG. 26E). In particular, IL13RA2 is a decoy receptor with high affinity for IL-13, suggesting that these cells may reinforce inflammation by neutralizing IL-13. Consistent with this hypothesis, deletion of IL13RA2 led to attenuated colitis in mice treated with dextran sodium sulfate (DSS). CAIFs also express high levels of chitinase 3-like-1 (CHI3L1), a biomarker of chronic inflammation and IBD-associated colonic dysplasia that is also associated with increased cancer-related mortality. CHI3L1 and IL13RA2 are known binding partners that can activate downstream MAPK and Akt signaling, and CAIFs have the greatest mean expression of the PI3K-Akt signaling pathway across all cell subsets ($p<10^{-6}$ in all comparisons, Mann-Whitney test). CAIFs are also enriched for WNT2, one of the most upregulated genes in the intestinal stroma of colorectal cancer patients relative to healthy controls.

Example 7—Shift in Goblet Cell Differentiation May Explain Mucosal Changes in UC Defects in the mucus layer in UC patients is a diagnostic feature and is widely attributed to goblet cell mucin depletion. However, Applicants generally did not observe cell-intrinsic reductions in mucin gene expression, suggesting that these defects may arise from degradation of the mucus layer or changes in the proportions of mucus-producing cells. While Applicants observed no significant changes in the frequencies of mature goblet cells, inflamed biopsies from UC patients showed a loss of goblet cell progenitors (FIG. 27A), coincident with a reduction in epithelial "stemness." In particular, along the continuum of epithelial cell differentiation (FIGS. 26H and 27B), there were significantly reduced proportions of secretory progenitor cells ($p<10^{-4}$; likelihood ratio test on fixed effect in mixed linear model; STAR Methods), in inflamed samples of UC patients. Defects in the mucus layer may therefore be explained by reduction in goblet cell progenitors. Interestingly, these cells are major sources of antimicrobial peptides, including REG4, ITLN1, and RETNLB, and may therefore correspond to the "deep crypt secretory cells" that help maintain the colon ISC niche.

Figure 27C:
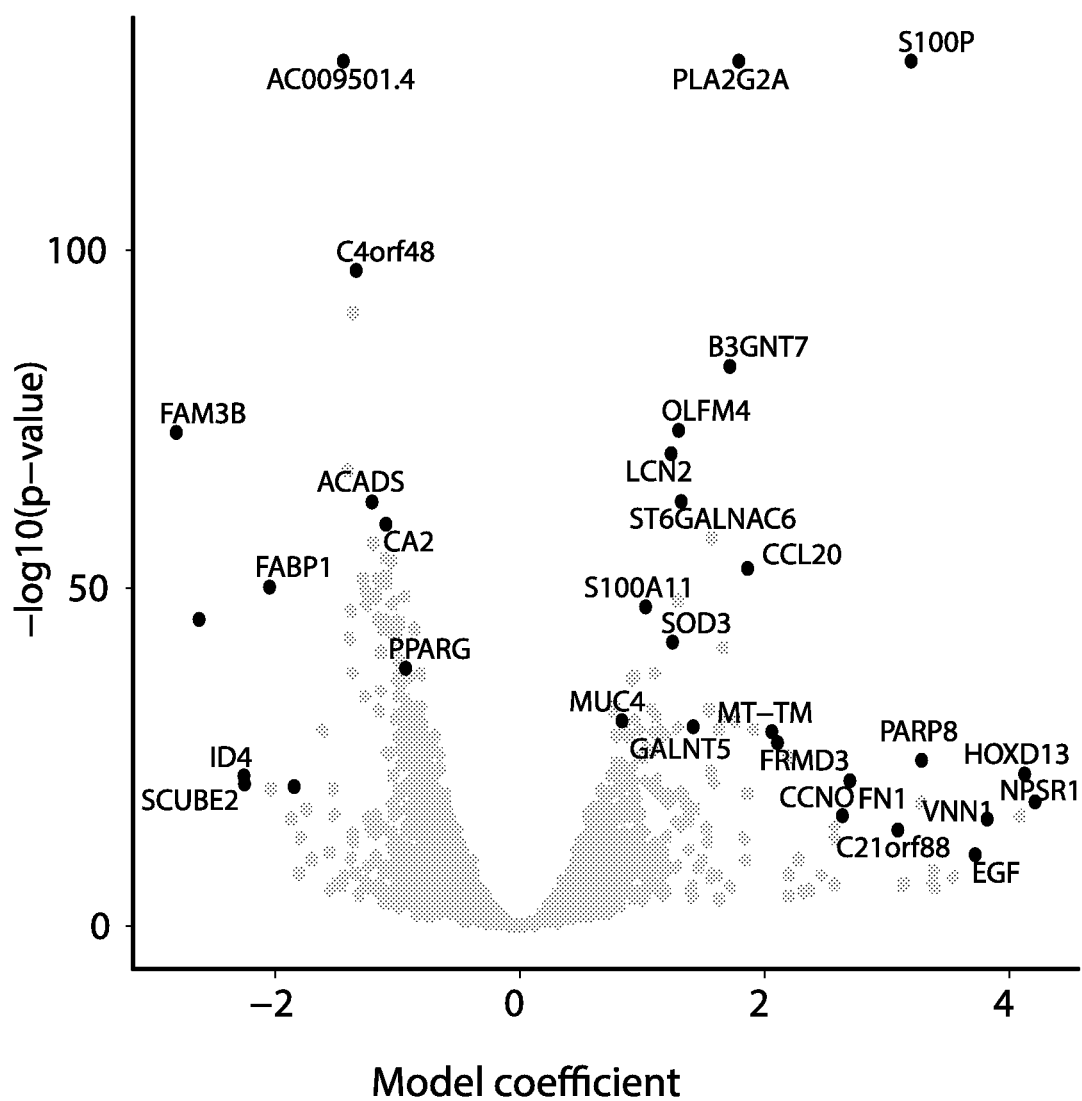
FIG. 27—Shifts in Cell Populations in UC. a. cell frequencies across samples. b. distribution of "pseudotime" values along each of the absorptive and secretory branches. c. general epithelial markers for inflamed cells. d. general innate immune markers for inflamed cells. e. general adaptive immune markers for inflamed cells. f. specific epithelial markers for inflamed cells. g. specific innate immune markers for inflamed cells. h. specific adaptive immune markers for inflamed cells. i. cell frequencies across samples. i. cell frequencies across samples.
Figure 27D:
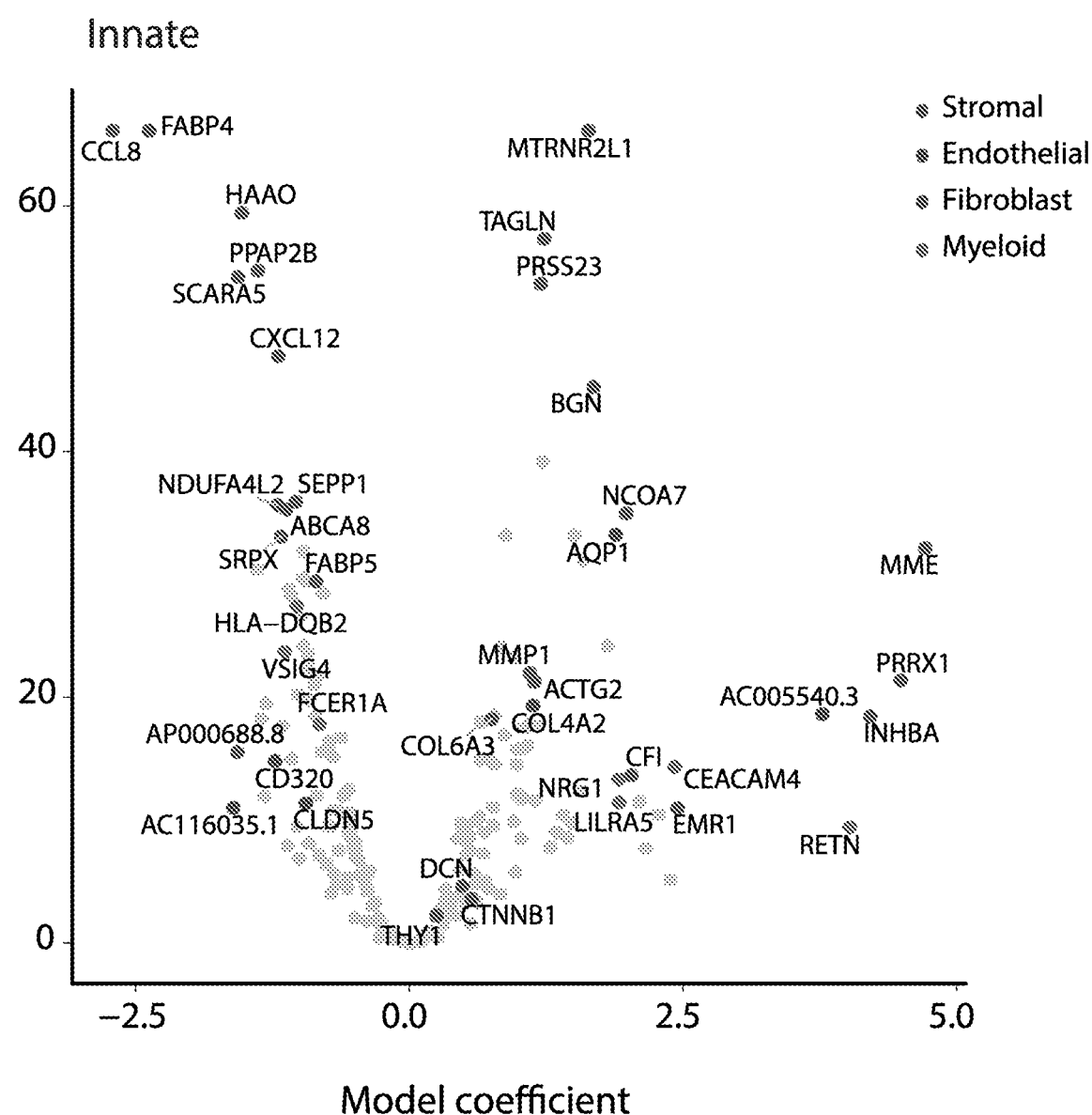
Figure 27E:
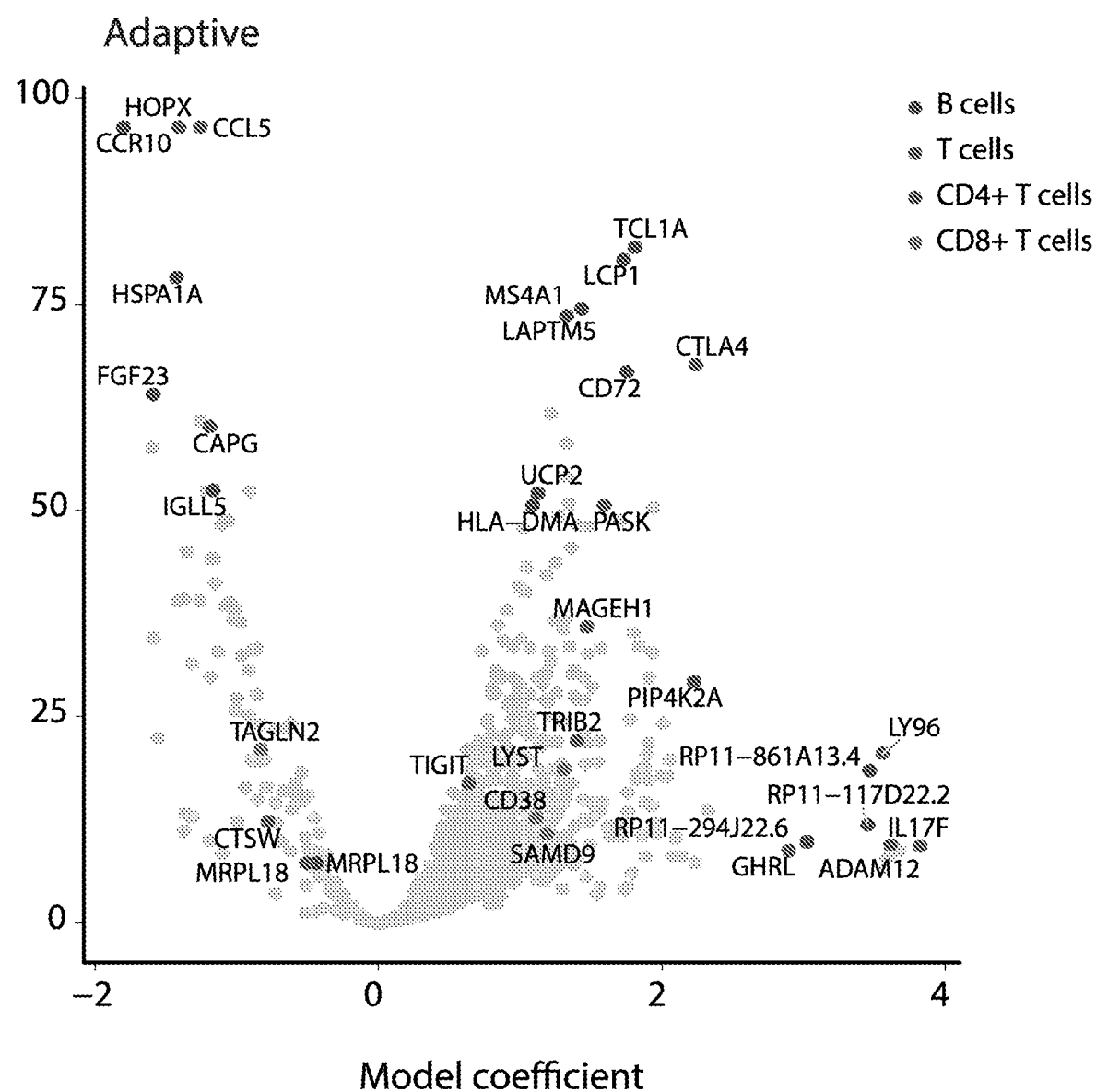

Example 8—Most Cell-Intrinsic Expression Changes in UC are Shared Between Inflamed and Uninflamed Regions Intestinal pathology during colitis is likely driven both by alterations in tissue composition and by changes in cell-intrinsic cellular programs. To explore the contribution of cell-intrinsic changes, Applicants modeled the expression of each gene as the sum of distinct components, reflecting cell subset, disease state (healthy, non-inflamed, or inflamed) and technical confounders, as well as correction for ambient RNA contamination in droplets (Macosko et al.) (STAR Methods). Fitting this model at different levels of the cell lineage, Applicants distinguished between general expression changes that are shared across an entire compartment (epithelial, stromal, immune, FIG. 27C-E) and unique changes within each subset (e.g. M cells, CAIFs, CD8$^+$IL-17$^+$ T cells) (FIG. 27F-H, Tables 3-9, 11 and 12, STAR Methods).

Despite being collected from grossly normal tissue, non-inflamed specimens shared much of the differential expression (DE) signature of inflamed tissue (FIG. 39A-F, Table 13-15), suggesting that the transcriptional signature of the disease may precede inflammation or persist after it resolved. Applicants therefore first focused on this shared signature, and then examined the minority of genes that were unique to inflamed tissue during active disease. (Applicants note that for the cell types which are nearly undetectable in healthy tissue, such as CAIFs and M cells, Applicants cannot robustly assess differential expression vs. healthy tissue).

Within epithelial cells, expression changes largely reflect the attempt of the disrupted epithelial barrier to regain tissue homeostasis by activating mucosal immune responses, antimicrobial defenses, tissue repair and antioxidant defense pathways, biosynthesis of O-glycans and alternative mucins (FIG. 27C), consistent with the remodeling of the mucosal environment, as well as the MHC class II machinery, which Applicants confirmed by RNA-FISH.

Figure 27F:
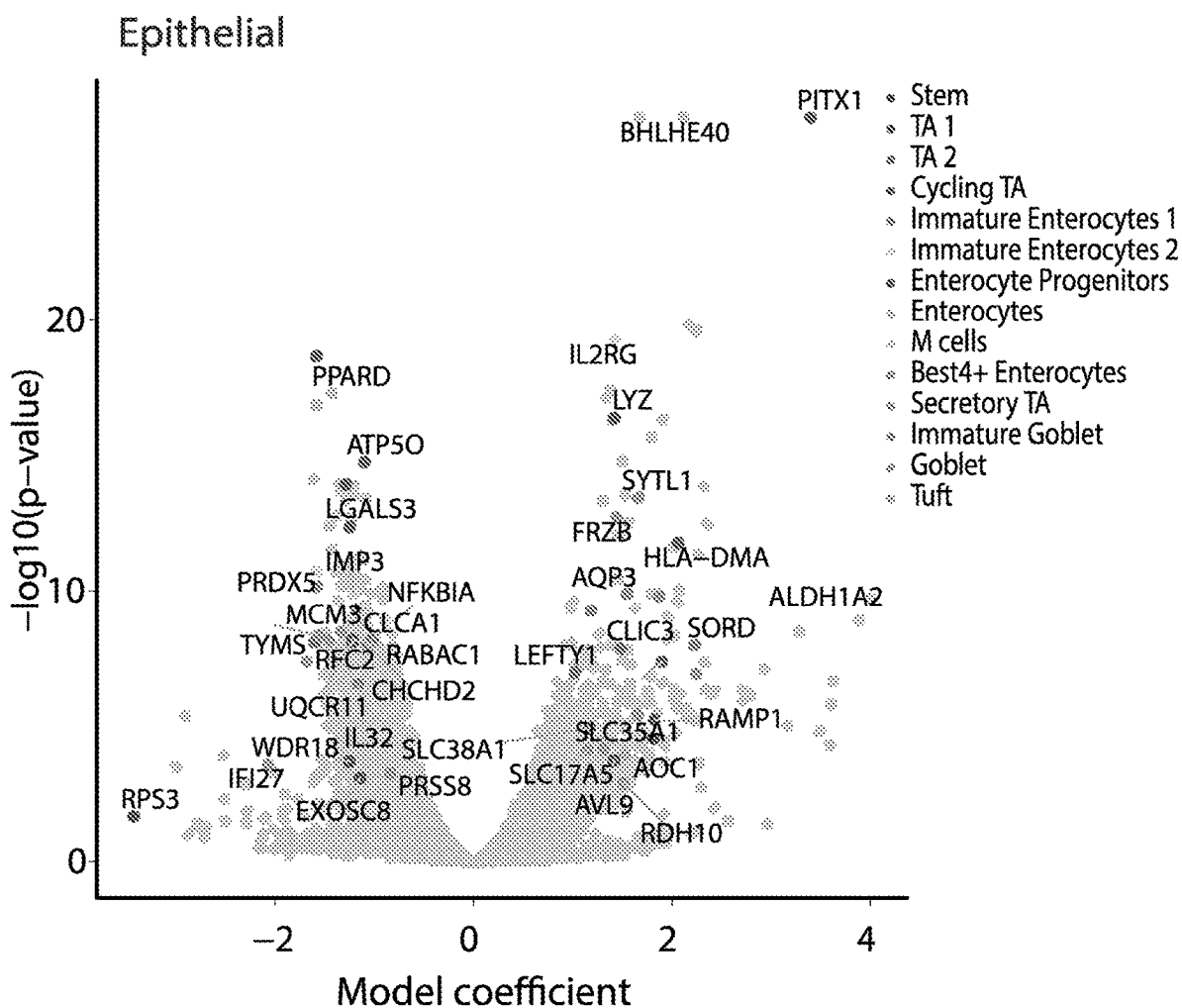

Epithelial subsets downregulated genes involved in fatty acid metabolism (FIG. 27C), possibly due to reduced production of short chain fatty acids by the gut microbiota. Within specific subsets, chemosensory tuft cells upregulated the diamine oxidase, AOC1, which may degrade mast cell-produced histamine (FIG. 27F); goblet cells increased importers of sialic acids (FIG. 27F), which may promote the growth of *Escherichia coli*; cycling TA cells upregulated IL-23, a key cytokine implicated in IBD through GWAS; and goblet cells and enterocytes upregulated genes for retinoic acid (RA) biosynthesis (FIG. 27F), while M cells induced the RA binding protein, CRABP2 (FIG. 27F). RA is known to suppress intestinal mucus production and to exacerbate colitis, suggesting that M cells may play an important role in this process.

Figure 27G:
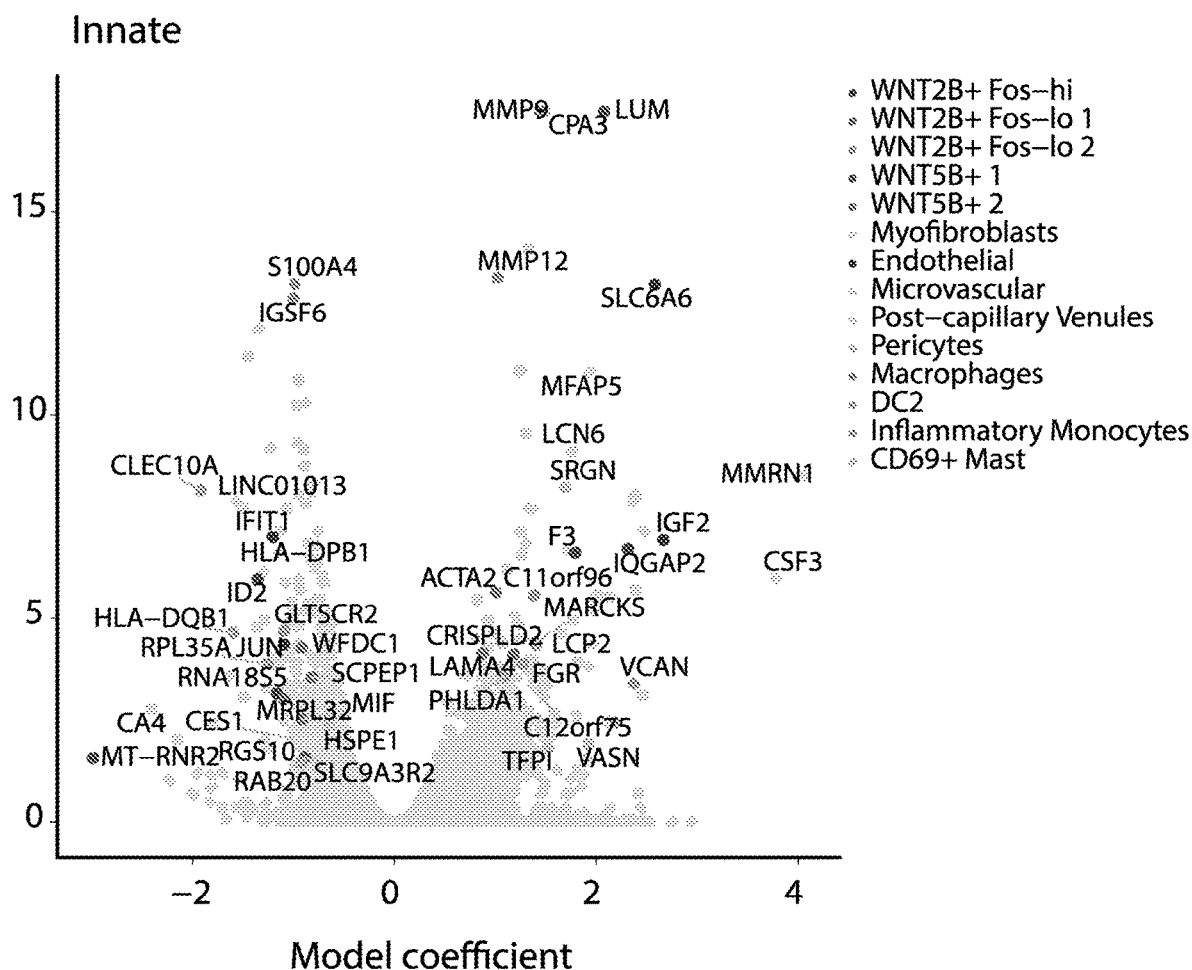
Figure 27H:
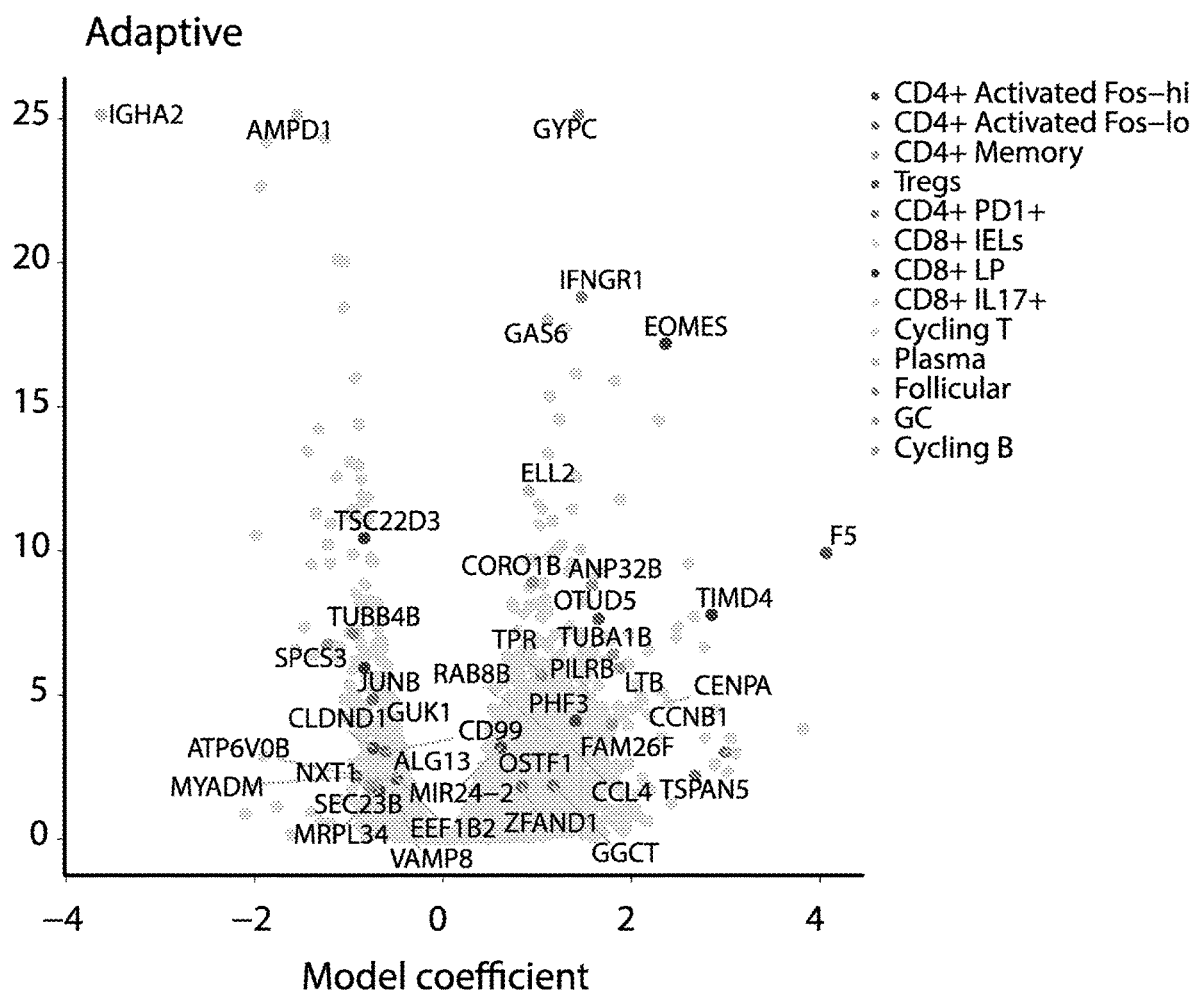
Figure 27I:
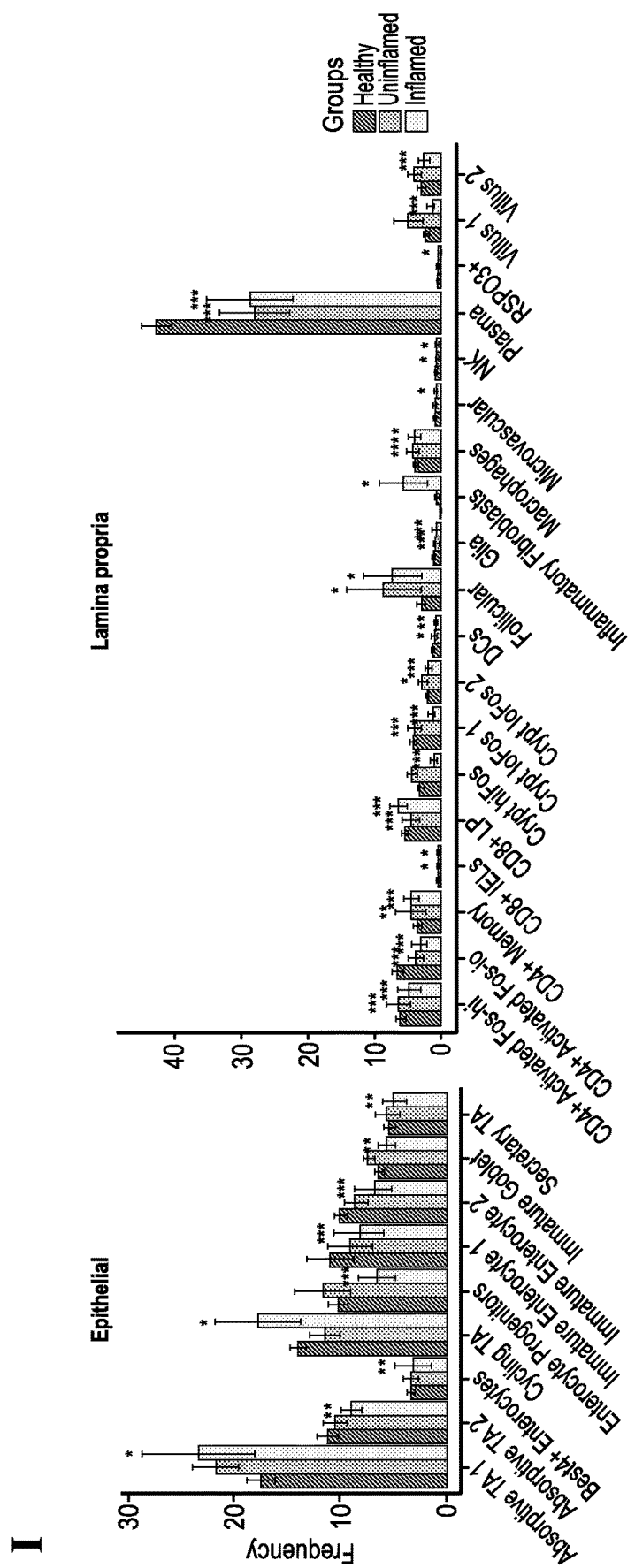

Within the stromal compartment, expression changes reflected induction of inflammatory cues, tissue repair and fibrosis, and of vascular expansion in the supporting tissue, suggesting a major role of the stroma in disease progression. Multiple subsets activate pro-fibrosis programs, including upregulation of genes involved in collagen deposition and fibrosis (FIG. 27D), expression of beta-catenin (CTNNB1; FIG. 27D), a mediator of pro-fibrotic WNT signaling by crypt-associated fibroblasts, and expression of fibrosis-associated ECM components that are normally restricted to the crypt (e.g. DCN, LUM; FIG. 27D,G) by villus-associated fibroblasts (FIG. 27D). In contrast to the dramatic increase in CAIFs, other fibroblast subsets downregulated the chemokines CCL8, CXCL12, and CCL13 (FIG. 27D,G) and produced neprilysin (MME), a metalloprotease that cleaves peptide hormones, including substance P, which could limit inflammation (FIG. 27D). Post-capillary venules induced CSF3 (FIG. 27G), which signals for the growth and differentiation of monocytes and granulocytes, and endothelial cell subsets induced angiopoietin 2 (ANGPT2; FIG. 27G) and the adhesion glycoprotein, THY1 (FIG. 27D), which may promote angiogenesis and leukocyte recruitment into the diseased tissue.

Figure 28A:
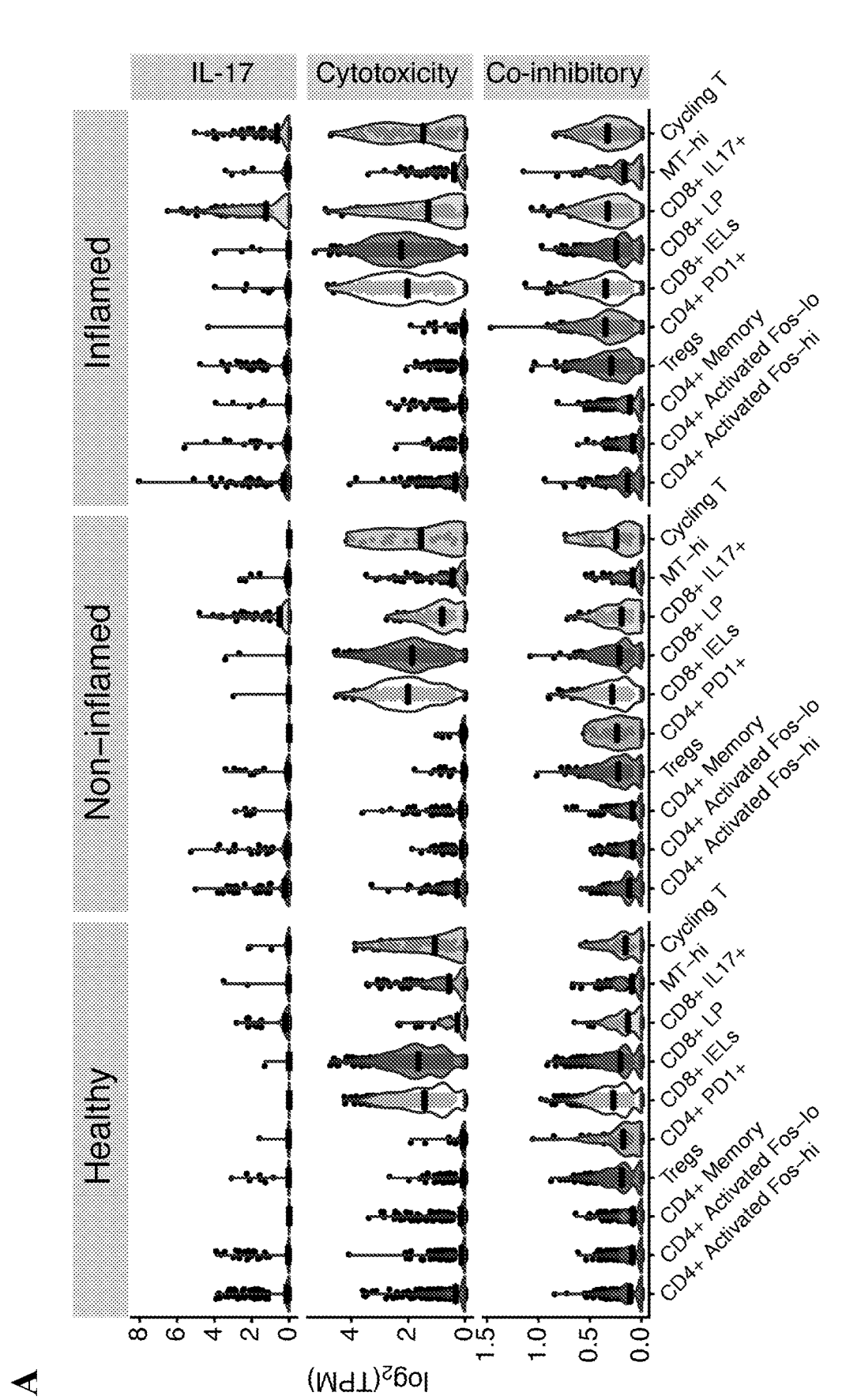
FIG. 28—Inflammatory pathways. a. Violin plots showing expression of IL-17, cytotoxicity, and co-inhibitory signatures in healthy, non-inflamed and inflamed samples. b. Heatmaps comparing cytokines between inflamed tissue, non-inflamed tissue and healthy tissue. c. Anti-TNF violin plots. Plot showing fold change of TNF signaling. d. TNF signature compared to the drug resistance signature and drug susceptibility signature in cell subsets. e. heatmap showing changes in the expression of pathways related to nutrient sensing, stress, and inflammation across all cell types. f. Expression of drug resistance signature genes in subsets.

Although innate immune responses seem to be a prerequisite for the excessive activation of adaptive immunity, the latter is the more proximate driver of tissue damage in UC. In particular, multiple subsets of CD4$^+$ and CD8$^+$ T cells adopted a Th17-like phenotype, with upregulation of both IL-17 (IL17A, IL17F; FIG. 27E) and of checkpoint genes (e.g. CTLA4, PDCD1, TIGIT; FIG. 27E). IL-17 expressing cells promote a pro-inflammatory and cytotoxic immune response, which may be reinforced by the expression of cytotoxic granule genes (e.g. GZMK, GNLY; FIG. 27E) in all subsets of CD8$^+$ T cells, and which may contribute to epithelial tissue damage. More generally, all CD8+ T cells induced cytotoxic programs in inflamed tissue that was accompanied by the expression of a co-inhibitory, checkpoint molecule (FIG. 28A). Notably, checkpoint activation was already apparent in healthy tissue, which may explain immunotherapy-induced colitis in some cancer patients. Within B cells, the increased expression of the TFs PAX5, IRF8, and BCL6 in multiple subsets and the expression of AICDA in GC B cells, which promotes affinity maturation and class switch recombination, help explain the reduction in plasma cells (FIG. 27A) and IgG class switching (FIG. 38). Finally, few changes were shared across the myeloid lineage, whereas subset specific changes reflected modulation of the innate immune response in monocytes (induced calprotectin, an inflammatory biomarker of UC and reduced FCER1A and MHC II), DCs (increased expression HTR3A and IL22R, suggesting increased interaction with mast cells and Th17 cells, respectively); and CD69$^+$ mast cells (up-regulated secretory granule genes).

Example 9—Shift in Carbon Metabolism, Fatty Acid Oxidation and Amino Acid Metabolism in Epithelial Cells in UC Comparison of non-inflamed and inflamed tissue within UC patients revealed several metabolic changes within epithelial cells that may underlie tissue inflammation (FIG.

28E). The expression of purine metabolism genes (e.g. XDH, URAD; FIG. 27C,F) was altered in epithelial subsets, likely leading to the production of uric acid. Uric acid is induced by *S. cerevisiae* colonization, leading to epithelial damage in mice, and inhibition of uric acid synthesis can ameliorate colitis (e.g., damage is reversed upon inhibition of uric acid synthesis). Epithelial cells in inflamed tissue also reduce HMGCS2, the limiting rate enzyme that catalyzes the first reaction in ketosis, and increased the expression of enzymes in the kynurenine pathway, a pathway that is associated with disease severity [REF] and is thought to promote mucosal inflammation through the rewiring of tryptophan metabolism and the abrogation of IL-22 synthesis (e.g. IDO1, KYNU), which may replenish NAD+ levels for oxidative phosphorylation. Diminished CLCA1 expression by secretory TA cells in inflamed tissue may help explain defects in the mucus layer thickness during inflammation. Such rewiring of epithelial cell metabolism in inflammation in UC is consistent with studies suggesting that stress and inflammation are coupled to the upstream sensing of nutrients, such as carbohydrates, lipids, and amino acids.

Previous studies suggest that stress and inflammation pathways induced in IBD and consisting of many IBD GWAS genes may be coupled to upstream environmental sensing of nutrients, such as oxygen, fatty acids, and amino acids, which in turn may be impacted by the microbiota. To identify such metabolic changes systematically, Applicants scored changes in the expression of 239 pathways related to nutrient sensing, stress, and inflammation across all cell types (FIG. 28E), relative to a background set of genes selected to have similar expression profiles across all samples.

Figure 28B:
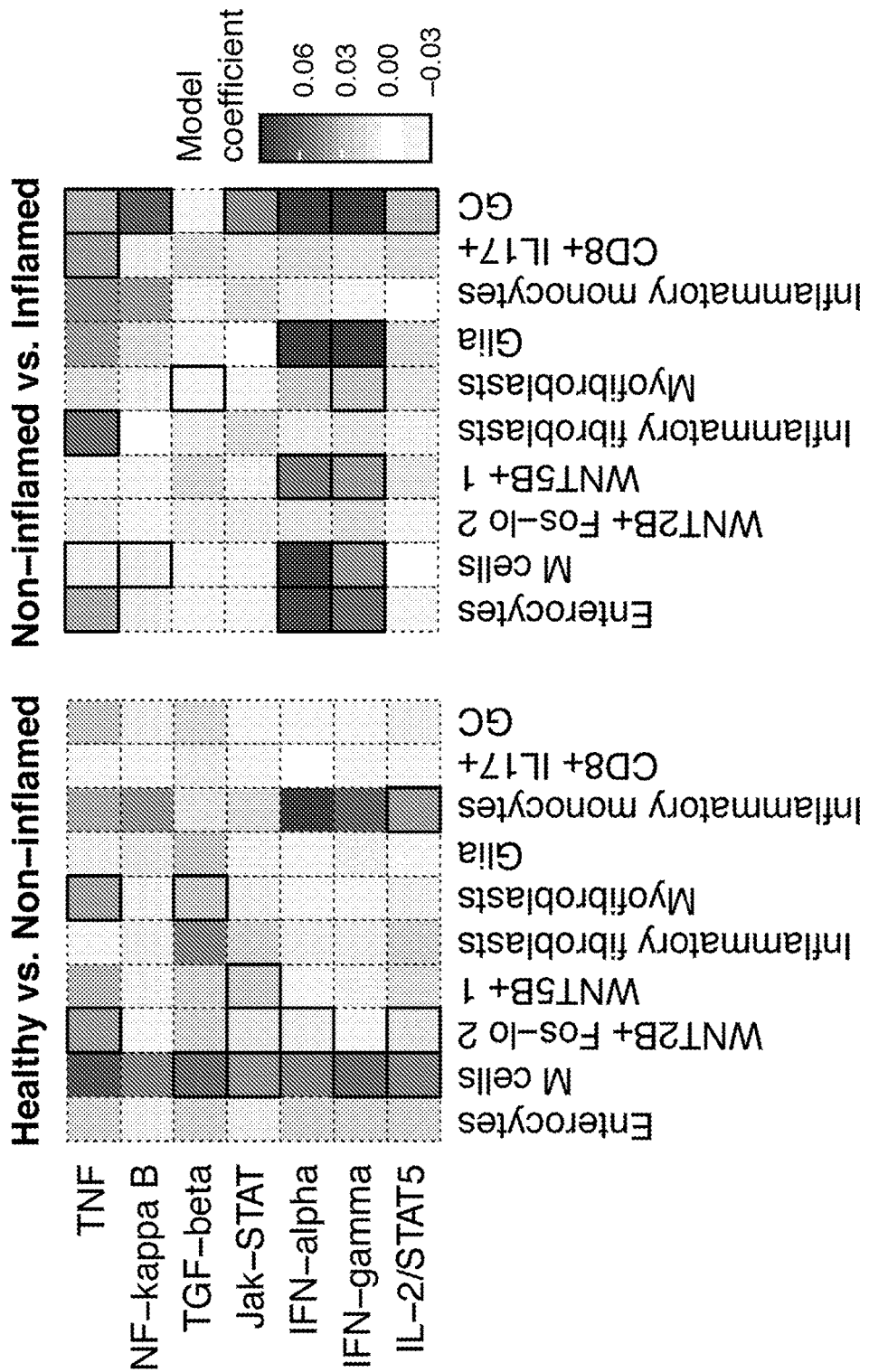
Figure 28C:
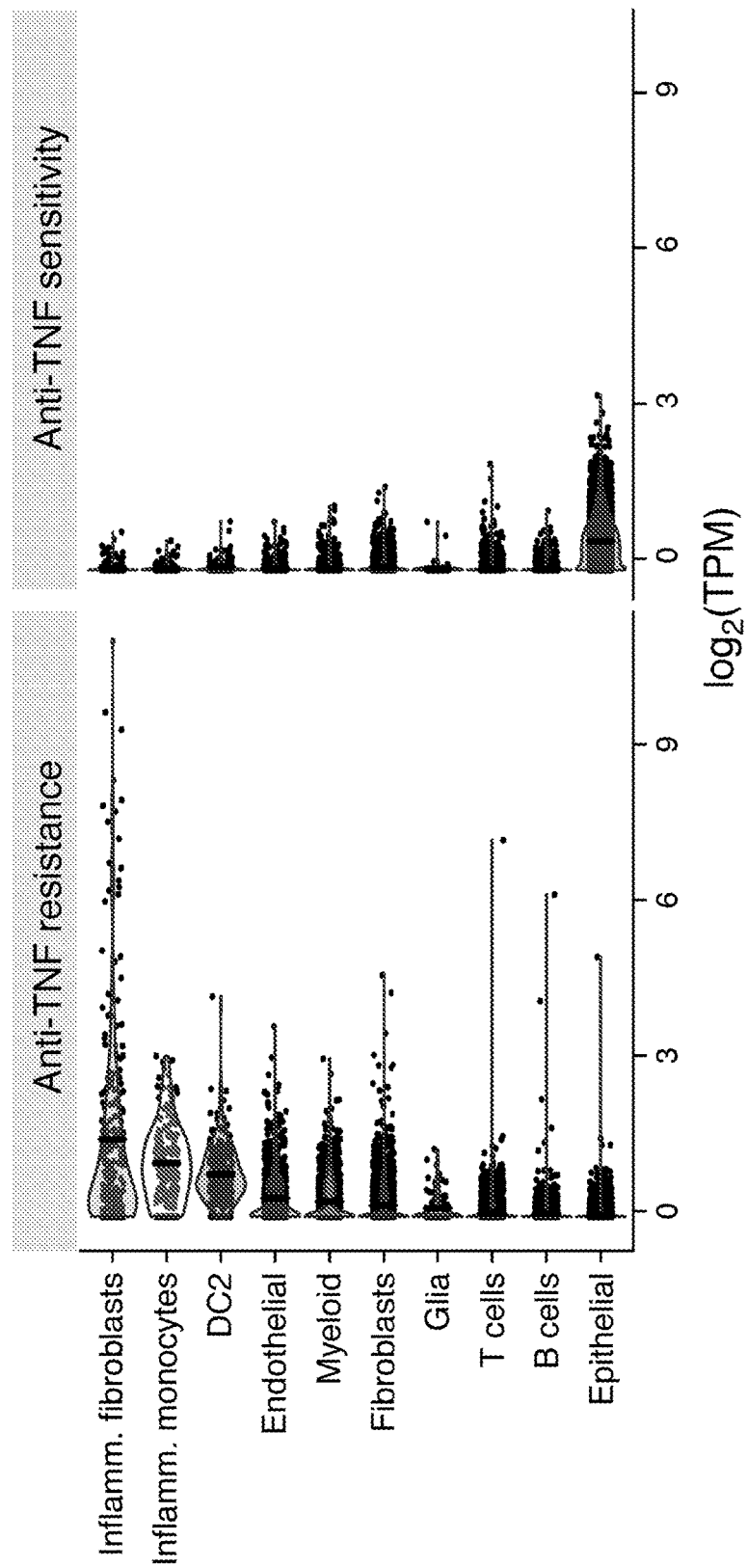
Figure 28D:
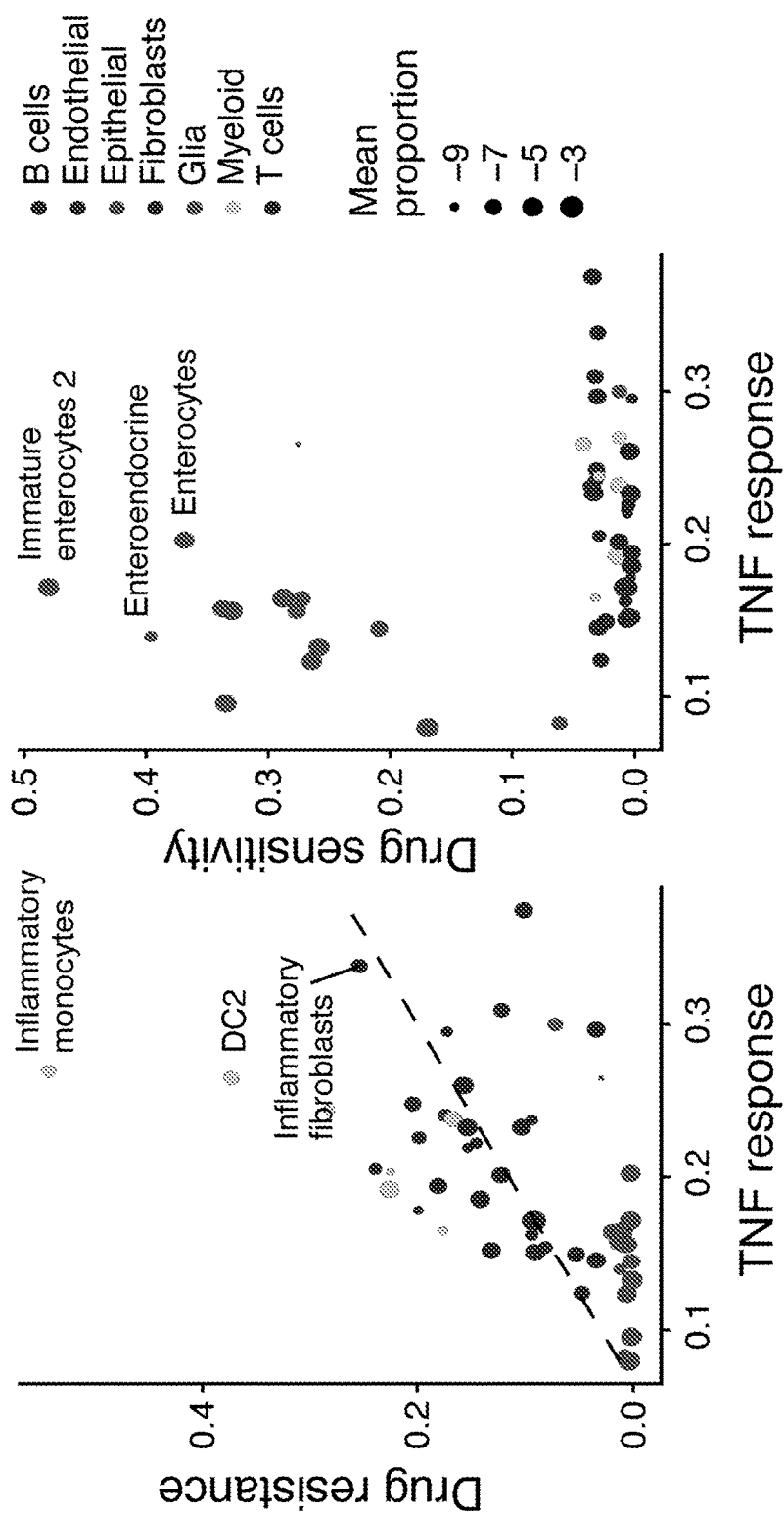
Figure 28E:
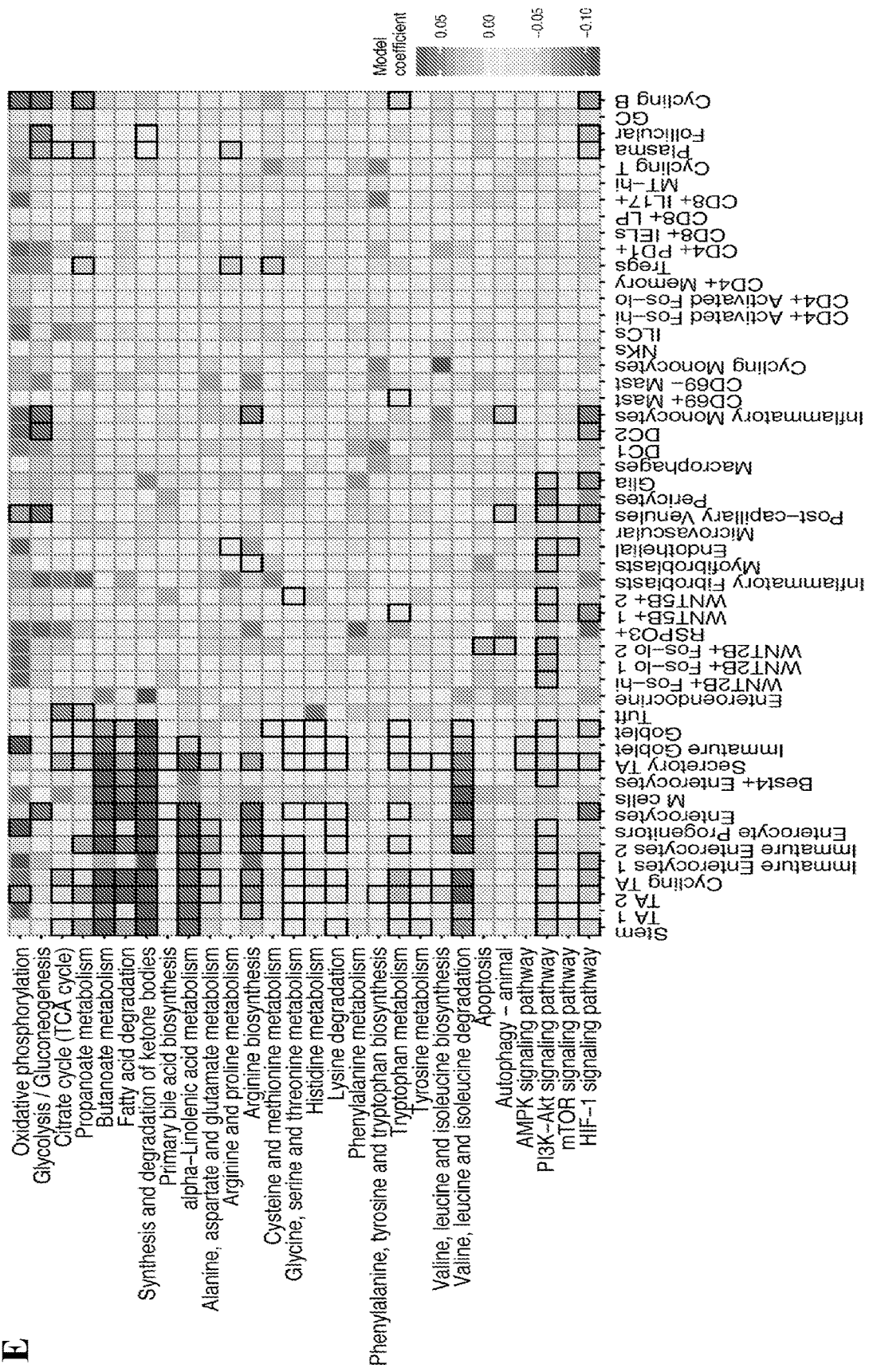
Figure 28F:
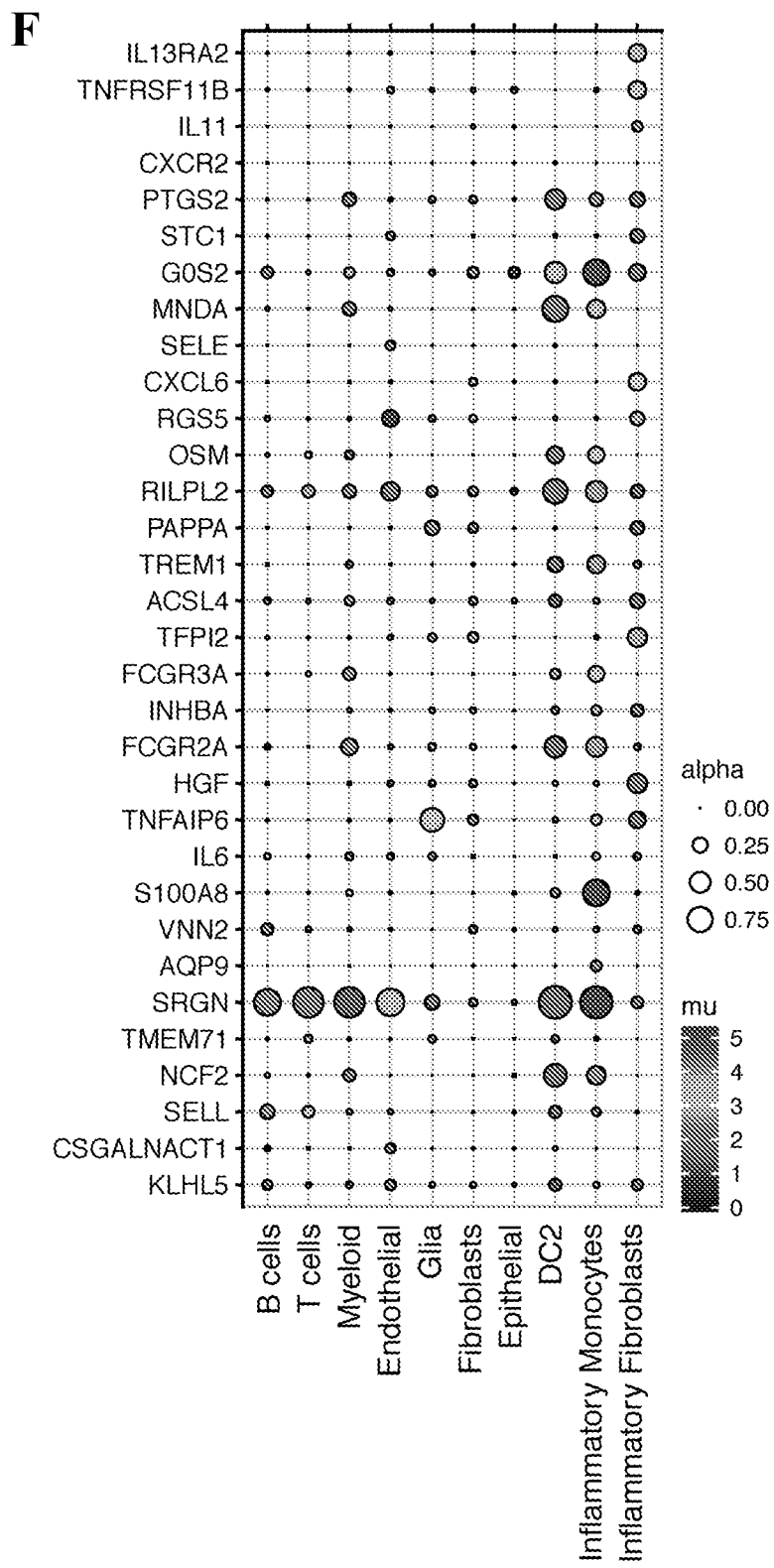

This analysis revealed metabolic shifts between oxidative phosphorylation and glycolysis, and changes in fatty acid and amino acid metabolism. First, in UC, epithelial cells shifted their metabolism from oxidative phosphorylation to glycolysis and the pentose phosphate pathway (FIG. 28E), while immune cells shifted towards oxidative phosphorylation, which may reflect efforts to quell immune activity, often coupled to glycolysis, which reflect efforts to quell immune activity, often coupled to glycolysis. Second, across multiple subsets Applicants infer a switch from microbial to dietary sources of fatty acids. There is reduced expression of pathways for beta-oxidation and the metabolism of butyrate and propionate (FIG. 28E), likely driven by impaired production of short chain fatty acids (SCFAs) by the gut microbiota, along with increased expression of dietary fatty acids metabolism genes (FIG. 28E) by epithelial cells in non-inflamed and inflamed tissue. Finally, epithelial cells from non-inflamed and inflamed tissue increased expression of pathways for the biosynthesis of arginine and the metabolism of alanine, aspartate, and glutamate, and reduced the metabolism of valine, leucine, isoleucine, lysine, and histidine (FIG. 28E). Changes in amino acid sensing may explain elevated levels of mTORC1 signaling across multiple subsets (FIG. 28E). Although metabolism of tryptophan through the kynurenine pathway increased, the combined gene signature for tryptophan metabolism decreased in epithelial cells and fibroblasts (FIG. 28E).

Example 10—Induction of a Strong IL17 Response and Checkpoints in CD8+ Cells in UC Although the innate immune response seems to be a prerequisite for the excessive activation of adaptive immunity, the latter is the more proximate driver of tissue damage in UC [REF]. In particular, multiple subsets of CD4$^+$ and CD8$^+$ T cells adopted a Th17-like phenotype, with upregulation of IL-17 (IL17A, IL17F; FIG. 27E) and checkpoint genes (e.g. CTLA4, PDCD1, TIGIT; FIG. 27E). The CD8$^+$ IL-17$^+$ cells promote a pro-inflammatory and cytotoxic immune response, as well as induce the expression of IL23R in non-inflamed and inflamed tissue. This may be further reinforced by the expression of cytotoxic granule genes (e.g. GZMK, GNLY; FIG. 27E) in all subsets of CD8$^+$ T cells, and which may contribute to epithelial tissue damage. More generally, all CD8+ T cells induced cytotoxic programs in inflamed tissue that were accompanied by the expression of a co-inhibitory, checkpoint molecule (FIG. 28A). Notably, checkpoint activation was already apparent in healthy tissue, which may explain immunotherapy-induced colitis in some cancer patients.

Example 11—A Shift of TNF Responding Cells to CAIFs May Underlie the Resistance to Anti-TNF Therapy The differentially expressed genes highlight inflammatory processes occurring in the different stages of colitis from non-inflamed to inflamed tissue across diverse cells. TNF signaling is one of the key pathways contributing to the onset and progression of UC, and monoclonal anti-TNF antibodies have been a major breakthrough in the treatment of IBD. Despite this success, non-response rates are high and treated patients eventually develop resistance to treatment, suggesting that there are both intrinsic and acquired causes of resistance. Additional inflammatory pathways could participate in gut inflammation as etiological causes, effects, or exacerbating factors. To assess those, Applicants compared each cell subset for the change between healthy, non-inflamed and inflamed tissue in seven inflammation signatures, as well as in expression of the TNF response (FIG. 28B,C).

The transition from healthy to non-inflamed tissue was mostly marked by induction of pathways within fibroblasts. For example, TNFα signaling increased in WNT2B+Fos$^{lo}$ fibroblasts and myofibroblasts, Jak-STAT signaling increased in WNT2B$^+$ and WNT5B$^+$ subsets, and TGFβ signaling increased in myofibroblasts (FIG. 28B). Additional pathways were induced in inflamed tissues across multiple lineages, including increases in IFNα/β and IFNγ signaling in epithelial subsets, B cells and CD69$^+$ mast cells, and increases in TNF signaling among some epithelial cells, CD8$^+$IL-17$^+$ T cells, GC B cells, and CAIFs. This suggests that TNFα, TGFβ, and Jak-STAT responses in fibroblasts are more related to disease etiology, whereas additional pathways in epithelial cells, mast cells, and B cells are secondary aspects that exacerbate tissue inflammation. This may explain why anti-TNF drugs effectively treat UC symptoms, whereas anti-IFNγ therapy does not.

Remarkably, the largest change in TNF signaling between non-inflamed and inflamed tissue was found in CAIFs (FIG. 28C), suggesting that these cells may underlie resistance to anti-TNF therapy. To test this hypothesis, Applicants scored each subset for gene signatures related to drug resistance and sensitivity, based on a meta-analysis of bulk expression profiles from 55 drug responders and 55 non-responders to anti-TNF blockade (STAR Methods). Supporting the hypothesis, the drug resistance signature was strongly enriched in CAIFs (FIG. 28D,F; e.g. IL13RA2, IL11, and TNFRSF11B) and inflammatory monocytes (FIG. 28D,F; e.g., G0S2, OSM, TREM1), while the drug sensitivity signature was enriched in epithelial cells (FIG. 28D,E; e.g., LGR5, PYY, RETNLB). In fact, the three genes whose expression is most significantly associated with drug resistance, IL13RA2, IL11, and TNFRSF11B, are highly specific markers of CAIFs, and are not expressed by any other cell subsets. Confirming these results, deletion of IL13RA2 ameliorates colitis in mice [REF], while pre-treatment expression of OSM is predictive of anti-TNF resistance in a human clinical trial, although the specific cell subsets or pathways mediating this resistance are unknown.

Moreover, after removing overlapping genes between the gene signatures (STAR Methods), the TNFα signature score was strongly correlated to the drug resistance score (FIG. 28D, left) and mutually exclusive with the drug sensitivity score (FIG. 28D, right), suggesting a direct relationship between TNF signaling and clinical resistance. Thus, TNF signaling by these cell subsets, particularly CAIFs, may reflect disease severity or even underlie drug non-responsiveness.

Example 12—Inter-Compartmental Re-Wiring of Cell-Cell Interactions in UC Through CAIFs, Inflammatory Monocytes, and M Cells Both cell subset proportions and intrinsic expression levels are changed in UC relative to healthy controls. Applicants hypothesized that alterations in cell subset proportions could be explained, at least in part, by cell intrinsic changes in cell-cell interaction genes, such as cytokines, chemokines, growth factors, and their cognate receptors. For example, immune signaling in inflamed tissue was impacted by changes in both stroma and immune cells compared to non-inflamed tissue. For example with multiple fibroblast subsets decreased expression of CCL13 and increased expression of the CGRP receptor (RAMP1) (FIG. 33) or T cell subsets increasing expression of the B cell chemoattractant, CXCL13 (FIG. 39C) and the checkpoint gene, PDCD1. For example, several expression changes targeted immune signaling within inflamed tissue, including the downregulation of CCL13 in fibroblast subsets (FIG. 33) and the upregulation of CXCL13 in T cell subsets (FIG. 39C), which can propagate into the infiltration, expansion, or inhibition of other cell types. Such intrinsic changes in expression in one cell type, can propagate into the infiltration, migration or expansion of another cell type, reflected in turn by a change it its proportion and/or its state. To test this hypothesis, Applicants first mapped thousands of literature-supported receptor-ligand pairs onto the cell subsets to construct a putative cell-cell network (STAR Methods) for healthy (FIG. 29A), non-inflamed (FIG. 29B), and inflamed (FIG. 29C) tissue, and identified those cell subset pairs with a statistically significant excess of receptor-ligand connections compared to a null model.

Whereas the healthy cellular network was mostly compartmentalized, with cell-cell interactions enriched among subsets from the same lineage (FIG. 29A,D), differential expression in disease preferentially targeted cross talk across compartments, and reduced compartmentalization (FIG. 29B-D), with colitis-associated subsets, such as CAIFs, inflammatory monocytes, and M cells, as key cross-compartment connectors. Intra-compartment interactions in health delineated the epithelial compartment ($P<10^{-4}$; all p-values for interactions from network permutation tests, STAR Methods) and spanned many connections reflecting homeostatic tissue organization, such as between DCIs and T cells (e.g. $P<10^{-3}$ for $T_{regs}$, CD8+ LP, and CD4+ Activated Fos-hi T cells), glia, endothelial cells, and pericytes (possibly comprising the gut-vascular barrier; $P<0.05$ for all pairs), and M cells and T cells ($P<0.05$ for cycling and CD8+ IEL subsets) (FIG. 29A). Conversely, in both non-inflamed and inflamed UC tissue, CAIFs, M cells, and inflammatory monocytes are the nexus of multiple intracompartmental connections. Differential expression in non-inflamed UC tissue (FIG. 29B,D) significantly targeted cross-talk between epithelial cells and T cells ($P<10^{-4}$) and fibroblasts ($P<10^{-4}$). Interactions between enterocytes and other cell subsets were especially targeted in non-inflamed UC tissue, including with several subsets of T cells ($P<0.05$ for $T_{regs}$ and CD8+ IELs, $P<10^{-3}$ for $MT^{hi}$ T cells) and fibroblasts (e.g. $P<10^{-4}$ for $WNT2B^+$ $Fos^{lo}$ subsets, $P<10^{-3}$ for $WNT5B^+$ subsets). Inflamed mucosal tissue (FIG. 29C,D) showed significant re-wiring of communication between B cells and T cells ($P<10^{-4}$; e.g. $P<0.05$ for $PD1^+$ T cells and all B cell subsets), macrophages and $CD8^+IL-17^+$ T cells ($P<0.05$), and enterocytes and post-capillary venules ($P<10^{-4}$).

Example 13—Cell-Intrinsic Changes that Underlie Immune Cells Infiltration, Stromal Cell and CAIF Proliferation and Epithelial Cell Differentiation Changes in UC Next, Applicants systematically queried all pairs of cell subsets, by testing, for each ligand-receptor pair that was differentially expressed during disease, whether the ligand's expression level in one cell type was correlated with the frequency of the cells expressing its cognate receptor across samples (including cells of the same type, to capture both autocrine and paracrine interactions).

The results strongly support the hypothesis that re-wiring of the cell-cell signaling network may drive changes in the cell subset proportions in UC. One set of interactions explains changes in immune cell proportions by effects on their migration and infiltration. For example, the increase in FO B cell proportions within the immune compartment, one of the most significant changes Applicants observed in UC (FIG. 27A), is correlated with strong upregulation of CXCL12 in $WNT2B^+$ $Fos^{lo}$ fibroblasts in UC (FIG. 29D), known to recruit B cells and induce follicle formation, and whose receptor, CXCR4, is expressed on plasma cells, (FIG. 29D, Spearman's $\rho=0.44$). In another example, the expression of IL-18, an epithelial-derived cytokine induced in enterocytes within inflamed tissue, is correlated with the frequencies of $T_{regs}$ across samples, which express its receptor IL18R1 (FIG. 29D, Spearman's $\rho=0.68$). IL18R1, inhibits colonic Th17 differentiation, is critical for $T_{reg}$-mediated control of intestinal inflammation, and has been associated with IBD through GWAS.

Second, within the stroma, multiple interactions reflect expansion of a stromal cell subset through growth factors expressed by other cells. For example, there is a high correlation across samples between the induction of platelet-derived growth factor (PDGFD) in $WNT2B^+Fos^{hi}$ fibroblasts and the frequency of pericytes, which express its receptor, PDGFRB (FIG. 29D, Spearman's $\rho=0.59$). PDGF plays an important role in blood vessel formation.

Third, some interactions reflect an impact of immune cells or fibroblasts on cell differentiation or state transition among epithelial cells, which can impact epithelial repair. For example, the frequency of enterocytes across samples was correlated with the expression by $CD4^+$ Activated $Fos^{hi}$ T cells of IL-22, a cytokine that promotes mucosal healing and epithelial renewal known to be reduced in (FIG. 29D, Spearman's $\rho=0.55$). Conversely, there is a negative correlation between CAIFs expression of CYR61 and the proportion of enterocytes, which express its receptor, ITGAV (FIG. 29D, Spearman's ρ=. −0.76). Interestingly, RBP4 expression in enterocytes is positively regulated with the proportions of CAIF, which express its receptor (FIG. 29D), suggesting a negative feedback loop between these two cell types.

Finally, autocrine signals may regulate cell frequencies both positively and negatively. For example, BEST4+ enterocytes expression of the hepatocyte growth factor-like gene, MST1, is strongly correlated to their frequencies across samples (FIG. 29D, Spearman's ρ=0.66), and they express its receptor, MST1R (implicated in IBD through GWAS). Similarly, post-capillary venule expression of TRAIL, for which they express the receptors, TNFSF10B, C and D, is negatively correlated to their frequencies across samples (FIG. 29D, Spearman's rho=0.38).

Figure 37:
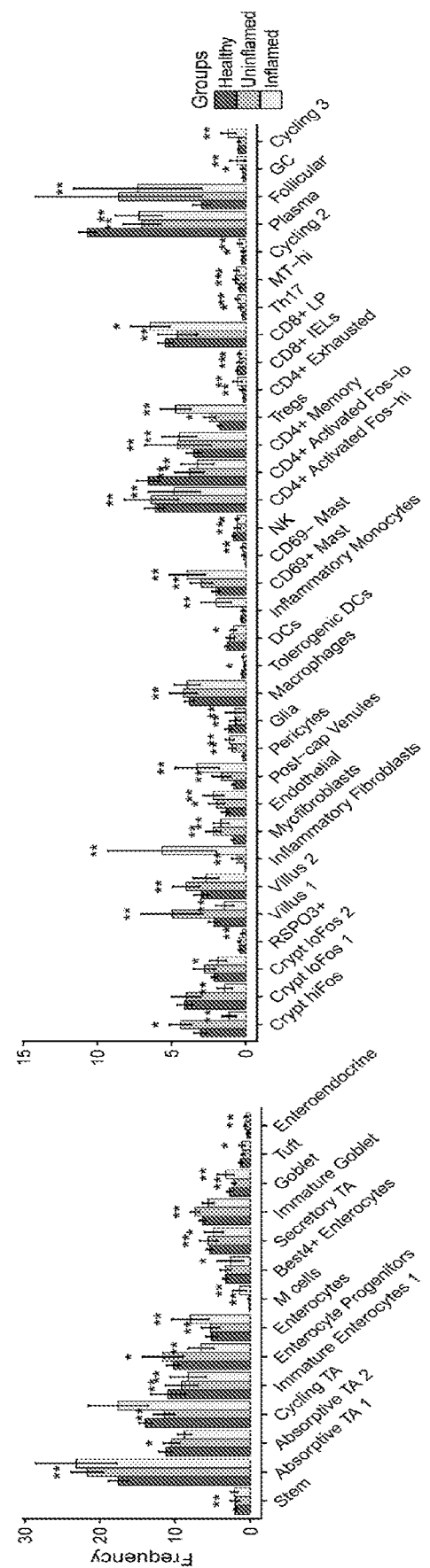
FIG. 37—Univariate analysis (with Fisher's exact test) on each cell frequency.

Applicants integrated this analysis across multiple interactions with LASSO regression, to predict the frequency of each cell subset using the expression levels of all cognate ligands of its receptors in other cells (FIG. 29E, STAR Methods). These provided highly significant explanation to the variance in the proportion of some of the key interacting cells, including inflammatory fibroblasts, CD8+IL17+ T cells, and M cells (FIG. 29E and FIG. 37). For example, the frequencies of CD8$^+$IL-17$^+$ T cells were explained by the combination of positive signals from (1) autocrine sources through CCL5, and FASLG; (2) CDH1 by absorptive TA cells, which may mediate adhesion between these cells and epithelial cells; (3) CCL4 by CD8$^+$ IELs and (4) IL-18 by immature enterocytes, both are known T cell chemoattractants; and (5) negatively regulation by CCL13 from WNT2B$^+$Fos$^{lo}$ fibroblasts and (6) plasma phospholipid transfer protein (PLTP) from glia.

Example 14—Mapping Disease Associated Variants to Cells of Action and Putative Function Tissue profiling of patients with active disease captures the pathological state of the tissue, but cannot directly distinguish between cause and effect. Conversely, Genome Wide Association Studies (GWAS) can identify genetic variants that are causally associated with disease risk, but cannot readily determine the molecular, cellular and physiological function of each variant. Tissue profiling by scRNA-Seq can help map variants to function at scale, by determining the cell of action for each associated gene and the genes' differential expression pattern in disease.

Figure 30A:
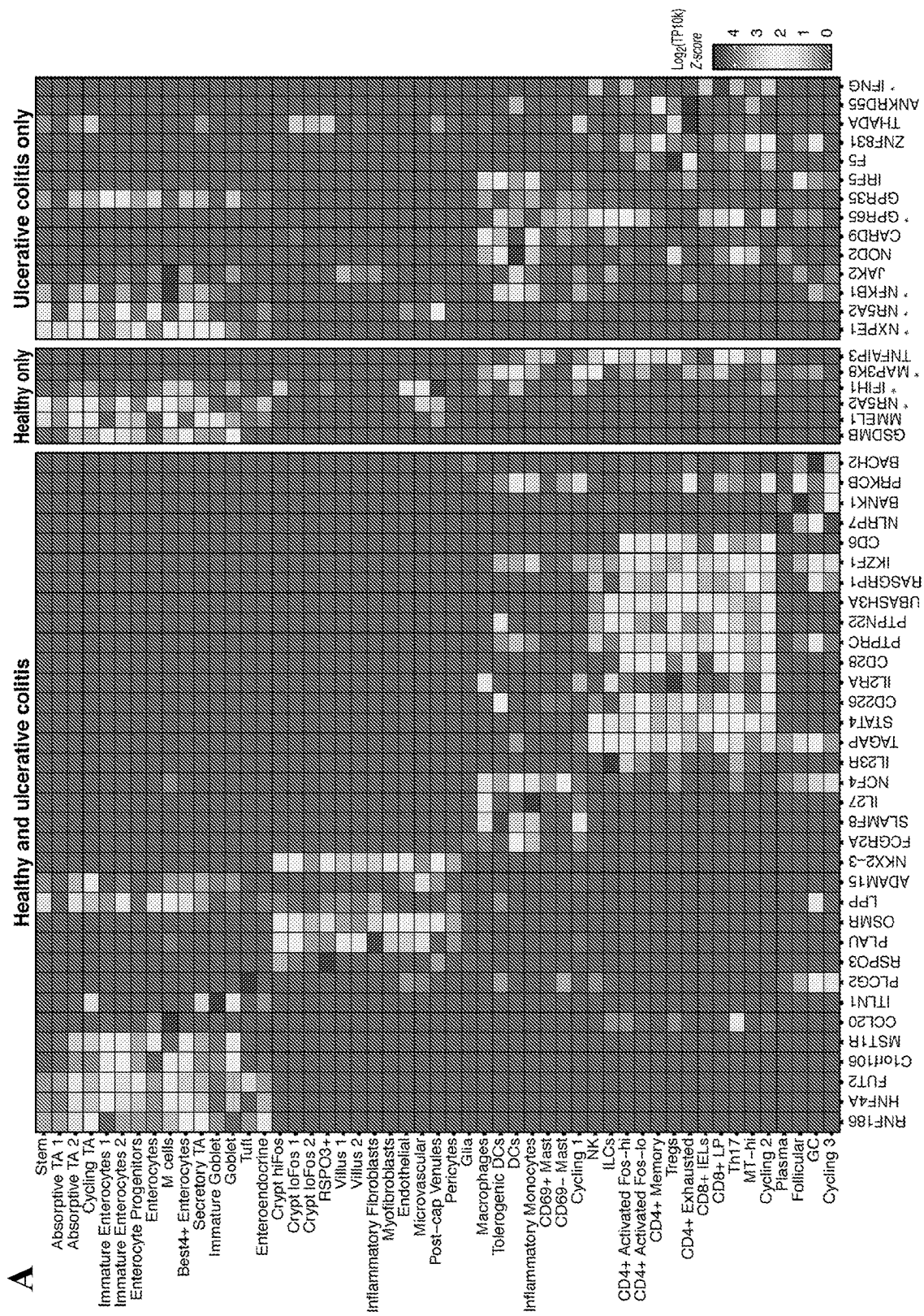
FIG. 30—a. Heatmap of 53 IBD-associated GWAS genes onto the colon cell atlas. b,c. plot comparing GWAS expression in subsets for healthy and inflamed cells.

Mapping 117 IBD-associated GWAS genes onto the colon cell atlas showed that 53 of the genes were strongly enriched within specific cell lineages (FIG. 30A), with 40 genes significantly differentially expressed in the cells between health and UC (FIG. 30A, Table 2, Table 13). In addition to many known associations (e.g. RNF186 in epithelial cells, CARD9 in monocytes), Applicants recovered many previously unappreciated associations. For example, Omentin (ITLN1), a receptor for bacterial arabinoglycans and lactoferrin, is expressed specifically by immature goblet cells that decreased in frequency with disease (FIG. 27A), rather than by all goblet cells; and plasma B cells expressed high levels of the NOD-like receptor, NLRP7, which is thought to recognize microbial acylated lipoproteins and activate the NLRP7 inflammasome in macrophages.

Figure 30B:
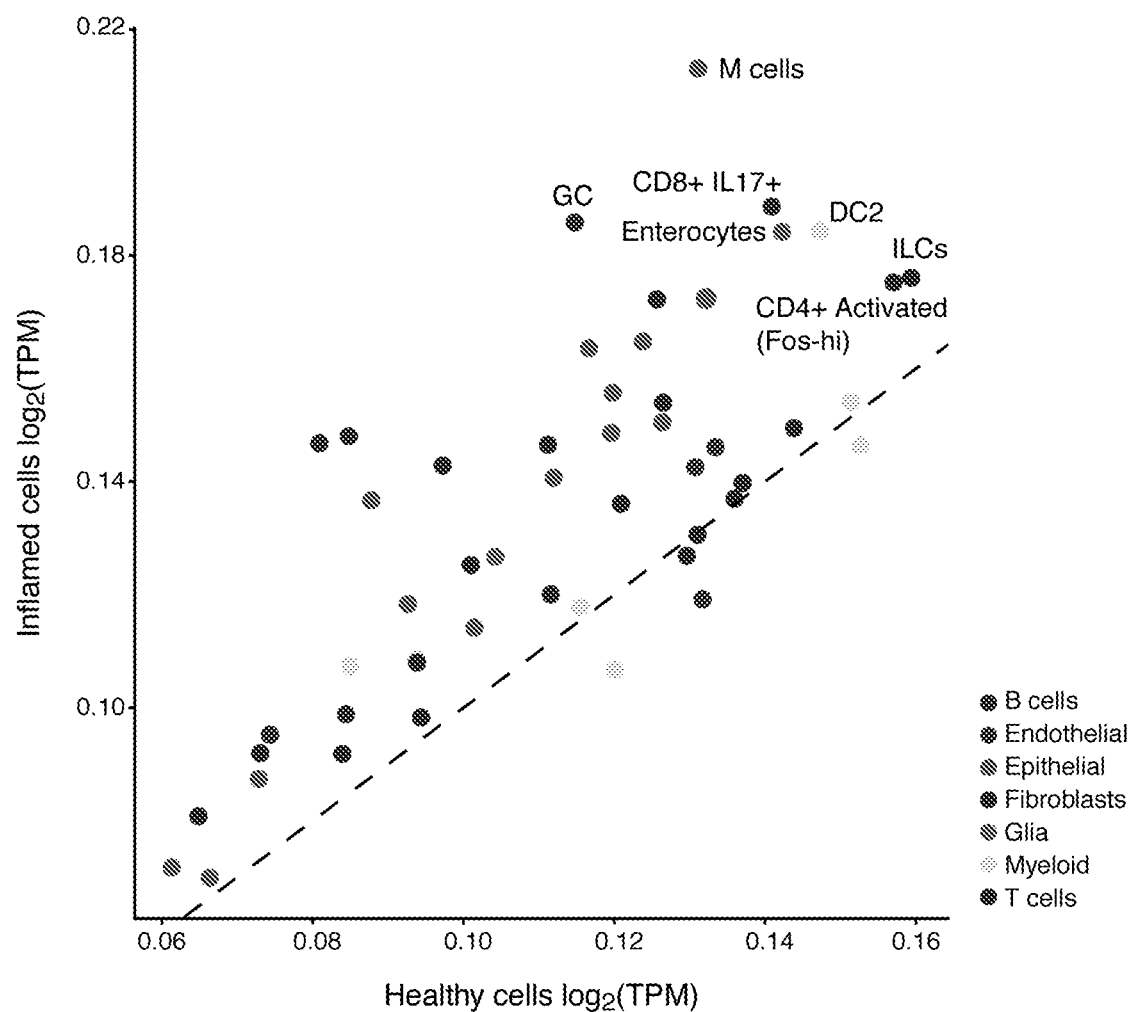

Some cell types are particularly enriched for UC-induced GWAS genes, most notably M cells, CD8$^+$IL-17$^+$ T cells, GC B cells, enterocytes, DC2s, and ILCs (FIG. 30B). In particular, multiple IBD-associated GWAS genes were significantly higher in M cells than in all other cell subsets, including MST1R, the receptor for macrophage-stimulating protein, CCL20, NR5A2, NFKB1, and JAK2 (FIG. 30A,B), and those genes were induced in M cells in UC vs. healthy tissue (FIG. 30B). Other cells with high mean expression levels of GWAS genes include many UC-related cell subsets, such as CD8$^+$IL-17$^+$ T cells, GC B cells, enterocytes, DC2s, and ILCs (FIG. 30B,C). Taken together with the changes in M cell proportions, their central cross-compartment interactions and overall differential expression patterns, this suggests that M cell dysfunction may play an underappreciated but pivotal role in UC.

Next, Applicants hypothesized that the variation in expression across individual cells of the same subset can power us to predict the function of GWAS genes. Past approaches to infer function from expression data often use "guilt by association" across bulk tissue samples, but those cannot distinguish between expression and cell proportions changes. In contrast, Applicants can measure the co-variation of genes across single cells within one cell subset, allowing us to isolate co-regulated biological processes (STAR Methods).

Using this approach, Applicants annotated many GWAS genes with new putative biological functions. For example, the function of C1orf106, expressed specifically by epithelial cells, was unknown until Applicants recently showed it was involved in cell-cell junctions. The gene module for this gene within epithelial cells contains many other genes involved in cell adhesion, including E-cadherin (CDH1), tight junction protein 3 (TJP3), and LAMB3, and is significantly enriched for the GO term "cell adhesion" (q-value<10$^{-3}$, Fisher exact test), second only to the response to interferon-gamma, which may reflect a relevant physiological pathway. NLRP7 is a NOD-like receptor that has been shown in macrophages to trigger the assembly of the inflammasome, activation of caspase 1, maturation of IL-1B and IL-18, and rapid pyroptosis. However, the analysis suggests that within plasma B cells, NLRP7 may activate caspase 3, the highest scoring gene in the module. Other top genes include pro- and anti-apoptotic factors, including death-associated protein (DAP), Fas apoptotic inhibitory molecule (FAIM), and BIM (BCL2L11), a key regulator of BCR-mediated apoptosis. Inflammasome assembly can lead to the activation of caspase 3 in cells that do not express caspase 1, which may explain the differential responses observed in macrophages and B cells.

RNF186 is an E3 ubiquitin ligase that is thought to participate in ER stress-mediated apoptosis and is expressed uniquely in epithelial cells (FIG. 30A).

Figure 30C:
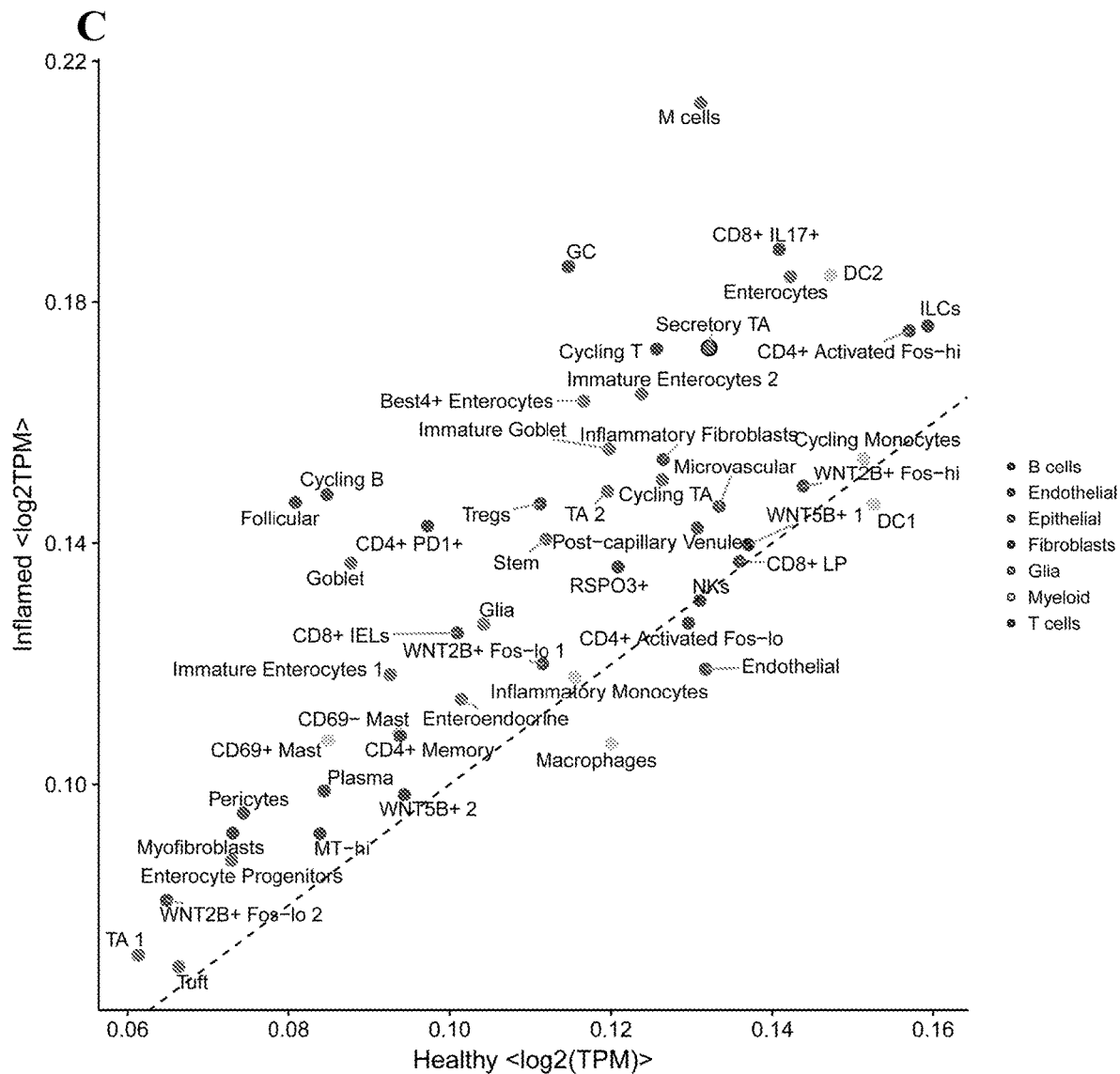

Example 15—GWAS Genes are Explained by a Small Number of Modules Spanning Key Pathways and Cells Remarkably, in many cases, multiple IBD-associated GWAS genes map into each others' modules, allowing us to arrange 10 meta-modules that together span nearly 50% of all IBD genetic associations, and may reflect some of the key pathways in the disease (FIG. 30C). In particular, the PTPN22 module in UC T$_{regs}$ contains 8 IBD-linked genes, including PTPN22, IL23R, RORC, CCL20, ATG16L1, SKAP2, PRDM1, and RASGRP1 (ranks 1, 2, 5, 17, 39, 40, 50, and 98 out of 16,801 analyzed genes, respectively). PTPN22, IL23R, RORC, and ATG16L1 are among the strongest risk factors of IBD, yet their precise roles in the disease are unknown. However, this module also contains caspase-8, BIM, and several other genes enriched in the KEGG terms for apoptosis and TNF signaling (q-value<10⁻⁴ for both terms, Fisher's exact test), suggesting that it may reflect pathways that regulate $T_{reg}$ apoptosis vs. survival in response to TNF. In another example, the TNFAIP3 module in healthy DC2s contains 7 IBD-linked genes, including TNFAIP3, TNFSF15, PLAU, STAT4, AHR, NDFIP1, and NCF4 (ranks 1, 11, 12, 21, 25, 88, and 96 out of 15,685 analyzed genes, respectively). This module was significantly enriched for KEGG terms related to TNF and NFκB signaling (q-value<10⁻⁴ for both terms, Fisher's exact test), along with the expression of several pro-inflammatory and anti-inflammatory cytokines and their receptors (e.g. IL-8, CXCR3, IL-10, IFNGR2, IL10RB), suggesting that this module may regulate DC responses in healthy tissue. In many cases, the genes in these modules are most highly expressed in other cell types, suggesting that the co-regulation of genes within single cells, rather than their absolute levels of expression, may reveal the cell-of-action for at least some GWAS-implicated genes. Some gene modules, such as the TNFAIP3 module in DC2s, were only found in healthy cells and may thus contribute to IBD onset, but the majority of gene modules, such as the PTPN22 module in $T_{regs}$, were only found in UC cells and may thus contribute to IBD progression (FIG. 30D). Notably, while, GWAS-enriched gene modules were found in subsets of epithelial cells, microvascular cells, myeloid cells, T cells, and B cells, but not fibroblasts, other endothelial cells, or glia (FIG. 30D), suggesting that stromal cells may contribute less to the overall genetic disease risk.

Example 16—Co-Regulation of Genes within Single Cells, Rather than their Absolute Expression Levels, Helps Recovers Causal Genes from Candidate Regions of Genetic Association Finally, Applicants hypothesized that cell type specific expression and co-expression modules can help pinpoint the specific genes that underlie the signal of association for each IBD-related SNP haplotype. To this end, Applicants retrieved all genes associated with each original associated region variant, and for each such candidate gene set, then examined whether the gene's expression level, degree of differential expression, or co-regulation with other candidate genes could be used to successfully recover the "causal" IBD-associated gene, as defined separately by fine mapping (STAR Methods), relative to a null model in which genes were randomly selected. In the null model, the "causal" IBD gene was selected 18 out of 53 total times from gene sets ranging in size from 2-10 genes (mean=4 genes). However, using scRNA-Seq data, Applicants successfully recovered 24 "causal" genes by selecting genes with the highest gene expression from each set of candidate genes (i.e. 33% increase in accuracy), and recovered 28 "causal" genes by selecting genes that were found in the largest co-regulated gene modules consisting of other candidate genes (i.e. 56% increase in accuracy). Importantly, the latter method constructs modules using only candidate genes as seeds, and thus does not rely on any a priori knowledge of disease associations, aside from the genetic regions and the scRNA-seq data. Furthermore, scRNA-seq data can also help prune candidate gene sets to reduce the number of potential hits, by removing genes with no detectable expression in the colon cells, genes that were not differentially expressed, or genes that were not found in any gene modules of candidate genes. Filtering by expression, Applicants successfully eliminated 18 out of 139 total genes, while incorrectly eliminating 5 true hits. Using modules, Applicants successfully eliminated 45 of 139 total genes, while incorrectly eliminating 9 true hits. Taken together, these results suggest that the co-regulation of genes within single cells, rather than their absolute levels of expression, can help recover the causal genes from candidate gene sets. Combining both ranking by co-expression and filtering, Applicants inferred the IBD-associated genes for all regions where the underlying variant is not known (FIG. 30E). This analysis suggests roles for NCF4, PDGFB, IL10, and CCRL2 in IBD.

Example 17—Discussion

The single cell census of the healthy and IBD colon generated a comprehensive cellular and molecular map of health and disease. This revealed nearly all known cell types, with the notable exception of neutrophils, revealed new cell types and states in the colon, including a subset of chemosensory epithelial cells that may detect pH and contribute to sour taste perception in the colon. Comparison of the cellular composition between healthy, uninflamed and inflamed UC tissue highlighted key disease-specific cell subsets whose contributions to IBD were largely unknown. Analysis of cell intrinsic programs showed that transcriptional programs are larger similarly changed in non-inflamed and inflamed tissue compared to healthy tissue, suggested that non-UC tissue, albeit histologically seemingly normal, is substantially modified, either as a "pre-inflamed" state or as "post-resolution". Analysis of cell interactions showed substantial rewiring from healthy to uninflamed to inflamed, with increased cross-talk between compartments, and allowed to explain some of the most dramatic changes in cellular proportions through cell-cell interactions that impact cell infiltration, proliferation and differentiation. The magnitudes of these reported changes—in cell proportions, intrinsic programs, and cell-cell interactions, emphasize the layer of complexity of colitis in which the three major components of the colon; the epithelial, stromal and immune cell are able to contribute to the initiation and progression of the disease, both inherently and through their effects on each other.

Several cell types, including M cells, CAIFs, inflammatory monocytes, B cells, and CD8⁺IL-17⁺ T cells—stand out as particularly prominent in disease and are often the locus of expression of GWAS genes—and manifest both changes in proportions, expression programs, and cell-cell interactions, that can play a role in disease initiation, progression and drug resistance, thus substantially revising the cellular and molecular narrative of disease.

BEST4+ Enterocytes are a New Subset of Chemosensory Epithelial Cells

Within the colon, pH sensing and sour taste perception may help detect members of the gut microbiota, for example, the lactic acid bacteria, many of which have established long-term symbioses with the human host and are thought to inhabit colonic crypts. Recent studies have highlighted the role of tuft cells in chemosensation at the microbiota-epithelium interface. The atlas uncovered also BEST4+ enterocytes, a new subset of chemosensory epithelial cells, which Applicants validated in the colons of healthy subjects and IBD patients (FIG. 26B). These cells may help detect and modulate salts and acids, and may work alongside tuft cells to transduce taste signals in the intestine. Supporting this hypothesis, they share the TF, SPIB, with tuft cells and M cells, suggesting either a developmental link or a common regulon for their shared functions. That this cell type has not been observed in the earlier census of the mouse small intestine may relate to either species-specific differences or to pH differences between the small and large intestines. Alternatively, as regulators of salt balance, these cells could be involved in water absorption, a key function of the colon, but not the small intestine. This interpretation is supported by low expression of renin in these cells. The proportion of BEST4+ enterocytes, along with those of several other epithelial subsets, are modestly decreases in inflamed tissue (FIG. 27A) and few differentially expressed genes with disease. Applicants found significant autocrine and paracrine signals controlling their abundances; most notably, their expression levels of MST1, for which they express the receptor, MST1R, were strongly correlated to their proportions across samples (FIG. 29D).

Microfold Cells are Expanded in Disease, Mediate Epithelial-T Cell Interactions, Especially with $T_{regs}$, and are Enriched for GWAS Genes Microfold cells are critical for the recognition of the gut microbiota by the adaptive immune system and were previously reported to reside in GALT (e.g. isolated lymphoid follicles) in healthy subjects. Microfold cells were rarely detected in healthy subjects, but expanded substantially in multiple inflamed tissue samples (FIG. 27A), which was unexpected because most biopsy specimens do not capture GALT (e.g. isolated lymphoid follicles). Their expansion during disease may either reflect the development of tertiary lymphoid structures or expansion of small sentinel populations of M cells within normal epithelium, and suggests that they may play an important and previously unrecognized role in the disease. In the cell-cell network, M cells are the sole epithelial cell type in the T cell compartment in healthy tissue, and are a central hub leading to the increased cross-compartment connectivity in non-inflamed and inflamed tissue, especially through connections to myeloid cells (FIG. 29A-C). Notably, within inflamed tissue, as epithelial cells overall increase production of RA, M cells upregulate the RA binding protein, CRABP2. RA production by DCs leads to the development of gut-homing $T_{regs}$ and it is possible that RA sequestration by CRABP2 from M cells plays a similar role, which also present antigen and form intimate associations with T cells. Moreover, M cells were major producers of CCL20, a cytokine whose expression in enterocytes and M cells was correlated in the analysis to the frequency of $T_{regs}$ across samples (FIG. 29D). Finally, the analysis implicates M cells causally in IBD through their expression of "GWAS genes": Indeed, they have the highest mean expression of all IBD-associated GWAS genes (FIG. 30A), including the highest expression levels of CCL20, JAK2, NFKB1, and NR5A2 (FIG. 30A), and an M-cell expressed gene module consist of 5 IBD-associated, co-regulated GWAS genes, including CCL20, ERAP1, PTGER4, JAK2, and TMEM135.

Inflammatory Fibroblasts and Inflammatory Monocytes are Key Hubs and May be Associated with Response and Resistance to Anti-TNF Therapy CAIFs are a new subset of fibroblasts that were barely detectable in healthy tissue, increased in non-inflamed tissue from UC patients, and dramatically expanded in inflamed tissue from UC patients (FIG. 27A). Together with inflammatory monocytes, the two cell types were strongly associated with signatures of clinical resistance to TNF blockade (FIG. 28D). This association may arise either because these cells are biomarkers of disease severity or are actively involved in drug resistance. Supporting the latter possibility, CAIFs uniquely express several genes that may promote resistance, including IL13RA2 and IL11, while inflammatory monocytes highly express OSM and IL1RN. Both subsets also express high levels of IL-8 and kynureninase (KYNU), which is a known biomarker of disease severity. Applicants additionally found: CAIFs interact with enterocytes; CAIFs and monocytes are "hubs" in disease interaction networks; and Few GWAS genes map to CAIFs.

T Cells

Applicants uncover strong evidence for the role of CD8+ IL-17+ T cells and Tregs in in IBD, which both progressively increase in frequency from healthy to non-inflamed to inflamed tissue (FIG. 27A). CD8+IL-17+ T cells were previously found in UC patients, but their role in the disease was unclear and they were not known to comprise a large fraction of colon-resident T cells. Surprisingly, these and other T cells simultaneously induce cytotoxic and co-inhibitory pathways. Applicants additionally found: Tregs upregulate TNF with disease; CD8 cells interactions (autocrine+paracrine interactions); and Re-wiring of T cell interactions with disease; GWAS modules show that Tregs and CD8 T cells are important (apoptosis).

This analysis provides a framework for using scRNA-Seq to understand complex diseases, from a census of cell types and states within healthy and diseased tissue, to identifying changes in cell proportions with disease, and partitioning changes in gene expression into those that are shared by cell lineages or unique to cell subsets or to drug responses; then, integrating these analyses to understand how changes in gene expression propagate into changes in cell-cell interactions, identifying the "cell-of-action" for GWAS genes, and understanding the complex genetic risk factors for the disease.

TABLE 3

| Epithelial Healthy specific markers for indicated cell types |
| --- |
| E.Enterocyte_Immature_1 |
| SLC16A12, TAC1, EFCAB5 |
| E.Enterocyte_Immature_2 |
| RP11-525K10.3, RP11-576I22.2, DRD5, LINC00974, GDPD2 |
| E.Enterocyte_Progenitor, |
| RP11-800A18.4 |
| E.Enterocytes |
| KIAA1239, RP11-396O20.1, DUSP21, SLC7A9, ARTN, SAA1, RP11-266L9.5, RP11-77K12.7, RBP2, SLC14A2, ADAMTSL4-AS1, RNU6-1016P, HAS3, LINC00955, G6PC, SAA2, CTB-58E17.9, KCTD4, SLC22A1, CELA3A, SLC6A20, CELA3B, CTC-490G23.2, CTB-171A8.1, GPR110, MAB21L3, RP11-30P6.6, SLC45A2, RAB6B, RP11-202A13.1, RP11-116O18.1, EMP1 |

TABLE 3-continued

Epithelial Healthy specific markers for indicated cell types

E.Enteroendocrine

DNAH2, MNX1, TNNC1, DACT2, FBXL16, RAB26, RP11-17M24.1, CNNM3, RP11-279F6.1, SYT13,
AC114730.3, ADPRHL1, KIAA1456, DDC, C19orf77, SNORD3D, SEZ6L2, STX1A, NAGS, KIF12, C14orf93,
ZNF311, PTPRD, MEX3A, PPL, COLCA1, CYP4F3, HOXB9

E.Epithelial

PRSS8, VIL1, PRR15L, PPP1R1B, AQP8, CCL15, SLC26A3, PCK1, CKMT1B, PRAP1, CKMTIA, LYPD8,
PKP3, AKR1B10, AP1M2, PLA2G10, NXPE4, MYO1A, TMEM171, PRR15, USH1C, MS4A12, PDZK1IP1,
KLK1, GGT6, FUT3, TMPRSS2, CBLC, MUC2, GUCA2B, LAD1, CDH1, MUC1, GJB1, C1orG10, LINC00035,
DSG2, LINC00483, C1orf106, GPRC5A, MUC4, LAMB3, ITLN1, CLRN3, CLCA4, LINC00675, MEP1A,
CYP3A5, AGR3, TRIM31, MARVELD3, ERN2, CES3, PLA2G2A, MUC5B, RP11-519G16.5, SATB2, CLCA1,
MAL2, CGN, NEU4, CFTR, RAPGEFL1, FERMT1, BAIAP2L2, DDC, HNF4A, PLEKHG6, BTNL3, ARL14,
CDHR2, FABP2, LCN2, SLC17A4, TM4SF5, ENTPD8, SPINK4, POF1B, MYO5B, C9orf152, VIPR1, PDZD3,
COL17A1, LAMA1, PLS1, IHH, B3GNT3, TMIGD1, OVOL1, REP15, RP11-395B7.2, RETNLB, CDKN2B-
AS1, GSTA1, MOGAT2, A1CF, SEMA4G, UGT2A3, BTNL8, SGK2, CEACAM6, SLC51A, YBX2, HHLA2,
TFF1, TRIM15, NOX1, C11orf86, OLFM4, LRRC19, PITX2, C1orf172, RNF43, PPP1R14C, U47924.27, LIPH,
CWH43, EDN3, ANXA13, CAMSAP3, PI3, TMEM184A, F2RL1, CAPN8, SMIM6, HEPACAM2, SH3RF2,
TMEM82, ISX, ANKS4B, RBBP8NL, GRB7, SPDEF, ESRP1, EPB41L4B, SLC3A1, AC106876.2, LINC00668,
HNF1B, RP11-747D18.1, NGEF, RP11-465B22.8, EPHA10, MB, ZBTB7C, STX19, CA7, SATB2-AS1, ASPG,
RP11-680F8.1, PRAC1, NXPE2, REG1A, C12orf36, RP11-465N4.4, CTD-2626G11.2, RP11-708H21.4,
SLC9A2, S100P, RP1-278O22.1, L1TD1, KIF12, INPP5J, OVOL2, AC005355.2, WNK4, NR1I2, NAT2,
SMIM2-AS1, LINC00992, EDN2, BARX2, C1orf116, HNF1A-AS1, RAP1GAP, SCGB2A1, BEST2, TINAG,
GPRIN2, B4GALNT2, RP11-234B24.2, TMEM236, FOXD2, RP11-349K16.1, RHOV, IL22RA1, DMBT1,
RP11-304L19.1, RP11-627G23.1, SLC5A1, BEST4, XDH, AC066593.1, RASEF, GLOD5, TMED6, CELA3B,
OTOP2, CAPN13, GOLT1A, TMEM61, RP11-59E19.1, GDPD2, ADH6, CYP2B6, IYD, HNF4G, CAPN9,
FOXA1, WWC1, SLC30A10, SERPINA6, RP5-881L22.5, IGSF3, PLA2G4F, SLC6A7, FOXA2, MIR194-2,
RP3-523K23.2, TMEM92, NOS2, RP11-30P6.6, C3orf83, SLC13A2, SYT13, AGXT, CELA3A, CTD-
2547H18.1, CTSE, EPPK1, MYRF, RBP2, TMEM72, FAM83E, GPR39, LINC00704, ACE2, FIBCD1, HOXA13,
RP11-297L17.2, RP11-284F21.10, SH2D6, AC009133.21, CTD-2196E14.5, GALNT5, MEP1B, MT3, UGT2B7,
CYP2C18, TUBAL3, APOBEC1, CLDN8, RP11-408H20.1, USP43, CTC-210G5.1, HAS3, CTD-2566J3.1,
AC011298.2, GLRA4, HSD3B2, CTD-2047H16.2, FAM83B, HOXB13, KRT14, LINC00261, PRAC2,
SLC6A19, CASC9, MUC3A, RP11-328M4.2, TM4SF20, PRLR, C6orf41, RP11-150O12.3, RP11-187E13.1,
MSLN, ALPI, SI, SOWAHA, GJB3, TBX10, CHAD, RP11-191G24.1, C1QTNF1-AS1, KLK15, PYY, MRAP2,
ALDOB, CYP4F2, RP11-91K11.2, RP11-567C2.1, AP000344.3, CASC8, CYP3A4, FAM151A, GRHL2,
SLC1A7, TTPA, LCN12, AC007182.6, KLK3, PF4, PVRL4, RP11-542M13.2, TREH, CYP4F11, AC011523.2,
GPR115, RP11-1260E13.2, RP11-519G16.3, RP11-6N17.6, MESP2, DMRTA1, AC005152.2, BRINP3, CTA-
363E6.2, GPD1, MUC17, NOVA1-AS1, OTOP3, RP11-470P21.2, RP11-595B24.2, RP11-800A3.4, TRPM5,
WFIKKN1, BCMO1, GPR128, RP1-170O19.14, RP11-801F7.1, AC005550.3, ACSM1, DPP10, GPR143,
HMGA2, KCNE2, LRRC66, PCSK9, PSCA, RP11-202A13.1, RP13-616I3.1, AP001610.9, DACT2, FAM160A1,
HTR3E, OGDHL, RP11-28H5.2, RP11-627G18.4, RP11-64K12.10, RP11-800A18.4, SLC5A11, TRIM10,
XXyac-YM21GA2.4, B3GALT1, LGR5, RP11-223I10.1, RP11-290F24.6, RP11-379B18.6, RP11-93B14.5,
RXFP4, UGT1A10, CHGA, DNAH3, C19orf45, CTD-3010D24.3, GNG13, KRT12, LINC00520, NR0B2, RP11-
116O18.1, RP11-135A1.2, RP11-276H7.3, RP11-509E16.1, SHH, TFF2, TNNT2, UCA1, RP11-125B21.2,
ABHD12B, CTA-221G9.11, CTC-55802.1, DAO, GPR98, LGR6, RP11-432J24.2, RP11-644F5.10, RP4-
680D5.8, RP5-1057J7.7, SLC15A1, SLC9A3, TAC1, TRPC7-AS1, LHX4, CASC16, CCDC108, CHRM3, CTD-
2611O12.7, KCNK10, KNG1, LINC01071, OXGR1, PHYHIP, POU2F3, RP11-1069G10.1, RP11-1220K2.2,
RP11-188P20.3, RP11-339B21.15, RP11-695J4.2, RP11-771K4.1, RP11-809C18.4, SLC45A2, XX-CR54.3,
AC024592.9, AC083900.1, AC090673.1, CTD-2026G6.3, CTD-2589M5.4, DUOXA2, GALNT8, HSD17B3,
INSL5, KCNV1, KLHL34, LA16c-395F10.2, LINC00941, MAB21L3, RP11-227H15.4, RP11-416N2.4,
SLC5A10, SYTL5, FRRS1, AC064834.1, AQP12A, C12orf56, C1orf177, C4BPA, CHST5, CTB-25B13.6,
DEFA5, DLG3-AS1, FAM83H-AS1, FEV, GLTPD2, HIST1H4B, LINC00114, LINC00570, MT-TS2, POU5F1B,
PRDM7, RP11-209E8.1, RP11-320N21.2, RP11-392E22.12, RP11-426L16.3, RP11-74C1.4, RP11-757F18.5,
RP11-806O11.1, RP11-844P9.2, SLC38A4

E.Goblet

CTD-2231E14.4, PLA2G2F, TFF1, TBX10, AC093642.3, RP11-95M15.1, FER1L6, S100P, LINC01022,
RN7SKP127, SYTL5, FFAR4, MUC2, SBF2-AS1, RASEF, MUC1, TFF2, NRAP, GALNT5, RP11-379B8.1,
HIST1H4A, LINC00842, RP11-363E7.4, AC011718.2, GPR153, RP11-845C23.2, CHAD, CHRNA7, CLDN8,
GPRIN2, AC009133.21, FAM101A, SYTL2, RP11-757F18.5, BCAS1, AN RD36C, ZG16, CAPN8, SMIM6,
HIST1H2BG, AN RD18A, TM4SF5, RNF39, GLTPD2, LRRC31, EIF2AK3, RECQL5, RP11-276H7.3, RP11-
196G18.22, AC147651.3, USP54, LGALS9B, DHX32, CTD-2589M5.4, TSNARE1, CYorf17, NEDD4L,
HIST1H2BE, ENTPD8, SCNN1A, GALE, LINC00543, RP11-92K15.3, FAM177B, KAZALD1, HIST1H2BC,
LGALS9C, FCGBP, HIST1H3D E.Immature_Enterocytes CA1, RP11-439E19.9, XXyac-YM21GA2.7, SLC26A2

E.Immature_Goblet

TMEM210, ITLN1, CLCA1, LA16c-321D4.2, SPINK4, KLK15, LRRC26, KLK1, RP11-234B24.2, RETNLB,
WFDC2, GNE, CCDC60, AC011523.2, LA16c-395F10.2, UGT2B7, RAP1GAP, ST6GALNAC1, AGR2, CTD-
2547H18.1, KLK3, LINC00261, CACNA2D2, GALNT8, KLK4, GMDS, TMEM61, SPINK1, PFKFB4

E.Secretory

ABCC8, CTD-2231E14.4, HTR3C, NKX2-2, PAX6, PLA2G2F, PRAME, RP11-69G7.1, VWA5B2, HTR3E,
GNG13, SCGN, SST, GCG, SH2D6, CHGA, TPH1, FEV, PYY, CRYBA2, SH2D7, TRPM5, TNNI1, OGDHL,
POU2F3, NCMAP, TAS1R3, KLHDC7A, TFF1, TBX10, HMX2, AZGP1, TREH, AC093642.3, IL17RB,
AC053503.4, FER1L6, KLK11, KCNQ4, PRSS22, SCG5, S100P, AVIL, PROC, RP11-93B14.5, LINC01022,

TABLE 3-continued

Epithelial Healthy specific markers for indicated cell types

C11orf53, SYTL5, ARHGEF38, TGM3, FFAR4, SHB, LCN15, ARX, MUC2, SBF2-AS1, BMX, RASEF, MUC1, TFF2, NRAP, ATP2A3, RP11-384L8.1, GPR153, PSTPIP2, RP11-700H6.1, TMEM198, HIST1H4A, GALNT5, PART1, RP11-379B8.1, 7SK, RP11-845C23.2, RP5-821D11.7, CTA-221G9.11, IGSF21, TM4SF5, LINC00842, RP11-363E7.4, SYT7, CHGB, AC011718.2, CHAD, GPRIN2, RP11-122G18.5, HCG9, MYCBPAP, CNTD1, CHRNA7, FAM101A, CLDN8, GFI1B, RECQL5, ANKRD36C, SYTL2, RP11-757F18.5, CTD-3051D23.4, AC009133.21, GRASP, BCAS1, ANKRD18A, SMIM6, RP11-498E2.9, RAB3B, FAM106A, CAPN8, MYRF, ARHGEF11, FUT6, ZG16, HIST1H2BG, MYO5C, ESPL1, PRUNE2, HCK
E.Secretory_All HTR3C, GCG, HTR3E, GNG13, SH2D6, FEV, CHGA, SCGN, CRYBA2, ZG16, TBX10, SH2D7, TRPM5, MUC2, PYY, OGDHL, BEST2, LA16c-321D4.2, AC009133.21, CAPN9, REP15, KCNQ4, POU2F3, AC011523.2, NCMAP, MB, FCGBP, SCGB2A1, SYTL5, FFAR4, KLK12, ITLN1, CLCA1, TFF3, TAS1R3, REG4, HMX2, TMEM61, TFF1, SPINK4, FER1L6, TPSG1, RP11-234B24.2, RETNLB, KLK15, RP11-384L8.1, ANXA13, ANO7, CCDC60, HOXA-AS3, KLK1, KLK3, AC093642.3, AZGP1, LRRC26, SPDEF, IL17RB, TREH, CTD-2589M5.4, CCDC108, RAP1GAP, WFDC2, LINC00238, LA16c-395F10.2, FOXA3, LINC00261, RXFP4, CTA-221G9.11, CA9, PFKFB4, CREB3L1, S100P, GPR153, C11orf53, ST6GALNAC1, PROC, FOXP4, ARHGEF38, RP11-93B14.5, WNK4
E.Secretory_TA RP11-350J20.12
E.Stem LEFTY1, ASCL2, RGMB, CDCA7, ALDH1B1, EPHB3, OLFM4, SMOC2, PTPRO, SLC39A2, LGR5, CELF5, OXGR1, RP11-84C10.4, FAM201A, TERT, RP11-43505.2, RP11-219E7.4, FMN2, DEC1, TMPRSS13, CLDN1, SNTN, RP11-396C23.2, TRIM74, RP11-22L13.1

TABLE 4

Epithelial UC specific markers for indicated cell types

E.Enterocyte_Progenitor

SLC38A4, AC013268.5, AGMO
E.Enterocytes

BEAN1, CYP24A1, KLK8, MYZAP, PLA2G4E, PNCK, RP11-103J17.2, RP11-317L10.1, RP11-626P14.2, SERPINB4, SLC47A2, ANXA10, INSL4, SERPINB7, RP11-79H23.3, MMP7, FOXE3, SAA4, RP11-381O7.3, KIAA1239, MGAM, C8G, AC104135.3, FAM83A, GLRA4, TPRXL, RP11-30P6.6, PHYHIP, RP11-73G16.1, RP11-345J4.3, RP11-28H5.2, SLC6A14, LINC00955, RP5-1086K13.1, RAB6B, TCHP, PDZK1IP1, RP11-35P15.1, AQP11, LINC00479, CRABP1, LY6D, BMP3, KCNG1, RP11-542M13.2, ABTB2, SLC6A20, TM4SF20, PLIN1
E.Enteroendocrine MIR7-3HG, NTS, PAX4, PAX6, VWA5B2, PYY, INSL5, SCGN, GCG, FEV, CHGA, CRYBA2, PRPH, SST, TPH1, SCG3, LCN15, KCNH6, KCNJ6, EYS, INSM1, SCG2, CPB1, RFX6, CHGB, NKX2-2, NEUROD1, CNIH2, SLC18A1, LINC00470, SCG5, NEUROG3, PCSK1N, TGM3, MEGT1, MAFA, TNNC1, PCSK1, RTBDN, CACNA1A, RP13-131K19.6, AC034243.1, SYT13, MS4A8, PDX1, ARX, SLC29A4, MAPK8IP2, STX1A, LRRC24, SCT, CTD-3193013.9, MLXIPL, BAIAP3, RIMS2, RIMBP2, DDC, C6orf141, MANEAL, AMBP, CAMK2B, CYP2W1, RXFP4, PELI3, ASCL1, RUNDC3A, PNPO, ATP6V1C2, ACVR2B, NPW, LY6H, PSCA, PPL, CADPS, PAPPA2, DUSP26, NT5DC3, RP11-279F6.1, CXXC4, DNAJC12, NOP9, Z83851.1, CELF4, PEMT, RAB26, GIPR, PGAM2
E.Epithelial ABCA12, ABO, AC005152.2, AC005550.3, AC007182.6, AC007255.8, AC007292.6, AC009133.21, AC010745.1, AC011298.2, AC011523.2, AC011718.2, AC011747.7, AC024592.9, AC026471.6, AC053503.4, AC066593.1, AC069277.2, AC090673.1, AC104667.3, AC106876.2, AC110619.2, ACE2, AGXT, AL133373.1, ALDH1A2, ALOX12B, AMBP, ANKRD18A, ANKS4B, ANO5, AP001610.9, AQP5, ARTN, B3GALT1, B4GALNT2, BCMO1, BEST2, C12orf56, C1QTNF1-AS1, C1orf168, C21orf88, C2orf54, C2orf70, C3orf83, C4BPA, C5orf52, CALN1, CASC16, CASC9, CASP16, CCDC108, CCDC60, CELA3A, CELF5, CHAD, CHRNA7, CHST5, CNTN3, COL2A1, CRABP1, CRYBA2, CRYBB3, CTA-363E6.2, CTB-175P5.4, CTC-210G5.1, CTC-436P18.3, CTC-490G23.2, CTC-558O2.1, CTD-2377D24.6, CTD-2547H18.1, CTD-2566J3.1, CTD-2589M5.4, CTD-3010D24.3, CTD-3118D7.1, CWH43, CYP2B6, CYP2C18, CYP3A4, CYP4F11, CYP4F2, CYorf17, DACT2, DAO, DEFB4A, DMRTA1, DNAJC6, DPP10, EDN2, EGF, ENKUR, FAM151A, FAM160A1, FAM83A, FAM83B, FAM83H-AS1, FEV, FOXH1, FOXN1, FRMD5, GABRB2, GABRB3, GABRP, GAL3ST1, GALNT8, GJB4, GJB5, GLRA2, GLRA4, GNG13, GPD1, GPR110, GPR115, GPR128, GPR37L1, HMGA2, HS3ST6, HSD3B2, HSPB3, HTR3E, HTR4, IGFALS, IL37, IRX2, ISX, KCNE2, KCNK10, KIAA0319, KLHDC7A, KLK12, KLK15, KLK3, KLK4, KNG1, KRT12, KRT13, KRT14, KRT6B, KRTAP13-2, LA16c-395F10.2, LECT1, LGR5, LHX4, LINC00114, LINC00238, LINC00639, LINC00842, LINC00896, LINC00940, LL22NC03-32F9.1, LRRC66, LRRIQ4, LYPD6, MAB21L3, MAMDC2-AS1, MEP1B, MESP2, MIR194-2, MNX1, MNX1-AS2, MT-TY, MT3, NAT2, NAT8, NKX2-2, NOVA1-AS1, NPSR1, NR0B2, NRI2, NRAP, OGDHL, PCAT7, PLA2G12B, PLA2G4F, PLCH1, PLSCR2, RBP2, RNF183, RNU1-134P, RP1-170O19.21, RP1-240K6.3, RP1-60O19.1, RP11-1069G10.1, RP11-1157N2_B.2, RP11-11N5.3, RP11-120K24.3, RP11-1220K2.2, RP11-150O12.3, RP11-150O12.6, RP11-164P12.4, RP11-187E13.1, RP11-188P20.3, RP11-202A13.1, RP11-206L10.3, RP11-209E8.1, RP11-211G23.2, RP11-21L23.2, RP11-223I10.1, RP11-231E6.1, RP11-244F12.3, RP11-275F13.1, RP11-307C12.11, RP11-30P6.6, RP11-349K16.1, RP11-352G9.1, RP11-35P15.1,

TABLE 4-continued

Epithelial UC specific markers for indicated cell types

RP11-380P13.1, RP11-382B18.4, RP11-41O4.1, RP11-432J24.2, RP11-439E19.7, RP11-440I14.3, RP11-44F14.8, RP11-465N4.5, RP11-469H8.6, RP11-470P21.2, RP11-511I2.2, RP11-519G16.3, RP11-542M13.2, RP11-595B24.2, RP11-627G18.4, RP11-627G23.1, RP11-63P12.7, RP11-64K12.10, RP11-680F8.1, RP11-6N17.6, RP11-708H21.4, RP11-747D18.1, RP11-757F18.5, RP11-77K12.7, RP11-789C1.1, RP11-796E10.1, RP11-798K3.2, RP11-800A18.4, RP11-801F7.1, RP11-844P9.2, RP11-84C10.4, RP11-93B14.5, RP11-963H4.3, RP13-497K6.1, RP13-616I3.1, RP4-680D5.8, RP5-1013A22.5, RP5-1057J7.7, S100A7, SAA4, SCEL, SCGB2A1, SCGN, SEMA3B-AS1, SERPINA6, SHH, SLC10A5, SLC13A2, SLC15A1, SLC18A1, SLC1A7, SLC28A3, SLC30A10, SLC38A4, SLC39A2, SLC5A11, SLC6A19, SLC6A7, ST6GAL2, SYT8, SYTL5, TMEM72, TNNT2, TRIM10, TRIM40, TRPC7-AS1, TRPM5, TSPO2, TTC6, TTPA, TUBAL3, U47924.27, UCA1, UGT1A1, UGT2B15, UGT2B7, VSTM5, WFIKKN1, WNT11, XX-CR54.3, YBX2, SH2D6, A1CF, TMEM61, TREH, C12orf36, UGT2A3, RP11-465B22.8, NXPE2, TMIGD1, ESRP1, TBX10, FAM83E, TFF2, CDHR2, SI, GRHL2, ZG16, TMEM82, PDZD3, TM4SF5, STX19, TFF1, RETNLB, POU2F3, CELA3B, GUCA2B, RP11-234B24.2, PRAP1, C4orf19, LRRC19, APOBEC1, TRIM31, FCGBP, GUCA2A, TFF3, MUC2, GOLT1A, PCK1, LINC00992, SHD, IL22RA1, CKMT1B, MYH14, PHGR1, CDH1, HSD17B3, CEACAM5, ERN2, KBTBD12, FABP2, LAMA1, ASPG, EPB41L4B, LYPD8, SLC26A3, FERMT1, SLC17A4, CA7, HHLA2, MISP, C9orf152, ELF3, MUC13, TTLL6, TSPAN1, OVOL2, LRRC26, PPP1R14D, REP15, MSLN, C11orf86, PITX2, S100A14, AGR3, CBLC, CDHR5, CAPN8, SMIM22, KRT8, GPT, MEP1A, LCN2, LINC00675, GPRIN2, MS4A12, EPPK1, HOXB13, GCNT3, GDPD2, NXPE4, IRF6, LGALS4, OTOP2, DQX1, FUT3, XDH, NXPE1, SLC9A2, PROM2, MAL2, IGSF9, LIPH, HNF4A, RAB25, CLCA4, SERPINB5, PIGR, HEPACAM2, CCDC64B, GGT6, MS4A8, SLC5A1, MYO1A, PRR15L, MYO5B, FUT2, C10orf99, FAM3D, AGR2, B3GALT5, PRR15, RP5-881L22.5, SPINK4, SLC39A5, CLDN8, PLS1, NOX1, HNF1A-AS1, RP3-406A7.7, ANXA13, RP11-96D1.11, FABP1, EPCAM, PRKCG, CAPN9, PRAC1, RP11-665N17.4, LEFTY1, CLDN7, CYP2C9, CDX1, CHP2, TMPRSS4, AOC1, RP11-22C11.2, FOXA3, URAD, HNF4G, LDHD, C1orf106, POF1B, CCL15, JPH1, TSPAN8, AMN, CAMSAP3, MUC5AC, EFNA2, PLA2G10, GRB7, PI3, SLC44A4, CTD-2196E14.5, LCN12, TMC5, CEACAM7, KRT19, DSG2, EPHA10, AC083900.1, GDA, SEMA4G, SLC6A14, SCNN1A, HMGCS2, AC079602.1, AQP8, TINAG, COL17A1, KLK1, S100P, TMEM54, CNGA1, CLDN3, RP11-304L19.1, SLPI, AKR1B10, KRT20, CA1, SPINK1, RP11-797A18.4, MB, TFCP2L1, RP11-305L7.6, FRMD1, SPDEF, PTPRH, RP11-395B7.2, GPX2, RBBP8NL, GPA33, PDE11A, LINC00483, FZD5, DSP, CA12, ITLN1, NOS2, FFAR4, TMEM184A, SFN, CLRN3, MTIG
E.Goblet C11orf52, RP11-120K24.5, RP11-43N5.1, RP11-542B15.1, CTD-2231E14.4, LGSN, RN7SKP127, NUTM2E, TBX10, SYTL5, RP11-363E7.4, RP11-143K11.1, TFF1, SCEL, RN7SL676P, FER1L6, SLC25A30-AS1, PCDH20, ANKRD36C, RP11-805I24.1, FAM177B, MUC5AC, LINC00342, RP11-845C23.2, RP11-730K11.1, STXBP5-AS1, FRY-AS1, SYTL2, TFF2, SBF2-AS1, RASD2, RP11-757F18.5, AC011718.2, ZG16, MUC1, SYTL4, MUC2, LGALS9B, FAM101A, MLLT3, FFAR4, RP11-452L6.1, TCTEX1D4, RP11-574K11.28, LGALS9C, GPR153, CAPN8, SHH, ADM2, AC007382.1, RP11-167J8.3, LINC01022, SMIM6, MFSD4, GALNT5, TEP1, BCAS1, GPRIN2, SDR16C5, ASPHD2, ZG16B, AC009133.21, C4orD6, GAN, FCGBP, GAREM, LNX1-AS1, MUC4
E.Immature_Enterocytes F11, RP11-525K10.3, RP11-576122.2, CA1, WFDC12, RP11-164P12.3
E.Immature_Goblet RP11-7115.4, IGFALS, AC015849.13, CLCA2, GALNTL6, IL37, AC073133.1, PRKCG, ITLN1, RETNLB, SPINK4, TMEM210, DLGAP1, CLCA1, LA16c-425C2.1, LINC00238, CREB3L4, LRRC26, CHRNA3, GALNT8, RP11-234B24.2, CTD-2547H18.1, AGR2, WFDC2, KLK15, KLK1, LINC00261, GIF, ST6GALNAC1, LINC00570, REG4
E.Secretory C11orf52, HTR3C, KLK13, MIR7-3HG, PAX4, PAX6, RP11-43N5.1, TAS1R1, TNNI1, VWA5B2, HTR3E, B4GALNT4, PYY, SH2D6, INSL5, SCGN, SH2D7, GCG, TRPM5, FEV, CHGA, CRYBA2, GNG13, PRPH, SST, CCDC129, PCP4, TPH1, SCG3, LCN15, KLHDC7A, OGDHL, KCNH6, POU2F3, AZGP1, TAS1R3, EYS, CTD-2231E14.4, KCNJ6, RP11-131L12.2, INSM1, ALOX12B, RAB3B, NCMAP, CCSER1, SCG2, CYP3A7, CPB1, IL17RB, RFX6, RN7SKP127, RIMBP2, CTD-2410N18.3, NKX2-2, NEUROD1, TBX10, SYTL5, SLC25A30-AS1, CNIH2, SLC18A1, C11orf53, RP11-143K11.1, RP11-363E7.4, RP11-93B14.5, MAFA, NRTN, AVIL, TFF1, LINC00470, KCNQ4, ABCA13, SCEL, TREH, GPR153, FER1L6, BMX, SCG5, RN7SK, NEUROG3, PSTPIP2, TGM3, PCDH20, ANKRD36C, KLB, ATP2A3, MEGT1, RASSF6, RP11-805I24.1, KLK11, FAM177B, PAQR7, PROC, ATP8A2, RP11-809C18.4, AC023490.1, RP11-730K11.1, TM4SF5, CACNA1A, HMX2, IGSF21, ADH6, SYTL2, TNNC1, RTBDN, PRSS22, FRY-AS1, GFI1B, FOXP4, RASD2, FAM101A, HOTAIRM1, AGAP1-IT1, HIP1R, SYT7
E.Secretory_All EYS, KCNH6, LINC01022, NEUROG3, TNNI1, VWA5B2, CRYBA2, HTR3E, SCGN, B4GALNT4, SH2D6, FEV, GCG, CHGA, PRPH, SH2D7, TRPM5, GNG13, RIMBP2, AC009133.21, ZG16, SLC18A1, LCN15, TPH1, SCG3, TBX10, RFX6, INSM1, SCEL, RP11-575A19.2, PKP1, MUC2, MUC5AC, BEST2, PCP4, KLHDC7A, REP15, TGM3, AC011523.2, TAS1R3, AC110619.2, SCG2, CTD-2231E14.4, RAB3B, RAD51AP2, POU2F3, CCDC60, AZGP1, KLK15, FCGBP, CCDC129, KLHL32, ALOX12B, ANO7, CLCA1, OGDHL, B3GNT6, KLK3, MB, ITLN1, TFF3, RN7SKP127, RETNLB, SNORA77, RAB26, CLCA2, NCMAP, KLK11, NKX2-2, KLK1, GALNT8, IL37, ANXA13, SPINK4, RP11-234B24.2, KLK12, TPSG1, CHRNA3, STXBP5-AS1, RAP1GAP, TMEM61, GPR153, IGFALS, TMEM210, SPDEF, CAPN9, SYTL5, SLC25A30-AS1, FOXA3,

TABLE 4-continued

Epithelial UC specific markers for indicated cell types

ABCA13, FFAR4, LRRC26, GALNTL6, LA16c-321D4.2, AGAP1-IT1, SYT7, TFF1, LINC00261, RP11-363E7.4, SCG5, FAM177B, SCGB2A1, KLB, CCDC108, NRTN, GIF, PCDH20, LINC01001, ST6GALNAC1, WFDC2, TFF2, MLLT3, DNAJC12, ATP2A3, PRKCG, CREB3L4, CTD-2547H18.1
E.Secretory_TA ARHGAP36, DLX4, SIK3-IT1, RP11-430G17.3, RP11-363J20.1, SBSPON, RP11-231G3.1, RP11-396C23.4
E.Stem RGMB, SMOC2, PTPRO, LPCAT3, LGR5, LGR6, SNX32, RP11-760H22.2, C1orf95, RP11-21817.2, IZUMO2, NANOG, SLC22A11, SHISA6, RP11-219E7.4, HYDIN, RP11-2E11.9, SCN8A, TDRD6, MURC, GABRA4, PARD3-AS1, AC006159.3, RP11-645C24.5, AC068499.10, SERHL, RP1-20N2.6, RP11-130C19.3, FNDC5, RP11-132A1.4, RP11-268P4.4, LINC00924, RN7SL215P, AC078883.4
E.Tuft KRT18, SH2D6, AZGP1, LRMP, HCK, IFI6, PTPN18, PTGS1, AVIL, ATP2A3, GNG13, TRPM5, PLCG2, BMX, EIF1B, LUC7L3, MATK, BIK, HOTAIRM1, IL17RB, PSTPIP2, ANXA13, SH2D7, AKAP9, HTR3E, DEFB1, RASSF6, PPAP2C, IL13RA1, POU2F3, SPTLC2, SOX9, DPYSL3, IFT172, KLK11, COL27A1, CC2D1A, TREH, TMEM63A, TAS1R3, ZFHX3, CASP6, NCMAP, GRASP, MAP7, VAV1, C11orf53, CHDH, CCSER1, AFAP1L2, CD300LF, OGDHL, 7SK, HIP1R, DEGS2, LIMD1, CRYM, RP11-93B14.5, IGSF21, KCNQ1, GFI1B, SRGAP1, FAM171A1, PRSS22, LRP5, CCDC129, B4GALNT4, PIK3CG, PLCB2, PCP4, RALGAPA2, CTD-3094K11.1, MTSS1, PART1, KCNQ4, KLHDC7A, KDM4A, IRAK1, RN7SK, PAK3, SHB, hsa-mir-1199, FOXP4, ALOX12B, ADH6, CAMP, FUT6, NRTN, PHF12, U47924.27, PROX1, FHDC1, GANC, ZSWIM8, HOXA3, CCM2L, TNNI1, IGSF3, LRRC16A, ARHGEF5, COLCA2, HTR3C, KREMEN2, ARHGEF38, ATP8A2, HMX2, SHF, FAM229A, ABCB9, GKAP1, MADD, KLK13, AC023490.1, TRHDE, ARHGEF11, CEACAM19, RP11-285F7.2, TMEM191C, PAQR7, TAS1R1, TBC1D32, FMN1, USP35, GDPD1, RP11-440L14.1, RP11-1220K2.2, C2orf15, RP1-140A9.1, LINC01001, CDH26, AMER1, SHROOM2, LINC01071, RP11-72M17.1, HIST1H4A, HOXA1, ZNF490, RP1-199J3.7, PLA2G4D, TMEM211, RP11-298I3.4, RP11-219G17.4, CABP4, RP11-712L6.5

TABLE 5

Immune Healthy specific markers for indicated cell types

B.Bcells

CDH15, CR2, CTB-43E15.4, GH1, GLDC, GPRC5D, HBD, HTR3A, IGHE, IGLJ2, IGLV3-12, IGLV5-48, NLRP7, OSTN-AS1, PAX5, RP1-148H17.1, RP11-1084E5.1, RP11-164H13.1, RP11-297B17.3, RP11-301L8.2, RP11-390F4.6, RP4-536B24.4, RP5-921G16.2, SERPINA9, SLC22A31, TRIM55, TSHR, UBE2QL1, ZC2HC1B, FCRLA, IGLL1, TCL1A, IGHD, IGLC2, RP5-887A10.1, FAM92B, CD19, MS4A1, VPREB3, IGKC, AL928768.3, IGHM, IGHA2, IGHG1, CD79A, IGHA1, IGHG2, IGLL5, IGLC7, AC104699.1, MZB1, IGJ, BANK1, CTA-250D10.23, DERL3, RP11-693J15.5, hsa-mir-5195, AC096579.7, TNFRSF17, IGHG3, WT1-AS, MIXL1, IGLV3-1, IGLV6-57, IGLV1-40, IGLV2-8, IGLV2-14, FGF23, IGLV2-11, IGLV3-16, FCRL5, LMTK3, AMPD1, IGLV1-47, TNFRSF13C, AF127936.3, FAM129C, AC104024.1, IGHV1-24, IGLV5-45, IGLV3-21, PKHD1L1, FCER2, AC096579.13, IGLV8-61, E2F5, IGKV1OR2-108, IGLV3-25, RP11-1070N10.3, IGLV3-10, KIAA0125, MEF2BNB-MEF2B, AC079767.4, CCR10, RP11-492E3.2, RP11-325K4.2, MYL2, RP11-138I18.2, IGLV2-23, IGLV4-60, EAF2, RP11-290F5.1, AP001058.3, CNR2, FCRL2, RP11-77H9.8, IGLV1-51, SSR4, CD79B, BLK, IGKV2D-28, IGLV3-9, P2RX5, AICDA, MEF2B, IGLV3-19, CRYBA4, AC096559.1, UBE2J1, RP11-16E12.2, AC007386.2, TEX9, ESR2, RAB30, IGKV4-1, SNX29P2, TXNDC5, RP3-402G11.25, IGKV1-12, IGLV10-54, IGKV1-5
B.Cycling

MIOX, HBD, IGLV3-9, HIST1H1B
B.FO

COL19A1, RP5-887A10.1, FCRL4, IGHE, OSTN-AS1, GYLTL1B, SIDT1, BANK1, TNFRSF13B, IGHD, SELL, TEX9, CCDC50
B.GC

RP11-485G7.5, RP11-624C23.1, RP11-138I18.2, SERPINA9, ANK1, C7orf10, HTR3A, RP11-511B23.1, BACH2, RP1-148H17.1, AC023590.1, IGKV6D-21, DBNDD1, AICDA, ANKLE1, BCL7A, TCL6, TRIM55, RP11-164H13.1, RP11-160H22.5, EYA3, BFSP2, SNX29P2, RP11-558F24.4, RP11-1070N10.3, CCDC144A, TCL1A, ACY3, RP11-960L18.1, NEIL1, WDR66, P2RX5, STAG3, GPR114, RPRD1B, HCAR1, SYVN1, IL21R, SMIM14, KLHL6, SEL1L3, TPD52, TERF2, TRIM59, TIGD1, RP4-739H11.4, BCAS4, LIMD2, LSM10, STAP1, MTMR14, CD180, RP11-16E12.2, GGA2, TNKS2-AS1, STX7, HMCES, DCAF12, MBD4, FBXO16, CD79B, FCRLA, STRBP, IQCB1, NGLY1, PARN, ST6GAL1, FCRL3, DEF8, TCEA1, TMEM156, CD53, RRAS2, NCF1, ZNF296, TOR3A, CD72, RFC1, EPS15, CYB561A3, LYPLAL1
B.Plasma IGLC3, IGLC7, FGF23, IGLV6-57, IGLV1-40, IGLV2-11, IGLV2-23, IGLV1-51, RP11-492E3.2, PSAT1, IGLV4-69, IGLV3-25, IGLV7-43, LINC00582, IGLV3-10, IGLV8-61, DNAAF1, IGLV10-54, IGLV5-45, IGLV4-60, IGLV3-16, CDH15, SLC22A31, IGLV1-50, RP11-1084E5.1, IGKV1OR2-108, ZC2HC1B, GH1, IGLV3-12, AF127936.3, LINC00525, UGT3A2, IGHV3OR16-9, NLRP11, RNF148, RP11-428K3.1

TABLE 5-continued

Immune Healthy specific markers for indicated cell types

I.Immune

AC004791.2, AC013264.2, AC104820.2, APOC2, ASGR2, ATP6V0D2, BTLA, CA10, CASS4, CATSPER1,
CCL18, CCL3L1, CCL4L1, CCL4L2, CD180, CD1E, CD207, CD226, CD28, CD300C, CD300LB, CLEC4E,
CLEC4F, CLEC9A, CLECL1, CRHBP, CTLA4, CXCR5, ELAVL4, FAM92B, FCER2, FCGR1A, FCGR1B,
FCGR3A, FCN1, FCRL1, FCRL6, FCRLA, FLT3, FPR1, GAPT, GCSAM, GPR34, GPR84, GPRC5D, ICOS,
IGHD, IL17A, IL18RAP, IL21R, IL22, ITGAX, JAKMIP1, KIR2DL3, KIR3DL2, KLHDC7B, KRT81, KRT86,
LAMP3, LILRA2, LILRA3, LILRA5, LILRB2, LILRB5, LRRC25, LTA, MSR1, NLRC4, NLRP7, OSTN-AS1,
P2RY13, PGLYRP2, PIK3R6, PKD2L1, RP11-18H21.1, RP11-291B21.2, RP11-327F22.2, RP11-354E11.2,
RP11-365O16.3, RP11-367G6.3, RP11-542M13.3, RP11-556E13.1, RP5-1091N2.9, RP5-899E9.1, S100Z,
SIGLEC1, SIGLEC12, SIRPB1, SNAI3, TBX21, TFEC, TIFAB, TNFRSF9, TNFSF8, TRAV4, UBASH3A,
ZNF683, RUNX3, CD1C, FASLG, CD160, GZMK, TRDC, CD3D, XCL1, CTSG, CD3E, AC092580.4, TRGC1,
TRBC2, KLRB1, TIGIT, CD300A, TPSAB1, IFNG, CD8A, GZMA, SNX20, SH2D1A, CST7, CD52, CCL4,
CD247, XCL2, CD2, CCL5, DOK2, GZMB, TMIGD2, GZMM, TRAF3IP3, GNLY, NKG7, SIRPG, THEMIS,
CD3G, CD7, ADORA3, MPEG1, KRT1, HCST, PLD4, LTB, TRGC2, IL2RB, SIT1, MAP4K1, RGL4, P2RY10,
PTPRC, NCKAP1L, GRAP2, CSF2, CD37, CXCR6, S100A9, GPR18, SLA2, TNFSF14, CTSW, AMICA1, PRF1,
ARHGAP9, GPR171, CD86, TBC1D10C, MARCH 1, SAMSN1, GPR183, LCP1, BCL2A1, SDS, RASGRP1,
CD5, CMA1, TNFAIP8L2, HDC, LINC00402, FCER1A, IL1B, RP11-455F5.5, STAT4, CD244, IL7R, CD19,
ARHGAP30, PCED1B-AS1, KLRD1, TRAT1, PTPN22, KLRC1, GZMH, AC109826.1, CCR5, LINC00996,
PARVG, MS4A6A, TNIP3, CD48, NCR3, ITGAM, VPREB3, RNASE6, LCK, FPR3, GNA15, LY86, SASH3,
CRTAM, MS4A4A, C1QB, LAPTM5, NCF1, WAS, HOPX, IGHV1OR15-1, CD6, FAM159A, MEFV,
CACNA2D3, IGSF6, IKZF1, LY9, CYTIP, MIR142, CSF1R, EVI2A, DUSP2, BFSP2, HLA-DOB, PTPRCAP,
PTPN7, SPI1, RHOH, TLR10, CSF3R, TNF, FCER1G, BTK, MYO1F, AC020571.3, CHRM3-AS2, GPR65,
CD53, CXCR3, C1orf162, SPN, ITGAL, TXK, CCL3, ADAM8, TCL1A, AIF1, CD96, KLRC2, PDCD1, CPA3,
MYO1G, IL10RA, HAVCR2, LILRB4, MMP12, CD40LG, SCIMP, CSF2RA, EVI2B, TREM2, LINC00892,
TREM1, DOCK2, EMB, PILRA, CYBB, RGS1, MS4A7, CHI3L2, RP3-522D1.1, C1QC, IL8, KCNA3,
SLFN12L, CARD11, CD69, PYHIN1, ITK, LAT2, CORO1A, DNASE1L3, ITGB2, GPR132, KLRG1, RP11-
190C22.9, LAIR1, FGD3, SCML4, BLK, SLC18A2, LRRN3, CD8B, FAM26F, PLA2G7, CLEC10A, CD209,
C5AR1, SLAMF8, SP140, TESPA1, CD200R1, PRAM1, CXorf21, VSIG4, SKAP1, LPXN, C1orf186, SYTL3,
CD163, IFI30, WDFY4, SH2D2A, RP6-91H8.3, RP11-94L15.2, LST1, CD79A, CD27, HLA-DQB2, LYZ,
DENND1C, CD70, RP11-222K16.2, CYTH4, RASSF5, CLEC2D, SH2D1B, CLEC4A, C1QA, MS4A1, CCR2,
OSCAR, C3AR1, CD101, BATF, ACAP1, CD33, IGLC2, RP3-477O4.14, CD38, CSTA, PIM2, IL4I1, OSM,
MMP9, SLAMF7, NCF2, RP11-489E7.4, IFNG-AS1, ITGB7, IL1RN, ZAP70, ITGB2-AS1, STK17A, DUSP4,
RP11-693J15.5, FAIM3, FAM179A, CD83, TMEM156, IGLL5, DAPP1, IGFLR1, SLAMF1, CXorf65, RAC2,
BIN2, F13A1, C1orf61, OLR1, SAMD3, IGKC, KYNU, AL928768.3, ZNF331, TNNI2, TLR7, OXNAD1,
IGLC7, IL16, TAGAP, SLAMF6, WNT10A, P2RY6, NLRP3, KCNAB2, KMO, APBB1IP, CCR1, CD72,
RASAL3, EVL, LAT, LIMD2, CREM, POU2F2, ADPGK-AS1, UPK3A, SLC7A5, TNFAIP3, TLR2, HLA-
DQA1, SELL, HCLS1, IL23A, AC017104.6, TRAC, GHRL, IRF4, RELT, SEPT1, HLA-DQB1, FAM46C,
AC006129.4, TMC8, AP001058.3, SNX10, PLEK, IGHG1, PNOC, LINC00528, CD84, STAP1, IGJ, FGD2,
FAM49B, CTA-384D8.34, HENMT1, RGS18, PARP15, MNDA, PHACTR1, P2RY11, EBI3, MZB1, YPEL5,
FMNL1, STK4, AOAH, COTL1, MMP25, RP11-324I22.3, SPNS3, IL2RA, PKHD1L1, GATA3, DUSP10,
TNFAIP8, SLA, MYBL1, RAB33A, EAF2, FGF23, P2RX5, CRLF3, HLA-DPB1, SEPT6, ARL4C, GPR114,
UTS2, RP11-70C1.1, IGLL1, DENND2D, LCP2, RGS19, ARRB2, CLIC3, TYROBP, AIM2, RORA, TC2N,
RP11-539L10.2, PDE4B, RP11-347P5.1, IL2RG, PRMT10, PIK3CD, TNFRSF18, SIGLEC10, IL1RAPL1,
NCF4, GLIPR1, SMAP2, RP11-863P13.3, CKLF, IGHG2, GALR2, TRAF1, HLA-DRA, ICAM3, PRR7, PRKCB,
MAP3K8, PIK3AP1

I.Lymphoid

AC013264.2, AC104820.2, CA10, CR2, CXCR5, DTHD1, GPRC5D, IGHD, IGLV5-48, IL22, JAKMIP1,
KIR3DL2, KRT81, KRT86, LINC00861, NCR2, NLRP7, OSTN-AS1, RP11-18H21.1, RP11-291B21.2, RP11-
403A21.2, RP11-664D1.1, TBX21, TRAV4, ZNF683, CD160, XCL1, XCL2, GZMK, AC092580.4, TIGIT,
GZMA, TRGC1, GNLY, CD3D, IFNG, CD3E, CD2, CD7, CCL5, IL2RB, TRGC2, CD3G, RASGRP1, TRDC,
CD247, CD8A, IL18RAP, CXCR6, KLRB1, GZMM, TRBC2, FCRLA, PRF1, KLRC1, VPREB3, ICOS, TRAT1,
KLRD1, SIRPG, GZMH, LCK, LINC00402, SLA2, IL17A, HOPX, IGHV1OR15-1, KLRC2, SIT1, FASLG,
RGL4, BLK, CHRM3-AS2, CD96, TMIGD2, CD40LG, LRRN3, CD6, PYHIN1, NKG7, SH2D1A, CHI3L2,
RP11-542M13.3, TXK, IL7R, SCML4, TCL1A, UBASH3A, IGLL5, THEMIS, FCRL6, SH2D1B, RP11-
222K16.2, CD8B, MS4A1, GZMB, STAT4, CD79A, CD27, SLFN12L, SH2D2A, CD70, TNFSF14, IGHG3,
IGLC2, CLEC2D, AC017104.6, CD19, IGLL1, FAM179A, RP11-94L15.2, FAM92B, FAM159A, SLAMF1,
ZAP70, CD244, RP11-553L6.2, RP11-489E7.4, C1orf61, CD5, PGLYRP2, SLAMF6, PTPRCAP, RP11-284N8.3,
IFNG-AS1, AL928768.3, CD28, IGJ, IGKC, SMKR1, GPR171, IGHG1, SAMD3, TRAC, EVL, GATA3, IL23R,
LTA, IGHA2, MZB1, AP001058.3, BCL11B, P2RX5, IGHA1, ITK, PARP15, APOBEC3H, CARD11,
TBC1D10C, PCED1B-AS1, AC069363.1, CCR7, LINC00426, RP11-539L10.2, STK17A, TC2N, TPRG1, RP11-
279F6.3, CLIC3, CXorf65, IGLC7, AC104699.1, SEPT1, TNFRSF18, AC078883.3, TNFRSF13B, IL2RG,
IGHG2, POU2AF1, PLCH2, RORA, MYBL1, CD52, ACAP1, CTLA4, FAM46C, GPR18, DERL3, CACNA1C-
AS2, PTPN4, RP11-693J15.5, CCDC65, DENND2D, ESR2, LTB, TNFRSF17, IGLV2-14, S1PR4, FGF23,
NCR3, MIXL1, SPOCK2, OXNAD1, CCR5, AC096579.7, NUGGC, WT1-AS, PKHD1L1, PCED1B, RCAN3,
CTSW, KLHDC7B, PARP8, ANKRD44-IT1, FKBP11, SYTL1, TAGAP, PPP1R18, IGLV5-45, ZBP1, EMB,
TNFRSF13C, LINC00649, PRKCQ-AS1, FAIM3, RP11-277L2.4, AAK1, P2RY11, GRK6, SPINK2, CYTIP,
SASH3, ORMDL3, FYN, LEPROTL1, PTPN22

M.CD69neg_Mast

NTRK1, IL9R, ADAM22, CATSPER1, FAM21B, ABCB8, NSMCE1, AJ271736.10, ARHGEF6, FECH, ACLY,
NCOA4, UBA7, BRAP, KRT1, FAM212A, MAML1, SLC43A3, SAMSN1, LPCAT2, GMPR, SPACA3, LTC4S,
HPGDS, HSD17B12

TABLE 5-continued

Immune Healthy specific markers for indicated cell types

M.CD69pos_Mast

ADCYAP1, CALB2, RP11-501J20.5, TPSD1, IL13, RP11-557H15.4, IL1RL1, RP4-794H19.2, ARL5B-AS1, RP11-705O1.8, AF213884.2, IL1RAPL1, DKFZP434E1119, IL5RA, ENPP3, PPP1R15A, NFKBIZ, FER, AC020571.3, HDC, FAM46A, EGR3, ANXA1

M.Cycling

SYCE2, ZMYND10, FAM72C, CDC25B, HTR7, SIGLEC15, CDK1, TUBA1B, KPNA2, HJURP, COQ2, FAM64A, H2AFZ, TPK1, RAD51AP1, RP11-556E13.1, TROAP

M.DCs

BAI1, CD1B, CTD-2514K5.2, RFPL4A, RP11-117D22.2, RP11-667K14.3, RUFY4, XCR1, SFTPD, TMEM170B, FLT3, UPK3A, SLAMF9, FAM230A, CLEC4F, NAMPTL, CLEC9A, CD207, RYR1, TBX19, CD1E, CTD-2619J13.17, CX3CR1, SERPINF2, INHBA-AS1, CD1C, CPVL, CTD-2319I12.1, FAM46B, RP11-248J18.2, HLA-DQB2, MYCL, LEKR1, NME8, CD1D

M.Macrophages

AC005082.12, LILRA6, RN7SL138P, GRIN2D, AZU1, KCNC3, SIGLEC11, SLC7A8, FABP3, PLA2G2D, SLC40A1, RP3-414A15.10, FOLR2, CRHBP, TREM2, OTOA, HSD17B14, RP11-848P1.2, RNASE1

M.Mast

ADCYAP1, AMHR2, CALB2, GATA1, GCSAML, MS4A2, NTRK1, RP11-501J20.5, TPSD1, XXbac-BPG13B8.10, IL1RAPL1, ST8SIA6, C1orf186, TPSAB1, RP11-354E11.2, IL13, RP11-557H15.4, SLC45A3, HDC, SLC18A2, CMA1, AC004791.2, SIGLEC8, SVOPL, IL1RL1, CPA3, CTSG, MAOB, KRT1, VWA5A, GATA2, RP4-794H19.2, CTD-3203P2.2, RAB27B, LTC4S, ATP6V0A2, ARL5B-AS1, SPACA3, RP11-705O1.8, HS3ST1, AF213884.2, ADRB2, DKFZP434E1119, LEO1, MITF, IL5RA, CTNNBL1, SMYD3, ENPP3, TIAM2, PPP1R15A, VWC2, NFKBIZ, FER, AC020571.3, GMPR, CAPG, TESPA1, BTK, FAM46A, UBXN10, PLIN2, RP11-169D4.2, CRBN, ANXA1, ALS2, BACE2, LMO4, GLUL, RP11-443B7.1

M.Monocytes

FTL, HLA-DRA, HLA-DRB1, HLA-DPB1, CST3, SAT1, HLA-DPA1, GPX1, AIF1, HLA-DQA1, LYZ, HLA-DQB1, HLA-DRB5, RNASET2, C1QA, HLA-DMB, TYMP, MS4A6A, C1QC, CTSS, DNASE1L3, C1QB, CTSB, SPI1, CTSZ, CPVL, IGSF6, PLAUR, MS4A7, FAM26F, HLA-DQA2, RNASE6, HLA-DQB2, LGMN, IL1B, CLEC10A, FUCA1, IFI30, BID, LGALS2, MPEG1, SLC40A1, VSIG4, STAB1, SDS, MS4A4A, CD68, FCGR2A, MNDA, IL8, PLA2G7, CSF1R, RB1, GM2A, CECR1, CD86, ADORA3, HBEGF, P2RY6, ADAP2, FOLR2, CSF2RA, MMP12, C5AR1, SLAMF8, HLA-DOA, AP1B1, CFP, SLC31A2, G0S2, VMO1, PILRA, S100A9, CD209, TTYH3, NAIP, LILRB4, CLEC7A, CD163, FPR3, TREM2, IL18BP, NCF2, CLEC4A, CLEC9A, ATP6V0D2, NUP214, OTOA, RAB42, LILRB5, CXCL3, LRRC25, CMKLR1, EBI3, P2RY13, FCGR1A, SLC7A8, CACNA2D3, LILRB2, CD1E, EMILIN2, SIGLEC1, RN7SL368P, CSF3R, BATF3, MYCL, DAPK1, TRPM2, CSTA, IL1RN, CRHBP, CD300C, RGS18, OLR1, RP11-426C22.5, TREM1, LY96, RP11-365O16.3, RP3-522D1.1, TIFAB, RP11-1143G9.4, PKD2L1, CCL18, TLR2, HCAR2, ITGAX, MSR1, ASGR2, F13A1, CLEC4G, FLT3, FCN1, RP11-290F20.3, OSCAR, LILRA2, GHRL, CD207, HCAR3, RP3-399L15.3, APOC2, RP5-899E9.1, RP11-863P13.3, CCL3L3, CLEC4E, LILRA3, RP11-556E13.1, FCGR1B, CCDC170, GPR84, RP11-760N9.1, CD300LB, ELAVL4, S100A8, GALR2, CLEC4F, FPR1, NLRC4, RP11-472N13.3, LILRA5, C19orf59, GSDMA, INHBA, GRIP1, RP11-426L16.8, SFTPD, RP11-190C22.9, ALOX15B, MRC1L1, TLR8, XCR1, UPK3A, SYCE2, RP11-680A11.5, CD1B, LILRA6, MS4A14, SLAMF9, CX3CR1, IL27, KCNK13, RNASE2, RP11-701P16.5, GRIN2D, RP11-848P1.2, AC005082.12, RYR1

M.Myeloid

AC004791.2, AC011899.9, AMHR2, ASGR2, ATP6V0D2, CALB2, CD300LB, CLEC4E, CLEC4F, ELAVL4, FCGR1A, FCGR1B, FCN1, FPR1, GATA1, GCSAML, GPR84, INHBA, LILRA3, LILRA5, LILRB2, LILRB5, MS4A2, NLRC4, RP11-365O16.3, RP11-472N13.3, RP11-556E13.1, RP11-760N9.1, RP5-899E9.1, S100A8, SIGLEC12, SIGLEC8, TIFAB, XXbac-BPG13B8.10, CTSG, CLEC9A, CMA1, SLC18A2, P2RY13, RP11-557H15.4, SDS, MSR1, FPR3, MS4A4A, MS4A6A, KRT1, CDIE, ADORA3, IGSF6, S100A9, MMP12, IL1B, TREM2, C1QB, FCER1A, C1QC, CD209, CACNA2D3, PLA2G7, CD163, RP3-522D1.1, TPSAB1, AIF1, CSF3R, CD207, DNASE1L3, PKD2L1, C1QA, C5AR1, SIGLEC1, IL1RAPL1, HDC, F13A1, LILRB4, VSIG4, IL8, CLEC10A, MS4A7, LYZ, CSTA, C1orf186, CCL18, SVOPL, TREM1, SFTPD, OSCAR, RP11-190C22.9, TLR2, CSF2RA, IL1RN, CRHBP, RP11-354E11.2, IL13, CPA3, OLR1, P2RY6, SLC45A3, APOC2, LILRA2, PILRA, RAB42, CFP, RASGRP4, FLT3, MNDA, CPVL, MPEG1, IFI30, GSDMA, STAB1, RP11-426L16.8, LRRC25, CCL3L3, CD68, RP11-76E17.3, GALR2, MAOB, LINC00884, CD300C, SLAMF8, IL10RB-AS1, NCF2, RP11-1143G9.4, FAM26F, HCAR3, VWA5A, FTL, HS3ST1, FUCA1, GM2A, SLC40A1, RNASE6, HLA-DPB1, FOLR, CLEC4A, GLUL, GRIP1, CD86, IL18BP, RP11-426C22.5, ALOX15B, HLA-DRB1, PIK3R6, RP11-42I10.1, RGS18, LY96, FCGR2A, GATA2, RP11-70C1.1, GHRL, CST3, CASS4, TBXAS1, HLA-DPA1, CTD-3203P2.2, CXCL16, C19orf59, TNFAIP8L2, TNNI2, HLA-DQA1, HLA-DRB5, PLAUR, RNU1-60P, RAB27B, TTYH3, VMO1, ATP6V0A2, CD33, NUP214, TRPM2, RP11-863P13.3, DAPK1, CTSS, CTSB, SGK1, ARL5B-AS1, HCAR2, CMKLR1, OTOA, RENBP, ATP6V1F, NCF4

M.Neutrophils

S100A8, RP11-701P16.5, S100A9, FCN1, EREG, NLRP3, CSTA, APOBEC3A, G0S2, TLR2, C5AR1, LILRB2, OLR1, FCGR1A, EMILIN2

M.Tissue_DCs

CDIB, CTD-2514K5.2, RFPL4A, RP11-117D22.2, RP11-667K14.3, SFTPD, TMEM170B, SLAMF9, FAM230A, CLEC4F, NAMPTL, CD207, RYR1, TBX19, CD1E, CTD-2619J13.17, CX3CR1, INHBA-AS1, CD1C, GHRL, RP11-248J18.2, LEKR1, NME8, TMEM52B, CD1D, MS4A14, PLD4, FCER1A, CACNA2D3

TABLE 5-continued

Immune Healthy specific markers for indicated cell types

M.Tolerogenic_DCs

XCR1, CLEC9A, CTD-2319I12.1, CLCN4, FBXO27, DGAT2, IDO1, BATF3, WDFY4, FLT3, SERPINF2, FKBP1B, DSCAML1, CPNE3, SNX3, PPM1J, RP11-661A12.7, CPVL, KIAA1598, KIAA0226L, C1orf54, FNIP2, C8orf47, TNNI2, TACSTD2, TOMM34, UCP3, VAC14

T.Activated_CD4_loFos

AC006369.2

T.CD4

CTLA4, LAIR2, RP11-664D1.1, ATG9B, CD40LG, IL17A

T.CD8

CD8B, RP11-291B21.2, DRAXIN, CD8A

T.CD8_IELs

TRBV20-1, RP11-535A5.1, PAGE5, KLRC2, NCR2, TRGC1, TRGC2, DRAXIN

T.CD8_LP

RP11-291B21.2, CD8B

T.CXCR6_Th17

RP11-85K15.2, IL12RB1, CCL20, SLAMF1, KLRB1, ZFYVE28

T.Cycling_T

ABCD2, CCT6B, C11orf82, C16orf59, A1BG, C5orf17, ZNF682

T.ILCs

LINC00299, TNFSF11, IL23R, SPINK2, SLC4A10, SAMD10, OTUD5, TRGV9, RP11-425D10.10, IL4I1, LINC00176, ALDOC, FXYD7, CASP3, AREG, KRT86, HINT3, CSF2, PRMT10, LTA4H, FAM167A, ZNF385C, PDZK1, MED30, ZMYM2

T.MT

FSCN3, BZRAP1, AP000350.4, AC132872.2

T.Memory_CD4

RP11-664D1.1

T.NK

PADI4, SPTSSB, KLRF1, RP11-401F2.3, BCO2, SH2D1B, EOMES, XCL1, XCL2, KLRC1, IL2RB, CLIC3, FGR, RP11-222K16.2, AC069363.1, NKG7, GZMB, KLRD1, AC017104.6, PRF1, GEMIN5, EIF3G, FCGR3A, CMC1, GNLY, B3GNT7, CHST12, APOBEC3G

T.PD1_CD4

RP5-1028K7.2, NMB, CD200, KIF2A, PDCD1, MPP7, RP11-455F5.5, PVALB, CDK5R1, PRKRIR

T.Tcells

CA10, CPA5, FOXP3, RP11-664D1.1, TRAV4, RP11-291B21.2, IL2, IL17A, LINC00402, BCL11B, CD8B, CD3G, CD3D, CTLA4, AC104820.2, CD5, RP11-279F6.3, CD6, CACNA1C-AS2, CD28, CCDC65, TRAT1, TRGC2, SIRPG, GPR171, LINC00649, CD8A, CD3E, FAM115C, TRAC, ACSL6, TNIP3

T.Tregs

RP11-316P17.2, LAIR2, MCF2L2, ANKS1B, FANK1, FOXP3, RP11-580116.2, DUSP16, TRAV8-2, TNFRSF9, IL10, BATF, CTLA4, RP11-382J12.1

TABLE 6

Immune UC specific markers for indicated cell types

B.Bcells

AC007381.3, AC007880.1, AC073072.5, AC104699.1, AL109761.5, AP005530.2, BEND4, C7orf72, CCL25, CHIA, CHIT1, COL19A1, COL24A1, CTB-43E15.4, FAM92B, GPRC5D, HCFC1-AS1, IGHE, IGKV1D-43, IGLV5-48, LINC00494, LINC00582, LINC00643, LRRC4, MYF6, OVOL3, RP1-148H17.1, RP11-138I18.2, RP11-203B7.2, RP11-297B17.3, RP11-301G19.1, RP11-301L8.2, RP11-390F4.6, RP11-428G5.5, RP11-493L12.3, RP11-511B23.1, RP11-624C23.1, RP11-625L16.3, RP11-689B22.2, TREML2, UBE2QL1, UGT3A2, UTS2B, hsa-mir-5195, hsa-mir-5571, HTR3A, IGLL5, IGLC3, CR2, IGLC2, SERPINA9, MED12L, MS4A1, CLEC17A, AC104024.1, AC096579.13, IGHG2, RN7SL17P, IGHA2, PAX5, IGLC7, CD19, IGKC, AL928768.3, AC096579.7, IGHA1, TCL1A, FCRLA, DERL3, IGHD, IGLL1, VPREB3, DKK1, MIXL1, IGHG1, MZB1, WT1-AS, IGHG4, IGLV3-16, FCRL5, IGLV6-57, LINC00525, RP5-887A10.1, BLK, FCER2, RP11-159H10.3, PKHD1L1, TNFRSF17, IGJ, FGF23, NLRP7, RP11-290F5.1, AC009473.1, TNFRSF13C, OSTN-AS1, CD79A, MRVI1-AS1, AF127936.3, FAM129C, IGLV1-40, IGLV2-11, MYL2, RP11-693J15.5, CD79B, IGLV10-54, WDR66, CTD-2306M10.1, FCRL1, IGLV3-1, IGKV2D-30, RP11-485G7.5, AC096559.1, IGHV1-24, KIAA0125, RP11-1070N10.3, AICDA, CD72, C7orf10, BANK1, RP11-492E3.2, DNAAF1, SNX29P2, RP11-480C16.1, EAF2, CLECL1, PNMA6C, IGLV3-25, HVCN1, CRYBA4, BLNK, FCRL4, CD180, AC023590.1, TABLE 6-continued Immune UC specific markers for indicated cell types MEF2BNB-MEF2B , IGKV1-6, SPAG4, CCDC144A, AC007386.2, ZCCHC7, IGKV2-30, UBE2J1, AMPD1, NEIL1, POU2AF1, FCRL2, HBD, SSR4, RP11-960L18.1, IGKV5-2, RP11-16E12.2, XBP1, IGKV1-12, TNFRSF13B, POU2F2, C12orf77, CTC-378H22.1, CD22, AP001058.3, ESR2
B.Cycling C7orf72, GLT1D1, RP11-301G19.1, STK4-AS1, ZNF730, BTN1A1, CTD-2561J22.5, AKAP2, RP13-494C23.1, RP11-553K8.2, CTC-332L22.1, KCNQ5-IT1, KLLN, RP11-286H14.6, SNORA70, CENPI, STOX1, C6orf99, RP13-20L14.6, RP11-449H11.1, IGHE, WDR76, C11orf65
B.FO AC002480.5, CCDC78, RP11-444D3.1, COL19A1, RP11-624C23.1, RP5-887A10.1, AC073072.5, RP11-445F6.2, OSTN-AS1, WASIR2, UTS2B, AC007880.1, FCRL4, TNFRSF13B, CLECL1, RP3-455J7.4
B.GC RP11-567J20.3, RN7SL17P, LRRC4, SERPINA9, RP11-138I18.2, RP11-203B7.2, HRK, NEIL1, C9orf66, PUS10, NPAS1, AC096559.1, RP11-72I8.1, CD22, HTR3A, MIXL1, CD180, C7orf10, CCDC144A, SEMA4A, TRAF4, CD79B, USP6NL, KLHL14, RP11-960L18.1, RP11-542M13.3, IGF2BP3, IFNG-AS1, P2RX5, IL4R, ADORA2A-AS1, RP11-511B23.2, BFSP2, GPR18, RP11-307E17.8, AC023590.1, SMIM14, CYB561A3, SNX29P2, ESR2, GPR114, BCL11A, RP11-164H13.1, BCL7A, AP003419.16, CR2, CNR2, RP11-413H22.2, SYVN1, SYPL1, PLEKHF2, KMO, AMFR, RANBP2, ZNF581, RFTN1, SLC38A9, NCOA3, WDR66, BLNK, HLA-DOB, CD53, FCRLA, FAM105B, VNN2, CD40, AC145110.1, KIAA0922, RP11-158I9.5, ICOSLG, PXK, XKR6, RN7SL172P, VCPKMT, ITSN2, PKHD1L1, MS4A1, TMEM206, CPNE5, LIMD2, RP11-248J18.3, CD72, RAB30, RASGRP3, SYNGR2, MTMR14, GGA2, RNGTT, MGAT3, TMED8, SNX8, MOAP1
B.Plasma DCC, GH1, IGHJ2, IGKV1D-43, MYBPC2, MYF6, PRRG3, RP11-301L8.2, RP11-625L16.3, RP11-689B22.2, SCARNA16, TNN, TPTE2, TRIM55, UBE2QL1, UGT3A2, hsa-mir-5571, IGLV4-60, IGLV3-16, IGHG2, DKK1, IGLV1-40, AF127936.3, IGKV5-2, IGLV2-8, IGLV3-1, AC096579.7, IGLV6-57, IGHV1-24, FAM92B, IGHA2, DNAAF1, IGLL1, CTB-43E15.4, IGLV10-54, IGKV3-11, IGKV2D-30, AMPD1, IGHG3, PNMA6C, IGLC2, IGHG1, IGKV3-20, IGLV7-43, IGLV7-46, IGKV2-30, IGKV6-21, SPAG4, AL109761.5, IGLV9-49, IGLV3-25, IGLV2-11, IGKV1D-13, IGHG4, IGKV4-1, RP11-390F4.6, RP11-290F5.1, IGLC7, DERL3, SLC22A31, IGHA1, IGLV5-48, GPRC5D, IGKC, RP11-492E3.2, SSR4, IGKV1-6, JSRP1, IGLC3, IGJ, IGKV2-24, IGLL5, XBP1, GUSBP11, LINC00582, RP11-554E23.4, FKBP11, IGHM, TNFRSF17, CHAC1, WNT10A, LINC00525, HERPUD1, LMTK3, IGKV3D-15, IGLV1-36, SEC11C, IGLV2-18, AC093818.1, IGKV1D-39, PDK1
I.Immune ABCD2, AC004791.2, AC011899.9, AC104699.1, AC104820.2, AC109826.1, AMPD1, AQP9, C11orf21, C19orf59, C20orf201, CA10, CASS4, CCL3L1, CCL3L3, CCL4L1, CCL4L2, CCR2, CCR5, CD1A, CD1B, CD226, CD300C, CD300E, CD300LB, CD80, CEACAM4, CLEC4E, CLEC4F, CLEC5A, CLEC9A, CMA1, CR1, CR2, CRYBB1, CSF3R, CTB-138E5.1, CTC-378H22.1, CTD-2337J16.1, DPEP3, EMR3, F5, FAM92B, FCGR1A, FCGR1B, FCN1, FCRL1, FLT3, FOXP3, FPR2, GPR141, HBD, HK3, IGHV1OR15-1, IKZF3, IL18RAP, IL22RA2, IL26, IL2RA, JAKMIP1, KCNK13, KRT1, LILRA1, LILRA2, LILRA3, LILRA4, LILRA5, LILRA6, LILRB2, LINC00402, LINC00582, LRRN3, MARCO, MEFV, MS4A14, MSR1, NLRC4, OSTN-AS1, P2RY13, PGLYRP2, PIK3R6, PKD2L1, PTCRA, PVALB, RASGRP4, RETN, RN7SL138P, RNASE2, RP11-138I18.2, RP11-169D4.2, RP11-265P11.2, RP11-291B21.2, RP11-297B17.3, RP11-316P17.2, RP11-354E11.2, RP11-365O16.3, RP11-367G6.3, RP11-403A21.2, RP11-472N13.3, RP11-542M13.3, RP11-556E13.1, RP11-701P16.5, RP11-737O24.5, RP11-76E17.3, RP11-798K3.3, RP11-8L8.2, RP11-960L18.1, RP5-1091N2.9, RP5-899E9.1, RYR1, SIGLEC1, SIGLEC12, SIGLEC14, SIRPB1, SUCNR1, TCHH, TFEC, TIFAB, TLR8, TNFRSF13C, TNFSF8, TRAV4, TREM2, ZFP57, ZNF831, PLD4, FPR1, CD1E, FASLG, OSM, RUNX3, CD1C, KLRB1, GCSAM, GZMH, ITGAX, CD86, LINC00892, C3AR1, CD207, CHRM3-AS2, IL17A, DOCK2, CTLA4, BTLA, CLECL1, HCST, NKG7, NLRP3, FCER1G, CXCR4, CD3D, RP5-1028K7.2, CD247, CD2, SIRPG, GPR34, CCL5, CD52, HDC, AIF1, CD28, GZMA, XCL1, HTR3A, TRDC, FOLR2, SDS, LRRC25, SIT1, SPI1, SH2D1A, UBASH3A, MS4A6A, CD3E, DOK2, CXCR5, THEMIS, C1QA, GPR18, LY9, FCER2, RGL4, AC013264.2, CCL3, MPEG1, STAP1, GZMM, CSF1R, PRF1, TIGIT, CST7, CD209, C1QC, TRGC1, SASH3, CCL4, IFNG, TRGC2, CD3G, CLEC10A, RP11-664D1.1, CTSG, NUGGC, AC092580.4, C1QB, P2RX5, S100A8, LCK, SAMSN1, CTA-250D10.23, TRAF3IP3, LST1, TIMD4, ZBTB32, RP11-164H13.1, GTSF1, ITGB2, PTPRC, IL1B, APOBEC3H, CD69, TXK, RP11-190C22.9, PLA2G7, GNLY, AMICA1, HAVCR2, ATP6V0D2, IKZF1, PTPRCAP, MMP12, MS4A7, XCL2, CD53, RP11-553L6.2, GZMK, C1orf162, TNFAIP8L2, TBC1D10C, IGSF6, LTB, IL22, FXYD7, CD40LG, IGHD, LILRB5, WAS, LCP1, NCR3, TPSAB1, LILRB4, MS4A4A, IGHG2, CYTIP, TRAT1, CD6, CD5, EVI2A, BTK, LAPTM5, TMIGD2, CACNA2D3, TRBC2, IGLL5, CD79A, RGS1, IGLC2, MS4A1, KMO, CYBB, IGHG3, FCER1A, GZMB, CD163, LY86, FAM26F, CD7, FPR3, AC079767.4, PCED1B-AS1, SNX20, CD180, ZAP70, CD300A, SP140, EVI2B, ITGB7, EBI3, NCF2, IFI30, MAP4K1, IGLC3, ITGB2-AS1, CSTA, FCGR3A, GPR183, OLR1, DENND1C, CSF2RA, CCL22, TNF, CD244, STAT4, LAIR1, GPR171, PDCD1, DNASE1L3, NCKAP1L, AC006129.4, NOD2, SERPINA9, RP11-455F5.5, RNASE6, CP A3, BCL2A1, TCL1A, PYHIN1, DUSP2, CD19, C12orf42, IL2RB, MIXL1, LTA, PARVG, CRTAM, CCL18, LAX1, CXorf21, FAIM3, NCF1, VSIG4, GAPT, GRAP2, SLC18A2, FGD2, BFSP2, CD160, TLR10, CD37, MIR142, PRKCB, RP11-693J15.5, RHOH, BLK, TNNI2, TYROBP, IGHG4, PAX5, LINC00861, CX3CR1, CLEC4A, CD38, FAM129C, AC020571.3, C16orf54, CORO1A, IGHG1, ITK, IFNG-AS1, GPR65, SPN, DNAJC5B, LAT2, P2RY10, F13A1, MYO1F, AGAP2, CCR7, TNFSF14, ADORA3, TMEM156, KLRD1, RIC3, BATF, CD8A, IL10RA, SLA2, CD48, ARHGAP30, IL10, SELPLG, ADAM8, RP11-637A17.2, CD84, SNAI3, AL928768.3, CD101, CATSPER1, SKAP1, IL16, HLA-DQA1, TBX21, HLA-DOB, CD96, RASGRP1, SLAMF6, CXCR3, CD22, SH2D2A, CTA-384D8.34, CD70, CD72, ARHGAP9, AIM2, PLEK, TESPA1, FCRL3, RP11-134P9.1, CYTH4, PTPN7, PTPN22, P0U2AF1, AC104024.1, IGKC, SLA, GPR132, MYO1G, STAC3, C1orf186, MZB1, RP11-493L12.4, RP11-284N8.3, PNOC, SLAMF7, FERMT3, PHACTR1, KLHDC7B, AP000783.1, SELL, UTS2, IL12RB1, CD8B, RASSF5, LINC00996, ITGAL, NCF4, AC096579.7, RASGRF1, CLEC2D, S100A9, IGHA2, GHRL, SERPINB9, IGLC7, SCML4, IGHM, CLEC12A, IGJ, AC096579.13, LYZ, HCLS1, TNFRSF18, SIGLEC10, RAC2, TAGAP, BIN2, LPXN, RASAL3, TABLE 6-continued Immune UC specific markers for indicated cell types HCAR3, MYBL1, CD27, SLAMF8, ICOS, RP3-477O4.14, RP11-1143G9.4, SIGLEC7, GATA3, CARD11, CD200R1, PCED1B, CFP, BZRAP1-AS1, CTD-2514K5.2, KLRC2, FGD3, WNT10A, FCRL5, BCL11B, MARCH1, HLA-DPB1, SEPT1, IGLV6-57, MRC1L1, KBTBD8, RP11-158G18.1, EPHA1-AS1, KLRG1, GNA15, ACAP1, TNFRSF13B, FAM110A, HLA-DQB1, TRAC, AC104653.1, HAMP, HLA-DMB, TNFRSF17, BANK1, ATP8B4
I.Lymphoid AC002331.1, AC006369.2, AC104699.1, AL109761.5, AMPD1, C15orf53, C4orf26, CA10, CCL25, CCR6, DTHD1, F5, FAM179A, FAM92B, FCRL1, FOXP3, GPRC5D, IGHE, IGLV5-48, IL17F, IL2, IL26, JAKMIP1, KISS1R, KRT81, LINC00402, LINC00582, LRRN3, OSTN-AS1, RP11-104L21.3, RP11-222K16.2, RP11-265P11.2, RP11-275I4.2, RP11-291B21.2, RP11-297B17.3, RP11-403A21.2, RP11-686F15.2, RP11-936I5.1, TRAV4, TRBV28, FASLG, XCL1, GZMH, RP5-1028K7.2, CHRM3-AS2, RP11-664D1.1, SIRPG, CD247, CCL5, IL17A, CXCR5, THEMIS, AC013264.2, SH2D1A, IGHV1OR15-1, CD3D, IFNG, GZMM, TIGIT, AC092580.4, LCK, GZMA, XCL2, HTR3A, CD3G, NUGGC, TRGC2, KLRB1, RP11-553L6.2, CD3E, FXYD7, TXK, LINC00861, CD40LG, CD6, GZMK, FCRL4, IGLL5, CD2, TRBC2, FCRL3, EOMES, ZAP70, TRAT1, AC104820.2, LTA, IGLC2, IGHG2, KRT86, CD7, IGLC3, TBX21, GNLY, TRDC, CD160, PYHIN1, IGLV4-60, SERPINA9, CD28, RP4-539M6.22, PGLYRP2, CR2, IL22, SLAMF6, CD8A, P2RX5, IGHG1, MS4A1, RP11-305L7.3, IGHG4, SIT1, KLRD1, CD70, IGLC7, RASGRP1, CD96, TNFRSF13B, TMIGD2, AC096579.13, CLEC2D, CTLA4, IFNG-AS1, RP11-455F5.5, ATG9B, POU2AF1, ABCD2, RGL4, UBASH3A, CARD11, IGKC, AC104024.1, CD8B, IGHD, CD19, PAX5, SCML4, CTC-378H22.1, GATA3, RP11-279F6.3, TCL1A, TRGC1, IGHA2, KLRC2, PTPRCAP, AGAP2, FCRL6, ICOS, CD27, BLK, CXCR6, SLA2, WNT10A, CDK5R1, FCRLA, BCL11B, AL928768.3, MZB1, NELL2, GPR171, IL2RB, KLRC1, PCED1B, TRAC, DERL3, FCRL5, TSHR, RP11-284N8.3, TBC1D10C, VPREB3, GPR18, PRF1, PCED1B-AS1, RP11-290F5.1, MIXL1, AC006129.2, AC096579.7, SAMD3, PDCD1, IL18RAP, AC017104.6, CPA5, SH2D2A, ACAP1, ZNF831, RP11-861A13.4, IGKV6D-21, WT1-AS, SEPT1, FAIM3, IGLL1, BFSP2, IKZF3, IGLV6-57, BCAS4, KCNA3, TNFRSF13C, GZMB, IL23R, CNR2, LAIR2, IGLV2-11, SLFN12L, TPRG1, STAT4, BACH2, PKHD1L1, SPOCK2, RP3-455J7.4, ZBED2, DENND2D, RP11-693J15.5, RP11-316P17.2, RP11-493L12.4, LINC00426, TNFRSF17, TNFSF8, CRTAM, LINC00525, IL7R, FCER2, RORA, STK17A, NKG7, ANKRD44-IT1, CPNE7, RP11-18H21.1, RIC3, LY9, RP11-492E3.2, SLAMF1, CCR4, TNFRSF18, IGJ, RP11-489E7.4, NLRP7, CD79A, RP11-382J12.1, LAG3, HOPX, TNFSF14, RP11-542M13.3, P2RX5-TAX1BP3, FGF23, SUSD4, CD79B, RP11-94L15.2, PIM2, SELL, FAM129C, RP11-539L10.2, SEPT6, EVL, SP140, LINC00649, AP001046.5, P2RY11, TMC8, AC069363.1, MYL2, BZRAP1-AS1, TTC39C, PPP2R2B, SPINK2, SYNGR3, RP3-370M22.8, NCR3, RP11-117D22.2, CD5, TAGAP, ICAM3, RP11-413H22.2, FAM46C, LTB, IKZF2, TMEM156, RAPGEF6, PPP2R5C, OXNAD1, MYBL1, ITGAL, FAM65B, PHTF2, PRKCQ-AS1, BIN2, XKR6
M.CD69neg_Mast ASIC3, AD000671.6, SIGLEC8, ITGA2B, AMHR2, TSTD3, CYP51A1, EXD3, CDK15, ABCB8, SLC4A2, NSMCE1, FAM212A, KRT1, RSAD2, IL9R, WBP1, NCOA4, MAML1, MS4A2, GPR35, GALNT6, UBA7, ARHGEF6, CAPG, GRAP2, AJ271736.10, IGFLR1, PAQR5
M.CD69pos_Mast CTC-537E7.3, LINC00323, IL1RAPL1, C19orf81, ATP1A4, PTGER3, ENPP3, IL5RA, RP11-16E12.1, CMA1, AC020571.3, PPM1H, AC004510.3, PPP1R15A, RAB27B, MIR3188, GPR65, RP4-794H19.2, ALAS1, RP11-422J8.1, ST8SIA6
M.Cycling RP11-6F2.5, HSF2BP, RP11-798K3.3, ZNF565, RP11-190C22.8, RP11-212I21.4, RNASE2, COQ2, RP11-792D21.2, IQGAP3, ZNF724P, RP13-270P17.1, TIMM21, E2F7, C20orf201
M.DCs RP11-404O13.5, RP11-863P13.4, SLAMF9, CTD-2006K23.1, CLEC4F, CYSLTR2, CD207, RUFY4, CTD-2319I12.1, CD1E, RP11-379F4.9, RN7SL472P, CD1C, RP11-863P13.3, CLEC10A, FLT3, RP11-24F11.2, RP3-399L15.3, CLEC9A, RYR1, AP003774.6, AC144521.1, SIRPB1, CD1B, PPM1J, RN7SL698P, HCAR3, CD80, HCAR2, RP11-192H23.8
M.Macrophages AC005082.12, ACSM5, NT5DC4, RP11-426L16.8, RP11-452C13.1, RP11-489O18.1, RP11-760N9.1, PLA2G2D, CCL24, CCL18, MERTK, FABP3, MSR1, SIGLEC1, TMEM86A, CTB-138E5.1, CTD-2337J16.1, NPL, ATOX1, FOLR2, ACP5, NR1H3, DNAJC5B, TCHH
M.Mast AMHR2, CDK15, CTC-537E7.3, GCSAML, RP11-501J20.5, TACR1, XXbac-BPG13B8.10, LINC00323, AC004791.2, MS4A2, TPSD1, GATA1, IL1RAPL1, CALB2, RP11-354E11.2, TPSAB1, SLC45A3, C1orf186, CMA1, HDC, SVOPL, CTSG, CTD-3203P2.2, MAOB, KRT1, CPA3, IL13, LTC4S, GATA2, SLC18A2, ATP1A4, DKFZP434E1119, ADCYAP1, VWA5A, SIGLEC8, LEO1, ITGA2B, NTRK1, UTS2, EFHC2, AJ271736.10, RAB27B, RP11-557H15.4, SMYD3, STXBP6, ADRB2, IL9R, HS3ST1, ATP6V0A2, AC020571.3, SAMSN1, P2RX1, GMPR, IL5RA, TIAM2, PLIN2, CTNNBL1, TDRD3, MITF, PIK3R6, MAML1, PPM1H, ACOT7, NSMCE1, ST8SIA6, CATSPER1, CRBN, RP11-620J15.3, SMIM1, GLUL, PPP1R15A, NDST2, CAPG, BMP2K, FAIM, GPR65, ALAS1, RP11-422J8.1
M.Monocytes ACSM5, AP003774.6, AQP9, C19orf59, CD1B, CD300E, CD300LB, CEACAM4, CLEC4D, CLEC4F, CLEC5A, CLEC9A, CRHBP, CTB-138E5.1, CTD-2337J16.1, EMR3, FCGR1A, FCGR1B, FPR2, HK3, IL22RA2, IL27, KCNK13, LILRA1, LILRA3, LILRA5, LILRA6, MARCO, MEFV, MRC1, MS4A14, NT5DC4, PKD2L1, RETN, RN7SL138P, RNASE2, RP11-365O16.3, RP11-404O13.5, RP11-472N13.3, RP11-489O18.1, RP11-556E13.1, RP11-737O24.5, RP11-760N9.1, RP11-798K3.3, RP5-899E9.1, S100A12, SIGLEC1, SLAMF9, SUCNR1, TCHH, TIFAB, TREM2, VSTM1, ZDHHC19, FCN1, CD1E, LILRB2, CD207, CLEC4E, SDS, C1QA, C1QC, CSF1R, CD209, MS4A6A, C1QB, MSR1, CLEC10A, S100A8, PLA2G7, IGSF6, ATP6V0D2, RP11-190C22.9, TABLE 6-continued Immune UC specific markers for indicated cell types CCL18, CSTA, FPR3, CD163, DNASE1L3, FPR1, MMP12, AIF1, CACNA2D3, CSF2RA, OLR1, VSIG4, F13A1, LILRB5, IL1B, P2RY13, NCF2, LILRB4, GSDMA, RP11-290F20.3, CSF3R, PLA2G2D, MS4A4A, DLEU7, RP11-1143G9.4, LYZ, S100A9, PILRA, MRC1L1, SLAMF8, OSCAR, FCGR2A, HCAR3, CFP, LILRB3, CPVL, CLEC4A, RP11-6F2.5, FLT3, MS4A7, C5AR1, KB-1507C5.4, VMO1, MPEG1, MNDA, FOLR2, GPR84, RP11-426C22.5, RAB42, IL1RN, FUCA1, IFI30, SIGLEC12, G0S2, RP3-460G2.2, MMP9, FTL, RNU5B-1, NLRP3, AURKC, TREM1, SIGLEC15, CLEC7A, TLR2, CD14, SLC7A7, CD68, MERTK, ACP5, NLRC4, RNASE6, TLR4, RP11-792D21.2, CD163L1, TFEC, RRAGD, FAM26F, CTSS, TLR8, ATP6V1B2, STAB1, GPX1, NFAM1, LIP A, TTYH3, SAT1, APOC1, CMKLR1, THEMIS2, ATF5, CTD-2319I12.1, LGMN, SPI1, FABP3, CTSB, CTD-2319I12.2, TNFAIP8L2, CLEC4G, CTD-2006K23.1, NAIP, CTC-205M6.5, TNNI2, OTOA, CST3, MYCL, SLCO2B1, CCL3L1, RB1, HLA-DPB1, RGS18, GRN, HLA-DPA1, EREG, P2RY6, PLAUR, CD1A, SLC31A2, CXCL3, LILRA2, CARD9, NAGA, TYMP, FZD2, GM2A, TRPM2, NUP214
M.Myeloid AC004791.2, AC011899.9, ADCYAP1, AMHR2, AQP9, C19orf59, CD1B, CD300E, CD300LB, CDK15, CEACAM4, CLEC4D, CLEC4F, CLEC5A, CLEC9A, CMA1, CRHBP, CTB-138E5.1, CTD-2337J16.1, EMR3, FCGR1A, FCGR1B, FPR2, GATA1, GCSAML, GPR141, HK3, IL22RA2, IL27, KCNK13, LILRA1, LILRA3, LILRA5, LILRA6, MARCO, MEFV, MS4A14, MS4A2, PKD2L1, RETN, RN7SL138P, RNASE2, RP11-354E11.2, RP11-365O16.3, RP11-472N13.3, RP11-489O18.1, RP11-501J20.5, RP11-556E13.1, RP11-760N9.1, RP11-798K3.3, RP5-899E9.1, S100A12, SIGLEC1, SIGLEC8, SUCNR1, TCHH, TIFAB, TREM2, XXbac-BPG13B8.10, FCN1, CD1E, LILRB2, HDC, CTSG, CPA3, CD207, SLC18A2, CLEC4E, SDS, C1QA, C1QC, CSF1R, MS4A6A, CD209, FCER1A, C1QB, MSR1, MMP12, CLEC10A, S100A8, LINC00323, IL1B, PLA2G7, IGSF6, ATP6V0D2, RP11-190C22.9, MS4A4A, CCL18, FPR3, AIF1, CD163, DNASE1L3, FPR1, SIGLEC12, SVOPL, CSTA, CACNA2D3, TPSD1, CSF2RA, OLR1, ATP1A4, VSIG4, ADORA3, F13A1, LILRA2, TPSAB1, LILRB5, IL1RAPL1, NCF2, P2RY13, KRT1, RP11-290F20.3, CSF3R, LILRB4, DLEU7, CALB2, S100A9, SLC45A3, GSDMA, LYZ, PLA2G2D, NLRP3, PILRA, RP11-1143G9.4, C1orf186, MRC1L1, UTS2, HCAR3, FCGR2A, SLAMF8, CFP, LILRB3, OSCAR, CTD-3203P2.2, CPVL, CLEC4A, FTL, MAOB, C5AR1, IL13, MS4A7, GPR84, VMO1, CD68, MNDA, RENBP, IL1RN, MPEG1, RP11-426C22.5, RAB42, FLT3, FOLR2, IL10RB-AS1, LTC4S, G0S2, DKFZP434E1119, FUCA1, IFI30, RP3-460G2.2, GATA2, CST6, MMP9, TREM1, ATP6V1B2, GLUL, PLIN2, VWA5A, ACP5, CLEC7A, MERTK, TLR2, AURKC, RRAGD, CD14, RP11-792D21.2, SLC7A7, SLC11A1, CXCL16, RP11-76E17.3, RNASE6, EMILIN2, TLR4, SAT1, LEO1, GM2A, CD163L1, TLR8, GPX1, FAM26F, CTSS, TBXAS1, TNNI2, HS3ST1, ATP6V1F, NLRC4, TFEC, RNF130, CTD-2514K5.2, STAB1, TTYH3, LIPA, NFAM1, ITGA2B, MPP1, RASGRP4
M.Neutrophils AQP9, C19orf59, S100A8, MARCO, S100A12, FPR2, CD300E, VSTM1, S100A9, APOBEC3A, RP11-290F20.3, RETN, IL1RN, SLC11A1, LILRA3, FCN1, RP11-701P16.5, G0S2, RP4-613B23.1, EREG, NLRP3, RP11-598F7.3, CXCL10, NUP214, FPR1, C5AR1, LUCAT1, TREM1, PLAUR, RP11-47I22.2, CLEC4D, LILRA5, SOD2, KYNU, TLR2, ACSL1, CLEC4E, LILRB2, KB-1507C5.4, STXBP2, CSF3R, CDC42EP2, P2RY2, STX11, OLR1, IL10RB-AS1, CEACAM4, OSM, TYMP, SLC43A2
M.Tissue_DCs RP11-404O13.5, RP11-863P13.4, SLAMF9, CTD-2006K23.1, CLEC4F, CYSLTR2, CD207, RUFY4, CD1E, RP11-379F4.9, CD1C, RP11-863P13.3, CLEC10A, RP11-24F11.2, RP1-90J20.12, RP3-399L15.3, RYR1, AP003774.6, CTB-113P19.5, SIRPB1, AC144521.1, CD1B, HCAR3, HCAR2, RP11-192H23.8, RP11-737O24.5, UTF1
M.Tolerogenic_DCs GPR157, PTGES3L, RP3-508I15.22, CTD-2319I12.1, FBXO27, BATF3, CLEC9A, DGAT2, PPM1J, IDO1, AC120194.1, TNNI2, TOMM34, SERPINF2, CPVL, SLAMF7, DICER1-AS1, C1orf54, WDFY4, CPNE3, MREG, CD3EAP, KIAA0226L, VAC14, LGALS2, PPT1, CAMK2D, SNX3
T.Activated_CD4_hiFos

CYP2E1
T.CD4

CCDC81, LINC00880, CCR4, GNG8, FOXP3, F5, RN7SL443P, RP11-265P11.2, ITPKB-AS1, AC013264.2, CDKL2
T.CD8

KIR2DL4, RP11-713M15.1, TMEM155, AC131056.3, ADRB1, RP11-535A5.1, TRGC2, TPRG1, CD8B, CACNA1C-AS2, CCL4L1
T.CD8_IELs

KIR2DL4, RP11-713M15.1, ADRB1, MUCL1, DPH1, KLRC2, DRAXIN, RP11-535A5.1, TRGC1, TRGC2, FBXO2, RP11-446N19.1
T.CD8_LP

TMEM155, AC131056.3, CCL4L1, TRAV38-2DV8, GZMK
T.CXCR6_Th17

TRAV17, BTBD16, TMPRSS3, IL17A, INSL3, MATN1-AS1, CA10, CTD-2007H13.3, KLRB1, SMG8, NMRK1, IL17F, AC092580.4, ADAM12

TABLE 6-continued

Immune UC specific markers for indicated cell types

T.Cycling_T

PKHD1, RP11-631N16.2, PRIM1, ASPM, CDCA4, AC010761.8, AC109333.10, CENPF

T.ILCs

LINC00299, SPINK2, RP4-673M15.1, LEKR1, CSF2, ALDOC, RUNX2, IL4I1, RP11-977G19.12, PRAM1, FXYD7, KRT86, COL9A2, LTB4R, ETV3, RP1-102K2.8, BEX2, ARL5B, CASP3, PRMT10, KRT81, CAT, TLR1, LDLRAD4

T.MT

SMC5-AS1, PAQR3, PDE7A, EPHA1-AS1, RP11-277L2.4, ZNF740, BCL11B, LINC00680, ANKRD44, ZNF736, CTB-31N19.3, LSM11

T.NK

KLRF1, GPR97, KIR3DX1, TEX22, CLIC3, KLRC1, S1PR5, SH2D1B, BCO2, C21orf67, SCXA, XCL2, PRF1, GZMB, ZNF114, IL2RB, CTSW, ZNF852, FCGR3A

T.PD1_CD4

IL4, RP11-148O21.6, PHEX, RP11-279F6.3, CXCL13, RP11-431M7.3, TSHR, RP5-1028K7.2, ECEL1, BTLA, AC011893.3, CXXC11, SARDH, RP11-219B17.1, CD200, AC006129.4, SCGB3A1, BZRAP1-AS1, RP11-455F5.5, FKBP5, PDCD1, TMEM232, ANKRD55, TOX, PVALB, XXYLT1-AS2, AP006621.5, MYO7A, NMB, PVRIG, THADA, GAREML, GNG4, NFATC1, KSR2, IL21, PVT1, RNF19A, SYNJ1

T.Tcells

AC002331.1, AC006369.2, CA10, CXXC11, ECEL1, F5, FOXP3, IL17F, IL2, IL26, PAGE5, RP11-104L21.3, RP11-265P11.2, TMEM155, TRAV13-2, TRAV36DV7, TRAV4, TRBV28, CHRM3-AS2, IL17A, RP11-664D1.1, THEMIS, LINC00402, AC131056.3, C15orf53, RP11-291B21.2, RP4-539M6.22, CTLA4, CD8B, NELL2, CD3G, AC013264.2, CD6, CD3D, PDCD1, CPA5, LINC00243, BCL11B, BHLHE40-AS1, SUSD4, RP11-18H21.1, GNG8, LAG3, C12orf79, ABCD2, LINC00649, TRAT1, CD8A, CTC-505O3.3, CD5, HAR1B, CXCR6, CD3E, SLFN12L, PBX4, TRAC, RN7SL443P, SIRPG, GPR171, TRBC2, RP11-85K15.2, C4orf26, RP13-977J11.2, MORN3, BATF, CD28, C14orf64, AC104820.2

T.Tregs

AHSP, PNMA3, SLC8A1-AS1, CARD17, FOXP3, TTBK1, RP4-533D7.5, F5, TNFRSF8, FANK1, RTKN2, IL2RA, CTLA4, CUL9, PPP1R3F, LAIR2, NINJ2, CTD-2325P2.4, BATF, TNFRSF9, AC017002.1, TNFRSF4

TABLE 7

Stromal Healthy specific markers for indicated cell types

F.Crypt

CFD, ADAMDEC1, MFAP4, CCL13, CCL11, HAPLN1, PTGDS, SFTA1P, CXCL1, ABCA6, ELANE, CP, CCL7, NR2F1-AS1, CXCL6, SLIT3, FZD1, CCL19, CFHR3, ADAMTS2, EPHA7, RBFOX1, RP11-93L9.1, GPC3, PTGFR, ABCA10, HAS2, SLCO1C1, FZD10-AS1, RNF112, COL6A5, RP11-222A11.1, AL132709.5, SORCS2, LCE2A, FGF10, RP11-135D11.2, CHODL, RP11-1008C21.2, GALNT9, TWIST2, AC092652.1, TNN, RP11-572C15.6

F.Crypt_RSPO3

CFH, CXCL12, CCL11, EFEMP1, ADH1B, CCDC80, C7, DPT, RSPO3, ASPN, SERPINE2, ANGPTL1, CXCL6, CP, GPC6, CHODL, CCL19, SLIT3, APOD, OGN, GREM2, MAPKAP1, PTGER1, PDE5A, GPC3, RP11-135D11.2, RGMA, C1QTNF3, OSR2, FAIM2, PTGFR, MFAP5, BDKRB1, CAPN6, ECM2, DACT1, SHISA3, CDO1, SFRP2, SFRP4, PI16, RBBP9, FLRT2, CTD-2014B16.3, IL17RD, AL035610.1, APCDD1L-AS1, FOLH1, SORCS2, ENTPD1-AS1, GPC2, AP001626.2, CTD-2085J24.4, CTD-2083E4.4, RP4-545C24.1

F.Crypt_hiFos

CNTN1, ZIC1, TMEM232, AC005592.2, ZDHHC11, SHBG, CECR5-AS1, WASF1, RNU6-450P

F.Crypt_loFos_1

RN7SL374P, BVES, KCNS2, MRAP, RP11-98I9.4

F.Crypt_loFos_2

ZNF836, FAM102B

F.Endothelial

AC004540.4, AC116035.1, APLN, AVPR2, CCDC178, CNTNAP3B, COX4I2, FAM155A, FCN3, FOXC1, GABRD, GIPC3, GJA4, GPIHBP1, INHBB, KCNJ8, KRT222, KRT27, LCN6, LYVE1, NOVA2, NPR1, PGM5-AS1, PLA1A, RASSF9, ROPN1L, RP11-1024P17.1, RP11-536018.1, SCN3B, SELE, SELP, SNTG2, SOX18, STC1, STC2, TLL1, TSPAN18, KDR, FAM110D, TM4SF18, H19, DARC, MMRN2, C1QTNF9, RAMP3, ZNF833P, FAM167B, PLVAP, BCL6B, AC011526.1, CLDN5, MYCT1, HIGD1B, SHANK3, CXorf6, FLT1, ECSCR, RP11-251M1.1, SLC14A1, ROBO4, VWF, RP11-536O18.2, CYYR1, CDH5, TMEM88, ZNF385D, GPR116, THSD7A, ESAM, APLNR, USHBP1, SOX17, ADM5, SNCG, CD320, RAMP2, ARHGEF15, CD34, CALCRL, EGFL7, GALNT15, NOS3, MADCAM1, FLT4, ANGPT2, ELTD1, THSD1, PODXL, KANK3, GPRC5B, ARAP3, SERPINE1, TNNT1, CYP1B1-AS1, KIAA1462, RP11-23P13.7, TPO, TEK, JAM2, VEGFC, HYAL1, CKMT2, RAPGEF3, MKL2, PALMD, RGS5, CLEC14A, CCL14, NOTCH3, PTPRB, NOSTRIN, TABLE 7-continued Stromal Healthy specific markers for indicated cell types LRRC46, PCDH12, TSPAN7, GPR4, EXOC3L2, SEMA6C, RUNDC3B, S1PR1, CD36, TDRD10, FABP5, ERG, NOTCH4, GRB10, GPR1, EHD4, MAPK11, EXOC3L1, RASIP1, SEMA3F, IGFBP4, PKN3, BTNL9, HSPA12B, RND1, GNG11, ZNF541, FGD5, NUAK1, PKP4, HYAL2, ACE, EVA1C, RP11-473M20.9, SLC35G2, HRC, IPO11, SLC9A3R2, ENPP2, SHE, ARC, MPZL2, ZNF676, RBP7, EPM2A, JAG2, RP11-768F21.1, CD93, SEMA3G, SLC7A2, LINC01013, EPAS1, MASP1, ASB9, ADCY4, MYRIP, RP11-435O5.5, LINC00162, AIF1L, DOCK9, KIF19, SPTBN5, DYSF, CYPIBI, OAZ3, FAM189A2, ENG, PRX, STXBP1, CORT, RAPGEF4, CLIC2, MEOX1, PRSS23, SOX7, SMAD1, CFI, APBB2, ARHGAP29, SH3BP5, FAM84B, ADAM15, TEAD4, CYP26B1, SERPINI1, TGFBR2, HLX, SLC25A25, AC009336.24, MIER2, TIE1, CDC37, ICAM2, CRIP2, CBX2, FILIP1, STOM, EBF1, FZD4, TNFAIP1, EPB41L4A, RIN1, IL33, TMEM255B, HTR2B, BAALC, TACC1, PLLP, CABP1, RP11-830F9.6, PTPN14, RPGR, SLCO2A1, FAM107A, APOLD1, CCDC85B, ALPL, MANSC1, ITGA5, EPHB4, MFAP3, EMCN, MYBBPIA, FAM213A, DOCK4, CX3CL1, PLXND1, CELSR1, SHROOM4, RBP5, TINAGL1, LDB2, C10orf10, RASAL2, TMTC1, ARL15, DGKE, RP11-806H10.4, CSGALNACT1, ACVRL1, C16orf80, BCAM, PDE1C, VAMP5, TNFRSF10D, SLC16A14, MSMP, NES, KLHDC8B
F.Endothelial_1

GAS1, RP11-15A1.7, SEMA3G, FCN3, STC1, MASP1, RP11-671J11.4, RP11-105C19.1, ALPL, PRDM16, ARL15, ANO2, BTNL9, RP11-435O5.5, RP11-806H10.4, AC007292.3, EFNB2, C10orf10, RBP7, SOX17, RUNDC3B, C22orf26, MECOM, RTN4R, NOV, HEY1, LCN6, TBC1D13, SSUH2
F.Fibroblast CFD, FBLN1, PROCR, BMP4, ADAMDEC1, CXCL12, DMKN, CCL8, PLAC9, SPON2, HAAO, CCL13, ADH1B, SCARA5, HAPLN1, PTGDS, CCL11, NSG1, GLT8D2, F3, GADD45G, TMEM119, LRP1, ENHO, VCAM1, FAM150B, VSTM2A, PDGFRA, AGT, SFTA1P, DPT, LOXL1, PDGFD, CXCL1, APOD, PCDH18, FARP1, PRR16, CRISPLD2, TPBG, PXDN, MXRA5, FGF7, CDH11, HTRA3, BAMBI, PLAGL1, TSLP, TDO2, GPC6, TRPA1, FGFR1, ELANE, TNC, LRRN4CL, CP, GLP2R, HSD11B1, LANCL2, SVEP1, NMNAT3, CXCL6, CCL7, REEP2, COL4A5, CIB2, WNT5B, SCUBE2, ALDH1A3, RP11-112H10.4, FZD1, FAM65C, CCL19, PCSK6, LTBP2, C3, SRPX2, FGF9, RP11-1260E13.4, NPY, DACT1, SEMA3E, GPC3, COL4A6, RP11-449D8.1, OBSCN, RP11-93L9.1, SPOCK1, BICC1, BMPER, AC003090.1, RP11-367J11.3, PTGFR, FZD10-AS1, CRABP2, C1QTNF7, WNT5A, LOXL4, FAM19A1, RNF112, C22orf31, HMGCLL1, SAMD14, PDGFRL, AC002511.2, RP11-2E17.1, C3orf55, ATP6V1G2, COL6A5, CLSTN2, PAPLN, FOXL1, KRTDAP, C1QL1, CTB-92J24.3, LRRC15, ADAMTSL3, CTD-2314B22.3, CHODL, RN7SL336P, LCE2A, LRRC18, HS3ST3A1, GSG1L, PGR, RP11-473E2.4, ETNK2, CHI3L1, KIF7, RP11-222A11.1, AC104654.2, OGN, EDAR, MC1R, AMPH, FGF10, RBMS3-AS3, CNNM1, ZNF334, RSPO2, RP11-1008C21.2, AC004538.3, EFCAB1, GALNT9, GS1-18A18.1, RP4-755D9.1, SORCS2, RP11-135D11.2, ADCY2, LPAR3, LRRC8E, RP11-157J24.2
F.Glia ANGPTL7, CAP2, CDH19, CTD-2325P2.4, CYP27C1, DLX1, DYNC1I1, FAM181B, FGF1, FOXD3, HAND2, LINC00982, LRRC4C, LRRTM1, MGAT4C, NDP, NKAIN3, NRXN3, PCSK2, PMP2, PTPRZ1, RASGEF1C, RORB, RP11-21A7A.4, RP11-713P17.3, RP4-792G4.2, SERPINA5, SHC4, SOX10, SOX2, SRCIN1, STEAP1B, TENM3, TMEM155, VGLL3, CADM2, L1CAM, MYOT, SBSPON, TFAP2A, LINC00632, NRXN1, COL28A1, HPR, TTYH1, TMEM178A, GPM6B, PLP1, SCN7A, MPZ, CMTM5, XKR4, HAND2-AS1, C10orf82, CRYAB, SPP1, TUBB2B, LRAT, NTM, SORCS1, DLX2, NLGN4X, TMEM132B, TSPAN11, BAI3, S100A1, SOX8, ST6GALNAC2, NIM1, AC144449.1, NGFR, KCNMB4, FLRT3, RP11-166D19.1, COL8A1, AATK, SEMA3B, TMOD2, WISP2, KCTD1, TMEM59L, CAPS, CAB39L, COL9A3, SH3BGR, SCN9A, ART3, WDR86, RP11-20J15.3, MMP17, S100B, PRIMA1, GRIK3, MAB21L1, MFAP3L, ALDH1A1, COL21A1, LEPREL1, LINC00882, SNCA, AP001631.9, GPR155, ENTPD2, CPEB1, PRNP, RFTN2, ZNF853, C1orf198, RP11-235E17.4, CNP, RP11-187C18.2, MFSD2A, FST, OLFML2A, ASPA, ABL2, CADM4, SLC16A4, BEX1, CHADL, RCAN1, GFRA3, PCBP4, FXYD1, LGI4, ARHGEF26, CYR61, FGFBP2, EHBP1, RASSF4, COMT, TUBB4A, SECISBP2L, ITPR1, PMP22, SCCPDH, ANK3, SLC22A17, SLC16A8, NCAM1, UCHL1, ARHGAP15, FIBIN, ASTN2, MAL, AP1S2, ENDOD1, POU3F1, GRAMD3, FEZ1, SMIM5, ATL1, SEMA3C, AK5, GFRA1, SREBF1, IL11RA, KDSR, PMEPA1, FBLN2, LINC00894, RBM43, NUP188, NXPH3, ADK, CADM3, USP6, RP4-777D9.2, MATN2, C1orf204, TUBA1A, PDK4, CYP27A1, TPCN2, LAMP5, FADS3, PON2, LINC00263, ANXA2, DKK3, TTLL4, CD9, NDRG2, RTDR1, PEBP1, PAQR6, CNN3, MAPRE2, CLU, SLC15A3, LMBRD2, DEPDC7, MIIP, SPARC, SIPA1L2, ZFYVE1, TIMP3, C8orf4, GNG2, ARHGAP12, ITGB1BP1, NPTX2, CXXC5, PLSCR4, SORBS2, GATM, CRTAC1, TSPAN15, HSPA2, ALCAM, CDC42EP4, TPT1-AS1, ZBTB5, CBR1, RHOB, STARD13, SLC39A6, PLA2G16, PDLIM4
F.Inflammatory CHI3L1, MMP3, SIRT4, GBP1, TRAFD1, ZCCHC4, BLOC1S5, CDC23, VTA1, PLAU, PSME3, PAQR5, GSTT1, APOL2, CAMKK2, COMMD2, BYSL, UBIAD1, STX5, BCDIN3D, RRP1
F.Microvascular GABRD, STC2, SPTBN5, F2RL3, PASK, RP11-536O18.2, APLN, MSMP, C11orf95, IVNS1ABP, LYPD5, GIPC3, ME3, PRX, RP11-575F12.1, VWA1, RGCC, PRSS23, SEMA3F, MCPH1, ADARB1, SETD4, AC112693.2, RNF44, PGS1, EXOC3L2, BAALC, TBC1D8, DYSF, NRP1, CIT, TP53I11, WWTR1, NUP43, MICALL1, HSPG2, TBCD, HTRA1, RAPGEF4, ANRD65, SCARB1, RARG, ITGA6, ARHGAP23, JAM3, EGLN3
F.Myofibroblasts SOGA2, SOSTDC1, HSD17B6, DES, ACTG2, NPNT, AF131217.1, RP11-611D20.2, RAB9B, LUZP2, CNN1, MYLK, TAGLN, RP13-143G15.4, MYH11, SYT10, SNCAIP, LMOD1, DIO2, TMEM158, LINC00595, RP11-356C4.3, HHIP, PDLIM3, C20orf166-AS1, SLC2A4, FBXL22, TGM2, ACTA2, LRRC17, FHL1, SLMAP, NEXN, PDLIM7, LRFN3, BVES-AS1, NAA60, TPM2, SPAG8, LPP, MIR145, KCNMB1, SMTN, MACROD2, SPESP1, TGFB1I1, AOC3, FAT4, DSTN, FLNA, RP11-344E13.3, NDUFA4, TCEAL4, MIR143HG, TRPC6, HMG20B, TES, TTLL7, SLC12A8, PDIA5, LTBP1, TCEAL1, WRN, AKAP6, PLN, SVIL, RP11-196G18.23, VAT1L, TCEAL3, TPM1, TEAD3

TABLE 7-continued

Stromal Healthy specific markers for indicated cell types

F.Pcap_Venules

FOXC1, LYVE1, RASSF9, SCN3B, SELE, TLL1, DARC, MADCAM1, SELP, VEGFC, CCL14, LRRC46,
FAM155A, ZNF385D, RAB3C, CELSR1, UBD, LINC01013, C2CD4B, ACKR4, PLA1A, TSPAN18,
FAM189A2, RP13-395E19.3, GALNT15, RP5-1021I20.5, CITED4, DUSP23, GPR126, TIAM1, CPE, DTL,
ZSCAN31, ICAM1, AMDHD1, ICAM4, KCNMB3, CORT, HTR2B, PMEL, CYP1B1, KLHL3, HESX1,
LPCAT4, ZNF521, APLNR, KIAA1683, NR5A2, PRKAR1B, FAM84B, MEOX1, IFIH1, SEMA6A

F.Pericytes

EDNRA, CYP4X1, KCNJ8, COX4I2, STEAP4, RP11-714L20.1, GJC1, CCDC3, HRC, NOTCH3, FAM162B,
CDC7, RGS5, ITGA7, PRDM11, BGN, HIGD1B, LDB3, JRKL, NR2F2-AS1, NDUFA4L2, NR1H4, PDGFRB,
PGF, ATXN7L2, LINC00883, TEPP, ARHGEF17, UBA2, REM1, ISYNA1, FZD7, TNS1, PLXDC1, CSRP2,
OLFM2, GJA4, TMEM38A, NUP133, SERPINI1, TINAGL1, RNF208, EBF1, HES4, SUSD2, CNNM2,
ADAMTS1, ATP1B2, EPS8, MCAM, RP11-110I1.12, RP11-349A22.5, ADIRF, TPPP3

F.Stromal

CXCL14, A2M, CALD1, C1S, MFAP4, COL6A2, COL3A1, PLAT, CFD, DCN, TM4SF1, CYGB, TCF21, LUM,
FBLN1, SOD3, ADAMDEC1, MMP2, PROCR, COL6A1, BMP4, CXCL12, TPM2, FABP5, MFGE8, CLEC11A,
EPHX1, CFH, CTSK, SLC9A3R2, PTN, PPAP2B, SDC2, PCOLCE, CAV1, EMILIN1, DMKN, CCL8, STMN2,
LINC01082, POSTN, HAAO, FRZB, FOXF1, ADH1B, PLAU, CCL13, WFDC1, SNAI2, GGT5, PTGDS,
SCARA5, CCL11, HAPLN1, ACTA2, EFEMP1, FXYD6, GLT8D2, PITX1, CAV2, FENDRR, RBP5, NKX2-3,
NDUFA4L2, EHD2, CTC-276P9.1, RAMP2, CD320, NSG1, MGP, TFPI, THY1, CLEC14A, F3, FILIP1L,
TMEM109, FABP4, EDIL3, TMEM204, EMID1, LHFP, TMEM199, VCAN, RCAN2, ENHO, IL34, PLVAP,
BMP5, AGT, SFTA1P, FAM150B, COL6A3, LOXL1, VSTM2A, TAGLN, IGFBP5, CCDC80, PDLIM3,
CLDN5, CERCAM, PTCH1, FN1, DPT, PDGFD, PDGFRA, MYLK, FGF7, EGFL7, RAMP3, CRISPLD2,
PCDH18, TNXB, NEGR1, TAC3, GSTM5, SEPT4, PXDN, PGF, VWF, ESAM, OLFML1, MMP11, TUSC3,
ECSCR, VASN, DDR2, SMYD4, EMCN, PRR16, COLEC11, MXRA5, TMEM150C, TMEM88, LRRC32,
AC011526.1, C16orf89, FGFR1, VSTM4, RP11-332H18.4, NEXN, PDGFRB, NID1, FOXF2, FAM167B,
COLEC12, CYYR1, HTRA3, EVA1A, ADAMTS1, SNCG, CD34, ELANE, FBN1, TDO2, MMP1, CDH11,
TRIL, ELTD1, PODXL, PAMR1, RP11-532F6.3, HHIP, RUNX1T1, TRPA1, TBX2, GPC6, TEAD2, TSLP,
LAMA5, RP4-665J23.1, LRRN4CL, RP11-514D23.3, HOXA11, AKAP12, TM4SF18, ARHGAP29, NR2F1-
AS1, SGCA, RPS6KA2, MIR497HG, MAB21L2, HHIP-AS1, PRKG1, PLEKHH2, NTF3, PDE1A, RASIP1,
GPR124, CCL7, APLNR, C7, ACTG2, CCDC102B, EFCC1, EFHD1, CP, LIFR, FAM107A, HOXD11, TFPI2,
FLT1, CXCL6, SVEP1, CDH5, CH25H, HOXD8, LOX, MMRN2, SLC14A1, HSPB6, PTGES, MAPK10,
ANGPT2, PTGDR2, SPON1, GLP2R, NKD2, LAMC3, CLMP, ROB04, SLIT3, MRVI1, FAM110D, CALCRL,
MYCT1, NUAK1, CXorf36, PTPRM, RHOJ, ENPP6, NR2F1, RP11-112H10.4, OSMR, KDR, RGS5, GPR63,
COL12A1, COL4A5, MIR143HG, LTBP2, ARHGEF25, HOXD9, C3, DARC, WNT5B, RP11-383H13.1, NXN,
SOSTDC1, GPR116, REEP2, RP3-323P13.2, AC131025.8, FZD4, GLI1, TNFRSF10D, SYNDIG1, MIR145,
PCDH7, CFHR3, LPHN2, RP11-536O18.2, FGD5, GRB10, SOBP, MADCAM1, PALMD, SULF1, PCSK6,
HSPA12B, ZP1, ALPL, AC124789.1, TEK, SOX17, SOX18, VAT1L, FAM162B, USHBP1, DACT1, PTPRG,
PDE7B, AC156455.1, CHST1, SALL1, PEAR1, C1orf167, SEMA3E, ASPN, OSR1, CLEC3B, FNDC1, FILIP1,
FAM13C, LEPR, AC116035.1, GPRC5B, PREX2, PCDH12, CCL21, CABP1, ROR2, DZIP1, HIGD1B,
COL4A6, RSPO3, WDFY3-AS2, PDGFC, LCN6, AMOTL1, HYAL1, KCNE4, TMTC1, NPY, PRX, ADM5,
TBXA2R, LRRC17, RBFOX1, GLIS2, SYNPO2, FAM110B, RP11-264B14.1, AP000330.8, GPR4, NTN1,
EDA2R, BOC, ISL2, DHRS7C, EXOC3L2, LINC00961, RP11-449D8.1, PCDH19, C16orf46, RBPMS2, NOS3,
HOXC9, SEMA3A, BCL6B, KLHL13, SEMA6C, ARHGEF15, ACSS3, HOXC6, PTGFR, WNT5A, IGF2,
SPOCK1, ADAMTS4, HSD17B6, CPAMD8, HIF3A, COX4I2, FAM19A1, PPP1R3C, TEKT3, CLSTN2, NPR2,
FOXL1, LINC00839, RGMA, MFAP5, PHACTR3, SLCO1C1, LCA5, AC017048.4, BICC1, ZNF423, SLC16A2,
AC003090.1, ANGPT1, C1QL1, COL6A5, KRT222, NPR1, MUSK, NOTCH3, THSD1, FMO3, NDNF,
SAMD14, APLN, AVPR2, PABPC5, ZNF833P, SCGB1B2P, ZNF385D, GALNT15, AC061992.2, AC002511.2,
CRMP1, FAM171B, HOXC8, HMGCLL1, FBXL7, SERPINE1, C22orf31, FGF13, PDGFRL, ADAMTS5,
C1QTNF7, GSG1L, KRTDAP, NAP1L3, RP11-2E17.1, ADAMTSL3, FAT4, ARHGAP28, TRPC6, CASP12,
RNF112, EVC, FOLR1, CHODL, CTB-92J24.3, LINC00475, OGN, CDO1, ETNK2, PAPLN, IL33, KIF7, DIO2,
GJA4, HS3ST3A1, INHBB, KIAA1462, LRRC3B, PTH1R, CORT, C3orf55, C1QTNF9, MMP3, AC116366.6,
C10orf107, CHRD, NAALAD2, RP11-572C15.6, RP4-755D9.1, STC1, INMT, BHMT2, SUSD2, CTD-
2314B22.3, GLIS1, RP11-774O3.3, AGTR1, CILP, ECM2, FCN3, GRIA4, GRID1, HPSE2, LRRC18, OMG,
RAET1G, RP11-54O7.3, RP11-135D11.2, SHANK3, GPR176, RP11-486G15.2, ZDHHC15, RP11-1008C21.2,
CNNM1, TTLL11, CCDC178, FAM180A, LRRC15, RP11-395L14.4, SELP, SORCS2, TRPC1, H19, NUDT10,
CHI3L1, MIR503HG, AC092652.1, FGF10, GPIHBP1, LCE2A, LIFR-AS1, MYL3, NOVA2, RBMS3-
AS3, RNF150, RP11-710C12.1, RSPO2, GPR133, RP11-251M1.1, LINC00595, ZNF667, CACHD1,
AL132709.5, PARD6G, RP11-69I8.3, FLT4, RP11-314C16.1, SLC45A1, C17orf51

F.Villus

DNAI1, F2RL2, GRIN2A, GS1-18A18.1, NEFM, NOTO, RP11-157P1.4, RP11-804A23.4, RP4-755D9.1,
RSPO2, REEP2, COL4A6, GLP2R, DLEU7, EDAR, SCN3A, PCSK6, SCUBE2, WNT5B, AC002511.2, RP11-
1002K11.1, HS3ST3A1, LPAR3, FGF9, LANCL2, DHRS7C, C22orf31, AC003090.1, ENHO, EGOT, BAMBI,
TSLP, SCUBE1, KCNK17, BMP7, VSTM2A, FAM150B, ADAMTS13, MMP11, KREMEN1, SRPX2, RBP4,
CBLN2, POSTN, CHST1, NRIP3, NSG1, OBSCN, NMNAT3, TSPAN33, CNTFR, SEMA4D, SEMA3A,
FAM218A, C1QL1, EDNRB, PDGFRA, PTGIS, MFAP2, SHANK2, TSHZ2, SDK1, DDHD1, GSG1L, CTD-
2334D19.1, ZNF407, LAMC3, GADD45G, TPBG, RP11-449D8.1, WFS1, CNIH3

F.Villus_1

IP6K3, MSX2, NTRK3, TTC25, AC019171.1, MAST1, AC022007.5, ARHGEF33, EGOT, KB-1125A3.11,
RP11-473M20.16, AL163953.3, XXbac-BPG252P9.10, EDAR, NHS, CASC14, ADCY2, AC009480.3, CPM,
RN7SL336P, FBXW7, BDNF, CTD-3093M3.1, FGF9, HUS1B, RP11-309M23.1, C10orf107

TABLE 7-continued

Stromal Healthy specific markers for indicated cell types

F.Villus_2

GRIN2A, NEFM, VPS37D, F2RL2, LEF1-AS1, DHRS7C, AC096772.6, RP11-86H7.7, RP11-97O12.7, LAMTOR5-AS1, ZNF646, EFHB, RP11-144G6.12

TABLE 8

Stromal UC specific markers for indicated cell types

F.Crypt

AC004538.3, AL132709.8, CILP, COL6A5, FMO2, GRIK4, HHIPL1, MPP2, OMG, RN7SKP295, RP5-1172A22.1, SHISA3, SLC17A7, TEKT3, TMEFF2, CNTN1, CCL13, GAS6-AS2, LPAR4, CCL7, OGN, AL035610.1, ABCA8, ABCA9, CP, CCL11, SVEP1, ELANE, ADAMDEC1, ANGPTL1, RP11-572C15.6, RP11-473E2.4, GPC3, HAPLN1, CFD, SFTA1P, NAALAD2, ADH1B, CCL8, SCGB1B2P, ANKRD13B, CCDC80, FBLN1, ABCA10, ADAMTSL3, CPEB1, DNM1, APOE, PTGDS, SCARA5

F.Crypt_RSPO3

SMAD5-AS1, OGN, CCL19, CAPN6, GREM1, SFRP4, CCL21, C7, PCOLCE2, GREM2, RP11-339B21.13, RP11-195F19.9, PI16, NAALAD2, RP11-572C15.6, CHODL, RSPO3, CCDC80, MAPKAP1, RGMA, NPB, OSR2, GNB3, SFRP1, RP11-597D13.9, FLRT2, ZNF3, C1QTNF9B-AS1, CTC-559E9.6, ADAMTSL3, RNF146, SIMC1, CP, PTGDS, ANGPTL1, DPT, FMR1, SRPX, CXCL12, ADH1B, EFEMP1, COL14A1, IRF2BP1, ZNF398, CFH, COPRS

F.Crypt_hiFos

RP11-173B14.5, TMEFF2, BCDIN3D-AS1, LPAR4, CTD-2651B20.3, RP11-420L9.5, CPEB1

F.Crypt_loFos_1

BPI, AL132709.8, RP11-216B9.6, PNMA2

F.Crpt_loFos_2

RP11-588K22.2, RN7SKP295, PIP4K2B, MAP3K10

F.Endothelial

AC116035.1, C1QTNF9, C1QTNF9B, CASC10, CTD-2536I1.1, CYP1A1, ESM1, FAM69B, GABRD, GALNT15, GJA5, GPIHBP1, GSDMC, KRT222, KRT5, LHX6, LYVE1, MMRN1, NOVA2, NOX4, PDE10A, RASSF9, RP11-286H15.1, RP11-676J12.6, STC2, ZNF541, ZNF833P, ZNF385D, LCN6, KDR, H19, HIGD1B, CXorf36, TM4SF18, AC011526.1, ECSCR, PLVAP, APLNR, SELE, FAM110D, CLDN5, DARC, RP11-251M1.1, VWF, SNCG, FCN3, ESAM, GPR4, FAM167B, COX4I2, MADCAM1, GPR116, SOX17, SHANK3, CDH5, CLEC14A, TLL1, ARHGEF15, EXOC3L2, CORT, RP11-536O18.2, RP11-536O18.1, ROBO4, AVPR2, INHBB, GAS1, MYCT1, BCL6B, THSD1, EGFL7, RAMP2, FLT1, RAMP3, SOX7, CD34, TMEM88, SOX18, TPO, CD320, MMRN2, RP11-23P13.7, KL, FUT1, SLC14A1, RP11-159D12.10, HSPA12B, PODXL, USHBP1, ADM5, CCL14, ANGPT2, ANKRD29, ELTD1, RND1, CCDC3, JAG2, PCDH12, TNFRSF10C, TEK, KCNJ8, KIAA1462, KANK3, ADCY4, RBP7, CYYR1, FOXS1, APLN, SELP, VEGFC, GRB10, CPLX1, JAM2, BFSP1, CALCRL, NPR1, GPRC5B, BTNL9, TSPAN7, C22orf34, PALMD, NPR3-473L9.4, RASIP1, IGSF9B, F2RL3, RTN4RL2, RAPGEF3, ERG, ARHGAP29, BAALC, GJA4, EMCN, DYSF, FGD5, FABP5, HYAL2, PKN3, ENG, CTD-2135D7.5, CD36, TIE1, ALPL, SFTA2, SLC9A3R2, EPAS1, RP11-355F16.1, CD93, ACE, NUAK1, TSPAN18, DOCK9, PTPRB, SNTG2, AC009336.24, LEPR, CABP1, RAPGEF4, GPR146, NOSTRIN, EVA1C, ADAMTS4, ICAM2, SEMA3F, TNFAIP1, CSGALNACT1, MIER2, CRIP2, RASA4, MPZL2, KIF26A, SMAD1, SHROOM4, CPXM2, GNG11, EXOC3L1, IFI44L, RP11-830F9.6, SERPINI1, RGS5, DGKE, SHE, LTF, NDST1, LDB2, ADAM15, OAZ3, MYBBP1A, PLA1A, FZD4, C4orf32, SLCO2A1, RP11-92C4.6, AQP1, CACNG8, DLL4, CYP1B1-AS1, TGFBR2, GIMAP8, NOTCH4, IPO11, PCDH17, KCNC4, CUBN, NDUFA4L2, MAPK11, MKL2, PLCB1, APBB2, CFI, C2CD4B, STOM, TMEM204, CASP12, FAM107A, RBP5, SEMA6C, FAM65A, HEG1, PKP4, SLC35G2, PEAR1, SCARF1, EDN1, FAM219A, ARAP3, SYNPO, RAI14, SH2D3C, S1PR1, EHD4, CCDC85B, MTUS1, FAM13C, CLEC3B, RUNDC3B, ENPP2, C11orf95, BCAM, ASB9, IGHV3-64, FKBP1A, TINAGL1, LIFR, PTRF F.Endothelial_1

FGF12, GJA5, SEMA3G, PDE10A, IGFBP7-AS1, PRODH, RP11-789C17.1, FCN3, TNMD, GPIHBP1, IGF2, SLC6A6, JAG2, ARL15, ALPL, EDN1, HEY1, AQP1, CTD-2035E11.4, RP11-225B17.2, AIF1L, SOX7, RP11-576D8.4, ANKRD29, RBP7, SRP14

F.Fibroblast

AC002511.2, AC004538.3, AKNAD1, AL132709.8, CHRM2, CILP, CLSTN2, COL6A5, CTD-2078B5.2, CTD-2334D19.1, FAM19A1, FAM216B, FGF10, FGF14, FMO2, GLIS1, GREM1, GRIK4, HOXC8, HTR2A, KRTDAP, LIFR-AS1, LRRC15, LRRC18, NACAD, NKX3-2, NPY, OMG, PPAPDC1A, RBMS3-AS3, RN7SKP295, RP11-129B22.1, RP11-395L14.4, RP11-473E2.4, RP11-473L15.2, RP11-7O14.1, RP11-800A3.7, RP3-323P13.2, RP4-530I15.6, RP5-1172A22.1, RSPO2, SHISA3, SLC17A7, STRA6, TCEAL5, TEKT3, WISP1, DPT, SEMA3E, CCL13, CNTN1, FAM19A5, CCL11, AC104654.2, LTBP2, THBS2, ADORA1, HS3ST3A1, IL13RA2, ADAMTSL3, MMP3, VSTM2A, IL11, FAM150B, GLP2R, CHI3L1, GAS6-AS2, SCUBE1, CCL7, RP11-449D8.1, SFTAIP, COL4A5, CHODL, AL035610.1, RP11-112H10.4, DMKN, PDGFRA, RP11-588K22.2, PCOLCE2, NSG1, COL4A6, OXT, WNT5B, SVEP1, OGN, C3, REEP2, CPXM1, SYNDIG1, CYP27C1, F3, LRRN4CL, TNFRSF11B, RP11-572C15.6, SDK1, MMP1, ARL9, ENHO, LRCH2, CP, RNF150, MXRA5, SCARA5, DACT1, FAM65C, ABCA9, TMEM119, RP11-1002K11.1, CYS1, CCL19, SRRM3, COL7A1, SCUBE2, ABCA8, HTRA3, ADH1B, PCSK6, APOD, HAS1, DNM1, FGF7, VCAM1, HMGCLL1, ELANE,

TABLE 8-continued

Stromal UC specific markers for indicated cell types

ADAMTS13, STMN2, BMP4, RP11-69I8.3, PRR16, RP11-152P17.2, BMP7, PIEZO2, CTSK, NPPC, AKR1C1, CTD-2269F5.1, C1QL1, C10orf107, GPC3, FIGN, LOXL1, CCDC71L, CFD, DZIP1L, RP11-204M4.2, FGF9, PI15, DHRS7C, ANGPTL1, GLT8D2, FANCC, BMP5, PROCR, ADAMDEC1, TRPA1, NAALAD2, GPR133, PTGIS, RP11-284F21.8, KB-1125A3.11, GSTM5, LOX, HAPLN1, FBLN1, LAMA2, PLAU, RARRES2, LRP1, CCDC80, PRTG, WNT2
F.Glia ADAMTS8, ANGPTL7, CADM2, CDH2, CMTM5, CRTAC1, FOXD3, L1CAM, NRXN1, PCSK2, PMP2, RP11-189B4.6, RP4-792G4.2, SERPINA5, SOX10, TENM3, TFAP2A, CDH19, MYOT, GPR17, PLP1, SOX2, LRRTM1, MPZ, COL28A1, XKR4, PPT2-EGFL8, DLX2, PRIMA1, HAND2-AS1, STEAP1B, NTM, GPM6B, AKAP6, LINC00162, SHC4, AC004466.1, CRYAB, DYNC1I1, WISP2, MAB21L1, TMEM59L, ST6GALNAC2, KIRREL3, HAND2, KCNMB4, NRXN3, RP11-262H14.3, TGFB2, SORCS1, NXF3, CADM4, TUBB2B, NGFR, HOXC6, MFAP3L, HOXC9, S100A1, LOXL3, ART3, TTYH1, CAPS, KCTD1, SEMA3B, MMP17, MEGF6, SPP1, COL8A1, RP11-18H7.1, FSTL3, COL9A3, COL21A1, NLGN4X, PMEPA1, DHH, RP4-635E18.6, RP5-1126H10.2, PRNP, TPT1-AS1, UBR4, GAS7, MIA, TSPAN11, GPR155, GFRA3, SLC22A17, SCN7A, SCRG1, EGFL8, TTR, NPTX2, ANKRD53, SNCA, SH3BGR, FHOD3, TIMP4, C1orf198, ITGB8, DEPDC7, GALNT2, LGI4, TSPAN15, RASSF4, TNFAIP6, SCCPDH, NUP188, OLFML2A, LAMP5, ALDH1A1, TMEM17, SEMA3C, RP5-1007M22.2, SCN9A, CNP, CAB39L, DAG1, KCNAB3, RCAN1, SLC15A3, SMIM5, CDKN2A, PMP22, BPGM, MAL, FEZ1, ARHGAP15, GDNF, RIPK4, FBLN2, CHADL, PHLDA3, S100B, SIPA1L2, CYTL1, HSPB2, DKK3, FAM210B, LEPREL1, C12orf43, IMMP2L, FAM124A, SORBS2, ITPR1, ARHGEF26, KCTD11, IER3, BMP8B, COMT, PCDH9, FST, FADS3, TXNRD2, CCL2, VPS52, PON2, CADM3, LPAR1, NRN1, ABL2, LINC00672, SREBF1, ANXA2, FRMD4A, SDC3, PDLIM4, MATN2, SLITRK6, RP11-374M1.5, RXRG, PEBP1, NLRP1, AP1S2, KCNS3, STARD13, JKAMP, GATM, CYR61, CBR1, GPC1, FXYD1, HES1, PCID2, PEPD, ADK, UPB1, CNPY2, MARCH2, S100A3, AP000688.8, B4GALT6, SPARC
F.Inflammatory C22orf15, IL24, SBSN, TMEM215, TRPC4, ZNF295-AS1, TNFRSF11B, IL13RA2, CHRM2, MMP3, PI15, WNT2, CHI3L1, RP1-90J20.8, MMP10, LBP, RP4-530I15.6, STRA6, GALNT16, WISP1, TWIST2, RASL11B, PLAU, STK32B, PTGES, PPAPDC1A, TFPI2, STEAP1, BDNF, MMP1, CXCL6, HGF, RP11-204M4.2, SORCS2, GAL, LINC00944, KIAA1199, PTHLH, PPIL1
F.Microvascular SCHIP1, MEGF11, RP11-536O18.2, F2RL3, AKR1E2, ME3, FABP5, AK7, CD36, RP11-540B6.6, RIN1, PCDH12, RGCC, SDPR, CTD-2319112.4, PRX, RAPGEF4, PRSS23, BAALC, WWTR1, TSPAN12, CABP1, HLX, VWA1, SEMA3F, C16orf80, ITGA6, MPV17L2, AC116035.1, PLVAP, ANKRD65, SH3BP5, RP11-509E16.1, PASK, PLIN5, FLT1, KIFC3
F.Myofibroblasts SYT10, SOSTDC1, TRDN, RAB9B, NPNT, HSD17B6, RP11-344E13.3, ACTG2, MYOCD, CTB-47B11.3, AF131217.1, TACR2, CNN1, SPOCD1, HHIP, DES, MYH11, ADAMTS6, KCNMB1, MBNL1-AS1, PDLIM3, MFAP5, LTBP1, FAM150A, MYLK, SLC2A4, LUZP2, FAM74A6, ADCY2, FAM168A, RP11-379B18.5, LPP, TMSB15A, ULK2, SMTN, KANK1, FLNA, TAGLN, LMOD1, ARHGEF25, SLMAP, PDLIM7, CAP2, APCDD1, FHL1, TCEAL1, HFE, HHIP-AS1, TGM2, NDUFA4, GRM7, DPEP2, PLN, NEXN, THSD4, LRRC73, NEO1, CSRP1, RP11-611D20.2, PDIA5, CES1, TGFB1I1, TPM2
F.Pcap__Venules SELE, DARC, GAS1, MADCAM1, CCL14, MMRN1, RP11-355F16.1, PLA1A, SNTG2, SELP, MEOX2, ZNF385D, C2CD4B, DUSP23, CSF3, RAB3C, LINC00312, SNORA40, LINC01013, RP4-607J23.2, TUBB3, RP11-782C8.5, CPXM2, SMAD1, IL33, PRCP, PKD1L1, TLL1, LHX6, RP11-417J8.6, SYT15, TSPAN7, GABRD, CACNG8, MED24, RASSF9, ICAM1, REM2, TPD52L1, MEOX1
F.Pericytes FOXS1, NOTCH3, KCNJ8, COX4I2, RGS5, NDUFA4L2, HIGD1B, STEAP4, HEYL, GJC1, CTD-3247F14.2, HRC, LPL, EFHD1, OLFML2B, C1QTNF1, ITGA7, EDNRA, ARVCF, LDB3, FAM162B, RP11-85A1.3, PDGFRB, ENPEP, NR2F2, CTD-3193K9.4, CENPP, HES4, PGF, SEPT4, BGN, AC022007.5, OLFM2, NRIP2, ADCY3, PTGIR, MAP3K7CL, CSRP2, NR1H4, C2orf40, ANO1, SERPINI1, ANGPT2, PLXDC1, LHFP, CYP4X1, HEY2, MEST, TINAGL1, SNAPC3, ADIRF
F.Stromal AC002511.2, AC004538.3, AC092652.1, AC116035.1, AC140912.1, ADAM33, ANGPTL1, AP000525.9, BHLHE22, C1QTNF7, C1QTNF9, C1QTNF9B, C22orf31, CAND2, CCDC178, CCDC8, CDO1, CFHR3, CHRD, CHRDL2, CHRM2, CHST1, CLSTN2, COL6A5, CORO6, CTB-92J24.3, CTD-2135D7.5, CTD-2334D19.1, CTD-2536I1.1, CYP1A1, EDNRA, EGFL6, EXOC3L2, FAM155A, FAM162B, FAM171B, FAM19A1, FAM26E, FAM69B, FBXL7, FGF10, FGF14, FIGN, FLRT2, FMO2, FMO3, FNDC1, FOXL1, FOXS1, GALNT15, GALNT16, GIPC3, GJA4, GJA5, GLI2, GLIS1, GLP2R, GPIHBP1, GREM1, GRIA4, GSG1L, HPSE2, HS3ST3A1, IGDCC4, IGF2, IL17B, ITGB3, KCNJ8, KIAA1755, KIRREL, KRT222, KRTDAP, LAMC3, LBP, LHX6, LIFR-AS1, LOXL4, LPHN3, LRCH2, LRRC15, LRRC3B, LYVE1, MAB21L2, MASP1, MATN3, MEOX2, MMRN1, MUSK, MYOCD, NAALAD2, NKX3-2, NOVA2, NPY, NR2F2-AS1, NUDT11, OGN, OMG, PABPC5, PCDHB4, PCDHB7, PGR, PIEZO2, PKNOX2, PLN, PPAPDC1A, PRRX1, PTGFR, PTH1R, RASSF9, RBMS3-AS3, RGMA, RN7SKP295, RNF112, RP11-129B22.1, RP11-152P17.2, RP11-264B14.1, RP11-395L14.4, RP11-473L15.2, RP11-514D23.3, RP11-536O18.1, RP11-572C15.6, RP11-676J12.6, RP11-710C12.1, RP11-7O14.1, RP11-800A3.7, RP11-804A23.4, RP11-92C4.6, RP3-323P13.2, RSPO2, SALL1, SLC27A6, SLC45A1, SPOCD1, STC2, STRA6, TCEAL5, TEK, TEKT3, TWIST2, VAT1L, VEGFC, WBSCR17, WNT2, ZNF541, ZNF833P, NOTCH3, VSTM2A, CCL21, ASPN, COX4I2, ZNF385D, CTC-276P9.1, CLEC3B, TBX2, DHRS7C, LCN6, KDR, MPDZ, HSPA12B, SFTA1P, MGP, APLNR, PDE1A, SYNDIG1, LMOD1, RAMP3, PAMR1, TNXB, TCF21, FCN3, SRRM3, ZP1, CLDN5, FAM107A, PODN, NTF3, PGM5, RP11-332H18.4, NR2F1, IL13RA2, DCN, RBPMS2, EMCN, H19, HIGD1B, NKX2-3, AC131025.8, TMEM100, SLIT3, ARHGAP28, DPT, TMTC1, POSTN, OLFML1, PRR16, FENDRR, FOXF2, LINC01082, VWF, FILIP1, TABLE 8-continued Stromal UC specific markers for indicated cell types PDGFRA, BMP4, AGT, HSPB6, SEMA3E, PCDH19, RP11-449D8.1, CXorf36, PREX2, CXCL14, AC003090.1,
COL4A5, CD34, LUM, STMN2, MMRN2, RAET1G, ACSS3, SOSTDC1, AC011526.1, ECSCR, TM4SF18,
SVEP1, LIFR, PLVAP, BCL6B, TDO2, NEXN, FAM110D, MFAP5, ELANE, MFAP4, C1QL1, RGS5, SNCG,
SNAI2, FAM150B, KIAA1462, DARC, NTN1, GPR63, ACTG2, ACTA2, RBP5, NXN, MADCAM1, PCOLCE,
MRVI1, TRIL, TMEM200B, ADORA1, SCARA5, FAM13C, AC124789.1, SEPT4, SULF1, CLEC14A, CDH11,
ESAM, PCDH7, CYGB, PCDH18, PLEKHH2, DNM3OS, ADAMTSL3, TMEM119, CCL13, FOXF1, GPR4, CP,
FAM167B, ENPP6, GPR116, CCL7, ITGA11, TLL1, EPHA3, COL4A6, ECM2, RAMP2, LPHN2, MIR145,
RP11-251M1.1, LOXL1, SGCD, CFH, RP11-736K20.5, FAM19A5, VASN, MMP3, SULT1C4, CAV1, NID1,
SELE, SOX17, EFEMP1, IL11, HSD17B6, PDGFRB, PYGO1, HTRA3, CYS1, SHANK3, LRRC17, RASIP1,
ADH1B, ADAMDEC1, BICC1, BMP5, CCDC3, RCAN2, TAGLN, NDNF, TAC3, LRRN4CL, SELP,
CCDC74B, DIO2, THBS2, GLIS2, C17orf82, FBLN1, HHIP, SEMA3A, MYH11, CAV2, CDH5, COLEC11,
CCL11, MMP2, C16orf89, ARHGEF15, RP11-351D16.3, RP11-536O18.2, SGCA, TRAM1L1, DMKN, LTBP2,
OSMR, FJX1, COLEC12, GPRC5B, FGF7, ROBO4, AC100830.3, MIR497HG, GLI1, STC1, EDIL3, USHBP1,
COL7A1, KCNE4, EGFL7, THSD1, INHBB, CNTN1, COL6A3, HAPLN1, MAPK10, PRICKLE2, PTCH1,
PCDHB10, LOX, RP11-157P1.4, MYCT1, MXRA5, EFHD1, TPO, TRPA1, ARHGAP29, TPM2, AHNAK2,
BOC, ABLIM3, ADAMTS5, MFAP2, MYOZ3, DCLK1, SOX7, SNCAIP, DCHS1, HMGCLL1, OSR1, AVPR2,
AMPH, C14orf37, FLT1, PPAP2B, SYNPO2, SCARF2, SLC9A3R2, PTGDR2, CRISPLD2, SLC16A2, WNT2B,
CHODL, LCA5, CNTNAP3B, ADAMTS12, SNED1, RUSC2, PITX1, CFD, CALD1, THY1, CTHRC1, CCL8,
TNFRSF10C, RP11-611D20.2, FGF13, HIF3A, FUT1, RP11-23P13.7, WNT5A, FGD5, FAP, MMP11, TRPC6,
DACT1, LAMA5, COX7A1, ARHGEF25, JAM2, GGT5, PEAR1, RPS6KA2, LPL, TMEM88, SCUBE1,
IGFBP3, CD320, TCF7L1, CACHD1, HOXD3, TFPI, SOX18, MIR143HG, JAG2, TRPC1, TSPAN9,
NDUFA4L2, CTD-2314B22.3, HAS1, ARL9, ACKR3, CD248, HOXA11, AASS, CTSK, EVA1A, TNFRSF11B,
CTD-2269F5.1, AL590822.1, A2M, NLGN4Y, DES, CCDC80, GRIP2, WNT5B, P4HA3, FBN2, PLAU, EML1,
MMP1, FXYD6, MDFI, COL3A1, TM4SF1, RP11-112H10.4, LAMB1, COL9A1, RP11-204M4.2, ADM5,
SOD3, CCL14, CLMP, CCL19, NSG1, PPP1R14A, SLC14A1, ROBO1, EMILIN1, RHOJ, MDGA1, C11orf96,
ZC3HAV1L, TMEM150C, RP11-486G15.2, F3, CPXM1, RP11-532F6.3, ANGPT1, FGD1, LPAR3, PRKG1,
VCAM1, FZD4, SDK1, SCGB1B2P, IGSF9B
F.Villus GS1-18A18.1, RP11-804A23.4, REEP2, ENHO, VSTM2A, NPY, PCSK6, FGF9, LPAR3, GSG1L, GLP2R,
PTGIS, COL4A5, FAM150B, TTC25, AC002511.2, AC003090.1, CNTFR, AC079779.4, SOX6, BMP5, POSTN,
WNT5B, NSG1, PDGFRA, PDGFD, DHRS7C, PTGDR2, RP11-231D20.2, SCUBE1, LANCL2, ZBTB20-AS2,
MMP11, DMKN, COL4A6, PTCHD1, EDNRB, C10orf107, RP11-423H2.3, RP4-755D9.1, BMP4, GADD45G,
CTC-349C3.1, SEMA3A, KRTDAP, TNFSF15, C1QL1, OBSCN, INSC, F3, APOD
F.Villus_1

EFCAB1, TTC25, TSNAXIP1, FAM178B, GDF15
F.Villus_2

RP11-626G11.3, LGALS8-AS1, CTD-2651B20.1, RP11-231D20.2, LPAR3, RP11-834C11.5, AC079779.4, NPY,
RP4-794H19.4, ZC3HAV1L, C14orf23, FOLR1

TABLE 9A

| Epithelial | | | | | | |
|---|---|---|---|---|---|---|
| identE.Absorptive | identE.Absorptive_All | identE.Absorptive_TA | identE.Absorptive_TA_1 | identE.Absorptive_TA_2 | identE.Best4_Enterocytes | identE.Cycling_TA |
| CA4 | C15orf48 | C15orf48 | LGALS4 | COX4I1 | BEST4 | TUBA1B |
| CEACAM5 | C19orf33 | LGALS4 | C15orf48 | LGALS4 | CA7 | H2AFZ |
| CLDN3 | CA2 | PHGR1 | PIGR | C15orf48 | SPIB | GSTP1 |
| CLDN7 | CES2 | PIGR | KRT8 | AGR2 | OTOP2 | PRDX5 |
| EPCAM | CLDN7 | TXN | MT-ND1 | TXN | MT1G | UBE2C |
| FABP1 | EPCAM | KRT8 | MT-CO3 | FABP1 | CA4 | HMGB2 |
| FTH1 | ETHE1 | FABP1 | EPCAM | ATP5G1 | MT2A | RPS2 |
| FXYD3 | FABP1 | ATP5G1 | MT-CYB | MGST1 | KRT8 | CENPM |
| GUCA2A | FXYD3 | EPCAM | KRT18 | ATP5G3 | MT1H | RPS3 |
| GUCA2B | KRT19 | AGR2 | TXN | EPCAM | SDCBP2 | RPL36A |
| KRT20 | KRT8 | MT1G | MT-ND4 | PIGR | MT1E | RPS5 |
| KRT8 | LGALS3 | GPX2 | MT1G | GPX2 | KRT19 | STMN1 |
| LGALS3 | LGALS4 | MGST1 | MT-CO2 | TMSB10 | LGALS3 | TK1 |
| LYPD8 | MT-CO2 | MT-ND1 | MT-ATP6 | COX5B | PHGR1 | RPLP0 |
| PHGR1 | PHGR1 | SELENBP1 | MT-ND2 | PHGR1 | KRT20 | RPL8 |
| PLAC8 | PIGR | KRT18 | AGR2 | CYC1 | LYPD8 | RPS10 |
| SDCBP2 | PRSS3 | FXYD3 | CLDN7 | S100A14 | NEURL | MIF |
| SRI | SDCBP2 | MT-CO3 | SELENBP1 | KRT8 | FXYD3 | RPL36 |
| TSPAN1 | SLC26A2 | COX5B | GPX2 | MT1G | LGALS4 | PTTG1 |
| CLDN4 | SLC26A3 | ATP5G3 | ATP5G1 | URAD | FABP1 | RPS18 |
| CEACAM1 | SRI | HMGCS2 | PPP1R1B | SELENBP1 | HES2 | RPS9 |
| CEACAM7 | TMEM54 | CLDN7 | PRDX5 | COX5A | CTSE | RPS6 |
| PRSS3 | TSPAN1 | CHCHD10 | COX5B | LGALS3 | MT1X | ATP5G1 |
| AQP8 | KRT20 | MT-CYB | HMGCS2 | UGT2B17 | EPCAM | C17orf76-AS1 |
| C19orf33 | MS4A12 | CYC1 | MT-ND5 | CHCHD10 | HRCT1 | TMSB10 |
| MISP | GUCA2A | PRDX5 | TSPAN8 | CA2 | S100A10 | RPL7A |

TABLE 9A-continued

| Epithelial | | | | | | | |
|---|---|---|---|---|---|---|---|
| IFI27 | SMIM22 | MT-ND4 | MT-CO1 | COX6C | CKB | RPL35 | |
| PRAP1 | SELENBP1 | PPP1R1B | MT1E | HMGCS2 | ITM2C | RPS15 | |
| CLCA4 | TST | MT-CO2 | LGALS3 | COX6A1 | GUCA2A | BIRC5 | |
| HSD17B2 | CHP2 | COX5A | MGST1 | CLDN7 | MSLN | RPL12 | |
| MUC13 | KRT18 | TSPAN8 | CLDN3 | TSPO | CLDN3 | RPS8 | |
| LGALS4 | CYSTM1 | S100A14 | CHCHD10 | TMEM141 | CLDN4 | COX4I1 | |
| CA2 | S100A10 | TMSB10 | KRTCAP3 | TSPAN8 | TSPAN1 | CENPW | |
| CDHR5 | CLDN3 | COX4I1 | ATP5G3 | KRT18 | SRI | HMGB1 | |
| S100A10 | CA4 | TSPO | S100A14 | FXYD3 | KRT18 | RANBP1 | |
| TMEM54 | PKIB | LGALS3 | KRT19 | C10orf99 | CLDN7 | RPS19 | |
| ITM2C | C10orf99 | CLDN3 | ELF3 | UQCR10 | S100A6 | RPL13 | |
| CYSTM1 | S100A6 | KRTCAP3 | MT-ND3 | C19orf33 | DMBT1 | HIST1H4C | |
| PPDPF | TSPAN8 | CA2 | CA2 | SMIM22 | MT1M | CDKN3 | |
| MYO15B | CA1 | COX6C | CYC1 | COX6B1 | PPDPF | RPL10A | |
| SMIM22 | PLAC8 | C10orf99 | C10orf99 | PPP1R1B | C10orf99 | AGR2 | |
| GPA33 | MISP | MT1E | COX5A | UQCRQ | TMEM54 | CDC20 | |
| AOC1 | CDHR5 | UGT2B17 | KLF5 | ATP5D | CYSTM1 | RPL37A | |
| S100A6 | SLC51B | MT-ATP6 | COX6C | CLDN3 | ELF3 | IGFBP2 | |
| TRIM31 | CEACAM7 | MT-ND2 | MT-RNR1 | RPL8 | PRSS3 | RPSA | |
| CDHR2 | MT-CO3 | TMEM141 | ATP5B | KRTCAP3 | PCSK1N | TYMS | |
| SPINT2 | MT-CO1 | ELF3 | UGT2B17 | KRT19 | CEACAM5 | AURKB | |
| CFDP1 | ANPEP | KRT19 | STARD10 | UQCRH | C15orf48 | RPS21 | |
| EMP1 | S100A14 | ATP5B | TSPO | ATP5B | NOTCH2NL | RPS14 | |
| MEPIA | CKB | STARD10 | FAM3D | AKR1C3 | PIGR | DTYMK | |

| identE.Enterocyte_Immature_1 | identE.Enterocyte_Immature_2 | identE.Enterocyte_Progenitor |
|---|---|---|
| ANPEP | CA1 | CA1 |
| AQP8 | CA2 | CA2 |
| C19orf33 | ETHE1 | FABP1 |
| CA4 | FABP1 | FXYD3 |
| CEACAM5 | FXYD3 | KRT19 |
| CEACAM7 | KRT19 | KRT8 |
| CLCA4 | KRT20 | LGALS4 |
| CTD-2228K2.5 | KRT8 | PHGR1 |
| FABP1 | LGALS3 | SELENBP1 |
| FXYD3 | MS4A12 | C15orf48 |
| GUCA2A | PHGR1 | CKB |
| GUCA2B | SLC26A2 | PIGR |
| LYPD8 | SLC26A3 | LGALS3 |
| MT-CO1 | SLC51B | SLC26A2 |
| MT-RNR2 | TMEM54 | CLDN7 |
| PHGR1 | SRI | KRT18 |
| PLAC8 | PLAC8 | HSD11B2 |
| PRAP1 | MALL | CES2 |
| SDCBP2 | TSPAN1 | ETHE1 |
| SLC26A3 | SELENBP1 | MT1G |
| TSPAN1 | LGALS4 | EPCAM |
| CDHR5 | CTD-2228K2.5 | TSPAN1 |
| CLDN7 | C19orf33 | C19orf33 |
| MISP | PRAP1 | UQCRQ |
| MT-RNR1 | CEACAM7 | TMEM54 |
| MYO15B | SDCBP2 | S100A14 |
| TRIM31 | CKB | HMGCS2 |
| IFI27 | AKR1B10 | MT-CO3 |
| LGALS4 | GUCA2A | COX5B |
| CEACAM1 | TST | C10orf99 |
| NEAT1 | PKIB | MT-CO2 |
| PIGR | SLC25A5 | CHCHD10 |
| KRT8 | GCNT3 | ADIRF |
| KRT20 | CEACAM1 | SMIM22 |
| MT-CO2 | MYL6 | MT-ND1 |
| CLDN4 | CLDN7 | CLDN3 |
| SMIM22 | CES2 | SLC26A3 |
| FTH1 | SULT1A2 | TST |
| SFN | FLNB | CHP2 |
| RP11-48O20.4 | AQP8 | MT-ND4 |
| MS4A12 | UQCRQ | AMN |
| ELF3 | CHP2 | ATP5G3 |
| HIST1H1C | RP11-48O20.4 | MT1E |
| MUC12 | ANPEP | KRT20 |
| PRSS3 | C2orf88 | SRI |
| TMEM54 | CYSTM1 | S100A6 |
| CA2 | CDHR5 | MT-ND5 |
| SLC51B | BSG | AKR1C3 |
| AMN | IFI27 | MT-ATP6 |
| MUC13 | COX6A1 | MT1M |

TABLE 9A-continued

| Epithelial | | | | | |
|---|---|---|---|---|---|
| identE.Enterocytes | identE.Enteroendocrine | identE.Epithelial | identE.Goblet | identE.Immature_Enterocytes | identE.Immature_Goblet |
| ANPEP | PCSK1N | AGR2 | CEACAM5 | AQP8 | AGR2 |
| APOBEC3B | SCGN | AMN | CLDN4 | C15orf48 | CLCA1 |
| AQP8 | CHGA | C10orf99 | FAM3D | C19orf33 | FCGBP |
| C19orf33 | CRYBA2 | C15orf48 | FCGBP | CA1 | ITLN1 |
| CA4 | PYY | C19orf33 | FXYD3 | CA2 | KLK1 |
| CEACAM1 | FEV | CA2 | GSN | CDHR5 | KRT18 |
| CEACAM5 | SCG5 | CDHR5 | IFI27 | CEACAM7 | LRRC26 |
| CEACAM7 | GCG | CKB | LYPD8 | CES2 | MUC2 |
| CFDP1 | TTR | CLDN3 | MUC1 | CKB | REP15 |
| CLCA4 | MS4A8 | CLDN4 | MUC2 | CLDN7 | RETNLB |
| CLDN23 | NEUROD1 | CLDN7 | TFF1 | CTD-2228K2.5 | RNASE1 |
| CLDN7 | CACNA1A | COX5B | TFF3 | EPCAM | SERPINA1 |
| CTD-2228K2.5 | STARD10 | ELF3 | TSPAN1 | ETHE1 | SPINK1 |
| EMP1 | HOXB9 | EPCAM | ZG16 | FABP1 | SPINK4 |
| FTH1 | MLXIPL | FABP1 | MUC13 | FXYD3 | ST6GALNAC1 |
| FXYD3 | PRDX5 | FAM3D | REP15 | GUCA2A | TFF3 |
| GPRC5A | RAB26 | FCGBP | S100P | KRT18 | WFDC2 |
| GUCA2A | CPE | FXYD3 | PHGR1 | KRT19 | ZG16 |
| GUCA2B | KIF12 | HMGCS2 | MT-RNR2 | KRT20 | LGALS4 |
| HIST1H1C | SLC29A4 | IFI27 | CLDN7 | KRT8 | TPSG1 |
| HPGD | FXYD3 | KRT18 | ENTPD8 | LGALS3 | PHGR1 |
| IFI27 | CHGB | KRT19 | ELF3 | LGALS4 | FXYD3 |
| IL32 | SCT | KRT20 | NEAT1 | MALL | STARD10 |
| KRT20 | VWA5B2 | KRT8 | KRT18 | MISP | GMDS |
| LYPD8 | MDK | LGALS3 | MALAT1 | MS4A12 | KRT8 |
| MISP | CES1 | LGALS4 | SERPINA1 | MT-CO2 | FAM3D |
| MS4A12 | KIAA1324 | MT-ATP6 | VSIG2 | PHGR1 | HEPACAM2 |
| MYO15B | C15orf48 | MT-CO1 | PLAC8 | PIGR | MT-ND1 |
| NLN | DDC | MT-CO2 | LGALS4 | PLAC8 | RPL36 |
| PKIB | HOXB8 | MT-CO3 | SDCBP2 | PRAP1 | NPDC1 |
| PLAC8 | LGALS4 | MT-CYB | KLK1 | PRSS3 | EPCAM |
| PRAP1 | ERI3 | MT-ND1 | TM4SF5 | SDCBP2 | MB |
| RP11-48020.4 | SOX4 | MT-ND2 | MT-RNR1 | SELENBP1 | C15orf48 |
| SDCBP2 | MARCKSL1 | MT-ND4 | BCAS1 | SLC26A2 | SMIM22 |
| SLC26A3 | REG4 | MT-RNR1 | KRT8 | SLC26A3 | ANG |
| SLC51B | TFF3 | MT-RNR2 | AMN | SLC51B | ANXA13 |
| SRI | KRT8 | MT1E | CLDN3 | SMIM22 | MT-CO3 |
| TMEM37 | RTN1 | MT1G | SPATS2L | SRI | TSPAN13 |
| TRIM31 | CXXC4 | PHGR1 | GUCA2B | TMEM54 | NANS |
| TSPAN1 | TPH1 | PIGR | SMIM6 | TSPAN1 | IFI27 |
| TMIGD1 | C19orf77 | PRSS3 | TPSG1 | TST | CREB3L1 |
| MALL | RAMP1 | S100A14 | CREB3L1 | IFI27 | COX6C |
| MUC13 | SPINK1 | S100A6 | C19orf33 | AMN | PRDX5 |
| HSD17B2 | ARX | SELENBP1 | CLTB | S100A6 | C2orf82 |
| FABP1 | DNAJC12 | SMIM22 | MT-CO1 | PKIB | RP11-234B24.2 |
| SFN | RAB3B | SPINT2 | MLPH | ANPEP | SPDEF |
| NEAT1 | RP11-279F6.1 | TMEM54 | SMIM22 | CA4 | TMEM141 |
| PRSS3 | NPDC1 | TSPAN1 | ZG16B | CHP2 | TCEA3 |
| MEP1A | TMEM141 | TSPAN8 | CAPN8 | MT-CO1 | CLDN7 |
| CDA | CLDN7 | STAP2 | EPCAM | CYSTM1 | URAD |

| | | identE.Secretory | identE.Secretory_AII | identE.Secretory_TA | identE.Stem | identE.Tuft |
|---|---|---|---|---|---|---|
| | | FCGBP | CLCA1 | TFF3 | PRDX5 | KRT18 |
| | | KRT18 | FCGBP | ITLN1 | LEFTY1 | AZGP1 |
| | | MUC2 | FXYD3 | RPL36 | ASCL2 | SH2D6 |
| | | TFF1 | ITLN1 | KLK1 | GPX2 | MARCKSL1 |
| | | TFF3 | KLK1 | PRDX5 | C17orf76-AS1 | BIK |
| | | ZG16 | KRT18 | SPINK4 | RPLP0 | LRMP |
| | | ELF3 | KRT8 | CLCA1 | CDCA7 | HCK |
| | | KRT8 | LGALS4 | LRRC26 | RGMB | PTPN18 |
| | | MT-RNR2 | MUC2 | MUC2 | RPS18 | ANXA13 |
| | | CLDN4 | REP15 | RETNLB | RPL12 | KRT8 |
| | | MUC1 | SERPINA1 | RPL12 | SMOC2 | ATP2A3 |
| | | GSN | SPINK1 | RPS18 | RPS6 | AVIL |
| | | MALAT1 | SPINK4 | WFDC2 | RPS3 | IL17RB |
| | | FXYD3 | TFF3 | FCGBP | PPP1R1B | TRPM5 |
| | | LGALS4 | WFDC2 | RPL8 | GAS5 | ALOX5 |
| | | CEACAM5 | ZG16 | AGR2 | GNB2L1 | SH2D7 |
| | | LYPD8 | LRRC26 | RPS9 | RPS2 | BMX |
| | | MT-CO1 | PHGR1 | GPX2 | MARCKSL1 | PTGS1 |
| | | IFI27 | AGR2 | RPS2 | LGALS4 | ELF3 |
| | | FAM3D | TPSG1 | RPS3 | NUPR1 | PPDPF |
| | | S100P | RNASE1 | SPINK1 | RPS5 | EIF1B |
| | | MT-RNR1 | RETNLB | RPS15 | ETS2 | TPM1 |
| | | TSPAN1 | STARD10 | ZG16 | PIGR | GNG13 |

TABLE 9A-continued

| Epithelial | | | | |
|---|---|---|---|---|
| REP15 | MT-ND1 | RPS14 | RPL29 | PSTPIP2 |
| MUC13 | FAM3D | TMSB10 | SLC25A6 | MALAT1 |
| S100A6 | SMIM22 | RPS5 | CLDN7 | HOTAIRM1 |
| CLDN7 | EPCAM | PIGR | RPL31 | SPIB |
| TM4SF5 | MT-CO3 | C17orf76-AS1 | RPS9 | TFF3 |
| CLDN3 | C15orf48 | RPL35 | RPL8 | CC2D1A |
| PHGR1 | MT-ND4 | STARD10 | EPHB3 | HTR3E |
| SERPINA1 | ELF3 | CLDN7 | RPL36A | IFT172 |
| SMIM22 | CLDN7 | RPS8 | RPL3 | PLCG2 |
| SPATS2L | CLDN3 | RNASE1 | RPL10A | DEFB1 |
| ENTPD8 | IFI27 | LGALS4 | RPL5 | RASSF6 |
| MT-CO3 | NPDC1 | RPL18 | RPL36 | HPGDS |
| MARCKSL1 | PIGR | RPL37A | RPS4X | MATK |
| MT-ND4 | ST6GALNAC1 | RPL13 | RPS24 | MT-CO3 |
| TPM1 | CLDN4 | URAD | RPL14 | MT-CO1 |
| KLK1 | MT-CYB | MT-ND1 | IMPDH2 | ANXA4 |
| MT-CO2 | MT-ATP6 | RPL13A | EPCAM | PPAP2C |
| BCAS1 | MT-ND2 | C15orf48 | RPL7A | AOC1 |
| EPCAM | MT-CO1 | RPL7A | RPL13 | OGDHL |
| AZGP1 | MT-CO2 | REP15 | RPS3A | ATPIF1 |
| MT-ND5 | MARCKSL1 | RPS6 | RPL13A | EPS8L3 |
| PRSS3 | MB | MT1G | ALDH1B1 | S100A6 |
| NEAT1 | CREB3L1 | EPCAM | RPS8 | FURIN |
| SMIM6 | S100A6 | RPL32 | SLC12A2 | H2AFJ |
| ZG16B | ANG | COX4I1 | C15orf48 | TMEM63A |
| MT-ND1 | MUC1 | RPL29 | RPS19 | IFI6 |
| VSIG2 | SPINT2 | RPL18A | SPINK1 | EHF |

TABLE 9B

| Fibroblast | | | | |
|---|---|---|---|---|
| identF.Crypt | identF.Crypt_RSPO3 | identF.Crypt_hiFos | identF.Crypt_loFos_1 | identF.Crypt_loFos_2 |
| A2M | DCN | A2M | A2M | APOE |
| ABCA8 | LUM | ABCA8 | ABCA8 | CFD |
| ADAM28 | EFEMP1 | ADAMDEC1 | ADAMDEC1 | IGFBP7 |
| ADAMDEC1 | FBLN1 | APOE | APOE | IFITM3 |
| ADH1B | CFH | C1R | C1R | DCN |
| APOE | CFD | C1S | C1S | ADAMDEC1 |
| BMP4 | CCDC80 | CCL2 | CALD1 | TMEM176B |
| C1R | C1R | CCL8 | CCL13 | FBLN1 |
| C1S | C1S | CFD | CCL2 | MFAP4 |
| CALD1 | CCL11 | COL1A1 | CCL8 | LUM |
| CCL11 | ADH1B | COL1A2 | CFD | SOD3 |
| CCL13 | COL1A2 | COL3A1 | CFH | CXCL14 |
| CCL2 | CXCL12 | COL6A2 | CLEC11A | A2M |
| CCL8 | GSN | CTSC | COL1A1 | C1S |
| CD63 | MFAP4 | CXCL12 | COL1A2 | GSN |
| CFD | IGFBP7 | CXCL14 | COL3A1 | C1R |
| CFH | SOD3 | CYGB | COL6A2 | RARRES2 |
| CLEC11A | C7 | DCN | CTSC | LGALS1 |
| COL1A1 | SERPINF1 | FBLN1 | CTSK | COL1A2 |
| COL1A2 | PLAC9 | GPX3 | CXCL12 | COL3A1 |
| COL3A1 | MGP | GSN | CXCL14 | RNA28S5 |
| COL6A1 | ADAMDEC1 | HAPLN1 | CYGB | TCF21 |
| COL6A2 | SERPING1 | IFITM3 | DCN | CCL13 |
| CTSC | TCF21 | IGFBP7 | DKK3 | CTSC |
| CTSK | CTSK | LUM | FBLN1 | CCL8 |
| CXCL12 | PTGDS | MFAP4 | GGT5 | LTBP4 |
| CXCL14 | IFITM3 | PPAP2B | GPX3 | CCL11 |
| CYGB | LTBP4 | PROCR | GSN | COL6A2 |
| DCN | THY1 | RBP1 | IFITM3 | CD63 |
| DKK3 | COL3A1 | SERPINF1 | IGFBP7 | CD81 |
| EFEMP1 | RSPO3 | SOD3 | LGALS1 | NGFRAP1 |
| EFEMP2 | PMP22 | TCF21 | LINC01082 | RBP1 |
| EMILIN1 | VIM | TMEM176B | LUM | TMEM176A |
| FABP4 | RARRES2 | VIM | MFAP4 | SELM |
| FBLN1 | C3 | CALD1 | MMP2 | PTGDS |
| GGT5 | APOE | STMN2 | PLAC9 | CALD1 |
| GNG11 | LGALS1 | PTN | PMP22 | COL1A1 |
| GPX3 | TMEM176B | LINC01082 | PPAP2B | CCL2 |
| GSN | ASPN | CTSK | PROCR | TIMP1 |
| HAAO | COL6A2 | CCL13 | PTN | QSOX1 |
| HAPLN1 | CALD1 | CFH | RARRES2 | PLAC9 |

TABLE 9B-continued

| Fibroblast | | | | |
|---|---|---|---|---|
| IFITM3 | CCL2 | PMP22 | RBP1 | RAB13 |
| IGFBP6 | TIMP1 | CCL11 | SERPINF1 | S100A13 |
| IGFBP7 | A2M | DKK3 | SERPING1 | CYGB |
| LAPTM4A | GPX3 | LGALS1 | SOD3 | GPX3 |
| LGALS1 | LAPTM4A | SEPP1 | SPARC | ABCA8 |
| LINC01082 | COL14A1 | PLAC9 | TCF21 | PPAP2B |
| LTBP4 | PCOLCE | GGT5 | TIMP1 | CST3 |
| LUM | DPT | RARRES2 | TMEM176A | CLEC11A |
| MATN2 | CD63 | SERPING1 | TMEM176B | VKORC1 |

| | identF.Endothelial | identF.Endothelial_1 | identF.Fibroblast | identF.Glia |
|---|---|---|---|---|
| | BCAM | CD320 | A2M | ALDH1A1 |
| | CAV1 | CLDN5 | ABCA8 | CD9 |
| | CCDC85B | FABP5 | ADAMDEC1 | CLU |
| | CD320 | GNG11 | APOE | CRYAB |
| | CD36 | IGFBP4 | BMP4 | S100B |
| | CD59 | PLVAP | BST2 | TUBA1A |
| | CLDN5 | RAMP2 | C1R | GPM6B |
| | CLEC14A | SLC9A3R2 | C1S | PMP22 |
| | CRIP2 | CRIP2 | CALD1 | PLP1 |
| | ECSCR | SPARCL1 | CCL11 | SPARC |
| | EGFL7 | ESAM | CCL13 | SPP1 |
| | ENG | EGFL7 | CCL2 | PRNP |
| | ESAM | IFITM3 | CCL8 | SEMA3B |
| | FABP5 | VAMP5 | CD63 | JUN |
| | FKBP1A | GSN | CFD | MATN2 |
| | GIMAP7 | TMEM88 | CFH | FOS |
| | GNG11 | CD36 | CLEC11A | CYR61 |
| | HLA-C | CLEC14A | COL1A1 | CD59 |
| | HLA-E | CAV1 | COL1A2 | COMT |
| | IFITM3 | RAMP3 | COL3A1 | IGFBP7 |
| | IGFBP4 | HLA-E | COL6A1 | CALM2 |
| | IGFBP7 | ENPP2 | COL6A2 | HES1 |
| | ITM2B | TXNIP | CTSC | MPZ |
| | JAM2 | JAM2 | CTSK | LGALS1 |
| | MGP | ECSCR | CXCL12 | ANXA2 |
| | NPDC1 | SEPW1 | CXCL14 | LGI4 |
| | PLVAP | IGFBP7 | CYGB | GFRA3 |
| | RAMP2 | CD59 | DCN | TUBB2B |
| | RAMP3 | MGP | DKK3 | CNN3 |
| | RBP5 | TM4SF1 | DMKN | C8orf4 |
| | SEPW1 | BCAM | ECM1 | PEBP1 |
| | SLC9A3R2 | NPDC1 | EFEMP2 | TIMP3 |
| | SNCG | CCDC85B | EID1 | DKK3 |
| | SPARCL1 | VWF | EMILIN1 | NRXN1 |
| | TM4SF1 | CD74 | FBLN1 | IFITM3 |
| | TMEM88 | GIMAP7 | GGT5 | TMEM176B |
| | VWF | ICAM2 | GPX3 | CCL2 |
| | FAM167B | FKBP1A | GSN | IER2 |
| | AC011526.1 | RBP7 | HAAO | JUNB |
| | SDPR | IFITM2 | HAPLN1 | VIM |
| | IFITM2 | SDPR | IFITM3 | EGR1 |
| | ENPP2 | HLA-C | IGFBP6 | NDRG2 |
| | CYYR1 | HLA-DRB1 | IGFBP7 | RGS16 |
| | PRSS23 | CYYR1 | LAMA4 | PMEPA1 |
| | GSN | ENG | LAPTM4A | SOCS3 |
| | HSPB1 | ITM2B | LGALS1 | RHOB |
| | CTGF | IFI27 | LGALS3BP | CBR1 |
| | SPARC | A2M | LINC01082 | S100A4 |
| | CD34 | RBP5 | LTBP4 | SORBS2 |
| | TSPAN7 | HES1 | LUM | AP1S2 |

| identF.Inflammatory | identF.Microvascular | identF.Myofibrobiasts | identF.Pcap_Venules | identF.Pericytes |
|---|---|---|---|---|
| NNMT | CD320 | ACTA2 | CLDN5 | RGS5 |
| LUM | FABP5 | TAGLN | NPC2 | MYL9 |
| C1S | PLVAP | MYL9 | DARC | TINAGL1 |
| MMP2 | GNG11 | TPM2 | CLU | CSRP2 |
| COL3A1 | PRSS23 | ACTG2 | TSPAN7 | NDUFA4L2 |
| IFITM3 | CD36 | PDLIM3 | GNG11 | IGFBP7 |
| CXCL14 | GSN | TPM1 | VWF | HIGD1B |
| C1R | SLC9A3R2 | MYLK | FABP5 | BGN |
| DCN | RAMP2 | SOSTDC1 | RAMP3 | COX4I2 |
| IGFBP7 | CRIP2 | DSTN | CPE | ADIRF |
| RARRES2 | RAMP3 | NDUFA4 | IGFBP4 | FRZB |
| COL1A2 | ESAM | MYH11 | PLVAP | TSC22D1 |
| LGALS1 | SPARCL1 | MYL6 | RAMP2 | CD36 |

TABLE 9B-continued

| Fibroblast | | | | |
|---|---|---|---|---|
| SPARC | VWF | FHL1 | LY6E | SOD3 |
| PLAT | VWA1 | HHIP | ECSCR | PDGFRB |
| FBLN1 | RGCC | PRKCDBP | JAM2 | TPPP3 |
| TIMP1 | ECSCR | SELM | ITM2B | MGP |
| COL1A1 | ITM2B | LGALS1 | EGFL7 | NOTCH3 |
| MFGE8 | EGFL7 | TGFB1I1 | SPARCL1 | MFGE8 |
| TSPAN4 | ENG | IGFBP7 | CD320 | HSPB1 |
| COL6A2 | RBP5 | CXCL14 | MADCAM1 | ACTA2 |
| MFAP4 | SDPR | HSPB1 | IGFBP7 | IFITM3 |
| COL6A1 | VAMP5 | TM4SF1 | HLA-E | EGR1 |
| SERPING1 | TMEM88 | HSD17B6 | APLNR | BCAM |
| TMEM176B | IGFBP4 | DCN | CLEC14A | GPX3 |
| LY6E | FKBP1A | FLNA | IFITM3 | HLA-C |
| PROCR | CLEC14A | CNN1 | DUSP23 | CALD1 |
| RBP1 | IGFBP7 | PPIC | HHEX | LGALS1 |
| CCL2 | CAV1 | NPNT | CTGF | PKIG |
| SOD3 | MGP | PDLIM7 | NNMT | HES4 |
| DMKN | BCAM | COL1A2 | NPDC1 | CAV1 |
| PLAU | SPARC | CES1 | TM4SF1 | PRKCDBP |
| SELM | CCDC85B | CSRP1 | ICAM1 | GEM |
| APOE | PLAT | ILK | GIMAP7 | ZFP36L1 |
| CALD1 | IFITM3 | ADAMDEC1 | AC011526.1 | FAM162B |
| F3 | CA4 | CAV1 | SNCG | PGF |
| CTSK | TM4SF18 | COL3A1 | CD74 | NR2F2 |
| PKIG | TMEM204 | LUM | CRIP2 | TPM2 |
| TPM2 | HLA-E | PPP1R14A | FAM167B | MAP1LC3A |
| CTSC | HSPG2 | SPARC | FAM213A | EPHX1 |
| A2M | EMCN | SMTN | SDCBP | PRSS23 |
| TMEM176A | PASK | APOE | CAV1 | CALM2 |
| TCF21 | FAM167B | C1S | TNFSF10 | MCAM |
| GPX3 | ELTD1 | C1R | CTNNAL1 | STEAP4 |
| PCOLCE | SLC14A1 | NBL1 | HLA-DRB1 | GADD45B |
| MYL9 | SNCG | TMEM176B | FKBP1A | STOM |
| CYGB | PODXL | WFDC1 | HLA-DRA | LHFP |
| WARS | FLT1 | NEXN | GIMAP4 | NDUFAF4 |
| RNA28S5 | CAV2 | SPARCL1 | BCAM | COL18A1 |
| STMN2 | CLDN5 | LINC01082 | CD34 | EPAS1 |

| | identF.Stromal | identF.Villus | identF.Villus_1 | identF.Villus_2 |
|---|---|---|---|---|
| | A2M | AGT | CXCL14 | BMP4 |
| | ADAMDEC1 | BMP4 | FRZB | COL6A2 |
| | APOE | C1S | PLAT | CXCL14 |
| | BMP4 | CALD1 | POSTN | DMKN |
| | BST2 | CAV1 | DMKN | F3 |
| | C1R | COL1A2 | NSG1 | FRZB |
| | C1S | COL3A1 | NBL1 | MMP2 |
| | CALD1 | COL6A1 | MMP2 | NSG1 |
| | CCL2 | COL6A2 | COL6A1 | PLAT |
| | CCL8 | CXCL14 | FOS | RARRES2 |
| | CD63 | CYGB | CAV1 | LGALS1 |
| | CFD | DMKN | VSTM2A | COL6A1 |
| | CFH | EDNRB | COL6A2 | TMEM176B |
| | CLEC11A | ENHO | TMEM176B | POSTN |
| | COL1A1 | F3 | BMP4 | ENHO |
| | COL1A2 | FRZB | IGFBP7 | IGFBP3 |
| | COL3A1 | GPX3 | ENHO | IGFBP7 |
| | COL6A1 | HSD17B2 | CYGB | IFITM3 |
| | COL6A2 | IFITM3 | LGALS1 | CALD1 |
| | CRIP2 | IGFBP3 | SDC2 | CAV1 |
| | CTSC | IGFBP7 | EDNRB | VSTM2A |
| | CTSK | LGALS1 | MFAP4 | COL3A1 |
| | CXCL12 | MFAP4 | CALD1 | GPX3 |
| | CXCL14 | MMP2 | IGFBP3 | MFGE8 |
| | CYGB | NBL1 | RARRES2 | TPM2 |
| | DCN | NSG1 | GADD45B | TIMP1 |
| | ECM1 | PLAT | GPX3 | SDC2 |
| | EFEMP2 | POSTN | JUNB | CYGB |
| | EID1 | RARRES2 | TPM2 | SPARC |
| | EMILIN1 | SDC2 | SERPINF1 | COL1A2 |
| | FBLN1 | SERPINF1 | EGR1 | MFAP4 |
| | GNG11 | SPARC | HSD17B2 | HSD17B2 |
| | GPX3 | TIMP1 | IER2 | NBL1 |
| | GSN | TMEM176B | SPARC | AGT |
| | HSPB1 | TPM2 | IFITM3 | EDNRB |
| | IFITM1 | VSTM2A | COL3A1 | FENDRR |
| | IFITM3 | FOXF1 | C1S | S100A13 |
| | IGFBP6 | FENDRR | | FOXF1 |

TABLE 9B-continued

| Fibroblast | | | |
|---|---|---|---|
| IGFBP7 | COL1A1 | COL1A2 | COL1A1 |
| LAPTM4A | SCPEP1 | MYL9 | C1S |
| LGALS1 | MFGE8 | HSPA1A | SERPINF1 |
| LINC01082 | C1R | JUN | LGALS3BP |
| LTBP4 | PPP1R14A | AGT | SCPEP1 |
| LUM | LAPTM4A | PDGFD | ECM1 |
| MFAP4 | ECM1 | FOXF1 | APLP2 |
| MFGE8 | MYL9 | ID1 | WFDC1 |
| MMP2 | PKIG | C11orf96 | PPP1R14A |
| MYL9 | TMEM176A | PKIG | PKIG |
| NGFRAP1 | TMEM119 | LAPTM4A | C1R |
| NNMT | S100A13 | FENDRR | LTBP4 |

TABLE 9C

| Immune | | | | |
|---|---|---|---|---|
| identB.Bcells | identB.Cycling | identB.FO | identB.GC | identB.Plasma |
| AC096579.7 | IGHA1 | CD74 | CD79A | AC096579.7 |
| AL928768.3 | IGJ | CD79A | CD79B | AL928768.3 |
| CCR10 | CD79A | HLA-DRA | AL928768.3 | CCR10 |
| CD27 | AL928768.3 | MS4A1 | TCL1A | CD27 |
| CD74 | MZB1 | VPREB3 | SMIM14 | CD79A |
| CD79A | DERL3 | HLA-DPB1 | MS4A1 | CHPF |
| DERL3 | EAF2 | HLA-DRB1 | CD74 | CRELD2 |
| DNAJB9 | IGKC | HLA-DPA1 | LIMD2 | CYTIP |
| EAF2 | IGHA2 | HLA-DQA1 | C7orf10 | DERL3 |
| FAM46C | TNFRSF17 | HLA-DQB1 | MARCKSL1 | DNAJB9 |
| FCRL5 | HERPUD1 | CD79B | VPREB3 | DPP7 |
| FKBP11 | UBE2J1 | CD37 | FCRLA | DUSP5 |
| GNG7 | SSR4 | HERPUD1 | IRF8 | EAF2 |
| HERPUD1 | SEC11C | CXCR4 | SERPINA9 | EVI2B |
| ICAM2 | AC096579.7 | RPS27 | EAF2 | FAM46C |
| IGHA1 | IGLC2 | LTB | CD53 | FCRL5 |
| IGHA2 | DNAJB9 | AL928768.3 | RGS13 | FGF23 |
| IGJ | CD74 | BANK1 | NCF1 | FKBP11 |
| IGKC | CD27 | CD52 | BCAS4 | GNG7 |
| IGLC2 | CCR10 | CD83 | CD40 | GYPC |
| IGLC3 | XBP1 | LINC00926 | SNX29P2 | HERPUD1 |
| IGLL5 | SDF2L1 | RPS23 | PTPRCAP | ICAM2 |
| MEI1 | POU2AF1 | IGKC | ISG20 | IFNAR2 |
| MZB1 | FKBP11 | RPS25 | RHOH | IGHA1 |
| PIM2 | IGLC3 | IGHM | CD37 | IGHA2 |
| POU2AF1 | CYTIP | RPL23A | POU2AF1 | IGJ |
| PTPRCAP | MANF | RPLP2 | LTB | IGKC |
| SEC11C | GNG7 | RPL21 | HTR3A | IGLC2 |
| SSR4 | SPCS3 | RP5-887A10.1 | HMCES | IGLC3 |
| TNFRSF17 | PNOC | CD19 | AC023590.1 | IGLL5 |
| UBE2J1 | FAM46C | FCRLA | GPR18 | IGLV3-1 |
| SPAG4 | DUSP5 | SMIM14 | CD72 | ISG20 |
| CYTIP | SSR3 | BTG1 | HERPUD1 | LMAN1 |
| CD79B | ISG20 | HLA-DMA | LAPTM5 | MANF |
| EVI2B | RGS2 | LY86 | UBE2J1 | MEI1 |
| GYPC | IGLL5 | RPS8 | HMGN1 | MZB1 |
| DUSP5 | LSP1 | PTPRCAP | CD22 | NUCB2 |
| IGLC7 | TRAM1 | HLA-DRB5 | CD19 | PABPC4 |
| TRAM1 | CD79B | RPS27A | LRMP | PDIA4 |
| SPCS3 | SPCS2 | RPS20 | NEIL1 | PIM2 |
| LSP1 | GYPC | RPS5 | HLA-DMA | PPAPDC1B |
| XBP1 | PIM2 | RPL18A | LY86 | PRDX4 |
| TPST2 | RGS1 | RPL32 | TPD52 | RGCC |
| TXNDC15 | CD38 | RPL3 | IGKC | RGS1 |
| CHPF | PDIA4 | RPL13A | HLA-DQA1 | SDF2L1 |
| SLAMF7 | IFNAR2 | FAU | CD27 | SEC11C |
| PPAPDC1B | TPST2 | CYBA | P2RX5 | SLAMF7 |
| PNOC | ARHGDIB | SELL | HLA-DRA | SPAG4 |
| IGLV3-1 | TSC22D3 | HVCN1 | HLA-DOB | SPCS3 |
| ISG20 | CRELD2 | RPS3A | BASP1 | SSR3 |
| identI.Immune | identI.Lymphoid | identM.CD69neg_Mast | identM.CD69pos_Mast | identM.Cycling |
| ARHGDIB | ARHGDIB | TPSAB1 | H3F3B | TUBA1B |
| CCL5 | CCL5 | VWA5A | NFKBIA | AIF1 |
| CD37 | CD2 | CAPG | PPP1R15A | FTL |

TABLE 9C-continued

| Immune | | | | |
|---|---|---|---|---|
| CD3D | CD3D | LTC4S | TPSAB1 | GPX1 |
| CD3E | CD3E | KRT1 | VWA5A | CST3 |
| CD48 | CD52 | MAOB | ANXA1 | CD74 |
| CD52 | CD69 | HPGDS | JUN | C1QC |
| CD53 | CD7 | CTSG | CTSG | HLA-DRB1 |
| CD69 | CORO1A | GATA2 | GLUL | LYZ |
| CD7 | CYTIP | CLU | CAPG | HLA-DPA1 |
| CORO1A | EVL | SAMSN1 | DNAJA1 | MS4A6A |
| CYBA | IL32 | RP11-354E11.2 | UBB | C1QA |
| CYTIP | LTB | FCER1G | LMNA | HLA-DPB1 |
| EVL | PTPRCAP | ALOX5AP | NFKBIZ | HLA-DRA |
| HCST | RAC2 | SLC18A2 | LTC4S | C1QB |
| LAPTM5 | TRAC | FCER1A | FTH1 | TYROBP |
| LTB | TRBC2 | NSMCE1 | LAPTM4A | PSAP |
| PTPRCAP | SRGN | ANXA1 | C1orf186 | DNASE1L3 |
| RAC2 | IL2RG | ADRB2 | FCER1G | HLA-DQA1 |
| RGS1 | LCK | BTK | HSP90AB1 | HLA-DRB5 |
| SRGN | CD27 | C1orf186 | HPGDS | NPC2 |
| TRBC2 | CD79A | GMPR | CLU | H2AFZ |
| ALOX5AP | NKG7 | CPA3 | DUSP1 | FCER1G |
| TRAC | HCST | ATP6V1F | GATA2 | HLA-DMA |
| NCF1 | CD37 | GLUL | DDX5 | STMN1 |
| TMSB4X | SEPT1 | TSC22D1 | SERPINB1 | LST1 |
| COTL1 | HOPX | SLC45A3 | ASAH1 | MS4A7 |
| DUSP2 | GZMA | HS3ST1 | BTG2 | IGSF6 |
| LCK | CD53 | SVOPL | HSPA1B | HLA-DQB1 |
| IL2RG | ACAP1 | MITF | FCER1A | TUBB |
| EVI2B | RGS1 | TYROBP | HSPA8 | CTSB |
| CKLF | PCED1B-AS1 | CD9 | RPL36AL | IL1B |
| IL32 | CD48 | ALOX5 | DNAJB1 | HLA-DMB |
| HCLS1 | AL928768.3 | SDPR | HPGD | SPI1 |
| CD2 | BTG1 | LMO4 | IER2 | CPVL |
| SAMSN1 | RPS19 | CD44 | HDC | FAM26F |
| NKG7 | TNFRSF17 | NCOA4 | MAOB | VSIG4 |
| PTPRC | CTSW | FAM212A | KRT1 | MS4A4A |
| GPSM3 | B2M | VIM | LMO4 | RNASE6 |
| HOPX | ICAM3 | MLPH | HSPA5 | SAT1 |
| ARPC1B | FKBP11 | FXYD5 | EIF1 | CCL3 |
| ACAP1 | TSC22D3 | S100A11 | JUNB | AP2S1 |
| ARPC2 | RHOH | RGS10 | EGR1 | RNASET2 |
| PCED1B-AS1 | TBC1D10C | ARHGDIB | SLC45A3 | NCF4 |
| RHOH | IGHV1OR15-1 | QPCT | RPL7 | FGL2 |
| ITGB7 | CXCR4 | S100A4 | DYNLL1 | CYBA |
| LIMD2 | RPLP1 | CATSPER1 | MALAT1 | LAPTM5 |
| CD27 | STK17A | ASAH1 | SELK | CTSH |
| GZMA | RPL10 | PKM | MIR24-2 | HLA-DQB2 |
| LCP1 | RPL3 | LAPTM4A | FOSB | COTL1 |

| identM.DCs | identM.Macrophages | identM.Mast | identM.Monocytes | identM.Myeloid |
|---|---|---|---|---|
| AIF1 | ACP5 | CAPG | ACP5 | AIF1 |
| CD74 | AIF1 | H3F3B | AIF1 | C1QA |
| CPVL | C1QA | NFKBIA | AMICA1 | C1QB |
| CST3 | C1QB | PPP1R15A | C1QA | C1QC |
| HLA-DMA | C1QC | TPSAB1 | C1QB | CD74 |
| HLA-DMB | CD74 | VWA5A | C1QC | CLEC10A |
| HLA-DPA1 | CST3 | ANXA1 | C1orf162 | CPVL |
| HLA-DPB1 | CTSB | GLUL | CD74 | CST3 |
| HLA-DQA1 | CTSD | CTSG | CLEC10A | CTSB |
| HLA-DQB1 | CTSZ | JUN | COTL1 | CYBA |
| HLA-DRA | CYBA | LTC4S | CPVL | DNASE1L3 |
| HLA-DRB1 | DNASE1L3 | DNAJA1 | CST3 | FAM26F |
| HLA-DRB5 | FCGRT | UBB | CTSB | FCER1G |
| LST1 | FTL | LMNA | CYBA | FGL2 |
| LYZ | FUCA1 | CLU | DNASE1L3 | FTH1 |
| SPI1 | GPX1 | GATA2 | FAM26F | FTL |
| CLEC10A | HLA-DMA | NFKBIZ | FCER1G | GLUL |
| HLA-DQB2 | HLA-DMB | LAPTM4A | FGL2 | GPX1 |
| LGALS2 | HLA-DPA1 | FTH1 | FTL | HLA-DMA |
| AMICA1 | HLA-DPB1 | C1orf186 | GPX1 | HLA-DMB |
| COTL1 | HLA-DQA1 | HSP90AB1 | GRN | HLA-DPA1 |
| TYROBP | HLA-DQB1 | HPGDS | HLA-DMA | HLA-DPB1 |
| FCER1G | HLA-DRA | FCER1G | HLA-DMB | HLA-DQA1 |
| FCER1A | HLA-DRB1 | KRT1 | HLA-DPA1 | HLA-DQA2 |
| IL1B | HLA-DRB5 | MAOB | HLA-DPB1 | HLA-DQB1 |
| HLA-DQA2 | IGSF6 | ASAH1 | HLA-DQA1 | HLA-DQB2 |
| MS4A6A | LGMN | FCER1A | HLA-DQA2 | HLA-DRA |
| CD83 | | SERPINB1 | HLA-DQB1 | HLA-DRB1 |

TABLE 9C-continued

| Immune | | | | |
|---|---|---|---|---|
| DNASE1L3 | LST1 | DUSP1 | HLA-DQB2 | HLA-DRB5 |
| GPX1 | LYZ | BTG2 | HLA-DRA | IFI30 |
| FGL2 | MS4A4A | DDX5 | HLA-DRB1 | IGSF6 |
| SRGN | MS4A6A | RP11-354E11.2 | HLA-DRB5 | IL1B |
| C1orf162 | MS4A7 | HDC | IFI30 | LST1 |
| ACTB | NPC2 | SLC45A3 | IGSF6 | LYZ |
| ITGB2 | PSAP | IER2 | IL1B | MPEG1 |
| FAM26F | RNASE1 | CPA3 | ITGB2 | MS4A4A |
| MNDA | RNASET2 | LMO4 | LAPTM5 | MS4A6A |
| SGK1 | S100A11 | HSPA8 | LGALS1 | MS4A7 |
| CFP | SAT1 | HSPA1B | LST1 | NPC2 |
| SAT1 | SEPP1 | HSPA5 | LYZ | PSAP |
| PLAUR | STAB1 | HPGD | MPEG1 | RNASE6 |
| IFI30 | TMSB4X | SLC18A2 | MS4A4A | RNASET2 |
| GPR183 | TYROBP | RPL7 | MS4A6A | S100A11 |
| RNASET2 | CD14 | EGR1 | MS4A7 | SAT1 |
| MPEG1 | SDS | DNAJB1 | NPC2 | SPI1 |
| IGSF6 | GRN | RPL36AL | PLAUR | SRGN |
| RGS2 | CTSS | ATP6V1F | PSAP | TMSB4X |
| LSP1 | APOC1 | MALAT1 | RGS10 | TYROBP |
| LY86 | SPI1 | MIR24-2 | RNASE6 | VSIG4 |
| RNASE6 | AP2S1 | CLIC1 | RNASET2 | SDS |

| identM.Neutrophils | identM.Tissue_DCs | identM.Tolerogenic_DCs | identT.Activated_CD4_hiFos | identT.Activated_CD4_loFos |
|---|---|---|---|---|
| CST3 | AIF1 | CST3 | TRBC2 | ANXA1 |
| LYZ | CD74 | CPVL | TRAC | TRAC |
| AIF1 | CLEC10A | IDO1 | CD69 | CD3D |
| LST1 | CST3 | CD74 | ANXA1 | LTB |
| HLA-DRB1 | HLA-DMA | SNX3 | CD3D | S100A4 |
| HLA-DRA | HLA-DPA1 | HLA-DPB1 | IL32 | TRBC2 |
| FTL | HLA-DPB1 | CLEC9A | S100A4 | IL32 |
| HLA-DPB1 | HLA-DQA1 | HLA-DPA1 | CD52 | CD52 |
| IL1B | HLA-DQB1 | DNASE1L3 | LTB | RPLP1 |
| PLAUR | HLA-DRA | HLA-DRB1 | CD2 | EEF1A1 |
| TYROBP | HLA-DRB1 | LGALS2 | TSC22D3 | ARHGDIB |
| SOD2 | LST1 | HLA-DRA | DNAJA1 | RPL10 |
| CD74 | LYZ | HLA-DQB1 | CD3E | RPS27A |
| HLA-DPA1 | FCER1A | HLA-DQA1 | ARHGDIB | RPS25 |
| FCER1G | TYROBP | CTD-2319I12.1 | KLF6 | RPL21 |
| HLA-DQB1 | CPVL | LYZ | BTG1 | CD3E |
| GPX1 | HLA-DRB5 | HLA-DRB5 | EIF1 | CXCR4 |
| HLA-DRB5 | IL1B | C1orf54 | RPLP1 | RPS19 |
| HLA-DMA | HLA-DMB | HLA-DQB2 | HSPA8 | RPL32 |
| G0S2 | AMICA1 | COTL1 | SRGN | CD2 |
| HLA-DQA1 | FCER1G | SPI1 | CORO1A | RPL3 |
| TYMP | MS4A6A | LSP1 | EEF1A1 | RPS3 |
| MS4A6A | SPI1 | IRF8 | CCL5 | RPS15A |
| SAT1 | HLA-DQB2 | HLA-DQA2 | DUSP1 | RPL13 |
| CLEC10A | PLAUR | AIF1 | B2M | BTG1 |
| FCN1 | LGALS2 | MPEG1 | YPEL5 | RPLP2 |
| SPI1 | HLA-DQA2 | HLA-DMA | TNFAIP3 | RPS12 |
| S100A9 | GPX1 | ACTB | TMEM66 | RPL9 |
| LGALS2 | IGSF6 | BATF3 | TMSB4X | RPS3A |
| CFP | CD83 | CD83 | CXCR4 | TMEM66 |
| COTL1 | SRGN | HLA-DMB | ID2 | RPS6 |
| CYBA | COTL1 | SGK1 | RGCC | CORO1A |
| HLA-DMB | CFP | FGL2 | RPS27A | RPS27 |
| NPC2 | IFI30 | C1orf162 | RPL10 | TMSB4X |
| SRGN | MNDA | LST1 | PTPRCAP | RPL23A |
| IGSF6 | DNASE1L3 | RGCC | H3F3B | TPT1 |
| C1orf162 | FGL2 | RGS10 | RPL21 | SRGN |
| FAM26F | FAM26F | CADM1 | RPS19 | RPL11 |
| CPVL | C1orf162 | HLA-DOB | MYL12A | RPSA |
| STX11 | ITGB2 | PLEK | RPS3 | RPL19 |
| C1QA | RGS2 | PPT1 | EVL | RPS4X |
| FTH1 | CD1C | HCK | DNAJB1 | RPS14 |
| FGL2 | SAT1 | BASP1 | IL7R | RPL4 |
| ITGB2 | RNASE6 | PTPRE | ACTB | GPR183 |
| CTSS | GPR183 | ITGB2 | ZFP36L2 | RPS2 |
| OAZ1 | CTSH | S100B | DDX5 | B2M |
| MS4A7 | SGK1 | CST7 | RPS25 | RPL30 |

TABLE 9C-continued

| Immune | | | | | | |
|---|---|---|---|---|---|---|
| PSAP | ACTB | GLIPR1 | | RPL32 | RPL28 | |
| S100A11 | RNASET2 | ASB2 | | SH3BGRL3 | RPL31 | |
| IFI30 | C1QA | LY86 | | JUNB | IL7R | |

| identT.CD4 | identT.CD8 | identT.CD8_IELs | identT.CD8_LP | identT.CXCRB_Th17 | identT.Cycling_T | identT.ILCs |
|---|---|---|---|---|---|---|
| ARHGDIB | ACTB | CCL5 | CCL5 | CD2 | CD52 | LST1 |
| B2M | ARHGDIB | CD3D | NKG7 | CD52 | STMN1 | LTB |
| BTG1 | B2M | CD52 | IL32 | CD3D | CCL5 | KRT86 |
| CD2 | CCL5 | CD7 | DUSP2 | LTB | CD3D | FXYD5 |
| CD3D | CD3D | HOPX | GZMA | TRAC | CORO1A | NFKBIA |
| CD3E | CD3E | IL32 | CD3D | TRBC2 | IL32 | IL4I1 |
| CD52 | CD52 | NKG7 | CCL4 | IL32 | CD3E | ID2 |
| EEF1A1 | CD7 | TMSB4X | B2M | S100A4 | ARHGDIB | CASP3 |
| IL32 | CORO1A | PTPRCAP | TRBC2 | CD3E | GZMA | DUSP1 |
| LTB | CTSW | GZMA | GZMK | ID2 | TRBC2 | ZFP36L1 |
| RPL10 | GZMA | TRDC | BTG1 | ARHGDIB | HMGB2 | TYROBP |
| RPL21 | HCST | HCST | CD8A | CXCR6 | TUBB | EIF1 |
| RPLP1 | HOPX | CORO1A | TRAC | KLRB1 | TRAC | CD52 |
| RPS19 | IL32 | CD3E | TMSB4X | ACTB | CD2 | H2AFY |
| RPS25 | NKG7 | ACTB | CD52 | CORO1A | ACTB | FOS |
| RPS27 | PTPRCAP | ARHGDIB | CXCR4 | TMSB4X | TYMS | HSPA8 |
| RPS27A | TMSB4X | TRBC2 | ARHGDIB | CKLF | EVL | ZFP36 |
| RPS3 | TRAC | TRGC2 | HCST | TNFRSF25 | KIAA0101 | HNRNPA0 |
| TMEM66 | TRBC2 | CKLF | CD8B | B2M | HMGN2 | SPINK2 |
| TMSB4X | EVL | EVL | ZFP36L2 | LCK | TMSB4X | BTG1 |
| TRAC | SH3BGRL3 | CD160 | CD3E | SH3BGRL3 | LCK | BTG2 |
| TRBC2 | GZMB | RAC2 | CD2 | CD69 | TUBA1B | CXCR4 |
| RPL32 | CKLF | TRAC | CST7 | GZMA | COTL1 | IL2RG |
| CORO1A | RAC2 | CTSW | PTPRCAP | AC092580.4 | PFN1 | OTUD5 |
| RPL3 | CST7 | TMIGD2 | HLA-C | PTPRCAP | RAC2 | DDIT4 |
| RPLP2 | CD8A | KLRC2 | CORO1A | ARPC1B | NKG7 | TNFRSF25 |
| RPS15A | ID2 | GZMB | SH3BGRL3 | RPS19 | TK1 | KRT81 |
| RPL13 | MYL12A | SH3BGRL3 | CD7 | OSTF1 | PTMA | ARL4A |
| S100A4 | CD8B | LCK | CD69 | HCST | CD69 | JUNB |
| PTPRCAP | CCL4 | ABI3 | TMEM66 | IL2RG | PTPRCAP | SRGN |
| RPL28 | LCK | ID2 | YPEL5 | MYL12A | ARPC2 | DNAJA1 |
| EIF1 | RPS19 | ARPC2 | EIF1 | BTG1 | DUT | MAFF |
| RPL23A | CD160 | TRGC1 | CTSW | PCBP1 | H2AFV | MIR24-2 |
| RPL19 | TRGC2 | XCL1 | SRGN | CACYBP | ASF1B | TMIGD2 |
| RPS6 | CD2 | RARRES3 | RGCC | SPOCK2 | HOPX | CD69 |
| RPS3A | ARPC2 | CD96 | ACTB | GIMAP7 | CD7 | ALDOC |
| RPL11 | CD69 | PRF1 | HLA-B | RPLP1 | SRGN | LTA4H |
| RPL3O | SRGN | RPS19 | MYL12A | SEPT1 | B2M | FOSB |
| LCK | PFN1 | AC092580.4 | HOPX | ODF2L | SH3BGRL3 | AMICA1 |
| RPL13A | RARRES3 | STK17A | GZMH | PFN1 | HCST | IL7R |
| CXCR4 | XCL1 | ALOX5AP | ID2 | CCL5 | ARPC1B | H3F3B |
| RPS4X | ALOX5AP | MYL12A | H3F3B | SLAMF1 | SLBP | PRMT10 |
| RPL9 | TRDC | B2M | NR4A2 | CCL20 | H2AFZ | IER2 |
| SRGN | BTG1 | CD247 | ANXA1 | AMICA1 | CKLF | SRSF2 |
| RPL4 | ZFP36L2 | GNLY | GZMB | CALM1 | SRSF7 | NR4A2 |
| ANXA1 | PRF1 | PFN1 | EVL | CD6 | RGS1 | EEF1A1 |
| CD69 | HLA-C | CST7 | IL2RG | EVL | HSPA8 | HMGN3 |
| RPSA | RPS27 | ACTG1 | RPS27 | ABRACL | RRM2 | NCOA7 |
| RPL31 | DUSP2 | TBC1D10C | MCL1 | EEF1A1 | CLSPN | YPEL5 |
| RPS2 | IL2RG | GIMAP7 | LCK | ARPC2 | CTSW | NR4A1 |

| | | identT.MT | identT.Memory_CD4 | identT.NK | identT.PD1_CD4 | identT.Tcells | identT.Tregs |
|---|---|---|---|---|---|---|---|
| | | MALAT1 | RPS27 | NKG7 | TRBC2 | ACTB | IL32 |
| | | CCL5 | RPL21 | FCER1G | CD3D | ARHGDIB | TRBC2 |
| | | MT-CYB | BTG1 | TYROBP | ARHGDIB | B2M | TRAC |
| | | SON | RPS3 | CCL4 | TRAC | BTG1 | BTG1 |
| | | MT-ND2 | RPS25 | XCL1 | LTB | CCL5 | ARHGDIB |
| | | IL32 | RPL32 | CTSW | ITM2A | CD2 | CD3D |
| | | MT-ND4 | RPS27A | GNLY | RP5-1028K7.2 | CD3D | LTB |
| | | SF1 | RPS15A | GZMA | CORO1B | CD3E | B2M |
| | | VAMP2 | RPL10 | CD7 | ICA1 | CD3G | RGS1 |
| | | ARHGEF1 | EEF1A1 | GZMK | CD52 | CD52 | SRGN |
| | | C1orf63 | RPL3 | IL2RB | BTG1 | CD7 | ARPC1B |
| | | ZFP36L2 | RPL13 | XCL2 | TIGIT | CKLF | IL2RG |
| | | FUS | RPLP2 | CLIC3 | PTPN7 | CORO1A | ACTB |
| | | MT-ATP6 | RPS4X | TRDC | RPL21 | EVL | CORO1A |
| | | ILF3 | RPS19 | KLRC1 | JUNB | GZMA | CD2 |
| | | C9orf142 | RPL9 | GZMB | CD200 | HCST | PFN1 |
| | | MYH9 | RPL19 | SRGN | LDHB | HOPX | PTPRCAP |
| | | SRSF2 | TRBC2 | HCST | RPS15A | IL2RG | CD52 |
| | | TRABD | | CCL5 | EEF1D | IL32 | BATF |

TABLE 9C-continued

Immune

| | | | | | |
|---|---|---|---|---|---|
| KLF6 | RPS20 | IFITM2 | CD52 | LCK | CD27 |
| MT-ND5 | ARHGDIB | KLRD1 | COTL1 | LTB | CREM |
| TSC22D4 | RPL31 | APOBEC3G | RPS4X | MYL12A | UBC |
| MT-CO3 | RPL30 | BTG1 | CD2 | NKG7 | RGCC |
| DDX5 | RPL23A | PRF1 | CD27 | PTPRCAP | TIGIT |
| SSU72 | TRAC | CST7 | RPS15 | RAC2 | CORO1B |
| ANKRD12 | CD52 | EIF3G | B2M | RPLP1 | CARD16 |
| SRSF7 | RPS3A | CCL3 | RPS27 | RPS19 | CD3E |
| TRAPPC1 | RPL11 | DUSP2 | RPL32 | RPS27 | LCK |
| RBM39 | RPL13A | HOPX | ARPC1B | RPS27A | UCP2 |
| PPP2R5C | RPS6 | H3F3B | CD3E | SH3BGRL3 | EIF1 |
| TMEM66 | RPS13 | CORO1A | PTPRCAP | TMEM66 | RPS27 |
| MIR24-2 | RPS14 | NR4A2 | GIMAP7 | TMSB4X | S100A4 |
| FOSB | RPS12 | STK17A | CD37 | TRAC | TMEM66 |
| BTG1 | CD3D | ZFP36 | C9orf16 | TRBC2 | SPOCK2 |
| ICAM3 | LDHB | PFN1 | LCK | PFN1 | HLA-A |
| HNRNPK | RPL27A | ZFP36L2 | H3F3B | RPL21 | TNFRSF4 |
| MT-CO1 | RPL4 | DUSP1 | RPS25 | RPS3 | RAP1A |
| SUN2 | RPL28 | CD160 | PDCD1 | ARPC2 | TMSB4X |
| PNISR | ZFP36L2 | TMSB4X | RPL6 | SRGN | C9orf16 |
| EIF4G2 | LTB | MATK | RPS13 | RPLP2 | CD44 |
| ABRACL | RPL18A | CD69 | RPL3 | SEPT1 | RAC2 |
| MRPL20 | RPL35A | KLRF1 | ACTB | CD69 | BIRC3 |
| HLA-F | RPLP1 | CD97 | RPS27A | CD247 | TSC22D3 |
| BUB3 | RPL41 | ARHGDIB | RPS3A | EEF1A1 | EEF1D |
| PRPF38B | RPL14 | FGR | RPL28 | ID2 | ARPC2 |
| MT-CO2 | IL32 | ARPC5L | RPL7 | RPL13 | DUSP4 |
| IDS | TMSB4X | ID2 | IL32 | ARPC1B | HSPA8 |
| PPP1R2 | RPS15 | MYL12A | TMSB4X | GIMAP7 | PBXIP1 |
| KMT2E | RPS18 | B2M | FXYD5 | RPL10 | PCBP1 |
| HLA-E | RPL7 | FAM46C | GPSM3 | CST7 | CALM3 |

TABLE 10

GWAS Gene List and Cell Subtype

| | |
|---|---|
| MEI1 | identB.Plasma |
| SLC26A3 | identE.Absorptive_All |
| ITLN1 | identE.Immature_Goblet |
| ITLN1 | identE.Secretory_All |
| CCL11 | identF.Crypt |
| CCDC85B | identF.Endothelial |
| CCL11 | identF.Fibroblast |
| PROCR | identF.Fibroblast |
| CCL2 | identF.Stromal |
| EFEMP2 | identF.Stromal |
| PROCR | identF.Stromal |
| GPX1 | identM.Monocytes |
| MXRA8 | identF.Stromal |
| SLC26A3 | identE.Epithelial |
| PTPRC | identI.Immune |
| SEMA3B | identF.Glia |
| NKX2-3 | identF.Stromal |
| PKIG | identF.Stromal |
| FCGR2A | identM.Myeloid |
| PLAU | identF.Stromal |
| FCGR2A | identM.Monocytes |
| CCL11 | identF.Stromal |
| VWA1 | identF.Microvascular |
| CTSW | identI.Immune |
| SULT1A1 | identE.Absorptive_All |
| GPR183 | identI.Immune |
| SLAMF8 | identM.Myeloid |
| SLAMF8 | identM.Monocytes |
| HYAL2 | identF.Endothelial |
| TAGAP | identI.Immune |
| CXCL1 | identF.Fibroblast |
| PDLIM4 | identF.Stromal |
| SULT1A2 | identE.Epithelial |
| ITLN1 | identE.Epithelial |
| C1orf106 | identE.Epithelial |
| CTSW | identT.NK |
| CD6 | identT.Tcells |
| LPXN | identI.Immune |
| CCL7 | identF.Crypt |
| IL10RA | identI.Immune |
| RNF186 | identE.Epithelial |
| CD19 | identB.Bcells |
| MEI1 | identI.Immune |
| CREM | identI.Immune |
| CXCL1 | identF.Stromal |
| TTYH3 | identM.Monocytes |
| FUT2 | identE.Epithelial |
| ESRRA | identE.Epithelial |
| CHP1 | identE.Epithelial |
| LY9 | identI.Immune |
| HNF4A | identE.Epithelial |
| NEU4 | identE.Epithelial |
| GSDMB | identE.Epithelial |
| PLCG2 | identE.Tuft |
| VDR | identE.Epithelial |
| CCL7 | identF.Fibroblast |
| NEXN | identF.Myofibroblasts |
| NEXN | identF.Stromal |
| GPR65 | identI.Immune |
| SCNN1A | identE.Epithelial |
| TNNI2 | identM.Myeloid |
| LAMB2 | identF.Stromal |
| OVOL1 | identE.Epithelial |
| PTPN22 | identI.Immune |
| CXCL6 | identF.Fibroblast |
| SP140 | identI.Immune |
| RSPO3 | identF.Crypt_RSPO3 |
| RAPGEF3 | identF.Endothelial |
| IKZF1 | identI.Immune |
| ANKRD65 | identF.Stromal |
| CCL7 | identF.Stromal |
| SLC26A6 | identE.Epithelial |
| THEMIS | identT.Tcells |
| GRB7 | identE.Epithelial |
| NLRP7 | identB.Bcells |
| CD6 | identI.Lymphoid |
| CD28 | identT.Tcells |
| MST1R | identE.Epithelial |

TABLE 10-continued

GWAS Gene List and Cell Subtype

| Gene | Cell Subtype |
|---|---|
| CD19 | identI.Lymphoid |
| CD6 | identI.Immune |
| FADS3 | identF.Glia |
| ANKRD65 | identF.Microvascular |
| SLAMF8 | identI.Immune |
| TAS1R3 | identE.Tuft |
| STAT4 | identI.Lymphoid |
| TNNI2 | identM.Tolerogenic_DCs |
| CXCL6 | identF.Stromal |
| SNX20 | identI.Immune |
| IFNG | identI.Lymphoid |
| SEMA3F | identF.Microvascular |
| CD40 | identB.GC |
| CD244 | identI.Immune |
| CD244 | identI.Lymphoid |
| CD19 | identI.Immune |
| IFNG | identI.Immune |
| HYAL1 | identF.Endothelial |
| STAT4 | identI.Immune |
| OSMR | identF.Stromal |
| SEMA3F | identF.Endothelial |
| IRF4 | identI.Immune |
| MMEL1 | identE.Best4_Enterocytes |
| CIT | identF.Microvascular |
| NLRP7 | identI.Lymphoid |
| RSPO3 | identF.Stromal |
| ITGAL | identI.Immune |
| CCR5 | identI.Immune |
| TNNI2 | identI.Immune |
| DGKE | identF.Endothelial |
| IL23R | identT.ILCs |
| THEMIS | identI.Lymphoid |
| CSF2 | identT.ILCs |
| TAS1R3 | identE.Secretory |
| THEMIS | identI.Immune |
| FAM212A | identM.CD69neg_Mast |
| CD28 | identI.Immune |
| CD28 | identI.Lymphoid |
| TNFRSF9 | identT.Tregs |
| CXCR5 | identI.Lymphoid |
| MYRF | identE.Epithelial |
| BACH2 | identB.GC |
| CCR2 | identI.Immune |
| NLRP7 | identI.Immune |
| CARD11 | identI.Immune |
| IL2RA | identI.Immune |
| PRKCB | identI.Immune |
| RASGRP1 | identI.Lymphoid |
| CD226 | identI.Immune |
| KIR3DL2 | identI.Lymphoid |
| CXCR5 | identI.Immune |
| TNFRSF9 | identI.Immune |
| CARD11 | identI.Lymphoid |
| KIR3DL2 | identI.Immune |
| COL7A1 | identF.Stromal |
| CCRL2 | identM.Neutrophils |
| IL10 | identI.Immune |
| RASGRP1 | identI.Immune |
| IKZF3 | identI.Lymphoid |
| ACSL6 | identT.Tcells |
| RFTN2 | identF.Stromal |
| IL27 | identM.Monocytes |
| PF4 | identE.Epithelial |
| IKZF3 | identI.Immune |
| ZMYND10 | identM.Cycling |
| IL27 | identM.Neutrophils |
| TNFSF8 | identI.Immune |
| IL2 | identT.Tcells |
| IL23R | identI.Lymphoid |
| IL2 | identI.Lymphoid |
| CELSR3 | identE.Enteroendocrine |

Table 11. Specific Cell Gene Lists

TABLE 11A

Epithelial

| identE.Absorptive | identE.Absorptive_All | identE.Absorptive_TA | identE.Absorptive_TA_1 | identE.Absorptive_TA_2 | identE.Best4_Enterocytes | identE.Cycling_TA |
|---|---|---|---|---|---|---|
| CLDN3 | C15orf48 | TXN | MT-ND3 | COX4I1 | BEST4 | MIF |
| CLDN7 | CA2 | MGST1 | SUCLG2 | TXN | CA7 | HIST1H4C |
| EPCAM | CES2 | UQCRFS1 | LCN2 | MGST1 | OTOP2 | IGFBP2 |
| GUCA2A | ETHE1 | PLA2G2A | NGEF | ATP5G3 | MT1G | TUBB4B |
| GUCA2B | FABP1 | LCN2 | DEFA6 | CYC1 | MT2A | RPSAP58 |
| LYPD8 | KRT19 | ATP5O | AC092620.2 | TMEM141 | MT1H | STRA13 |
| PLAC8 | LGALS3 | SUCLG2 | #N/A | UQCR10 | MT1E | CTD-2090113.1 |
| SDCBP2 | MT-CO2 | CTD-2228K2.7 | #N/A | ATP5D | NEURL | CCDC34 |
| CEACAM1 | PIGR | TLN2 | #N/A | UQCRH | CTSE | REG1A |
| ITM2C | SLC26A2 | PITPNM3 | #N/A | DBI | MT1X | RP11-519G16.5 |
| CEACAM6 | SLC26A3 | XXyac-YM21GA2.4 | #N/A | COX7C | HRCT1 | SAPCD2 |
| CLDN23 | SRI | RP1-102H19.8 | #N/A | ATP5EP2 | MSLN | GMNN |
| CA7 | KRT20 | AC013268.5 | #N/A | UQCRFS1 | DMBT1 | C18orf56 |
| TMEM171 | MS4A12 | CTA-363E6.2 | #N/A | MESP1 | MT1M | MZT2B |
| BEST4 | GUCA2A | AL133245.2 | #N/A | ATP5O | NOTCH2NL | NUDT8 |
| NLN | SELENBP1 | RN7SL485P | #N/A | BOLA3 | MT1F | GGCT |
| PRR15L | TST | RP11-7K24.3 | #N/A | MRPS33 | MYOM1 | FOXP1 |
| OTOP2 | CHP2 | RP11-57H14.4 | #N/A | CTD-2228K2.7 | STAP2 | F12 |
| APOBEC3B | CYSTM1 | CTD-2256P15.4 | #N/A | GJB1 | NBPF10 | TOMM40 |
| TMPRSS2 | C10orf99 | SNORD3B-1 | #N/A | GOT1 | OTOP3 | TSFM |
| C12orf36 | CA1 | FITM1 | #N/A | MFSD3 | GPRC5C | CTC-524C5.2 |
| SCIN | SLC51B | AC007255.8 | #N/A | APEH | CDX1 | CDC25C |
| CELA3B | CEACAM7 | RP11-214N9.1 | #N/A | LINC00668 | SCIN | GCAT |
| TDP2 | ANPEP | RP11-31506.1 | #N/A | UBAC1 | ADCY5 | KIF4A |
| CHMP4B | S100A14 | REG3A | #N/A | MRPL21 | RHOV | ATAD3A |
| PTTG1IP | CTD-2228K2.5 | PLCH1 | #N/A | SH2D4A | TDP2 | EMC9 |
| RP11-680F8.1 | PRAP1 | ATP13A4 | #N/A | TLN2 | CDK18 | SNRPF |
| PTPRR | PPP1R14D | ZSCAN20 | #N/A | XRCC6BP1 | C2orf54 | TCOF1 |
| APOBEC1 | HMGCS2 | CTD-2619J13.14 | #N/A | C1orf53 | CRYL1 | NDUFA7 |
| CTSE | TMEM45B | RP11-192H23.8 | #N/A | SPRYD4 | ALDH2 | CECR5 |
| GNG12 | SFN | #N/A | #N/A | RP1-102H19.8 | CEACAM3 | HPDL |

TABLE 11A-continued

| Epithelial | | | | | | | |
|---|---|---|---|---|---|---|---|
| TRIM15 | DHRS11 | #N/A | #N/A | XXyac-YM21GA2.4 | NOTCH2 | YBX2 | |
| MT1H | CEACAM1 | #N/A | #N/A | PITPNM3 | MEIS1 | RCC1 | |
| MSLN | AKR1B10 | #N/A | #N/A | YY2 | CCNYL1 | MYO19 | |
| TMCC3 | AGPAT2 | #N/A | #N/A | ATP13A4 | MMEL1 | WDR90 | |
| B3GNT3 | UQCRQ | #N/A | #N/A | RP11-50E11.3 | A1CF | CTB-175P5.4 | |
| CHMP2B | SULT1A1 | #N/A | #N/A | CTA-363E6.2 | SMPDL3B | HMBS | |
| HSD17B11 | SULT1A2 | #N/A | #N/A | LL22NC03-86G7.1 | SULT1E1 | SERPINA6 | |
| CELA3A | STAP2 | #N/A | #N/A | RP11-52112.3 | RP11-44N21.1 | PTBP1 | |
| CTC-490G23.2 | AKR1C3 | #N/A | #N/A | RP11-7K24.3 | CPA6 | PLEK2 | |
| DMBT1 | MT1G | #N/A | #N/A | UNC79 | NBPF14 | ACAD9 | |
| PARP4 | SLC22A18 | #N/A | #N/A | RP11-73M18.9 | HR | ICT1 | |
| RHPN2 | TMEM171 | #N/A | #N/A | SNORD3B-1 | REN | MCM8 | |
| MYOM1 | ACAA2 | #N/A | #N/A | RP1-80N2.2 | RP11-771K4.1 | RP11-304L19.1 | |
| MT1G | TMIGD1 | #N/A | #N/A | RN7SL485P | SAMD13 | C12orf54 | |
| VDAC2 | MPST | #N/A | #N/A | RP5-914P20.5 | NPY1R | RAC3 | |
| CEBPA | LINC00483 | #N/A | #N/A | HTR4 | TNFRSF11A | NMRAL1 | |
| IL10RB | GNA11 | #N/A | #N/A | PLCH1 | AGXT | TONSL | |
| GPRC5C | MT1E | #N/A | #N/A | CTD-2256P15.4 | TLDC2 | C9orf24 | |
| C2orf54 | SLC22A18AS | #N/A | #N/A | RP11-57H14.4 | AC069277.2 | POLE | |

| | identE.Enterocyte_Immature_1 | identE.Enterocyte_Immature_2 | identE.Enterocyte_Progenitor | identE.Enterocytes |
|---|---|---|---|---|
| | MT-CO1 | ETHE1 | SELENBP1 | ANPEP |
| | MT-RNR1 | FABP1 | AKR7A3 | APOBEC3B |
| | MT-CO2 | KRT19 | GOLM1 | AQP8 |
| | MT-ND2 | KRT20 | ACADS | C19orf33 |
| | MT-ATP6 | KRT8 | CMBL | CEACAM1 |
| | MT-ND5 | LGALS3 | SLC39A5 | CEACAM5 |
| | MT-ND4L | PHGR1 | CKMT1B | CEACAM7 |
| | SIRT6 | SLC26A2 | CKMT1A | CFDP1 |
| | VPS13A | TMEM54 | ASL | CLCA4 |
| | RP11-747D18.1 | LGALS4 | TRPM4 | CLDN23 |
| | SIRT7 | AKR1B10 | HADH | CLDN7 |
| | PHYKPL | TST | SDHA | CTD-2228K2.5 |
| | BAIAP2L2 | SLC25A5 | LIMA1 | EMP1 |
| | MT-TL1 | CES2 | NAPRT1 | FTH1 |
| | TAC1 | FLNB | UGDH | GPRC5A |
| | KRTAP13-2 | UQCRQ | BCL2L15 | GUCA2A |
| | HIST1H3F | CHP2 | ACO2 | HIST1H1C |
| | MT-TN | BSG | AIFM3 | IFI27 |
| | RP11-505E24.2 | COX6A1 | PKP2 | LYPD8 |
| | STAB2 | S100A14 | MOGAT2 | MISP |
| | RNU1-134P | AHCYL2 | ETFA | MS4A12 |
| | #N/A | COX5B | OPLAH | NLN |
| | #N/A | SULT1A1 | CAPN1 | PKIB |
| | #N/A | PLCD3 | OSBPL7 | PLAC8 |
| | #N/A | MGST3 | TTLL12 | PRAP1 |
| | #N/A | SLC22A18AS | LPIN3 | RP11-48020.4 |
| | #N/A | UQCR11 | VPS9D1 | SDCBP2 |
| | #N/A | SGK2 | SLC23A1 | SLC26A3 |
| | #N/A | TPRN | EME2 | SLC51B |
| | #N/A | TP53I3 | TRIM66 | SRI |
| | #N/A | ACAA1 | GLDN | TMEM37 |
| | #N/A | ATP1A1 | AF127936.7 | TRIM31 |
| | #N/A | ETNK1 | C21orf88 | TSPAN1 |
| | #N/A | IGSF9 | #N/A | TMIGD1 |
| | #N/A | NDUFA1 | #N/A | MALL |
| | #N/A | TNNC2 | #N/A | SFN |
| | #N/A | CYP4F12 | #N/A | PRSS3 |
| | #N/A | ATP5J | #N/A | MEP1A |
| | #N/A | TMEM82 | #N/A | CDA |
| | #N/A | LDHD | #N/A | RHOC |
| | #N/A | SHD | #N/A | SMIM22 |
| | #N/A | ZBTB7B | #N/A | SULT1A2 |
| | #N/A | PPARG | #N/A | ASS1 |
| | #N/A | RAPGEFL1 | #N/A | C11orf86 |
| | #N/A | AXDND1 | #N/A | SLC6A8 |
| | #N/A | ITPKA | #N/A | TMEM171 |
| | #N/A | MPST | #N/A | SPINT2 |
| | #N/A | LETM1 | #N/A | RHOF |
| | #N/A | CYCS | #N/A | GCNT3 |
| | #N/A | GDPD2 | #N/A | GPA33 |

| identE.Enteroendocrine | identE.Epithelial | identE.Goblet | identE.Immature_Enterocytes | identE.Immature_Goblet |
|---|---|---|---|---|
| PCSK1N | AGR2 | FAM3D | CA1 | AGR2 |
| SCGN | AMN | FCGBP | CES2 | CLCA1 |
| CHGA | C10orf99 | MUC1 | ETHE1 | ITLN1 |

TABLE 11A-continued

| Epithelial | | | | | |
|---|---|---|---|---|---|
| CRYBA2 | C15orf48 | MUC2 | KRT19 | KLK1 | |
| PYY | C19orf33 | TFF1 | MT-CO2 | LRRC26 | |
| FEV | CA2 | ZG16 | PIGR | RETNLB | |
| SCG5 | CDHR5 | MUC13 | SELENBP1 | SERPINA1 | |
| GCG | CLDN3 | REP15 | SLC26A2 | SPINK1 | |
| MS4A8 | CLDN4 | S100P | TST | SPINK4 | |
| NEUROD1 | CLDN7 | ENTPD8 | CHP2 | ST6GALNAC1 | |
| CACNA1A | COX5B | MALAT1 | HSD11B2 | TFF3 | |
| HOXB9 | ELF3 | VSIG2 | FLNB | WFDC2 | |
| MLXIPL | EPCAM | TM4SF5 | AKR1B10 | TPSG1 | |
| RAB26 | FABP1 | BCAS1 | SULT1A1 | GMDS | |
| KIF12 | FAM3D | AMN | MVP | HEPACAM2 | |
| SLC29A4 | FCGBP | SPATS2L | MGAT4B | MB | |
| CHGB | FXYD3 | SMIM6 | SLC22A18AS | ANG | |
| VWA5B2 | HMGCS2 | CREB3L1 | MYO1A | TSPAN13 | |
| KIAA1324 | KRT18 | ZG16B | PLCD3 | NANS | |
| DDC | KRT19 | CAPN8 | ATP1A1 | RP11-234B24.2 | |
| HOXB8 | KRT20 | FFAR4 | GPT | TCEA3 | |
| ERI3 | KRT8 | GDPD3 | ABCC3 | URAD | |
| CXXC4 | LGALS3 | SYTL2 | PAPSS2 | IL1R2 | |
| TPH1 | LGALS4 | PARM1 | CMBL | CDC42EP5 | |
| C19orf77 | MT-ATP6 | TBX10 | PPARG | TSTA3 | |
| ARX | MT-CO1 | FOXA3 | SHD | RAP1GAP | |
| RP11-279F6.1 | MT-CO2 | LGALS9B | IGSF9 | TMEM61 | |
| ABCC8 | MT-CO3 | PLA2G10 | VIL1 | HES6 | |
| CADPS | MT-ND1 | SCNN1A | TMPRSS4 | FABP2 | |
| ETV1 | MT-ND4 | TP53INP2 | CYP4F12 | CREB3L4 | |
| LCN15 | MT-RNR1 | BEST2 | ACADVL | EFCAB4A | |
| PELI3 | MT1E | MLLT3 | LETM1 | AC011523.2 | |
| SST | MT1G | GALE | DGAT1 | RAB15 | |
| NKX2-2 | PHGR1 | GPR153 | LDHD | ERGIC1 | |
| PEMT | PIGR | SPDEF | SHROOM1 | DYRK4 | |
| CYP2W1 | PRSS3 | SCGB2A1 | MAP2K2 | CTD-2547H18.1 | |
| PAX6 | S100A14 | AC009133.21 | MOGAT3 | SNHG18 | |
| QDPR | SELENBP1 | NEDD4L | RAPGEFL1 | LINC00261 | |
| C6orf141 | SMIM22 | VILL | LIMA1 | KLK15 | |
| COL2A1 | SPINT2 | RAB27A | NAPRT1 | PYCR1 | |
| BRAT1 | TMEM54 | DNM2 | PACSIN2 | C9orf152 | |
| SYT13 | TSPAN1 | FAM101A | ITPKA | ZNF511 | |
| SSTR5-AS1 | TSPAN8 | GPRIN2 | VDR | ABLIM1 | |
| SEZ6L2 | STAP2 | FUT3 | PFKL | KLK4 | |
| RXFP4 | TFF3 | MTMR11 | ACO2 | GNE | |
| PSCA | SLC44A4 | ACSS2 | MMP15 | HDLBP | |
| KIAA1456 | GUCA2A | KCNK1 | ZBTB7A | HES2 | |
| MNX1 | ETHE1 | VIPR1 | AXDND1 | KDELR2 | |
| STX1A | TST | DST | ITGA3 | FOXA2 | |
| INSL5 | PRAP1 | RASEF | SLC27A4 | TRPT1 | |

| identE.Secretory | identE.Secretory_All | identE.Secretory_TA | identE.Stem | identE.Tuft |
|---|---|---|---|---|
| FCGBP | CLCA1 | RPL36 | PRDX5 | KRT18 |
| MUC2 | FCGBP | RPL35 | LEFTY1 | AZGP1 |
| TFF1 | ITLN1 | RPL37A | ASCL2 | SH2D6 |
| ZG16 | KLK1 | AC112229.7 | GPX2 | MARCKSL1 |
| ELF3 | KRT18 | ANKS6 | C17orf76-AS1 | BIK |
| MUC1 | MUC2 | KCNJ12 | RPLP0 | LRMP |
| MALAT1 | REP15 | ZSCAN22 | CDCA7 | HCK |
| S100P | SPINK1 | FAM183A | RGMB | PTPN18 |
| TM4SF5 | SPINK4 | TTC4 | RPS18 | ANXA13 |
| ENTPD8 | TFF3 | RP4-610C12.3 | RPL12 | ATP2A3 |
| BCAS1 | WFDC2 | KRTAP4-1 | SMOC2 | AVIL |
| AZGP1 | ZG16 | RGMB-AS1 | RPS6 | IL17RB |
| SMIM6 | LRRC26 | RP11-884K10.7 | PPP1R1B | TRPM5 |
| ZG16B | AGR2 | RP11-199F11.2 | GNB2L1 | ALOX5 |
| SH2D6 | TPSG1 | SLC25A30-AS1 | RPS2 | SH2D7 |
| FFAR4 | RETNLB | B4GALT6 | RPS5 | BMX |
| CAPN8 | STARD10 | CTA-797E19.1 | RPL29 | PTGS1 |
| FOXA3 | FAM3D | CACNA1F | SLC25A6 | ELF3 |
| ATP2A3 | ST6GALNAC1 | AP001462.6 | EPHB3 | EIF1B |
| TBX10 | MB | RP11-548H3.1 | RPS24 | GNG13 |
| SYTL2 | CREB3L1 | KIAA1875 | IMPDH2 | PSTPIP2 |
| GALE | ANG | CITF22-1A6.3 | RPL7A | HOTAIRM1 |
| LGALS9B | MUC1 | RP4-565E6.1 | ALDH1B1 | SPIB |
| GPR153 | GMDS | SLC35G5 | OLFM4 | CC2D1A |
| HCK | BEST2 | RNVU1-14 | FERMT1 | HTR3E |
| ANXA13 | ANXA13 | CTD-2196E14.4 | AP003774.1 | IFT172 |
| AVIL | SPDEF | CTC-360G5.1 | KCNN4 | PLCG2 |
| H1F0 | FOXA3 | ZNF334 | EPHB2 | DEFB1 |

TABLE 11A-continued

| Epithelial | | | | |
|---|---|---|---|---|
| RASSF7 | ZG16B | RP11-677M14.2 | GPR160 | RASSF6 |
| SCNN1A | TFF1 | RP11-391M1.4 | APEX1 | MATK |
| IL17RB | CDC42EP5 | AP001619.2 | PTPRO | ANXA4 |
| MLLT3 | RP11-234B24.2 | LINC00959 | RNF186 | PPAP2C |
| TRPM5 | KIAA1324 | ANKUB1 | CDK6 | AOC1 |
| NEDD4L | REG4 | CTD-2196E14.6 | EXOSC5 | OGDHL |
| AC009133.21 | TMEM61 | RP11-188P20.3 | ADCK3 | ATPIF1 |
| BMX | RAP1GAP | CTB-75G16.3 | ARSE | EPS8L3 |
| SH2D7 | S100P | AC073133.2 | REPIN1 | FURIN |
| GNG13 | BCAS1 | FAM221B | ZNF814 | TMEM63A |
| FAM101A | CAPN9 | RP11-932O9.9 | NOX1 | EHF |
| IFT172 | SCGB2A1 | HP | CDHR1 | C2orf82 |
| GPRIN2 | TM4SF5 | RP11-361F15.2 | MACROD1 | ESPN |
| HOTAIRM1 | AZGP1 | OTUB2 | SH3YL1 | POU2F3 |
| CBFA2T2 | ERN2 | LRRC16B | LGR5 | SPTLC2 |
| KCNK1 | FFAR4 | RP11-163N6.2 | UGT2A3 | CDH17 |
| EHF | ERI3 | RP11-13K12.1 | SLC39A2 | NT5C |
| PSTPIP2 | AC009133.21 | #N/A | ACSM3 | BLOC1S1 |
| HTR3E | ATP2A3 | #N/A | SFXN4 | IL13RA1 |
| SCGN | SH2D6 | #N/A | LRIG1 | CENPV |
| DDR1 | TSTA3 | #N/A | TSPAN6 | ASMTL |
| SYT7 | ANO7 | #N/A | CRLS1 | FYB |

TABLE 11B

| Fibroblast | | | | |
|---|---|---|---|---|
| identF.Crypt | identF.Crypt_RSPO3 | identF.Crypt_hiFos | identF.Crypt_loFos_1 | identF.Crypt_loFos_2 |
| A2M | DCN | ADAMDEC1 | APOE | IFI27L2 |
| ABCA8 | LUM | CCL8 | SCARA5 | PKDCC |
| ADAM28 | EFEMP1 | HAPLN1 | COLEC11 | DTX4 |
| ADAMDEC1 | FBLN1 | STMN2 | RP11-54O7.3 | ABCA6 |
| APOE | CFH | CCL7 | ANKRD53 | C1RL |
| CCL11 | CCDC80 | IL7 | RP11-107N15.1 | TEKT3 |
| CCL13 | CCL11 | EPHA7 | LNP1 | ROBO1 |
| CCL8 | ADH1B | PHACTR3 | MFI2-AS1 | LINC00663 |
| CFD | CXCL12 | BPI | C17orf51 | #N/A |
| CFH | MFAP4 | GALNT9 | AC144449.1 | #N/A |
| CXCL12 | C7 | AL117190.3 | PNMA2 | #N/A |
| DCN | SERPINF1 | RP11-374M1.5 | RN7SKP295 | #N/A |
| FABP4 | PLAC9 | LINC00309 | RP11-422P24.11 | #N/A |
| FBLN1 | SERPING1 | LRRC8E | L3MBTL1 | #N/A |
| HAPLN1 | PTGDS | ZKSCAN7 | FLNC | #N/A |
| MFAP4 | RSPO3 | RP11-556N21.1 | ZNF510 | #N/A |
| PLTP | C3 | RP11-88H9.2 | LPP-AS2 | #N/A |
| PTGDS | ASPN | RP11-774O3.3 | BVES | #N/A |
| PTN | COL14A1 | RP11-353B9.1 | DNHD1 | #N/A |
| SCARA5 | DPT | ATP6V0E2-AS1 | ZC3H12B | #N/A |
| SFTA1P | GSTM3 | ZNF114 | MARK1 | #N/A |
| TCF21 | GSTM5 | MAATS1 | RP11-112L6.4 | #N/A |
| SNAI2 | PRELP | C9orf96 | RP3-510D11.2 | #N/A |
| EDIL3 | ANGPTL1 | LIN7A | SEC24B-AS1 | #N/A |
| CXCL1 | C16orf89 | NBPF15 | RP11-267N12.3 | #N/A |
| C6orf48 | CXCL6 | ZNF660 | #N/A | #N/A |
| TNXB | CHODL | RP11-326C3.11 | #N/A | #N/A |
| PROS1 | SERPINE2 | ANKRD6 | #N/A | #N/A |
| SERPINE2 | OGN | CMYA5 | #N/A | #N/A |
| ABCA6 | NFIA | PRTG | #N/A | #N/A |
| IFI27L2 | GREM2 | RP11-475I24.3 | #N/A | #N/A |
| CP | CCL19 | CNTNAP1 | #N/A | #N/A |
| CCL7 | CP | WASF1 | #N/A | #N/A |
| ELANE | GPC6 | FAM184B | #N/A | #N/A |
| ANGPTL1 | CCL21 | DNM3OS | #N/A | #N/A |
| HOXB-AS3 | PAM | RP11-173B14.5 | #N/A | #N/A |
| NR2F1-AS1 | RGMA | #N/A | #N/A | #N/A |
| GPC6 | APOD | #N/A | #N/A | #N/A |
| CXCL6 | RP11-135D11.2 | #N/A | #N/A | #N/A |
| FMOD | GPC3 | #N/A | #N/A | #N/A |
| SLIT3 | TMEM59 | #N/A | #N/A | #N/A |
| BCL3 | PTGER1 | #N/A | #N/A | #N/A |
| CRYBG3 | FAIM2 | #N/A | #N/A | #N/A |
| PRCD | MAPKAP1 | #N/A | #N/A | #N/A |
| FNDC1 | PTGFR | #N/A | #N/A | #N/A |
| EPHA7 | SFRP2 | #N/A | #N/A | #N/A |

TABLE 11B-continued

| Fibroblast | | | | |
|---|---|---|---|---|
| CCL19 | CAPN6 | #N/A | #N/A | #N/A |
| ADAMTS2 | OSR2 | #N/A | #N/A | #N/A |
| RP3-323P13.2 | SFRP4 | #N/A | #N/A | #N/A |
| CFHR3 | CDO1 | #N/A | #N/A | #N/A |

| identF.Endothelial | identF.Endothelial_1 | identF.Fibroblast | identF.Glia |
|---|---|---|---|
| BCAM | CD320 | ABCA8 | ALDH1A1 |
| CCDC85B | IGFBP4 | ADAMDEC1 | CD9 |
| CD320 | ENPP2 | APOE | CLU |
| CD36 | TXNIP | BMP4 | CRYAB |
| CLDN5 | ICAM2 | C1R | S100B |
| CLEC14A | RBP7 | C1S | TUBA1A |
| CRIP2 | CYYR1 | CCL11 | GPM6B |
| ECSCR | CD34 | CCL13 | PMP22 |
| EGFL7 | MMRN2 | CCL8 | PLP1 |
| ENG | GPR146 | CFD | SPARC |
| ESAM | IL3RA | CFH | SPP1 |
| FABP5 | SOX17 | CLEC11A | PRNP |
| FKBP1A | SRP14 | COL6A1 | SEMA3B |
| GIMAP7 | FAM107A | COL6A2 | JUN |
| GNG11 | OAZ2 | CTSK | MATN2 |
| HLA-C | C10orf54 | CXCL12 | FOS |
| HLA-E | SYNPO | CYGB | CYR61 |
| IGFBP4 | C10orf10 | DCN | CD59 |
| ITM2B | HEY1 | DMKN | COMT |
| JAM2 | LPAR6 | ECM1 | CALM2 |
| NPDC1 | TIE1 | EMILIN1 | HES1 |
| PLVAP | KLF2 | FBLN1 | MPZ |
| RAMP2 | AIF1L | GGT5 | ANXA2 |
| RAMP3 | ADAM15 | HAAO | LGI4 |
| RBP5 | COL15A1 | HAPLN1 | GFRA3 |
| SEPW1 | NOV | LAMA4 | TUBB2B |
| SLC9A3R2 | PLLP | LTBP4 | CNN3 |
| SNCG | ALPL | LUM | C8orf4 |
| SPARCL1 | SEMA3G | MFAP4 | PEBP1 |
| TMEM88 | BTNL9 | MMP2 | TIMP3 |
| VWF | EFNB2 | PCOLCE | DKK3 |
| FAM167B | MECOM | PLAC9 | NRXN1 |
| AC011526.1 | SHE | PROCR | CCL2 |
| ENPP2 | STC1 | PTN | IER2 |
| CYYR1 | RUNDC3B | RARRES2 | JUNB |
| PRSS23 | C1QTNF9 | RBP1 | VIM |
| CTGF | INHBB | SCARA5 | EGR1 |
| CD34 | FCN3 | SERPINF1 | NDRG2 |
| TSPAN7 | ARL15 | SPON2 | RGS16 |
| ICAM2 | GPIHBP1 | STMN2 | PMEPA1 |
| PTRF | OAZ3 | TCF21 | SOCS3 |
| VAMP5 | RP11-536O18.1 | SNAI2 | RHOB |
| TGFBR2 | SSUH2 | ADH1B | CBR1 |
| CAV2 | PRDM16 | PTGDS | S100A4 |
| FAM213A | FGF12 | PLTP | SORBS2 |
| EMCN | RP11-105C19.1 | ADAM28 | AP1S2 |
| ELTD1 | RP11-1379J22.5 | GLT8D2 | FXYD1 |
| TM4SF18 | SNORA7 | TMEM119 | ANXA5 |
| HLA-A | AC007161.5 | VCAM1 | S100A1 |
| TXNIP | RP4-569M23.2 | CTC-276P9.1 | PLEKHB1 |

| identF.Inflammatory | identF.Microvascular | identF.Myofibrobiasts | identF.Pcap_Venules | identF.Pericytes |
|---|---|---|---|---|
| CHI3L1 | FABP5 | ACTA2 | CLDN5 | RGS5 |
| RHBDD3 | PLVAP | TAGLN | NPC2 | TINAGL1 |
| RCVRN | GNG11 | MYL9 | DARC | CSRP2 |
| MMP3 | PRSS23 | TPM2 | TSPAN7 | NDUFA4L2 |
| RP11-676J12.7 | CD36 | ACTG2 | CPE | IGFBP7 |
| LRCH2 | GSN | PDLIM3 | LY6E | HIGD1B |
| MMP10 | RAMP3 | TPM1 | MADCAM1 | BGN |
| AP000688.29 | SPARCL1 | MYLK | APLNR | COX4I2 |
| ZC3HAV1L | VWF | SOSTDC1 | DUSP23 | ADIRF |
| #N/A | VWA1 | DSTN | HHEX | PDGFRB |
| #N/A | RGCC | NDUFA4 | ICAM1 | TPPP3 |
| #N/A | ITM2B | MYH11 | TNFSF10 | NOTCH3 |
| #N/A | ENG | MYL6 | LINC01013 | HES4 |
| #N/A | RBP5 | FHL1 | GPR126 | GEM |
| #N/A | SDPR | HHIP | ZNF385D | FAM162B |
| #N/A | TMEM88 | PRKCDBP | KCTD12 | PGF |
| #N/A | FKBP1A | TGFB1I1 | CCL14 | NR2F2 |
| #N/A | TM4SF18 | HSD17B6 | CYP1B1 | MCAM |

TABLE 11B-continued

| Fibroblast | | | | |
|---|---|---|---|---|
| #N/A | TMEM204 | FLNA | RPS28 | STEAP4 |
| #N/A | HSPG2 | CNN1 | ADM5 | STOM |
| #N/A | EMCN | PPIC | PIR | LHFP |
| #N/A | PASK | NPNT | LPCAT4 | EPS8 |
| #N/A | ELTD1 | PDLIM7 | IL33 | SERPINI1 |
| #N/A | SLC14A1 | CES1 | KRT222 | REM1 |
| #N/A | PODXL | CSRP1 | SELP | ISYNA1 |
| #N/A | FLT1 | ILK | MEOX1 | TNS1 |
| #N/A | CAV2 | SMTN | MTUS1 | UBA2 |
| #N/A | C16orf80 | NEXN | SEMA6A | PLXDC1 |
| #N/A | SH3BP5 | LINC01082 | SMAD1 | ADAMTS1 |
| #N/A | KDR | TCEAL4 | GALNT15 | ITGA7 |
| #N/A | ARHGAP29 | HHIP-AS1 | VGLL4 | NFATC4 |
| #N/A | CDC37 | C9orf3 | ENY2 | MEST |
| #N/A | APP | RBPMS | TNFRSF10D | EDNRA |
| #N/A | RP11-536O18.2 | KCNMB1 | LEPR | NR1H4 |
| #N/A | HTRA1 | LMOD1 | ICAM4 | EBF1 |
| #N/A | EHD4 | CD151 | FAM84B | OLFM2 |
| #N/A | KANK3 | PDIA5 | RAB3C | KCNE4 |
| #N/A | CXorf36 | UBE2E3 | C2CD4B | LDB3 |
| #N/A | BAALC | LPP | ZNF521 | HEY2 |
| #N/A | HLX | AOC3 | PLA1A | HRC |
| #N/A | ROBO4 | TTLL7 | MMP28 | RASL12 |
| #N/A | NQO1 | RCN1 | SLC41A3 | ARHGEF17 |
| #N/A | GAS6 | HMG20B | FAM155A | GJC1 |
| #N/A | LXN | MIR145 | CORT | KCNJ8 |
| #N/A | SLCO2A1 | MFAP5 | VEGFC | LINC00883 |
| #N/A | WWTR1 | AC131025.8 | CA8 | HEYL |
| #N/A | GALNT18 | PARVA | KLK10 | C1QTNF1 |
| #N/A | MGLL | TCEAL1 | PRKAR1B | FZD7 |
| #N/A | PTPRB | CALU | BCAT1 | NTF3 |
| #N/A | NRP1 | CCDC107 | TIAM1 | GJA4 |

| | identF.Stromal | identF.Villus | identF.Villus_1 | identF.Villus_2 |
|---|---|---|---|---|
| | A2M | BMP4 | POSTN | BMP4 |
| | ADAMDEC1 | COL6A1 | NSG1 | F3 |
| | APOE | EDNRB | NBL1 | IGFBP3 |
| | BMP4 | ENHO | MMP2 | APLP2 |
| | C1R | F3 | VSTM2A | MMP11 |
| | C1S | HSD17B2 | GADD45B | BMP5 |
| | CALD1 | IGFBP3 | PDGFD | BAMBI |
| | CCL2 | MMP2 | C11orf96 | LANCL2 |
| | CCL8 | NBL1 | LAMA4 | TSPAN33 |
| | CFD | NSG1 | PLK2 | ITGA8 |
| | CFH | POSTN | CPM | NKD2 |
| | CLEC11A | VSTM2A | RBP4 | GBGT1 |
| | COL1A1 | FOXF1 | PROM1 | BMP7 |
| | COL1A2 | SCPEP1 | SOX6 | C22orf31 |
| | COL3A1 | APLP2 | FGF9 | RP11-2E17.1 |
| | COL6A1 | BMP5 | TSHZ2 | NEFM |
| | COL6A2 | FAM150B | GLP2R | LEF1-AS1 |
| | CRIP2 | PDGFD | CRISPLD2 | F2RL2 |
| | CTSK | MMP11 | MAFB | GRIN2A |
| | CXCL12 | LAMA4 | KLF10 | LPAR3 |
| | CXCL14 | MRPS6 | PCSK6 | FZD8 |
| | CYGB | PITX1 | FAM92A1 | RP11-157P1.4 |
| | DCN | ISCU | SCUBE2 | POU6F1 |
| | ECM1 | C1orf21 | NMNAT3 | SOX5 |
| | EFEMP2 | INSC | DDHD1 | EFHB |
| | EMILIN1 | RBP4 | FRY | ARL10 |
| | FBLN1 | GLP2R | RN7SL832P | AGAP10 |
| | GNG11 | GLT8D2 | CCDC68 | KDM8 |
| | GPX3 | TSHZ2 | FBXO21 | RSG1 |
| | HSPB1 | BAMBI | POLA2 | RP11-298J20.3 |
| | IFITM1 | TSLP | ADAMTS13 | ISPD |
| | IFITM3 | KREMEN1 | AC061992.2 | KANSL1L |
| | IGFBP6 | CRISPLD2 | CTD-2035E11.3 | #N/A |
| | IGFBP7 | REEP2 | C10orf107 | #N/A |
| | LINC01082 | FGF9 | RP11-108M9.6 | #N/A |
| | LTBP4 | TPBG | WBSCR17 | #N/A |
| | LUM | LANCL2 | HUS1B | #N/A |
| | MFAP4 | PLBD1 | EDAR | #N/A |
| | MFGE8 | PCSK6 | AP000769.1 | #N/A |
| | MMP2 | SCUBE2 | EFCAB1 | #N/A |
| | MYL9 | WNT5B | EGOT | #N/A |
| | NGFRAP1 | SEMA4D | NOTO | #N/A |
| | NNMT | MFAP2 | SRPK3 | #N/A |

TABLE 11B-continued

| Fibroblast | | | |
|---|---|---|---|
| PCOLCE | LAMA5 | RP11-473M20.16 | #N/A |
| PLAC9 | COL4A6 | KCNK17 | #N/A |
| PLAT | WFS1 | ZCCHC18 | #N/A |
| PMP22 | CCDC68 | ZNF410 | #N/A |
| PPAP2A | SRPX2 | BDNF | #N/A |
| PPAP2B | CNTFR | COLGALT2 | #N/A |
| PPP1R14A | RP11-449D8.1 | ZNF594 | #N/A |

TABLE 11C

| Immune | | | | | | | |
|---|---|---|---|---|---|---|---|
| identB.Bcells | identB.Cycling | identB.FO | identB.GC | identB.Plasma | identI.Immune | identI.Lymphoid | |
| AC096579.7 | PBK | BANK1 | CD79A | AC096579.7 | ARHGDIB | CCL5 | |
| AL928768.3 | SEC23B | RP5-887A10.1 | CD79B | AL928768.3 | CCL5 | CD2 | |
| CCR10 | NDC1 | SELL | TCL1A | CCR10 | CD37 | CD3D | |
| CD79A | ZBTB8OS | ARHGAP24 | SMIM14 | CHPF | CD3D | CD3E | |
| DERL3 | HBD | TNFRSF13B | MS4A1 | CRELD2 | CD3E | CD52 | |
| DNAJB9 | ZFAT | CCDC50 | LIMD2 | DERL3 | CD48 | CD7 | |
| EAF2 | IGLV3-9 | RALGPS2 | C7orf10 | DNAJB9 | CD52 | CYTIP | |
| FCRL5 | KIF14 | SIDT1 | VPREB3 | DUSP5 | CD53 | EVL | |
| GNG7 | ZNF264 | OSTN-AS1 | FCRLA | FCRL5 | CD69 | LTB | |
| HERPUD1 | ZNF215 | FCRL4 | SERPINA9 | FGF23 | CD7 | PTPRCAP | |
| IGHA1 | ZNF66 | GYLTL1B | EAF2 | FKBP11 | CORO1A | TRAC | |
| IGHA2 | HIST1H1B | CLECL1 | CD53 | HERPUD1 | CYBA | TRBC2 | |
| IGJ | AP000569.9 | IGHE | NCF1 | IFNAR2 | CYTIP | IL2RG | |
| IGKC | RP11-166B2.5 | DENND5B | BCAS4 | IGHA1 | EVL | LCK | |
| IGLC2 | C4orf21 | AP001046.5 | CD40 | IGHA2 | HCST | CD27 | |
| IGLC3 | RP11-382J12.1 | BEND4 | SNX29P2 | IGJ | LAPTM5 | CD79A | |
| IGLL5 | HIST1H2AH | C2ORF15 | ISG20 | IGKC | LTB | NKG7 | |
| MEI1 | AC090587.5 | SMKR1 | POU2AF1 | IGLC2 | PTPRCAP | SEPT1 | |
| MZB1 | CECR7 | ZBED2 | HTR3A | IGLC3 | RAC2 | HOPX | |
| POU2AF1 | ACSBG1 | KCNIP2 | HMCES | IGLL5 | RGS1 | GZMA | |
| SEC11C | UBE2NL | RP11-861A13.4 | AC023590.1 | IGLV3-1 | TRBC2 | ACAP1 | |
| SSR4 | RP4-536B24.3 | #N/A | CD72 | LMAN1 | TRAC | PCED1B-AS1 | |
| TNFRSF17 | TTF2 | #N/A | UBE2J1 | MANF | NCF1 | AL928768.3 | |
| UBE2J1 | MDH1B | #N/A | HMGN1 | MEI1 | COTL1 | BTG1 | |
| SPAG4 | RP11-46H11.12 | #N/A | NEIL1 | MZB1 | DUSP2 | TNFRSF17 | |
| CD79B | RP11-266K4.9 | #N/A | TPD52 | PDIA4 | LCK | CTSW | |
| EVI2B | DNMT3B | #N/A | P2RX5 | PPAPDC1B | IL2RG | ICAM3 | |
| DUSP5 | RP11-347C18.3 | #N/A | HLA-DOB | PRDX4 | EVI2B | FKBP11 | |
| IGLC7 | #N/A | #N/A | BFSP2 | SDF2L1 | CKLF | TSC22D3 | |
| SPCS3 | #N/A | #N/A | HVCN1 | SEC11C | HCLS1 | TBC1D10C | |
| XBP1 | #N/A | #N/A | GNG7 | SPAG4 | CD2 | IGHV1OR15-1 | |
| PPAPDC1B | #N/A | #N/A | EZR | SPCS3 | SAMSN1 | STK17A | |
| PNOC | #N/A | #N/A | MTMR14 | SSR3 | NKG7 | POU2AF1 | |
| IGLV3-1 | #N/A | #N/A | AICDA | SSR4 | PTPRC | TNFRSF18 | |
| FGF23 | #N/A | #N/A | TCEA1 | TNFRSF17 | GPSM3 | FCRL5 | |
| CRELD2 | #N/A | #N/A | MBD4 | TRAM1 | HOPX | CD247 | |
| TNFRSF13B | #N/A | #N/A | CYB561A3 | TXNDC15 | ACAP1 | MZB1 | |
| IGLV6-57 | #N/A | #N/A | RP11-138118.2 | WT1-AS | ARPC2 | DERL3 | |
| RP11-290F5.1 | #N/A | #N/A | CD180 | XBP1 | PCED1B-AS1 | CD3G | |
| WT1-AS | #N/A | #N/A | CCDC144A | IGKV4-1 | RHOH | CD96 | |
| IGHM | #N/A | #N/A | GGA2 | IGLV6-57 | ITGB7 | PIM2 | |
| IGKV4-1 | #N/A | #N/A | SEL1L3 | IGLC7 | LIMD2 | GZMB | |
| PDIA4 | #N/A | #N/A | BCL7A | DNAJB11 | CD27 | TRDC | |
| C16orf74 | #N/A | #N/A | LSM10 | SPCS2 | GZMA | TRGC2 | |
| MANF | #N/A | #N/A | TMEM156 | ANKRD37 | LCP1 | TMIGD2 | |
| SSR3 | #N/A | #N/A | RP11-164H13.1 | ERLEC1 | CTSW | MEI1 | |
| TPD52 | #N/A | #N/A | BACH2 | ALG5 | TMEM66 | TAGAP | |
| ANKRD37 | #N/A | #N/A | ZNF581 | RP11-290F5.1 | FCER1G | FAM46C | |
| PRDX4 | #N/A | #N/A | CD38 | UAP1 | CST7 | AC092580.4 | |
| SPCS2 | #N/A | #N/A | STX7 | SPCS1 | TBC1D10C | GZMM | |

| | identM.CD69neg_Mast | identM.CD69pos_Mast | identM.Cycling | identM.DCs |
|---|---|---|---|---|
| | CAPG | H3F3B | TUBA1B | CD74 |
| | LTC4S | NFKBIA | H2AFZ | CPVL |
| | KRT1 | PPP1R15A | STMN1 | CST3 |
| | MAOB | ANXA1 | AP2S1 | HLA-DPA1 |
| | HPGDS | GLUL | UBE2C | HLA-DPB1 |
| | SAMSN1 | DNAJA1 | CENPM | HLA-DQA1 |
| | ALOX5AP | UBB | CKS1B | HLA-DQB1 |
| | SLC18A2 | LMNA | YWHAH | HLA-DRA |

TABLE 11C-continued

| Immune | | | |
|---|---|---|---|
| NSMCE1 | NFKBIZ | CDK1 | HLA-DRB1 |
| ADRB2 | C1orf186 | ATP6V0B | HLA-DRB5 |
| BTK | HSP90AB1 | KPNA2 | CLEC10A |
| GMPR | DDX5 | NUDT1 | HLA-DQB2 |
| SVOPL | HDC | TOP2A | LGALS2 |
| CD44 | HSPA5 | SNRNP25 | AMICA1 |
| NCOA4 | FAM46A | TROAP | FCER1A |
| FAM212A | HSP90AA1 | EIF4EBP1 | HLA-DQA2 |
| CATSPER1 | STXBP6 | LSM4 | SGK1 |
| LYL1 | HSPH1 | COMMD4 | CD1C |
| ARL6IP5 | IL1RAPL1 | SYCE2 | PLD4 |
| HSD17B12 | ELF1 | GGH | CD1E |
| BEX4 | UBBP4 | NCAPD3 | CLEC9A |
| MAML1 | AC020571.3 | FAM64A | PHACTR1 |
| AJ271736.10 | DNAJB4 | AC009005.2 | CD1D |
| NTRK1 | RP11-620J15.3 | FAM72C | IFNGR1 |
| SLC43A3 | IL1RL1 | ZMYND10 | CACNA2D3 |
| PABPC4 | EGR3 | C20orf201 | IDO1 |
| ABCB8 | CALB2 | SIGLEC15 | CTD-2319112.1 |
| IL9R | ADCYAP1 | GPR42 | TNNI2 |
| PSMD1 | IL13 | RP11-327F22.2 | FLT3 |
| CASS4 | ARL5B-AS1 | INCENP | C12orf5 |
| RN7SL243P | FER | RP11-1100L3.8 | SERPINF2 |
| ADAM22 | RP11-293M10.2 | PIPOX | CD207 |
| ASIC4 | RP4-794H19.2 | RP11-421L21.2 | NABP1 |
| RP4-669L17.10 | TPSD1 | #N/A | GHRL |
| RP5-1013A22.5 | DKFZP434E1119 | #N/A | TBC1D9 |
| ACAD11 | HIST1H2AG | #N/A | CLEC4F |
| RP11-336K24.12 | #N/A | #N/A | TATDN3 |
| ST8SIA6 | #N/A | #N/A | DGAT2 |
| ZNF709 | #N/A | #N/A | ELAVL4 |
| #N/A | #N/A | #N/A | XCR1 |
| #N/A | #N/A | #N/A | TOMM34 |
| #N/A | #N/A | #N/A | SLAMF9 |
| #N/A | #N/A | #N/A | UPK3A |
| #N/A | #N/A | #N/A | CD1B |
| #N/A | #N/A | #N/A | SFTPD |
| #N/A | #N/A | #N/A | RFPL4A |
| #N/A | #N/A | #N/A | CEACAM4 |
| #N/A | #N/A | #N/A | AP003774.6 |
| #N/A | #N/A | #N/A | CTD-2514K5.2 |
| #N/A | #N/A | #N/A | CLCN4 |

| identM.Macrophages | identM.Mast | identM.Monocytes | identM.Myeloid | identM.Neutrophils | identM.Tissue_DCs |
|---|---|---|---|---|---|
| ACP5 | CAPG | ACP5 | AIF1 | IL1B | CLEC10A |
| C1QA | H3F3B | AIF1 | C1QA | PLAUR | FCER1A |
| C1QB | NFKBIA | C1QA | C1QB | SOD2 | AMICA1 |
| C1QC | PPP1R15A | C1QB | C1QC | G0S2 | RGS2 |
| CTSB | TPSAB1 | C1QC | CLEC10A | TYMP | CD1C |
| CTSD | VWA5A | C1orf162 | CPVL | FCN1 | GPR183 |
| CTSZ | ANXA1 | CD74 | CST3 | S100A9 | PLD4 |
| FCGRT | GLUL | CLEC10A | CTSB | CYBA | CD1E |
| FTL | CTSG | CPVL | CYBA | STX11 | CXCL16 |
| FUCA1 | LTC4S | CST3 | DNASE1L3 | OAZ1 | CD1D |
| HLA-DMB | DNAJA1 | CTSB | FAM26F | C5AR1 | PHACTR1 |
| IGSF6 | UBB | CYBA | FTL | EREG | CACNA2D3 |
| LGMN | LMNA | DNASE1L3 | GLUL | CXCL2 | LITAF |
| MS4A4A | GATA2 | FAM26F | GPX1 | NCF2 | P2RY13 |
| MS4A7 | NFKBIZ | FTL | HLA-DPA1 | LILRB2 | CD207 |
| PSAP | C1orf186 | GPX1 | HLA-DPB1 | IL1RN | GHRL |
| RNASE1 | HSP90AB1 | GRN | HLA-DQA1 | GLRX | TBC1D9 |
| RNASET2 | HPGDS | HLA-DMA | HLA-DQA2 | CSTA | CLEC4F |
| SEPP1 | KRT1 | HLA-DMB | HLA-DQB1 | RAB20 | ELAVL4 |
| STAB1 | MAOB | HLA-DPA1 | HLA-DQB2 | ASGR1 | PLB1 |
| TYROBP | ASAH1 | HLA-DPB1 | HLA-DRA | S100A8 | SLAMF9 |
| CD14 | SERPINB1 | HLA-DQA1 | HLA-DRB1 | UBE2D1 | CD1B |
| SDS | DDX5 | HLA-DQA2 | HLA-DRB5 | ATF5 | CEACAM4 |
| GRN | RP11-354E11.2 | HLA-DQB1 | IFI30 | JUND | RFPL4A |
| APOC1 | HDC | HLA-DQB2 | IGSF6 | FCGR1A | AP003774.6 |
| SLC40A1 | SLC45A3 | HLA-DRA | IL1B | CXCL3 | CTD-2514K5.2 |
| GPNMB | CPA3 | HLA-DRB1 | LYZ | LILRA2 | RP11-667K14.3 |
| PLD3 | LMO4 | HLA-DRB5 | MPEG1 | APOBEC3A | RASGRF1 |
| FOLR2 | HSPA5 | IFI30 | MS4A4A | EMILIN2 | TBX19 |
| CD68 | HPGD | IGSF6 | MS4A6A | FPR1 | RP11-196G11.2 |
| ADORA3 | SLC18A2 | IL1B | MS4A7 | SCO2 | RUFY4 |
| LIPA | RPL36AL | LYZ | PSAP | NLRP3 | RP11-13811.2 |
| IGF1 | CLIC1 | MPEG1 | RNASE6 | CCRL2 | MS4A14 |

TABLE 11C-continued

| Immune | | | | | |
|---|---|---|---|---|---|
| CD163L1 | CTNNBL1 | MS4A4A | RNASET2 | ARL8B | TMEM170B |
| CSTB | DAD1 | MS4A6A | S100A11 | LILRA3 | RP11-117D22.2 |
| CREG1 | ADRB2 | MS4A7 | SAT1 | RNF19B | ZDHHC19 |
| TREM2 | ALOX5AP | PLAUR | SPI1 | FCGR1B | ANKRD55 |
| MMP12 | PLIN2 | PSAP | TYROBP | RP11-701P16.5 | RP11-248J18.2 |
| GM2A | STX3 | RNASE6 | VSIG4 | IL27 | NAMPTL |
| ATOX1 | HS3ST1 | RNASET2 | SDS | LILRA5 | CTC-428H11.2 |
| CD4 | PRKAR1A | SAT1 | C1orf162 | RP11-686D22.8 | GRAMD1B |
| ATP6V0D2 | HNRNPM | SDS | ATP6V1F | #N/A | RP11-147L13.2 |
| CD209 | FAM46A | SPI1 | FCER1A | #N/A | LEKR1 |
| BRI3 | CD44 | TYMP | TYMP | #N/A | CTD-2619J13.17 |
| ADAP2 | CMA1 | TYROBP | GRN | #N/A | LUCAT1 |
| CD163 | STXBP6 | VSIG4 | STAB1 | #N/A | RP11-73K9.2 |
| DAB2 | BTK | STAB1 | PLAUR | #N/A | RN7SL605P |
| LILRB5 | EIF3D | OAZ1 | RNF130 | #N/A | AC144652.1 |
| OTOA | SAMSN1 | AP2S1 | CTSS | #N/A | RP11-128M1.1 |
| NPL | GMPR | CTSZ | CTSD | #N/A | #N/A |

| | identM.Tolerogenic_DCs | identT.Activated_CD4_hiFos | identT.Activated_CD4_loFos | identT.CD4 | identT.CD8 |
|---|---|---|---|---|---|
| | CST3 | TSC22D3 | RPLP1 | RPL10 | CCL5 |
| | CPVL | KLF6 | ZDBF2 | RPL21 | CD8A |
| | IDO1 | TNFAIP3 | AC006369.2 | RPLP1 | CD8B |
| | CD74 | CITED2 | #N/A | RPS25 | TRGC2 |
| | SNX3 | RP11-302B13.5 | #N/A | RPS27A | TRGC1 |
| | HLA-DPB1 | #N/A | #N/A | TRAC | LYAR |
| | CLEC9A | #N/A | #N/A | RPL32 | RP11-291B21.2 |
| | HLA-DPA1 | #N/A | #N/A | RPS15A | NCR2 |
| | DNASE1L3 | #N/A | #N/A | RPL19 | RP11-713M15.1 |
| | LGALS2 | #N/A | #N/A | RPL30 | AC131056.3 |
| | CTD-2319I12.1 | #N/A | #N/A | RPL9 | RP11-305L7.3 |
| | C1orf54 | #N/A | #N/A | CD40LG | SLC25A5-AS1 |
| | HLA-DQB2 | #N/A | #N/A | RORA | CACNA1C-AS2 |
| | COTL1 | #N/A | #N/A | CD5 | GSG2 |
| | LSP1 | #N/A | #N/A | FLT3LG | CCR9 |
| | HLA-DQA2 | #N/A | #N/A | CTLA4 | #N/A |
| | MPEG1 | #N/A | #N/A | PDCD1 | #N/A |
| | ACTB | #N/A | #N/A | LAIR2 | #N/A |
| | BATF3 | #N/A | #N/A | RP11-664D1.1 | #N/A |
| | SGK1 | #N/A | #N/A | SUSD4 | #N/A |
| | PPT1 | #N/A | #N/A | IL26 | #N/A |
| | PTPRE | #N/A | #N/A | RP11-265P11.2 | #N/A |
| | GLIPR1 | #N/A | #N/A | CDKL2 | #N/A |
| | ASB2 | #N/A | #N/A | HAR1A | #N/A |
| | KIAA0226L | #N/A | #N/A | AC006369.2 | #N/A |
| | TMSB4X | #N/A | #N/A | RP4-594I10.3 | #N/A |
| | SERPINF2 | #N/A | #N/A | F5 | #N/A |
| | TNNI2 | #N/A | #N/A | CCDC157 | #N/A |
| | SLAMF7 | #N/A | #N/A | LA16c-431H6.6 | #N/A |
| | FLT3 | #N/A | #N/A | C15orf53 | #N/A |
| | WDFY4 | #N/A | #N/A | #N/A | #N/A |
| | SMCO4 | #N/A | #N/A | #N/A | #N/A |
| | VMO1 | #N/A | #N/A | #N/A | #N/A |
| | CPNE3 | #N/A | #N/A | #N/A | #N/A |
| | CKS2 | #N/A | #N/A | #N/A | #N/A |
| | RAB32 | #N/A | #N/A | #N/A | #N/A |
| | GSTP1 | #N/A | #N/A | #N/A | #N/A |
| | FKBP1B | #N/A | #N/A | #N/A | #N/A |
| | TACSTD2 | #N/A | #N/A | #N/A | #N/A |
| | CCND1 | #N/A | #N/A | #N/A | #N/A |
| | C12orf5 | #N/A | #N/A | #N/A | #N/A |
| | NABP1 | #N/A | #N/A | #N/A | #N/A |
| | FNIP2 | #N/A | #N/A | #N/A | #N/A |
| | KIAA1598 | #N/A | #N/A | #N/A | #N/A |
| | VAC14 | #N/A | #N/A | #N/A | #N/A |
| | LSM6 | #N/A | #N/A | #N/A | #N/A |
| | XCR1 | #N/A | #N/A | #N/A | #N/A |
| | PPM1M | #N/A | #N/A | #N/A | #N/A |
| | PPM1J | #N/A | #N/A | #N/A | #N/A |
| | IER5 | #N/A | #N/A | #N/A | #N/A |

| identT.CD8_IELs | identT.CD8_LP | identT.CXCR6_Th17 | identT.Cycling_T | identT.ILCs | identT.MT |
|---|---|---|---|---|---|
| CCL5 | CD8A | CD2 | TYMS | LST1 | ACAP1 |
| HOPX | CD8B | CXCR6 | KIAA0101 | LTB | PAK6 |
| GZMA | ZFP36L2 | KLRB1 | DUT | KRT86 | CTD-2035E11.5 |
| TRDC | GZMH | AC092580.4 | GINS2 | FXYD5 | RN7SL55P |

TABLE 11C-continued

| Immune | | | | | |
|---|---|---|---|---|---|
| TRGC2 | LYAR | SLAMF1 | PCNA | IL4I1 | #N/A |
| KLRC2 | IFNG | CCL20 | DNAJC9 | ID2 | #N/A |
| ABI3 | CRTAM | IL12RB1 | SMC4 | CASP3 | #N/A |
| TRGC1 | RP11-291B21.2 | ZNRD1 | MCM3 | H2AFY | #N/A |
| RARRES3 | RP11-305L7.3 | ZFYVE28 | CENPF | HNRNPA0 | #N/A |
| CD96 | ZNF80 | RP11-403A21.1 | YEATS4 | SPINK2 | #N/A |
| CD244 | ATP1A3 | RP11-85K15.2 | NRM | OTUD5 | #N/A |
| NCR2 | #N/A | RP11-415F23.2 | RAD51 | DDIT4 | #N/A |
| KIR2DL3 | #N/A | RP11-401F2.3 | CDCA5 | ARL4A | #N/A |
| RP11-713M15.1 | #N/A | OVCH1-AS1 | TCTEX1D2 | ALDOC | #N/A |
| DRAXIN | #N/A | #N/A | MTFR2 | LTA4H | #N/A |
| URB2 | #N/A | #N/A | ACAT2 | PRMT10 | #N/A |
| RP11-535A5.1 | #N/A | #N/A | VSIG1 | SRSF2 | #N/A |
| SEC14L6 | #N/A | #N/A | ABCD2 | HMGN3 | #N/A |
| RP11-104L21.3 | #N/A | #N/A | A1BG | MAP3K8 | #N/A |
| AL590452.1 | #N/A | #N/A | C5orf17 | AREG | #N/A |
| ADAMTS17 | #N/A | #N/A | AC027307.3 | MPG | #N/A |
| SEMA4F | #N/A | #N/A | #N/A | IL23R | #N/A |
| LRRIQ3 | #N/A | #N/A | #N/A | CD164 | #N/A |
| KLRC4 | #N/A | #N/A | #N/A | CSF2 | #N/A |
| ALG11 | #N/A | #N/A | #N/A | HINT3 | #N/A |
| CCDC7 | #N/A | #N/A | #N/A | MED30 | #N/A |
| #N/A | #N/A | #N/A | #N/A | LINC00299 | #N/A |
| #N/A | #N/A | #N/A | #N/A | OSTC | #N/A |
| #N/A | #N/A | #N/A | #N/A | DLL1 | #N/A |
| #N/A | #N/A | #N/A | #N/A | TNFSF11 | #N/A |
| #N/A | #N/A | #N/A | #N/A | TCTN3 | #N/A |
| #N/A | #N/A | #N/A | #N/A | SLC4A10 | #N/A |
| #N/A | #N/A | #N/A | #N/A | TEX30 | #N/A |
| #N/A | #N/A | #N/A | #N/A | FXYD7 | #N/A |
| #N/A | #N/A | #N/A | #N/A | SAMD10 | #N/A |
| #N/A | #N/A | #N/A | #N/A | PLEKHN1 | #N/A |
| #N/A | #N/A | #N/A | #N/A | ZNF724P | #N/A |
| #N/A | #N/A | #N/A | #N/A | ZNF385C | #N/A |
| #N/A | #N/A | #N/A | #N/A | RP11-403113.5 | #N/A |
| #N/A | #N/A | #N/A | #N/A | RP11-77P16.4 | #N/A |
| #N/A | #N/A | #N/A | #N/A | SYDE2 | #N/A |
| #N/A | #N/A | #N/A | #N/A | RNU2-63P | #N/A |
| #N/A | #N/A | #N/A | #N/A | RP11-53O19.3 | #N/A |
| #N/A | #N/A | #N/A | #N/A | FAM169A | #N/A |
| #N/A | #N/A | #N/A | #N/A | #N/A | #N/A |
| #N/A | #N/A | #N/A | #N/A | #N/A | #N/A |
| #N/A | #N/A | #N/A | #N/A | #N/A | #N/A |
| #N/A | #N/A | #N/A | #N/A | #N/A | #N/A |

| identT.Memory_CD4 | identT.NK | identT.PD1_CD4 | identT.Tcells | identT.Tregs |
|---|---|---|---|---|
| RPS27 | NKG7 | RP5-1028K7.2 | CD2 | IL32 |
| RPL21 | CCL4 | CORO1B | CD3D | TRBC2 |
| RPS25 | XCL1 | ICA1 | CD3E | RGS1 |
| RPL32 | CTSW | PTPN7 | CD3G | BATF |
| TMEM66 | GNLY | CD200 | LCK | CREM |
| RPLP2 | IL2RB | PDCD1 | RPS19 | TNFRSF4 |
| RPL9 | XCL2 | KIF2A | TRAC | CTLA4 |
| RPL19 | CLIC3 | RP11-455F5.5 | TRBC2 | GBP2 |
| RPS20 | KLRC1 | GNG4 | AC092580.4 | TNFRSF1B |
| RPL31 | GZMB | RP11-566E18.3 | ACAP1 | FOXP3 |
| RPL30 | HCST | RP11-479G22.8 | SIRPG | LAIR2 |
| RPL11 | KLRD1 | RP11-126K1.2 | TRGC2 | MIR4435-1HG |
| RPL13A | APOBEC3G | IQSEC3 | ICAM3 | NINJ2 |
| RPL27A | PRF1 | NTRK3 | RGL4 | LINC00649 |
| RPL35A | EIF3G | #N/A | CYTIP | TNFRSF9 |
| RPS29 | CCL3 | #N/A | CD8A | CUL9 |
| CCR7 | STK17A | #N/A | TIGIT | DUSP16 |
| NOSIP | CD160 | #N/A | CXCR6 | CDKL2 |
| LEF1 | KLRF1 | #N/A | TRAT1 | ANKS1B |
| RP11-664D1.1 | FGR | #N/A | C9orf78 | TRAV36DV7 |
| AC013264.2 | VPS37B | #N/A | CD8B | RN7SL443P |
| RP11-166B2.3 | CMC1 | #N/A | CD6 | C15orf53 |
| #N/A | CHST12 | #N/A | GPR171 | TRAV13-2 |
| #N/A | LINC00996 | #N/A | LAG3 | TRAV8-2 |
| #N/A | SH2D1B | #N/A | LYAR | RP11-53B2.6 |
| #N/A | BCO2 | #N/A | OXNAD1 | #N/A |
| #N/A | SLC35E1 | #N/A | DDX24 | #N/A |
| #N/A | FCRL6 | #N/A | IGHV1OR15-1 | #N/A |
| #N/A | RP11-222K16.2 | #N/A | SSBP4 | #N/A |

TABLE 11C-continued

Immune

| | | | | |
|---|---|---|---|---|
| #N/A | AC017104.6 | #N/A | RCAN3 | #N/A |
| #N/A | EOMES | #N/A | CD40LG | #N/A |
| #N/A | IL12RB2 | #N/A | THEMIS | #N/A |
| #N/A | TRIM54 | #N/A | RGS14 | #N/A |
| #N/A | PADI4 | #N/A | FLT3LG | #N/A |
| #N/A | RP11-449P15.2 | #N/A | CD28 | #N/A |
| #N/A | RP11-24B19.3 | #N/A | CISH | #N/A |
| #N/A | KIF21B | #N/A | CD5 | #N/A |
| #N/A | #N/A | #N/A | CA10 | #N/A |
| #N/A | #N/A | #N/A | CHRM3-AS2 | #N/A |
| #N/A | #N/A | #N/A | BCL11B | #N/A |
| #N/A | #N/A | #N/A | UBASH3A | #N/A |
| #N/A | #N/A | #N/A | LRRN3 | #N/A |
| #N/A | #N/A | #N/A | RP11-291B21.2 | #N/A |
| #N/A | #N/A | #N/A | CTLA4 | #N/A |
| #N/A | #N/A | #N/A | CCR5 | #N/A |
| #N/A | #N/A | #N/A | TNIP3 | #N/A |
| #N/A | #N/A | #N/A | MIAT | #N/A |
| #N/A | #N/A | #N/A | LINC00649 | #N/A |
| #N/A | #N/A | #N/A | AC013264.2 | #N/A |
| #N/A | #N/A | #N/A | AC104820.2 | #N/A |

| Tables 12-15 Column | Description |
|---|---|
| ident | cell subset ID |
| gene | gene name |
| contrast | DE comparison |
| coefD | discrete coefficient of model |
| pvalD | discrete p-value |
| coefC | continuous coefficient of model |
| pvalC | continuous p-value |
| mastfc | fold-change of gene estimated by MAST |
| pvalH | combined p-value (discrete and continuous) |
| ref | name of reference group |
| n | number of expressing cells |
| ref_n | for reference group |
| | alpha fraction of expressing cells |
| | ref_alpha for reference group |
| mu | mean expression level within expressing cells |
| ref_mu | for reference group |
| | mean mean expression |
| | ref_mean for reference group |
| total | fraction of total expression within group |
| ref_total | for reference group |
| | log2fc log2(fold-change) relative to reference group |
| | padjD adjusted p-value for discrete term |
| | padjC adjusted p-value for continuous term |
| | padjH adjusted p-value (combined) |
| | contam.res residual from contamination fit |
| | contam fraction of total expression within group |
| | nsamps number of samples gene is expressed in |

TABLE 12

Additional Cell Type Markers

| ident | gene | coefD | pvalD | coefC | pvalC | mastfc |
|---|---|---|---|---|---|---|
| B.Bcells | AC096579.7 | 3.268 | 0.00E+00 | 2.04E+00 | 2.22E−31 | 2.073248198 |
| B.Bcells | AL928768.3 | 6.364 | 0.00E+00 | 9.39E−01 | 2.47E−04 | 1.917529901 |
| B.Bcells | CD27 | 3.202 | 0.00E+00 | −5.04E−01 | 4.30E−13 | 1.454640372 |
| B.Bcells | CD74 | 4.682 | 0.00E+00 | 6.43E−01 | 1.98E−18 | 3.951093813 |
| B.Bcells | CD79A | 7.006 | 0.00E+00 | 8.64E−01 | 3.04E−04 | 2.727051658 |
| B.Bcells | CFL1 | −0.738 | 1.34E−20 | −1.64E+00 | 0.00E+00 | −1.184421042 |
| B.Bcells | DERL3 | 4.997 | 0.00E+00 | 1.27E+00 | 1.40E−26 | 1.221885789 |
| B.Bcells | DNAJB9 | 2.666 | 0.00E+00 | 1.02E−01 | 3.58E−02 | 1.403867423 |
| B.Bcells | FKBP11 | 2.607 | 0.00E+00 | 8.26E−01 | 1.12E−69 | 1.333818231 |
| B.Bcells | HERPUD1 | 2.593 | 0.00E+00 | 1.74E+00 | 0.00E+00 | 2.631118963 |
| B.Bcells | IGHA1 | 2.237 | 1.67E−211 | 4.66E+00 | 0.00E+00 | 5.929899096 |
| B.Bcells | IGHA2 | 2.087 | 4.56E−255 | 4.18E+00 | 0.00E+00 | 4.806875561 |
| B.Bcells | IGJ | 2.338 | 5.24E−289 | 4.55E+00 | 0.00E+00 | 5.565921598 |
| B.Bcells | IGKC | 2.917 | 0.00E+00 | 4.37E+00 | 4.37E−196 | 5.440840209 |
| B.Bcells | IGLC2 | 2.701 | 0.00E+00 | 2.24E+00 | 1.28E−34 | 2.653469053 |
| B.Bcells | IGLC3 | 2.590 | 0.00E+00 | 2.07E+00 | 3.89E−31 | 2.686736798 |
| B.Bcells | MZB1 | 4.212 | 0.00E+00 | 1.98E+00 | 3.72E−74 | 2.231289984 |
| B.Bcells | PTPRCAP | 2.259 | 3.03E−294 | −9.81E−01 | 5.62E−61 | 1.530286416 |
| B.Bcells | SEC11C | 2.343 | 8.29E−272 | 1.01E+00 | 7.87E−140 | 1.081174331 |
| B.FO | CD74 | 4.460 | 2.85E−280 | 2.49E+00 | 3.51E−181 | 5.354121926 |
| B.FO | CD79A | 3.737 | 0.00E+00 | 7.69E−01 | 1.09E−17 | 2.695535941 |
| B.FO | HLA-DRA | 3.473 | 0.00E+00 | 1.31E+00 | 2.57E−31 | 4.584234603 |
| B.Plasma | AC096579.7 | 4.338 | 0.00E+00 | 1.87E+00 | 1.20E−28 | 4.119453937 |
| B.Plasma | AL928768.3 | 6.031 | 0.00E+00 | −3.82E−01 | 4.82E−03 | 2.80561746 |
| B.Plasma | CCR10 | 5.264 | 0.00E+00 | −3.53E−01 | 6.29E−03 | 1.099736317 |
| B.Plasma | CD27 | 4.354 | 0.00E+00 | −6.00E−01 | 3.05E−17 | 2.032701947 |

TABLE 12-continued

Additional Cell Type Markers

| | | | | | | |
|---|---|---|---|---|---|---|
| B.Plasma | CD79A | 6.105 | 0.00E+00 | −6.42E−01 | 8.21E−10 | 2.569609064 |
| B.Plasma | CRELD2 | 3.642 | 0.00E+00 | −7.49E−02 | 7.62E−02 | 1.521987695 |
| B.Plasma | CYTIP | 2.801 | 8.56E−287 | −1.12E+00 | 4.40E−108 | 1.172161746 |
| B.Plasma | DERL3 | 7.160 | 0.00E+00 | 1.06E+00 | 1.28E−27 | 3.432708536 |
| B.Plasma | DNAJB9 | 4.516 | 0.00E+00 | 2.31E−01 | 1.13E−06 | 2.751694035 |
| B.Plasma | DUSP5 | 3.550 | 0.00E+00 | −5.31E−01 | 8.87E−15 | 1.084131907 |
| B.Plasma | EAF2 | 4.763 | 0.00E+00 | −3.45E−01 | 1.57E−06 | 1.626266352 |
| B.Plasma | EMP3 | 2.523 | 1.73E−240 | −1.18E+00 | 4.28E−175 | 1.039438032 |
| B.Plasma | EVI2B | 2.894 | 3.61E−279 | −9.89E−01 | 4.61E−76 | 1.091108309 |
| B.Plasma | FAM46C | 3.600 | 0.00E+00 | −6.89E−01 | 3.30E−41 | 1.056523747 |
| B.Plasma | FGF23 | 4.651 | 0.00E+00 | −2.47E−01 | 4.23E−02 | 1.271037067 |
| B.Plasma | FKBP11 | 5.774 | 0.00E+00 | 9.52E−01 | 3.02E−96 | 3.37615678 |
| B.Plasma | GNG7 | 4.228 | 0.00E+00 | −5.70E−01 | 3.94E−21 | 1.273964782 |
| B.Plasma | GYPC | 2.905 | 0.00E+00 | −9.97E−01 | 2.47E−119 | 1.374166018 |
| B.Plasma | HERPUD1 | 5.656 | 0.00E+00 | 1.96E+00 | 0.00E+00 | 4.539832048 |
| B.Plasma | IGHA1 | 5.916 | 8.02E−264 | 6.74E+00 | 0.00E+00 | 8.832840744 |
| B.Plasma | IGHA2 | 5.673 | 0.00E+00 | 5.34E+00 | 0.00E+00 | 8.005763853 |
| B.Plasma | IGJ | 6.775 | 0.00E+00 | 5.95E+00 | 0.00E+00 | 8.446894928 |
| B.Plasma | IGKC | 4.405 | 0.00E+00 | 5.28E+00 | 2.45E−275 | 7.801070323 |
| B.Plasma | IGLC2 | 3.773 | 0.00E+00 | 2.28E+00 | 4.98E−32 | 4.275847217 |
| B.Plasma | IGLC3 | 3.401 | 0.00E+00 | 2.02E+00 | 6.17E−26 | 3.981855127 |
| B.Plasma | IGLL5 | 4.075 | 0.00E+00 | 5.73E−01 | 6.19E−02 | 2.106667448 |
| B.Plasma | IL2RG | 2.386 | 1.07E−225 | −9.48E−01 | 1.03E−106 | 1.018567961 |
| B.Plasma | ISG20 | 3.760 | 0.00E+00 | −2.47E−01 | 5.63E−09 | 2.1133028 |
| B.Plasma | MANF | 3.944 | 0.00E+00 | 1.73E−01 | 1.39E−05 | 2.022112695 |
| B.Plasma | MZB1 | 8.081 | 0.00E+00 | 1.70E+00 | 2.09E−87 | 4.636645997 |
| B.Plasma | NUCB2 | 2.932 | 4.18E−299 | −4.76E−01 | 4.17E−31 | 1.121345488 |
| B.Plasma | PDIA4 | 3.344 | 0.00E+00 | −1.51E−01 | 2.50E−04 | 1.089626914 |
| B.Plasma | PIM2 | 3.954 | 0.00E+00 | −6.11E−01 | 4.80E−16 | 1.249090523 |
| B.Plasma | PPAPDC1B | 3.473 | 0.00E+00 | −1.84E−01 | 9.65E−06 | 1.180769265 |
| B.Plasma | PRDX4 | 3.794 | 0.00E+00 | 2.13E−01 | 2.49E−08 | 1.908367774 |
| B.Plasma | RGCC | 2.955 | 0.00E+00 | −1.39E+00 | 3.65E−86 | 1.671612761 |
| B.Plasma | RGS1 | 2.958 | 0.00E+00 | −6.46E−01 | 3.21E−24 | 2.027928073 |
| B.Plasma | SDF2L1 | 3.816 | 0.00E+00 | 2.29E−01 | 7.68E−09 | 2.12000614 |
| B.Plasma | SEC11C | 5.065 | 0.00E+00 | 1.06E+00 | 1.35E−157 | 3.257253887 |
| B.Plasma | SPCS3 | 3.550 | 0.00E+00 | −2.48E−01 | 6.75E−09 | 1.303454494 |
| B.Plasma | SSR3 | 3.937 | 0.00E+00 | 2.78E−01 | 1.50E−14 | 1.985908248 |
| B.Plasma | SSR4 | 5.407 | 2.05E−119 | 2.36E+00 | 0.00E+00 | 4.875540628 |
| B.Plasma | TNFRSF17 | 7.053 | 0.00E+00 | 3.55E−01 | 2.28E−03 | 2.775933525 |
| B.Plasma | TRAM1 | 3.600 | 0.00E+00 | −3.83E−01 | 2.34E−25 | 1.594121993 |
| B.Plasma | TXNDC15 | 3.410 | 0.00E+00 | −3.88E−01 | 1.71E−18 | 1.24259521 |
| B.Plasma | UBE2J1 | 4.889 | 0.00E+00 | 3.20E−02 | 5.13E−01 | 2.040155386 |
| B.Plasma | WT1-AS | 3.838 | 0.00E+00 | 7.54E−01 | 2.19E−08 | 1.850996813 |
| B.Plasma | XBP1 | 5.257 | 0.00E+00 | 9.96E−01 | 1.20E−110 | 3.416010759 |
| E.Absorptive | CA4 | 3.869 | 0.00E+00 | 2.23E+00 | 5.83E−168 | 4.966152183 |
| E.Absorptive | CEACAM5 | 3.040 | 0.00E+00 | 1.32E+00 | 4.22E−101 | 2.471517978 |
| E.Absorptive | CLDN3 | 3.520 | 2.44E−265 | 7.28E−01 | 1.38E−70 | 2.849876849 |
| E.Absorptive | CLDN7 | 3.451 | 3.17E−254 | 9.20E−01 | 2.72E−114 | 3.239205689 |
| E.Absorptive | EPCAM | 3.611 | 8.10E−263 | 8.16E−01 | 3.65E−76 | 3.498387043 |
| E.Absorptive | FABP1 | 4.261 | 3.07E−269 | 2.02E+00 | 1.43E−129 | 5.705513317 |
| E.Absorptive | FTH1 | 1.212 | 4.19E−02 | 2.26E+00 | 0.00E+00 | 2.904022981 |
| E.Absorptive | FXYD3 | 4.139 | 9.84E−269 | 1.43E+00 | 1.68E−142 | 4.637026365 |
| E.Absorptive | GUCA2A | 3.019 | 0.00E+00 | 2.71E+00 | 2.07E−158 | 5.019707907 |
| E.Absorptive | GUCA2B | 2.911 | 0.00E+00 | 2.15E+00 | 2.49E−91 | 3.832151794 |
| E.Absorptive | KRT20 | 3.141 | 0.00E+00 | 9.79E−01 | 2.09E−53 | 3.027566969 |
| E.Absorptive | KRT8 | 4.729 | 1.42E−270 | 1.04E+00 | 9.65E−86 | 4.383298523 |
| E.Absorptive | LGALS3 | 3.504 | 1.18E−100 | 1.55E+00 | 9.06E−244 | 3.952510867 |
| E.Absorptive | LYPD8 | 3.338 | 0.00E+00 | 1.55E+00 | 2.72E−88 | 3.510660931 |
| E.Absorptive | PHGR1 | 5.683 | 1.10E−267 | 1.69E+00 | 9.76E−127 | 5.833162008 |
| E.Absorptive | PLAC8 | 2.520 | 5.24E−261 | 1.32E+00 | 1.29E−80 | 2.780344753 |
| E.Absorptive | SDCBP2 | 3.592 | 0.00E+00 | 1.25E+00 | 1.13E−118 | 3.146564742 |
| E.Absorptive | SRI | 2.653 | 1.32E−117 | 1.49E+00 | 1.05E−263 | 3.080149952 |
| E.Absorptive | TSPAN1 | 3.255 | 3.14E−288 | 1.28E+00 | 8.98E−120 | 3.449336247 |
| E.Absorptive_All | C15orf48 | 3.617 | 0.00E+00 | 9.36E−01 | 1.72E−112 | 3.001269361 |
| E.Absorptive_All | C19orf33 | 2.845 | 0.00E+00 | 1.00E+00 | 5.63E−118 | 1.314768165 |
| E.Absorptive_All | CA2 | 3.138 | 0.00E+00 | 1.71E+00 | 2.24E−195 | 2.609090429 |
| E.Absorptive_All | CLDN7 | 3.105 | 0.00E+00 | 7.51E−01 | 4.22E−84 | 2.010379557 |
| E.Absorptive_All | EPCAM | 3.213 | 0.00E+00 | 4.23E−01 | 3.37E−23 | 2.504645735 |
| E.Absorptive_All | ETHE1 | 2.302 | 2.35E−221 | 1.03E+00 | 1.66E−142 | 1.039613635 |
| E.Absorptive_All | FABP1 | 3.780 | 0.00E+00 | 3.21E+00 | 0.00E+00 | 5.586554967 |
| E.Absorptive_All | FXYD3 | 3.402 | 0.00E+00 | 1.63E+00 | 9.61E−216 | 3.576992003 |
| E.Absorptive_All | KRT19 | 2.755 | 0.00E+00 | 1.55E+00 | 8.44E−143 | 1.818399526 |
| E.Absorptive_All | KRT8 | 3.698 | 0.00E+00 | 1.16E+00 | 6.91E−128 | 3.836768245 |
| E.Absorptive_All | LGALS3 | 2.848 | 3.50E−188 | 1.60E+00 | 0.00E+00 | 3.461283056 |
| E.Absorptive_All | LGALS4 | 4.384 | 0.00E+00 | 7.03E−01 | 3.02E−50 | 4.211537187 |
| E.Absorptive_All | PHGR1 | 5.445 | 0.00E+00 | 2.14E+00 | 9.74E−280 | 5.851633306 |
| E.Absorptive_All | PIGR | 3.492 | 0.00E+00 | 9.55E−01 | 5.70E−99 | 2.40099232 |
| E.Absorptive_All | SDCBP2 | 2.672 | 5.76E−306 | 7.80E−01 | 1.60E−30 | 1.124968887 |

TABLE 12-continued

Additional Cell Type Markers

| | | | | | | |
|---|---|---|---|---|---|---|
| E.Absorptive_All | SLC26A3 | 2.567 | 5.04E−296 | 1.53E+00 | 9.49E−54 | 1.462101925 |
| E.Absorptive_All | SRI | 2.120 | 2.05E−168 | 1.20E+00 | 2.42E−223 | 1.743839617 |
| E.Absorptive_All | TMEM54 | 2.793 | 0.00E+00 | 9.67E−01 | 1.34E−104 | 1.077198575 |
| E.Absorptive_All | TSPAN1 | 2.599 | 2.92E−308 | 9.87E−01 | 1.25E−67 | 1.638371845 |
| E.Absorptive_TA_1 | LGALS4 | 3.972 | 0.00E+00 | −2.12E−01 | 4.36E−04 | 3.560085632 |
| E.Best4_Enterocytes | BEST4 | 5.329 | 0.00E+00 | 1.91E+00 | 8.10E−12 | 2.425352878 |
| E.Best4_Enterocytes | CA7 | 5.258 | 0.00E+00 | 1.69E+00 | 9.89E−17 | 2.608165149 |
| E.Best4_Enterocytes | SPIB | 4.611 | 0.00E+00 | 5.00E−01 | 4.09E−06 | 1.727259355 |
| E.Enterocyte_Immature_1 | ANPEP | 3.273 | 0.00E+00 | 4.23E−01 | 3.34E−10 | 2.255957196 |
| E.Enterocyte_Immature_1 | AQP8 | 5.529 | 0.00E+00 | 2.22E+00 | 6.64E−104 | 5.678449028 |
| E.Enterocyte_Immature_1 | C19orf33 | 3.309 | 3.92E−279 | 7.66E−01 | 4.51E−54 | 2.553397084 |
| E.Enterocyte_Immature_1 | CA4 | 4.624 | 0.00E+00 | 9.84E−01 | 2.85E−28 | 4.39738035 |
| E.Enterocyte_Immature_1 | CEACAM5 | 3.877 | 0.00E+00 | 7.92E−01 | 1.17E−33 | 2.717411561 |
| E.Enterocyte_Immature_1 | CEACAM7 | 3.601 | 0.00E+00 | 2.86E−01 | 6.89E−05 | 2.272494617 |
| E.Enterocyte_Immature_1 | CLCA4 | 3.608 | 0.00E+00 | 5.71E−01 | 5.87E−10 | 1.903154797 |
| E.Enterocyte_Immature_1 | CTD-2228K2.5 | 3.928 | 0.00E+00 | 2.35E−01 | 3.99E−04 | 2.663088343 |
| E.Enterocyte_Immature_1 | FABP1 | 6.525 | 1.00E−301 | 1.58E+00 | 1.78E−63 | 5.694861283 |
| E.Enterocyte_Immature_1 | FXYD3 | 5.069 | 0.00E+00 | 1.02E+00 | 1.47E−58 | 4.485597281 |
| E.Enterocyte_Immature_1 | GUCA2A | 4.903 | 0.00E+00 | 1.94E+00 | 1.25E−79 | 5.559428295 |
| E.Enterocyte_Immature_1 | GUCA2B | 3.889 | 0.00E+00 | 8.26E−01 | 3.33E−16 | 3.558658878 |
| E.Enterocyte_Immature_1 | LYPD8 | 3.820 | 0.00E+00 | 6.53E−01 | 1.07E−15 | 3.082198702 |
| E.Enterocyte_Immature_1 | MT-RNR2 | 2.292 | 2.30E−14 | 2.71E+00 | 0.00E+00 | 4.854022399 |
| E.Enterocyte_Immature_1 | PHGR1 | 5.718 | 2.20E−275 | 1.58E+00 | 1.98E−86 | 5.828514036 |
| E.Enterocyte_Immature_1 | PLAC8 | 3.821 | 0.00E+00 | 9.36E−01 | 8.51E−43 | 3.344273115 |
| E.Enterocyte_Immature_1 | PRAP1 | 3.639 | 0.00E+00 | 6.96E−01 | 3.88E−21 | 2.616769997 |
| E.Enterocyte_Immature_1 | SDCBP2 | 3.416 | 0.00E+00 | 5.58E−01 | 4.57E−22 | 2.47146566 |
| E.Enterocyte_Immature_1 | SLC26A3 | 3.960 | 0.00E+00 | 5.28E−01 | 9.36E−11 | 3.105329195 |
| E.Enterocyte_Immature_1 | TSPAN1 | 4.105 | 0.00E+00 | 8.49E−01 | 3.42E−44 | 3.553346713 |
| E.Enterocyte_Immature_2 | CA1 | 3.617 | 7.44E−271 | 1.90E+00 | 2.14E−95 | 4.022433153 |
| E.Enterocyte_Immature_2 | CA2 | 6.076 | 2.56E−210 | 1.82E+00 | 5.16E−196 | 5.018877036 |
| E.Enterocyte_Immature_2 | ETHE1 | 3.172 | 2.56E−107 | 1.61E+00 | 2.65E−288 | 3.031843788 |
| E.Enterocyte_Immature_2 | FABP1 | 6.700 | 3.73E−169 | 3.54E+00 | 0.00E+00 | 7.466412634 |
| E.Enterocyte_Immature_2 | FXYD3 | 6.468 | 3.46E−163 | 2.11E+00 | 5.90E−304 | 5.521904327 |
| E.Enterocyte_Immature_2 | KRT19 | 4.212 | 5.25E−177 | 2.29E+00 | 3.79E−280 | 4.943887282 |
| E.Enterocyte_Immature_2 | KRT20 | 4.317 | 0.00E+00 | 1.31E+00 | 3.19E−87 | 3.976800169 |
| E.Enterocyte_Immature_2 | KRT8 | 5.494 | 7.38E−149 | 2.01E+00 | 2.61E−259 | 5.358446529 |
| E.Enterocyte_Immature_2 | LGALS3 | 3.960 | 5.85E−49 | 2.24E+00 | 0.00E+00 | 4.773676172 |
| E.Enterocyte_Immature_2 | MS4A12 | 4.243 | 0.00E+00 | 1.01E+00 | 4.80E−42 | 3.534180442 |
| E.Enterocyte_Immature_2 | PHGR1 | 6.551 | 1.19E−151 | 2.63E+00 | 7.99E−271 | 6.710120779 |
| E.Enterocyte_Immature_2 | SLC26A2 | 4.441 | 1.25E−277 | 1.03E+00 | 1.22E−65 | 2.835807204 |
| E.Enterocyte_Immature_2 | SLC26A3 | 4.350 | 0.00E+00 | 9.07E−01 | 2.06E−30 | 3.660394983 |
| E.Enterocyte_Immature_2 | SLC51B | 3.934 | 0.00E+00 | 4.63E−01 | 1.35E−17 | 2.37432504 |
| E.Enterocyte_Immature_2 | TMEM54 | 4.061 | 8.68E−165 | 1.39E+00 | 1.73E−199 | 3.480691951 |
| E.Enterocyte_Progenitor | CA1 | 3.386 | 0.00E+00 | 1.50E+00 | 8.58E−55 | 3.281612499 |
| E.Enterocyte_Progenitor | CA2 | 3.952 | 0.00E+00 | 8.98E−01 | 5.54E−42 | 3.742427108 |
| E.Enterocyte_Progenitor | FABP1 | 6.816 | 0.00E+00 | 2.32E+00 | 2.12E−145 | 6.384233482 |
| E.Enterocyte_Progenitor | FXYD3 | 4.646 | 0.00E+00 | 9.74E−01 | 2.64E−57 | 4.403240028 |
| E.Enterocyte_Progenitor | KRT19 | 4.065 | 0.00E+00 | 1.24E+00 | 4.89E−73 | 3.955605149 |
| E.Enterocyte_Progenitor | KRT8 | 4.971 | 0.00E+00 | 1.07E+00 | 3.04E−69 | 4.573460965 |
| E.Enterocyte_Progenitor | LGALS4 | 5.934 | 0.00E+00 | 1.03E+00 | 1.02E−70 | 4.817857244 |
| E.Enterocyte_Progenitor | PHGR1 | 7.475 | 0.00E+00 | 1.88E+00 | 8.07E−133 | 6.100770415 |
| E.Enterocyte_Progenitor | SELENBP1 | 4.211 | 0.00E+00 | 1.33E+00 | 4.51E−136 | 3.135115956 |
| E.Enterocytes | ANPEP | 4.276 | 0.00E+00 | 9.70E−01 | 4.37E−49 | 3.4334963 |
| E.Enterocytes | APOBEC3B | 3.764 | 0.00E+00 | 6.10E−01 | 1.70E−21 | 1.781460279 |
| E.Enterocytes | AQP8 | 7.060 | 0.00E+00 | 3.38E+00 | 2.11E−268 | 7.177138737 |
| E.Enterocytes | C19orf33 | 5.584 | 3.11E−198 | 1.36E+00 | 2.22E−188 | 4.137577174 |
| E.Enterocytes | CA4 | 6.565 | 0.00E+00 | 2.15E+00 | 2.95E−149 | 5.939432428 |
| E.Enterocytes | CEACAM1 | 4.695 | 0.00E+00 | 7.73E−01 | 9.35E−25 | 3.045247994 |
| E.Enterocytes | CEACAM5 | 6.519 | 0.00E+00 | 1.84E+00 | 4.95E−199 | 4.700907519 |
| E.Enterocytes | CEACAM7 | 5.715 | 0.00E+00 | 9.49E−01 | 4.29E−43 | 3.622341305 |
| E.Enterocytes | CFDP1 | 4.497 | 6.15E−231 | 1.06E+00 | 1.38E−132 | 3.245164922 |
| E.Enterocytes | CLCA4 | 5.018 | 0.00E+00 | 1.15E+00 | 1.95E−32 | 3.503102339 |
| E.Enterocytes | CLDN23 | 4.089 | 0.00E+00 | 5.26E−01 | 2.60E−16 | 2.160346928 |
| E.Enterocytes | CLDN7 | 5.365 | 2.79E−173 | 1.42E+00 | 9.21E−207 | 4.427110007 |
| E.Enterocytes | CTD-2228K2.5 | 5.362 | 0.00E+00 | 1.21E+00 | 9.92E−83 | 3.877284229 |
| E.Enterocytes | EMP1 | 4.123 | 0.00E+00 | 4.12E−01 | 1.24E−09 | 2.047517041 |
| E.Enterocytes | FTH1 | 1.916 | 1.32E−01 | 3.29E+00 | 0.00E+00 | 4.290842634 |
| E.Enterocytes | FXYD3 | 6.057 | 2.22E−164 | 1.91E+00 | 5.88E−195 | 5.426847174 |
| E.Enterocytes | GPRC5A | 4.048 | 0.00E+00 | 5.24E−01 | 1.70E−19 | 1.525511114 |
| E.Enterocytes | GUCA2A | 6.907 | 0.00E+00 | 3.09E+00 | 6.58E−220 | 7.354492732 |
| E.Enterocytes | GUCA2B | 6.330 | 0.00E+00 | 1.83E+00 | 4.32E−82 | 5.559777218 |
| E.Enterocytes | HIST1H1C | 4.085 | 0.00E+00 | 7.94E−01 | 2.15E−36 | 2.894643396 |
| E.Enterocytes | HPGD | 4.238 | 0.00E+00 | 5.12E−01 | 2.25E−16 | 2.509509481 |
| E.Enterocytes | IFI27 | 6.392 | 3.05E−125 | 2.53E+00 | 0.00E+00 | 5.895091164 |
| E.Enterocytes | IL32 | 5.937 | 3.27E−218 | 1.59E+00 | 1.14E−139 | 4.756889198 |
| E.Enterocytes | KRT20 | 5.007 | 0.00E+00 | 8.96E−01 | 8.40E−40 | 3.876747723 |
| E.Enterocytes | LYPD8 | 5.363 | 0.00E+00 | 1.79E+00 | 1.38E−122 | 4.928965265 |
| E.Enterocytes | MISP | 4.804 | 3.19E−301 | 7.87E−01 | 4.27E−65 | 2.937076305 |

TABLE 12-continued

Additional Cell Type Markers

| | | | | | | |
|---|---|---|---|---|---|---|
| E.Enterocytes | MS4A12 | 4.286 | 0.00E+00 | 9.91E-01 | 6.77E-37 | 3.637728367 |
| E.Enterocytes | MYO15B | 4.284 | 0.00E+00 | 3.86E-01 | 5.87E-14 | 2.331334816 |
| E.Enterocytes | NLN | 3.914 | 0.00E+00 | 5.51E-01 | 5.98E-17 | 1.748615136 |
| E.Enterocytes | PKIB | 3.969 | 1.63E-252 | 1.03E+00 | 3.43E-94 | 2.846373547 |
| E.Enterocytes | PLAC8 | 6.696 | 0.00E+00 | 2.10E+00 | 6.90E-230 | 5.029379735 |
| E.Enterocytes | PRAP1 | 5.954 | 0.00E+00 | 1.34E+00 | 1.28E-81 | 4.30079732 |
| E.Enterocytes | RP11-48O20.4 | 3.959 | 0.00E+00 | 5.85E-01 | 4.40E-29 | 2.478995999 |
| E.Enterocytes | SDCBP2 | 5.657 | 0.00E+00 | 1.52E+00 | 7.07E-168 | 4.352042706 |
| E.Enterocytes | SLC26A3 | 5.722 | 0.00E+00 | 1.77E+00 | 1.86E-111 | 4.84897002 |
| E.Enterocytes | SLC51B | 3.996 | 0.00E+00 | 4.22E-01 | 1.66E-15 | 2.404698069 |
| E.Enterocytes | SRI | 4.171 | 7.04E-80 | 1.82E+00 | 5.05E-295 | 4.265517134 |
| E.Enterocytes | TMEM37 | 3.713 | 1.33E-299 | 6.67E-01 | 5.75E-41 | 2.013255733 |
| E.Enterocytes | TRIM31 | 4.538 | 0.00E+00 | 4.75E-01 | 1.39E-11 | 2.802587786 |
| E.Enterocytes | TSPAN1 | 6.413 | 1.57E-228 | 1.94E+00 | 2.82E-237 | 5.148729385 |
| E.Epithelial | AGR2 | 3.949 | 0.00E+00 | 1.01E+00 | 8.09E-10 | 1.253081377 |
| E.Epithelial | ANXA1 | -4.217 | 0.00E+00 | -1.04E+00 | 7.40E-07 | -1.710241201 |
| E.Epithelial | BTG1 | -1.582 | 1.48E-130 | -1.36E+00 | 2.91E-239 | -1.367126527 |
| E.Epithelial | C15orf48 | 4.669 | 0.00E+00 | 1.59E+00 | 8.27E-80 | 2.960253603 |
| E.Epithelial | C19orf33 | 4.647 | 0.00E+00 | 9.18E-01 | 1.35E-10 | 1.134930377 |
| E.Epithelial | CA2 | 3.288 | 0.00E+00 | 1.19E+00 | 2.03E-32 | 2.331379028 |
| E.Epithelial | CKB | 3.289 | 0.00E+00 | 8.62E-01 | 2.47E-12 | 1.146140076 |
| E.Epithelial | CLDN3 | 4.663 | 0.00E+00 | 9.77E-01 | 1.82E-24 | 1.215653124 |
| E.Epithelial | CLDN4 | 4.347 | 0.00E+00 | 7.77E-01 | 6.52E-13 | 1.15526912 |
| E.Epithelial | CLDN7 | 4.624 | 0.00E+00 | 1.00E+00 | 6.15E-31 | 1.876200849 |
| E.Epithelial | COX5B | 2.214 | 5.36E-161 | 1.11E+00 | 8.18E-267 | 1.799641559 |
| E.Epithelial | DUSP1 | -1.288 | 2.69E-97 | -1.53E+00 | 2.48E-242 | -1.135839708 |
| E.Epithelial | EIF1 | -1.762 | 2.34E-66 | -1.40E+00 | 0.00E+00 | -2.021194885 |
| E.Epithelial | ELF3 | 4.803 | 0.00E+00 | 7.95E-01 | 2.09E-12 | 1.239636169 |
| E.Epithelial | EPCAM | 4.613 | 0.00E+00 | 1.62E+00 | 1.40E-82 | 2.59722632 |
| E.Epithelial | FABP1 | 3.453 | 0.00E+00 | 2.94E+00 | 3.19E-179 | 4.955159628 |
| E.Epithelial | FCGBP | 3.946 | 0.00E+00 | 1.37E+00 | 2.63E-10 | 1.688693541 |
| E.Epithelial | FXYD3 | 4.263 | 0.00E+00 | 2.08E+00 | 2.40E-125 | 3.385670825 |
| E.Epithelial | H3F3B | -1.872 | 3.49E-99 | -1.42E+00 | 0.00E+00 | -1.851301465 |
| E.Epithelial | HMGCS2 | 4.819 | 0.00E+00 | 2.68E-01 | 7.29E-02 | 1.305286854 |
| E.Epithelial | IFI27 | 2.816 | 0.00E+00 | 6.65E-01 | 1.44E-17 | 2.137897548 |
| E.Epithelial | IFITM2 | -2.952 | 0.00E+00 | -1.39E+00 | 2.78E-77 | -1.263956467 |
| E.Epithelial | JUNB | -1.448 | 3.67E-98 | -1.77E+00 | 0.00E+00 | -1.744661197 |
| E.Epithelial | KRT18 | 4.848 | 0.00E+00 | 1.75E+00 | 9.68E-103 | 3.014353055 |
| E.Epithelial | KRT19 | 3.783 | 0.00E+00 | 1.05E+00 | 1.11E-15 | 1.678360125 |
| E.Epithelial | KRT20 | 3.500 | 0.00E+00 | 9.49E-01 | 1.35E-09 | 1.692310998 |
| E.Epithelial | KRT8 | 4.853 | 0.00E+00 | 2.26E+00 | 2.77E-200 | 4.101240322 |
| E.Epithelial | LGALS1 | -3.516 | 0.00E+00 | -1.95E+00 | 2.98E-52 | -1.780792681 |
| E.Epithelial | LGALS3 | 2.748 | 1.14E-241 | 1.69E+00 | 9.68E-287 | 3.079368421 |
| E.Epithelial | LGALS4 | 5.445 | 0.00E+00 | 2.59E+00 | 5.11E-274 | 4.781743305 |
| E.Epithelial | MT-ATP6 | 0.934 | 7.28E-19 | 2.05E+00 | 0.00E+00 | 2.293028029 |
| E.Epithelial | MT-ND2 | 0.492 | 5.82E-05 | 1.81E+00 | 0.00E+00 | 1.625662978 |
| E.Epithelial | MT-RNR1 | 1.652 | 3.50E-62 | 2.20E+00 | 0.00E+00 | 3.082297281 |
| E.Epithelial | MT1G | 3.638 | 0.00E+00 | 7.00E-01 | 7.15E-06 | 1.243604189 |
| E.Epithelial | PIGR | 4.870 | 0.00E+00 | 1.44E+00 | 1.80E-40 | 2.220870574 |
| E.Epithelial | RPL21 | -2.431 | 6.34E-73 | -1.21E+00 | 1.28E-260 | -3.027643271 |
| E.Epithelial | S100A6 | 2.947 | 4.26E-150 | 1.71E+00 | 0.00E+00 | 3.608164898 |
| E.Epithelial | SMIM22 | 6.002 | 0.00E+00 | 5.78E-01 | 3.52E-04 | 1.024792323 |
| E.Epithelial | SPINT2 | 3.019 | 0.00E+00 | 7.90E-01 | 1.76E-51 | 1.075499988 |
| E.Epithelial | TSPAN1 | 4.132 | 0.00E+00 | 1.01E+00 | 2.20E-11 | 1.756588332 |
| E.Epithelial | ZFP36 | -1.608 | 8.96E-149 | -1.59E+00 | 3.30E-285 | -1.438143355 |
| E.Goblet | CEACAM5 | 4.002 | 0.00E+00 | 1.03E+00 | 4.78E-45 | 2.968738633 |
| E.Goblet | CLDN4 | 3.623 | 3.64E-260 | 9.79E-01 | 4.81E-70 | 2.991613153 |
| E.Goblet | FAM3D | 3.571 | 1.62E-260 | 8.96E-01 | 3.82E-68 | 2.437979965 |
| E.Goblet | FCGBP | 5.018 | 0.00E+00 | 2.85E+00 | 2.31E-219 | 5.921268619 |
| E.Goblet | FXYD3 | 4.708 | 3.13E-259 | 1.30E+00 | 6.86E-74 | 4.686719039 |
| E.Goblet | GSN | 4.114 | 1.01E-263 | 1.45E+00 | 1.95E-107 | 4.26091539 |
| E.Goblet | IFI27 | 5.113 | 2.73E-240 | 1.79E+00 | 3.67E-134 | 5.086890298 |
| E.Goblet | LYPD8 | 4.063 | 0.00E+00 | 8.87E-01 | 2.31E-25 | 3.43572456 |
| E.Goblet | MUC1 | 3.744 | 2.28E-303 | 1.06E+00 | 8.46E-49 | 1.779435114 |
| E.Goblet | MUC2 | 6.322 | 0.00E+00 | 3.25E+00 | 1.13E-201 | 6.142438491 |
| E.Goblet | TFF1 | 5.714 | 0.00E+00 | 2.47E+00 | 3.84E-54 | 4.455223547 |
| E.Goblet | TFF3 | 5.667 | 0.00E+00 | 3.29E+00 | 5.07E-166 | 6.864284391 |
| E.Goblet | TSPAN1 | 4.367 | 0.00E+00 | 1.20E+00 | 8.68E-69 | 4.020758556 |
| E.Goblet | ZG16 | 6.895 | 0.00E+00 | 5.45E+00 | 0.00E+00 | 9.067037516 |
| E.Immature_Enterocytes | AQP8 | 2.562 | 0.00E+00 | 1.17E+00 | 3.17E-29 | 2.608741765 |
| E.Immature_Enterocytes | C15orf48 | 3.540 | 0.00E+00 | 4.76E-01 | 3.03E-29 | 3.057877917 |
| E.Immature_Enterocytes | C19orf33 | 3.153 | 0.00E+00 | 7.95E-01 | 4.84E-85 | 2.007697328 |
| E.Immature_Enterocytes | CA1 | 2.744 | 0.00E+00 | 1.90E+00 | 4.64E-101 | 2.192458205 |
| E.Immature_Enterocytes | CA2 | 3.825 | 0.00E+00 | 1.35E+00 | 3.12E-132 | 3.555364117 |
| E.Immature_Enterocytes | CDHR5 | 2.788 | 0.00E+00 | 4.38E-01 | 4.00E-25 | 1.143355387 |
| E.Immature_Enterocytes | CEACAM7 | 2.742 | 0.00E+00 | 3.30E-01 | 1.42E-05 | 1.247437806 |
| E.Immature_Enterocytes | CKB | 2.424 | 1.57E-270 | 1.35E+00 | 1.05E-108 | 1.574412494 |
| E.Immature_Enterocytes | CLDN7 | 3.489 | 0.00E+00 | 5.32E-01 | 2.73E-47 | 2.705758523 |

TABLE 12-continued

Additional Cell Type Markers

| | | | | | | |
|---|---|---|---|---|---|---|
| E.Immature_Enterocytes | CTD-2228K2.5 | 2.752 | 0.00E+00 | 3.71E-01 | 9.67E-09 | 1.49783796 |
| E.Immature_Enterocytes | EPCAM | 2.955 | 0.00E+00 | -1.17E-02 | 7.87E-01 | 2.427057509 |
| E.Immature_Enterocytes | ETHE1 | 2.453 | 4.30E-258 | 9.99E-01 | 1.05E-132 | 1.482997692 |
| E.Immature_Enterocytes | FABP1 | 7.054 | 0.00E+00 | 3.05E+00 | 0.00E+00 | 6.557149922 |
| E.Immature_Enterocytes | FXYD3 | 4.961 | 0.00E+00 | 1.70E+00 | 1.42E-287 | 4.711504101 |
| E.Immature_Enterocytes | GUCA2A | 2.653 | 0.00E+00 | 1.35E+00 | 9.17E-43 | 2.839818034 |
| E.Immature_Enterocytes | KRT18 | 3.119 | 0.00E+00 | 2.67E-01 | 6.93E-10 | 2.756402712 |
| E.Immature_Enterocytes | KRT19 | 3.054 | 0.00E+00 | 1.74E+00 | 3.42E-197 | 2.892412398 |
| E.Immature_Enterocytes | KRT20 | 3.095 | 0.00E+00 | 8.75E-01 | 2.59E-40 | 2.309331115 |
| E.Immature_Enterocytes | KRT8 | 4.742 | 0.00E+00 | 1.46E+00 | 1.61E-217 | 4.522895646 |
| E.Immature_Enterocytes | LGALS3 | 3.227 | 6.30E-211 | 1.53E+00 | 3.05E-290 | 3.780959158 |
| E.Immature_Enterocytes | LGALS4 | 4.998 | 0.00E+00 | 6.64E-01 | 1.01E-44 | 4.280123818 |
| E.Immature_Enterocytes | MS4A12 | 3.085 | 0.00E+00 | 7.42E-01 | 4.17E-20 | 1.717936251 |
| E.Immature_Enterocytes | PHGR1 | 6.879 | 0.00E+00 | 2.49E+00 | 0.00E+00 | 6.287397388 |
| E.Immature_Enterocytes | PIGR | 3.423 | 0.00E+00 | 6.49E-01 | 5.35E-50 | 2.774586468 |
| E.Immature_Enterocytes | PLAC8 | 2.738 | 0.00E+00 | 5.60E-01 | 2.45E-18 | 2.073305121 |
| E.Immature_Enterocytes | PRAP1 | 2.623 | 0.00E+00 | 4.30E-01 | 3.61E-10 | 1.510711869 |
| E.Immature_Enterocytes | SDCBP2 | 2.707 | 0.00E+00 | 3.15E-01 | 1.19E-09 | 1.418862701 |
| E.Immature_Enterocytes | SELENBP1 | 2.469 | 8.53E-272 | 1.20E+00 | 7.94E-130 | 1.298087006 |
| E.Immature_Enterocytes | SLC26A2 | 3.134 | 0.00E+00 | 9.92E-01 | 3.09E-61 | 1.123729159 |
| E.Immature_Enterocytes | SLC26A3 | 3.427 | 0.00E+00 | 8.97E-01 | 7.27E-31 | 2.292018359 |
| E.Immature_Enterocytes | SLC51B | 3.063 | 0.00E+00 | 3.81E-01 | 8.85E-11 | 1.024945086 |
| E.Immature_Enterocytes | SMIM22 | 2.809 | 0.00E+00 | 5.17E-01 | 4.28E-49 | 1.685183951 |
| E.Immature_Enterocytes | SRI | 2.507 | 5.04E-209 | 1.08E+00 | 3.30E-176 | 2.332610674 |
| E.Immature_Enterocytes | TMEM54 | 2.975 | 0.00E+00 | 9.87E-01 | 2.95E-121 | 1.645157143 |
| E.Immature_Enterocytes | TSPAN1 | 3.329 | 0.00E+00 | 7.60E-01 | 1.30E-51 | 2.602637796 |
| E.Immature_Goblet | AGR2 | 3.431 | 1.31E-304 | 1.75E+00 | 4.76E-122 | 3.413884158 |
| E.Immature_Goblet | CLCA1 | 4.350 | 0.00E+00 | 2.34E+00 | 1.17E-98 | 3.288406852 |
| E.Immature_Goblet | FCGBP | 4.495 | 0.00E+00 | 2.12E+00 | 8.68E-176 | 4.957987636 |
| E.Immature_Goblet | ITLN1 | 5.156 | 0.00E+00 | 2.32E+00 | 3.48E-92 | 4.367175216 |
| E.Immature_Goblet | KLK1 | 5.385 | 0.00E+00 | 1.96E+00 | 2.94E-163 | 3.739014763 |
| E.Immature_Goblet | KRT18 | 3.877 | 1.01E-269 | 8.78E-01 | 9.19E-60 | 3.753416847 |
| E.Immature_Goblet | LRRC26 | 4.285 | 0.00E+00 | 8.34E-01 | 8.76E-29 | 1.36967859 |
| E.Immature_Goblet | MUC2 | 4.313 | 0.00E+00 | 4.61E-01 | 2.10E-06 | 3.154373567 |
| E.Immature_Goblet | REP15 | 3.858 | 0.00E+00 | 4.12E-01 | 3.84E-08 | 1.607019236 |
| E.Immature_Goblet | RETNLB | 4.214 | 0.00E+00 | 1.69E+00 | 7.13E-42 | 1.929546104 |
| E.Immature_Goblet | RNASE1 | 4.048 | 0.00E+00 | 8.71E-01 | 3.95E-38 | 2.827005292 |
| E.Immature_Goblet | SERPINA1 | 3.421 | 0.00E+00 | 8.22E-01 | 3.24E-31 | 1.633161619 |
| E.Immature_Goblet | SPINK1 | 3.753 | 0.00E+00 | 1.08E+00 | 1.84E-48 | 1.913114833 |
| E.Immature_Goblet | SPINK4 | 3.885 | 0.00E+00 | 1.57E+00 | 1.52E-19 | 2.475188133 |
| E.Immature_Goblet | TFF3 | 6.904 | 0.00E+00 | 4.93E+00 | 0.00E+00 | 8.29841861 |
| E.Immature_Goblet | WFDC2 | 4.563 | 0.00E+00 | 1.82E+00 | 1.43E-85 | 2.003880612 |
| E.Immature_Goblet | ZG16 | 3.631 | 0.00E+00 | 2.46E+00 | 4.56E-78 | 5.239192724 |
| E.Secretory | FCGBP | 2.255 | 1.76E-180 | 2.51E+00 | 2.12E-170 | 2.685649637 |
| E.Secretory | KRT18 | 3.797 | 0.00E+00 | 9.56E-01 | 2.03E-60 | 3.870979692 |
| E.Secretory | MUC2 | 3.090 | 8.90E-300 | 2.88E+00 | 1.05E-153 | 2.97529401 |
| E.Secretory | TFF1 | 3.677 | 0.00E+00 | 2.22E+00 | 2.45E-45 | 2.433519046 |
| E.Secretory | TFF3 | 3.887 | 0.00E+00 | 2.43E+00 | 7.95E-106 | 5.096886913 |
| E.Secretory | ZG16 | 2.414 | 1.69E-209 | 4.64E+00 | 6.23E-264 | 4.51896634 |
| E.Secretory_All | CLCA1 | 3.005 | 0.00E+00 | 1.59E+00 | 1.20E-45 | 1.398794545 |
| E.Secretory_All | FCGBP | 3.151 | 0.00E+00 | 2.22E+00 | 4.83E-247 | 3.402013896 |
| E.Secretory_All | FXYD3 | 2.648 | 7.25E-302 | -6.63E-01 | 6.00E-37 | 2.27714686 |
| E.Secretory_All | ITLN1 | 3.479 | 0.00E+00 | 1.50E+00 | 5.99E-33 | 1.898258706 |
| E.Secretory_All | KLK1 | 4.279 | 0.00E+00 | 1.28E+00 | 5.36E-62 | 1.43230919 |
| E.Secretory_All | KRT18 | 3.810 | 0.00E+00 | 8.00E-01 | 1.08E-74 | 3.69599281 |
| E.Secretory_All | KRT8 | 3.729 | 0.00E+00 | -1.29E-01 | 7.04E-03 | 3.307698873 |
| E.Secretory_All | LGALS4 | 3.259 | 0.00E+00 | 3.38E-02 | 4.74E-01 | 3.402953324 |
| E.Secretory_All | MUC2 | 3.811 | 0.00E+00 | 1.65E+00 | 7.54E-54 | 2.531118742 |
| E.Secretory_All | REP15 | 3.631 | 0.00E+00 | 5.12E-01 | 1.68E-07 | 1.007908306 |
| E.Secretory_All | SPINK4 | 3.264 | 0.00E+00 | 7.97E-01 | 2.70E-05 | 1.333729761 |
| E.Secretory_All | TFF3 | 4.523 | 0.00E+00 | 4.34E+00 | 0.00E+00 | 6.403931399 |
| E.Secretory_All | ZG16 | 2.819 | 0.00E+00 | 3.35E+00 | 1.31E-190 | 4.477100018 |
| E.Tuft | KRT18 | 5.434 | 7.28E-158 | 2.62E+00 | 1.91E-209 | 5.752838414 |
| F.Crypt | A2M | 4.284 | 0.00E+00 | 1.17E+00 | 1.85E-72 | 3.492074115 |
| F.Crypt | ABCA8 | 5.496 | 0.00E+00 | 7.50E-01 | 5.75E-06 | 1.688536779 |
| F.Crypt | ADAM28 | 3.648 | 0.00E+00 | 7.34E-01 | 1.73E-17 | 1.3316427 |
| F.Crypt | ADAMDEC1 | 5.668 | 0.00E+00 | 4.47E+00 | 0.00E+00 | 5.70918829 |
| F.Crypt | ADH1B | 3.617 | 0.00E+00 | 1.26E+00 | 1.14E-43 | 1.243902457 |
| F.Crypt | APOE | 6.298 | 0.00E+00 | 3.31E+00 | 0.00E+00 | 6.688838049 |
| F.Crypt | BMP4 | 3.215 | 0.00E+00 | -5.22E-01 | 6.37E-13 | 1.570952671 |
| F.Crypt | C1R | 5.051 | 0.00E+00 | 1.27E+00 | 6.77E-60 | 3.743899141 |
| F.Crypt | C1S | 5.165 | 0.00E+00 | 1.18E+00 | 2.98E-50 | 3.879547488 |
| F.Crypt | CALD1 | 3.961 | 0.00E+00 | 1.27E+00 | 7.55E-02 | 2.800815759 |
| F.Crypt | CCL11 | 5.288 | 0.00E+00 | 2.77E+00 | 9.04E-12 | 3.068255858 |
| F.Crypt | CCL13 | 5.690 | 0.00E+00 | 3.29E+00 | 1.88E-14 | 2.738743783 |
| F.Crypt | CCL2 | 4.486 | 0.00E+00 | 1.01E+00 | 7.78E-15 | 3.492339648 |
| F.Crypt | CCL8 | 5.709 | 0.00E+00 | 2.86E+00 | 1.14E-33 | 2.701919577 |
| F.Crypt | CD63 | 2.718 | 4.96E-122 | 1.43E+00 | 0.00E+00 | 3.486481313 |

TABLE 12-continued

Additional Cell Type Markers

| | | | | | | |
|---|---|---|---|---|---|---|
| F.Crypt | CFD | 6.712 | 0.00E+00 | 4.21E+00 | 0.00E+00 | 6.838074558 |
| F.Crypt | CFH | 4.252 | 0.00E+00 | 6.33E-01 | 7.26E-09 | 1.853771933 |
| F.Crypt | CLEC11A | 3.606 | 0.00E+00 | 5.62E-01 | 1.03E-18 | 1.895949104 |
| F.Crypt | COL1A1 | 4.065 | 0.00E+00 | 1.86E-01 | 3.22E-02 | 2.600863122 |
| F.Crypt | COL1A2 | 4.802 | 0.00E+00 | 5.71E-01 | 1.78E-13 | 3.478176115 |
| F.Crypt | COL3A1 | 4.651 | 0.00E+00 | 6.79E-01 | 1.20E-13 | 3.464081884 |
| F.Crypt | COL6A1 | 3.150 | 0.00E+00 | -4.52E-01 | 3.79E-10 | 1.63183674 |
| F.Crypt | COL6A2 | 4.071 | 0.00E+00 | -1.23E-01 | 1.12E-01 | 2.870797734 |
| F.Crypt | CTSC | 3.442 | 0.00E+00 | 2.00E+00 | 0.00E+00 | 3.77792912 |
| F.Crypt | CTSK | 4.270 | 0.00E+00 | 6.12E-01 | 9.43E-11 | 2.07068938 |
| F.Crypt | CXCL12 | 4.295 | 0.00E+00 | 8.91E-01 | 2.89E-17 | 2.357940547 |
| F.Crypt | CXCL14 | 3.894 | 0.00E+00 | 2.81E+00 | 0.00E+00 | 5.192128961 |
| F.Crypt | CYGB | 4.307 | 0.00E+00 | 3.91E-02 | 6.32E-01 | 2.398157949 |
| F.Crypt | DCN | 6.004 | 0.00E+00 | 2.79E+00 | 2.10E-201 | 4.989098789 |
| F.Crypt | DKK3 | 4.247 | 0.00E+00 | -2.46E-01 | 1.45E-02 | 1.25655402 |
| F.Crypt | EFEMP1 | 4.062 | 0.00E+00 | 3.40E-01 | 2.66E-02 | 1.037851843 |
| F.Crypt | EFEMP2 | 3.540 | 0.00E+00 | -4.70E-02 | 5.51E-01 | 1.084607071 |
| F.Crypt | EMILIN1 | 3.650 | 0.00E+00 | 6.55E-02 | 4.18E-01 | 1.522259058 |
| F.Crypt | FABP4 | 5.111 | 0.00E+00 | 2.30E-01 | 5.01E-01 | 1.194045652 |
| F.Crypt | FBLN1 | 5.764 | 0.00E+00 | 1.54E+00 | 1.40E-46 | 3.438001639 |
| F.Crypt | GGT5 | 5.016 | 0.00E+00 | 4.02E-01 | 5.03E-03 | 1.343247026 |
| F.Crypt | GNG11 | 3.200 | 0.00E+00 | -8.10E-01 | 2.01E-23 | 1.5347982 |
| F.Crypt | GPX3 | 4.218 | 0.00E+00 | 5.13E-01 | 4.53E-11 | 2.829560076 |
| F.Crypt | GSN | 3.608 | 0.00E+00 | 1.86E+00 | 0.00E+00 | 4.01570815 |
| F.Crypt | HAAO | 3.538 | 0.00E+00 | 4.78E-01 | 1.81E-09 | 1.117489226 |
| F.Crypt | IFITM3 | 4.587 | 0.00E+00 | 1.81E+00 | 2.24E-305 | 4.693229283 |
| F.Crypt | IGFBP6 | 3.447 | 0.00E+00 | 2.88E-01 | 2.45E-03 | 1.802560823 |
| F.Crypt | IGFBP7 | 6.374 | 0.00E+00 | 2.12E+00 | 1.07E-150 | 6.278605 |
| F.Crypt | LAPTM4A | 2.172 | 1.00E-225 | 1.15E+00 | 9.11E-216 | 1.650359625 |
| F.Crypt | LGALS1 | 4.361 | 0.00E+00 | 1.20E+00 | 2.63E-129 | 4.014277197 |
| F.Crypt | LINC01082 | 4.891 | 0.00E+00 | 3.90E-01 | 1.26E-03 | 1.832126089 |
| F.Crypt | LTBP4 | 2.845 | 0.00E+00 | 7.67E-01 | 5.61E-53 | 1.55451071 |
| F.Crypt | LUM | 5.474 | 0.00E+00 | 2.63E+00 | 5.18E-131 | 4.610864086 |
| F.Crypt | MFAP4 | 5.218 | 0.00E+00 | 1.51E+00 | 8.79E-64 | 4.233927469 |
| F.Crypt | MFGE8 | 2.986 | 0.00E+00 | -2.47E-01 | 1.09E-03 | 1.347363767 |
| F.Crypt | MMP2 | 3.597 | 0.00E+00 | -2.95E-01 | 9.94E-05 | 1.902455796 |
| F.Crypt | MYL9 | 2.778 | 0.00E+00 | -5.15E-01 | 1.34E-11 | 1.502286202 |
| F.Crypt | NGFRAP1 | 2.528 | 0.00E+00 | 6.10E-01 | 5.49E-56 | 1.354437953 |
| F.Crypt | NNMT | 3.431 | 0.00E+00 | -2.14E-01 | 1.54E-02 | 1.388286729 |
| F.Crypt | PCOLCE | 3.816 | 0.00E+00 | 1.40E+00 | 1.41E-01 | 1.520934896 |
| F.Crypt | PLAC9 | 4.658 | 0.00E+00 | 3.18E-01 | 7.56E-03 | 2.119682525 |
| F.Crypt | PLAT | 2.836 | 0.00E+00 | -9.77E-01 | 1.02E-31 | 1.714357364 |
| F.Crypt | PLTP | 3.245 | 0.00E+00 | 4.97E-01 | 2.42E-12 | 1.128031708 |
| F.Crypt | PMP22 | 3.549 | 0.00E+00 | 4.10E-01 | 5.72E-09 | 1.968640894 |
| F.Crypt | PPAP2A | 2.665 | 0.00E+00 | 8.91E-01 | 1.70E-84 | 1.654665665 |
| F.Crypt | PPAP2B | 4.323 | 0.00E+00 | 8.74E-01 | 8.59E-24 | 1.672913736 |
| F.Crypt | PPP1R14A | 2.882 | 0.00E+00 | 3.39E-01 | 7.24E-09 | 2.075006444 |
| F.Crypt | PRKCDBP | 3.358 | 0.00E+00 | -1.01E-01 | 1.34E-01 | 1.868623908 |
| F.Crypt | PROCR | 4.040 | 0.00E+00 | 6.40E-01 | 2.77E-18 | 2.45588358 |
| F.Crypt | PTGDS | 4.801 | 0.00E+00 | 1.38E+00 | 3.35E-07 | 2.157176738 |
| F.Crypt | PTN | 4.436 | 0.00E+00 | 4.86E-01 | 3.27E-05 | 1.90716397 |
| F.Crypt | RARRES2 | 3.704 | 0.00E+00 | 7.23E-01 | 1.11E-43 | 2.949004193 |
| F.Crypt | RBP1 | 4.222 | 0.00E+00 | 6.90E-01 | 1.61E-19 | 2.667468 |
| F.Crypt | S100A13 | 2.452 | 2.98E-301 | 5.56E-01 | 1.24E-40 | 1.18901627 |
| F.Crypt | SELM | 2.910 | 0.00E+00 | 7.91E-01 | 8.90E-74 | 2.662116539 |
| F.Crypt | SEPPI | 2.702 | 0.00E+00 | 8.41E-01 | 1.07E-55 | 2.690236454 |
| F.Crypt | SERPINF1 | 3.865 | 0.00E+00 | 3.20E-01 | 1.08E-05 | 2.625543209 |
| F.Crypt | SERPING1 | 3.525 | 0.00E+00 | 3.51E-01 | 1.15E-07 | 2.202321285 |
| F.Crypt | SGCE | 3.394 | 0.00E+00 | 9.98E-02 | 1.93E-01 | 1.318068281 |
| F.Crypt | SOD3 | 4.535 | 0.00E+00 | 1.32E+00 | 1.26E-57 | 2.867761402 |
| F.Crypt | SPARC | 3.291 | 0.00E+00 | -2.81E-01 | 8.62E-05 | 2.178834875 |
| F.Crypt | SPARCL1 | 2.885 | 0.00E+00 | -7.17E-01 | 2.83E-19 | 1.289030226 |
| F.Crypt | SPON2 | 3.311 | 0.00E+00 | 4.11E-01 | 2.88E-08 | 1.109871188 |
| F.Crypt | STMN2 | 4.214 | 0.00E+00 | 7.72E-01 | 9.69E-10 | 1.298791061 |
| F.Crypt | TCF21 | 5.007 | 0.00E+00 | 9.02E-01 | 3.64E-21 | 3.133263086 |
| F.Crypt | TIMP1 | 3.158 | 0.00E+00 | 8.42E-01 | 7.64E-62 | 3.071014624 |
| F.Crypt | TM4SF1 | 2.743 | 0.00E+00 | 1.77E-02 | 7.98E-01 | 1.620288745 |
| F.Crypt | TMEM176A | 2.953 | 0.00E+00 | 1.16E+00 | 1.88E-195 | 2.275110559 |
| F.Crypt | TMEM176B | 3.878 | 0.00E+00 | 1.81E+00 | 0.00E+00 | 4.09743926 |
| F.Crypt | TPM2 | 2.939 | 0.00E+00 | -6.77E-01 | 5.60E-19 | 1.538165952 |
| F.Crypt | TSPAN4 | 3.028 | 0.00E+00 | -1.37E-02 | 8.11E-01 | 1.529585907 |
| F.Crypt | VIM | 3.222 | 0.00E+00 | 1.35E+00 | 8.69E-224 | 3.162898723 |
| F.Crypt_hiFos | A2M | 4.512 | 0.00E+00 | 8.15E-01 | 3.22E-33 | 3.676893205 |
| F.Crypt_hiFos | ABCA8 | 4.194 | 0.00E+00 | -4.76E-02 | 6.20E-01 | 2.649916107 |
| F.Crypt_hiFos | ADAMDEC1 | 7.088 | 0.00E+00 | 2.83E+00 | 4.26E-106 | 7.218882666 |
| F.Crypt_hiFos | APOE | 6.567 | 0.00E+00 | 2.01E+00 | 3.43E-76 | 6.615669035 |
| F.Crypt_hiFos | C1R | 5.565 | 0.00E+00 | 8.50E-01 | 2.64E-30 | 4.216039635 |
| F.Crypt_hiFos | C1S | 5.634 | 0.00E+00 | 9.16E-01 | 5.97E-39 | 4.521134396 |

TABLE 12-continued

Additional Cell Type Markers

| | | | | | | |
|---|---|---|---|---|---|---|
| F.Crypt_hiFos | CCL2 | 6.150 | 0.00E+00 | 1.27E+00 | 1.29E-30 | 5.123848379 |
| F.Crypt_hiFos | CCL8 | 4.875 | 0.00E+00 | 9.76E-01 | 3.13E-13 | 4.529100706 |
| F.Crypt_hiFos | CFD | 6.860 | 0.00E+00 | 2.89E+00 | 9.60E-176 | 7.220630374 |
| F.Crypt_hiFos | COL1A1 | 4.013 | 0.00E+00 | -1.52E-01 | 6.42E-02 | 2.82946601 |
| F.Crypt_hiFos | COL1A2 | 5.086 | 0.00E+00 | 2.94E-02 | 6.96E-01 | 3.494207311 |
| F.Crypt_hiFos | COL3A1 | 4.638 | 0.00E+00 | 1.50E-01 | 7.55E-02 | 3.596814435 |
| F.Crypt_hiFos | COL6A2 | 3.948 | 0.00E+00 | -3.21E-01 | 2.07E-05 | 2.806908085 |
| F.Crypt_hiFos | CTSC | 4.500 | 6.34E-256 | 1.89E+00 | 1.98E-199 | 4.569762818 |
| F.Crypt_hiFos | CXCL12 | 4.235 | 0.00E+00 | 3.80E-01 | 1.02E-06 | 3.1951176 |
| F.Crypt_hiFos | CXCL14 | 5.349 | 1.31E-258 | 2.52E+00 | 3.41E-138 | 5.763443334 |
| F.Crypt_hiFos | CYGB | 4.188 | 0.00E+00 | 9.68E-02 | 1.58E-01 | 2.819846584 |
| F.Crypt_hiFos | DCN | 6.287 | 0.00E+00 | 1.31E+00 | 1.48E-43 | 5.283090907 |
| F.Crypt_hiFos | FBLN1 | 5.461 | 0.00E+00 | 4.82E-01 | 5.93E-10 | 3.726786119 |
| F.Crypt_hiFos | GPX3 | 4.276 | 0.00E+00 | 2.55E-01 | 4.12E-04 | 3.3265932 |
| F.Crypt_hiFos | GSN | 4.198 | 3.26E-202 | 1.61E+00 | 1.66E-141 | 4.426932662 |
| F.Crypt_hiFos | HAPLN1 | 4.502 | 0.00E+00 | 4.15E-01 | 2.32E-05 | 2.524390098 |
| F.Crypt_hiFos | IFITM3 | 4.767 | 2.69E-230 | 1.50E+00 | 3.30E-120 | 4.706261067 |
| F.Crypt_hiFos | IGFBP7 | 7.507 | 0.00E+00 | 1.40E+00 | 9.36E-43 | 6.303383638 |
| F.Crypt_hiFos | LUM | 6.169 | 0.00E+00 | 1.29E+00 | 9.03E-34 | 5.351962011 |
| F.Crypt_hiFos | MFAP4 | 5.988 | 0.00E+00 | 7.99E-01 | 5.26E-23 | 4.555224313 |
| F.Crypt_hiFos | PPAP2B | 3.920 | 0.00E+00 | 3.93E-01 | 9.26E-09 | 2.394203067 |
| F.Crypt_hiFos | PROCR | 4.081 | 0.00E+00 | 2.87E-01 | 1.61E-05 | 3.077806433 |
| F.Crypt_hiFos | RBP1 | 4.194 | 0.00E+00 | 4.28E-01 | 5.10E-10 | 3.130240169 |
| F.Crypt_hiFos | SERPINF1 | 4.010 | 0.00E+00 | 4.87E-02 | 4.85E-01 | 3.045950154 |
| F.Crypt_hiFos | SOD3 | 4.488 | 0.00E+00 | 7.24E-01 | 1.16E-19 | 3.463482129 |
| F.Crypt_hiFos | TCF21 | 4.584 | 0.00E+00 | 2.38E-01 | 1.31E-03 | 3.283744234 |
| F.Crypt_hiFos | TMEM176B | 4.410 | 7.82E-165 | 1.71E+00 | 1.08E-197 | 4.527681262 |
| F.Crypt_hiFos | VIM | 4.984 | 3.19E-214 | 1.39E+00 | 1.13E-121 | 3.48544695 |
| F.Crypt_loFos_1 | A2M | 4.566 | 0.00E+00 | 5.85E-01 | 2.88E-20 | 3.471644048 |
| F.Crypt_loFos_1 | ABCA8 | 4.248 | 0.00E+00 | 2.03E-01 | 4.13E-02 | 2.55026446 |
| F.Crypt_loFos_1 | ADAMDEC1 | 7.160 | 0.00E+00 | 3.05E+00 | 9.68E-134 | 6.568413627 |
| F.Crypt_loFos_1 | APOE | 8.389 | 0.00E+00 | 2.58E+00 | 2.82E-151 | 7.136783921 |
| F.Crypt_loFos_1 | C1R | 5.496 | 0.00E+00 | 7.93E-01 | 1.24E-30 | 4.131494165 |
| F.Crypt_loFos_1 | C1S | 5.837 | 0.00E+00 | 6.91E-01 | 4.03E-22 | 4.237252058 |
| F.Crypt_loFos_1 | CALD1 | 4.220 | 0.00E+00 | 9.82E-03 | 8.86E-01 | 3.150459876 |
| F.Crypt_loFos_1 | CCL13 | 3.859 | 0.00E+00 | 7.60E-01 | 1.35E-04 | 3.58486718 |
| F.Crypt_loFos_1 | CCL2 | 4.141 | 0.00E+00 | 2.30E-01 | 4.37E-02 | 3.733752357 |
| F.Crypt_loFos_1 | CCL8 | 4.449 | 0.00E+00 | 2.59E-01 | 5.58E-02 | 3.576080936 |
| F.Crypt_loFos_1 | CFD | 7.081 | 0.00E+00 | 3.01E+00 | 2.68E-209 | 7.152385774 |
| F.Crypt_loFos_1 | CFH | 3.783 | 0.00E+00 | 1.85E-01 | 2.47E-02 | 2.220815228 |
| F.Crypt_loFos_1 | CLEC11A | 3.494 | 0.00E+00 | 2.04E-01 | 4.21E-04 | 2.258975783 |
| F.Crypt_loFos_1 | COL1A1 | 4.014 | 0.00E+00 | 7.08E-02 | 3.52E-01 | 2.963298302 |
| F.Crypt_loFos_1 | COL1A2 | 5.242 | 0.00E+00 | 3.40E-01 | 2.62E-06 | 3.602018387 |
| F.Crypt_loFos_1 | COL3A1 | 4.942 | 0.00E+00 | 5.30E-01 | 7.50E-11 | 3.873803804 |
| F.Crypt_loFos_1 | COL6A2 | 3.984 | 0.00E+00 | -2.72E-01 | 1.28E-04 | 2.837098282 |
| F.Crypt_loFos_1 | CTSC | 4.685 | 0.00E+00 | 1.83E+00 | 1.10E-208 | 4.520244292 |
| F.Crypt_loFos_1 | CTSK | 4.130 | 0.00E+00 | 2.49E-01 | 1.66E-03 | 2.620660286 |
| F.Crypt_loFos_1 | CXCL12 | 3.721 | 0.00E+00 | 3.29E-01 | 9.35E-05 | 2.775507108 |
| F.Crypt_loFos_1 | CXCL14 | 5.123 | 0.00E+00 | 2.51E+00 | 6.71E-163 | 5.704823079 |
| F.Crypt_loFos_1 | CYGB | 4.375 | 0.00E+00 | -5.80E-03 | 9.33E-01 | 2.860992966 |
| F.Crypt_loFos_1 | DCN | 7.822 | 0.00E+00 | 1.52E+00 | 2.00E-63 | 5.238131885 |
| F.Crypt_loFos_1 | DKK3 | 3.769 | 0.00E+00 | -2.18E-01 | 4.21E-03 | 1.908342802 |
| F.Crypt_loFos_1 | FBLN1 | 5.573 | 0.00E+00 | 3.66E-01 | 7.01E-06 | 3.461190649 |
| F.Crypt_loFos_1 | GGT5 | 3.900 | 0.00E+00 | 2.03E-01 | 9.92E-03 | 1.851084854 |
| F.Crypt_loFos_1 | GPX3 | 4.330 | 0.00E+00 | 4.80E-01 | 7.17E-13 | 3.458058087 |
| F.Crypt_loFos_1 | GSN | 3.859 | 1.47E-254 | 1.60E+00 | 6.27E-159 | 4.263567086 |
| F.Crypt_loFos_1 | IFITM3 | 6.560 | 0.00E+00 | 1.77E+00 | 2.23E-192 | 5.166646778 |
| F.Crypt_loFos_1 | IGFBP7 | 7.514 | 0.00E+00 | 1.59E+00 | 6.62E-66 | 6.290186933 |
| F.Crypt_loFos_1 | LGALS1 | 5.430 | 1.44E-306 | 1.08E+00 | 1.33E-67 | 3.918497227 |
| F.Crypt_loFos_1 | LINC01082 | 4.011 | 0.00E+00 | -2.52E-03 | 9.74E-01 | 2.466725414 |
| F.Crypt_loFos_1 | LUM | 6.948 | 0.00E+00 | 1.46E+00 | 2.78E-44 | 5.224703375 |
| F.Crypt_loFos_1 | MFAP4 | 5.686 | 0.00E+00 | 9.07E-01 | 5.35E-29 | 4.455406471 |
| F.Crypt_loFos_1 | MMP2 | 3.547 | 0.00E+00 | -3.40E-01 | 2.88E-07 | 2.36769262 |
| F.Crypt_loFos_1 | PLAC9 | 3.828 | 0.00E+00 | 1.85E-02 | 8.08E-01 | 2.327666003 |
| F.Crypt_loFos_1 | PMP22 | 3.692 | 0.00E+00 | 8.69E-02 | 2.23E-01 | 2.538680468 |
| F.Crypt_loFos_1 | PPAP2B | 3.844 | 0.00E+00 | 3.25E-01 | 2.22E-06 | 2.317632739 |
| F.Crypt_loFos_1 | PROCR | 4.373 | 0.00E+00 | 3.95E-01 | 6.81E-09 | 3.195637587 |
| F.Crypt_loFos_1 | PTN | 3.804 | 0.00E+00 | 7.31E-02 | 3.62E-01 | 2.563456235 |
| F.Crypt_loFos_1 | RARRES2 | 3.874 | 0.00E+00 | 5.14E-01 | 2.99E-18 | 3.294341143 |
| F.Crypt_loFos_1 | RBP1 | 4.074 | 0.00E+00 | 3.93E-01 | 7.33E-10 | 3.101702956 |
| F.Crypt_loFos_1 | SERPINF1 | 3.726 | 0.00E+00 | 2.23E-01 | 6.29E-04 | 2.970864106 |
| F.Crypt_loFos_1 | SERPING1 | 3.431 | 0.00E+00 | 2.52E-01 | 4.68E-05 | 2.610215112 |
| F.Crypt_loFos_1 | SOD3 | 4.177 | 0.00E+00 | 7.64E-01 | 1.37E-23 | 3.282749538 |
| F.Crypt_loFos_1 | SPARC | 3.802 | 0.00E+00 | -1.66E-01 | 2.29E-02 | 2.730098195 |
| F.Crypt_loFos_1 | TCF21 | 4.897 | 0.00E+00 | 2.46E-01 | 9.84E-04 | 3.412667084 |
| F.Crypt_loFos_1 | TIMP1 | 4.084 | 0.00E+00 | 8.14E-01 | 5.04E-42 | 3.536639892 |
| F.Crypt_loFos_1 | TMEM176A | 3.351 | 4.02E-211 | 1.10E+00 | 2.76E-128 | 2.998762433 |
| F.Crypt_loFos_1 | TMEM176B | 4.864 | 8.48E-225 | 1.74E+00 | 1.12E-245 | 4.741101922 |

TABLE 12-continued

Additional Cell Type Markers

| | | | | | | |
|---|---|---|---|---|---|---|
| F.Crypt_loFos_1 | VIM | 5.295 | 5.46E−276 | 1.18E+00 | 1.88E−108 | 3.248254715 |
| F.Crypt_loFos_2 | APOE | 5.899 | 0.00E+00 | 1.76E+00 | 1.67E−43 | 6.466993305 |
| F.Crypt_loFos_2 | CFD | 5.299 | 0.00E+00 | 2.35E+00 | 3.36E−92 | 6.443773934 |
| F.Endothelial | BCAM | 4.293 | 0.00E+00 | 1.23E+00 | 9.84E−42 | 1.212070381 |
| F.Endothelial | CAV1 | 4.086 | 0.00E+00 | 7.55E−01 | 1.03E−14 | 2.963859243 |
| F.Endothelial | CCDC85B | 2.406 | 2.79E−184 | 1.30E+00 | 1.32E−165 | 1.989479948 |
| F.Endothelial | CD320 | 3.689 | 0.00E+00 | 3.25E+00 | 0.00E+00 | 3.29103572 |
| F.Endothelial | CD36 | 4.135 | 0.00E+00 | 1.90E+00 | 4.90E−39 | 2.182349023 |
| F.Endothelial | CD59 | 2.172 | 1.73E−130 | 1.53E+00 | 2.54E−236 | 1.506163126 |
| F.Endothelial | CLDN5 | 6.137 | 0.00E+00 | 3.07E+00 | 1.45E−25 | 3.333557396 |
| F.Endothelial | CLEC14A | 5.319 | 0.00E+00 | 9.66E−01 | 3.87E−12 | 1.451043092 |
| F.Endothelial | CRIP2 | 4.642 | 0.00E+00 | 1.27E+00 | 2.67E−42 | 3.236897944 |
| F.Endothelial | EGFL7 | 6.013 | 0.00E+00 | 1.41E+00 | 5.14E−12 | 1.84382156 |
| F.Endothelial | ENG | 3.721 | 0.00E+00 | 1.00E+00 | 3.27E−30 | 1.859620568 |
| F.Endothelial | ESAM | 5.913 | 0.00E+00 | 1.59E+00 | 1.49E−18 | 1.438464574 |
| F.Endothelial | FABP5 | 3.117 | 1.32E−228 | 3.41E+00 | 0.00E+00 | 4.374347395 |
| F.Endothelial | FKBP1A | 2.022 | 2.10E−112 | 1.50E+00 | 1.63E−264 | 1.788766568 |
| F.Endothelial | GIMAP7 | 3.221 | 1.42E−300 | 7.65E−01 | 2.55E−28 | 2.842038719 |
| F.Endothelial | GNG11 | 4.738 | 0.00E+00 | 1.85E+00 | 1.78E−120 | 4.14121094 |
| F.Endothelial | HLA-C | 1.469 | 1.65E−11 | 1.59E+00 | 0.00E+00 | 2.645174636 |
| F.Endothelial | HLA-E | 1.845 | 1.35E−74 | 1.66E+00 | 0.00E+00 | 2.607209735 |
| F.Endothelial | IFITM3 | 3.985 | 1.50E−298 | 1.75E+00 | 2.69E−201 | 4.533520832 |
| F.Endothelial | IGFBP4 | 3.576 | 0.00E+00 | 1.85E+00 | 8.00E−222 | 1.952179734 |
| F.Endothelial | IGFBP7 | 4.755 | 0.00E+00 | 1.67E+00 | 1.53E−71 | 5.974854235 |
| F.Endothelial | ITM2B | 1.752 | 3.79E−56 | 1.97E+00 | 0.00E+00 | 2.756111513 |
| F.Endothelial | JAM2 | 5.981 | 0.00E+00 | 1.15E+00 | 3.42E−05 | 1.121967689 |
| F.Endothelial | MGP | 4.392 | 0.00E+00 | 8.05E−01 | 8.10E−07 | 1.998657704 |
| F.Endothelial | NPDC1 | 3.004 | 3.12E−242 | 1.16E+00 | 6.47E−87 | 1.254551441 |
| F.Endothelial | PLVAP | 6.365 | 0.00E+00 | 3.94E+00 | 8.19E−45 | 4.167360966 |
| F.Endothelial | RAMP2 | 5.270 | 0.00E+00 | 2.14E+00 | 8.66E−61 | 2.914625288 |
| F.Endothelial | RAMP3 | 8.188 | 0.00E+00 | 2.19E+00 | 5.51E−05 | 1.424899143 |
| F.Endothelial | RBP5 | 4.299 | 0.00E+00 | 5.14E−01 | 2.73E−05 | 1.573217657 |
| F.Endothelial | SEPW1 | 2.111 | 5.35E−106 | 1.47E+00 | 3.05E−269 | 2.044916625 |
| F.Endothelial | SLC9A3R2 | 3.082 | 2.77E−266 | 1.84E+00 | 1.69E−126 | 2.09792238 |
| F.Endothelial | SPARCL1 | 4.167 | 0.00E+00 | 1.32E+00 | 1.29E−55 | 3.33841819 |
| F.Endothelial | TM4SF1 | 3.406 | 0.00E+00 | 1.01E+00 | 7.43E−40 | 2.817273257 |
| F.Endothelial | TMEM88 | 5.627 | 0.00E+00 | 1.27E+00 | 3.57E−06 | 1.415444312 |
| F.Endothelial | VWF | 8.023 | 0.00E+00 | 2.22E+00 | 2.29E−02 | 1.464896788 |
| F.Endothelial_1 | CD320 | 4.615 | 3.19E−220 | 3.53E+00 | 0.00E+00 | 4.954668807 |
| F.Endothelial_1 | CLDN5 | 5.988 | 0.00E+00 | 5.24E−01 | 1.28E−02 | 4.442027574 |
| F.Endothelial_1 | FABP5 | 4.513 | 1.86E−151 | 3.03E+00 | 2.87E−248 | 5.598134063 |
| F.Endothelial_1 | GNG11 | 4.944 | 2.31E−270 | 1.61E+00 | 5.47E−66 | 4.383616677 |
| F.Endothelial_1 | IGFBP4 | 3.758 | 3.71E−187 | 1.85E+00 | 3.16E−146 | 2.636215458 |
| F.Endothelial_1 | PLVAP | 6.417 | 0.00E+00 | 1.88E+00 | 3.88E−21 | 5.305889624 |
| F.Fibroblast | A2M | 3.869 | 0.00E+00 | 1.17E+00 | 1.10E−57 | 2.858008192 |
| F.Fibroblast | ADAMDEC1 | 3.583 | 0.00E+00 | 4.98E+00 | 1.90E−267 | 3.594023618 |
| F.Fibroblast | APOE | 4.039 | 0.00E+00 | 3.22E+00 | 3.38E−168 | 4.921162902 |
| F.Fibroblast | BMP4 | 5.864 | 0.00E+00 | 1.00E+00 | 6.50E−07 | 1.42480642 |
| F.Fibroblast | C1R | 5.580 | 0.00E+00 | 2.31E+00 | 7.05E−71 | 2.692699318 |
| F.Fibroblast | C1S | 5.850 | 0.00E+00 | 2.13E+00 | 3.11E−49 | 2.913093084 |
| F.Fibroblast | CALD1 | 5.259 | 0.00E+00 | 6.73E−01 | 1.84E−07 | 2.814729165 |
| F.Fibroblast | CCL11 | 4.991 | 0.00E+00 | 2.97E+00 | 7.98E−08 | 1.681673822 |
| F.Fibroblast | CCL13 | 4.265 | 0.00E+00 | 3.42E+00 | 6.41E−26 | 1.449036254 |
| F.Fibroblast | CCL2 | 3.541 | 0.00E+00 | 1.41E+00 | 1.38E−22 | 2.112347447 |
| F.Fibroblast | CCL8 | 4.674 | 0.00E+00 | 2.67E+00 | 2.49E−26 | 1.387750615 |
| F.Fibroblast | CD63 | 2.229 | 2.01E−114 | 1.43E+00 | 0.00E+00 | 2.975250752 |
| F.Fibroblast | CFD | 3.800 | 0.00E+00 | 4.03E+00 | 1.33E−289 | 4.028336506 |
| F.Fibroblast | CFH | 5.163 | 0.00E+00 | 8.04E−01 | 2.06E−05 | 1.034054406 |
| F.Fibroblast | CLEC11A | 4.337 | 0.00E+00 | 7.52E−01 | 1.23E−16 | 1.281757763 |
| F.Fibroblast | COL1A1 | 5.087 | 0.00E+00 | 1.51E+00 | 2.53E−25 | 2.075687041 |
| F.Fibroblast | COL1A2 | 5.820 | 0.00E+00 | 1.32E+00 | 1.22E−19 | 2.962132038 |
| F.Fibroblast | COL3A1 | 5.960 | 0.00E+00 | 2.06E+00 | 3.13E−30 | 2.867219098 |
| F.Fibroblast | COL6A1 | 4.892 | 0.00E+00 | 1.29E+00 | 1.08E−20 | 1.674302912 |
| F.Fibroblast | COL6A2 | 5.960 | 0.00E+00 | 1.49E+00 | 1.19E−17 | 2.844489178 |
| F.Fibroblast | CTSC | 2.217 | 6.04E−280 | 1.78E+00 | 5.98E−242 | 2.19902085 |
| F.Fibroblast | CXCL12 | 4.276 | 0.00E+00 | 1.52E+00 | 1.55E−32 | 1.645919137 |
| F.Fibroblast | CXCL14 | 4.288 | 0.00E+00 | 4.13E+00 | 0.00E+00 | 5.862818394 |
| F.Fibroblast | CYGB | 6.236 | 0.00E+00 | 1.22E+00 | 4.60E−12 | 1.721814926 |
| F.Fibroblast | DCN | 5.155 | 0.00E+00 | 3.87E+00 | 3.97E−112 | 3.204355181 |
| F.Fibroblast | DMKN | 3.898 | 0.00E+00 | 1.59E+00 | 1.34E−20 | 1.008034114 |
| F.Fibroblast | EID1 | 1.941 | 2.83E−209 | 9.60E−01 | 2.83E−165 | 1.465413201 |
| F.Fibroblast | EMILIN1 | 5.819 | 0.00E+00 | 1.04E+00 | 1.19E−07 | 1.055725268 |
| F.Fibroblast | FBLN1 | 6.416 | 0.00E+00 | 2.15E+00 | 1.21E−20 | 1.654953126 |
| F.Fibroblast | GNG11 | 2.966 | 3.60E−305 | −1.21E+00 | 4.11E−46 | 1.064901305 |
| F.Fibroblast | GPX3 | 4.875 | 0.00E+00 | 1.03E+00 | 3.28E−22 | 2.355348742 |
| F.Fibroblast | GSN | 2.553 | 0.00E+00 | 1.45E+00 | 9.12E−168 | 2.612701254 |
| F.Fibroblast | IFITM3 | 4.287 | 0.00E+00 | 1.91E+00 | 0.00E+00 | 4.209536056 |
| F.Fibroblast | IGFBP6 | 4.030 | 0.00E+00 | 4.48E−01 | 3.06E−04 | 1.420392445 |

TABLE 12-continued

Additional Cell Type Markers

| | | | | | | |
|---|---|---|---|---|---|---|
| F.Fibroblast | IGFBP7 | 5.423 | 0.00E+00 | 1.92E+00 | 1.34E-86 | 5.704163002 |
| F.Fibroblast | LAMA4 | 4.389 | 0.00E+00 | 1.00E-01 | 4.76E-01 | 1.039331541 |
| F.Fibroblast | LAPTM4A | 2.132 | 3.25E-223 | 1.30E+00 | 7.56E-280 | 1.339834069 |
| F.Fibroblast | LGALS1 | 4.316 | 0.00E+00 | 1.63E+00 | 7.62E-267 | 4.303949742 |
| F.Fibroblast | LGALS3BP | 2.142 | 2.57E-224 | 1.08E+00 | 2.12E-204 | 1.091162389 |
| F.Fibroblast | LTBP4 | 3.130 | 0.00E+00 | 1.18E+00 | 5.17E-104 | 1.309909843 |
| F.Fibroblast | LUM | 5.009 | 0.00E+00 | 3.79E+00 | 7.61E-97 | 2.964227078 |
| F.Fibroblast | MFAP4 | 6.497 | 0.00E+00 | 3.15E+00 | 4.74E-64 | 3.285006765 |
| F.Fibroblast | MFGE8 | 4.113 | 0.00E+00 | 9.42E-01 | 1.57E-13 | 1.289214426 |
| F.Fibroblast | MMP2 | 6.500 | 0.00E+00 | 1.66E+00 | 3.72E-12 | 1.747981548 |
| F.Fibroblast | MYL9 | 3.785 | 0.00E+00 | 4.76E-01 | 2.51E-04 | 1.942377438 |
| F.Fibroblast | NGFRAP1 | 2.546 | 0.00E+00 | 7.85E-01 | 3.46E-78 | 1.005472029 |
| F.Fibroblast | NNMT | 4.284 | 0.00E+00 | -6.65E-02 | 6.52E-01 | 1.043271273 |
| F.Fibroblast | PLAC9 | 5.422 | 0.00E+00 | 6.10E-01 | 6.25E-03 | 1.166274382 |
| F.Fibroblast | PLAT | 3.585 | 0.00E+00 | 7.36E-01 | 4.31E-11 | 2.298300837 |
| F.Fibroblast | PMP22 | 3.499 | 0.00E+00 | 3.66E-01 | 2.39E-05 | 1.310460807 |
| F.Fibroblast | PPP1R14A | 3.624 | 0.00E+00 | 8.61E-01 | 8.44E-31 | 2.050855445 |
| F.Fibroblast | PRKCDBP | 3.972 | 0.00E+00 | 2.19E-01 | 2.86E-02 | 1.653768965 |
| F.Fibroblast | PROCR | 5.144 | 0.00E+00 | 1.17E+00 | 2.40E-19 | 1.662380716 |
| F.Fibroblast | PTN | 5.707 | 0.00E+00 | 5.65E-01 | 1.10E-02 | 1.06748513 |
| F.Fibroblast | RARRES2 | 4.164 | 0.00E+00 | 1.33E+00 | 4.13E-118 | 2.422426722 |
| F.Fibroblast | RBP1 | 4.610 | 0.00E+00 | 1.05E+00 | 1.54E-21 | 1.771585228 |
| F.Fibroblast | S100A13 | 2.664 | 0.00E+00 | 8.65E-01 | 3.26E-84 | 1.068941824 |
| F.Fibroblast | SDC2 | 4.548 | 0.00E+00 | 6.00E-01 | 2.34E-05 | 1.04905118 |
| F.Fibroblast | SELM | 2.801 | 0.00E+00 | 1.18E+00 | 4.03E-158 | 2.474691328 |
| F.Fibroblast | SERPINF1 | 4.562 | 0.00E+00 | 1.04E+00 | 2.49E-24 | 2.265134228 |
| F.Fibroblast | SERPING1 | 3.893 | 0.00E+00 | 6.95E-01 | 1.18E-17 | 1.766270888 |
| F.Fibroblast | SOD3 | 4.119 | 0.00E+00 | 1.79E+00 | 1.53E-81 | 1.7043373 |
| F.Fibroblast | SPARC | 3.920 | 0.00E+00 | -5.69E-02 | 5.24E-01 | 2.258898195 |
| F.Fibroblast | TCF21 | 6.571 | 0.00E+00 | 1.33E+00 | 1.05E-10 | 1.816207729 |
| F.Fibroblast | TIMP1 | 3.012 | 0.00E+00 | 1.16E+00 | 1.19E-104 | 2.839662172 |
| F.Fibroblast | TM4SF1 | 3.104 | 0.00E+00 | 2.91E-01 | 8.34E-04 | 1.581472528 |
| F.Fibroblast | TMEM176A | 2.830 | 0.00E+00 | 1.40E+00 | 1.16E-277 | 1.769196047 |
| F.Fibroblast | TMEM176B | 3.791 | 0.00E+00 | 2.20E+00 | 0.00E+00 | 3.832911655 |
| F.Fibroblast | TPM2 | 4.664 | 0.00E+00 | 9.64E-01 | 4.00E-09 | 1.939714308 |
| F.Fibroblast | TSPAN4 | 3.186 | 0.00E+00 | 2.44E-01 | 2.05E-04 | 1.26975591 |
| F.Fibroblast | VIM | 2.603 | 0.00E+00 | 1.23E+00 | 1.46E-198 | 2.867719694 |
| F.Glia | ALDH1A1 | 4.071 | 2.33E-198 | 2.62E+00 | 2.02E-201 | 3.761789138 |
| F.Glia | CD9 | 4.124 | 2.25E-110 | 2.31E+00 | 2.70E-220 | 4.789181961 |
| F.Glia | CLU | 6.270 | 0.00E+00 | 2.13E+00 | 1.12E-48 | 5.703214125 |
| F.Glia | CRYAB | 7.727 | 0.00E+00 | 3.82E+00 | 1.03E-142 | 6.612674122 |
| F.Glia | S100B | 6.472 | 0.00E+00 | 2.20E+00 | 2.22E-23 | 4.64832577 |
| F.Microvascular | CD320 | 5.109 | 3.81E-136 | 3.11E+00 | 9.49E-225 | 5.155185625 |
| F.Microvascular | FABP5 | 5.789 | 1.22E-94 | 4.26E+00 | 0.00E+00 | 7.141265843 |
| F.Microvascular | PLVAP | 8.376 | 5.02E-296 | 2.99E+00 | 2.61E-58 | 6.877072514 |
| F.Myofibroblasts | ACTA2 | 6.853 | 1.08E-258 | 3.42E+00 | 1.21E-118 | 6.872108933 |
| F.Myofibroblasts | TAGLN | 6.260 | 1.93E-256 | 3.28E+00 | 2.29E-94 | 6.533966568 |
| F.Stromal | A2M | 4.108 | 0.00E+00 | 1.73E+00 | 3.25E-93 | 2.420855705 |
| F.Stromal | ADAMDEC1 | 2.954 | 0.00E+00 | 4.68E+00 | 1.14E-198 | 2.910515351 |
| F.Stromal | APOE | 2.975 | 0.00E+00 | 3.07E+00 | 1.74E-148 | 3.827897438 |
| F.Stromal | BMP4 | 5.111 | 0.00E+00 | 1.74E+00 | 3.18E-15 | 1.30003534 |
| F.Stromal | BST2 | 2.012 | 3.45E-242 | 9.82E-01 | 4.04E-122 | 1.935227746 |
| F.Stromal | C1R | 5.080 | 0.00E+00 | 2.41E+00 | 1.09E-47 | 2.145519647 |
| F.Stromal | C1S | 5.202 | 0.00E+00 | 2.60E+00 | 5.03E-47 | 2.33056005 |
| F.Stromal | CALD1 | 6.181 | 0.00E+00 | 1.95E+00 | 7.99E-15 | 1.966047523 |
| F.Stromal | CCL2 | 3.734 | 0.00E+00 | 2.05E+00 | 1.56E-30 | 1.986582677 |
| F.Stromal | CCL8 | 4.304 | 0.00E+00 | 2.83E+00 | 1.77E-24 | 1.144580585 |
| F.Stromal | CD63 | 1.819 | 1.79E-89 | 1.29E+00 | 0.00E+00 | 2.406521128 |
| F.Stromal | CFD | 2.806 | 0.00E+00 | 4.00E+00 | 2.05E-268 | 2.868892416 |
| F.Stromal | CLEC11A | 3.739 | 0.00E+00 | 9.36E-01 | 1.75E-24 | 1.025199717 |
| F.Stromal | COL1A1 | 5.431 | 0.00E+00 | 2.03E+00 | 7.75E-16 | 1.75794711 |
| F.Stromal | COL1A2 | 5.603 | 0.00E+00 | 2.25E+00 | 4.89E-26 | 2.478102984 |
| F.Stromal | COL3A1 | 5.196 | 0.00E+00 | 2.72E+00 | 2.58E-39 | 2.355722526 |
| F.Stromal | COL6A1 | 5.454 | 0.00E+00 | 1.47E+00 | 1.18E-09 | 1.375024981 |
| F.Stromal | COL6A2 | 5.503 | 0.00E+00 | 1.70E+00 | 9.14E-15 | 2.21250568 |
| F.Stromal | CTSC | 1.583 | 3.43E-152 | 1.64E+00 | 1.13E-199 | 1.629643567 |
| F.Stromal | CXCL12 | 4.310 | 0.00E+00 | 1.60E+00 | 9.03E-26 | 1.242570645 |
| F.Stromal | CXCL14 | 2.342 | 0.00E+00 | 3.87E+00 | 0.00E+00 | 4.433021518 |
| F.Stromal | CYGB | 5.565 | 0.00E+00 | 1.80E+00 | 1.20E-19 | 1.380616503 |
| F.Stromal | DCN | 3.977 | 0.00E+00 | 3.86E+00 | 5.63E-126 | 2.624796179 |
| F.Stromal | EID1 | 1.833 | 2.53E-189 | 1.04E+00 | 1.08E-203 | 1.386022122 |
| F.Stromal | FBLN1 | 5.291 | 0.00E+00 | 2.51E+00 | 6.46E-23 | 1.542104205 |
| F.Stromal | GNG11 | 5.522 | 0.00E+00 | 2.03E+00 | 6.87E-16 | 1.024915045 |
| F.Stromal | GPX3 | 5.203 | 0.00E+00 | 2.14E+00 | 7.78E-41 | 1.908920129 |
| F.Stromal | GSN | 2.806 | 0.00E+00 | 1.85E+00 | 1.20E-258 | 2.671887439 |
| F.Stromal | HSPB1 | 2.089 | 9.10E-212 | 1.13E+00 | 6.26E-190 | 1.97223964 |
| F.Stromal | IFITM1 | 2.098 | 3.42E-252 | 9.15E-01 | 3.94E-101 | 1.630880521 |
| F.Stromal | IFITM3 | 4.606 | 0.00E+00 | 2.62E+00 | 0.00E+00 | 4.057873527 |

TABLE 12-continued

| | | | Additional Cell Type Markers | | | |
|---|---|---|---|---|---|---|
| F.Stromal | IGFBP6 | 4.614 | 0.00E+00 | 1.46E+00 | 9.98E-16 | 1.209098122 |
| F.Stromal | IGFBP7 | 6.204 | 0.00E+00 | 4.58E+00 | 0.00E+00 | 5.88712189 |
| F.Stromal | LAPTM4A | 2.041 | 3.57E-211 | 1.29E+00 | 5.86E-279 | 1.268032666 |
| F.Stromal | LGALS1 | 3.180 | 0.00E+00 | 1.70E+00 | 5.11E-250 | 4.001715701 |
| F.Stromal | LTBP4 | 2.655 | 1.13E-299 | 1.25E+00 | 5.14E-109 | 1.044916065 |
| F.Stromal | LUM | 3.968 | 0.00E+00 | 3.64E+00 | 9.21E-91 | 2.418426911 |
| F.Stromal | MFAP4 | 4.998 | 0.00E+00 | 3.05E+00 | 1.99E-66 | 2.65491401 |
| F.Stromal | MMP2 | 6.151 | 0.00E+00 | 1.66E+00 | 1.03E-06 | 1.45210403 |
| F.Stromal | MYL9 | 4.791 | 0.00E+00 | 1.68E+00 | 1.22E-14 | 1.659548772 |
| F.Stromal | PLAT | 4.548 | 0.00E+00 | 1.94E+00 | 1.74E-28 | 2.167799271 |
| F.Stromal | PMP22 | 3.820 | 0.00E+00 | 1.13E+00 | 6.81E-21 | 1.283005003 |
| F.Stromal | PPP1R14A | 3.223 | 0.00E+00 | 1.01E+00 | 2.56E-39 | 1.700199238 |
| F.Stromal | PRKCDBP | 5.658 | 0.00E+00 | 1.34E+00 | 3.79E-10 | 1.243717165 |
| F.Stromal | PROCR | 4.810 | 0.00E+00 | 1.12E+00 | 6.77E-15 | 1.252978763 |
| F.Stromal | RARRES2 | 3.237 | 0.00E+00 | 1.40E+00 | 2.15E-110 | 1.838084217 |
| F.Stromal | RBP1 | 4.332 | 0.00E+00 | 1.30E+00 | 2.48E-27 | 1.423203449 |
| F.Stromal | SELM | 2.476 | 0.00E+00 | 1.14E+00 | 4.80E-134 | 2.053452374 |
| F.Stromal | SERPINF1 | 3.472 | 0.00E+00 | 1.01E+00 | 1.47E-27 | 1.720141644 |
| F.Stromal | SERPING1 | 4.471 | 0.00E+00 | 1.20E+00 | 1.82E-26 | 1.455173755 |
| F.Stromal | SOD3 | 3.747 | 0.00E+00 | 2.28E+00 | 7.79E-96 | 1.301466108 |
| F.Stromal | SPARC | 6.089 | 0.00E+00 | 2.11E+00 | 1.77E-23 | 2.08492746 |
| F.Stromal | SPARCL1 | 5.397 | 0.00E+00 | 2.19E+00 | 3.29E-18 | 1.157334608 |
| F.Stromal | TCF21 | 5.231 | 0.00E+00 | 1.98E+00 | 9.17E-25 | 1.514343398 |
| F.Stromal | TIMP1 | 2.749 | 0.00E+00 | 1.17E+00 | 1.48E-91 | 2.447949478 |
| F.Stromal | TM4SF1 | 3.823 | 0.00E+00 | 1.34E+00 | 1.41E-32 | 1.422652756 |
| F.Stromal | TMEM176A | 1.962 | 3.88E-209 | 1.38E+00 | 9.94E-242 | 1.2868717 |
| F.Stromal | TMEM176B | 2.318 | 1.97E-286 | 2.07E+00 | 0.00E+00 | 2.548034924 |
| F.Stromal | TPM2 | 4.510 | 0.00E+00 | 1.38E+00 | 1.36E-12 | 1.570324457 |
| F.Stromal | TSPAN4 | 3.521 | 0.00E+00 | 7.00E-01 | 8.16E-21 | 1.059144752 |
| F.Stromal | VIM | 2.599 | 0.00E+00 | 1.27E+00 | 2.09E-203 | 2.963469114 |
| F.Villus | AGT | 5.191 | 0.00E+00 | 7.61E-01 | 2.86E-03 | 1.565337446 |
| F.Villus | BMP4 | 4.133 | 0.00E+00 | 9.55E-01 | 3.23E-35 | 3.04641886 |
| F.Villus | C1S | 3.052 | 0.00E+00 | -6.76E-01 | 9.73E-21 | 2.265592255 |
| F.Villus | CALD1 | 3.626 | 0.00E+00 | 3.40E-01 | 8.31E-07 | 3.076513343 |
| F.Villus | CAV1 | 3.940 | 0.00E+00 | 3.44E-01 | 6.33E-04 | 2.679407949 |
| F.Villus | COL1A2 | 3.222 | 0.00E+00 | -2.45E-01 | 7.00E-04 | 2.508175055 |
| F.Villus | COL3A1 | 3.337 | 0.00E+00 | -3.69E-02 | 6.47E-01 | 2.699343963 |
| F.Villus | COL6A1 | 4.045 | 0.00E+00 | 9.09E-01 | 5.49E-33 | 3.105851972 |
| F.Villus | COL6A2 | 4.186 | 0.00E+00 | 8.33E-01 | 1.96E-28 | 3.587072611 |
| F.Villus | CXCL14 | 5.331 | 0.00E+00 | 3.87E+00 | 0.00E+00 | 6.639737212 |
| F.Villus | CYGB | 3.575 | 0.00E+00 | 2.25E-01 | 6.46E-04 | 2.448508799 |
| F.Villus | DMKN | 4.682 | 0.00E+00 | 1.76E+00 | 2.36E-49 | 3.100766685 |
| F.Villus | EDNRB | 4.259 | 0.00E+00 | 6.52E-01 | 5.45E-10 | 1.964731755 |
| F.Villus | ENHO | 5.765 | 0.00E+00 | 5.60E-01 | 5.06E-03 | 2.037996647 |
| F.Villus | F3 | 5.091 | 0.00E+00 | 1.41E+00 | 9.73E-25 | 2.111992756 |
| F.Villus | FRZB | 4.758 | 0.00E+00 | 1.68E+00 | 4.91E-58 | 3.163962402 |
| F.Villus | GPX3 | 3.409 | 0.00E+00 | 2.34E-01 | 1.77E-04 | 2.723044038 |
| F.Villus | HSD17B2 | 2.813 | 2.90E-286 | 1.07E+00 | 4.46E-80 | 1.978660202 |
| F.Villus | IFITM3 | 3.410 | 0.00E+00 | 8.60E-01 | 6.14E-52 | 3.534780337 |
| F.Villus | IGFBP3 | 4.041 | 0.00E+00 | 1.30E+00 | 1.17E-25 | 2.513313933 |
| F.Villus | IGFBP7 | 4.072 | 0.00E+00 | -3.70E-01 | 7.67E-05 | 4.395528895 |
| F.Villus | LGALS1 | 4.297 | 0.00E+00 | 1.49E+00 | 2.96E-146 | 4.260881439 |
| F.Villus | MFAP4 | 3.452 | 0.00E+00 | -4.94E-01 | 6.77E-11 | 2.767660733 |
| F.Villus | MMP2 | 3.936 | 0.00E+00 | 7.39E-01 | 1.11E-27 | 3.105311214 |
| F.Villus | NBL1 | 2.298 | 8.07E-190 | 1.43E+00 | 2.84E-212 | 1.288462163 |
| F.Villus | NSG1 | 5.310 | 0.00E+00 | 1.17E+00 | 1.93E-16 | 2.688454505 |
| F.Villus | PLAT | 4.548 | 0.00E+00 | 1.53E+00 | 4.34E-75 | 4.300004313 |
| F.Villus | POSTN | 4.627 | 0.00E+00 | 1.79E+00 | 1.11E-35 | 3.366108575 |
| F.Villus | RARRES2 | 3.600 | 0.00E+00 | 9.47E-01 | 7.40E-62 | 3.155237799 |
| F.Villus | SDC2 | 3.610 | 0.00E+00 | 6.90E-01 | 1.47E-19 | 2.172949162 |
| F.Villus | SERPINF1 | 3.086 | 0.00E+00 | 3.73E-01 | 2.39E-08 | 2.484627191 |
| F.Villus | SPARC | 3.176 | 0.00E+00 | 1.08E-01 | 1.27E-01 | 2.582445259 |
| F.Villus | TIMP1 | 2.751 | 2.30E-277 | 1.00E+00 | 1.07E-62 | 2.948613606 |
| F.Villus | TMEM176B | 3.213 | 2.56E-272 | 1.64E+00 | 3.08E-240 | 3.649384031 |
| F.Villus | TPM2 | 3.507 | 0.00E+00 | 6.95E-01 | 1.29E-16 | 2.708057439 |
| F.Villus | VSTM2A | 6.302 | 0.00E+00 | 1.17E+00 | 3.87E-05 | 1.94824354 |
| F.Villus_1 | CXCL14 | 5.215 | 1.74E-209 | 3.59E+00 | 4.77E-225 | 6.731692814 |
| F.Villus_1 | FRZB | 4.374 | 0.00E+00 | 1.21E+00 | 1.92E-33 | 3.44591024 |
| F.Villus_1 | PLAT | 4.344 | 2.06E-300 | 1.19E+00 | 6.68E-41 | 4.3838881 |
| F.Villus_1 | POSTN | 4.774 | 0.00E+00 | 1.43E+00 | 4.92E-25 | 4.224144974 |
| F.Villus_2 | BMP4 | 4.055 | 0.00E+00 | 7.81E-01 | 1.46E-21 | 3.18144352 |
| F.Villus_2 | COL6A2 | 4.047 | 0.00E+00 | 7.36E-01 | 1.95E-22 | 3.663402198 |
| F.Villus_2 | CXCL14 | 5.188 | 1.56E-257 | 3.53E+00 | 1.21E-262 | 6.468476855 |
| F.Villus_2 | DMKN | 4.194 | 0.00E+00 | 1.14E+00 | 1.96E-25 | 3.122402938 |
| F.Villus_2 | F3 | 4.600 | 0.00E+00 | 8.82E-01 | 1.40E-13 | 2.378018518 |
| F.Villus_2 | FRZB | 4.341 | 0.00E+00 | 1.31E+00 | 1.27E-36 | 3.273271947 |
| F.Villus_2 | MMP2 | 3.863 | 0.00E+00 | 5.82E-01 | 1.14E-15 | 3.004724044 |
| F.Villus_2 | NSG1 | 4.447 | 0.00E+00 | 4.64E-01 | 1.67E-05 | 2.733631613 |

TABLE 12-continued

Additional Cell Type Markers

| | | | | | | |
|---|---|---|---|---|---|---|
| F.Villus_2 | PLAT | 4.234 | 0.00E+00 | 1.42E+00 | 9.20E-57 | 4.328991007 |
| F.Villus_2 | RARRES2 | 3.647 | 4.28E-284 | 9.70E-01 | 4.92E-50 | 3.333240445 |
| I.Immune | ARHGDIB | 4.207 | 0.00E+00 | 7.82E-01 | 6.32E-22 | 3.181654331 |
| I.Immune | CCL5 | 3.713 | 0.00E+00 | 2.86E+00 | 5.61E-41 | 3.227650679 |
| I.Immune | CD37 | 5.394 | 0.00E+00 | 2.57E-01 | 2.73E-01 | 1.385527254 |
| I.Immune | CD3D | 4.743 | 0.00E+00 | 1.63E+00 | 1.37E-11 | 2.656028184 |
| I.Immune | CD3E | 5.114 | 0.00E+00 | 1.25E+00 | 4.63E-06 | 2.008260655 |
| I.Immune | CD52 | 5.341 | 0.00E+00 | 1.58E+00 | 2.86E-13 | 3.098900803 |
| I.Immune | CD69 | 3.468 | 0.00E+00 | 9.81E-01 | 7.45E-15 | 2.209932935 |
| I.Immune | CD7 | 4.101 | 0.00E+00 | 2.28E+00 | 1.90E-27 | 1.902035143 |
| I.Immune | CORO1A | 5.181 | 0.00E+00 | 1.37E+00 | 1.40E-16 | 2.294753907 |
| I.Immune | CST3 | -3.303 | 0.00E+00 | 5.57E-01 | 1.48E-17 | -2.400189989 |
| I.Immune | CYBA | 1.716 | 1.86E-131 | 1.11E+00 | 2.74E-244 | 1.660237626 |
| I.Immune | EVL | 3.462 | 0.00E+00 | 6.54E-01 | 2.05E-11 | 1.493950621 |
| I.Immune | HCST | 5.437 | 0.00E+00 | 7.94E-01 | 6.19E-04 | 1.609957297 |
| I.Immune | LAPTM5 | 5.136 | 0.00E+00 | 8.70E-01 | 3.17E-05 | 1.184622899 |
| I.Immune | LTB | 4.541 | 0.00E+00 | 1.46E+00 | 5.87E-07 | 1.551222258 |
| I.Immune | PTPRCAP | 5.120 | 0.00E+00 | 1.23E+00 | 1.08E-11 | 2.166023611 |
| I.Immune | RAC2 | 4.648 | 0.00E+00 | 6.56E-01 | 5.34E-07 | 1.313198 |
| I.Immune | RGS1 | 3.798 | 0.00E+00 | 1.15E+00 | 3.62E-22 | 2.015574355 |
| I.Immune | SRGN | 3.581 | 0.00E+00 | 3.14E-01 | 1.61E-04 | 2.825816153 |
| I.Immune | TRBC2 | 4.401 | 0.00E+00 | 1.45E+00 | 5.26E-12 | 2.825938206 |
| I.Lymphoid | ARHGDIB | 3.161 | 0.00E+00 | 2.32E+00 | 4.47E-05 | 3.051707434 |
| I.Lymphoid | CCL5 | 4.003 | 0.00E+00 | 2.91E+00 | 4.01E-44 | 3.723272334 |
| I.Lymphoid | CD2 | 4.995 | 0.00E+00 | 7.92E-01 | 5.47E-03 | 2.213341168 |
| I.Lymphoid | CD3D | 4.827 | 0.00E+00 | 1.84E+00 | 1.44E-17 | 3.248239337 |
| I.Lymphoid | CD3E | 5.611 | 0.00E+00 | 1.26E+00 | 2.42E-05 | 2.497000932 |
| I.Lymphoid | CD52 | 3.726 | 0.00E+00 | 1.10E+00 | 2.79E-32 | 3.478443808 |
| I.Lymphoid | CD69 | 2.848 | 0.00E+00 | 5.09E-02 | 5.93E-01 | 2.43959911 |
| I.Lymphoid | CD7 | 4.040 | 0.00E+00 | 2.42E+00 | 1.15E-39 | 2.231958553 |
| I.Lymphoid | CORO1A | 3.316 | 0.00E+00 | 7.40E-01 | 7.28E-22 | 2.580002303 |
| I.Lymphoid | CYTIP | 3.486 | 0.00E+00 | 2.17E-01 | 1.62E-02 | 1.083215597 |
| I.Lymphoid | EVL | 3.009 | 2.49E-308 | 8.04E-01 | 1.35E-25 | 1.719868351 |
| I.Lymphoid | IL32 | 1.886 | 7.28E-217 | 1.53E+00 | 1.65E-150 | 2.754297032 |
| I.Lymphoid | LTB | 3.458 | 0.00E+00 | 1.22E+00 | 6.33E-15 | 1.960757541 |
| I.Lymphoid | PTPRCAP | 5.483 | 0.00E+00 | 9.99E-01 | 1.59E-11 | 2.664468478 |
| I.Lymphoid | RAC2 | 3.576 | 0.00E+00 | 4.91E-01 | 2.55E-09 | 1.619586858 |
| I.Lymphoid | TRAC | 3.277 | 0.00E+00 | 9.75E-01 | 4.22E-23 | 2.970592688 |
| I.Lymphoid | TRBC2 | 4.628 | 0.00E+00 | 1.31E+00 | 8.72E-12 | 3.495017388 |
| M.CD69pos Mast | H3F3B | 3.540 | 1.14E-70 | 2.04E+00 | 0.00E+00 | 4.709127236 |
| M.CD69pos Mast | NFKBIA | 2.588 | 4.21E-135 | 2.26E+00 | 3.68E-261 | 3.816864413 |
| M.CD69pos Mast | PPP1R15A | 2.241 | 4.32E-119 | 1.88E+00 | 3.12E-235 | 2.716247642 |
| M.CD69pos Mast | TPSAB1 | 8.102 | 0.00E+00 | 5.34E+00 | 1.96E-81 | 8.759937866 |
| M.CD69pos Mast | VWA5A | 4.147 | 4.01E-306 | 2.24E+00 | 2.67E-153 | 2.804627246 |
| M.DCs | AIF1 | 5.554 | 0.00E+00 | 6.91E-02 | 5.32E-01 | 4.109607894 |
| M.DCs | CD74 | 6.686 | 1.89E-172 | 4.31E+00 | 0.00E+00 | 7.361182144 |
| M.DCs | CPVL | 5.451 | 0.00E+00 | 9.74E-01 | 1.72E-13 | 3.259858496 |
| M.DCs | CST3 | 5.077 | 1.81E-84 | 3.22E+00 | 0.00E+00 | 6.239191066 |
| M.DCs | HLA-DMA | 5.034 | 0.00E+00 | 1.19E+00 | 1.06E-60 | 3.949279865 |
| M.DCs | HLA-DMB | 4.713 | 0.00E+00 | 2.68E-02 | 7.46E-01 | 2.996355003 |
| M.DCs | HLA-DPA1 | 7.499 | 0.00E+00 | 3.16E+00 | 3.81E-219 | 6.620670842 |
| M.DCs | HLA-DPB1 | 7.613 | 0.00E+00 | 3.30E+00 | 1.84E-212 | 7.191760426 |
| M.DCs | HLA-DQA1 | 7.085 | 0.00E+00 | 1.57E+00 | 3.77E-47 | 5.548948208 |
| M.DCs | HLA-DQB1 | 6.326 | 0.00E+00 | 1.65E+00 | 9.64E-76 | 4.944199971 |
| M.DCs | HLA-DRA | 7.705 | 0.00E+00 | 3.77E+00 | 2.22E-196 | 7.875311998 |
| M.DCs | HLA-DRB1 | 7.430 | 4.72E-272 | 3.62E+00 | 5.06E-285 | 7.13770053 |
| M.DCs | HLA-DRB5 | 4.876 | 0.00E+00 | 1.85E+00 | 3.04E-68 | 4.910951864 |
| M.DCs | LST1 | 5.039 | 0.00E+00 | 2.99E-01 | 1.74E-03 | 3.486090838 |
| M.DCs | LYZ | 5.747 | 0.00E+00 | 2.04E+00 | 1.56E-44 | 5.88694392 |
| M.Macrophages | ACP5 | 3.187 | 4.27E-303 | 1.34E+00 | 6.76E-73 | 2.590818222 |
| M.Macrophages | AIF1 | 5.576 | 0.00E+00 | 1.04E+00 | 1.07E-22 | 4.307976358 |
| M.Macrophages | C1QA | 6.150 | 0.00E+00 | 2.87E+00 | 1.46E-84 | 5.300031996 |
| M.Macrophages | C1QB | 6.052 | 0.00E+00 | 2.86E+00 | 7.25E-75 | 4.677009635 |
| M.Macrophages | C1QC | 6.172 | 0.00E+00 | 2.57E+00 | 1.21E-69 | 4.762331438 |
| M.Macrophages | CD74 | 5.009 | 7.44E-287 | 3.39E+00 | 0.00E+00 | 6.179449074 |
| M.Macrophages | CST3 | 3.100 | 2.80E-150 | 2.47E+00 | 0.00E+00 | 4.680553349 |
| M.Macrophages | CTSB | 2.952 | 8.47E-251 | 1.92E+00 | 7.20E-294 | 2.192366953 |
| M.Macrophages | CTSD | 2.222 | 5.30E-145 | 1.99E+00 | 0.00E+00 | 2.293098548 |
| M.Macrophages | CTSZ | 2.801 | 8.27E-225 | 1.20E+00 | 1.03E-124 | 1.283964758 |
| M.Macrophages | CYBA | 1.691 | 7.98E-52 | 1.72E+00 | 0.00E+00 | 2.742799342 |
| M.Macrophages | DNASE1L3 | 5.106 | 0.00E+00 | 9.20E-01 | 3.60E-09 | 2.994302955 |
| M.Macrophages | FCER1G | 4.663 | 0.00E+00 | 9.35E-01 | 2.28E-28 | 4.105822052 |
| M.Macrophages | FCGRT | 2.078 | 1.29E-112 | 1.35E+00 | 1.21E-221 | 1.42923146 |
| M.Macrophages | FTL | 4.189 | 2.32E-26 | 4.10E+00 | 0.00E+00 | 6.501041387 |
| M.Macrophages | FUCA1 | 2.678 | 3.03E-209 | 1.80E+00 | 1.44E-157 | 1.444883944 |
| M.Macrophages | GPX1 | 3.408 | 1.48E-239 | 2.08E+00 | 0.00E+00 | 3.660866748 |
| M.Macrophages | HLA-DMA | 3.705 | 0.00E+00 | 1.27E+00 | 2.39E-89 | 2.908577367 |
| M.Macrophages | HLA-DMB | 3.933 | 0.00E+00 | 8.50E-01 | 4.73E-26 | 2.265503073 |

TABLE 12-continued

Additional Cell Type Markers

| | | | | | | |
|---|---|---|---|---|---|---|
| M.Macrophages | HLA-DPA1 | 4.231 | 0.00E+00 | 2.53E+00 | 1.04E−207 | 5.115407151 |
| M.Macrophages | HLA-DPB1 | 5.213 | 0.00E+00 | 2.35E+00 | 5.56E−166 | 5.724454744 |
| M.Macrophages | HLA-DQA1 | 4.701 | 0.00E+00 | 1.18E+00 | 3.01E−30 | 4.031618355 |
| M.Macrophages | HLA-DQB1 | 3.829 | 0.00E+00 | 9.39E−01 | 1.29E−31 | 3.050844971 |
| M.Macrophages | HLA-DRA | 5.837 | 0.00E+00 | 2.84E+00 | 4.85E−170 | 6.499764955 |
| M.Macrophages | HLA-DRB1 | 5.097 | 0.00E+00 | 2.83E+00 | 1.57E−257 | 5.910780843 |
| M.Macrophages | HLA-DRB5 | 3.390 | 0.00E+00 | 1.74E+00 | 1.88E−77 | 3.498438452 |
| M.Macrophages | IGSF6 | 5.196 | 0.00E+00 | 5.53E−01 | 2.67E−04 | 1.625886678 |
| M.Macrophages | LGMN | 2.996 | 7.35E−263 | 1.72E+00 | 2.49E−165 | 1.837166624 |
| M.Macrophages | LST1 | 4.287 | 0.00E+00 | −1.14E−01 | 2.10E−01 | 2.582366499 |
| M.Macrophages | LYZ | 4.983 | 0.00E+00 | 1.99E+00 | 1.85E−41 | 4.35619307 |
| M.Macrophages | MS4A4A | 5.392 | 0.00E+00 | 7.67E−01 | 3.65E−05 | 1.044712017 |
| M.Macrophages | MS4A6A | 5.055 | 0.00E+00 | 8.89E−01 | 1.94E−13 | 2.624760555 |
| M.Macrophages | MS4A7 | 5.211 | 0.00E+00 | 7.97E−01 | 2.20E−07 | 1.824855194 |
| M.Macrophages | NPC2 | 2.844 | 1.41E−177 | 2.19E+00 | 0.00E+00 | 2.979535936 |
| M.Macrophages | PSAP | 2.931 | 2.19E−193 | 2.40E+00 | 0.00E+00 | 3.379791933 |
| M.Macrophages | RNASE1 | 2.869 | 2.01E−246 | 2.02E+00 | 4.73E−141 | 2.33910545 |
| M.Macrophages | RNASET2 | 2.002 | 5.77E−127 | 1.47E+00 | 1.81E−255 | 1.746194062 |
| M.Macrophages | S100A11 | 2.110 | 1.58E−119 | 1.51E+00 | 1.50E−219 | 2.530747738 |
| M.Macrophages | SAT1 | 3.003 | 8.08E−149 | 2.35E+00 | 0.00E+00 | 4.071450542 |
| M.Macrophages | SEPP1 | 2.949 | 9.84E−254 | 1.64E+00 | 5.90E−136 | 3.60554335 |
| M.Macrophages | STAB1 | 5.244 | 0.00E+00 | 4.85E−01 | 3.14E−03 | 1.299766554 |
| M.Macrophages | TMSB4X | 3.375 | 2.03E−05 | 2.11E+00 | 0.00E+00 | 2.573438479 |
| M.Macrophages | TYROBP | 5.234 | 0.00E+00 | 1.63E+00 | 7.88E−86 | 4.732860448 |
| M.Mast | CAPG | 2.432 | 4.98E−146 | 1.70E+00 | 6.15E−192 | 2.17915183 |
| M.Mast | H3F3B | 3.313 | 3.21E−65 | 1.93E+00 | 0.00E+00 | 4.47755371 |
| M.Mast | NFKBIA | 2.271 | 1.45E−118 | 2.20E+00 | 2.86E−255 | 3.455658808 |
| M.Mast | PPP1R15A | 2.033 | 2.06E−108 | 1.87E+00 | 1.26E−240 | 2.476327326 |
| M.Mast | TPSAB1 | 8.512 | 0.00E+00 | 6.42E+00 | 4.45E−163 | 8.639427859 |
| M.Mast | VWA5A | 4.283 | 0.00E+00 | 2.45E+00 | 7.39E−197 | 2.846401762 |
| M.Monocytes | ACP5 | 2.724 | 8.51E−303 | 9.53E−01 | 3.39E−33 | 1.882241762 |
| M.Monocytes | AIF1 | 6.739 | 0.00E+00 | 2.17E+00 | 9.08E−46 | 4.232871977 |
| M.Monocytes | AMICA1 | 3.065 | 0.00E+00 | 8.74E−02 | 2.31E−01 | 1.677961646 |
| M.Monocytes | C1QA | 5.492 | 0.00E+00 | 4.03E+00 | 2.99E−69 | 4.155816971 |
| M.Monocytes | C1QB | 5.282 | 0.00E+00 | 3.70E+00 | 7.83E−53 | 3.441937672 |
| M.Monocytes | C1QC | 5.400 | 0.00E+00 | 3.19E+00 | 9.69E−45 | 3.642706749 |
| M.Monocytes | C1orf162 | 3.733 | 0.00E+00 | −1.04E−01 | 2.85E−01 | 1.170437832 |
| M.Monocytes | CD74 | 5.291 | 0.00E+00 | 3.98E+00 | 0.00E+00 | 6.598762611 |
| M.Monocytes | COTL1 | 2.597 | 7.05E−307 | 9.03E−01 | 5.44E−85 | 2.212565365 |
| M.Monocytes | CPVL | 5.896 | 0.00E+00 | 1.33E+00 | 3.40E−11 | 1.189459222 |
| M.Monocytes | CST3 | 3.513 | 6.58E−239 | 2.90E+00 | 0.00E+00 | 5.233170493 |
| M.Monocytes | CTSB | 2.202 | 2.93E−211 | 1.55E+00 | 9.60E−204 | 1.356719163 |
| M.Monocytes | CYBA | 1.897 | 2.10E−81 | 1.50E+00 | 0.00E+00 | 2.769627973 |
| M.Monocytes | DNASE1L3 | 6.099 | 0.00E+00 | 2.45E+00 | 9.24E−18 | 2.563358103 |
| M.Monocytes | FAM26F | 4.957 | 0.00E+00 | 2.28E−01 | 1.99E−01 | 1.145484272 |
| M.Monocytes | FCER1G | 4.804 | 0.00E+00 | 7.06E−01 | 9.51E−13 | 3.864097586 |
| M.Monocytes | FGL2 | 3.941 | 0.00E+00 | 9.35E−01 | 4.92E−21 | 1.291638448 |
| M.Monocytes | FTL | 3.690 | 6.14E−25 | 3.33E+00 | 0.00E+00 | 5.135226719 |
| M.Monocytes | GPX1 | 3.523 | 0.00E+00 | 1.94E+00 | 0.00E+00 | 3.477841098 |
| M.Monocytes | HLA-DMA | 4.277 | 0.00E+00 | 1.60E+00 | 7.42E−148 | 3.137660058 |
| M.Monocytes | HLA-DMB | 4.587 | 0.00E+00 | 8.74E−01 | 1.14E−22 | 2.298238533 |
| M.Monocytes | HLA-DPA1 | 4.926 | 0.00E+00 | 3.06E+00 | 0.00E+00 | 5.55420434 |
| M.Monocytes | HLA-DPB1 | 5.650 | 0.00E+00 | 3.21E+00 | 0.00E+00 | 6.141157002 |
| M.Monocytes | HLA-DQA1 | 5.332 | 0.00E+00 | 2.21E+00 | 8.84E−99 | 4.355634178 |
| M.Monocytes | HLA-DQA2 | 3.920 | 0.00E+00 | 8.37E−01 | 3.45E−10 | 1.7733194 |
| M.Monocytes | HLA-DQB1 | 4.715 | 0.00E+00 | 1.86E+00 | 4.05E−100 | 3.47409069 |
| M.Monocytes | HLA-DQB2 | 4.951 | 0.00E+00 | 3.95E−01 | 2.47E−02 | 1.429331185 |
| M.Monocytes | HLA-DRA | 6.364 | 0.00E+00 | 3.77E+00 | 0.00E+00 | 6.90336385 |
| M.Monocytes | HLA-DRB1 | 5.624 | 0.00E+00 | 3.53E+00 | 0.00E+00 | 6.291170635 |
| M.Monocytes | HLA-DRB5 | 4.212 | 0.00E+00 | 2.13E+00 | 2.24E−103 | 3.906936969 |
| M.Monocytes | IL1B | 5.314 | 0.00E+00 | 2.02E+00 | 1.23E−09 | 1.362160979 |
| M.Monocytes | ITGB2 | 3.243 | 0.00E+00 | 1.26E−01 | 7.84E−02 | 1.46825593 |
| M.Monocytes | LAPTM5 | 2.698 | 0.00E+00 | 1.33E−01 | 1.19E−02 | 2.055128002 |
| M.Monocytes | LGALS1 | 3.002 | 0.00E+00 | 8.09E−01 | 9.54E−44 | 3.344243506 |
| M.Monocytes | LST1 | 5.286 | 0.00E+00 | 6.40E−01 | 1.30E−07 | 2.821686152 |
| M.Monocytes | LYZ | 5.942 | 0.00E+00 | 3.45E+00 | 2.44E−87 | 4.680781408 |
| M.Monocytes | MS4A6A | 6.354 | 0.00E+00 | 1.78E+00 | 9.88E−17 | 2.246168647 |
| M.Monocytes | MS4A7 | 5.854 | 0.00E+00 | 1.02E+00 | 6.74E−05 | 1.332493787 |
| M.Monocytes | NPC2 | 2.814 | 2.22E−246 | 1.78E+00 | 0.00E+00 | 2.574957856 |
| M.Monocytes | PLAUR | 2.657 | 3.67E−283 | 1.12E+00 | 3.46E−56 | 1.648644174 |
| M.Monocytes | PSAP | 2.534 | 5.30E−224 | 1.91E+00 | 0.00E+00 | 2.503500359 |
| M.Monocytes | RGS10 | 2.565 | 0.00E+00 | 4.82E−01 | 4.78E−31 | 2.150189084 |
| M.Monocytes | RNASE6 | 4.098 | 0.00E+00 | 9.94E−01 | 4.50E−21 | 1.036740582 |
| M.Monocytes | RNASET2 | 2.270 | 2.04E−218 | 1.30E+00 | 6.18E−257 | 1.751116723 |
| M.Monocytes | S100A11 | 2.204 | 3.20E−179 | 1.28E+00 | 2.47E−222 | 2.369494044 |
| M.Monocytes | SAT1 | 3.237 | 2.41E−232 | 2.09E+00 | 0.00E+00 | 3.959712325 |
| M.Monocytes | SPI1 | 4.890 | 0.00E+00 | 1.01E+00 | 2.42E−17 | 1.592825824 |
| M.Monocytes | TMSB4X | 3.136 | 8.25E−06 | 2.05E+00 | 0.00E+00 | 2.614405699 |

TABLE 12-continued

Additional Cell Type Markers

| | | | | | | |
|---|---|---|---|---|---|---|
| M.Monocytes | TYMP | 2.489 | 3.09E−282 | 9.52E−01 | 2.47E−101 | 1.861697922 |
| M.Monocytes | TYROBP | 5.333 | 0.00E+00 | 1.66E+00 | 1.01E−62 | 4.513467018 |
| M.Myeloid | AIF1 | 5.813 | 0.00E+00 | 2.02E+00 | 1.09E−33 | 2.305919495 |
| M.Myeloid | C1QA | 4.690 | 0.00E+00 | 3.98E+00 | 1.50E−84 | 2.293597851 |
| M.Myeloid | C1QB | 4.688 | 0.00E+00 | 4.01E+00 | 5.78E−68 | 1.93454735 |
| M.Myeloid | C1QC | 5.203 | 0.00E+00 | 3.75E+00 | 2.68E−46 | 1.994680241 |
| M.Myeloid | CD74 | 1.729 | 2.70E−174 | 3.83E+00 | 0.00E+00 | 3.96445085 |
| M.Myeloid | CST3 | 1.583 | 1.20E−114 | 2.55E+00 | 0.00E+00 | 2.496545122 |
| M.Myeloid | CYBA | 0.845 | 3.74E−30 | 1.30E+00 | 0.00E+00 | 1.355375364 |
| M.Myeloid | DNASE1L3 | 5.938 | 0.00E+00 | 2.54E+00 | 5.07E−17 | 1.357649186 |
| M.Myeloid | FCER1G | 5.155 | 0.00E+00 | 7.53E−01 | 6.05E−10 | 3.351878581 |
| M.Myeloid | FTH1 | 2.972 | 6.58E−17 | 1.58E+00 | 0.00E+00 | 3.161764242 |
| M.Myeloid | FTL | 3.481 | 2.47E−46 | 2.81E+00 | 0.00E+00 | 5.143530637 |
| M.Myeloid | GLUL | 2.625 | 9.29E−308 | 1.05E+00 | 2.08E−81 | 1.104516091 |
| M.Myeloid | GPX1 | 2.294 | 7.45E−245 | 1.92E+00 | 0.00E+00 | 1.892173705 |
| M.Myeloid | HLA-DMA | 3.140 | 0.00E+00 | 1.61E+00 | 8.42E−166 | 1.804731204 |
| M.Myeloid | HLA-DMB | 4.269 | 0.00E+00 | 1.05E+00 | 1.83E−26 | 1.310971013 |
| M.Myeloid | HLA-DPA1 | 2.822 | 0.00E+00 | 3.07E+00 | 0.00E+00 | 3.603351858 |
| M.Myeloid | HLA-DPB1 | 3.000 | 0.00E+00 | 3.42E+00 | 0.00E+00 | 3.960321522 |
| M.Myeloid | HLA-DQA1 | 4.043 | 0.00E+00 | 2.04E+00 | 1.83E−73 | 2.645131811 |
| M.Myeloid | HLA-DQA2 | 3.981 | 0.00E+00 | 7.23E−01 | 8.78E−06 | 1.096108771 |
| M.Myeloid | HLA-DQB1 | 3.588 | 0.00E+00 | 1.90E+00 | 8.14E−107 | 2.070477499 |
| M.Myeloid | HLA-DRA | 3.065 | 0.00E+00 | 3.69E+00 | 0.00E+00 | 4.339804481 |
| M.Myeloid | HLA-DRB1 | 2.879 | 0.00E+00 | 3.40E+00 | 0.00E+00 | 3.753125817 |
| M.Myeloid | HLA-DRB5 | 3.170 | 0.00E+00 | 2.12E+00 | 1.23E−103 | 2.390321388 |
| M.Myeloid | LST1 | 4.767 | 0.00E+00 | 4.39E−01 | 7.52E−04 | 1.650785876 |
| M.Myeloid | LYZ | 4.702 | 0.00E+00 | 3.68E+00 | 7.62E−110 | 2.556327471 |
| M.Myeloid | MS4A6A | 6.737 | 0.00E+00 | 1.99E+00 | 1.24E−17 | 1.009965999 |
| M.Myeloid | NPC2 | 2.140 | 6.05E−205 | 1.71E+00 | 0.00E+00 | 1.557639793 |
| M.Myeloid | PSAP | 1.917 | 4.55E−178 | 1.82E+00 | 0.00E+00 | 1.557168286 |
| M.Myeloid | S100A11 | 1.592 | 1.63E−131 | 1.21E+00 | 1.01E−219 | 1.623417727 |
| M.Myeloid | SAT1 | 1.885 | 4.03E−151 | 2.00E+00 | 0.00E+00 | 2.378322556 |
| M.Myeloid | SRGN | 2.346 | 3.11E−303 | 6.68E−01 | 2.24E−51 | 2.663800303 |
| M.Myeloid | TMSB4X | 3.924 | 1.08E−11 | 1.61E+00 | 0.00E+00 | 2.455257638 |
| M.Myeloid | TYROBP | 4.999 | 0.00E+00 | 1.22E+00 | 2.51E−22 | 3.317457944 |
| M.Tissue_DCs | AIF1 | 5.733 | 0.00E+00 | 3.04E−01 | 6.77E−03 | 4.343902986 |
| M.Tissue_DCs | CD74 | 6.537 | 8.69E−147 | 4.22E+00 | 0.00E+00 | 7.317250586 |
| M.Tissue_DCs | CLEC10A | 5.783 | 0.00E+00 | 1.04E+00 | 4.56E−13 | 3.638767911 |
| M.Tissue_DCs | CST3 | 4.913 | 7.85E−72 | 3.17E+00 | 0.00E+00 | 6.099017935 |
| M.Tissue_DCs | HLA-DMA | 5.111 | 5.40E−280 | 1.36E+00 | 1.87E−71 | 4.010612012 |
| M.Tissue_DCs | HLA-DPA1 | 7.274 | 3.20E−256 | 3.23E+00 | 2.20E−206 | 6.561614831 |
| M.Tissue_DCs | HLA-DPB1 | 7.476 | 3.55E−290 | 3.09E+00 | 4.68E−164 | 7.139900132 |
| M.Tissue_DCs | HLA-DQA1 | 6.883 | 0.00E+00 | 1.65E+00 | 1.64E−46 | 5.545865153 |
| M.Tissue_DCs | HLA-DQB1 | 6.394 | 0.00E+00 | 1.75E+00 | 1.37E−75 | 4.964711147 |
| M.Tissue_DCs | HLA-DRA | 7.540 | 1.52E−267 | 3.88E+00 | 3.58E−183 | 7.91753476 |
| M.Tissue_DCs | HLA-DRB1 | 7.352 | 5.21E−243 | 3.50E+00 | 5.44E−237 | 7.1857139 |
| M.Tissue_DCs | LST1 | 5.239 | 0.00E+00 | 4.97E−01 | 7.18E−08 | 3.72542232 |
| M.Tissue_DCs | LYZ | 5.579 | 0.00E+00 | 2.14E+00 | 3.62E−44 | 5.80083893 |
| T.CD4 | ARHGDIB | 2.714 | 0.00E+00 | 6.95E−01 | 5.09E−60 | 2.948999621 |
| T.CD4 | B2M | 2.524 | 4.10E−11 | 1.31E+00 | 0.00E+00 | 3.181207891 |
| T.CD4 | BTG1 | 2.081 | 8.64E−201 | 1.29E+00 | 3.42E−241 | 2.666942355 |
| T.CD4 | CD2 | 3.325 | 0.00E+00 | −4.30E−02 | 5.70E−01 | 2.361888134 |
| T.CD4 | CD3D | 3.865 | 0.00E+00 | −1.53E−01 | 3.12E−02 | 3.285517157 |
| T.CD4 | CD3E | 3.298 | 0.00E+00 | −1.03E−01 | 9.38E−02 | 2.441937608 |
| T.CD4 | CD52 | 3.093 | 0.00E+00 | 4.27E−01 | 6.58E−15 | 3.285206277 |
| T.CD4 | EEF1A1 | 1.811 | 1.44E−18 | 1.29E+00 | 0.00E+00 | 2.913519854 |
| T.CD4 | IL32 | 3.257 | 0.00E+00 | 9.29E−01 | 7.35E−73 | 3.875940105 |
| T.CD4 | LTB | 3.303 | 0.00E+00 | 5.68E−01 | 2.19E−11 | 2.960038975 |
| T.CD4 | RPL10 | 1.878 | 5.33E−17 | 1.19E+00 | 0.00E+00 | 2.933302608 |
| T.CD4 | RPL21 | 2.075 | 2.43E−43 | 1.20E+00 | 0.00E+00 | 3.077829574 |
| T.CD4 | RPLP1 | 2.061 | 3.31E−25 | 1.22E+00 | 0.00E+00 | 2.97564638 |
| T.CD4 | RPS19 | 2.122 | 1.71E−40 | 1.24E+00 | 0.00E+00 | 3.029170811 |
| T.CD4 | RPS25 | 1.749 | 4.46E−50 | 1.10E+00 | 0.00E+00 | 2.510200315 |
| T.CD4 | RPS27 | 1.969 | 2.14E−30 | 1.29E+00 | 0.00E+00 | 3.052783949 |
| T.CD4 | RPS27A | 1.880 | 5.73E−50 | 1.22E+00 | 0.00E+00 | 2.910333285 |
| T.CD4 | RPS3 | 1.822 | 1.75E−33 | 1.14E+00 | 0.00E+00 | 2.909904991 |
| T.CD4 | TMEM66 | 1.634 | 1.36E−148 | 9.77E−01 | 2.12E−191 | 1.516743632 |
| T.CD4 | TMSB4X | 2.596 | 3.91E−08 | 1.50E+00 | 0.00E+00 | 2.234471623 |
| T.CD4 | TRAC | 3.572 | 0.00E+00 | 6.66E−01 | 7.52E−26 | 3.57637506 |
| T.CD4 | TRBC2 | 3.692 | 0.00E+00 | 4.12E−01 | 1.65E−08 | 3.684828708 |
| T.CD8 | ACTB | 2.475 | 3.60E−42 | 1.50E+00 | 0.00E+00 | 3.50971244 |
| T.CD8 | ARHGDIB | 2.865 | 0.00E+00 | 6.08E−01 | 1.44E−49 | 2.982840619 |
| T.CD8 | B2M | 3.216 | 1.13E−08 | 1.43E+00 | 0.00E+00 | 2.404427044 |
| T.CD8 | CCL5 | 5.160 | 0.00E+00 | 2.00E+00 | 4.92E−151 | 5.905248855 |
| T.CD8 | CD3D | 3.462 | 0.00E+00 | 4.53E−01 | 6.24E−15 | 3.394691814 |
| T.CD8 | CD3E | 3.001 | 0.00E+00 | 2.17E−01 | 1.56E−05 | 2.761361085 |
| T.CD8 | CD52 | 3.267 | 0.00E+00 | 7.59E−01 | 2.58E−46 | 3.532187537 |
| T.CD8 | CD7 | 3.358 | 0.00E+00 | 9.13E−01 | 2.79E−31 | 3.042456161 |

TABLE 12-continued

Additional Cell Type Markers

| | | | | | | |
|---|---|---|---|---|---|---|
| T.CD8 | CORO1A | 2.680 | 0.00E+00 | 6.16E-01 | 3.12E-38 | 2.743977822 |
| T.CD8 | EVL | 2.487 | 2.00E-302 | 5.33E-01 | 1.11E-29 | 2.184459445 |
| T.CD8 | GZMA | 3.738 | 0.00E+00 | 1.48E+00 | 1.48E-21 | 3.352055654 |
| T.CD8 | HCST | 2.860 | 0.00E+00 | 5.95E-01 | 1.90E-34 | 2.695248321 |
| T.CD8 | HOPX | 3.414 | 0.00E+00 | 5.97E-01 | 1.12E-13 | 2.402446002 |
| T.CD8 | IL32 | 3.922 | 0.00E+00 | 1.20E+00 | 3.71E-150 | 4.279234749 |
| T.CD8 | NKG7 | 4.290 | 0.00E+00 | 6.17E-01 | 7.86E-08 | 3.272826393 |
| T.CD8 | PTPRCAP | 2.633 | 0.00E+00 | 8.49E-01 | 1.44E-69 | 2.810217158 |
| T.CD8 | SH3BGRL3 | 1.886 | 5.60E-118 | 1.05E+00 | 5.36E-212 | 2.458584789 |
| T.CD8 | TMSB4X | 4.143 | 4.19E-11 | 1.88E+00 | 0.00E+00 | 2.661426524 |
| T.CD8 | TRAC | 2.825 | 0.00E+00 | 2.81E-01 | 2.77E-07 | 3.041416989 |
| T.CD8 | TRBC2 | 3.074 | 0.00E+00 | 1.88E-01 | 1.58E-03 | 3.233102921 |
| T.CD8_IELs | CCL5 | 6.114 | 0.00E+00 | 1.88E+00 | 2.57E-123 | 6.194585882 |
| T.CD8_IELs | CD3D | 3.256 | 0.00E+00 | 5.35E-01 | 1.20E-18 | 3.441592568 |
| T.CD8_IELs | CD52 | 3.451 | 1.72E-306 | 7.40E-01 | 1.11E-37 | 3.498103129 |
| T.CD8_IELs | CD7 | 3.988 | 0.00E+00 | 1.24E+00 | 4.14E-68 | 4.046757488 |
| T.CD8_IELs | HOPX | 3.762 | 0.00E+00 | 5.68E-01 | 3.21E-13 | 3.314436098 |
| T.CD8_IELs | IL32 | 4.020 | 2.09E-271 | 1.38E+00 | 4.88E-124 | 4.322274876 |
| T.CD8_IELs | NKG7 | 3.841 | 0.00E+00 | -3.01E-02 | 7.46E-01 | 3.446184383 |
| T.CD8 LP | CCL5 | 5.676 | 0.00E+00 | 1.27E+00 | 5.56E-57 | 5.633700535 |
| T.CD8 LP | NKG7 | 3.722 | 0.00E+00 | 4.11E-01 | 3.52E-05 | 3.486023674 |
| T.Tcells | ACTB | 2.020 | 4.86E-40 | 1.65E+00 | 0.00E+00 | 3.316981313 |
| T.Tcells | ARHGDIB | 3.191 | 0.00E+00 | 1.10E+00 | 3.46E-131 | 3.341126137 |
| T.Tcells | B2M | 2.272 | 1.17E-09 | 1.50E+00 | 0.00E+00 | 3.065937757 |
| T.Tcells | BTG1 | 1.763 | 8.44E-157 | 1.26E+00 | 2.58E-229 | 2.123789859 |
| T.Tcells | CCL5 | 4.279 | 0.00E+00 | 2.74E+00 | 1.64E-83 | 4.302419639 |
| T.Tcells | CD2 | 5.172 | 0.00E+00 | 6.17E-01 | 7.82E-05 | 2.052746914 |
| T.Tcells | CD3D | 6.166 | 0.00E+00 | 2.08E+00 | 5.91E-46 | 3.397618572 |
| T.Tcells | CD3E | 6.421 | 0.00E+00 | 7.92E-01 | 4.38E-07 | 2.370389625 |
| T.Tcells | CD52 | 4.108 | 0.00E+00 | 1.20E+00 | 1.58E-68 | 3.95478922 |
| T.Tcells | CD7 | 4.693 | 0.00E+00 | 9.36E-01 | 1.78E-11 | 2.221062807 |
| T.Tcells | CKLF | 2.025 | 3.39E-207 | 1.20E+00 | 2.90E-176 | 1.080775129 |
| T.Tcells | CORO1A | 3.262 | 0.00E+00 | 1.09E+00 | 7.57E-77 | 2.860991596 |
| T.Tcells | EVL | 3.434 | 0.00E+00 | 9.82E-01 | 1.41E-49 | 2.035932542 |
| T.Tcells | GZMA | 3.945 | 0.00E+00 | 2.12E+00 | 1.82E-18 | 1.960681705 |
| T.Tcells | HCST | 3.243 | 0.00E+00 | 7.05E-01 | 4.60E-27 | 2.173769075 |
| T.Tcells | HOPX | 4.032 | 0.00E+00 | 6.86E-01 | 5.98E-07 | 1.726884514 |
| T.Tcells | IL2RG | 2.193 | 7.47E-228 | 1.17E+00 | 1.41E-136 | 1.152000617 |
| T.Tcells | IL32 | 4.161 | 0.00E+00 | 1.81E+00 | 8.41E-260 | 4.656688606 |
| T.Tcells | LCK | 4.921 | 0.00E+00 | 6.42E-01 | 8.05E-07 | 1.507134026 |
| T.Tcells | LTB | 3.053 | 0.00E+00 | 3.90E-01 | 3.13E-04 | 2.116429025 |
| T.Tcells | MYL12A | 1.681 | 2.24E-123 | 1.06E+00 | 3.94E-231 | 1.746942368 |
| T.Tcells | NKG7 | 4.103 | 0.00E+00 | 2.56E-01 | 1.48E-01 | 1.791038239 |
| T.Tcells | PTPRCAP | 3.216 | 0.00E+00 | 1.41E+00 | 4.57E-128 | 2.773769069 |
| T.Tcells | RAC2 | 2.651 | 0.00E+00 | 1.13E+00 | 2.04E-99 | 1.676182044 |
| T.Tcells | RPLP1 | 1.843 | 1.24E-20 | 1.12E+00 | 0.00E+00 | 2.762677204 |
| T.Tcells | RPS19 | 2.379 | 6.55E-43 | 1.34E+00 | 0.00E+00 | 3.222843513 |
| T.Tcells | RPS27 | 2.047 | 1.14E-31 | 1.22E+00 | 0.00E+00 | 3.079388618 |
| T.Tcells | RPS27A | 1.878 | 5.06E-50 | 1.19E+00 | 0.00E+00 | 2.82253802 |
| T.Tcells | SH3BGRL3 | 1.894 | 7.78E-139 | 1.22E+00 | 1.42E-266 | 2.177941405 |
| T.Tcells | TMEM66 | 1.554 | 3.21E-135 | 1.03E+00 | 2.83E-211 | 1.23170526 |
| T.Tcells | TMSB4X | 3.485 | 6.22E-17 | 2.01E+00 | 0.00E+00 | 3.017818451 |
| T.Tcells | TRAC | 4.649 | 0.00E+00 | 1.34E+00 | 9.50E-47 | 3.593010994 |
| T.Tcells | TRBC2 | 5.165 | 0.00E+00 | 1.21E+00 | 3.55E-24 | 3.838266308 |

| ident | pvalH | n | ref_n | mu | ref_mu | total | ref_total |
|---|---|---|---|---|---|---|---|
| B.Bcells | 0 | 2578 | 359 | 5.641 | 2.160 | 0.988 | 0.012 |
| B.Bcells | 0 | 2871 | 54 | 3.440 | 2.038 | 0.993 | 0.007 |
| B.Bcells | 0 | 2822 | 654 | 2.141 | 3.245 | 0.667 | 0.333 |
| B.Bcells | 0 | 4698 | 3412 | 6.225 | 5.422 | 0.706 | 0.294 |
| B.Bcells | 0 | 4236 | 96 | 3.539 | 2.601 | 0.988 | 0.012 |
| B.Bcells | 0 | 3975 | 6433 | 3.404 | 4.208 | 0.261 | 0.739 |
| B.Bcells | 0 | 2866 | 202 | 3.310 | 1.484 | 0.980 | 0.020 |
| B.Bcells | 0 | 2886 | 1147 | 2.490 | 2.410 | 0.727 | 0.273 |
| B.Bcells | 0 | 2838 | 1234 | 3.073 | 2.136 | 0.815 | 0.185 |
| B.Bcells | 0 | 4045 | 2898 | 4.309 | 2.510 | 0.829 | 0.171 |
| B.Bcells | 0 | 4090 | 3927 | 10.531 | 4.627 | 0.984 | 0.016 |
| B.Bcells | 0 | 3316 | 1856 | 8.718 | 3.178 | 0.988 | 0.012 |
| B.Bcells | 0 | 3809 | 2394 | 8.956 | 3.375 | 0.987 | 0.013 |
| B.Bcells | 0 | 4051 | 2015 | 9.672 | 3.306 | 0.994 | 0.006 |
| B.Bcells | 0 | 3141 | 970 | 9.006 | 2.698 | 0.996 | 0.004 |
| B.Bcells | 0 | 3104 | 1057 | 8.945 | 2.694 | 0.996 | 0.004 |
| B.Bcells | 0 | 3236 | 327 | 4.523 | 2.282 | 0.979 | 0.021 |
| B.Bcells | 0 | 3514 | 1633 | 3.061 | 3.806 | 0.562 | 0.438 |
| B.Bcells | 0 | 3115 | 1862 | 3.082 | 2.014 | 0.778 | 0.222 |
| B.FO | 0 | 1636 | 3662 | 7.169 | 5.408 | 0.602 | 0.398 |
| B.FO | 0 | 1329 | 611 | 4.069 | 3.148 | 0.805 | 0.195 |

TABLE 12-continued

| Additional Cell Type Markers | | | | | | | |
|---|---|---|---|---|---|---|---|
| B.FO | 0 | 1424 | 1964 | 6.368 | 5.807 | 0.517 | 0.483 |
| B.Plasma | 0 | 1938 | 476 | 5.757 | 3.326 | 0.956 | 0.044 |
| B.Plasma | 0 | 1952 | 187 | 3.086 | 3.582 | 0.881 | 0.119 |
| B.Plasma | 0 | 1446 | 67 | 1.049 | 1.739 | 0.930 | 0.070 |
| B.Plasma | 0 | 1965 | 694 | 1.883 | 3.067 | 0.555 | 0.445 |
| B.Plasma | 0 | 2232 | 415 | 2.837 | 3.768 | 0.738 | 0.262 |
| B.Plasma | 0 | 2047 | 1483 | 1.669 | 1.866 | 0.546 | 0.454 |
| B.Plasma | 0 | 1614 | 1080 | 0.998 | 2.928 | 0.282 | 0.718 |
| B.Plasma | 0 | 2257 | 308 | 3.404 | 2.046 | 0.949 | 0.051 |
| B.Plasma | 0 | 2175 | 1211 | 2.502 | 2.401 | 0.658 | 0.342 |
| B.Plasma | 0 | 1575 | 464 | 1.118 | 2.147 | 0.625 | 0.375 |
| B.Plasma | 0 | 1896 | 390 | 1.327 | 2.039 | 0.748 | 0.252 |
| B.Plasma | 0 | 1938 | 2367 | 1.332 | 3.351 | 0.168 | 0.832 |
| B.Plasma | 0 | 1464 | 743 | 0.806 | 2.612 | 0.360 | 0.640 |
| B.Plasma | 0 | 1743 | 692 | 0.998 | 1.926 | 0.570 | 0.430 |
| B.Plasma | 0 | 987 | 57 | 0.872 | 1.673 | 0.909 | 0.091 |
| B.Plasma | 0 | 2264 | 1310 | 3.132 | 2.155 | 0.773 | 0.227 |
| B.Plasma | 0 | 1711 | 310 | 0.885 | 1.806 | 0.745 | 0.255 |
| B.Plasma | 0 | 1812 | 1347 | 1.099 | 2.730 | 0.303 | 0.697 |
| B.Plasma | 0 | 2289 | 2972 | 4.600 | 2.649 | 0.749 | 0.251 |
| B.Plasma | 0 | 2277 | 3971 | 11.091 | 6.041 | 0.950 | 0.050 |
| B.Plasma | 0 | 2191 | 1943 | 9.110 | 4.205 | 0.971 | 0.029 |
| B.Plasma | 0 | 2276 | 2508 | 9.345 | 5.235 | 0.940 | 0.060 |
| B.Plasma | 0 | 2236 | 2285 | 10.236 | 5.820 | 0.954 | 0.046 |
| B.Plasma | 0 | 2004 | 1122 | 9.451 | 5.412 | 0.967 | 0.033 |
| B.Plasma | 0 | 1949 | 1188 | 9.318 | 5.456 | 0.960 | 0.040 |
| B.Plasma | 0 | 1489 | 229 | 7.071 | 4.038 | 0.982 | 0.018 |
| B.Plasma | 0 | 1665 | 1897 | 0.949 | 2.751 | 0.201 | 0.799 |
| B.Plasma | 0 | 2132 | 1910 | 1.991 | 2.682 | 0.409 | 0.591 |
| B.Plasma | 0 | 2167 | 1989 | 2.174 | 2.088 | 0.536 | 0.464 |
| B.Plasma | 0 | 2288 | 444 | 4.708 | 3.157 | 0.938 | 0.062 |
| B.Plasma | 0 | 1847 | 1542 | 1.330 | 2.140 | 0.406 | 0.594 |
| B.Plasma | 0 | 1994 | 1742 | 1.575 | 1.818 | 0.492 | 0.508 |
| B.Plasma | 0 | 1754 | 530 | 1.437 | 2.396 | 0.630 | 0.370 |
| B.Plasma | 0 | 1913 | 1076 | 1.259 | 1.678 | 0.571 | 0.429 |
| B.Plasma | 0 | 2173 | 1824 | 2.321 | 2.002 | 0.598 | 0.402 |
| B.Plasma | 0 | 1876 | 1532 | 2.366 | 4.316 | 0.241 | 0.759 |
| B.Plasma | 0 | 1935 | 1939 | 3.018 | 4.263 | 0.296 | 0.704 |
| B.Plasma | 0 | 2188 | 2170 | 2.399 | 2.306 | 0.518 | 0.482 |
| B.Plasma | 0 | 2257 | 1916 | 3.186 | 2.059 | 0.720 | 0.280 |
| B.Plasma | 0 | 1997 | 1374 | 1.537 | 1.815 | 0.545 | 0.455 |
| B.Plasma | 0 | 2186 | 2124 | 2.197 | 2.042 | 0.534 | 0.466 |
| B.Plasma | 0 | 2304 | 4597 | 5.264 | 3.048 | 0.700 | 0.300 |
| B.Plasma | 0 | 2144 | 159 | 2.368 | 2.270 | 0.935 | 0.065 |
| B.Plasma | 0 | 2074 | 1697 | 1.437 | 2.029 | 0.448 | 0.552 |
| B.Plasma | 0 | 1851 | 906 | 1.197 | 1.820 | 0.570 | 0.430 |
| B.Plasma | 0 | 2142 | 1136 | 1.859 | 1.783 | 0.665 | 0.335 |
| B.Plasma | 0 | 1182 | 181 | 3.150 | 2.281 | 0.923 | 0.077 |
| B.Plasma | 0 | 2269 | 2366 | 3.808 | 2.402 | 0.718 | 0.282 |
| E.Absorptive | 0 | 2419 | 1210 | 5.657 | 4.012 | 0.862 | 0.138 |
| E.Absorptive | 0 | 2368 | 1676 | 4.134 | 3.090 | 0.744 | 0.256 |
| E.Absorptive | 0 | 2543 | 2453 | 3.920 | 3.230 | 0.626 | 0.374 |
| E.Absorptive | 0 | 2538 | 2572 | 4.215 | 3.389 | 0.636 | 0.364 |
| E.Absorptive | 0 | 2569 | 2856 | 4.828 | 4.237 | 0.575 | 0.425 |
| E.Absorptive | 0 | 2586 | 3229 | 7.343 | 6.378 | 0.610 | 0.390 |
| E.Absorptive | 0 | 2636 | 7360 | 8.704 | 6.761 | 0.579 | 0.421 |
| E.Absorptive | 0 | 2604 | 2999 | 5.836 | 4.833 | 0.635 | 0.365 |
| E.Absorptive | 0 | 2291 | 1543 | 6.851 | 4.898 | 0.852 | 0.148 |
| E.Absorptive | 0 | 1915 | 864 | 6.005 | 3.687 | 0.917 | 0.083 |
| E.Absorptive | 0 | 2319 | 1549 | 3.931 | 3.630 | 0.648 | 0.352 |
| E.Absorptive | 0 | 2625 | 3403 | 5.557 | 5.034 | 0.526 | 0.474 |
| E.Absorptive | 0 | 2615 | 4913 | 5.677 | 4.600 | 0.529 | 0.471 |
| E.Absorptive | 0 | 2255 | 1042 | 4.595 | 3.340 | 0.838 | 0.162 |
| E.Absorptive | 0 | 2629 | 3625 | 7.680 | 6.559 | 0.612 | 0.388 |
| E.Absorptive | 0 | 2235 | 1712 | 4.390 | 3.443 | 0.716 | 0.284 |
| E.Absorptive | 0 | 2413 | 1313 | 3.557 | 2.644 | 0.776 | 0.224 |
| E.Absorptive | 0 | 2552 | 3904 | 4.571 | 3.259 | 0.619 | 0.381 |
| E.Absorptive | 0 | 2510 | 2308 | 4.466 | 3.800 | 0.633 | 0.367 |
| E.Absorptive_All | 0 | 6268 | 2463 | 4.694 | 3.733 | 0.832 | 0.168 |
| E.Absorptive_All | 0 | 5395 | 1757 | 3.378 | 2.208 | 0.874 | 0.126 |
| E.Absorptive_All | 0 | 5581 | 1642 | 4.383 | 2.304 | 0.935 | 0.065 |
| E.Absorptive_All | 0 | 5855 | 2149 | 3.753 | 2.912 | 0.830 | 0.170 |
| E.Absorptive_All | 0 | 6196 | 2409 | 4.475 | 3.788 | 0.805 | 0.195 |
| E.Absorptive_All | 0 | 5203 | 2380 | 3.467 | 2.281 | 0.833 | 0.167 |
| E.Absorptive_All | 0 | 6288 | 2771 | 7.262 | 4.198 | 0.950 | 0.050 |
| E.Absorptive_All | 0 | 6280 | 2556 | 5.411 | 4.074 | 0.861 | 0.139 |
| E.Absorptive_All | 0 | 5846 | 2079 | 4.970 | 3.024 | 0.915 | 0.085 |
| E.Absorptive_All | 0 | 6520 | 2928 | 5.497 | 4.207 | 0.845 | 0.155 |

TABLE 12-continued

| Additional Cell Type Markers | | | | | | | |
|---|---|---|---|---|---|---|---|
| E.Absorptive__All | 0 | 6456 | 4467 | 5.441 | 3.867 | 0.811 | 0.189 |
| E.Absorptive__All | 0 | 6540 | 2740 | 5.707 | 4.974 | 0.799 | 0.201 |
| E.Absorptive__All | 0 | 6653 | 3203 | 7.396 | 5.409 | 0.892 | 0.108 |
| E.Absorptive__All | 0 | 6008 | 2284 | 5.037 | 3.789 | 0.862 | 0.138 |
| E.Absorptive__All | 0 | 4148 | 778 | 2.897 | 2.025 | 0.907 | 0.093 |
| E.Absorptive__All | 0 | 4088 | 681 | 4.251 | 1.773 | 0.971 | 0.029 |
| E.Absorptive__All | 0 | 5736 | 3566 | 3.994 | 2.566 | 0.812 | 0.188 |
| E.Absorptive__All | 0 | 5391 | 1861 | 3.459 | 2.234 | 0.871 | 0.129 |
| E.Absorptive__All | 0 | 5464 | 1809 | 4.071 | 2.982 | 0.865 | 0.135 |
| E.Absorptive_TA__1 | 0 | 1888 | 3219 | 5.228 | 5.469 | 0.332 | 0.668 |
| E.Best4__Enterocytes | 0 | 883 | 79 | 4.152 | 1.316 | 0.988 | 0.012 |
| E.Best4__Enterocytes | 0 | 1008 | 159 | 4.234 | 2.208 | 0.963 | 0.037 |
| E.Best4__Enterocytes | 0 | 998 | 312 | 2.542 | 2.166 | 0.806 | 0.194 |
| E.Enterocyte_Immature__1 | 0 | 1208 | 986 | 3.636 | 2.657 | 0.707 | 0.293 |
| E.Enterocyte_Immature__1 | 0 | 1509 | 1055 | 6.138 | 4.740 | 0.790 | 0.210 |
| E.Enterocyte_Immature__1 | 0 | 1448 | 2202 | 3.934 | 2.974 | 0.561 | 0.439 |
| E.Enterocyte_Immature__1 | 0 | 1541 | 1211 | 5.270 | 4.437 | 0.694 | 0.306 |
| E.Enterocyte_Immature__1 | 0 | 1469 | 1685 | 4.045 | 3.252 | 0.602 | 0.398 |
| E.Enterocyte_Immature__1 | 0 | 1355 | 926 | 3.502 | 3.047 | 0.667 | 0.333 |
| E.Enterocyte_Immature__1 | 0 | 1160 | 562 | 3.641 | 2.825 | 0.784 | 0.216 |
| E.Enterocyte_Immature__1 | 0 | 1245 | 791 | 3.305 | 2.625 | 0.716 | 0.284 |
| E.Enterocyte_Immature__1 | 0 | 1649 | 3213 | 7.297 | 6.450 | 0.480 | 0.520 |
| E.Enterocyte_Immature__1 | 0 | 1624 | 2958 | 5.587 | 4.929 | 0.464 | 0.536 |
| E.Enterocyte_Immature__1 | 0 | 1576 | 1563 | 6.327 | 5.274 | 0.677 | 0.323 |
| E.Enterocyte_Immature__1 | 0 | 1375 | 869 | 4.845 | 4.491 | 0.669 | 0.331 |
| E.Enterocyte_Immature__1 | 0 | 1397 | 1101 | 4.274 | 3.659 | 0.660 | 0.340 |
| E.Enterocyte_Immature__1 | 0 | 1636 | 7064 | 9.382 | 7.272 | 0.500 | 0.500 |
| E.Enterocyte_Immature__1 | 0 | 1650 | 3582 | 7.715 | 6.569 | 0.505 | 0.495 |
| E.Enterocyte_Immature__1 | 0 | 1508 | 1743 | 4.271 | 3.450 | 0.604 | 0.396 |
| E.Enterocyte_Immature__1 | 0 | 1303 | 988 | 3.838 | 2.743 | 0.738 | 0.262 |
| E.Enterocyte_Immature__1 | 0 | 1364 | 1389 | 3.484 | 2.750 | 0.620 | 0.380 |
| E.Enterocyte_Immature__1 | 0 | 1511 | 1278 | 4.441 | 3.959 | 0.623 | 0.377 |
| E.Enterocyte_Immature__1 | 0 | 1585 | 2292 | 4.562 | 3.771 | 0.545 | 0.455 |
| E.Enterocyte_Immature__2 | 0 | 1613 | 1448 | 5.329 | 4.259 | 0.700 | 0.300 |
| E.Enterocyte_Immature__2 | 0 | 1733 | 2294 | 4.949 | 3.991 | 0.595 | 0.405 |
| E.Enterocyte_Immature__2 | 0 | 1706 | 2741 | 4.217 | 2.898 | 0.608 | 0.392 |
| E.Enterocyte_Immature__2 | 0 | 1742 | 3229 | 8.185 | 6.228 | 0.677 | 0.323 |
| E.Enterocyte_Immature__2 | 0 | 1741 | 2988 | 6.218 | 4.786 | 0.611 | 0.389 |
| E.Enterocyte_Immature__2 | 0 | 1728 | 2665 | 5.773 | 4.442 | 0.620 | 0.380 |
| E.Enterocyte_Immature__2 | 0 | 1686 | 1570 | 4.051 | 3.624 | 0.591 | 0.409 |
| E.Enterocyte_Immature__2 | 0 | 1740 | 3405 | 6.253 | 4.952 | 0.557 | 0.443 |
| E.Enterocyte_Immature__2 | 0 | 1739 | 4853 | 6.280 | 4.541 | 0.545 | 0.455 |
| E.Enterocyte_Immature__2 | 0 | 1651 | 1026 | 3.644 | 3.194 | 0.687 | 0.313 |
| E.Enterocyte_Immature__2 | 0 | 1742 | 3640 | 8.382 | 6.389 | 0.656 | 0.344 |
| E.Enterocyte_Immature__2 | 0 | 1657 | 1239 | 3.473 | 2.556 | 0.716 | 0.284 |
| E.Enterocyte_Immature__2 | 0 | 1681 | 1257 | 4.082 | 3.996 | 0.587 | 0.413 |
| E.Enterocyte_Immature__2 | 0 | 1563 | 722 | 2.284 | 2.256 | 0.688 | 0.312 |
| E.Enterocyte_Immature__2 | 0 | 1721 | 2289 | 4.045 | 3.026 | 0.604 | 0.396 |
| E.Enterocyte_Progenitor | 0 | 1449 | 1447 | 5.583 | 4.128 | 0.733 | 0.267 |
| E.Enterocyte_Progenitor | 0 | 1666 | 2312 | 5.128 | 3.860 | 0.634 | 0.366 |
| E.Enterocyte_Progenitor | 0 | 1775 | 3197 | 7.585 | 6.413 | 0.556 | 0.444 |
| E.Enterocyte_Progenitor | 0 | 1750 | 2962 | 5.506 | 4.937 | 0.467 | 0.533 |
| E.Enterocyte_Progenitor | 0 | 1732 | 2698 | 5.418 | 4.421 | 0.562 | 0.438 |
| E.Enterocyte_Progenitor | 0 | 1788 | 3407 | 5.829 | 4.994 | 0.483 | 0.517 |
| E.Enterocyte_Progenitor | 0 | 1794 | 3248 | 6.231 | 5.312 | 0.511 | 0.489 |
| E.Enterocyte_Progenitor | 0 | 1805 | 3625 | 7.738 | 6.539 | 0.533 | 0.467 |
| E.Enterocyte_Progenitor | 0 | 1571 | 2085 | 4.310 | 2.747 | 0.690 | 0.310 |
| E.Enterocytes | 0 | 1208 | 975 | 3.631 | 2.639 | 0.711 | 0.289 |
| E.Enterocytes | 0 | 917 | 355 | 1.979 | 1.221 | 0.814 | 0.186 |
| E.Enterocytes | 0 | 1300 | 1081 | 6.579 | 4.568 | 0.829 | 0.171 |
| E.Enterocytes | 0 | 1399 | 2198 | 4.012 | 2.940 | 0.572 | 0.428 |
| E.Enterocytes | 0 | 1373 | 1236 | 5.591 | 4.360 | 0.723 | 0.277 |
| E.Enterocytes | 0 | 1332 | 890 | 3.427 | 2.674 | 0.716 | 0.284 |
| E.Enterocytes | 0 | 1401 | 1679 | 4.545 | 3.150 | 0.687 | 0.313 |
| E.Enterocytes | 0 | 1365 | 915 | 3.753 | 2.942 | 0.724 | 0.276 |
| E.Enterocytes | 0 | 1357 | 1984 | 3.033 | 2.101 | 0.566 | 0.434 |
| E.Enterocytes | 0 | 1246 | 523 | 3.893 | 2.827 | 0.833 | 0.167 |
| E.Enterocytes | 0 | 1138 | 521 | 2.204 | 1.612 | 0.767 | 0.233 |
| E.Enterocytes | 0 | 1400 | 2545 | 4.586 | 3.458 | 0.546 | 0.454 |
| E.Enterocytes | 0 | 1287 | 769 | 3.495 | 2.429 | 0.778 | 0.222 |
| E.Enterocytes | 0 | 1163 | 628 | 2.203 | 2.004 | 0.680 | 0.320 |
| E.Enterocytes | 0 | 1407 | 7359 | 9.255 | 6.746 | 0.521 | 0.479 |
| E.Enterocytes | 0 | 1406 | 2957 | 6.072 | 4.857 | 0.525 | 0.475 |
| E.Enterocytes | 0 | 1245 | 840 | 2.147 | 1.559 | 0.690 | 0.310 |
| E.Enterocytes | 0 | 1360 | 1569 | 6.764 | 5.134 | 0.728 | 0.272 |
| E.Enterocytes | 0 | 1323 | 842 | 5.194 | 4.497 | 0.718 | 0.282 |
| E.Enterocytes | 0 | 1312 | 1210 | 3.191 | 2.445 | 0.645 | 0.355 |
| E.Enterocytes | 0 | 1273 | 867 | 2.494 | 2.449 | 0.602 | 0.398 |

TABLE 12-continued

| Additional Cell Type Markers | | | | | | | |
|---|---|---|---|---|---|---|---|
| E.Enterocytes | 0 | 1407 | 3535 | 6.492 | 4.715 | 0.577 | 0.423 |
| E.Enterocytes | 0 | 1396 | 3426 | 4.999 | 4.657 | 0.341 | 0.659 |
| E.Enterocytes | 0 | 1370 | 1546 | 3.900 | 3.754 | 0.495 | 0.505 |
| E.Enterocytes | 0 | 1329 | 1109 | 4.750 | 3.508 | 0.739 | 0.261 |
| E.Enterocytes | 0 | 1367 | 1283 | 2.746 | 2.110 | 0.623 | 0.377 |
| E.Enterocytes | 0 | 1296 | 1000 | 3.998 | 3.267 | 0.683 | 0.317 |
| E.Enterocytes | 0 | 1269 | 765 | 2.116 | 1.954 | 0.650 | 0.350 |
| E.Enterocytes | 0 | 1004 | 338 | 1.924 | 1.388 | 0.812 | 0.188 |
| E.Enterocytes | 0 | 1318 | 1256 | 3.092 | 2.264 | 0.651 | 0.349 |
| E.Enterocytes | 0 | 1400 | 1769 | 4.877 | 3.398 | 0.688 | 0.312 |
| E.Enterocytes | 0 | 1271 | 976 | 3.950 | 2.808 | 0.742 | 0.258 |
| E.Enterocytes | 0 | 1269 | 906 | 2.510 | 2.150 | 0.643 | 0.357 |
| E.Enterocytes | 0 | 1383 | 1375 | 3.797 | 2.739 | 0.677 | 0.323 |
| E.Enterocytes | 0 | 1361 | 1268 | 5.029 | 3.857 | 0.708 | 0.292 |
| E.Enterocytes | 0 | 1252 | 769 | 2.441 | 2.197 | 0.659 | 0.341 |
| E.Enterocytes | 0 | 1396 | 3893 | 4.751 | 3.276 | 0.499 | 0.501 |
| E.Enterocytes | 0 | 1189 | 699 | 2.159 | 1.498 | 0.729 | 0.271 |
| E.Enterocytes | 0 | 1282 | 561 | 2.649 | 2.497 | 0.718 | 0.282 |
| E.Enterocytes | 0 | 1405 | 2295 | 4.950 | 3.765 | 0.582 | 0.418 |
| E.Epithelial | 0 | 5973 | 612 | 4.662 | 2.328 | 0.980 | 0.020 |
| E.Epithelial | 0 | 307 | 3272 | 3.229 | 4.267 | 0.044 | 0.956 |
| E.Epithelial | 0 | 3989 | 5281 | 1.787 | 4.098 | 0.132 | 0.868 |
| E.Epithelial | 0 | 6692 | 739 | 4.464 | 2.690 | 0.969 | 0.031 |
| E.Epithelial | 0 | 5641 | 162 | 3.091 | 1.879 | 0.988 | 0.012 |
| E.Epithelial | 0 | 5315 | 529 | 4.057 | 2.477 | 0.968 | 0.032 |
| E.Epithelial | 0 | 5479 | 542 | 4.053 | 2.368 | 0.970 | 0.030 |
| E.Epithelial | 0 | 6025 | 324 | 3.331 | 2.067 | 0.978 | 0.022 |
| E.Epithelial | 0 | 5725 | 313 | 3.030 | 1.789 | 0.977 | 0.023 |
| E.Epithelial | 0 | 6329 | 341 | 3.514 | 2.357 | 0.976 | 0.024 |
| E.Epithelial | 0 | 6657 | 3899 | 3.928 | 2.819 | 0.787 | 0.213 |
| E.Epithelial | 0 | 2953 | 4393 | 1.575 | 4.053 | 0.108 | 0.892 |
| E.Epithelial | 0 | 6291 | 7064 | 3.410 | 4.852 | 0.247 | 0.753 |
| E.Epithelial | 0 | 5939 | 220 | 2.986 | 1.950 | 0.982 | 0.018 |
| E.Epithelial | 0 | 6749 | 538 | 4.356 | 2.299 | 0.981 | 0.019 |
| E.Epithelial | 0 | 6503 | 1475 | 6.761 | 2.996 | 0.984 | 0.016 |
| E.Epithelial | 0 | 4839 | 273 | 4.634 | 2.143 | 0.990 | 0.010 |
| E.Epithelial | 0 | 6836 | 736 | 5.030 | 2.380 | 0.983 | 0.017 |
| E.Epithelial | 0 | 6115 | 6812 | 3.156 | 4.678 | 0.238 | 0.762 |
| E.Epithelial | 0 | 4232 | 77 | 2.454 | 2.392 | 0.983 | 0.017 |
| E.Epithelial | 0 | 6506 | 1536 | 4.979 | 4.205 | 0.879 | 0.121 |
| E.Epithelial | 0 | 1130 | 3867 | 1.024 | 3.483 | 0.050 | 0.950 |
| E.Epithelial | 0 | 4787 | 5723 | 2.296 | 4.826 | 0.127 | 0.873 |
| E.Epithelial | 0 | 6932 | 773 | 4.516 | 2.208 | 0.978 | 0.022 |
| E.Epithelial | 0 | 6214 | 504 | 4.638 | 2.285 | 0.984 | 0.016 |
| E.Epithelial | 0 | 3967 | 188 | 3.602 | 2.227 | 0.982 | 0.018 |
| E.Epithelial | 0 | 7212 | 1063 | 5.228 | 2.254 | 0.982 | 0.018 |
| E.Epithelial | 0 | 536 | 4026 | 1.750 | 4.763 | 0.016 | 0.984 |
| E.Epithelial | 0 | 6974 | 3280 | 5.112 | 3.428 | 0.872 | 0.128 |
| E.Epithelial | 0 | 7167 | 943 | 5.524 | 2.568 | 0.983 | 0.017 |
| E.Epithelial | 0 | 6851 | 6095 | 6.555 | 4.769 | 0.795 | 0.205 |
| E.Epithelial | 0 | 6938 | 6665 | 6.706 | 4.903 | 0.784 | 0.216 |
| E.Epithelial | 0 | 6912 | 5562 | 6.655 | 5.153 | 0.779 | 0.221 |
| E.Epithelial | 0 | 4403 | 256 | 3.945 | 2.516 | 0.979 | 0.021 |
| E.Epithelial | 0 | 6432 | 562 | 4.723 | 2.396 | 0.983 | 0.017 |
| E.Epithelial | 0 | 6606 | 7339 | 4.757 | 5.640 | 0.328 | 0.672 |
| E.Epithelial | 0 | 7408 | 5397 | 6.193 | 4.281 | 0.838 | 0.162 |
| E.Epithelial | 0 | 6127 | 139 | 3.183 | 2.235 | 0.988 | 0.012 |
| E.Epithelial | 0 | 5976 | 1086 | 2.970 | 2.252 | 0.900 | 0.100 |
| E.Epithelial | 0 | 5745 | 240 | 3.827 | 2.062 | 0.988 | 0.012 |
| E.Epithelial | 0 | 3260 | 4585 | 1.622 | 4.032 | 0.118 | 0.882 |
| E.Goblet | 0 | 1014 | 1738 | 4.280 | 3.261 | 0.542 | 0.458 |
| E.Goblet | 0 | 1028 | 2386 | 4.238 | 2.967 | 0.510 | 0.490 |
| E.Goblet | 0 | 1019 | 2318 | 3.786 | 2.986 | 0.434 | 0.566 |
| E.Goblet | 0 | 1130 | 1888 | 6.958 | 3.952 | 0.828 | 0.172 |
| E.Goblet | 0 | 1139 | 2993 | 5.805 | 4.876 | 0.420 | 0.580 |
| E.Goblet | 0 | 1116 | 2845 | 5.250 | 3.470 | 0.574 | 0.426 |
| E.Goblet | 0 | 1144 | 3565 | 5.970 | 4.780 | 0.423 | 0.577 |
| E.Goblet | 0 | 1013 | 1161 | 4.358 | 3.537 | 0.606 | 0.394 |
| E.Goblet | 0 | 901 | 980 | 3.415 | 1.838 | 0.733 | 0.267 |
| E.Goblet | 0 | 1147 | 1035 | 6.701 | 3.303 | 0.921 | 0.079 |
| E.Goblet | 0 | 1047 | 874 | 5.978 | 3.644 | 0.858 | 0.142 |
| E.Goblet | 0 | 1155 | 2699 | 8.105 | 6.062 | 0.638 | 0.362 |
| E.Goblet | 0 | 1112 | 2295 | 4.690 | 3.832 | 0.468 | 0.532 |
| E.Goblet | 0 | 1152 | 1799 | 9.543 | 5.487 | 0.914 | 0.086 |
| E.Immature_Enterocytes | 0 | 2770 | 974 | 5.397 | 4.780 | 0.814 | 0.186 |
| E.Immature_Enterocytes | 0 | 4103 | 2842 | 4.682 | 4.247 | 0.661 | 0.339 |
| E.Immature_Enterocytes | 0 | 3737 | 2024 | 3.594 | 2.779 | 0.765 | 0.235 |
| E.Immature_Enterocytes | 0 | 3209 | 1234 | 5.279 | 3.343 | 0.909 | 0.091 |

TABLE 12-continued

| Additional Cell Type Markers | | | | | | | |
|---|---|---|---|---|---|---|---|
| E.Immature_Enterocytes | 0 | 3984 | 2104 | 4.839 | 3.403 | 0.837 | 0.163 |
| E.Immature_Enterocytes | 0 | 3148 | 1205 | 2.557 | 1.970 | 0.797 | 0.203 |
| E.Immature_Enterocytes | 0 | 2795 | 702 | 3.278 | 2.891 | 0.839 | 0.161 |
| E.Immature_Enterocytes | 0 | 3495 | 2259 | 4.787 | 3.428 | 0.799 | 0.201 |
| E.Immature_Enterocytes | 0 | 3987 | 2429 | 3.904 | 3.355 | 0.706 | 0.294 |
| E.Immature_Enterocytes | 0 | 2467 | 682 | 2.970 | 2.406 | 0.842 | 0.158 |
| E.Immature_Enterocytes | 0 | 4002 | 2792 | 4.364 | 4.240 | 0.610 | 0.390 |
| E.Immature_Enterocytes | 0 | 3518 | 2703 | 3.810 | 2.732 | 0.733 | 0.267 |
| E.Immature_Enterocytes | 0 | 4306 | 3066 | 7.752 | 5.616 | 0.861 | 0.139 |
| E.Immature_Enterocytes | 0 | 4259 | 2804 | 5.786 | 4.542 | 0.783 | 0.217 |
| E.Immature_Enterocytes | 0 | 3313 | 1399 | 5.742 | 5.195 | 0.776 | 0.224 |
| E.Immature_Enterocytes | 0 | 4043 | 3078 | 4.457 | 4.346 | 0.586 | 0.414 |
| E.Immature_Enterocytes | 0 | 3925 | 2492 | 5.394 | 3.918 | 0.814 | 0.186 |
| E.Immature_Enterocytes | 0 | 3478 | 1272 | 3.920 | 3.183 | 0.820 | 0.180 |
| E.Immature_Enterocytes | 0 | 4298 | 3250 | 5.891 | 4.632 | 0.760 | 0.240 |
| E.Immature_Enterocytes | 0 | 4231 | 4762 | 5.744 | 4.378 | 0.696 | 0.304 |
| E.Immature_Enterocytes | 0 | 4267 | 3099 | 5.988 | 5.204 | 0.703 | 0.297 |
| E.Immature_Enterocytes | 0 | 3067 | 767 | 3.589 | 2.881 | 0.867 | 0.133 |
| E.Immature_Enterocytes | 0 | 4339 | 3536 | 7.965 | 5.941 | 0.833 | 0.167 |
| E.Immature_Enterocytes | 0 | 3955 | 2610 | 4.983 | 4.291 | 0.710 | 0.290 |
| E.Immature_Enterocytes | 0 | 3423 | 1503 | 3.872 | 3.325 | 0.769 | 0.231 |
| E.Immature_Enterocytes | 0 | 2621 | 844 | 3.295 | 2.782 | 0.816 | 0.184 |
| E.Immature_Enterocytes | 0 | 3107 | 1191 | 2.956 | 2.634 | 0.765 | 0.235 |
| E.Immature_Enterocytes | 0 | 3242 | 1926 | 3.977 | 2.504 | 0.824 | 0.176 |
| E.Immature_Enterocytes | 0 | 3097 | 1082 | 3.413 | 2.109 | 0.876 | 0.124 |
| E.Immature_Enterocytes | 0 | 3549 | 972 | 4.198 | 3.576 | 0.849 | 0.151 |
| E.Immature_Enterocytes | 0 | 2613 | 579 | 2.414 | 1.908 | 0.865 | 0.135 |
| E.Immature_Enterocytes | 0 | 3743 | 2268 | 3.484 | 2.977 | 0.701 | 0.299 |
| E.Immature_Enterocytes | 0 | 3919 | 3787 | 4.221 | 3.085 | 0.695 | 0.305 |
| E.Immature_Enterocytes | 0 | 3721 | 2131 | 3.735 | 2.740 | 0.777 | 0.223 |
| E.Immature_Enterocytes | 0 | 3931 | 2068 | 4.145 | 3.590 | 0.736 | 0.264 |
| E.Immature_Goblet | 0 | 1551 | 2662 | 5.765 | 4.313 | 0.615 | 0.385 |
| E.Immature_Goblet | 0 | 1359 | 695 | 5.136 | 2.744 | 0.911 | 0.089 |
| E.Immature_Goblet | 0 | 1573 | 1880 | 5.942 | 4.318 | 0.720 | 0.280 |
| E.Immature_Goblet | 0 | 1565 | 966 | 5.946 | 3.560 | 0.894 | 0.106 |
| E.Immature_Goblet | 0 | 1530 | 954 | 4.467 | 2.127 | 0.890 | 0.110 |
| E.Immature_Goblet | 0 | 1605 | 3182 | 4.941 | 4.379 | 0.427 | 0.573 |
| E.Immature_Goblet | 0 | 1175 | 381 | 2.500 | 0.954 | 0.900 | 0.100 |
| E.Immature_Goblet | 0 | 1480 | 1003 | 4.504 | 4.612 | 0.578 | 0.422 |
| E.Immature_Goblet | 0 | 1191 | 439 | 2.826 | 1.954 | 0.832 | 0.168 |
| E.Immature_Goblet | 0 | 1193 | 409 | 4.378 | 1.993 | 0.938 | 0.062 |
| E.Immature_Goblet | 0 | 1408 | 1494 | 3.866 | 3.130 | 0.611 | 0.389 |
| E.Immature_Goblet | 0 | 1224 | 828 | 3.130 | 2.242 | 0.732 | 0.268 |
| E.Immature_Goblet | 0 | 1382 | 1364 | 3.880 | 2.933 | 0.661 | 0.339 |
| E.Immature_Goblet | 0 | 1236 | 768 | 6.140 | 4.371 | 0.846 | 0.154 |
| E.Immature_Goblet | 0 | 1658 | 2739 | 8.816 | 5.512 | 0.857 | 0.143 |
| E.Immature_Goblet | 0 | 1370 | 959 | 4.276 | 2.274 | 0.851 | 0.149 |
| E.Immature_Goblet | 0 | 1449 | 1816 | 7.937 | 6.485 | 0.686 | 0.314 |
| E.Secretory | 0 | 1291 | 1951 | 6.784 | 3.914 | 0.829 | 0.171 |
| E.Secretory | 0 | 1845 | 3181 | 5.589 | 4.243 | 0.596 | 0.404 |
| E.Secretory | 0 | 1231 | 1080 | 6.606 | 3.313 | 0.918 | 0.082 |
| E.Secretory | 0 | 1131 | 920 | 5.885 | 3.694 | 0.849 | 0.151 |
| E.Secretory | 0 | 1794 | 2690 | 7.582 | 6.100 | 0.651 | 0.349 |
| E.Secretory | 0 | 1349 | 1854 | 9.323 | 5.425 | 0.916 | 0.084 |
| E.Secretory_All | 0 | 2517 | 603 | 4.459 | 1.756 | 0.965 | 0.035 |
| E.Secretory_All | 0 | 3656 | 1746 | 5.947 | 2.828 | 0.948 | 0.052 |
| E.Secretory_All | 0 | 3924 | 2945 | 4.548 | 5.087 | 0.478 | 0.522 |
| E.Secretory_All | 0 | 3044 | 802 | 5.231 | 2.741 | 0.955 | 0.045 |
| E.Secretory_All | 0 | 3200 | 755 | 3.709 | 1.530 | 0.950 | 0.050 |
| E.Secretory_All | 0 | 4218 | 3113 | 5.026 | 4.144 | 0.714 | 0.286 |
| E.Secretory_All | 0 | 4234 | 3340 | 4.732 | 5.151 | 0.487 | 0.513 |
| E.Secretory_All | 0 | 4111 | 3186 | 5.379 | 5.488 | 0.545 | 0.455 |
| E.Secretory_All | 0 | 3391 | 817 | 5.311 | 1.951 | 0.977 | 0.023 |
| E.Secretory_All | 0 | 2389 | 240 | 2.570 | 0.913 | 0.969 | 0.031 |
| E.Secretory_All | 0 | 2326 | 612 | 5.647 | 3.504 | 0.944 | 0.056 |
| E.Secretory_All | 0 | 4234 | 2580 | 8.009 | 4.159 | 0.959 | 0.041 |
| E.Secretory_All | 0 | 3449 | 1682 | 8.247 | 3.561 | 0.981 | 0.019 |
| E.Tuft | 0 | 552 | 3208 | 6.765 | 4.217 | 0.502 | 0.498 |
| F.Crypt | 0 | 3156 | 920 | 4.099 | 3.199 | 0.865 | 0.135 |
| F.Crypt | 0 | 2386 | 78 | 3.398 | 2.781 | 0.979 | 0.021 |
| F.Crypt | 0 | 1779 | 316 | 2.763 | 1.870 | 0.913 | 0.087 |
| F.Crypt | 0 | 3497 | 556 | 7.247 | 3.992 | 0.984 | 0.016 |
| F.Crypt | 0 | 2123 | 327 | 3.330 | 1.894 | 0.946 | 0.054 |
| F.Crypt | 0 | 3623 | 868 | 7.043 | 5.086 | 0.942 | 0.058 |
| F.Crypt | 0 | 2087 | 487 | 2.812 | 3.595 | 0.713 | 0.287 |
| F.Crypt | 0 | 3308 | 639 | 4.365 | 3.670 | 0.893 | 0.107 |
| F.Crypt | 0 | 3341 | 614 | 4.536 | 3.693 | 0.907 | 0.093 |
| F.Crypt | 0 | 2951 | 718 | 3.608 | 3.828 | 0.779 | 0.221 |

TABLE 12-continued

| Additional Cell Type Markers | | | | | | | |
|---|---|---|---|---|---|---|---|
| F.Crypt | 0 | 2221 | 119 | 5.921 | 3.852 | 0.987 | 0.013 |
| F.Crypt | 0 | 1919 | 48 | 5.837 | 2.060 | 0.998 | 0.002 |
| F.Crypt | 0 | 2986 | 445 | 4.944 | 4.651 | 0.892 | 0.108 |
| F.Crypt | 0 | 2149 | 64 | 5.018 | 1.983 | 0.996 | 0.004 |
| F.Crypt | 0 | 3624 | 5585 | 5.307 | 4.208 | 0.582 | 0.418 |
| F.Crypt | 0 | 3596 | 926 | 6.711 | 3.192 | 0.978 | 0.022 |
| F.Crypt | 0 | 2375 | 360 | 3.327 | 2.554 | 0.919 | 0.081 |
| F.Crypt | 0 | 2375 | 500 | 2.948 | 2.424 | 0.872 | 0.128 |
| F.Crypt | 0 | 2949 | 618 | 3.768 | 3.722 | 0.831 | 0.169 |
| F.Crypt | 0 | 3310 | 671 | 4.189 | 3.910 | 0.857 | 0.143 |
| F.Crypt | 0 | 3281 | 671 | 4.522 | 4.262 | 0.854 | 0.146 |
| F.Crypt | 0 | 2324 | 591 | 3.038 | 3.498 | 0.741 | 0.259 |
| F.Crypt | 0 | 3069 | 706 | 3.715 | 3.901 | 0.793 | 0.207 |
| F.Crypt | 0 | 3322 | 2236 | 4.673 | 2.996 | 0.826 | 0.174 |
| F.Crypt | 0 | 2564 | 397 | 3.253 | 2.783 | 0.899 | 0.101 |
| F.Crypt | 0 | 2503 | 333 | 3.720 | 2.966 | 0.927 | 0.073 |
| F.Crypt | 0 | 3542 | 2197 | 6.261 | 5.187 | 0.772 | 0.228 |
| F.Crypt | 0 | 2782 | 488 | 3.451 | 3.339 | 0.860 | 0.140 |
| F.Crypt | 0 | 3546 | 596 | 5.853 | 4.297 | 0.946 | 0.054 |
| F.Crypt | 0 | 1979 | 213 | 2.670 | 3.009 | 0.880 | 0.120 |
| F.Crypt | 0 | 1732 | 188 | 3.131 | 2.839 | 0.919 | 0.081 |
| F.Crypt | 0 | 1789 | 319 | 2.403 | 2.658 | 0.825 | 0.175 |
| F.Crypt | 0 | 2102 | 375 | 2.752 | 2.686 | 0.854 | 0.146 |
| F.Crypt | 0 | 1146 | 42 | 3.718 | 3.221 | 0.975 | 0.025 |
| F.Crypt | 0 | 3283 | 344 | 4.242 | 2.792 | 0.963 | 0.037 |
| F.Crypt | 0 | 1902 | 156 | 2.727 | 2.171 | 0.947 | 0.053 |
| F.Crypt | 0 | 2145 | 630 | 2.846 | 3.905 | 0.620 | 0.380 |
| F.Crypt | 0 | 2755 | 567 | 3.695 | 3.335 | 0.862 | 0.138 |
| F.Crypt | 0 | 3351 | 2620 | 4.812 | 3.347 | 0.779 | 0.221 |
| F.Crypt | 0 | 1671 | 350 | 2.744 | 1.965 | 0.891 | 0.109 |
| F.Crypt | 0 | 3564 | 2640 | 4.917 | 3.851 | 0.739 | 0.261 |
| F.Crypt | 0 | 2196 | 511 | 3.312 | 3.323 | 0.810 | 0.190 |
| F.Crypt | 0 | 3646 | 1406 | 6.519 | 5.994 | 0.789 | 0.211 |
| F.Crypt | 0 | 3006 | 3294 | 3.700 | 2.735 | 0.641 | 0.359 |
| F.Crypt | 0 | 3604 | 2719 | 5.252 | 4.673 | 0.664 | 0.336 |
| F.Crypt | 0 | 2245 | 167 | 2.910 | 2.829 | 0.934 | 0.066 |
| F.Crypt | 0 | 2549 | 1084 | 3.174 | 2.069 | 0.835 | 0.165 |
| F.Crypt | 0 | 3454 | 597 | 5.922 | 4.575 | 0.936 | 0.064 |
| F.Crypt | 0 | 3320 | 521 | 4.843 | 3.536 | 0.940 | 0.060 |
| F.Crypt | 0 | 2033 | 554 | 2.858 | 3.439 | 0.710 | 0.290 |
| F.Crypt | 0 | 2459 | 506 | 3.042 | 3.445 | 0.786 | 0.214 |
| F.Crypt | 0 | 2088 | 727 | 2.818 | 4.133 | 0.536 | 0.464 |
| F.Crypt | 0 | 2587 | 1685 | 3.046 | 2.198 | 0.734 | 0.266 |
| F.Crypt | 0 | 2032 | 506 | 2.896 | 3.270 | 0.756 | 0.244 |
| F.Crypt | 0 | 2260 | 449 | 3.014 | 3.247 | 0.811 | 0.189 |
| F.Crypt | 0 | 2329 | 276 | 3.061 | 2.836 | 0.908 | 0.092 |
| F.Crypt | 0 | 2063 | 698 | 3.375 | 4.421 | 0.589 | 0.411 |
| F.Crypt | 0 | 1794 | 389 | 2.610 | 2.032 | 0.873 | 0.127 |
| F.Crypt | 0 | 2512 | 640 | 3.163 | 2.978 | 0.817 | 0.183 |
| F.Crypt | 0 | 2523 | 1293 | 3.135 | 2.224 | 0.786 | 0.214 |
| F.Crypt | 0 | 2286 | 337 | 3.137 | 1.894 | 0.941 | 0.059 |
| F.Crypt | 0 | 2383 | 721 | 3.249 | 3.040 | 0.793 | 0.207 |
| F.Crypt | 0 | 2258 | 647 | 2.978 | 3.157 | 0.755 | 0.245 |
| F.Crypt | 0 | 2622 | 560 | 3.322 | 2.862 | 0.866 | 0.134 |
| F.Crypt | 0 | 1947 | 119 | 4.614 | 3.985 | 0.962 | 0.038 |
| F.Crypt | 0 | 2273 | 250 | 3.298 | 3.244 | 0.904 | 0.096 |
| F.Crypt | 0 | 3290 | 1485 | 4.071 | 3.414 | 0.777 | 0.223 |
| F.Crypt | 0 | 2670 | 421 | 3.435 | 2.749 | 0.911 | 0.089 |
| F.Crypt | 0 | 2562 | 1770 | 3.036 | 2.263 | 0.712 | 0.288 |
| F.Crypt | 0 | 3087 | 1931 | 3.545 | 2.881 | 0.717 | 0.283 |
| F.Crypt | 0 | 2953 | 2154 | 4.010 | 3.961 | 0.586 | 0.414 |
| F.Crypt | 0 | 2780 | 656 | 3.501 | 3.499 | 0.809 | 0.191 |
| F.Crypt | 0 | 2554 | 666 | 3.133 | 3.021 | 0.806 | 0.194 |
| F.Crypt | 0 | 1797 | 361 | 2.604 | 2.770 | 0.816 | 0.184 |
| F.Crypt | 0 | 3091 | 938 | 4.135 | 2.948 | 0.882 | 0.118 |
| F.Crypt | 0 | 2800 | 943 | 3.632 | 4.166 | 0.672 | 0.328 |
| F.Crypt | 0 | 1879 | 588 | 2.948 | 3.943 | 0.616 | 0.384 |
| F.Crypt | 0 | 2024 | 517 | 2.767 | 2.396 | 0.835 | 0.165 |
| F.Crypt | 0 | 1997 | 215 | 3.327 | 2.866 | 0.928 | 0.072 |
| F.Crypt | 0 | 2985 | 366 | 3.792 | 2.967 | 0.935 | 0.065 |
| F.Crypt | 0 | 3299 | 2614 | 4.083 | 4.024 | 0.568 | 0.432 |
| F.Crypt | 0 | 2007 | 948 | 3.037 | 3.560 | 0.596 | 0.404 |
| F.Crypt | 0 | 3150 | 2348 | 3.853 | 2.738 | 0.744 | 0.256 |
| F.Crypt | 0 | 3498 | 2880 | 4.789 | 3.365 | 0.765 | 0.235 |
| F.Crypt | 0 | 2180 | 660 | 2.906 | 4.096 | 0.591 | 0.409 |
| F.Crypt | 0 | 2111 | 714 | 2.713 | 2.627 | 0.758 | 0.242 |
| F.Crypt | 0 | 3478 | 3224 | 5.026 | 4.148 | 0.665 | 0.335 |
| F.Crypt_hiFos | 0 | 1049 | 1083 | 4.022 | 3.446 | 0.591 | 0.409 |

TABLE 12-continued

Additional Cell Type Markers

| | | | | | | |
|---|---|---|---|---|---|---|
| F.Crypt_hiFos | 0 | 844 | 278 | 3.112 | 3.507 | 0.698 | 0.302 |
| F.Crypt_hiFos | 0 | 1134 | 794 | 7.597 | 5.955 | 0.817 | 0.183 |
| F.Crypt_hiFos | 0 | 1134 | 1087 | 6.856 | 5.919 | 0.666 | 0.334 |
| F.Crypt_hiFos | 0 | 1105 | 818 | 4.389 | 3.853 | 0.662 | 0.338 |
| F.Crypt_hiFos | 0 | 1111 | 784 | 4.675 | 3.976 | 0.697 | 0.303 |
| F.Crypt_hiFos | 0 | 1108 | 687 | 5.225 | 4.744 | 0.692 | 0.308 |
| F.Crypt_hiFos | 0 | 795 | 197 | 5.246 | 4.437 | 0.876 | 0.124 |
| F.Crypt_hiFos | 0 | 1136 | 1213 | 6.608 | 5.024 | 0.737 | 0.263 |
| F.Crypt_hiFos | 0 | 997 | 782 | 3.471 | 3.886 | 0.489 | 0.511 |
| F.Crypt_hiFos | 0 | 1083 | 826 | 3.970 | 4.166 | 0.534 | 0.466 |
| F.Crypt_hiFos | 0 | 1080 | 848 | 4.301 | 4.422 | 0.539 | 0.461 |
| F.Crypt_hiFos | 0 | 1001 | 860 | 3.368 | 3.938 | 0.440 | 0.560 |
| F.Crypt_hiFos | 0 | 1120 | 2480 | 4.771 | 3.249 | 0.565 | 0.435 |
| F.Crypt_hiFos | 0 | 936 | 514 | 3.479 | 3.169 | 0.693 | 0.307 |
| F.Crypt_hiFos | 0 | 1136 | 2226 | 6.269 | 5.371 | 0.487 | 0.513 |
| F.Crypt_hiFos | 0 | 985 | 628 | 3.315 | 3.356 | 0.604 | 0.396 |
| F.Crypt_hiFos | 0 | 1131 | 817 | 5.879 | 5.050 | 0.711 | 0.289 |
| F.Crypt_hiFos | 0 | 1089 | 606 | 4.156 | 3.697 | 0.712 | 0.288 |
| F.Crypt_hiFos | 0 | 965 | 715 | 3.482 | 3.394 | 0.589 | 0.411 |
| F.Crypt_hiFos | 0 | 1090 | 2798 | 4.676 | 3.594 | 0.452 | 0.548 |
| F.Crypt_hiFos | 0 | 867 | 214 | 3.125 | 2.672 | 0.847 | 0.153 |
| F.Crypt_hiFos | 0 | 1126 | 2791 | 4.687 | 3.886 | 0.413 | 0.587 |
| F.Crypt_hiFos | 0 | 1141 | 1517 | 6.456 | 6.170 | 0.478 | 0.522 |
| F.Crypt_hiFos | 0 | 1126 | 788 | 6.057 | 5.403 | 0.692 | 0.308 |
| F.Crypt_hiFos | 0 | 1110 | 725 | 4.771 | 4.184 | 0.697 | 0.303 |
| F.Crypt_hiFos | 0 | 863 | 519 | 3.017 | 2.422 | 0.715 | 0.285 |
| F.Crypt_hiFos | 0 | 946 | 706 | 3.151 | 2.989 | 0.600 | 0.400 |
| F.Crypt_hiFos | 0 | 952 | 550 | 3.255 | 3.030 | 0.669 | 0.331 |
| F.Crypt_hiFos | 0 | 981 | 742 | 3.297 | 3.443 | 0.544 | 0.456 |
| F.Crypt_hiFos | 0 | 1060 | 1107 | 4.028 | 3.266 | 0.619 | 0.381 |
| F.Crypt_hiFos | 0 | 1014 | 526 | 3.617 | 3.403 | 0.691 | 0.309 |
| F.Crypt_hiFos | 0 | 1131 | 3028 | 4.716 | 3.536 | 0.458 | 0.542 |
| F.Crypt_hiFos | 0 | 1134 | 3268 | 5.166 | 4.234 | 0.398 | 0.602 |
| F.Crypt_loFos_1 | 0 | 1250 | 1134 | 3.901 | 3.480 | 0.596 | 0.404 |
| F.Crypt_loFos_1 | 0 | 1022 | 281 | 3.158 | 3.451 | 0.748 | 0.252 |
| F.Crypt_loFos_1 | 0 | 1366 | 818 | 7.306 | 6.044 | 0.800 | 0.200 |
| F.Crypt_loFos_1 | 0 | 1376 | 1174 | 7.234 | 5.806 | 0.759 | 0.241 |
| F.Crypt_loFos_1 | 0 | 1327 | 881 | 4.308 | 3.896 | 0.667 | 0.333 |
| F.Crypt_loFos_1 | 0 | 1332 | 858 | 4.445 | 4.073 | 0.668 | 0.332 |
| F.Crypt_loFos_1 | 0 | 1216 | 918 | 3.499 | 3.798 | 0.518 | 0.482 |
| F.Crypt_loFos_1 | 0 | 787 | 185 | 5.923 | 5.332 | 0.865 | 0.135 |
| F.Crypt_loFos_1 | 0 | 1183 | 727 | 4.634 | 4.814 | 0.590 | 0.410 |
| F.Crypt_loFos_1 | 0 | 916 | 204 | 4.830 | 4.778 | 0.823 | 0.177 |
| F.Crypt_loFos_1 | 0 | 1358 | 1240 | 6.713 | 5.016 | 0.780 | 0.220 |
| F.Crypt_loFos_1 | 0 | 1001 | 520 | 3.080 | 2.914 | 0.684 | 0.316 |
| F.Crypt_loFos_1 | 0 | 1009 | 676 | 2.746 | 2.685 | 0.609 | 0.391 |
| F.Crypt_loFos_1 | 0 | 1199 | 837 | 3.662 | 3.906 | 0.547 | 0.453 |
| F.Crypt_loFos_1 | 0 | 1317 | 883 | 4.130 | 4.085 | 0.606 | 0.394 |
| F.Crypt_loFos_1 | 0 | 1307 | 902 | 4.577 | 4.438 | 0.615 | 0.385 |
| F.Crypt_loFos_1 | 0 | 1211 | 903 | 3.424 | 3.976 | 0.478 | 0.522 |
| F.Crypt_loFos_1 | 0 | 1343 | 2404 | 4.706 | 3.355 | 0.588 | 0.412 |
| F.Crypt_loFos_1 | 0 | 1090 | 562 | 3.120 | 3.084 | 0.665 | 0.335 |
| F.Crypt_loFos_1 | 0 | 1023 | 543 | 3.627 | 3.278 | 0.706 | 0.294 |
| F.Crypt_loFos_1 | 0 | 1364 | 2359 | 6.358 | 5.403 | 0.528 | 0.472 |
| F.Crypt_loFos_1 | 0 | 1197 | 671 | 3.404 | 3.343 | 0.651 | 0.349 |
| F.Crypt_loFos_1 | 0 | 1371 | 874 | 5.894 | 5.057 | 0.737 | 0.263 |
| F.Crypt_loFos_1 | 0 | 898 | 359 | 2.565 | 2.894 | 0.666 | 0.334 |
| F.Crypt_loFos_1 | 0 | 1301 | 618 | 4.125 | 3.797 | 0.725 | 0.275 |
| F.Crypt_loFos_1 | 0 | 853 | 286 | 2.556 | 2.363 | 0.773 | 0.227 |
| F.Crypt_loFos_1 | 0 | 1182 | 796 | 3.740 | 3.357 | 0.659 | 0.341 |
| F.Crypt_loFos_1 | 0 | 1310 | 2894 | 4.812 | 3.611 | 0.510 | 0.490 |
| F.Crypt_loFos_1 | 0 | 1370 | 2857 | 4.959 | 3.939 | 0.493 | 0.507 |
| F.Crypt_loFos_1 | 0 | 1374 | 1612 | 6.526 | 6.130 | 0.529 | 0.471 |
| F.Crypt_loFos_1 | 0 | 1365 | 2794 | 5.146 | 4.733 | 0.394 | 0.606 |
| F.Crypt_loFos_1 | 0 | 960 | 350 | 2.743 | 2.988 | 0.698 | 0.302 |
| F.Crypt_loFos_1 | 0 | 1365 | 826 | 5.956 | 5.358 | 0.714 | 0.286 |
| F.Crypt_loFos_1 | 0 | 1323 | 795 | 4.867 | 4.057 | 0.745 | 0.255 |
| F.Crypt_loFos_1 | 0 | 1044 | 692 | 2.856 | 3.290 | 0.528 | 0.472 |
| F.Crypt_loFos_1 | 0 | 958 | 475 | 2.702 | 2.874 | 0.642 | 0.358 |
| F.Crypt_loFos_1 | 0 | 1069 | 779 | 3.034 | 3.129 | 0.562 | 0.438 |
| F.Crypt_loFos_1 | 0 | 1015 | 529 | 3.017 | 2.494 | 0.734 | 0.266 |
| F.Crypt_loFos_1 | 0 | 1182 | 710 | 3.305 | 2.950 | 0.680 | 0.320 |
| F.Crypt_loFos_1 | 0 | 996 | 438 | 3.197 | 3.275 | 0.683 | 0.317 |
| F.Crypt_loFos_1 | 0 | 1300 | 1739 | 3.944 | 3.565 | 0.493 | 0.507 |
| F.Crypt_loFos_1 | 0 | 1136 | 595 | 3.285 | 3.027 | 0.695 | 0.305 |
| F.Crypt_loFos_1 | 0 | 1156 | 851 | 3.365 | 3.538 | 0.546 | 0.454 |
| F.Crypt_loFos_1 | 0 | 1088 | 846 | 3.023 | 3.037 | 0.560 | 0.440 |
| F.Crypt_loFos_1 | 0 | 1227 | 1199 | 4.022 | 3.296 | 0.629 | 0.371 |

TABLE 12-continued

| Additional Cell Type Markers | | | | | | | |
|---|---|---|---|---|---|---|---|
| F.Crypt_loFos_1 | 0 | 1208 | 1128 | 3.689 | 4.066 | 0.452 | 0.548 |
| F.Crypt_loFos_1 | 0 | 1223 | 588 | 3.747 | 3.373 | 0.729 | 0.271 |
| F.Crypt_loFos_1 | 0 | 1325 | 2772 | 4.035 | 4.051 | 0.321 | 0.679 |
| F.Crypt_loFos_1 | 0 | 1294 | 2583 | 3.807 | 2.807 | 0.500 | 0.500 |
| F.Crypt_loFos_1 | 0 | 1365 | 3132 | 4.845 | 3.565 | 0.514 | 0.486 |
| F.Crypt_loFos_1 | 0 | 1368 | 3268 | 4.997 | 4.262 | 0.411 | 0.589 |
| F.Crypt_loFos_2 | 0 | 949 | 1084 | 7.101 | 5.953 | 0.660 | 0.340 |
| F.Crypt_loFos_2 | 0 | 916 | 1243 | 6.828 | 5.015 | 0.721 | 0.279 |
| F.Endothelial | 0 | 1219 | 273 | 2.908 | 0.994 | 0.944 | 0.056 |
| F.Endothelial | 0 | 1559 | 618 | 3.985 | 3.482 | 0.781 | 0.219 |
| F.Endothelial | 0 | 1441 | 1881 | 3.510 | 2.125 | 0.667 | 0.333 |
| F.Endothelial | 0 | 1556 | 1426 | 5.383 | 1.472 | 0.943 | 0.057 |
| F.Endothelial | 0 | 951 | 148 | 4.156 | 1.856 | 0.969 | 0.031 |
| F.Endothelial | 0 | 1604 | 2782 | 4.064 | 2.214 | 0.675 | 0.325 |
| F.Endothelial | 0 | 1414 | 49 | 5.228 | 1.567 | 0.997 | 0.003 |
| F.Endothelial | 0 | 1281 | 59 | 3.399 | 2.168 | 0.981 | 0.019 |
| F.Endothelial | 0 | 1643 | 444 | 4.115 | 2.641 | 0.911 | 0.089 |
| F.Endothelial | 0 | 1351 | 58 | 3.331 | 1.770 | 0.986 | 0.014 |
| F.Endothelial | 0 | 1245 | 368 | 3.311 | 1.973 | 0.895 | 0.105 |
| F.Endothelial | 0 | 1282 | 78 | 3.259 | 0.870 | 0.989 | 0.011 |
| F.Endothelial | 0 | 1635 | 2518 | 6.400 | 3.120 | 0.863 | 0.137 |
| F.Endothelial | 0 | 1644 | 3414 | 4.059 | 2.462 | 0.593 | 0.407 |
| F.Endothelial | 0 | 1334 | 849 | 3.624 | 3.301 | 0.663 | 0.337 |
| F.Endothelial | 0 | 1722 | 601 | 4.684 | 2.860 | 0.910 | 0.090 |
| F.Endothelial | 0 | 1928 | 6769 | 5.707 | 4.574 | 0.384 | 0.616 |
| F.Endothelial | 0 | 1718 | 4543 | 4.333 | 3.002 | 0.488 | 0.512 |
| F.Endothelial | 0 | 1893 | 2711 | 5.196 | 3.748 | 0.656 | 0.344 |
| F.Endothelial | 0 | 1500 | 1206 | 3.811 | 1.626 | 0.850 | 0.150 |
| F.Endothelial | 0 | 1914 | 1455 | 6.984 | 5.874 | 0.739 | 0.261 |
| F.Endothelial | 0 | 1805 | 5038 | 5.020 | 3.334 | 0.536 | 0.464 |
| F.Endothelial | 0 | 1054 | 47 | 3.046 | 1.581 | 0.984 | 0.016 |
| F.Endothelial | 0 | 1345 | 206 | 4.033 | 2.843 | 0.937 | 0.063 |
| F.Endothelial | 0 | 1289 | 996 | 3.201 | 1.726 | 0.782 | 0.218 |
| F.Endothelial | 0 | 1579 | 72 | 5.687 | 1.269 | 0.998 | 0.002 |
| F.Endothelial | 0 | 1528 | 143 | 4.279 | 1.597 | 0.986 | 0.014 |
| F.Endothelial | 0 | 1331 | 15 | 3.868 | 0.963 | 0.998 | 0.002 |
| F.Endothelial | 0 | 1006 | 128 | 3.109 | 2.540 | 0.921 | 0.079 |
| F.Endothelial | 0 | 1676 | 3525 | 4.151 | 2.590 | 0.584 | 0.416 |
| F.Endothelial | 0 | 1305 | 906 | 4.166 | 1.802 | 0.881 | 0.119 |
| F.Endothelial | 0 | 1602 | 512 | 4.493 | 3.167 | 0.887 | 0.113 |
| F.Endothelial | 0 | 1513 | 909 | 4.155 | 3.150 | 0.770 | 0.230 |
| F.Endothelial | 0 | 905 | 47 | 3.234 | 1.512 | 0.985 | 0.015 |
| F.Endothelial | 0 | 1244 | 15 | 3.544 | 1.783 | 0.996 | 0.004 |
| F.Endothelial_1 | 0 | 652 | 1575 | 5.796 | 2.413 | 0.812 | 0.188 |
| F.Endothelial_1 | 0 | 585 | 172 | 5.192 | 4.948 | 0.801 | 0.199 |
| F.Endothelial_1 | 0 | 654 | 2665 | 6.229 | 3.695 | 0.587 | 0.413 |
| F.Endothelial_1 | 0 | 676 | 750 | 4.828 | 3.440 | 0.702 | 0.298 |
| F.Endothelial_1 | 0 | 586 | 1320 | 4.051 | 2.045 | 0.641 | 0.359 |
| F.Endothelial_1 | 0 | 666 | 217 | 5.705 | 5.102 | 0.823 | 0.177 |
| F.Fibroblast | 0 | 4029 | 635 | 3.832 | 3.104 | 0.913 | 0.087 |
| F.Fibroblast | 0 | 3456 | 408 | 6.974 | 2.269 | 0.995 | 0.005 |
| F.Fibroblast | 0 | 4106 | 607 | 6.605 | 4.675 | 0.963 | 0.037 |
| F.Fibroblast | 0 | 3267 | 73 | 3.344 | 1.646 | 0.993 | 0.007 |
| F.Fibroblast | 0 | 4326 | 213 | 4.183 | 2.021 | 0.989 | 0.011 |
| F.Fibroblast | 0 | 4410 | 163 | 4.300 | 2.446 | 0.990 | 0.010 |
| F.Fibroblast | 0 | 4239 | 261 | 3.842 | 3.442 | 0.955 | 0.045 |
| F.Fibroblast | 0 | 1873 | 92 | 5.972 | 1.932 | 0.997 | 0.003 |
| F.Fibroblast | 0 | 1422 | 59 | 5.806 | 1.785 | 0.997 | 0.003 |
| F.Fibroblast | 0 | 2929 | 351 | 4.833 | 4.585 | 0.908 | 0.092 |
| F.Fibroblast | 0 | 1563 | 61 | 4.966 | 2.517 | 0.993 | 0.007 |
| F.Fibroblast | 0 | 5111 | 5338 | 5.197 | 4.037 | 0.681 | 0.319 |
| F.Fibroblast | 0 | 3949 | 704 | 6.211 | 2.064 | 0.990 | 0.010 |
| F.Fibroblast | 0 | 2740 | 114 | 3.128 | 2.120 | 0.980 | 0.020 |
| F.Fibroblast | 0 | 2962 | 197 | 2.886 | 1.903 | 0.967 | 0.033 |
| F.Fibroblast | 0 | 4125 | 199 | 3.894 | 2.397 | 0.983 | 0.017 |
| F.Fibroblast | 0 | 4518 | 186 | 4.169 | 2.996 | 0.982 | 0.018 |
| F.Fibroblast | 0 | 4579 | 172 | 4.539 | 2.685 | 0.990 | 0.010 |
| F.Fibroblast | 0 | 3657 | 165 | 3.437 | 2.078 | 0.983 | 0.017 |
| F.Fibroblast | 0 | 4478 | 190 | 4.006 | 2.265 | 0.987 | 0.013 |
| F.Fibroblast | 0 | 3827 | 2143 | 4.427 | 2.818 | 0.845 | 0.155 |
| F.Fibroblast | 0 | 2679 | 184 | 3.600 | 2.643 | 0.966 | 0.034 |
| F.Fibroblast | 0 | 5077 | 1724 | 6.700 | 2.109 | 0.986 | 0.014 |
| F.Fibroblast | 0 | 3686 | 97 | 3.433 | 2.581 | 0.986 | 0.014 |
| F.Fibroblast | 0 | 4311 | 182 | 5.480 | 1.697 | 0.997 | 0.003 |
| F.Fibroblast | 0 | 2121 | 249 | 3.980 | 1.133 | 0.984 | 0.016 |
| F.Fibroblast | 0 | 3905 | 2725 | 3.376 | 2.406 | 0.737 | 0.263 |
| F.Fibroblast | 0 | 2953 | 59 | 2.846 | 1.676 | 0.991 | 0.009 |
| F.Fibroblast | 0 | 3645 | 58 | 3.945 | 1.554 | 0.997 | 0.003 |

TABLE 12-continued

| Additional Cell Type Markers | | | | | | | |
|---|---|---|---|---|---|---|---|
| F.Fibroblast | 0 | 2584 | 465 | 2.863 | 4.368 | 0.662 | 0.338 |
| F.Fibroblast | 0 | 3550 | 254 | 3.635 | 2.703 | 0.964 | 0.036 |
| F.Fibroblast | 0 | 4136 | 2346 | 4.358 | 3.393 | 0.775 | 0.225 |
| F.Fibroblast | 0 | 4971 | 2195 | 4.744 | 3.624 | 0.831 | 0.169 |
| F.Fibroblast | 0 | 3046 | 212 | 3.466 | 2.742 | 0.960 | 0.040 |
| F.Fibroblast | 0 | 5121 | 933 | 6.266 | 6.102 | 0.860 | 0.140 |
| F.Fibroblast | 0 | 2401 | 139 | 2.800 | 2.555 | 0.953 | 0.047 |
| F.Fibroblast | 0 | 4228 | 3014 | 3.706 | 2.526 | 0.761 | 0.239 |
| F.Fibroblast | 0 | 5158 | 2426 | 5.537 | 4.140 | 0.848 | 0.152 |
| F.Fibroblast | 0 | 3920 | 2336 | 3.479 | 2.320 | 0.789 | 0.211 |
| F.Fibroblast | 0 | 3415 | 811 | 3.148 | 1.349 | 0.936 | 0.064 |
| F.Fibroblast | 0 | 4072 | 234 | 5.743 | 1.786 | 0.996 | 0.004 |
| F.Fibroblast | 0 | 4268 | 103 | 4.481 | 1.355 | 0.997 | 0.003 |
| F.Fibroblast | 0 | 2988 | 230 | 3.363 | 2.578 | 0.957 | 0.043 |
| F.Fibroblast | 0 | 3714 | 77 | 3.343 | 1.563 | 0.994 | 0.006 |
| F.Fibroblast | 0 | 3349 | 331 | 3.886 | 3.831 | 0.913 | 0.087 |
| F.Fibroblast | 0 | 3281 | 1352 | 3.054 | 1.920 | 0.842 | 0.158 |
| F.Fibroblast | 0 | 2747 | 228 | 3.114 | 2.952 | 0.931 | 0.069 |
| F.Fibroblast | 0 | 2564 | 75 | 2.996 | 2.370 | 0.981 | 0.019 |
| F.Fibroblast | 0 | 3283 | 345 | 4.326 | 3.405 | 0.947 | 0.053 |
| F.Fibroblast | 0 | 2891 | 416 | 3.084 | 3.061 | 0.876 | 0.124 |
| F.Fibroblast | 0 | 3402 | 334 | 3.328 | 2.179 | 0.958 | 0.042 |
| F.Fibroblast | 0 | 2975 | 375 | 3.145 | 3.035 | 0.895 | 0.105 |
| F.Fibroblast | 0 | 3329 | 204 | 3.271 | 2.174 | 0.972 | 0.028 |
| F.Fibroblast | 0 | 2585 | 54 | 3.301 | 2.573 | 0.988 | 0.012 |
| F.Fibroblast | 0 | 4613 | 988 | 4.226 | 2.277 | 0.947 | 0.053 |
| F.Fibroblast | 0 | 3032 | 169 | 3.280 | 2.058 | 0.977 | 0.023 |
| F.Fibroblast | 0 | 3516 | 1433 | 3.177 | 1.918 | 0.855 | 0.145 |
| F.Fibroblast | 0 | 2875 | 151 | 3.076 | 2.437 | 0.967 | 0.033 |
| F.Fibroblast | 0 | 4317 | 1602 | 3.686 | 2.347 | 0.872 | 0.128 |
| F.Fibroblast | 0 | 3857 | 273 | 3.650 | 2.531 | 0.968 | 0.032 |
| F.Fibroblast | 0 | 3417 | 364 | 3.186 | 2.451 | 0.940 | 0.060 |
| F.Fibroblast | 0 | 3733 | 634 | 4.046 | 2.123 | 0.957 | 0.043 |
| F.Fibroblast | 0 | 4160 | 540 | 3.881 | 4.055 | 0.872 | 0.128 |
| F.Fibroblast | 0 | 3510 | 61 | 3.541 | 2.220 | 0.993 | 0.007 |
| F.Fibroblast | 0 | 4636 | 2280 | 4.656 | 3.474 | 0.822 | 0.178 |
| F.Fibroblast | 0 | 2901 | 671 | 3.427 | 3.580 | 0.795 | 0.205 |
| F.Fibroblast | 0 | 4235 | 1927 | 3.787 | 2.310 | 0.859 | 0.141 |
| F.Fibroblast | 0 | 4918 | 2415 | 4.735 | 2.770 | 0.888 | 0.112 |
| F.Fibroblast | 0 | 3694 | 196 | 3.854 | 3.302 | 0.965 | 0.035 |
| F.Fibroblast | 0 | 2773 | 496 | 2.761 | 2.469 | 0.873 | 0.127 |
| F.Fibroblast | 0 | 4853 | 3142 | 4.876 | 3.992 | 0.740 | 0.260 |
| F.Glia | 0 | 348 | 875 | 5.078 | 1.800 | 0.794 | 0.206 |
| F.Glia | 0 | 412 | 3823 | 5.854 | 3.599 | 0.340 | 0.660 |
| F.Glia | 0 | 380 | 452 | 5.884 | 3.738 | 0.788 | 0.212 |
| F.Glia | 0 | 422 | 256 | 6.580 | 2.417 | 0.967 | 0.033 |
| F.Glia | 0 | 377 | 118 | 5.034 | 3.083 | 0.925 | 0.075 |
| F.Microvascular | 0 | 395 | 1567 | 5.613 | 2.622 | 0.667 | 0.333 |
| F.Microvascular | 0 | 403 | 2618 | 7.296 | 3.566 | 0.671 | 0.329 |
| F.Microvascular | 0 | 405 | 241 | 6.509 | 4.671 | 0.857 | 0.143 |
| F.Myofibroblasts | 0 | 594 | 552 | 6.751 | 3.937 | 0.883 | 0.117 |
| F.Myofibroblasts | 0 | 586 | 486 | 6.561 | 3.942 | 0.881 | 0.119 |
| F.Stromal | 0 | 4699 | 323 | 3.769 | 2.021 | 0.980 | 0.020 |
| F.Stromal | 0 | 3224 | 434 | 6.862 | 2.089 | 0.995 | 0.005 |
| F.Stromal | 0 | 3873 | 667 | 6.467 | 4.709 | 0.952 | 0.048 |
| F.Stromal | 0 | 2981 | 52 | 3.325 | 1.280 | 0.996 | 0.004 |
| F.Stromal | 0 | 4083 | 1908 | 3.402 | 2.549 | 0.794 | 0.206 |
| F.Stromal | 0 | 4219 | 125 | 4.112 | 1.466 | 0.995 | 0.005 |
| F.Stromal | 0 | 4206 | 92 | 4.244 | 1.369 | 0.997 | 0.003 |
| F.Stromal | 0 | 4456 | 52 | 3.803 | 1.491 | 0.998 | 0.002 |
| F.Stromal | 0 | 3138 | 223 | 4.997 | 3.309 | 0.978 | 0.022 |
| F.Stromal | 0 | 1341 | 40 | 4.975 | 2.629 | 0.994 | 0.006 |
| F.Stromal | 0 | 6062 | 5255 | 5.051 | 3.987 | 0.707 | 0.293 |
| F.Stromal | 0 | 3536 | 750 | 6.157 | 1.994 | 0.988 | 0.012 |
| F.Stromal | 0 | 2758 | 202 | 2.865 | 1.552 | 0.971 | 0.029 |
| F.Stromal | 0 | 3999 | 99 | 3.904 | 0.760 | 0.997 | 0.003 |
| F.Stromal | 0 | 4386 | 98 | 4.164 | 1.264 | 0.997 | 0.003 |
| F.Stromal | 0 | 4396 | 114 | 4.521 | 1.678 | 0.996 | 0.004 |
| F.Stromal | 0 | 3587 | 69 | 3.430 | 1.068 | 0.996 | 0.004 |
| F.Stromal | 0 | 4371 | 87 | 3.975 | 1.532 | 0.996 | 0.004 |
| F.Stromal | 0 | 3962 | 2146 | 4.285 | 2.821 | 0.836 | 0.164 |
| F.Stromal | 0 | 2689 | 96 | 3.499 | 1.539 | 0.991 | 0.009 |
| F.Stromal | 0 | 5009 | 1743 | 6.560 | 2.060 | 0.985 | 0.015 |
| F.Stromal | 0 | 3480 | 42 | 3.414 | 1.739 | 0.996 | 0.004 |
| F.Stromal | 0 | 3982 | 197 | 5.413 | 1.504 | 0.997 | 0.003 |
| F.Stromal | 0 | 4636 | 2608 | 3.343 | 2.255 | 0.791 | 0.209 |
| F.Stromal | 0 | 3294 | 56 | 3.917 | 1.115 | 0.998 | 0.002 |
| F.Stromal | 0 | 3587 | 86 | 3.720 | 1.424 | 0.995 | 0.005 |

TABLE 12-continued

Additional Cell Type Markers

| | | | | | | | |
|---|---|---|---|---|---|---|---|
| F.Stromal | 0 | 3544 | 121 | 3.603 | 0.980 | 0.994 | 0.006 |
| F.Stromal | 0 | 4983 | 2076 | 4.421 | 2.935 | 0.871 | 0.129 |
| F.Stromal | 0 | 5515 | 3101 | 4.283 | 2.766 | 0.836 | 0.164 |
| F.Stromal | 0 | 3508 | 1426 | 3.269 | 2.276 | 0.830 | 0.170 |
| F.Stromal | 0 | 6010 | 1863 | 4.863 | 2.442 | 0.945 | 0.055 |
| F.Stromal | 0 | 3172 | 92 | 3.461 | 1.376 | 0.993 | 0.007 |
| F.Stromal | 0 | 6201 | 540 | 6.457 | 1.796 | 0.997 | 0.003 |
| F.Stromal | 0 | 4943 | 2914 | 3.611 | 2.444 | 0.792 | 0.208 |
| F.Stromal | 0 | 5847 | 2307 | 5.474 | 3.855 | 0.886 | 0.114 |
| F.Stromal | 0 | 3341 | 737 | 3.113 | 1.004 | 0.951 | 0.049 |
| F.Stromal | 0 | 3754 | 257 | 5.716 | 1.713 | 0.996 | 0.004 |
| F.Stromal | 0 | 3881 | 115 | 4.406 | 1.112 | 0.997 | 0.003 |
| F.Stromal | 0 | 3445 | 45 | 3.320 | 1.498 | 0.996 | 0.004 |
| F.Stromal | 0 | 3697 | 112 | 3.933 | 1.190 | 0.995 | 0.005 |
| F.Stromal | 0 | 3599 | 159 | 4.283 | 2.060 | 0.991 | 0.009 |
| F.Stromal | 0 | 3125 | 275 | 3.367 | 1.958 | 0.968 | 0.032 |
| F.Stromal | 0 | 3323 | 277 | 3.311 | 1.743 | 0.973 | 0.027 |
| F.Stromal | 0 | 3562 | 99 | 3.208 | 1.151 | 0.993 | 0.007 |
| F.Stromal | 0 | 3247 | 133 | 3.161 | 2.329 | 0.978 | 0.022 |
| F.Stromal | 0 | 4497 | 900 | 4.201 | 1.891 | 0.961 | 0.039 |
| F.Stromal | 0 | 2947 | 118 | 3.219 | 1.504 | 0.988 | 0.012 |
| F.Stromal | 0 | 4640 | 1511 | 3.613 | 2.214 | 0.890 | 0.110 |
| F.Stromal | 0 | 3498 | 279 | 3.641 | 2.437 | 0.967 | 0.033 |
| F.Stromal | 0 | 3728 | 181 | 3.137 | 1.846 | 0.981 | 0.019 |
| F.Stromal | 0 | 3590 | 561 | 4.073 | 1.321 | 0.977 | 0.023 |
| F.Stromal | 0 | 5071 | 127 | 4.105 | 1.102 | 0.997 | 0.003 |
| F.Stromal | 0 | 3314 | 63 | 3.793 | 1.337 | 0.997 | 0.003 |
| F.Stromal | 0 | 3169 | 39 | 3.500 | 0.992 | 0.998 | 0.002 |
| F.Stromal | 0 | 5320 | 2150 | 4.570 | 3.528 | 0.836 | 0.164 |
| F.Stromal | 0 | 3633 | 337 | 3.716 | 2.230 | 0.968 | 0.032 |
| F.Stromal | 0 | 4059 | 1930 | 3.743 | 2.244 | 0.856 | 0.144 |
| F.Stromal | 0 | 4772 | 2353 | 4.676 | 2.747 | 0.885 | 0.115 |
| F.Stromal | 0 | 3627 | 105 | 3.869 | 1.411 | 0.995 | 0.005 |
| F.Stromal | 0 | 3246 | 314 | 2.721 | 2.032 | 0.943 | 0.057 |
| F.Stromal | 0 | 5801 | 3009 | 4.853 | 3.850 | 0.794 | 0.206 |
| F.Villus | 0 | 1118 | 113 | 3.482 | 3.031 | 0.931 | 0.069 |
| F.Villus | 0 | 1755 | 429 | 3.858 | 2.664 | 0.903 | 0.097 |
| F.Villus | 0 | 1620 | 749 | 3.772 | 4.170 | 0.621 | 0.379 |
| F.Villus | 0 | 1785 | 760 | 3.998 | 3.616 | 0.754 | 0.246 |
| F.Villus | 0 | 1634 | 619 | 3.845 | 3.580 | 0.760 | 0.240 |
| F.Villus | 0 | 1701 | 774 | 3.820 | 4.191 | 0.630 | 0.370 |
| F.Villus | 0 | 1799 | 792 | 4.333 | 4.445 | 0.678 | 0.322 |
| F.Villus | 0 | 1785 | 592 | 3.789 | 3.151 | 0.824 | 0.176 |
| F.Villus | 0 | 1952 | 738 | 4.298 | 3.740 | 0.796 | 0.204 |
| F.Villus | 0 | 2185 | 2158 | 7.330 | 4.679 | 0.864 | 0.136 |
| F.Villus | 0 | 1641 | 565 | 3.540 | 3.345 | 0.769 | 0.231 |
| F.Villus | 0 | 1599 | 390 | 4.467 | 2.254 | 0.950 | 0.050 |
| F.Villus | 0 | 1319 | 208 | 3.234 | 2.430 | 0.917 | 0.083 |
| F.Villus | 0 | 1354 | 66 | 3.310 | 2.408 | 0.975 | 0.025 |
| F.Villus | 0 | 1575 | 269 | 3.591 | 1.921 | 0.949 | 0.051 |
| F.Villus | 0 | 1792 | 403 | 4.335 | 2.595 | 0.937 | 0.063 |
| F.Villus | 0 | 1669 | 662 | 3.683 | 3.272 | 0.770 | 0.230 |
| F.Villus | 0 | 1624 | 1098 | 3.742 | 2.252 | 0.806 | 0.194 |
| F.Villus | 0 | 2046 | 2669 | 4.561 | 3.963 | 0.537 | 0.463 |
| F.Villus | 0 | 1420 | 317 | 4.194 | 3.145 | 0.903 | 0.097 |
| F.Villus | 0 | 2089 | 1461 | 5.894 | 6.223 | 0.532 | 0.468 |
| F.Villus | 0 | 2165 | 2685 | 5.737 | 4.614 | 0.637 | 0.363 |
| F.Villus | 0 | 1608 | 676 | 3.810 | 4.416 | 0.610 | 0.390 |
| F.Villus | 0 | 1738 | 548 | 3.702 | 3.101 | 0.828 | 0.172 |
| F.Villus | 0 | 1617 | 2123 | 3.864 | 2.021 | 0.732 | 0.268 |
| F.Villus | 0 | 1545 | 159 | 3.557 | 2.182 | 0.962 | 0.038 |
| F.Villus | 0 | 1979 | 606 | 5.011 | 3.416 | 0.908 | 0.092 |
| F.Villus | 0 | 1771 | 333 | 4.989 | 3.348 | 0.943 | 0.057 |
| F.Villus | 0 | 1988 | 1564 | 4.363 | 3.326 | 0.723 | 0.277 |
| F.Villus | 0 | 1508 | 496 | 3.401 | 2.790 | 0.823 | 0.177 |
| F.Villus | 0 | 1642 | 703 | 3.859 | 3.280 | 0.777 | 0.223 |
| F.Villus | 0 | 1738 | 991 | 3.973 | 4.056 | 0.624 | 0.376 |
| F.Villus | 0 | 1939 | 2612 | 4.926 | 3.772 | 0.623 | 0.377 |
| F.Villus | 0 | 2050 | 2924 | 4.861 | 3.433 | 0.654 | 0.346 |
| F.Villus | 0 | 1657 | 632 | 3.869 | 3.723 | 0.744 | 0.256 |
| F.Villus | 0 | 1203 | 24 | 3.408 | 2.581 | 0.989 | 0.011 |
| F.Villus_1 | 0 | 982 | 2294 | 7.382 | 5.226 | 0.656 | 0.344 |
| F.Villus_1 | 0 | 836 | 564 | 4.269 | 3.244 | 0.751 | 0.249 |
| F.Villus_1 | 0 | 886 | 791 | 4.923 | 3.822 | 0.706 | 0.294 |
| F.Villus_1 | 0 | 858 | 467 | 5.104 | 3.865 | 0.813 | 0.187 |
| F.Villus_2 | 0 | 969 | 549 | 3.899 | 2.999 | 0.767 | 0.233 |
| F.Villus_2 | 0 | 1084 | 884 | 4.389 | 3.824 | 0.645 | 0.355 |
| F.Villus_2 | 0 | 1203 | 2333 | 7.286 | 5.180 | 0.690 | 0.310 |

TABLE 12-continued

| Additional Cell Type Markers | | | | | | | |
|---|---|---|---|---|---|---|---|
| | F.Villus_2 | 0 | 884 | 511 | 4.521 | 3.079 | 0.825 | 0.175 |
| | F.Villus_2 | 0 | 864 | 374 | 3.665 | 2.638 | 0.825 | 0.175 |
| | F.Villus_2 | 0 | 956 | 509 | 4.390 | 3.149 | 0.816 | 0.184 |
| | F.Villus_2 | 0 | 947 | 645 | 3.695 | 3.037 | 0.698 | 0.302 |
| | F.Villus_2 | 0 | 813 | 275 | 3.551 | 2.916 | 0.821 | 0.179 |
| | F.Villus_2 | 0 | 1093 | 757 | 5.078 | 3.833 | 0.774 | 0.226 |
| | F.Villus_2 | 0 | 1105 | 1727 | 4.490 | 3.435 | 0.571 | 0.429 |
| | I.Immune | 0 | 6020 | 912 | 4.060 | 2.685 | 0.945 | 0.055 |
| | I.Immune | 0 | 2923 | 198 | 5.993 | 1.342 | 0.997 | 0.003 |
| | I.Immune | 0 | 3578 | 85 | 3.206 | 1.336 | 0.994 | 0.006 |
| | I.Immune | 0 | 3612 | 91 | 4.454 | 1.223 | 0.997 | 0.003 |
| | I.Immune | 0 | 3063 | 50 | 3.608 | 1.035 | 0.997 | 0.003 |
| | I.Immune | 0 | 5000 | 160 | 4.518 | 1.339 | 0.996 | 0.004 |
| | I.Immune | 0 | 3952 | 245 | 4.383 | 1.564 | 0.991 | 0.009 |
| | I.Immune | 0 | 2831 | 115 | 4.230 | 1.067 | 0.995 | 0.005 |
| | I.Immune | 0 | 4900 | 234 | 3.876 | 1.264 | 0.992 | 0.008 |
| | I.Immune | 0 | 1786 | 6623 | 5.707 | 4.195 | 0.435 | 0.565 |
| | I.Immune | 0 | 6213 | 4853 | 4.296 | 3.229 | 0.728 | 0.272 |
| | I.Immune | 0 | 3302 | 276 | 3.332 | 1.746 | 0.973 | 0.027 |
| | I.Immune | 0 | 3552 | 79 | 3.464 | 0.713 | 0.997 | 0.003 |
| | I.Immune | 0 | 3745 | 128 | 3.391 | 1.254 | 0.992 | 0.008 |
| | I.Immune | 0 | 3265 | 181 | 4.581 | 1.703 | 0.993 | 0.007 |
| | I.Immune | 0 | 4538 | 170 | 3.795 | 0.812 | 0.995 | 0.005 |
| | I.Immune | 0 | 3824 | 294 | 3.168 | 0.746 | 0.986 | 0.014 |
| | I.Immune | 0 | 4472 | 331 | 4.275 | 2.045 | 0.984 | 0.016 |
| | I.Immune | 0 | 5777 | 805 | 4.342 | 3.298 | 0.937 | 0.063 |
| | I.Immune | 0 | 3800 | 145 | 4.546 | 1.690 | 0.995 | 0.005 |
| | I.Lymphoid | 0 | 6125 | 1705 | 4.081 | 3.443 | 0.848 | 0.152 |
| | I.Lymphoid | 0 | 3441 | 211 | 5.946 | 1.275 | 0.998 | 0.002 |
| | I.Lymphoid | 0 | 3474 | 55 | 3.773 | 1.342 | 0.997 | 0.003 |
| | I.Lymphoid | 0 | 4459 | 84 | 4.452 | 1.570 | 0.997 | 0.003 |
| | I.Lymphoid | 0 | 3794 | 36 | 3.590 | 1.424 | 0.998 | 0.002 |
| | I.Lymphoid | 0 | 5543 | 633 | 4.577 | 3.224 | 0.957 | 0.043 |
| | I.Lymphoid | 0 | 4340 | 623 | 4.262 | 4.865 | 0.821 | 0.179 |
| | I.Lymphoid | 0 | 3425 | 123 | 4.186 | 1.085 | 0.996 | 0.004 |
| | I.Lymphoid | 0 | 5360 | 766 | 3.943 | 2.738 | 0.942 | 0.058 |
| | I.Lymphoid | 0 | 3266 | 302 | 2.824 | 1.917 | 0.953 | 0.047 |
| | I.Lymphoid | 0 | 3701 | 469 | 3.393 | 1.843 | 0.959 | 0.041 |
| | I.Lymphoid | 0 | 5118 | 2541 | 5.374 | 3.490 | 0.881 | 0.119 |
| | I.Lymphoid | 0 | 3944 | 330 | 4.659 | 3.021 | 0.974 | 0.026 |
| | I.Lymphoid | 0 | 5618 | 178 | 3.758 | 1.359 | 0.994 | 0.006 |
| | I.Lymphoid | 0 | 4248 | 586 | 3.189 | 2.168 | 0.936 | 0.064 |
| | I.Lymphoid | 0 | 4692 | 364 | 4.507 | 2.525 | 0.981 | 0.019 |
| | I.Lymphoid | 0 | 4741 | 147 | 4.535 | 1.971 | 0.995 | 0.005 |
| | M.CD69pos Mast | 0 | 1123 | 6490 | 6.312 | 4.300 | 0.411 | 0.589 |
| | M.CD69pos Mast | 0 | 993 | 3547 | 5.806 | 3.295 | 0.615 | 0.385 |
| | M.CD69pos Mast | 0 | 813 | 2506 | 4.718 | 2.379 | 0.621 | 0.379 |
| | M.CD69pos Mast | 0 | 1124 | 144 | 9.027 | 7.355 | 0.961 | 0.039 |
| | M.CD69pos Mast | 0 | 835 | 630 | 4.462 | 1.515 | 0.911 | 0.089 |
| | M.DCs | 0 | 751 | 463 | 4.164 | 4.386 | 0.582 | 0.418 |
| | M.DCs | 0 | 794 | 3651 | 8.113 | 5.410 | 0.586 | 0.414 |
| | M.DCs | 0 | 690 | 242 | 3.712 | 2.844 | 0.839 | 0.161 |
| | M.DCs | 0 | 792 | 4441 | 7.237 | 4.407 | 0.559 | 0.441 |
| | M.DCs | 0 | 759 | 1369 | 3.847 | 2.861 | 0.523 | 0.477 |
| | M.DCs | 0 | 705 | 637 | 3.162 | 3.124 | 0.532 | 0.468 |
| | M.DCs | 0 | 793 | 1729 | 6.636 | 4.414 | 0.681 | 0.319 |
| | M.DCs | 0 | 792 | 1535 | 6.940 | 4.638 | 0.718 | 0.282 |
| | M.DCs | 0 | 785 | 775 | 5.480 | 4.250 | 0.704 | 0.296 |
| | M.DCs | 0 | 781 | 1025 | 4.857 | 3.358 | 0.683 | 0.317 |
| | M.DCs | 0 | 794 | 1950 | 7.880 | 5.598 | 0.665 | 0.335 |
| | M.DCs | 0 | 794 | 2305 | 6.995 | 4.605 | 0.644 | 0.356 |
| | M.DCs | 0 | 727 | 1079 | 5.291 | 3.724 | 0.666 | 0.334 |
| | M.DCs | 0 | 713 | 452 | 3.452 | 3.275 | 0.641 | 0.359 |
| | M.DCs | 0 | 761 | 779 | 6.025 | 4.610 | 0.723 | 0.277 |
| | M.Macrophages | 0 | 1259 | 981 | 4.367 | 2.516 | 0.822 | 0.178 |
| | M.Macrophages | 0 | 1604 | 315 | 4.880 | 3.984 | 0.905 | 0.095 |
| | M.Macrophages | 0 | 1604 | 193 | 6.399 | 4.403 | 0.971 | 0.029 |
| | M.Macrophages | 0 | 1551 | 182 | 6.180 | 4.112 | 0.973 | 0.027 |
| | M.Macrophages | 0 | 1591 | 168 | 5.922 | 4.068 | 0.972 | 0.028 |
| | M.Macrophages | 0 | 1779 | 3605 | 7.519 | 5.211 | 0.710 | 0.290 |
| | M.Macrophages | 0 | 1706 | 4504 | 6.494 | 4.310 | 0.632 | 0.368 |
| | M.Macrophages | 0 | 1350 | 2231 | 4.318 | 2.083 | 0.740 | 0.260 |
| | M.Macrophages | 0 | 1380 | 2970 | 4.750 | 2.506 | 0.688 | 0.312 |
| | M.Macrophages | 0 | 1138 | 1656 | 3.421 | 1.644 | 0.702 | 0.298 |
| | M.Macrophages | 0 | 1616 | 5507 | 5.357 | 3.728 | 0.476 | 0.524 |
| | M.Macrophages | 0 | 1356 | 167 | 4.750 | 3.405 | 0.954 | 0.046 |
| | M.Macrophages | 0 | 1529 | 569 | 4.931 | 4.204 | 0.816 | 0.184 |
| | M.Macrophages | 0 | 1354 | 3286 | 4.180 | 2.604 | 0.551 | 0.449 |

TABLE 12-continued

Additional Cell Type Markers

| | | | | | | | |
|---|---|---|---|---|---|---|---|
| M.Macrophages | | 0 | 1792 | 7034 | 9.465 | 5.572 | 0.791 | 0.209 |
| M.Macrophages | | 0 | 1114 | 1352 | 4.300 | 1.573 | 0.845 | 0.155 |
| M.Macrophages | | 0 | 1628 | 3460 | 4.771 | 2.665 | 0.669 | 0.331 |
| M.Macrophages | | 0 | 1398 | 1302 | 4.047 | 2.615 | 0.743 | 0.257 |
| M.Macrophages | | 0 | 1249 | 553 | 3.713 | 2.569 | 0.833 | 0.167 |
| M.Macrophages | | 0 | 1696 | 1686 | 6.184 | 4.077 | 0.813 | 0.187 |
| M.Macrophages | | 0 | 1741 | 1435 | 6.354 | 4.449 | 0.820 | 0.180 |
| M.Macrophages | | 0 | 1587 | 646 | 5.108 | 3.988 | 0.842 | 0.158 |
| M.Macrophages | | 0 | 1440 | 922 | 4.304 | 3.316 | 0.756 | 0.244 |
| M.Macrophages | | 0 | 1770 | 1877 | 7.374 | 5.256 | 0.804 | 0.196 |
| M.Macrophages | | 0 | 1741 | 2216 | 6.563 | 4.333 | 0.787 | 0.213 |
| M.Macrophages | | 0 | 1331 | 1031 | 5.158 | 3.414 | 0.812 | 0.188 |
| M.Macrophages | | 0 | 1000 | 96 | 3.324 | 2.648 | 0.943 | 0.057 |
| M.Macrophages | | 0 | 1129 | 1343 | 3.886 | 1.713 | 0.791 | 0.209 |
| M.Macrophages | | 0 | 1271 | 364 | 3.376 | 3.304 | 0.786 | 0.214 |
| M.Macrophages | | 0 | 1511 | 670 | 5.912 | 4.114 | 0.887 | 0.113 |
| M.Macrophages | | 0 | 890 | 68 | 2.914 | 1.915 | 0.963 | 0.037 |
| M.Macrophages | | 0 | 1342 | 175 | 4.006 | 3.216 | 0.930 | 0.070 |
| M.Macrophages | | 0 | 1099 | 121 | 3.368 | 2.594 | 0.940 | 0.060 |
| M.Macrophages | | 0 | 1572 | 3624 | 4.921 | 2.750 | 0.661 | 0.339 |
| M.Macrophages | | 0 | 1546 | 3595 | 5.063 | 2.492 | 0.719 | 0.281 |
| M.Macrophages | | 0 | 1008 | 1558 | 5.248 | 2.858 | 0.772 | 0.228 |
| M.Macrophages | | 0 | 1245 | 2803 | 3.727 | 2.193 | 0.563 | 0.437 |
| M.Macrophages | | 0 | 1527 | 4245 | 4.435 | 3.320 | 0.438 | 0.562 |
| M.Macrophages | | 0 | 1671 | 4532 | 5.541 | 3.360 | 0.626 | 0.374 |
| M.Macrophages | | 0 | 1471 | 2221 | 5.315 | 3.691 | 0.671 | 0.329 |
| M.Macrophages | | 0 | 898 | 90 | 2.765 | 1.742 | 0.953 | 0.047 |
| M.Macrophages | | 0 | 1801 | 7464 | 8.586 | 7.077 | 0.407 | 0.593 |
| M.Macrophages | | 0 | 1631 | 568 | 5.310 | 4.061 | 0.872 | 0.128 |
| M.Mast | | 0 | 892 | 2099 | 4.344 | 2.247 | 0.645 | 0.355 |
| M.Mast | | 0 | 1265 | 6569 | 6.234 | 4.296 | 0.425 | 0.575 |
| M.Mast | | 0 | 1076 | 3546 | 5.738 | 3.286 | 0.624 | 0.376 |
| M.Mast | | 0 | 869 | 2424 | 4.659 | 2.349 | 0.640 | 0.360 |
| M.Mast | | 0 | 1269 | 116 | 9.035 | 3.446 | 0.998 | 0.002 |
| M.Mast | | 0 | 965 | 593 | 4.446 | 0.972 | 0.948 | 0.052 |
| M.Monocytes | | 0 | 1897 | 874 | 4.019 | 2.490 | 0.862 | 0.138 |
| M.Monocytes | | 0 | 2857 | 156 | 4.719 | 2.195 | 0.991 | 0.009 |
| M.Monocytes | | 0 | 1815 | 508 | 2.944 | 3.082 | 0.764 | 0.236 |
| M.Monocytes | | 0 | 2307 | 114 | 6.165 | 2.078 | 0.997 | 0.003 |
| M.Monocytes | | 0 | 2133 | 103 | 5.989 | 2.142 | 0.997 | 0.003 |
| M.Monocytes | | 0 | 2209 | 95 | 5.739 | 2.159 | 0.996 | 0.004 |
| M.Monocytes | | 0 | 1463 | 275 | 2.488 | 2.625 | 0.829 | 0.171 |
| M.Monocytes | | 0 | 3091 | 3493 | 7.652 | 4.889 | 0.857 | 0.143 |
| M.Monocytes | | 0 | 2424 | 2140 | 3.732 | 2.793 | 0.685 | 0.315 |
| M.Monocytes | | 0 | 1908 | 80 | 3.354 | 1.253 | 0.990 | 0.010 |
| M.Monocytes | | 0 | 3008 | 4313 | 6.722 | 4.040 | 0.817 | 0.183 |
| M.Monocytes | | 0 | 2157 | 2153 | 3.992 | 1.897 | 0.811 | 0.189 |
| M.Monocytes | | 0 | 2909 | 5455 | 5.153 | 3.680 | 0.597 | 0.403 |
| M.Monocytes | | 0 | 2106 | 64 | 4.561 | 1.775 | 0.996 | 0.004 |
| M.Monocytes | | 0 | 1712 | 141 | 2.960 | 2.399 | 0.947 | 0.053 |
| M.Monocytes | | 0 | 2662 | 401 | 4.673 | 4.038 | 0.912 | 0.088 |
| M.Monocytes | | 0 | 1818 | 292 | 2.889 | 2.044 | 0.918 | 0.082 |
| M.Monocytes | | 0 | 3110 | 7054 | 9.015 | 5.357 | 0.848 | 0.152 |
| M.Monocytes | | 0 | 2856 | 3292 | 4.577 | 2.548 | 0.780 | 0.220 |
| M.Monocytes | | 0 | 2563 | 1179 | 3.945 | 2.455 | 0.859 | 0.141 |
| M.Monocytes | | 0 | 2288 | 465 | 3.482 | 2.480 | 0.908 | 0.092 |
| M.Monocytes | | 0 | 2982 | 1495 | 6.259 | 3.531 | 0.930 | 0.070 |
| M.Monocytes | | 0 | 3026 | 1289 | 6.486 | 3.739 | 0.940 | 0.060 |
| M.Monocytes | | 0 | 2772 | 544 | 5.172 | 3.422 | 0.945 | 0.055 |
| M.Monocytes | | 0 | 1395 | 205 | 3.329 | 2.362 | 0.930 | 0.070 |
| M.Monocytes | | 0 | 2620 | 767 | 4.448 | 2.817 | 0.914 | 0.086 |
| M.Monocytes | | 0 | 1336 | 110 | 2.684 | 2.345 | 0.939 | 0.061 |
| M.Monocytes | | 0 | 3082 | 1688 | 7.493 | 4.610 | 0.931 | 0.069 |
| M.Monocytes | | 0 | 3046 | 2056 | 6.647 | 3.831 | 0.913 | 0.087 |
| M.Monocytes | | 0 | 2468 | 850 | 5.151 | 2.923 | 0.932 | 0.068 |
| M.Monocytes | | 0 | 1602 | 70 | 4.341 | 1.876 | 0.992 | 0.008 |
| M.Monocytes | | 0 | 1725 | 547 | 2.594 | 2.639 | 0.754 | 0.246 |
| M.Monocytes | | 0 | 2208 | 1427 | 3.181 | 3.343 | 0.580 | 0.420 |
| M.Monocytes | | 0 | 2760 | 2651 | 5.009 | 4.777 | 0.550 | 0.450 |
| M.Monocytes | | 0 | 2437 | 224 | 3.487 | 2.716 | 0.949 | 0.051 |
| M.Monocytes | | 0 | 2709 | 513 | 5.972 | 2.582 | 0.982 | 0.018 |
| M.Monocytes | | 0 | 2287 | 51 | 3.900 | 2.227 | 0.993 | 0.007 |
| M.Monocytes | | 0 | 1745 | 54 | 3.150 | 2.092 | 0.985 | 0.015 |
| M.Monocytes | | 0 | 2775 | 3440 | 4.601 | 2.716 | 0.749 | 0.251 |
| M.Monocytes | | 0 | 1744 | 855 | 3.547 | 2.139 | 0.844 | 0.156 |
| M.Monocytes | | 0 | 2672 | 3468 | 4.656 | 2.351 | 0.792 | 0.208 |
| M.Monocytes | | 0 | 2279 | 1706 | 3.213 | 2.735 | 0.651 | 0.349 |
| M.Monocytes | | 0 | 1651 | 203 | 2.735 | 1.357 | 0.955 | 0.045 |

TABLE 12-continued

Additional Cell Type Markers

| | | | | | | | |
|---|---|---|---|---|---|---|---|
| M.Monocytes | 0 | 2301 | 2679 | 3.514 | 2.173 | 0.685 | 0.315 |
| M.Monocytes | 0 | 2739 | 4164 | 4.264 | 3.231 | 0.574 | 0.426 |
| M.Monocytes | 0 | 2962 | 4464 | 5.344 | 3.186 | 0.748 | 0.252 |
| M.Monocytes | 0 | 2057 | 196 | 2.895 | 1.824 | 0.957 | 0.043 |
| M.Monocytes | 0 | 3122 | 7474 | 8.491 | 7.064 | 0.529 | 0.471 |
| M.Monocytes | 0 | 2380 | 2020 | 3.528 | 2.135 | 0.756 | 0.244 |
| M.Monocytes | 0 | 2822 | 362 | 5.067 | 3.625 | 0.955 | 0.045 |
| M.Myeloid | 0 | 2919 | 140 | 4.702 | 2.218 | 0.992 | 0.008 |
| M.Myeloid | 0 | 2321 | 124 | 6.159 | 1.666 | 0.998 | 0.002 |
| M.Myeloid | 0 | 2150 | 125 | 5.980 | 1.824 | 0.997 | 0.003 |
| M.Myeloid | 0 | 2223 | 93 | 5.732 | 1.822 | 0.997 | 0.003 |
| M.Myeloid | 0 | 3288 | 3628 | 7.571 | 4.821 | 0.859 | 0.141 |
| M.Myeloid | 0 | 3580 | 4368 | 6.509 | 4.044 | 0.819 | 0.181 |
| M.Myeloid | 0 | 3625 | 5451 | 4.985 | 3.677 | 0.622 | 0.378 |
| M.Myeloid | 0 | 2111 | 81 | 4.559 | 1.796 | 0.994 | 0.006 |
| M.Myeloid | 0 | 3593 | 235 | 4.604 | 3.771 | 0.965 | 0.035 |
| M.Myeloid | 0 | 4393 | 7356 | 7.972 | 6.710 | 0.589 | 0.411 |
| M.Myeloid | 0 | 4387 | 7036 | 8.638 | 5.278 | 0.865 | 0.135 |
| M.Myeloid | 0 | 2545 | 1392 | 3.591 | 1.731 | 0.869 | 0.131 |
| M.Myeloid | 0 | 3403 | 3404 | 4.467 | 2.435 | 0.804 | 0.196 |
| M.Myeloid | 0 | 2644 | 1244 | 3.926 | 2.383 | 0.861 | 0.139 |
| M.Myeloid | 0 | 2300 | 439 | 3.484 | 2.295 | 0.923 | 0.077 |
| M.Myeloid | 0 | 3135 | 1526 | 6.198 | 3.482 | 0.931 | 0.069 |
| M.Myeloid | 0 | 3111 | 1304 | 6.454 | 3.554 | 0.947 | 0.053 |
| M.Myeloid | 0 | 2798 | 529 | 5.165 | 3.338 | 0.949 | 0.051 |
| M.Myeloid | 0 | 1400 | 208 | 3.331 | 2.234 | 0.935 | 0.065 |
| M.Myeloid | 0 | 2648 | 787 | 4.439 | 2.881 | 0.908 | 0.092 |
| M.Myeloid | 0 | 3181 | 1708 | 7.454 | 4.571 | 0.932 | 0.068 |
| M.Myeloid | 0 | 3202 | 2024 | 6.585 | 3.810 | 0.915 | 0.085 |
| M.Myeloid | 0 | 2535 | 866 | 5.121 | 2.926 | 0.931 | 0.069 |
| M.Myeloid | 0 | 2494 | 230 | 3.483 | 3.035 | 0.937 | 0.063 |
| M.Myeloid | 0 | 2749 | 527 | 5.960 | 2.455 | 0.983 | 0.017 |
| M.Myeloid | 0 | 2300 | 48 | 3.900 | 1.788 | 0.995 | 0.005 |
| M.Myeloid | 0 | 3387 | 3537 | 4.481 | 2.615 | 0.777 | 0.223 |
| M.Myeloid | 0 | 3206 | 3517 | 4.532 | 2.297 | 0.811 | 0.189 |
| M.Myeloid | 0 | 3391 | 4180 | 4.220 | 3.215 | 0.620 | 0.380 |
| M.Myeloid | 0 | 3745 | 4510 | 5.191 | 3.125 | 0.777 | 0.223 |
| M.Myeloid | 0 | 3737 | 2618 | 4.753 | 4.074 | 0.696 | 0.304 |
| M.Myeloid | 0 | 4407 | 7468 | 8.202 | 7.029 | 0.571 | 0.429 |
| M.Myeloid | 0 | 3501 | 255 | 4.897 | 3.573 | 0.972 | 0.028 |
| M.Tissue_DCs | 0 | 643 | 481 | 4.281 | 4.460 | 0.541 | 0.459 |
| M.Tissue_DCs | 0 | 672 | 3634 | 8.013 | 5.364 | 0.537 | 0.463 |
| M.Tissue_DCs | 0 | 578 | 146 | 3.803 | 3.080 | 0.867 | 0.133 |
| M.Tissue_DCs | 0 | 670 | 4472 | 7.124 | 4.451 | 0.489 | 0.511 |
| M.Tissue_DCs | 0 | 643 | 1368 | 3.884 | 2.767 | 0.505 | 0.495 |
| M.Tissue_DCs | 0 | 671 | 1759 | 6.577 | 4.420 | 0.630 | 0.370 |
| M.Tissue_DCs | 0 | 670 | 1484 | 6.863 | 4.773 | 0.658 | 0.342 |
| M.Tissue_DCs | 0 | 663 | 738 | 5.457 | 4.290 | 0.669 | 0.331 |
| M.Tissue_DCs | 0 | 662 | 1000 | 4.815 | 3.367 | 0.644 | 0.356 |
| M.Tissue_DCs | 0 | 672 | 1937 | 7.874 | 5.574 | 0.631 | 0.369 |
| M.Tissue_DCs | 0 | 672 | 2279 | 6.984 | 4.587 | 0.608 | 0.392 |
| M.Tissue_DCs | 0 | 622 | 462 | 3.581 | 3.366 | 0.610 | 0.390 |
| M.Tissue_DCs | 0 | 640 | 782 | 6.080 | 4.547 | 0.703 | 0.297 |
| T.CD4 | 0 | 5187 | 2552 | 4.312 | 3.578 | 0.772 | 0.228 |
| T.CD4 | 0 | 6115 | 7425 | 7.908 | 6.955 | 0.615 | 0.385 |
| T.CD4 | 0 | 5262 | 4406 | 4.793 | 3.354 | 0.764 | 0.236 |
| T.CD4 | 0 | 4067 | 522 | 3.823 | 3.702 | 0.894 | 0.106 |
| T.CD4 | 0 | 5156 | 643 | 4.361 | 4.376 | 0.888 | 0.112 |
| T.CD4 | 0 | 4233 | 549 | 3.570 | 3.491 | 0.891 | 0.109 |
| T.CD4 | 0 | 5137 | 1523 | 4.538 | 4.307 | 0.798 | 0.202 |
| T.CD4 | 0 | 6074 | 7227 | 6.822 | 5.836 | 0.625 | 0.375 |
| T.CD4 | 0 | 5533 | 2804 | 5.278 | 4.263 | 0.800 | 0.200 |
| T.CD4 | 0 | 4588 | 886 | 4.766 | 4.230 | 0.883 | 0.117 |
| T.CD4 | 0 | 6079 | 7288 | 7.129 | 6.260 | 0.604 | 0.396 |
| T.CD4 | 0 | 5989 | 6942 | 6.135 | 5.158 | 0.629 | 0.371 |
| T.CD4 | 0 | 6061 | 7192 | 6.695 | 5.717 | 0.624 | 0.376 |
| T.CD4 | 0 | 6034 | 7017 | 6.324 | 5.430 | 0.615 | 0.385 |
| T.CD4 | 0 | 5855 | 6596 | 5.349 | 4.369 | 0.637 | 0.363 |
| T.CD4 | 0 | 6030 | 7028 | 6.381 | 5.184 | 0.663 | 0.337 |
| T.CD4 | 0 | 5927 | 6769 | 5.913 | 4.944 | 0.631 | 0.369 |
| T.CD4 | 0 | 5988 | 6999 | 6.052 | 5.244 | 0.600 | 0.400 |
| T.CD4 | 0 | 4285 | 3675 | 3.757 | 2.468 | 0.740 | 0.260 |
| T.CD4 | 0 | 6122 | 7459 | 7.932 | 7.047 | 0.602 | 0.398 |
| T.CD4 | 0 | 5232 | 948 | 4.671 | 3.876 | 0.905 | 0.095 |
| T.CD4 | 0 | 5075 | 837 | 4.719 | 4.066 | 0.905 | 0.095 |
| T.CD8 | 0 | 4141 | 7129 | 6.459 | 5.447 | 0.540 | 0.460 |
| T.CD8 | 0 | 3679 | 2662 | 4.342 | 3.756 | 0.675 | 0.325 |
| T.CD8 | 0 | 4167 | 7446 | 8.044 | 7.029 | 0.531 | 0.469 |

TABLE 12-continued

Additional Cell Type Markers

| | | | | | | | |
|---|---|---|---|---|---|---|---|
| T.CD8 | 0 | 3896 | 699 | 6.285 | 4.684 | 0.944 | 0.056 |
| T.CD8 | 0 | 3622 | 1088 | 4.617 | 4.237 | 0.812 | 0.188 |
| T.CD8 | 0 | 3183 | 896 | 3.706 | 3.503 | 0.804 | 0.196 |
| T.CD8 | 0 | 3668 | 1773 | 4.811 | 4.187 | 0.761 | 0.239 |
| T.CD8 | 0 | 3012 | 783 | 4.335 | 3.569 | 0.867 | 0.133 |
| T.CD8 | 0 | 3458 | 1801 | 4.144 | 3.610 | 0.735 | 0.265 |
| T.CD8 | 0 | 2775 | 1166 | 3.555 | 2.976 | 0.780 | 0.220 |
| T.CD8 | 0 | 2956 | 344 | 5.852 | 4.682 | 0.951 | 0.049 |
| T.CD8 | 0 | 3117 | 1132 | 3.782 | 3.025 | 0.823 | 0.177 |
| T.CD8 | 0 | 2194 | 318 | 3.874 | 3.303 | 0.911 | 0.089 |
| T.CD8 | 0 | 4007 | 3265 | 5.519 | 4.367 | 0.732 | 0.268 |
| T.CD8 | 0 | 3166 | 315 | 4.585 | 4.231 | 0.928 | 0.072 |
| T.CD8 | 0 | 3384 | 1619 | 4.095 | 3.450 | 0.766 | 0.234 |
| T.CD8 | 0 | 3856 | 5624 | 4.736 | 3.749 | 0.576 | 0.424 |
| T.CD8 | 0 | 4168 | 7463 | 8.386 | 7.040 | 0.587 | 0.413 |
| T.CD8 | 0 | 3505 | 1405 | 4.545 | 4.333 | 0.743 | 0.257 |
| T.CD8 | 0 | 3498 | 1277 | 4.549 | 4.496 | 0.740 | 0.260 |
| T.CD8_IELs | 0 | 1582 | 1004 | 6.549 | 5.273 | 0.792 | 0.208 |
| T.CD8_IELs | 0 | 1364 | 1360 | 4.702 | 4.376 | 0.557 | 0.443 |
| T.CD8_IELs | 0 | 1486 | 1995 | 4.865 | 4.341 | 0.517 | 0.483 |
| T.CD8_IELs | 0 | 1414 | 1003 | 4.790 | 3.630 | 0.759 | 0.241 |
| T.CD8_IELs | 0 | 1211 | 424 | 4.054 | 3.412 | 0.817 | 0.183 |
| T.CD8_IELs | 0 | 1552 | 3461 | 5.772 | 4.518 | 0.517 | 0.483 |
| T.CD8_IELs | 0 | 1311 | 593 | 4.406 | 4.614 | 0.657 | 0.343 |
| T.CD8 LP | 0 | 1849 | 931 | 6.222 | 5.372 | 0.782 | 0.218 |
| T.CD8 LP | 0 | 1523 | 544 | 4.793 | 4.225 | 0.806 | 0.194 |
| T.Tcells | 0 | 7176 | 7092 | 6.254 | 5.363 | 0.652 | 0.348 |
| T.Tcells | 0 | 6214 | 2208 | 4.290 | 3.309 | 0.847 | 0.153 |
| T.Tcells | 0 | 7263 | 7424 | 7.915 | 6.800 | 0.679 | 0.321 |
| T.Tcells | 0 | 6125 | 4331 | 4.691 | 3.042 | 0.816 | 0.184 |
| T.Tcells | 0 | 4168 | 350 | 5.968 | 3.879 | 0.981 | 0.019 |
| T.Tcells | 0 | 4718 | 126 | 3.815 | 2.607 | 0.989 | 0.011 |
| T.Tcells | 0 | 6220 | 143 | 4.461 | 1.922 | 0.996 | 0.004 |
| T.Tcells | 0 | 5275 | 90 | 3.603 | 2.457 | 0.992 | 0.008 |
| T.Tcells | 0 | 6205 | 1100 | 4.606 | 3.906 | 0.902 | 0.098 |
| T.Tcells | 0 | 4463 | 217 | 4.085 | 3.492 | 0.969 | 0.031 |
| T.Tcells | 0 | 3661 | 2127 | 3.412 | 1.851 | 0.835 | 0.165 |
| T.Tcells | 0 | 5641 | 1278 | 4.004 | 3.324 | 0.876 | 0.124 |
| T.Tcells | 0 | 4420 | 669 | 3.464 | 2.212 | 0.940 | 0.060 |
| T.Tcells | 0 | 2751 | 189 | 5.826 | 4.113 | 0.979 | 0.021 |
| T.Tcells | 0 | 4351 | 749 | 3.584 | 2.617 | 0.919 | 0.081 |
| T.Tcells | 0 | 2136 | 218 | 3.775 | 3.224 | 0.935 | 0.065 |
| T.Tcells | 0 | 3819 | 1590 | 3.287 | 1.717 | 0.877 | 0.123 |
| T.Tcells | 0 | 6717 | 2386 | 5.388 | 3.569 | 0.909 | 0.091 |
| T.Tcells | 0 | 3982 | 177 | 3.294 | 2.299 | 0.978 | 0.022 |
| T.Tcells | 0 | 4454 | 687 | 4.631 | 4.205 | 0.897 | 0.103 |
| T.Tcells | 0 | 5665 | 5265 | 4.016 | 3.130 | 0.665 | 0.335 |
| T.Tcells | 0 | 2809 | 225 | 4.479 | 4.344 | 0.932 | 0.068 |
| T.Tcells | 0 | 5519 | 1057 | 3.917 | 2.940 | 0.911 | 0.089 |
| T.Tcells | 0 | 4119 | 1178 | 3.375 | 2.293 | 0.881 | 0.119 |
| T.Tcells | 0 | 7206 | 7197 | 6.564 | 5.647 | 0.654 | 0.346 |
| T.Tcells | 0 | 7191 | 7013 | 6.286 | 5.318 | 0.667 | 0.333 |
| T.Tcells | 0 | 7181 | 7033 | 6.297 | 5.052 | 0.708 | 0.292 |
| T.Tcells | 0 | 7057 | 6748 | 5.806 | 4.867 | 0.667 | 0.333 |
| T.Tcells | 0 | 6212 | 5466 | 4.504 | 3.586 | 0.682 | 0.318 |
| T.Tcells | 0 | 4941 | 3660 | 3.646 | 2.209 | 0.785 | 0.215 |
| T.Tcells | 0 | 7271 | 7444 | 8.103 | 6.826 | 0.703 | 0.297 |
| T.Tcells | 0 | 6163 | 451 | 4.592 | 2.553 | 0.983 | 0.017 |
| T.Tcells | 0 | 6049 | 358 | 4.642 | 2.673 | 0.985 | 0.015 |

TABLE 13

Inflamed vs Healthy Markers

| ident | gene | coefD | pvalD | coefC | pvalC | mastfc |
|---|---|---|---|---|---|---|
| B.Bcells | AC009501.4 | −0.840 | 3.95E−34 | 2.53E−01 | 2.55E−07 | −0.741 |
| B.Bcells | ACAP1 | 1.066 | 1.15E−42 | 6.23E−01 | 2.91E−34 | 0.707 |
| B.Bcells | ACP5 | 0.764 | 2.94E−22 | 8.02E−01 | 9.84E−33 | 0.540 |
| B.Bcells | ACTG1 | 0.518 | 8.84E−07 | 1.33E+00 | 2.04E−185 | 1.239 |
| B.Bcells | ACTR3 | 0.992 | 1.10E−43 | 6.71E−01 | 2.51E−48 | 0.544 |
| B.Bcells | ALOX5AP | 1.429 | 5.97E−60 | 4.36E−01 | 1.73E−10 | 1.430 |
| B.Bcells | ARHGDIB | 0.800 | 1.93E−23 | 8.96E−01 | 1.64E−90 | 1.398 |
| B.Bcells | ARPC1B | 0.824 | 2.50E−30 | 9.25E−01 | 1.70E−84 | 1.086 |
| B.Bcells | ARPC2 | 0.596 | 1.17E−08 | 9.73E−01 | 2.29E−138 | 0.656 |

TABLE 13-continued

| | Inflamed vs Healthy Markers | | | | | |
|---|---|---|---|---|---|---|
| B.Bcells | ARPC5 | 1.043 | 3.72E−46 | 7.81E−01 | 3.25E−61 | 0.815 |
| B.Bcells | ATP5E | 0.560 | 6.15E−08 | 7.70E−01 | 4.66E−104 | 0.767 |
| B.Bcells | BATF | 2.091 | 1.33E−43 | 5.98E−01 | 8.77E−06 | 0.637 |
| B.Bcells | CAP1 | 0.816 | 9.89E−29 | 5.78E−01 | 6.04E−39 | 0.511 |
| B.Bcells | CAPZB | 0.616 | 1.83E−16 | 7.46E−01 | 2.09E−66 | 0.575 |
| B.Bcells | CD37 | 0.709 | 1.90E−24 | 8.98E−01 | 7.79E−70 | 0.856 |
| B.Bcells | CD52 | 0.831 | 1.88E−32 | 1.34E+00 | 1.78E−101 | 1.800 |
| B.Bcells | CD53 | 0.836 | 1.56E−32 | 9.36E−01 | 3.51E−91 | 0.723 |
| B.Bcells | CFL1 | 0.552 | 6.13E−07 | 9.86E−01 | 2.82E−121 | 1.185 |
| B.Bcells | CORO1A | 1.217 | 3.24E−65 | 1.17E+00 | 4.13E−96 | 1.971 |
| B.Bcells | COTL1 | 1.254 | 1.98E−62 | 6.23E−01 | 4.95E−23 | 1.044 |
| B.Bcells | DHRS9 | 2.923 | 1.56E−85 | 5.75E−01 | 3.94E−04 | 1.495 |
| B.Bcells | DUOXA2 | 4.226 | 3.70E−21 | | 1.00E+00 | 2.568 |
| B.Bcells | EVL | 1.158 | 1.79E−47 | 6.17E−01 | 1.75E−27 | 1.267 |
| B.Bcells | GAPDH | 0.738 | 9.52E−08 | 1.03E+00 | 3.18E−140 | 1.167 |
| B.Bcells | GBP1 | 1.930 | 1.69E−33 | 6.71E−01 | 2.07E−07 | 0.656 |
| B.Bcells | GBP2 | 1.390 | 1.19E−22 | 9.89E−01 | 1.58E−21 | 0.920 |
| B.Bcells | GPSM3 | 0.679 | 8.63E−23 | 5.98E−01 | 4.20E−42 | 0.515 |
| B.Bcells | H3F3A | 0.586 | 1.26E−06 | 7.04E−01 | 4.66E−76 | 0.772 |
| B.Bcells | HLA-DMA | 1.086 | 8.58E−54 | 6.11E−01 | 1.35E−30 | 0.600 |
| B.Bcells | HLA-DPA1 | 0.602 | 1.74E−16 | 1.03E+00 | 7.98E−50 | 0.803 |
| B.Bcells | HLA-DPB1 | 0.797 | 5.81E−31 | 9.67E−01 | 2.04E−33 | 1.059 |
| B.Bcells | HLA-DQA1 | 0.880 | 5.41E−37 | 9.73E−01 | 5.18E−45 | 0.661 |
| B.Bcells | HLA-DRA | 0.580 | 5.76E−16 | 1.16E+00 | 4.34E−34 | 0.783 |
| B.Bcells | HLA-DRB1 | 0.686 | 1.94E−22 | 1.17E+00 | 1.06E−48 | 0.905 |
| B.Bcells | HOPX | 1.829 | 2.48E−45 | 5.15E−01 | 3.43E−05 | 1.804 |
| B.Bcells | IGHA1 | −1.355 | 4.90E−48 | −2.56E+00 | 7.40E−136 | −2.004 |
| B.Bcells | IGHA2 | −1.541 | 4.79E−99 | −2.61E+00 | 2.21E−114 | −0.952 |
| B.Bcells | IGJ | −1.186 | 3.38E−47 | −1.77E+00 | 8.06E−84 | −0.915 |
| B.Bcells | ITGB2 | 1.489 | 9.36E−57 | 7.06E−01 | 3.79E−24 | 0.847 |
| B.Bcells | LAPTM5 | 1.327 | 2.70E−77 | 8.69E−01 | 3.53E−46 | 1.557 |
| B.Bcells | LCP1 | 1.729 | 2.92E−84 | 3.32E−01 | 5.59E−07 | 0.967 |
| B.Bcells | LIMD2 | 1.040 | 1.95E−50 | 9.12E−01 | 1.30E−62 | 0.786 |
| B.Bcells | LSP1 | 0.374 | 2.12E−07 | 6.18E−01 | 3.73E−62 | 0.502 |
| B.Bcells | LST1 | 1.447 | 3.82E−25 | 3.84E−01 | 3.07E−03 | 0.703 |
| B.Bcells | LTB | 0.945 | 1.56E−39 | 5.70E−01 | 5.62E−14 | 1.258 |
| B.Bcells | MT-ND3 | 0.437 | 1.64E−09 | 9.87E−01 | 6.68E−38 | 0.631 |
| B.Bcells | MYL12A | 0.262 | 1.13E−03 | 6.57E−01 | 2.57E−55 | 0.513 |
| B.Bcells | PKM | 0.751 | 7.21E−24 | 8.45E−01 | 1.18E−69 | 0.595 |
| B.Bcells | PPIA | 0.727 | 4.42E−17 | 7.26E−01 | 8.00E−72 | 0.781 |
| B.Bcells | PPP1R18 | 1.280 | 7.03E−49 | 7.09E−01 | 5.00E−35 | 0.682 |
| B.Bcells | PSMB9 | 0.578 | 2.60E−15 | 6.89E−01 | 6.34E−69 | 0.502 |
| B.Bcells | PTPRC | 1.464 | 7.12E−70 | 4.40E−01 | 9.28E−13 | 1.071 |
| B.Bcells | PTPRCAP | 0.753 | 8.87E−21 | 1.05E+00 | 1.61E−120 | 1.056 |
| B.Bcells | RAC2 | 0.712 | 2.69E−24 | 7.58E−01 | 4.61E−74 | 0.552 |
| B.Bcells | RPL17 | −1.084 | 1.83E−41 | −1.24E−01 | 6.59E−04 | −0.663 |
| B.Bcells | RPS24 | 0.267 | 7.32E−02 | 7.49E−01 | 5.36E−76 | 0.556 |
| B.Bcells | SERF2 | 0.495 | 6.78E−03 | 5.69E−01 | 1.17E−96 | 0.752 |
| B.Bcells | SOCS1 | 1.066 | 8.64E−34 | 5.95E−01 | 2.20E−19 | 0.518 |
| B.Bcells | STMN1 | 0.845 | 9.34E−21 | 1.15E+00 | 2.85E−32 | 0.559 |
| B.Bcells | TTC39C | 1.991 | 1.01E−20 | 2.00E−01 | 2.17E−01 | 0.651 |
| B.Bcells | UCP2 | 1.124 | 2.55E−55 | 6.00E−01 | 1.13E−27 | 0.688 |
| B.Cycling | ACTB | 1.210 | 5.44E−02 | 2.80E+00 | 4.48E−85 | 3.533 |
| B.Cycling | ACTG1 | 1.344 | 2.46E−04 | 1.59E+00 | 2.71E−41 | 2.152 |
| B.Cycling | ACTR3 | 1.650 | 1.29E−13 | 8.00E−01 | 3.56E−12 | 1.051 |
| B.Cycling | ARHGDIB | 1.737 | 1.49E−10 | 1.54E+00 | 7.59E−35 | 2.945 |
| B.Cycling | ARPC1B | 1.372 | 1.64E−09 | 1.05E+00 | 5.92E−17 | 1.678 |
| B.Cycling | ARPC2 | 1.134 | 2.00E−03 | 1.47E+00 | 3.77E−46 | 1.514 |
| B.Cycling | ARPC3 | 1.198 | 2.47E−05 | 1.13E+00 | 1.48E−26 | 1.208 |
| B.Cycling | ARPC5 | 1.874 | 1.37E−16 | 7.33E−01 | 4.59E−09 | 1.374 |
| B.Cycling | CD53 | 1.217 | 3.35E−09 | 1.30E+00 | 4.46E−26 | 1.383 |
| B.Cycling | CORO1A | 2.167 | 8.33E−21 | 1.63E+00 | 1.66E−31 | 3.301 |
| B.Cycling | GAPDH | 3.021 | 2.42E−04 | 1.73E+00 | 1.17E−52 | 4.052 |
| B.Cycling | H2AFZ | 0.760 | 5.45E−02 | 1.46E+00 | 3.54E−40 | 0.961 |
| B.Cycling | HLA-DPA1 | 1.450 | 1.27E−11 | 1.31E+00 | 8.25E−10 | 1.891 |
| B.Cycling | HLA-DRA | 1.884 | 2.94E−17 | 1.66E+00 | 1.86E−09 | 2.805 |
| B.Cycling | HMGB1 | 2.006 | 3.96E−07 | 1.71E+00 | 6.45E−51 | 2.517 |
| B.Cycling | HMGB2 | 1.657 | 2.93E−12 | 1.13E+00 | 8.29E−17 | 1.265 |
| B.Cycling | HMGN1 | 1.706 | 4.25E−09 | 1.11E+00 | 1.15E−24 | 1.579 |
| B.Cycling | HMGN2 | 1.559 | 2.18E−07 | 1.80E+00 | 6.33E−57 | 1.922 |
| B.Cycling | HNRNPA1 | 0.889 | 1.13E−02 | 1.35E+00 | 2.77E−37 | 1.422 |
| B.Cycling | HNRNPA2B1 | 1.175 | 1.93E−05 | 1.28E+00 | 6.89E−32 | 1.187 |
| B.Cycling | HNRNPK | 1.101 | 8.09E−06 | 1.04E+00 | 1.77E−23 | 0.841 |
| B.Cycling | LAPTM5 | 1.865 | 3.52E−20 | 8.75E−01 | 1.07E−08 | 2.088 |
| B.Cycling | LAT2 | 2.014 | 5.93E−19 | 4.85E−01 | 9.69E−03 | 0.632 |
| B.Cycling | LCP1 | 2.072 | 5.27E−22 | −4.47E−02 | 7.54E−01 | 1.018 |
| B.Cycling | LDHA | 1.530 | 1.23E−09 | 9.28E−01 | 7.24E−14 | 1.346 |
| B.Cycling | LDHB | 1.097 | 7.52E−06 | 1.00E+00 | 8.69E−20 | 1.187 |

TABLE 13-continued

| | Inflamed vs Healthy Markers | | | | | |
|---|---|---|---|---|---|---|
| B.Cycling | LIMD2 | 1.883 | 2.98E−20 | 7.23E−01 | 2.17E−07 | 1.574 |
| B.Cycling | MS4A1 | 2.125 | 1.51E−22 | 5.90E−01 | 5.47E−03 | 0.516 |
| B.Cycling | NAP1L1 | 1.046 | 4.82E−07 | 9.50E−01 | 4.50E−17 | 0.916 |
| B.Cycling | NCF1 | 0.935 | 2.95E−06 | 1.04E+00 | 4.82E−20 | 0.622 |
| B.Cycling | NPM1 | 0.917 | 8.69E−03 | 1.09E+00 | 3.34E−24 | 1.375 |
| B.Cycling | PKM | 1.263 | 1.73E−07 | 1.33E+00 | 1.14E−28 | 1.033 |
| B.Cycling | RAC2 | 1.456 | 4.14E−12 | 1.06E+00 | 1.28E−18 | 1.554 |
| B.Cycling | RAN | 1.151 | 1.12E−05 | 1.10E+00 | 1.24E−24 | 0.943 |
| B.Cycling | RPL39 | 0.407 | 6.43E−02 | 1.85E+00 | 1.29E−21 | 0.602 |
| B.Cycling | STMN1 | 1.816 | 2.22E−15 | 7.47E−01 | 1.12E−07 | 1.165 |
| B.Cycling | TUBA1B | 1.809 | 5.39E−09 | 1.60E+00 | 3.95E−33 | 2.359 |
| B.Cycling | TUBB | 1.915 | 1.40E−13 | 1.43E+00 | 5.06E−31 | 2.022 |
| B.FO | ACAP1 | 1.242 | 4.69E−20 | 3.91E−01 | 2.55E−06 | 0.810 |
| B.FO | ACP5 | 1.487 | 1.63E−28 | 3.10E−01 | 5.22E−03 | 0.949 |
| B.FO | ACTB | 0.101 | 8.13E−01 | 1.25E+00 | 6.28E−44 | 0.799 |
| B.FO | ACTG1 | 0.573 | 3.21E−03 | 8.80E−01 | 3.05E−32 | 0.844 |
| B.FO | ALOX5AP | 1.327 | 1.53E−20 | 8.10E−02 | 4.32E−01 | 1.142 |
| B.FO | ARHGDIB | 1.129 | 5.19E−13 | 4.51E−01 | 1.28E−09 | 1.511 |
| B.FO | ARPC1B | 0.705 | 1.42E−07 | 5.79E−01 | 1.76E−14 | 0.757 |
| B.FO | BATF | 2.222 | 1.48E−21 | 3.48E−01 | 1.15E−01 | 0.878 |
| B.FO | BIRC3 | 1.205 | 3.46E−20 | 1.41E−01 | 1.32E−01 | 0.501 |
| B.FO | CD48 | 1.132 | 3.70E−19 | 3.05E−01 | 2.67E−05 | 0.952 |
| B.FO | CD52 | 0.743 | 2.15E−06 | 9.97E−01 | 5.23E−34 | 1.419 |
| B.FO | CD53 | 1.245 | 6.33E−21 | 4.51E−01 | 1.57E−10 | 1.043 |
| B.FO | CLEC2B | 1.793 | 2.09E−21 | 3.04E−01 | 2.69E−02 | 1.020 |
| B.FO | CORO1A | 1.454 | 2.43E−22 | 7.04E−01 | 3.11E−20 | 1.896 |
| B.FO | COTL1 | 1.048 | 4.20E−16 | 5.22E−01 | 8.07E−10 | 0.742 |
| B.FO | DHRS9 | 3.753 | 1.38E−33 | 5.78E−01 | 2.16E−01 | 2.150 |
| B.FO | EPSTI1 | 1.920 | 2.42E−19 | 1.41E−01 | 3.51E−01 | 0.503 |
| B.FO | EVL | 1.416 | 2.07E−26 | 1.64E−01 | 5.08E−02 | 1.268 |
| B.FO | GBP1 | 2.259 | 2.65E−20 | 2.87E−01 | 1.59E−01 | 0.853 |
| B.FO | GBP2 | 2.682 | 1.37E−30 | 5.04E−01 | 9.17E−03 | 1.837 |
| B.FO | GBP4 | 3.236 | 3.95E−29 | 9.92E−02 | 7.16E−01 | 1.130 |
| B.FO | GMFG | 1.019 | 7.41E−16 | 3.64E−01 | 1.86E−06 | 1.069 |
| B.FO | GYPC | 1.437 | 8.07E−29 | 5.61E−01 | 1.60E−14 | 1.382 |
| B.FO | HCLS1 | 1.059 | 2.60E−15 | 4.10E−01 | 1.73E−07 | 0.531 |
| B.FO | HCST | 1.403 | 3.21E−19 | 1.92E−01 | 8.82E−02 | 1.350 |
| B.FO | HLA-B | 0.225 | 5.45E−01 | 7.46E−01 | 9.81E−24 | 0.553 |
| B.FO | HOPX | 2.240 | 2.75E−28 | 4.97E−01 | 9.34E−03 | 2.321 |
| B.FO | IGJ | −1.260 | 2.53E−23 | 1.53E−01 | 5.27E−01 | −1.065 |
| B.FO | IRF1 | 1.113 | 3.14E−16 | 4.47E−01 | 5.43E−06 | 0.766 |
| B.FO | ITGB2 | 2.100 | 6.23E−40 | 1.20E−01 | 2.89E−01 | 1.190 |
| B.FO | LAPTM5 | 1.462 | 1.98E−27 | 5.88E−01 | 7.58E−16 | 1.526 |
| B.FO | LCP1 | 1.555 | 4.77E−26 | 2.13E−02 | 8.12E−01 | 0.755 |
| B.FO | LIMD2 | 1.238 | 6.56E−22 | 4.73E−01 | 7.16E−11 | 0.796 |
| B.FO | LSP1 | 1.126 | 2.19E−18 | 2.86E−01 | 7.86E−05 | 1.147 |
| B.FO | LY6E | 1.309 | 5.92E−21 | −4.74E−02 | 6.41E−01 | 1.071 |
| B.FO | PPP1R18 | 1.690 | 4.06E−29 | 1.40E−01 | 1.15E−01 | 0.801 |
| B.FO | PTPRC | 1.577 | 1.92E−30 | 2.07E−01 | 1.66E−02 | 1.058 |
| B.FO | PTPRCAP | 1.252 | 3.80E−17 | 7.36E−01 | 1.25E−22 | 1.585 |
| B.FO | RAC2 | 1.128 | 1.74E−18 | 3.32E−01 | 2.36E−06 | 0.899 |
| B.FO | RHOH | 0.947 | 7.00E−14 | 4.86E−01 | 4.32E−10 | 0.558 |
| B.FO | RPS4Y1 | 0.994 | 6.52E−12 | 7.54E−01 | 2.92E−10 | 0.866 |
| B.FO | 6-Sep | 1.453 | 5.58E−25 | 2.92E−01 | 1.55E−03 | 0.543 |
| B.FO | SOCS1 | 1.798 | 1.08E−25 | −5.09E−02 | 6.99E−01 | 0.987 |
| B.FO | VAMP5 | 1.550 | 7.55E−21 | 2.74E−01 | 4.35E−02 | 1.038 |
| B.GC | ACTB | 1.429 | 8.36E−02 | 1.66E+00 | 1.28E−20 | 2.884 |
| B.GC | CD52 | 2.524 | 1.96E−13 | 1.05E+00 | 7.19E−10 | 3.356 |
| B.GC | HLA-DQB1 | 2.254 | 2.57E−14 | 1.08E+00 | 6.51E−08 | 1.945 |
| B.Plasma | DHRS9 | 2.692 | 8.88E−27 | 9.71E−01 | 2.14E−04 | 1.535 |
| B.Plasma | IGHA1 | −3.590 | 2.13E−23 | −2.33E+00 | 3.21E−130 | −3.007 |
| B.Plasma | IGHA2 | −3.629 | 1.96E−55 | −2.81E+00 | 4.82E−125 | −1.563 |
| B.Plasma | IGJ | −4.003 | 1.81E−27 | −1.59E+00 | 2.78E−94 | −1.620 |
| B.Plasma | MS4A1 | 2.416 | 2.90E−17 | 1.58E+00 | 2.93E−05 | 1.191 |
| B.Plasma | RGS2 | −1.140 | 4.07E−23 | −2.48E−01 | 1.12E−04 | −0.544 |
| B.Plasma | RPL17 | −1.494 | 1.00E−23 | −1.48E−01 | 2.75E−03 | −0.956 |
| E.Absorptive | AC009501.4 | −2.051 | 2.54E−62 | 5.49E−01 | 9.89E−08 | −1.515 |
| E.Absorptive | B2M | −1.377 | 5.95E−02 | 7.43E−01 | 1.29E−21 | −1.703 |
| E.Absorptive | BIRC3 | 1.039 | 2.28E−17 | 8.71E−01 | 3.54E−28 | 0.513 |
| E.Absorptive | C2 | 2.730 | 2.21E−32 | 3.39E−01 | 5.88E−02 | 0.892 |
| E.Absorptive | C4orf3 | 0.745 | 1.22E−07 | 7.64E−01 | 1.16E−38 | 0.515 |
| E.Absorptive | CA2 | −1.604 | 6.80E−18 | −7.71E−01 | 3.08E−18 | −0.504 |
| E.Absorptive | CXCL1 | 3.150 | 1.07E−42 | 2.61E−01 | 2.15E−05 | 2.180 |
| E.Absorptive | F3 | 2.139 | 1.95E−20 | 7.40E−01 | 1.71E−03 | 0.721 |
| E.Absorptive | FSTL1 | 3.103 | 7.52E−19 | 1.01E+00 | 4.22E−03 | 1.251 |
| E.Absorptive | GBP4 | 2.153 | 7.68E−18 | 7.64E−01 | 1.26E−05 | 0.564 |
| E.Absorptive | GSN | 0.648 | 5.56E−04 | 8.55E−01 | 3.38E−31 | 0.705 |
| E.Absorptive | HLA-B | 0.505 | 3.69E−01 | 9.39E−01 | 8.66E−41 | 1.084 |

TABLE 13-continued

| | Inflamed vs Healthy Markers | | | | | |
|---|---|---|---|---|---|---|
| E.Absorptive | HLA-DRB1 | 1.843 | 7.53E−44 | 1.27E+00 | 3.16E−26 | 2.336 |
| E.Absorptive | HLA-E | 0.433 | 2.54E−02 | 6.42E−01 | 1.64E−28 | 0.564 |
| E.Absorptive | HSPB1 | −1.796 | 1.84E−30 | −4.37E−01 | 1.69E−07 | −0.732 |
| E.Absorptive | IDO1 | 4.788 | 4.77E−33 | | 1.00E+00 | 5.394 |
| E.Absorptive | IFI6 | 1.134 | 2.63E−10 | 1.05E+00 | 9.73E−13 | 0.541 |
| E.Absorptive | IFITM3 | 0.973 | 8.41E−13 | 1.35E+00 | 2.01E−33 | 1.180 |
| E.Absorptive | IL2RG | 1.161 | 3.70E−21 | 8.22E−01 | 1.34E−40 | 0.995 |
| E.Absorptive | ITM2B | 0.707 | 1.18E−03 | 9.07E−01 | 4.66E−44 | 0.935 |
| E.Absorptive | LAPTM4A | 0.723 | 4.42E−06 | 8.38E−01 | 1.24E−36 | 0.501 |
| E.Absorptive | LGALS4 | −0.690 | 2.11E−01 | −7.02E−01 | 3.14E−20 | −0.601 |
| E.Absorptive | LPCAT1 | 2.997 | 4.17E−24 | 5.03E−01 | 4.52E−02 | 0.520 |
| E.Absorptive | MMP7 | 4.751 | 1.86E−24 | | 1.00E+00 | 5.394 |
| E.Absorptive | MUC12 | 1.647 | 3.32E−17 | 1.41E+00 | 2.18E−100 | 0.726 |
| E.Absorptive | PARP8 | 3.844 | 1.43E−27 | −3.03E−01 | 5.12E−01 | 0.836 |
| E.Absorptive | PDLIM7 | 1.800 | 1.73E−18 | 7.62E−01 | 9.29E−09 | 0.596 |
| E.Absorptive | PFKFB3 | 2.431 | 9.07E−32 | 5.85E−01 | 1.06E−05 | 0.504 |
| E.Absorptive | PLA2G16 | 1.381 | 1.15E−15 | 5.83E−01 | 9.23E−07 | 0.585 |
| E.Absorptive | PLA2G2A | 1.639 | 6.27E−32 | 1.55E+00 | 9.26E−36 | 0.508 |
| E.Absorptive | PNRC1 | 0.757 | 9.17E−09 | 7.40E−01 | 3.96E−26 | 0.579 |
| E.Absorptive | PSMB9 | 0.626 | 6.99E−06 | 8.54E−01 | 3.79E−46 | 0.607 |
| E.Absorptive | PSME2 | 1.164 | 6.57E−08 | 8.15E−01 | 1.40E−45 | 1.088 |
| E.Absorptive | RARRES3 | 1.558 | 3.64E−33 | 9.72E−01 | 9.80E−54 | 1.625 |
| E.Absorptive | REG4 | 2.931 | 1.55E−43 | 1.65E+00 | 5.19E−05 | 1.418 |
| E.Absorptive | RNASE1 | 1.637 | 6.05E−30 | 1.30E+00 | 1.50E−41 | 0.982 |
| E.Absorptive | S100A11 | 0.839 | 5.39E−09 | 1.67E+00 | 3.16E−88 | 1.341 |
| E.Absorptive | S100A6 | 1.276 | 3.38E−01 | 7.96E−01 | 2.13E−21 | 1.728 |
| E.Absorptive | S100A9 | 3.985 | 1.12E−37 | 1.99E+00 | 9.81E−03 | 1.209 |
| E.Absorptive | SEPPI | 0.558 | 5.30E−05 | 1.09E+00 | 4.66E−33 | 0.759 |
| E.Absorptive | SLC25A6 | −1.779 | 6.80E−19 | −4.44E−01 | 1.48E−12 | −0.644 |
| E.Absorptive | SLC6A14 | 5.158 | 8.49E−41 | | 1.00E+00 | 5.394 |
| E.Absorptive | SOCS1 | 1.130 | 2.55E−12 | 1.33E+00 | 1.08E−27 | 0.710 |
| E.Absorptive | SOD3 | 1.634 | 7.87E−26 | 1.58E+00 | 2.74E−27 | 0.986 |
| E.Absorptive | TFF1 | 1.636 | 6.62E−37 | 1.62E+00 | 3.71E−43 | 0.619 |
| E.Absorptive | VAMP5 | 1.323 | 1.18E−22 | 7.36E−01 | 4.33E−15 | 0.969 |
| E.Absorptive | VNN1 | 4.531 | 1.58E−23 | | 1.00E+00 | 5.394 |
| E.Absorptive | WARS | 1.396 | 1.04E−14 | 9.54E−01 | 3.17E−13 | 0.538 |
| E.Absorptive_All | AC009501.4 | −1.792 | 1.15E−163 | 4.81E−01 | 1.04E−22 | −1.362 |
| E.Absorptive_All | AGR2 | 0.782 | 6.21E−23 | 1.04E+00 | 5.64E−84 | 0.507 |
| E.Absorptive_All | ANXA5 | 0.954 | 2.34E−18 | 6.57E−01 | 4.45E−13 | 0.676 |
| E.Absorptive_All | C2 | 2.754 | 1.09E−39 | 6.00E−01 | 4.15E−03 | 1.003 |
| E.Absorptive_All | COX4I1 | −0.853 | 3.27E−12 | −5.60E−01 | 1.37E−65 | −0.604 |
| E.Absorptive_All | CXCL1 | 2.908 | 9.82E−81 | 2.04E+00 | 1.38E−10 | 1.577 |
| E.Absorptive_All | DAPP1 | 3.328 | 2.96E−30 | 7.70E−01 | 5.62E−02 | 0.582 |
| E.Absorptive_All | DDX5 | 0.523 | 3.14E−12 | 6.62E−01 | 6.50E−02 | 0.579 |
| E.Absorptive_All | FABP1 | −2.045 | 3.38E−53 | −6.57E−01 | 4.44E−27 | −0.617 |
| E.Absorptive_All | FOS | −0.936 | 1.18E−35 | 1.75E−01 | 1.10E−03 | −0.671 |
| E.Absorptive_All | FSTL1 | 2.851 | 2.95E−25 | 9.20E−01 | 1.49E−03 | 0.968 |
| E.Absorptive_All | FTH1 | −0.974 | 6.31E−03 | −4.70E−01 | 1.01E−22 | −1.551 |
| E.Absorptive_All | FTL | −0.747 | 3.28E−07 | −7.28E−01 | 2.29E−67 | −1.280 |
| E.Absorptive_All | GLRA2 | 4.198 | 3.03E−23 | | 1.00E+00 | 4.481 |
| E.Absorptive_All | H3F3B | 0.244 | 8.30E−03 | 4.44E−01 | 1.01E−34 | 0.505 |
| E.Absorptive_All | HLA-DMA | 1.347 | 1.29E−40 | 7.79E−01 | 1.67E−16 | 0.784 |
| E.Absorptive_All | HLA-DMB | 1.612 | 3.18E−22 | 3.70E−01 | 2.49E−02 | 0.680 |
| E.Absorptive_All | HLA-DRB1 | 1.433 | 1.16E−88 | 1.14E+00 | 7.09E−40 | 1.590 |
| E.Absorptive_All | IDO1 | 3.952 | 7.80E−22 | | 1.00E+00 | 4.481 |
| E.Absorptive_All | IFI16 | 2.247 | 8.22E−31 | 4.37E−01 | 1.58E−02 | 0.943 |
| E.Absorptive_All | IFITM3 | 0.685 | 2.16E−19 | 1.08E+00 | 6.15E−57 | 0.795 |
| E.Absorptive_All | IL2RG | 1.007 | 9.58E−45 | 6.21E−01 | 2.87E−35 | 0.751 |
| E.Absorptive_All | JUN | −1.110 | 8.43E−48 | 2.69E−03 | 9.54E−01 | −0.593 |
| E.Absorptive_All | KYNU | 3.935 | 1.46E−21 | | 1.00E+00 | 4.481 |
| E.Absorptive_All | LYZ | 1.481 | 4.03E−35 | 8.61E−01 | 9.01E−06 | 0.718 |
| E.Absorptive_All | MMP7 | 4.430 | 1.64E−23 | | 1.00E+00 | 4.481 |
| E.Absorptive_All | MTRNR2L1 | 0.449 | 4.87E−11 | 1.43E+00 | 1.57E−43 | 0.538 |
| E.Absorptive_All | MYL6 | −0.955 | 7.44E−12 | −3.37E−01 | 8.80E−26 | −0.673 |
| E.Absorptive_All | OLFM4 | 1.788 | 7.27E−98 | 1.05E+00 | 4.42E−22 | 0.655 |
| E.Absorptive_All | PARP8 | 3.785 | 6.51E−41 | 1.48E−01 | 7.36E−01 | 1.034 |
| E.Absorptive_All | PHGR1 | −2.038 | 3.78E−17 | −6.91E−01 | 4.99E−42 | −0.784 |
| E.Absorptive_All | PLA2G2A | 2.131 | 4.09E−182 | 1.55E+00 | 5.54E−96 | 0.758 |
| E.Absorptive_All | PPDPF | −0.839 | 3.41E−14 | −2.78E−01 | 3.96E−17 | −0.508 |
| E.Absorptive_All | RARRES3 | 1.064 | 7.21E−50 | 6.87E−01 | 8.29E−39 | 1.037 |
| E.Absorptive_All | RBPMS | 3.743 | 7.60E−47 | 7.07E−01 | 1.04E−01 | 2.445 |
| E.Absorptive_All | REG4 | 2.831 | 9.24E−112 | 1.58E+00 | 6.02E−09 | 1.812 |
| E.Absorptive_All | RNASE1 | 1.207 | 2.86E−52 | 9.10E−01 | 3.07E−53 | 0.765 |
| E.Absorptive_All | S100A11 | 1.169 | 6.07E−58 | 1.23E+00 | 6.71E−148 | 1.584 |
| E.Absorptive_All | S100A6 | 0.331 | 2.90E−01 | 8.55E−01 | 1.16E−96 | 0.820 |
| E.Absorptive_All | S100A9 | 4.103 | 5.97E−66 | 1.24E+00 | 8.10E−02 | 1.174 |
| E.Absorptive_All | S100P | 3.310 | 5.39E−308 | 1.75E+00 | 2.53E−77 | 0.906 |
| E.Absorptive_All | SEPP1 | 0.543 | 5.00E−17 | 8.41E−01 | 1.28E−39 | 0.565 |

TABLE 13-continued

| | Inflamed vs Healthy Markers | | | | | |
|---|---|---|---|---|---|---|
| E.Absorptive_All | SLC25A6 | −1.053 | 1.01E−33 | −3.60E−01 | 2.98E−24 | −0.565 |
| E.Absorptive_All | SLC6A14 | 4.946 | 3.95E−49 | | 1.00E+00 | 4.481 |
| E.Absorptive_All | SOCS1 | 1.315 | 1.57E−27 | 1.10E+00 | 3.29E−27 | 0.793 |
| E.Absorptive_All | SOD3 | 1.638 | 8.80E−50 | 1.15E+00 | 1.53E−20 | 0.926 |
| E.Absorptive_All | TFF1 | 1.851 | 1.10E−135 | 1.27E+00 | 1.20E−35 | 1.028 |
| E.Absorptive_All | TIMP1 | 3.502 | 8.11E−199 | 1.28E+00 | 1.56E−09 | 3.673 |
| E.Absorptive_All | TNIP3 | 4.300 | 2.15E−59 | 1.38E+00 | 3.48E−02 | 0.639 |
| E.Absorptive_All | TRIM22 | 2.732 | 1.06E−24 | 8.20E−01 | 1.73E−03 | 0.823 |
| E.Absorptive_All | VAMP5 | 1.000 | 1.29E−23 | 5.06E−01 | 6.45E−10 | 0.612 |
| E.Absorptive_All | VNN1 | 3.903 | 9.55E−19 | | 1.00E+00 | 4.481 |
| E.Absorptive_All | XKR9 | 4.027 | 4.63E−21 | | 1.00E+00 | 4.481 |
| E.Absorptive_TA_1 | COX4I1 | −1.237 | 7.85E−14 | −4.51E−01 | 1.06E−10 | −0.813 |
| E.Absorptive_TA_1 | DUOX2 | 4.483 | 9.35E−22 | | 1.00E+00 | 3.487 |
| E.Absorptive_TA_1 | DUOXA2 | 4.970 | 1.86E−32 | | 1.00E+00 | 3.487 |
| E.Absorptive_TA_1 | LGALS3 | −1.243 | 2.05E−15 | −4.97E−01 | 1.55E−07 | −0.764 |
| E.Absorptive_TA_1 | LGALS4 | −1.865 | 1.50E−22 | −6.63E−01 | 2.27E−13 | −0.794 |
| E.Absorptive_TA_1 | MTRNR2L1 | 1.007 | 2.80E−13 | 1.46E+00 | 2.30E−12 | 1.006 |
| E.Absorptive_TA_1 | MUC12 | 1.924 | 1.08E−41 | 9.71E−01 | 2.25E−14 | 0.746 |
| E.Absorptive_TA_1 | PI3 | 2.873 | 3.95E−51 | 1.17E+00 | 8.61E−04 | 0.989 |
| E.Absorptive_TA_1 | REG4 | 3.493 | 3.77E−48 | 2.00E+00 | 3.91E−04 | 1.910 |
| E.Absorptive_TA_1 | RPL13A | −1.230 | 1.49E−06 | −6.81E−01 | 1.08E−19 | −1.944 |
| E.Absorptive_TA_1 | RPL15 | −1.123 | 3.27E−12 | −6.16E−01 | 1.90E−14 | −1.623 |
| E.Absorptive_TA_1 | RPL8 | −0.957 | 2.66E−06 | −5.23E−01 | 8.97E−15 | −0.952 |
| E.Absorptive_TA_1 | RPLP0 | −1.399 | 4.40E−17 | −4.28E−01 | 2.11E−08 | −1.250 |
| E.Absorptive_TA_1 | RPS14 | −1.078 | 2.20E−07 | −6.92E−01 | 1.13E−20 | −1.631 |
| E.Absorptive_TA_1 | RPS18 | −1.506 | 2.37E−07 | −6.14E−01 | 6.68E−15 | −2.203 |
| E.Absorptive_TA_1 | RPS2 | −1.112 | 1.30E−06 | −7.95E−01 | 2.76E−20 | −1.830 |
| E.Absorptive_TA_1 | RPS5 | −1.200 | 1.11E−16 | −3.71E−01 | 1.91E−06 | −1.125 |
| E.Absorptive_TA_1 | S100A11 | 0.801 | 2.56E−11 | 7.99E−01 | 9.69E−18 | 0.902 |
| E.Absorptive_TA_1 | S100P | 3.499 | 7.00E−64 | 5.73E−01 | 5.27E−02 | 0.608 |
| E.Absorptive_TA_1 | SAA1 | 4.759 | 1.88E−19 | | 1.00E+00 | 3.487 |
| E.Absorptive_TA_2 | AC009501.4 | −2.035 | 1.89E−46 | 4.32E−01 | 8.41E−06 | −1.587 |
| E.Absorptive_TA_2 | ARPC1B | 0.803 | 8.00E−06 | 6.70E−01 | 9.84E−23 | 0.861 |
| E.Absorptive_TA_2 | ATP6V1G1 | 0.696 | 1.44E−04 | 7.10E−01 | 1.93E−30 | 0.590 |
| E.Absorptive_TA_2 | CD44 | 1.225 | 3.74E−14 | 8.89E−01 | 2.59E−18 | 0.827 |
| E.Absorptive_TA_2 | CXCL1 | 2.030 | 4.68E−21 | 1.74E+00 | 7.62E−09 | 0.740 |
| E.Absorptive_TA_2 | FAM3B | −4.763 | 3.39E−26 | | 1.00E+00 | 5.362 |
| E.Absorptive_TA_2 | FOS | −2.217 | 1.09E−33 | 3.52E−01 | 1.33E−03 | −1.065 |
| E.Absorptive_TA_2 | GPX2 | 1.975 | 1.93E−06 | 1.18E+00 | 4.04E−59 | 0.988 |
| E.Absorptive_TA_2 | IFITM3 | 0.713 | 3.27E−05 | 1.14E+00 | 1.16E−33 | 0.780 |
| E.Absorptive_TA_2 | JUN | −2.140 | 1.07E−30 | 2.13E−01 | 2.99E−02 | −0.715 |
| E.Absorptive_TA_2 | KRT19 | 1.926 | 6.67E−05 | 1.04E+00 | 1.44E−24 | 2.057 |
| E.Absorptive_TA_2 | LGALS4 | −2.052 | 2.94E−03 | −8.31E−01 | 7.58E−21 | −1.057 |
| E.Absorptive_TA_2 | MUC12 | 2.943 | 6.71E−55 | 1.60E+00 | 2.73E−82 | 1.962 |
| E.Absorptive_TA_2 | OLFM4 | 2.263 | 2.18E−47 | 1.43E+00 | 8.82E−21 | 0.912 |
| E.Absorptive_TA_2 | PARP8 | 4.359 | 6.47E−27 | | 1.00E+00 | 5.362 |
| E.Absorptive_TA_2 | PDIA3 | 1.138 | 2.14E−07 | 9.74E−01 | 1.53E−58 | 0.682 |
| E.Absorptive_TA_2 | PI3 | 2.532 | 4.68E−55 | 2.03E+00 | 3.86E−22 | 1.026 |
| E.Absorptive_TA_2 | PITX2 | −5.183 | 2.15E−36 | | 1.00E+00 | 5.362 |
| E.Absorptive_TA_2 | PLA2G2A | 2.672 | 1.34E−35 | 2.35E+00 | 9.57E−124 | 1.526 |
| E.Absorptive_TA_2 | PRAC1 | 4.172 | 1.17E−107 | 6.60E−01 | 1.16E−14 | 0.845 |
| E.Absorptive_TA_2 | PSMB9 | 0.727 | 2.84E−06 | 8.15E−01 | 9.01E−28 | 0.702 |
| E.Absorptive_TA_2 | PSME2 | 0.656 | 5.51E−02 | 6.36E−01 | 2.68E−24 | 0.539 |
| E.Absorptive_TA_2 | REG4 | 2.978 | 5.55E−59 | 1.41E+00 | 1.65E−06 | 1.499 |
| E.Absorptive_TA_2 | RNASE1 | 1.197 | 5.71E−13 | 8.73E−01 | 1.38E−22 | 0.518 |
| E.Absorptive_TA_2 | RP11-708H21.4 | −5.510 | 1.52E−35 | | 1.00E+00 | 5.362 |
| E.Absorptive_TA_2 | RPS20 | −2.005 | 5.54E−05 | 6.04E−01 | 1.49E−17 | −1.030 |
| E.Absorptive_TA_2 | S100A10 | 0.724 | 4.05E−01 | 7.44E−01 | 1.05E−21 | 0.965 |
| E.Absorptive_TA_2 | S100A11 | 1.708 | 2.98E−07 | 1.34E+00 | 2.00E−79 | 2.043 |
| E.Absorptive_TA_2 | S100A6 | 0.806 | 6.47E−01 | 9.97E−01 | 1.50E−24 | 1.526 |
| E.Absorptive_TA_2 | S100A9 | 3.719 | 7.49E−29 | 1.11E+00 | 1.42E−01 | 0.636 |
| E.Absorptive_TA_2 | S100P | 4.775 | 7.32E−142 | 1.82E+00 | 9.71E−41 | 2.118 |
| E.Absorptive_TA_2 | 7-Sep | 0.806 | 1.11E−07 | 7.46E−01 | 4.33E−22 | 0.521 |
| E.Absorptive_TA_2 | SH3BGRL3 | 0.384 | 2.41E−01 | 7.49E−01 | 1.17E−24 | 0.694 |
| E.Absorptive_TA_2 | SOD3 | 1.752 | 2.49E−26 | 1.22E+00 | 5.87E−19 | 1.117 |
| E.Absorptive_TA_2 | SSR4 | 1.419 | 4.08E−05 | 6.51E−01 | 2.25E−21 | 1.212 |
| E.Absorptive_TA_2 | ST3GAL4 | 2.321 | 1.54E−21 | 7.09E−01 | 1.95E−04 | 0.503 |
| E.Absorptive_TA_2 | ST6GALNAC6 | 2.484 | 1.09E−44 | 7.02E−01 | 1.02E−13 | 0.740 |
| E.Best4_Enterocytes | AC009501.4 | −2.044 | 3.27E−22 | 4.88E−01 | 1.47E−02 | −1.532 |
| E.Best4_Enterocytes | AQP8 | −2.602 | 1.40E−28 | 1.56E−01 | 7.08E−01 | −0.517 |
| E.Best4_Enterocytes | ARF4 | 1.190 | 3.64E−05 | 8.83E−01 | 1.07E−19 | 0.584 |
| E.Best4_Enterocytes | EIF4G2 | 1.075 | 2.23E−04 | 9.59E−01 | 5.21E−27 | 0.515 |
| E.Best4_Enterocytes | ITM2B | 1.023 | 8.35E−03 | 1.05E+00 | 2.50E−21 | 1.406 |
| E.Best4_Enterocytes | LAPTM4A | 0.907 | 4.12E−03 | 1.03E+00 | 9.39E−21 | 0.701 |
| E.Best4_Enterocytes | MT-ND4L | 1.168 | 1.29E−04 | 1.06E+00 | 3.28E−29 | 0.614 |
| E.Best4_Enterocytes | MUC12 | 1.802 | 3.33E−09 | 1.07E+00 | 2.31E−19 | 0.784 |
| E.Best4_Enterocytes | RPL37 | 0.400 | 3.34E−01 | 1.03E+00 | 3.93E−20 | 0.714 |
| E.Best4_Enterocytes | RPL38 | 0.517 | 2.06E−01 | 9.36E−01 | 3.81E−20 | 0.648 |

TABLE 13-continued

| Inflamed vs Healthy Markers | | | | | | |
|---|---|---|---|---|---|---|
| E.Best4_Enterocytes | RPL39 | 0.270 | 3.66E-01 | 2.26E+00 | 6.86E-40 | 0.567 |
| E.Best4_Enterocytes | S100A11 | 1.141 | 3.66E-04 | 1.32E+00 | 1.10E-30 | 1.492 |
| E.Cycling_TA | AK1 | 2.364 | 2.05E-47 | 5.53E-01 | 1.75E-09 | 0.894 |
| E.Cycling_TA | ANXA5 | 0.741 | 1.64E-07 | 8.29E-01 | 2.42E-27 | 0.569 |
| E.Cycling_TA | ARPC1B | 0.754 | 4.22E-05 | 1.10E+00 | 2.61E-63 | 0.987 |
| E.Cycling_TA | C2 | 2.248 | 1.79E-22 | 1.01E+00 | 4.50E-09 | 0.707 |
| E.Cycling_TA | CAPG | 0.852 | 1.98E-06 | 8.04E-01 | 1.75E-39 | 0.507 |
| E.Cycling_TA | CLDN2 | 4.506 | 2.72E-21 | | 1.00E+00 | 5.347 |
| E.Cycling_TA | DDX5 | 0.446 | 4.03E-02 | 8.98E-01 | 1.59E-41 | 0.588 |
| E.Cycling_TA | DUOXA2 | 4.748 | 3.48E-46 | 1.70E+00 | 1.72E-01 | 0.584 |
| E.Cycling_TA | ENO1 | 1.107 | 8.45E-03 | 9.17E-01 | 1.33E-59 | 0.925 |
| E.Cycling_TA | FAM3B | -4.685 | 2.85E-25 | | 1.00E+00 | 5.347 |
| E.Cycling_TA | FN1 | 3.408 | 5.62E-29 | 1.26E+00 | 9.56E-03 | 1.190 |
| E.Cycling_TA | H3F3B | 1.033 | 1.94E-02 | 7.37E-01 | 1.81E-26 | 1.500 |
| E.Cycling_TA | HLA-DMA | 1.344 | 6.68E-20 | 1.22E+00 | 2.89E-27 | 0.881 |
| E.Cycling_TA | HLA-DRB1 | 1.673 | 5.80E-31 | 2.18E+00 | 1.38E-35 | 2.587 |
| E.Cycling_TA | HSPA5 | 1.222 | 7.03E-10 | 9.93E-01 | 1.89E-56 | 0.944 |
| E.Cycling_TA | IFI16 | 1.535 | 4.03E-16 | 8.25E-01 | 5.72E-11 | 0.564 |
| E.Cycling_TA | IFITM3 | 0.709 | 9.80E-04 | 1.29E+00 | 1.05E-52 | 0.800 |
| E.Cycling_TA | JUN | -1.938 | 2.62E-20 | 6.40E-02 | 4.41E-01 | -0.685 |
| E.Cycling_TA | LDHA | 0.582 | 4.22E-02 | 9.94E-01 | 8.79E-58 | 0.557 |
| E.Cycling_TA | LYZ | 1.419 | 4.50E-19 | 1.08E+00 | 2.71E-07 | 0.824 |
| E.Cycling_TA | MMP7 | 4.756 | 2.07E-20 | | 1.00E+00 | 5.347 |
| E.Cycling_TA | MTRNR2L1 | 1.059 | 7.81E-16 | 1.00E+00 | 4.48E-09 | 1.035 |
| E.Cycling_TA | MUC12 | 2.558 | 1.09E-34 | 1.34E+00 | 2.06E-78 | 1.307 |
| E.Cycling_TA | PDIA3 | 1.005 | 2.85E-04 | 1.12E+00 | 2.93E-88 | 0.712 |
| E.Cycling_TA | PI3 | 1.750 | 2.09E-26 | 2.36E+00 | 1.06E-25 | 0.573 |
| E.Cycling_TA | PITX1 | 3.389 | 2.83E-33 | 5.86E-01 | 3.64E-02 | 1.746 |
| E.Cycling_TA | PITX2 | -5.266 | 3.04E-38 | | 1.00E+00 | 5.347 |
| E.Cycling_TA | PLA2G2A | 2.181 | 6.66E-23 | 2.00E+00 | 3.70E-108 | 1.037 |
| E.Cycling_TA | PRAC1 | 4.338 | 1.08E-106 | 5.88E-01 | 1.59E-13 | 0.933 |
| E.Cycling_TA | PSMB9 | 0.574 | 7.69E-04 | 1.11E+00 | 1.52E-66 | 0.671 |
| E.Cycling_TA | PSME2 | 0.840 | 3.36E-02 | 1.01E+00 | 3.67E-64 | 0.783 |
| E.Cycling_TA | REG4 | 3.108 | 3.27E-91 | 2.18E+00 | 1.61E-22 | 2.029 |
| E.Cycling_TA | RPL36AL | 0.535 | 2.03E-01 | 7.16E-01 | 1.81E-43 | 0.691 |
| E.Cycling_TA | RPL38 | -1.396 | 1.21E-03 | 6.04E-01 | 5.50E-24 | -0.518 |
| E.Cycling_TA | S100A10 | 0.542 | 3.09E-01 | 6.87E-01 | 7.21E-20 | 0.728 |
| E.Cycling_TA | S100A11 | 1.278 | 1.93E-05 | 1.48E+00 | 9.57E-108 | 1.704 |
| E.Cycling_TA | S100P | 4.483 | 2.51E-135 | 1.53E+00 | 3.04E-29 | 1.934 |
| E.Cycling_TA | SAA1 | 4.886 | 3.06E-38 | | 1.00E+00 | 5.347 |
| E.Cycling_TA | SH3BGRL3 | 0.466 | 2.04E-01 | 9.51E-01 | 4.79E-42 | 0.896 |
| E.Cycling_TA | SPCS1 | 0.997 | 1.14E-03 | 7.51E-01 | 2.22E-49 | 0.702 |
| E.Cycling_TA | ST6GALNAC6 | 2.373 | 5.30E-36 | 7.72E-01 | 1.53E-11 | 0.641 |
| E.Cycling_TA | TESC | 3.977 | 5.68E-31 | 7.30E-01 | 1.78E-01 | 1.524 |
| E.Cycling_TA | UBL5 | 0.763 | 4.90E-02 | 7.22E-01 | 7.05E-46 | 0.562 |
| E.Enterocyte_Immature_1 | AC009501.4 | -1.578 | 1.07E-27 | 4.98E-01 | 4.99E-05 | -1.207 |
| E.Enterocyte_Immature_1 | MUC1 | 2.225 | 1.32E-28 | 1.25E+00 | 9.20E-14 | 0.989 |
| E.Enterocyte_Immature_1 | MUC4 | 2.580 | 1.36E-27 | 1.01E+00 | 7.66E-10 | 0.648 |
| E.Enterocyte_Immature_1 | OAZ1 | -0.919 | 2.43E-06 | -5.61E-01 | 4.55E-15 | -0.526 |
| E.Enterocyte_Immature_1 | PLA2G2A | 3.060 | 8.53E-55 | 1.01E+00 | 2.00E-04 | 1.432 |
| E.Enterocyte_Immature_1 | RNASE1 | 1.506 | 1.12E-19 | 7.19E-01 | 2.15E-06 | 0.652 |
| E.Enterocyte_Immature_1 | S100P | 3.636 | 1.24E-50 | 1.18E+00 | 3.28E-04 | 0.858 |
| E.Enterocyte_Immature_1 | TNIP3 | 4.533 | 1.08E-18 | | 1.00E+00 | 3.737 |
| E.Enterocyte_Immature_1 | XIST | 1.241 | 2.78E-11 | 9.86E-01 | 6.99E-12 | 0.558 |
| E.Enterocyte_Immature_2 | AC009501.4 | -2.768 | 2.25E-73 | 3.42E-01 | 6.64E-03 | -1.914 |
| E.Enterocyte_Immature_2 | AGR2 | 1.354 | 2.45E-08 | 1.63E+00 | 3.94E-52 | 1.375 |
| E.Enterocyte_Immature_2 | AQP8 | -2.453 | 1.34E-53 | -1.12E+00 | 4.78E-09 | -0.542 |
| E.Enterocyte_Immature_2 | BHLHE40 | 2.162 | 3.21E-25 | 7.35E-01 | 3.35E-08 | 0.747 |
| E.Enterocyte_Immature_2 | CCL20 | 2.820 | 5.35E-24 | 2.45E+00 | 5.30E-09 | 0.855 |
| E.Enterocyte_Immature_2 | CEACAM5 | 1.784 | 6.07E-09 | 1.20E+00 | 3.93E-42 | 1.233 |
| E.Enterocyte_Immature_2 | CEACAM6 | 1.929 | 1.16E-34 | 1.13E+00 | 1.89E-36 | 0.560 |
| E.Enterocyte_Immature_2 | CLIC3 | 2.244 | 5.14E-20 | 8.02E-01 | 3.27E-05 | 0.515 |
| E.Enterocyte_Immature_2 | CRIP1 | 1.028 | 3.37E-11 | 7.47E-01 | 1.57E-25 | 0.637 |
| E.Enterocyte_Immature_2 | CTSE | 3.988 | 1.76E-39 | 9.98E-01 | 2.51E-02 | 0.948 |
| E.Enterocyte_Immature_2 | CXCL1 | 3.232 | 4.63E-31 | 2.99E+00 | 2.20E-08 | 1.874 |
| E.Enterocyte_Immature_2 | CXCL2 | 2.355 | 1.36E-17 | 1.83E+00 | 1.06E-07 | 0.796 |
| E.Enterocyte_Immature_2 | DDX5 | 0.541 | 5.23E-03 | 7.54E-01 | 1.97E-23 | 0.608 |
| E.Enterocyte_Immature_2 | FAM3C | 1.790 | 9.09E-23 | 7.90E-01 | 1.03E-14 | 0.504 |
| E.Enterocyte_Immature_2 | FOSB | -2.318 | 3.62E-41 | 8.57E-02 | 3.99E-01 | -0.563 |
| E.Enterocyte_Immature_2 | FTL | -1.369 | 4.53E-02 | -9.90E-01 | 5.23E-26 | -1.925 |
| E.Enterocyte_Immature_2 | GPX2 | 1.336 | 1.26E-13 | 1.58E+00 | 2.45E-62 | 0.700 |
| E.Enterocyte_Immature_2 | HSPA5 | 0.720 | 3.48E-05 | 1.16E+00 | 4.47E-47 | 0.566 |
| E.Enterocyte_Immature_2 | HSPB1 | -1.098 | 2.00E-04 | -8.02E-01 | 3.51E-02 | -0.552 |
| E.Enterocyte_Immature_2 | IL2RG | 1.424 | 3.34E-22 | 6.95E-01 | 2.30E-18 | 1.183 |
| E.Enterocyte_Immature_2 | MDK | 1.022 | 1.38E-10 | 6.62E-01 | 6.49E-12 | 0.506 |
| E.Enterocyte_Immature_2 | MUC12 | 2.103 | 1.06E-18 | 1.75E+00 | 1.24E-108 | 1.048 |
| E.Enterocyte_Immature_2 | PDIA3 | 0.832 | 2.28E-05 | 8.17E-01 | 3.32E-34 | 0.527 |
| E.Enterocyte_Immature_2 | PITX2 | -5.108 | 9.63E-37 | | 1.00E+00 | 4.699 |

TABLE 13-continued

| | Inflamed vs Healthy Markers | | | | | |
|---|---|---|---|---|---|---|
| E.Enterocyte_Immature_2 | PLA2G2A | 3.223 | 1.25E−74 | 2.16E+00 | 1.22E−52 | 2.024 |
| E.Enterocyte_Immature_2 | RARRES3 | 1.373 | 2.76E−20 | 8.93E−01 | 1.94E−24 | 1.463 |
| E.Enterocyte_Immature_2 | RNASE1 | 1.490 | 3.23E−18 | 9.83E−01 | 8.18E−21 | 0.722 |
| E.Enterocyte_Immature_2 | S100A11 | 2.296 | 1.40E−34 | 1.73E+00 | 4.50E−84 | 3.042 |
| E.Enterocyte_Immature_2 | S100A6 | 0.487 | 8.95E−01 | 1.22E+00 | 1.13E−33 | 1.347 |
| E.Enterocyte_Immature_2 | S100A9 | 4.778 | 1.09E−35 | | 1.00E+00 | 4.699 |
| E.Enterocyte_Immature_2 | S100P | 4.403 | 5.49E−119 | 2.48E+00 | 1.80E−93 | 2.215 |
| E.Enterocyte_Immature_2 | SAA1 | 4.632 | 2.47E−25 | | 1.00E+00 | 4.699 |
| E.Enterocyte_Immature_2 | SDCBP | 1.046 | 2.94E−11 | 8.86E−01 | 2.61E−28 | 0.730 |
| E.Enterocyte_Immature_2 | SEC24D | 3.545 | 1.92E−21 | 7.11E−01 | 1.14E+00 | 0.740 |
| E.Enterocyte_Immature_2 | SEPP1 | 1.501 | 5.03E−16 | 1.06E+00 | 6.71E−25 | 1.821 |
| E.Enterocyte_Immature_2 | SERPINB5 | 4.888 | 2.54E−29 | | 1.00E+00 | 4.699 |
| E.Enterocyte_Immature_2 | SLC6A14 | 4.678 | 1.75E−25 | | 1.00E+00 | 4.699 |
| E.Enterocyte_Immature_2 | TFF1 | 2.726 | 2.86E−65 | 1.43E+00 | 2.79E−19 | 1.847 |
| E.Enterocyte_Immature_2 | TIMP2 | 1.921 | 1.69E−15 | 6.59E−01 | 1.42E−05 | 0.648 |
| E.Enterocyte_Immature_2 | TNIP3 | 4.989 | 2.93E−32 | | 1.00E+00 | 4.699 |
| E.Enterocyte_Immature_2 | TPM4 | 1.104 | 8.57E−11 | 6.95E−01 | 6.54E−26 | 0.528 |
| E.Enterocyte_Immature_2 | TRAM1 | 1.156 | 5.21E−12 | 7.44E−01 | 2.20E−18 | 0.621 |
| E.Enterocyte_Progenitor | AC009501.4 | −1.790 | 4.78E−28 | 8.23E−01 | 1.42E−07 | −1.363 |
| E.Enterocyte_Progenitor | AGR2 | 0.874 | 2.18E−07 | 1.07E+00 | 7.14E−15 | 0.618 |
| E.Enterocyte_Progenitor | CCL20 | 3.364 | 7.51E−25 | 9.45E−01 | 5.44E−02 | 0.971 |
| E.Enterocyte_Progenitor | CEACAM5 | 1.304 | 1.77E−16 | 1.11E+00 | 4.55E−19 | 0.797 |
| E.Enterocyte_Progenitor | CEACAM6 | 2.165 | 4.16E−21 | 1.25E+00 | 2.50E−09 | 0.725 |
| E.Enterocyte_Progenitor | CXCL1 | 3.601 | 2.78E−26 | 1.55E+00 | 2.06E−02 | 2.451 |
| E.Enterocyte_Progenitor | CXCL3 | 2.597 | 3.47E−20 | 1.69E+00 | 2.00E−06 | 0.832 |
| E.Enterocyte_Progenitor | DUOXA2 | 5.301 | 6.59E−34 | | 1.00E+00 | 4.362 |
| E.Enterocyte_Progenitor | GPX2 | 1.489 | 2.06E−20 | 1.17E+00 | 7.68E−23 | 0.648 |
| E.Enterocyte_Progenitor | HSPB1 | −1.810 | 3.57E−27 | −3.83E−01 | 2.31E−03 | −0.614 |
| E.Enterocyte_Progenitor | LCN2 | 2.265 | 4.40E−38 | 2.19E+00 | 1.65E−28 | 0.771 |
| E.Enterocyte_Progenitor | OLFM4 | 2.962 | 6.59E−34 | 1.43E+00 | 2.90E−05 | 1.256 |
| E.Enterocyte_Progenitor | PI3 | 2.248 | 6.99E−37 | 2.35E+00 | 3.39E−25 | 0.698 |
| E.Enterocyte_Progenitor | PLA2G2A | 2.744 | 4.26E−57 | 1.65E+00 | 8.27E−20 | 1.295 |
| E.Enterocyte_Progenitor | S100A11 | 1.487 | 1.34E−20 | 1.16E+00 | 5.79E−25 | 1.808 |
| E.Enterocyte_Progenitor | S100A6 | 1.420 | 2.81E−01 | 1.21E+00 | 5.11E−27 | 2.188 |
| E.Enterocyte_Progenitor | S100A9 | 4.821 | 1.22E−24 | | 1.00E+00 | 4.362 |
| E.Enterocyte_Progenitor | S100P | 4.217 | 7.74E−100 | 1.40E+00 | 3.88E−11 | 1.481 |
| E.Enterocyte_Progenitor | TFF1 | 2.396 | 4.72E−26 | 1.24E+00 | 2.37E−04 | 1.400 |
| E.Enterocyte_Progenitor | TNIP3 | 4.724 | 2.35E−19 | | 1.00E+00 | 4.362 |
| E.Enterocyte_Progenitor | TPT1 | 0.631 | 1.65E−03 | 7.81E−01 | 1.21E−19 | 0.944 |
| E.Enterocytes | AC009501.4 | −2.349 | 9.38E−52 | 5.09E−01 | 3.37E−05 | −1.707 |
| E.Enterocytes | BHLHE40 | 2.112 | 1.35E−30 | 7.65E−01 | 1.16E−10 | 0.777 |
| E.Enterocytes | C4orf3 | 1.121 | 3.18E−11 | 9.20E−01 | 7.30E−34 | 0.869 |
| E.Enterocytes | CA2 | −2.970 | 9.81E−18 | −1.13E+00 | 4.28E−27 | −0.602 |
| E.Enterocytes | CARD16 | 0.989 | 5.33E−08 | 1.40E+00 | 2.00E−33 | 0.754 |
| E.Enterocytes | CASP1 | 1.981 | 1.44E−22 | 1.42E+00 | 1.62E−24 | 1.256 |
| E.Enterocytes | CCNJL | −4.668 | 5.35E−22 | | 1.00E+00 | 5.613 |
| E.Enterocytes | CD55 | 1.595 | 2.02E−21 | 1.36E+00 | 4.01E−34 | 0.776 |
| E.Enterocytes | CTSE | 3.644 | 7.81E−41 | 1.38E+00 | 1.03E−04 | 0.623 |
| E.Enterocytes | CXCL1 | 3.416 | 1.52E−39 | 2.76E+00 | 2.35E−07 | 2.315 |
| E.Enterocytes | CXCL3 | 2.170 | 4.29E−24 | 2.21E+00 | 5.65E−16 | 0.668 |
| E.Enterocytes | FSTL1 | 4.180 | 4.28E−21 | | 1.00E+00 | 5.613 |
| E.Enterocytes | FTH1 | 0.338 | 8.97E−01 | −1.26E+00 | 5.68E−33 | −0.744 |
| E.Enterocytes | GLDN | 4.849 | 1.07E−29 | | 1.00E+00 | 5.613 |
| E.Enterocytes | GLUL | 1.393 | 2.71E−11 | 1.29E+00 | 2.02E−15 | 0.668 |
| E.Enterocytes | GPX2 | 1.242 | 1.22E−11 | 2.19E+00 | 2.23E−47 | 0.744 |
| E.Enterocytes | GPX4 | −2.068 | 3.20E−22 | −4.83E−01 | 1.02E−11 | −0.516 |
| E.Enterocytes | GUCA2A | −4.568 | 4.77E−31 | −8.72E−01 | 2.27E−11 | −0.540 |
| E.Enterocytes | HLA-B | 1.277 | 3.56E−01 | 8.45E−01 | 5.24E−23 | 2.037 |
| E.Enterocytes | HLA-F | 1.058 | 2.46E−10 | 7.24E−01 | 4.55E−27 | 0.529 |
| E.Enterocytes | IDO1 | 4.493 | 2.75E−27 | | 1.00E+00 | 5.613 |
| E.Enterocytes | IFITM3 | 1.886 | 4.92E−26 | 1.91E+00 | 2.31E−23 | 2.733 |
| E.Enterocytes | IL2RG | 0.819 | 4.99E−07 | 8.66E−01 | 1.06E−32 | 0.645 |
| E.Enterocytes | ITM2B | 0.372 | 1.66E−01 | 9.06E−01 | 1.02E−27 | 0.602 |
| E.Enterocytes | KDELR3 | 3.122 | 1.27E−19 | 7.14E−01 | 4.43E−02 | 0.587 |
| E.Enterocytes | LAPTM4A | 0.767 | 2.50E−05 | 8.99E−01 | 1.91E−24 | 0.575 |
| E.Enterocytes | LPCAT1 | 3.289 | 9.48E−23 | 4.78E−01 | 1.42E−01 | 0.543 |
| E.Enterocytes | MARCKSL1 | 1.542 | 2.40E−17 | 7.01E−01 | 1.60E−16 | 0.785 |
| E.Enterocytes | MMP7 | 4.672 | 5.17E−23 | | 1.00E+00 | 5.613 |
| E.Enterocytes | MUC1 | 1.629 | 4.62E−20 | 1.45E+00 | 4.47E−35 | 0.630 |
| E.Enterocytes | OLFM4 | 2.237 | 6.26E−23 | 1.76E+00 | 1.51E−08 | 0.670 |
| E.Enterocytes | PFKFB3 | 3.265 | 3.75E−34 | 9.27E−01 | 2.44E−04 | 1.121 |
| E.Enterocytes | PITX2 | −5.485 | 2.67E−47 | | 1.00E+00 | 5.613 |
| E.Enterocytes | PKM | 0.850 | 3.61E−06 | 1.44E+00 | 6.67E−61 | 0.716 |
| E.Enterocytes | PLA2G16 | 1.790 | 2.78E−18 | 7.22E−01 | 2.02E−06 | 0.863 |
| E.Enterocytes | PLA2G2A | 2.920 | 9.64E−57 | 2.21E+00 | 4.22E−24 | 1.774 |
| E.Enterocytes | PNRC1 | 0.761 | 1.47E−06 | 8.21E−01 | 1.00E−18 | 0.645 |
| E.Enterocytes | PSMB9 | 0.428 | 1.26E−02 | 1.05E+00 | 4.20E−44 | 0.502 |
| E.Enterocytes | PSME2 | 1.196 | 8.23E−06 | 1.13E+00 | 3.69E−54 | 1.201 |

TABLE 13-continued

| | Inflamed vs Healthy Markers | | | | | |
|---|---|---|---|---|---|---|
| E.Enterocytes | RARRES3 | 2.176 | 1.34E−22 | 1.02E+00 | 2.51E−48 | 2.320 |
| E.Enterocytes | REG4 | 3.497 | 2.26E−36 | 1.99E+00 | 3.33E−03 | 2.049 |
| E.Enterocytes | RNASE1 | 1.914 | 3.26E−29 | 1.36E+00 | 3.41E−27 | 1.372 |
| E.Enterocytes | S100A11 | 2.028 | 4.04E−28 | 2.69E+00 | 7.68E−72 | 3.482 |
| E.Enterocytes | S100A9 | 4.819 | 1.77E−36 | | 1.00E+00 | 5.613 |
| E.Enterocytes | S100P | 2.774 | 8.64E−45 | 1.83E+00 | 2.45E−21 | 0.527 |
| E.Enterocytes | SERPINB5 | 4.782 | 2.34E−28 | | 1.00E+00 | 5.613 |
| E.Enterocytes | SLC6A14 | 4.958 | 2.33E−32 | | 1.00E+00 | 5.613 |
| E.Enterocytes | SOCS1 | 1.172 | 1.49E−10 | 1.45E+00 | 2.99E−26 | 0.654 |
| E.Enterocytes | SRI | −1.855 | 1.09E−03 | −7.90E−01 | 8.80E−24 | −0.511 |
| E.Enterocytes | TC2N | 2.673 | 1.04E−24 | 6.58E−01 | 1.36E−03 | 0.608 |
| E.Enterocytes | TFF1 | 1.694 | 2.24E−24 | 1.78E+00 | 6.57E−38 | 0.631 |
| E.Enterocytes | TNIP3 | 4.597 | 1.38E−38 | 1.96E+00 | 4.96E−02 | 0.752 |
| E.Enterocytes | UBE2L6 | 1.501 | 2.38E−17 | 6.19E−01 | 8.51E−09 | 0.885 |
| E.Enterocytes | VAMP5 | 1.397 | 6.09E−19 | 7.76E−01 | 2.78E−12 | 1.132 |
| E.Enterocytes | WARS | 1.943 | 5.03E−16 | 1.11E+00 | 4.93E−08 | 0.904 |
| E.Epithelial | AC009501.4 | −1.443 | 7.79E−132 | 4.72E−01 | 6.10E−31 | −1.149 |
| E.Epithelial | ANXA1 | 1.532 | 1.71E−21 | 9.34E−01 | 5.59E−05 | 2.273 |
| E.Epithelial | C2 | 2.419 | 4.00E−35 | 4.07E−01 | 2.16E−02 | 0.718 |
| E.Epithelial | CLDN2 | 4.210 | 6.55E−22 | | 1.00E+00 | 3.712 |
| E.Epithelial | CLIC3 | 1.511 | 2.81E−16 | 7.55E−01 | 5.91E−06 | 0.730 |
| E.Epithelial | CLU | 1.765 | 3.90E−24 | 4.83E−01 | 2.92E−02 | 0.713 |
| E.Epithelial | CXCL1 | 2.124 | 3.72E−61 | 1.59E+00 | 4.85E−12 | 0.799 |
| E.Epithelial | CXCL14 | −0.977 | 1.47E−43 | 2.74E−01 | 1.18E−02 | −0.638 |
| E.Epithelial | DAPP1 | 3.360 | 3.08E−22 | 6.57E−01 | 3.29E−01 | 0.689 |
| E.Epithelial | DDX5 | 0.586 | 1.04E−15 | 5.38E−01 | 2.57E−53 | 0.735 |
| E.Epithelial | DUSP1 | −0.762 | 4.30E−29 | 1.82E−01 | 1.58E−04 | −0.600 |
| E.Epithelial | EMB | 2.867 | 8.44E−25 | 4.77E−01 | 2.03E−01 | 1.071 |
| E.Epithelial | FN1 | 2.696 | 7.40E−24 | 1.01E+00 | 1.27E−02 | 0.755 |
| E.Epithelial | FOS | −0.854 | 5.67E−35 | −3.32E−02 | 4.67E−01 | −0.748 |
| E.Epithelial | FTL | −0.865 | 1.12E−11 | −6.64E−01 | 1.34E−65 | −1.441 |
| E.Epithelial | FYB | 1.577 | 3.28E−24 | 3.85E−01 | 9.34E−03 | 1.069 |
| E.Epithelial | GNB2L1 | −0.865 | 6.70E−21 | −3.72E−01 | 1.89E−29 | −1.038 |
| E.Epithelial | HLA-DMA | 1.393 | 9.54E−48 | 6.45E−01 | 1.16E−13 | 0.980 |
| E.Epithelial | HLA-DMB | 1.558 | 1.95E−21 | 3.37E−01 | 3.23E−02 | 0.699 |
| E.Epithelial | HLA-DRB5 | 0.896 | 2.04E−19 | 7.32E−01 | 5.36E−10 | 0.744 |
| E.Epithelial | HLA-E | 0.299 | 1.23E−05 | 4.98E−01 | 1.09E−47 | 0.503 |
| E.Epithelial | HOXD13 | 4.124 | 7.08E−25 | | 1.00E+00 | 3.712 |
| E.Epithelial | IFI16 | 1.281 | 9.80E−16 | 5.37E−01 | 5.23E−06 | 0.583 |
| E.Epithelial | IFITM2 | 0.683 | 9.63E−14 | 4.51E−01 | 5.34E−09 | 0.863 |
| E.Epithelial | IL2RG | 1.125 | 7.11E−55 | 5.06E−01 | 3.53E−20 | 1.076 |
| E.Epithelial | JUN | −1.096 | 7.03E−55 | −1.23E−01 | 2.44E−03 | −0.544 |
| E.Epithelial | LYZ | 1.686 | 3.73E−65 | 7.01E−01 | 2.11E−05 | 1.159 |
| E.Epithelial | MMP7 | 4.672 | 5.73E−32 | | 1.00E+00 | 3.712 |
| E.Epithelial | MTRNR2L1 | 0.769 | 2.37E−35 | 1.50E+00 | 1.88E−65 | 0.583 |
| E.Epithelial | MYL6 | −0.723 | 1.96E−08 | −2.21E−01 | 7.35E−14 | −0.543 |
| E.Epithelial | NPSR1 | 4.209 | 1.31E−20 | | 1.00E+00 | 3.712 |
| E.Epithelial | PARP8 | 3.281 | 5.72E−27 | 5.60E−01 | 2.18E−01 | 1.215 |
| E.Epithelial | PDIA3 | 0.781 | 9.84E−26 | 7.38E−01 | 9.60E−107 | 0.577 |
| E.Epithelial | PITX1 | 3.327 | 1.93E−29 | 5.18E−01 | 2.50E−01 | 1.404 |
| E.Epithelial | PLA2G16 | 1.312 | 6.03E−16 | 5.71E−01 | 3.33E−05 | 0.818 |
| E.Epithelial | RARRES3 | 0.983 | 5.05E−46 | 5.61E−01 | 1.35E−26 | 1.172 |
| E.Epithelial | RBPMS | 3.215 | 8.44E−25 | 8.90E−01 | 8.58E−02 | 1.970 |
| E.Epithelial | RPL10A | −0.494 | 4.20E−10 | −2.63E−01 | 3.96E−12 | −0.638 |
| E.Epithelial | RPL11 | −0.604 | 4.93E−07 | −3.64E−01 | 4.47E−29 | −0.840 |
| E.Epithelial | RPL12 | −0.703 | 4.84E−12 | −3.45E−01 | 3.32E−22 | −0.949 |
| E.Epithelial | RPL15 | −0.607 | 3.55E−11 | −4.52E−01 | 6.87E−36 | −0.808 |
| E.Epithelial | RPL3 | −0.432 | 2.77E−05 | −3.97E−01 | 1.04E−27 | −0.599 |
| E.Epithelial | RPL8 | −0.453 | 1.38E−04 | −4.33E−01 | 2.01E−42 | −0.754 |
| E.Epithelial | RPLP0 | −0.670 | 5.02E−14 | −3.92E−01 | 3.93E−27 | −0.893 |
| E.Epithelial | RPS14 | −0.714 | 5.62E−09 | −5.30E−01 | 4.82E−55 | −1.072 |
| E.Epithelial | RPS3 | −0.562 | 8.06E−07 | −5.03E−01 | 6.89E−46 | −0.920 |
| E.Epithelial | RPS4X | −0.747 | 3.99E−15 | −3.57E−01 | 4.14E−22 | −0.793 |
| E.Epithelial | RPS5 | −0.778 | 1.04E−18 | −4.38E−01 | 2.13E−34 | −1.056 |
| E.Epithelial | RPS6 | −0.345 | 1.94E−03 | −4.07E−01 | 4.67E−25 | −0.516 |
| E.Epithelial | RPS7 | −0.553 | 1.08E−10 | −2.31E−01 | 3.16E−11 | −0.722 |
| E.Epithelial | RPS8 | −0.421 | 1.64E−06 | −2.92E−01 | 1.81E−14 | −0.608 |
| E.Epithelial | RPS9 | −0.499 | 6.83E−07 | −3.42E−01 | 6.59E−25 | −0.724 |
| E.Epithelial | S100A11 | 1.027 | 3.60E−50 | 1.14E+00 | 5.42E−174 | 1.438 |
| E.Epithelial | S100A6 | 0.316 | 2.20E−01 | 9.80E−01 | 7.47E−166 | 0.766 |
| E.Epithelial | S100A9 | 3.465 | 6.87E−51 | 1.36E+00 | 1.54E−02 | 0.852 |
| E.Epithelial | SEPP1 | 0.517 | 9.21E−18 | 6.80E−01 | 1.65E−25 | 0.513 |
| E.Epithelial | SLC25A6 | −0.922 | 1.36E−28 | −3.28E−01 | 2.06E−25 | −0.505 |
| E.Epithelial | SLC6A14 | 4.840 | 3.60E−45 | | 1.00E+00 | 3.712 |
| E.Epithelial | SOCS1 | 1.303 | 5.89E−25 | 9.77E−01 | 4.12E−19 | 1.015 |
| E.Epithelial | SOD3 | 1.247 | 7.61E−45 | 6.69E−01 | 1.58E−17 | 0.526 |
| E.Epithelial | TESC | 3.086 | 1.80E−29 | −1.68E−01 | 6.55E−01 | 0.938 |
| E.Epithelial | TGFBI | 2.541 | 1.53E−24 | 5.92E−01 | 4.34E−02 | 1.252 |

TABLE 13-continued

| Inflamed vs Healthy Markers | | | | | | |
|---|---|---|---|---|---|---|
| E.Epithelial | TGM2 | 3.983 | 1.26E−26 | | 1.00E+00 | 3.712 |
| E.Epithelial | TIMP1 | 2.832 | 3.53E−214 | 7.38E−01 | 1.84E−09 | 2.805 |
| E.Epithelial | TNIP3 | 4.624 | 1.56E−50 | | 1.00E+00 | 3.712 |
| E.Goblet | CD55 | 1.848 | 2.06E−17 | 5.48E−01 | 4.68E−04 | 0.782 |
| E.Goblet | REG4 | 2.119 | 7.02E−31 | 1.68E+00 | 2.41E−14 | 0.585 |
| E.Immature_Enterocytes | AC009501.4 | −1.996 | 2.17E−109 | 4.73E−01 | 9.38E−10 | −1.467 |
| E.Immature_Enterocytes | ACTB | 0.736 | 5.40E−03 | 4.95E−01 | 2.53E−18 | 1.195 |
| E.Immature_Enterocytes | AGR2 | 0.813 | 2.93E−16 | 1.11E+00 | 2.45E−51 | 0.652 |
| E.Immature_Enterocytes | ATP5G2 | −1.021 | 3.18E−20 | −1.40E−01 | 9.24E−03 | −0.522 |
| E.Immature_Enterocytes | BHLHE40 | 1.813 | 1.08E−28 | 6.05E−01 | 8.32E−08 | 0.533 |
| E.Immature_Enterocytes | C2 | 3.396 | 1.06E−23 | 6.41E−01 | 1.22E−01 | 1.513 |
| E.Immature_Enterocytes | CCL20 | 2.626 | 2.55E−53 | 1.72E+00 | 4.25E−13 | 0.694 |
| E.Immature_Enterocytes | CD55 | 1.431 | 4.60E−29 | 7.57E−01 | 8.67E−18 | 0.528 |
| E.Immature_Enterocytes | COX4I1 | −0.986 | 1.64E−10 | −6.32E−01 | 5.86E−41 | −0.656 |
| E.Immature_Enterocytes | CTSE | 3.705 | 4.13E−51 | 7.71E−01 | 2.08E−02 | 0.720 |
| E.Immature_Enterocytes | CXCL1 | 3.293 | 1.44E−60 | 1.96E+00 | 6.03E−07 | 2.170 |
| E.Immature_Enterocytes | CXCL2 | 2.244 | 3.20E−26 | 1.52E+00 | 6.15E−09 | 0.717 |
| E.Immature_Enterocytes | CXCL3 | 1.917 | 8.57E−32 | 2.03E+00 | 9.47E−24 | 0.675 |
| E.Immature_Enterocytes | DDX5 | 0.668 | 1.49E−11 | 5.71E−01 | 2.49E−26 | 0.688 |
| E.Immature_Enterocytes | FABP1 | −3.053 | 1.37E−11 | −4.59E−01 | 3.65E−10 | −0.930 |
| E.Immature_Enterocytes | FSTL1 | 3.298 | 1.82E−20 | 9.38E−01 | 2.20E−02 | 1.375 |
| E.Immature_Enterocytes | FTL | −0.984 | 2.24E−07 | −8.67E−01 | 1.10E−47 | −1.585 |
| E.Immature_Enterocytes | GLRA2 | 4.429 | 1.50E−22 | | 1.00E+00 | 3.780 |
| E.Immature_Enterocytes | GPX2 | 1.284 | 7.15E−38 | 1.34E+00 | 1.93E−78 | 0.727 |
| E.Immature_Enterocytes | GSN | 0.622 | 2.20E−11 | 5.12E−01 | 6.60E−17 | 0.566 |
| E.Immature_Enterocytes | H3F3B | 0.379 | 1.83E−03 | 4.65E−01 | 1.29E−20 | 0.648 |
| E.Immature_Enterocytes | HLA-DMA | 1.146 | 1.05E−14 | 7.23E−01 | 2.28E−07 | 0.629 |
| E.Immature_Enterocytes | HLA-DRB1 | 1.115 | 5.71E−32 | 8.99E−01 | 2.54E−16 | 1.133 |
| E.Immature_Enterocytes | IFITM3 | 0.996 | 1.88E−17 | 1.21E+00 | 1.10E−24 | 1.235 |
| E.Immature_Enterocytes | IL2RG | 1.050 | 2.54E−29 | 4.06E−01 | 1.21E−11 | 0.680 |
| E.Immature_Enterocytes | LCN2 | 1.652 | 5.00E−55 | 2.28E+00 | 2.32E−81 | 0.630 |
| E.Immature_Enterocytes | MUC12 | 1.575 | 2.63E−52 | 1.49E+00 | 5.82E−173 | 0.507 |
| E.Immature_Enterocytes | MYL6 | −1.070 | 8.96E−08 | −3.39E−01 | 2.58E−14 | −0.809 |
| E.Immature_Enterocytes | PARP8 | 4.286 | 2.54E−27 | | 1.00E+00 | 3.780 |
| E.Immature_Enterocytes | PITX2 | −5.336 | 1.15E−51 | | 1.00E+00 | 3.780 |
| E.Immature_Enterocytes | PLA2G2A | 2.792 | 1.36E−159 | 1.74E+00 | 1.05E−55 | 1.666 |
| E.Immature_Enterocytes | PPDPF | −0.764 | 4.22E−07 | −4.13E−01 | 7.60E−19 | −0.573 |
| E.Immature_Enterocytes | RARRES3 | 1.072 | 9.26E−31 | 5.27E−01 | 3.33E−18 | 0.946 |
| E.Immature_Enterocytes | REG4 | 2.421 | 2.29E−41 | 1.33E+00 | 3.34E−05 | 0.904 |
| E.Immature_Enterocytes | RNASE1 | 1.291 | 2.61E−34 | 8.99E−01 | 1.66E−28 | 0.679 |
| E.Immature_Enterocytes | S100A11 | 1.519 | 2.59E−54 | 1.36E+00 | 1.34E−88 | 2.079 |
| E.Immature_Enterocytes | S100A6 | 2.704 | 1.21E−03 | 9.85E−01 | 3.00E−65 | 2.484 |
| E.Immature_Enterocytes | S100A9 | 5.071 | 3.74E−55 | | 1.00E+00 | 3.780 |
| E.Immature_Enterocytes | S100P | 3.659 | 2.13E−223 | 2.01E+00 | 8.60E−74 | 1.180 |
| E.Immature_Enterocytes | SDCBP | 0.829 | 1.54E−15 | 6.27E−01 | 4.94E−22 | 0.519 |
| E.Immature_Enterocytes | SEC24D | 3.280 | 1.34E−28 | 5.32E−01 | 6.92E−02 | 0.541 |
| E.Immature_Enterocytes | SEPP1 | 1.092 | 5.01E−32 | 7.78E−01 | 7.85E−29 | 1.165 |
| E.Immature_Enterocytes | SLC25A6 | −1.100 | 2.75E−22 | −4.08E−01 | 2.29E−16 | −0.552 |
| E.Immature_Enterocytes | SLC6A14 | 4.944 | 1.67E−36 | | 1.00E+00 | 3.780 |
| E.Immature_Enterocytes | SOCS1 | 1.505 | 5.40E−20 | 1.04E+00 | 2.25E−15 | 0.930 |
| E.Immature_Enterocytes | SPINK1 | 0.967 | 9.15E−18 | 1.72E+00 | 8.72E−61 | 0.613 |
| E.Immature_Enterocytes | TFF1 | 2.048 | 8.47E−97 | 1.33E+00 | 4.98E−33 | 1.056 |
| E.Immature_Enterocytes | TGM2 | 3.379 | 1.71E−20 | 1.33E+00 | 3.61E−03 | 0.737 |
| E.Immature_Enterocytes | TNIP3 | 5.326 | 4.69E−59 | | 1.00E+00 | 3.780 |
| E.Immature_Goblet | AC009501.4 | −1.337 | 4.88E−18 | 5.82E−01 | 3.69E−05 | −1.044 |
| E.Immature_Goblet | CCL20 | 2.890 | 3.18E−19 | 8.86E−01 | 5.94E−02 | 0.727 |
| E.Immature_Goblet | COX4I1 | −1.191 | 5.15E−05 | −7.55E−01 | 6.18E−24 | −0.820 |
| E.Immature_Goblet | RPL10 | −1.902 | 2.44E−04 | −7.44E−01 | 1.13E−17 | −2.877 |
| E.Immature_Goblet | RPL8 | −1.005 | 8.44E−03 | −6.59E−01 | 2.58E−19 | −1.040 |
| E.Immature_Goblet | S100P | 3.344 | 8.37E−84 | 1.23E+00 | 1.13E−19 | 0.534 |
| E.Immature_Goblet | TFF1 | 2.786 | 6.36E−57 | 1.44E+00 | 6.23E−09 | 1.843 |
| E.Immature_Goblet | XIST | 1.805 | 3.50E−20 | 6.50E−01 | 1.68E−05 | 0.796 |
| E.Secretory | CD55 | 1.774 | 1.22E−18 | 5.78E−01 | 5.94E−05 | 0.720 |
| E.Secretory | MT-ND3 | 0.612 | 2.87E−04 | 1.74E+00 | 1.68E−42 | 0.840 |
| E.Secretory_All | AC009501.4 | −1.407 | 1.77E−55 | 2.10E−01 | 3.91E−04 | −1.175 |
| E.Secretory_All | ANXA5 | 0.814 | 6.68E−15 | 3.89E−01 | 4.64E−08 | 0.500 |
| E.Secretory_All | C2 | 2.862 | 7.54E−34 | 5.68E−01 | 4.29E−03 | 0.984 |
| E.Secretory_All | C2CD4A | 4.621 | 3.44E−22 | | 1.00E+00 | 3.977 |
| E.Secretory_All | COX4I1 | −1.041 | 3.46E−12 | −6.80E−01 | 3.70E−51 | −0.782 |
| E.Secretory_All | DDX5 | 0.746 | 3.77E−13 | 5.55E−01 | 2.80E−25 | 0.726 |
| E.Secretory_All | F3 | 2.004 | 6.47E−27 | 5.77E−01 | 1.18E−03 | 0.622 |
| E.Secretory_All | FN1 | 3.749 | 4.17E−30 | 1.04E+00 | 1.26E−01 | 1.293 |
| E.Secretory_All | GNB2L1 | −0.763 | 2.24E−08 | −4.37E−01 | 4.28E−18 | −0.718 |
| E.Secretory_All | GSN | 0.687 | 4.27E−12 | 5.83E−01 | 9.40E−19 | 0.760 |
| E.Secretory_All | HLA-E | 0.552 | 2.99E−08 | 5.37E−01 | 8.98E−28 | 0.710 |
| E.Secretory_All | HSPB1 | −0.997 | 2.07E−21 | −1.16E−01 | 1.00E−01 | −0.515 |
| E.Secretory_All | IGFALS | 4.692 | 1.58E−22 | | 1.00E+00 | 3.977 |
| E.Secretory_All | LGALS4 | −0.832 | 9.78E−07 | −6.12E−01 | 7.75E−26 | −0.554 |

TABLE 13-continued

Inflamed vs Healthy Markers

| | | | | | | |
|---|---|---|---|---|---|---|
| E.Secretory_All | LYZ | 2.134 | 6.69E−71 | 5.62E−01 | 1.37E−03 | 1.474 |
| E.Secretory_All | MTRNR2L1 | 0.697 | 1.03E−13 | 1.06E+00 | 5.67E−15 | 0.708 |
| E.Secretory_All | MUC5AC | 4.738 | 1.60E−25 | | 1.00E+00 | 3.977 |
| E.Secretory_All | MYL6 | −0.771 | 2.97E−05 | −3.64E−01 | 9.90E−17 | −0.611 |
| E.Secretory_All | RARRES3 | 0.880 | 8.46E−18 | 3.05E−01 | 1.87E−05 | 0.671 |
| E.Secretory_All | RPL10 | −0.754 | 6.30E−05 | −5.97E−01 | 4.67E−25 | −1.350 |
| E.Secretory_All | RPL11 | −0.775 | 1.13E−05 | −4.09E−01 | 2.73E−16 | −1.037 |
| E.Secretory_All | RPL12 | −0.637 | 3.49E−05 | −4.50E−01 | 4.19E−17 | −0.864 |
| E.Secretory_All | RPL13A | −0.451 | 2.29E−02 | −5.80E−01 | 8.75E−27 | −0.905 |
| E.Secretory_All | RPL15 | −0.448 | 1.20E−03 | −5.43E−01 | 3.56E−21 | −0.803 |
| E.Secretory_All | RPL8 | −0.363 | 3.38E−02 | −6.33E−01 | 4.82E−40 | −0.616 |
| E.Secretory_All | RPLP0 | −0.392 | 3.24E−03 | −5.07E−01 | 4.81E−21 | −0.541 |
| E.Secretory_All | RPS14 | −0.703 | 4.32E−05 | −5.44E−01 | 1.02E−24 | −1.105 |
| E.Secretory_All | RPS2 | −0.292 | 6.78E−02 | −8.30E−01 | 1.92E−36 | −0.895 |
| E.Secretory_All | RPS3 | −0.460 | 6.04E−03 | −6.15E−01 | 1.01E−29 | −0.814 |
| E.Secretory_All | RPS5 | −0.666 | 3.53E−07 | −5.84E−01 | 4.59E−27 | −0.790 |
| E.Secretory_All | RPS6 | −0.440 | 1.61E−02 | −5.67E−01 | 1.45E−21 | −0.859 |
| E.Secretory_All | S100A11 | 0.648 | 2.98E−10 | 6.82E−01 | 8.40E−38 | 0.632 |
| E.Secretory_All | TESC | 3.081 | 1.10E−26 | −3.44E−01 | 2.63E−01 | 0.640 |
| E.Secretory_All | TGFBI | 2.094 | 8.71E−26 | 4.21E−01 | 8.92E−03 | 0.906 |
| E.Secretory_All | TIMP1 | 2.353 | 1.54E−111 | 2.76E−01 | 1.43E−02 | 2.162 |
| E.Secretory_All | TRIM22 | 2.716 | 6.77E−21 | 4.84E−01 | 4.41E−02 | 0.720 |
| E.Secretory_TA | AC009501.4 | −1.922 | 8.21E−33 | 3.93E−01 | 1.28E−03 | −1.493 |
| E.Secretory_TA | AGR2 | 0.853 | 1.63E−01 | 1.34E+00 | 6.39E−32 | 0.743 |
| E.Secretory_TA | ATP6V1G1 | 0.927 | 1.17E−04 | 6.61E−01 | 1.05E−21 | 0.720 |
| E.Secretory_TA | CLDN2 | 4.820 | 2.51E−21 | | 1.00E+00 | 5.000 |
| E.Secretory_TA | FN1 | 4.014 | 5.26E−30 | 1.24E+00 | 6.58E−02 | 1.790 |
| E.Secretory_TA | FRZB | 1.444 | 1.41E−15 | 7.15E−01 | 2.96E−06 | 0.564 |
| E.Secretory_TA | HLA-F | 1.278 | 9.14E−13 | 8.25E−01 | 1.00E−22 | 0.711 |
| E.Secretory_TA | HSPA5 | 0.707 | 3.67E−04 | 9.37E−01 | 6.96E−31 | 0.504 |
| E.Secretory_TA | ID3 | −2.462 | 3.54E−33 | 1.86E−01 | 8.68E−01 | −0.521 |
| E.Secretory_TA | IFITM3 | 0.474 | 3.08E−02 | 1.19E+00 | 5.35E−29 | 0.552 |
| E.Secretory_TA | MUC12 | 1.620 | 1.67E−15 | 1.00E+00 | 1.50E−27 | 0.560 |
| E.Secretory_TA | PDIA3 | 1.223 | 6.40E−06 | 8.66E−01 | 1.63E−36 | 0.820 |
| E.Secretory_TA | PI3 | 1.933 | 5.42E−20 | 1.40E+00 | 7.05E−07 | 0.511 |
| E.Secretory_TA | PITX2 | −4.655 | 3.26E−22 | | 1.00E+00 | 5.000 |
| E.Secretory_TA | PRAC1 | 3.889 | 7.68E−69 | 8.65E−01 | 8.21E−21 | 0.641 |
| E.Secretory_TA | PSMB9 | 0.578 | 1.62E−03 | 1.09E+00 | 3.57E−40 | 0.664 |
| E.Secretory_TA | REG4 | 2.058 | 5.48E−35 | 2.08E+00 | 8.85E−28 | 0.795 |
| E.Secretory_TA | S100A11 | 0.914 | 2.80E−03 | 9.52E−01 | 9.56E−31 | 1.044 |
| E.Secretory_TA | S100P | 3.744 | 1.30E−76 | 1.55E+00 | 1.46E−27 | 1.083 |
| E.Secretory_TA | SAA1 | 4.764 | 3.13E−27 | | 1.00E+00 | 5.000 |
| E.Secretory_TA | ST6GALNAC6 | 2.139 | 6.48E−23 | 6.58E−01 | 3.40E−08 | 0.504 |
| E.Secretory_TA | SUB1 | 0.866 | 1.14E−04 | 8.38E−01 | 1.60E−30 | 0.578 |
| E.Secretory_TA | TESC | 4.021 | 2.87E−26 | 9.33E−01 | 7.33E−02 | 1.638 |
| E.Stem | PLA2G2A | 2.205 | 3.62E−15 | 1.30E+00 | 8.28E−11 | 0.780 |
| E.Stem | PRAC1 | 4.659 | 1.44E−42 | 8.96E−01 | 4.25E−10 | 1.215 |
| E.Stem | WFDC2 | 1.916 | 8.85E−11 | 1.27E+00 | 4.00E−15 | 0.610 |
| F.Crypt | MME | 4.670 | 1.98E−19 | | 1.00E+00 | 1.880 |
| F.Crypt | MT-ND2 | 0.554 | 5.48E−03 | 7.23E−01 | 6.74E−18 | 1.118 |
| F.Crypt | MTRNR2L1 | 1.470 | 7.43E−23 | 1.35E+00 | 9.35E−11 | 1.524 |
| F.Crypt | NEAT1 | 0.816 | 8.97E−11 | 6.22E−01 | 2.99E−14 | 0.697 |
| F.Crypt | TAGLN | 1.972 | 9.97E−40 | 7.73E−01 | 9.39E−06 | 0.919 |
| F.Crypt_hiFos | GSN | −2.426 | 2.22E−11 | −1.15E+00 | 1.94E−14 | −0.619 |
| F.Crypt_hiFos | TAGLN | 2.893 | 1.13E−27 | 7.76E−01 | 2.01E−02 | 1.916 |
| F.Crypt_loFos_1 | TAGLN | 2.131 | 3.20E−18 | 8.60E−01 | 3.21E−03 | 1.061 |
| F.Crypt_loFos_2 | APOE | −2.835 | 4.08E−17 | −1.43E+00 | 8.91E−15 | −0.785 |
| F.Crypt_loFos_2 | MTRNR2L1 | 2.610 | 1.48E−28 | 1.02E+00 | 6.59E−03 | 2.694 |
| F.Endothelial | AC005540.3 | 3.774 | 3.20E−22 | 5.85E−01 | 4.07E−01 | 0.660 |
| F.Endothelial | ANXA2 | 0.809 | 2.90E−09 | 1.02E+00 | 5.78E−45 | 0.721 |
| F.Endothelial | CD9 | 1.131 | 3.61E−20 | 3.90E−01 | 2.00E−05 | 1.049 |
| F.Endothelial | GAPDH | 0.640 | 1.38E−03 | 5.31E−01 | 1.38E−17 | 0.754 |
| F.Endothelial | HLA-A | −1.590 | 1.36E−06 | −6.64E−01 | 1.04E−24 | −1.462 |
| F.Endothelial | HLA-C | −0.617 | 9.10E−02 | −5.77E−01 | 5.04E−24 | −0.617 |
| F.Endothelial | LGALS1 | 0.527 | 1.88E−05 | 8.46E−01 | 4.01E−19 | 1.028 |
| F.Endothelial | MTRNR2L1 | 2.205 | 8.01E−57 | −6.75E−02 | 7.67E−01 | 1.668 |
| F.Endothelial | S100A6 | 0.691 | 5.92E−06 | 1.01E+00 | 2.42E−27 | 1.430 |
| F.Endothelial | TAGLN | 1.624 | 4.97E−20 | 9.22E−01 | 1.52E−03 | 0.651 |
| F.Endothelial | TIMP1 | 0.703 | 4.10E−08 | 6.73E−01 | 7.05E−17 | 0.694 |
| F.Endothelial | VIM | 0.938 | 3.36E−08 | 7.75E−01 | 2.34E−29 | 1.462 |
| F.Fibroblast | AREG | 2.762 | 2.41E−20 | 4.30E−01 | 2.17E−01 | 0.528 |
| F.Fibroblast | C12orf75 | 1.837 | 5.90E−28 | 3.48E−01 | 1.96E−02 | 0.659 |
| F.Fibroblast | EMP3 | 0.505 | 1.25E−09 | 4.92E−01 | 9.97E−34 | 0.590 |
| F.Fibroblast | GLIPR1 | 1.473 | 3.84E−31 | 2.25E−01 | 9.47E−03 | 0.866 |
| F.Fibroblast | IL13RA2 | 5.211 | 6.14E−32 | | 1.00E+00 | 2.254 |
| F.Fibroblast | INHBA | 4.213 | 2.59E−21 | | 1.00E+00 | 2.254 |
| F.Fibroblast | MME | 4.715 | 1.69E−35 | | 1.00E+00 | 2.254 |
| F.Fibroblast | MTRNR2L1 | 1.638 | 4.80E−70 | 8.33E−01 | 2.73E−10 | 1.487 |

TABLE 13-continued

Inflamed vs Healthy Markers

| Cell Type | Gene | | | | | |
|---|---|---|---|---|---|---|
| F.Fibroblast | PRRX1 | 4.491 | 2.38E−24 | | 1.00E+00 | 2.254 |
| F.Fibroblast | PRSS23 | 1.544 | 1.03E−52 | 6.89E−01 | 9.84E−13 | 0.783 |
| F.Fibroblast | PTMA | 0.290 | 8.33E−02 | 5.14E−01 | 5.87E−33 | 0.617 |
| F.Fibroblast | RPL7 | −0.783 | 2.22E−06 | −3.72E−01 | 4.41E−17 | −0.992 |
| F.Fibroblast | RPS26 | −0.737 | 2.77E−14 | −3.74E−01 | 1.63E−16 | −0.707 |
| F.Fibroblast | S100A6 | 0.310 | 7.37E−02 | 6.45E−01 | 2.95E−31 | 0.722 |
| F.Fibroblast | SGK1 | 1.600 | 2.79E−22 | 8.71E−01 | 2.31E−09 | 0.688 |
| F.Fibroblast | STC1 | 4.459 | 5.39E−24 | | 1.00E+00 | 2.254 |
| F.Fibroblast | TIMP1 | 0.803 | 1.52E−10 | 1.07E+00 | 1.73E−122 | 0.604 |
| F.Glia | ANXA1 | 2.251 | 1.06E−07 | 2.05E+00 | 2.20E−25 | 4.008 |
| F.Glia | S100A3 | 4.450 | 4.92E−21 | −3.87E−01 | 4.85E−01 | 0.677 |
| F.Pcap_Venules | ANXA2 | 0.635 | 1.29E−02 | 1.18E+00 | 6.99E−23 | 0.685 |
| F.Pcap_Venules | COL4A2 | 2.336 | 7.99E−27 | 5.62E−01 | 2.29E−04 | 0.910 |
| F.Pcap_Venules | FKBP1A | 1.402 | 3.44E−04 | 7.98E−01 | 1.52E−18 | 0.977 |
| F.Pcap_Venules | PRKCDBP | 1.778 | 5.49E−19 | 8.81E−01 | 2.11E−10 | 1.276 |
| F.Pcap_Venules | PRSS23 | 1.992 | 4.28E−22 | 1.13E+00 | 1.25E−12 | 1.271 |
| F.Pcap_Venules | VAMP5 | 2.074 | 1.37E−21 | 6.46E−01 | 4.93E−04 | 1.770 |
| F.Stromal | DEFA5 | 4.171 | 5.18E−27 | | 1.00E+00 | 2.053 |
| F.Stromal | GLIPR1 | 1.206 | 3.78E−21 | 1.32E−01 | 1.41E−01 | 0.620 |
| F.Stromal | IL13RA2 | 4.847 | 5.21E−26 | | 1.00E+00 | 2.053 |
| F.Stromal | LINC00152 | 0.880 | 1.35E−22 | 4.20E−01 | 1.13E−10 | 0.511 |
| F.Stromal | MME | 4.368 | 7.34E−28 | | 1.00E+00 | 2.053 |
| F.Stromal | MTRNR2L1 | 1.652 | 1.46E−93 | 5.61E−01 | 2.24E−06 | 1.346 |
| F.Stromal | PRRX1 | 4.419 | 1.14E−22 | | 1.00E+00 | 2.053 |
| F.Stromal | RGCC | 0.835 | 2.42E−22 | 2.70E−01 | 1.42E−02 | 1.006 |
| F.Stromal | RPL7 | −0.662 | 2.11E−06 | −3.05E−01 | 3.33E−15 | −0.852 |
| F.Stromal | RPS26 | −0.666 | 7.83E−15 | −3.25E−01 | 1.12E−16 | −0.646 |
| F.Stromal | S100A10 | 0.447 | 2.43E−09 | 4.83E−01 | 9.92E−23 | 0.558 |
| F.Stromal | S100A6 | 0.162 | 1.84E−01 | 5.76E−01 | 2.03E−30 | 0.503 |
| F.Stromal | TMSB10 | 0.385 | 2.10E−02 | 4.72E−01 | 3.46E−30 | 0.736 |
| F.Villus | COL3A1 | 1.221 | 2.23E−11 | 5.24E−01 | 5.11E−12 | 0.746 |
| F.Villus | DCN | 1.537 | 3.42E−30 | 3.62E−01 | 1.30E−03 | 1.307 |
| F.Villus | IGFBP7 | 1.049 | 1.07E−03 | 9.90E−01 | 4.40E−19 | 1.542 |
| F.Villus | PLAC9 | 1.552 | 8.20E−31 | 2.20E−01 | 2.27E−03 | 0.669 |
| F.Villus | TIMP1 | 1.228 | 3.53E−08 | 1.21E+00 | 1.69E−49 | 1.394 |
| F.Villus_1 | DCN | 2.175 | 1.34E−21 | 5.02E−01 | 6.38E−03 | 2.265 |
| F.Villus_1 | LUM | 2.080 | 7.39E−23 | 5.76E−01 | 3.15E−02 | 2.117 |
| F.Villus_1 | TIMP1 | 1.842 | 1.31E−06 | 1.49E+00 | 1.35E−30 | 2.426 |
| F.Villus_2 | PLAC9 | 1.583 | 1.57E−19 | 2.01E−01 | 4.07E−02 | 0.794 |
| F.Villus_2 | TIMP1 | 0.864 | 1.72E−03 | 1.01E+00 | 2.78E−20 | 0.965 |
| I.Immune | AC009501.4 | −0.856 | 2.31E−50 | 5.93E−02 | 1.52E−01 | −0.784 |
| I.Immune | IGHA2 | −0.760 | 7.42E−37 | −9.80E−01 | 3.00E−21 | −0.646 |
| I.Lymphoid | AC009501.4 | −0.789 | 3.67E−43 | 3.15E−02 | 4.45E−01 | −0.773 |
| I.Lymphoid | ANXA1 | −0.548 | 3.52E−20 | −1.52E−01 | 1.05E−02 | −0.526 |
| I.Lymphoid | DHRS9 | 1.968 | 3.85E−20 | −6.42E−02 | 7.68E−01 | 0.711 |
| I.Lymphoid | IGHA2 | −0.653 | 8.92E−28 | −7.76E−01 | 5.33E−13 | −0.522 |
| M.CD69pos_Mast | SAMSN1 | 1.332 | 4.44E−18 | 3.55E−01 | 2.81E−06 | 1.064 |
| M.CD69pos_Mast | SRGN | 1.688 | 7.65E−12 | 5.22E−01 | 1.72E−09 | 2.121 |
| M.Macrophages | FTL | −1.951 | 3.23E−03 | −6.58E−01 | 6.94E−21 | −2.086 |
| M.Mast | PPAP2A | 2.425 | 1.61E−23 | 1.70E−01 | 4.90E−01 | 1.631 |
| M.Mast | SAMSN1 | 1.258 | 1.50E−17 | 3.46E−01 | 9.27E−07 | 0.886 |
| M.Mast | SRGN | 1.668 | 2.53E−12 | 5.90E−01 | 3.29E−13 | 2.145 |
| M.Monocytes | AC009501.4 | −0.751 | 1.25E−16 | 2.40E−01 | 3.36E−05 | −0.601 |
| M.Monocytes | CD300E | 4.435 | 1.27E−19 | | 1.00E+00 | 2.268 |
| M.Monocytes | CD74 | −0.857 | 1.69E−02 | −6.80E−01 | 5.05E−25 | −0.651 |
| M.Monocytes | CST3 | −0.938 | 4.63E−06 | 1.04E+00 | 6.47E−92 | −0.611 |
| M.Monocytes | RGS1 | −0.963 | 9.92E−27 | 1.23E−01 | 1.00E−01 | −0.519 |
| M.Myeloid | CD300E | 4.420 | 1.39E−19 | | 1.00E+00 | 2.065 |
| M.Myeloid | IL2RG | 0.761 | 5.19E−14 | 4.04E−01 | 6.77E−08 | 0.550 |
| M.Myeloid | JUNB | −0.815 | 2.96E−18 | −1.46E−01 | 9.95E−03 | −0.708 |
| M.Myeloid | SH3BGRL3 | 0.359 | 2.28E−04 | 4.97E−01 | 3.22E−29 | 0.522 |
| M.Myeloid | TMEM176B | 0.775 | 8.35E−22 | 1.47E−01 | 1.92E−02 | 0.518 |
| M.Neutrophils | CST3 | −1.508 | 6.90E−03 | −1.84E+00 | 4.29E−28 | −1.016 |
| M.Neutrophils | TIMP1 | 0.622 | 6.08E−02 | 1.91E+00 | 6.49E−24 | 1.077 |
| T.Activated_CD4_hiFos | RPL39 | 0.601 | 2.66E−06 | 1.20E+00 | 1.09E−18 | 0.570 |
| T.Activated_CD4_loFos | ANXA1 | −2.040 | 5.80E−37 | −4.49E−01 | 1.65E−06 | −1.270 |
| T.Activated_CD4_loFos | RPL39 | 0.499 | 1.23E−04 | 1.29E+00 | 9.00E−22 | 0.557 |
| T.Activated_CD4_loFos | RPS29 | 0.391 | 9.55E−02 | 7.71E−01 | 1.98E−20 | 0.680 |
| T.CD4 | AC009501.4 | −0.674 | 2.50E−27 | 1.01E−01 | 3.23E−02 | −0.590 |
| T.CD4 | ACP5 | 1.065 | 7.77E−22 | 6.83E−02 | 5.52E−01 | 0.628 |
| T.CD4 | ANXA1 | −1.551 | 6.16E−138 | −4.15E−01 | 4.74E−14 | −0.969 |
| T.CD4 | CCL5 | −1.068 | 1.87E−64 | 5.50E−02 | 4.40E−01 | −0.675 |
| T.CD4 | CXCL13 | 4.921 | 3.71E−40 | | 1.00E+00 | 1.584 |
| T.CD4 | MT-ND3 | 0.741 | 2.99E−30 | 6.72E−01 | 1.16E−16 | 0.679 |
| T.CD4 | NPDC1 | 2.292 | 9.11E−30 | −3.40E−01 | 1.27E−01 | 0.730 |
| T.CD4 | RPL10 | −0.862 | 3.17E−03 | −3.97E−01 | 7.90E−40 | −1.413 |
| T.CD4 | RPL13A | −0.805 | 3.03E−03 | −2.81E−01 | 2.44E−21 | −1.161 |
| T.CD4 | RPL3 | −0.487 | 3.75E−02 | −3.65E−01 | 1.02E−31 | −0.779 |

TABLE 13-continued

Inflamed vs Healthy Markers

| | | | | | | |
|---|---|---|---|---|---|---|
| T.CD4 | RPS18 | −0.525 | 3.46E−02 | −3.14E−01 | 1.77E−22 | −0.857 |
| T.CD4 | RPS2 | −0.381 | 1.44E−01 | −3.47E−01 | 9.61E−25 | −0.701 |
| T.CD4 | RPS3 | −0.379 | 4.81E−02 | −3.89E−01 | 1.29E−38 | −0.531 |
| T.CD4 | RPS6 | −0.737 | 2.86E−03 | −3.12E−01 | 1.45E−22 | −1.117 |
| T.CD4 | SRGN | 0.451 | 3.54E−09 | 3.10E−01 | 8.66E−18 | 0.604 |
| T.CD4 | VIM | −0.782 | 2.19E−38 | −2.27E−01 | 3.69E−06 | −0.853 |
| T.CD8 | ANXA1 | −0.806 | 1.03E−25 | −3.22E−01 | 2.67E−06 | −0.760 |
| T.CD8 | CD2 | 0.761 | 8.07E−20 | 3.65E−01 | 3.50E−19 | 0.632 |
| T.CD8 | CD63 | −0.780 | 2.66E−21 | −3.56E−01 | 4.41E−11 | −0.689 |
| T.CD8 | FOS | −0.623 | 2.75E−15 | −3.31E−01 | 1.24E−06 | −0.559 |
| T.CD8 | GADD45G | 1.698 | 2.47E−22 | 1.85E−01 | 2.17E−01 | 0.548 |
| T.CD8 | HLA-B | 0.858 | 1.33E−03 | 4.19E−01 | 1.45E−22 | 1.265 |
| T.CD8 | RPL3 | −0.622 | 5.58E−02 | −4.10E−01 | 8.03E−22 | −1.003 |
| T.CD8 | RPL8 | −0.736 | 7.33E−05 | −3.74E−01 | 2.23E−23 | −0.824 |
| T.CD8 | RPS29 | 0.341 | 4.24E−03 | 4.98E−01 | 7.90E−24 | 0.524 |
| T.CD8 | TNFRSF4 | 1.540 | 7.08E−20 | 4.29E−01 | 2.87E−02 | 0.655 |
| T.CD8 | ZFP36 | −0.737 | 4.37E−20 | −2.73E−01 | 7.01E−07 | −0.535 |
| T.CD8_IELs | KLRB1 | 1.674 | 1.58E−25 | 1.11E+00 | 1.72E−14 | 1.381 |
| T.CD8_LP | ANXA1 | −1.174 | 2.14E−22 | −4.29E−01 | 1.37E−06 | −1.040 |
| T.CD8_LP | CD27 | 0.900 | 8.38E−15 | 4.65E−01 | 6.62E−10 | 0.522 |
| T.CD8_LP | CST7 | 0.910 | 7.31E−14 | 2.98E−01 | 3.74E−08 | 0.519 |
| T.CD8_LP | RPL39 | 0.594 | 1.71E−07 | 9.88E−01 | 4.26E−14 | 0.553 |
| T.Cycling_T | CXCR6 | 2.805 | 1.15E−19 | 7.05E−01 | 4.74E−03 | 1.903 |
| T.Memory_CD4 | ANXA1 | −1.660 | 1.40E−40 | −4.97E−01 | 2.42E−04 | −1.223 |
| T.Memory_CD4 | CCL5 | −1.316 | 1.96E−21 | −2.16E−01 | 2.97E−01 | −1.076 |
| T.Memory_CD4 | TOX2 | 3.301 | 9.76E−21 | 4.04E−01 | 3.30E−01 | 0.543 |
| T.Tcells | AC009501.4 | −0.910 | 4.89E−56 | 4.51E−02 | 2.76E−01 | −0.815 |
| T.Tcells | ANXA1 | −0.849 | 1.27E−49 | −1.73E−01 | 6.37E−04 | −0.615 |
| T.Tcells | CTSH | 1.589 | 1.59E−25 | −6.19E−02 | 6.77E−01 | 0.605 |
| T.Tcells | CXCL13 | 4.630 | 3.60E−29 | | 1.00E+00 | 1.874 |
| T.Tcells | NPDC1 | 2.424 | 2.51E−27 | −2.81E−01 | 3.16E−01 | 0.897 |
| T.Tcells | SRGN | 0.583 | 1.62E−16 | 3.28E−01 | 8.70E−22 | 0.664 |
| T.Tcells | TMSB4X | −1.614 | 6.61E−03 | −3.91E−01 | 8.77E−32 | −2.065 |
| T.Tcells | VIM | −0.618 | 2.92E−27 | −7.84E−02 | 6.91E−02 | −0.669 |
| T.Tregs | CD7 | 1.258 | 3.50E−22 | 6.20E−01 | 4.06E−14 | 1.382 |
| T.Tregs | LINC00152 | 1.269 | 6.98E−23 | 3.66E−01 | 1.55E−06 | 0.749 |
| T.Tregs | MIR4435-1HG | 1.248 | 1.64E−21 | 3.03E−01 | 7.06E−05 | 0.533 |

| ident | pvalH | n | ref_n | mu | ref_mu | total | ref_total |
|---|---|---|---|---|---|---|---|
| B.Bcells | 1.04E−38 | 483 | 1399 | 2.242 | 2.300 | 0.045 | 0.136 |
| B.Bcells | 8.87E−74 | 498 | 432 | 1.766 | 2.020 | 0.148 | 0.154 |
| B.Bcells | 5.35E−52 | 450 | 439 | 2.304 | 1.853 | 0.141 | 0.100 |
| B.Bcells | 4.21E−189 | 1205 | 1893 | 4.576 | 3.181 | 0.174 | 0.104 |
| B.Bcells | 8.84E−89 | 815 | 780 | 2.462 | 2.103 | 0.215 | 0.160 |
| B.Bcells | 1.73E−67 | 412 | 261 | 2.558 | 2.798 | 0.134 | 0.100 |
| B.Bcells | 1.01E−110 | 1105 | 1696 | 3.373 | 2.914 | 0.154 | 0.172 |
| B.Bcells | 1.50E−111 | 928 | 1091 | 3.250 | 2.626 | 0.175 | 0.134 |
| B.Bcells | 6.18E−144 | 1210 | 1891 | 3.572 | 2.654 | 0.192 | 0.159 |
| B.Bcells | 4.50E−104 | 802 | 713 | 2.586 | 2.009 | 0.182 | 0.109 |
| B.Bcells | 5.45E−109 | 1197 | 1847 | 3.031 | 2.347 | 0.109 | 0.105 |
| B.Bcells | 1.18E−46 | 174 | 44 | 1.913 | 1.716 | 0.163 | 0.036 |
| B.Bcells | 1.38E−64 | 757 | 743 | 2.158 | 1.906 | 0.152 | 0.126 |
| B.Bcells | 8.67E−80 | 750 | 806 | 2.343 | 1.813 | 0.120 | 0.089 |
| B.Bcells | 4.24E−91 | 854 | 1210 | 3.282 | 3.224 | 0.225 | 0.306 |
| B.Bcells | 1.35E−130 | 820 | 1150 | 4.566 | 4.059 | 0.211 | 0.209 |
| B.Bcells | 2.09E−120 | 933 | 1229 | 3.044 | 2.562 | 0.294 | 0.277 |
| B.Bcells | 3.30E−125 | 1225 | 1949 | 4.009 | 2.968 | 0.121 | 0.093 |
| B.Bcells | 7.49E−158 | 971 | 1157 | 3.959 | 3.249 | 0.250 | 0.182 |
| B.Bcells | 2.57E−82 | 640 | 451 | 3.255 | 3.056 | 0.199 | 0.122 |
| B.Bcells | 7.18E−87 | 277 | 27 | 2.057 | 1.822 | 0.302 | 0.025 |
| B.Bcells | 3.70E−21 | 48 | 0 | 0.632 | −17.176 | 0.031 | 0.000 |
| B.Bcells | 7.85E−72 | 470 | 383 | 2.264 | 2.448 | 0.113 | 0.105 |
| B.Bcells | 6.61E−145 | 1275 | 2048 | 4.351 | 3.203 | 0.117 | 0.085 |
| B.Bcells | 3.60E−38 | 154 | 39 | 1.755 | 1.769 | 0.148 | 0.038 |
| B.Bcells | 2.82E−41 | 155 | 68 | 1.830 | 0.739 | 0.079 | 0.016 |
| B.Bcells | 7.73E−62 | 708 | 864 | 2.165 | 2.088 | 0.173 | 0.200 |
| B.Bcells | 8.58E−80 | 1248 | 2005 | 3.488 | 2.912 | 0.109 | 0.118 |
| B.Bcells | 3.28E−81 | 865 | 854 | 2.952 | 2.811 | 0.260 | 0.233 |
| B.Bcells | 2.71E−63 | 992 | 1484 | 4.370 | 4.045 | 0.204 | 0.244 |
| B.Bcells | 2.64E−61 | 843 | 1074 | 4.756 | 4.445 | 0.214 | 0.220 |
| B.Bcells | 7.95E−79 | 779 | 908 | 4.032 | 3.601 | 0.276 | 0.239 |
| B.Bcells | 3.96E−47 | 957 | 1404 | 5.906 | 5.712 | 0.213 | 0.273 |
| B.Bcells | 4.69E−68 | 918 | 1220 | 5.136 | 4.581 | 0.230 | 0.208 |
| B.Bcells | 8.27E−48 | 204 | 77 | 2.496 | 2.746 | 0.119 | 0.054 |
| B.Bcells | 2.07E−180 | 992 | 2293 | 10.016 | 10.713 | 0.167 | 0.624 |
| B.Bcells | 8.01E−210 | 645 | 2002 | 7.927 | 9.053 | 0.111 | 0.750 |
| B.Bcells | 1.21E−127 | 911 | 2160 | 8.371 | 9.095 | 0.157 | 0.616 |

TABLE 13-continued

| | Inflamed vs Healthy Markers | | | | | | |
|---|---|---|---|---|---|---|---|
| B.Bcells | 9.10E−78 | 374 | 195 | 2.116 | 1.882 | 0.213 | 0.095 |
| B.Bcells | 4.00E−120 | 727 | 651 | 3.945 | 3.519 | 0.295 | 0.197 |
| B.Bcells | 2.59E−88 | 458 | 209 | 2.385 | 2.686 | 0.262 | 0.147 |
| B.Bcells | 9.96E−110 | 762 | 795 | 3.149 | 2.853 | 0.295 | 0.251 |
| B.Bcells | 1.12E−66 | 945 | 1525 | 2.304 | 1.948 | 0.149 | 0.188 |
| B.Bcells | 6.26E−26 | 156 | 73 | 1.943 | 2.469 | 0.087 | 0.059 |
| B.Bcells | 1.39E−50 | 631 | 748 | 4.703 | 4.629 | 0.216 | 0.244 |
| B.Bcells | 1.38E−44 | 838 | 1094 | 3.810 | 3.127 | 0.073 | 0.059 |
| B.Bcells | 2.52E−56 | 1010 | 1516 | 2.836 | 2.441 | 0.092 | 0.105 |
| B.Bcells | 2.40E−90 | 820 | 864 | 2.757 | 1.961 | 0.151 | 0.092 |
| B.Bcells | 8.51E−86 | 1095 | 1476 | 2.904 | 2.239 | 0.119 | 0.101 |
| B.Bcells | 1.01E−80 | 413 | 262 | 1.918 | 1.807 | 0.199 | 0.117 |
| B.Bcells | 3.65E−81 | 936 | 1235 | 2.460 | 1.948 | 0.163 | 0.151 |
| B.Bcells | 1.34E−79 | 484 | 297 | 2.028 | 2.371 | 0.138 | 0.107 |
| B.Bcells | 4.97E−138 | 1100 | 1723 | 3.484 | 2.776 | 0.236 | 0.226 |
| B.Bcells | 3.65E−95 | 910 | 1223 | 2.569 | 2.128 | 0.209 | 0.207 |
| B.Bcells | 9.44E−43 | 892 | 1968 | 1.978 | 2.456 | 0.060 | 0.183 |
| B.Bcells | 2.50E−75 | 1284 | 2234 | 3.998 | 3.235 | 0.115 | 0.118 |
| B.Bcells | 6.56E−68 | 1309 | 2259 | 4.110 | 3.482 | 0.110 | 0.123 |
| B.Bcells | 3.32E−50 | 380 | 272 | 2.055 | 1.696 | 0.163 | 0.091 |
| B.Bcells | 4.71E−50 | 352 | 269 | 3.503 | 2.736 | 0.235 | 0.106 |
| B.Bcells | 5.59E−20 | 85 | 20 | 1.440 | 2.189 | 0.086 | 0.034 |
| B.Bcells | 7.87E−80 | 688 | 594 | 2.676 | 2.613 | 0.241 | 0.199 |
| B.Cycling | 1.73E−84 | 247 | 174 | 7.126 | 5.318 | 0.092 | 0.018 |
| B.Cycling | 5.54E−43 | 240 | 144 | 5.178 | 4.016 | 0.073 | 0.020 |
| B.Cycling | 3.85E−23 | 209 | 76 | 2.861 | 2.359 | 0.112 | 0.029 |
| B.Cycling | 1.45E−42 | 231 | 133 | 3.844 | 2.892 | 0.070 | 0.021 |
| B.Cycling | 8.02E−24 | 212 | 91 | 3.597 | 3.114 | 0.076 | 0.023 |
| B.Cycling | 5.71E−47 | 240 | 151 | 4.273 | 3.328 | 0.093 | 0.030 |
| B.Cycling | 2.73E−29 | 229 | 120 | 3.523 | 2.612 | 0.064 | 0.018 |
| B.Cycling | 4.99E−23 | 206 | 61 | 2.958 | 2.422 | 0.088 | 0.018 |
| B.Cycling | 1.52E−32 | 190 | 93 | 3.093 | 2.225 | 0.132 | 0.035 |
| B.Cycling | 2.41E−49 | 222 | 99 | 4.402 | 3.454 | 0.135 | 0.031 |
| B.Cycling | 2.67E−54 | 249 | 171 | 5.563 | 4.394 | 0.067 | 0.020 |
| B.Cycling | 9.31E−40 | 240 | 162 | 4.498 | 3.578 | 0.140 | 0.050 |
| B.Cycling | 7.15E−19 | 206 | 93 | 3.988 | 3.518 | 0.063 | 0.021 |
| B.Cycling | 4.55E−24 | 217 | 86 | 5.384 | 4.656 | 0.071 | 0.017 |
| B.Cycling | 3.18E−55 | 244 | 143 | 4.953 | 3.918 | 0.136 | 0.039 |
| B.Cycling | 2.29E−26 | 221 | 94 | 4.563 | 4.045 | 0.293 | 0.087 |
| B.Cycling | 4.80E−31 | 235 | 119 | 3.988 | 3.437 | 0.131 | 0.045 |
| B.Cycling | 1.85E−61 | 236 | 128 | 4.838 | 3.643 | 0.207 | 0.049 |
| B.Cycling | 1.80E−37 | 238 | 153 | 4.078 | 3.108 | 0.068 | 0.022 |
| B.Cycling | 1.11E−34 | 227 | 117 | 3.716 | 2.806 | 0.081 | 0.022 |
| B.Cycling | 1.06E−26 | 216 | 102 | 2.854 | 1.895 | 0.069 | 0.017 |
| B.Cycling | 3.25E−26 | 173 | 53 | 3.612 | 3.180 | 0.109 | 0.025 |
| B.Cycling | 2.36E−19 | 140 | 24 | 2.164 | 1.371 | 0.228 | 0.023 |
| B.Cycling | 6.13E−21 | 154 | 31 | 2.328 | 2.730 | 0.136 | 0.036 |
| B.Cycling | 6.63E−21 | 220 | 91 | 3.354 | 2.544 | 0.064 | 0.015 |
| B.Cycling | 4.43E−23 | 220 | 115 | 3.195 | 2.347 | 0.073 | 0.021 |
| B.Cycling | 5.09E−25 | 188 | 61 | 2.981 | 2.794 | 0.134 | 0.038 |
| B.Cycling | 3.95E−23 | 161 | 31 | 3.630 | 2.981 | 0.363 | 0.045 |
| B.Cycling | 1.51E−21 | 187 | 80 | 2.718 | 2.124 | 0.076 | 0.021 |
| B.Cycling | 1.01E−23 | 173 | 85 | 2.356 | 1.536 | 0.148 | 0.041 |
| B.Cycling | 1.37E−24 | 238 | 154 | 4.104 | 3.464 | 0.070 | 0.029 |
| B.Cycling | 1.88E−33 | 213 | 91 | 3.527 | 2.469 | 0.090 | 0.018 |
| B.Cycling | 5.24E−28 | 201 | 90 | 2.794 | 2.002 | 0.093 | 0.024 |
| B.Cycling | 1.04E−27 | 224 | 114 | 3.694 | 2.991 | 0.110 | 0.034 |
| B.Cycling | 2.82E−21 | 187 | 96 | 4.783 | 3.306 | 0.068 | 0.013 |
| B.Cycling | 1.72E−20 | 218 | 84 | 3.978 | 3.890 | 0.237 | 0.086 |
| B.Cycling | 2.42E−39 | 238 | 124 | 4.983 | 4.198 | 0.137 | 0.041 |
| B.Cycling | 9.78E−42 | 230 | 99 | 4.397 | 3.556 | 0.175 | 0.042 |
| B.FO | 8.53E−24 | 157 | 191 | 2.338 | 2.889 | 0.082 | 0.146 |
| B.FO | 4.61E−29 | 185 | 172 | 2.828 | 2.996 | 0.103 | 0.108 |
| B.FO | 1.07E−42 | 346 | 886 | 6.547 | 5.472 | 0.077 | 0.093 |
| B.FO | 5.91E−33 | 320 | 636 | 4.777 | 3.888 | 0.067 | 0.071 |
| B.FO | 1.32E−19 | 135 | 153 | 2.756 | 3.301 | 0.060 | 0.099 |
| B.FO | 4.79E−20 | 308 | 663 | 3.749 | 3.828 | 0.071 | 0.162 |
| B.FO | 1.67E−19 | 256 | 441 | 3.575 | 3.342 | 0.077 | 0.113 |
| B.FO | 5.19E−21 | 64 | 22 | 2.335 | 2.708 | 0.086 | 0.038 |
| B.FO | 1.30E−19 | 185 | 216 | 3.051 | 3.392 | 0.120 | 0.178 |
| B.FO | 6.21E−22 | 216 | 330 | 2.583 | 3.130 | 0.086 | 0.191 |
| B.FO | 1.07E−37 | 298 | 736 | 4.974 | 4.587 | 0.122 | 0.231 |
| B.FO | 9.69E−29 | 269 | 464 | 3.294 | 3.481 | 0.140 | 0.274 |
| B.FO | 2.17E−21 | 86 | 46 | 2.090 | 2.916 | 0.068 | 0.064 |
| B.FO | 1.09E−39 | 305 | 593 | 4.035 | 3.817 | 0.113 | 0.189 |
| B.FO | 2.77E−23 | 222 | 293 | 3.507 | 3.312 | 0.104 | 0.120 |
| B.FO | 9.81E−33 | 71 | 3 | 2.270 | 2.417 | 0.112 | 0.005 |
| B.FO | 1.79E−18 | 76 | 28 | 1.912 | 2.337 | 0.106 | 0.052 |

TABLE 13-continued

| | Inflamed vs Healthy Markers | | | | | | |
|---|---|---|---|---|---|---|---|
| B.FO | 4.13E−26 | 174 | 198 | 2.430 | 3.137 | 0.057 | 0.106 |
| B.FO | 1.15E−19 | 63 | 17 | 2.007 | 2.685 | 0.081 | 0.035 |
| B.FO | 6.68E−31 | 81 | 15 | 2.190 | 2.182 | 0.062 | 0.011 |
| B.FO | 5.23E−28 | 65 | 6 | 1.842 | 2.346 | 0.148 | 0.019 |
| B.FO | 8.78E−20 | 199 | 311 | 2.591 | 2.886 | 0.058 | 0.112 |
| B.FO | 1.78E−40 | 209 | 240 | 2.609 | 2.695 | 0.101 | 0.124 |
| B.FO | 3.07E−20 | 158 | 202 | 2.279 | 2.676 | 0.104 | 0.175 |
| B.FO | 8.54E−19 | 109 | 105 | 2.143 | 2.803 | 0.031 | 0.047 |
| B.FO | 1.04E−22 | 347 | 882 | 5.567 | 5.194 | 0.053 | 0.104 |
| B.FO | 1.31E−28 | 81 | 34 | 2.751 | 2.799 | 0.066 | 0.029 |
| B.FO | 2.61E−22 | 135 | 655 | 8.300 | 7.716 | 0.080 | 0.258 |
| B.FO | 1.06E−19 | 165 | 171 | 2.806 | 2.748 | 0.078 | 0.078 |
| B.FO | 5.92E−39 | 140 | 70 | 2.395 | 2.901 | 0.121 | 0.086 |
| B.FO | 2.11E−40 | 278 | 466 | 4.067 | 3.725 | 0.161 | 0.213 |
| B.FO | 6.19E−25 | 139 | 115 | 2.181 | 2.949 | 0.097 | 0.137 |
| B.FO | 4.78E−30 | 249 | 388 | 3.235 | 3.400 | 0.145 | 0.254 |
| B.FO | 1.00E−20 | 251 | 426 | 2.947 | 3.109 | 0.083 | 0.157 |
| B.FO | 6.31E−20 | 149 | 153 | 2.368 | 3.076 | 0.047 | 0.079 |
| B.FO | 1.65E−28 | 139 | 97 | 1.987 | 2.737 | 0.099 | 0.116 |
| B.FO | 1.57E−30 | 166 | 157 | 2.351 | 2.981 | 0.072 | 0.105 |
| B.FO | 6.28E−37 | 301 | 615 | 4.006 | 3.826 | 0.125 | 0.226 |
| B.FO | 2.83E−22 | 249 | 406 | 2.957 | 3.220 | 0.098 | 0.192 |
| B.FO | 2.31E−21 | 205 | 336 | 3.024 | 3.304 | 0.142 | 0.283 |
| B.FO | 1.36E−19 | 131 | 137 | 3.426 | 2.895 | 0.069 | 0.050 |
| B.FO | 4.87E−26 | 157 | 137 | 2.445 | 2.712 | 0.124 | 0.131 |
| B.FO | 1.32E−24 | 107 | 60 | 2.219 | 2.971 | 0.061 | 0.058 |
| B.FO | 1.17E−20 | 109 | 72 | 1.997 | 2.474 | 0.043 | 0.040 |
| B.GC | 3.38E−20 | 184 | 94 | 7.326 | 6.520 | 0.079 | 0.023 |
| B.GC | 1.04E−20 | 176 | 62 | 4.966 | 4.158 | 0.107 | 0.021 |
| B.GC | 1.14E−19 | 168 | 48 | 4.267 | 3.147 | 0.187 | 0.025 |
| B.Plasma | 1.27E−28 | 72 | 11 | 1.428 | −0.956 | 0.061 | 0.002 |
| B.Plasma | 2.63E−150 | 513 | 1325 | 10.681 | 11.221 | 0.162 | 0.606 |
| B.Plasma | 5.56E−177 | 443 | 1319 | 8.371 | 9.410 | 0.118 | 0.720 |
| B.Plasma | 1.78E−118 | 509 | 1326 | 8.796 | 9.476 | 0.144 | 0.601 |
| B.Plasma | 5.02E−20 | 47 | 10 | 3.860 | 0.076 | 0.161 | 0.002 |
| B.Plasma | 2.94E−25 | 349 | 1113 | 2.132 | 2.616 | 0.056 | 0.252 |
| B.Plasma | 1.44E−24 | 430 | 1235 | 1.500 | 1.718 | 0.025 | 0.083 |
| E.Absorptive | 3.63E−67 | 96 | 1244 | 3.047 | 2.477 | 0.017 | 0.146 |
| E.Absorptive | 2.65E−21 | 368 | 1671 | 7.505 | 7.222 | 0.048 | 0.179 |
| E.Absorptive | 1.21E−42 | 190 | 387 | 1.659 | 1.214 | 0.063 | 0.094 |
| E.Absorptive | 5.55E−32 | 88 | 17 | −0.143 | 0.976 | 0.035 | 0.015 |
| E.Absorptive | 1.59E−43 | 258 | 628 | 1.227 | 0.982 | 0.034 | 0.071 |
| E.Absorptive | 2.53E−33 | 305 | 1551 | 3.289 | 4.431 | 0.035 | 0.393 |
| E.Absorptive | 3.05E−49 | 98 | 14 | 4.137 | 1.495 | 0.224 | 0.005 |
| E.Absorptive | 1.67E−21 | 65 | 25 | 0.004 | 0.987 | 0.017 | 0.013 |
| E.Absorptive | 1.41E−19 | 39 | 4 | 0.106 | 0.014 | 0.024 | 0.002 |
| E.Absorptive | 6.06E−21 | 53 | 21 | 0.786 | 0.777 | 0.060 | 0.023 |
| E.Absorptive | 1.28E−32 | 339 | 1314 | 3.011 | 2.752 | 0.057 | 0.184 |
| E.Absorptive | 9.74E−40 | 368 | 1639 | 5.426 | 4.978 | 0.048 | 0.156 |
| E.Absorptive | 5.58E−67 | 294 | 498 | 2.895 | 1.921 | 0.029 | 0.025 |
| E.Absorptive | 1.89E−28 | 336 | 1328 | 2.345 | 2.218 | 0.035 | 0.127 |
| E.Absorptive | 3.06E−35 | 251 | 1384 | 2.155 | 3.528 | 0.019 | 0.264 |
| E.Absorptive | 4.77E−33 | 54 | 0 | 2.628 | −16.350 | 0.305 | 0.000 |
| E.Absorptive | 1.89E−20 | 74 | 87 | 2.443 | 1.702 | 0.089 | 0.062 |
| E.Absorptive | 2.35E−43 | 219 | 378 | 2.533 | 1.516 | 0.027 | 0.023 |
| E.Absorptive | 9.93E−59 | 265 | 638 | 1.643 | 1.188 | 0.053 | 0.093 |
| E.Absorptive | 4.23E−45 | 344 | 1349 | 2.750 | 2.245 | 0.034 | 0.093 |
| E.Absorptive | 5.24E−40 | 291 | 857 | 1.725 | 1.341 | 0.034 | 0.077 |
| E.Absorptive | 1.68E−19 | 367 | 1664 | 5.041 | 5.531 | 0.048 | 0.303 |
| E.Absorptive | 7.19E−24 | 60 | 7 | −0.129 | 0.206 | 0.061 | 0.009 |
| E.Absorptive | 1.86E−24 | 54 | 0 | 4.033 | −16.350 | 0.787 | 0.000 |
| E.Absorptive | 2.07E−114 | 348 | 1120 | 3.784 | 2.433 | 0.184 | 0.233 |
| E.Absorptive | 1.59E−26 | 53 | 2 | −0.482 | 2.042 | 0.038 | 0.008 |
| E.Absorptive | 1.33E−24 | 69 | 44 | 0.194 | 0.781 | 0.030 | 0.029 |
| E.Absorptive | 8.20E−35 | 95 | 29 | 0.344 | 0.063 | 0.098 | 0.025 |
| E.Absorptive | 6.88E−20 | 85 | 89 | 0.778 | 0.921 | 0.042 | 0.049 |
| E.Absorptive | 1.36E−64 | 245 | 306 | 3.534 | 1.581 | 0.107 | 0.035 |
| E.Absorptive | 3.60E−32 | 198 | 380 | 0.437 | 0.549 | 0.017 | 0.035 |
| E.Absorptive | 2.80E−49 | 281 | 838 | 1.844 | 1.287 | 0.044 | 0.089 |
| E.Absorptive | 1.14E−50 | 346 | 1269 | 2.922 | 2.023 | 0.059 | 0.117 |
| E.Absorptive | 1.05E−83 | 298 | 675 | 2.781 | 2.124 | 0.100 | 0.144 |
| E.Absorptive | 7.50E−46 | 100 | 21 | 3.802 | 0.828 | 0.058 | 0.002 |
| E.Absorptive | 2.22E−68 | 249 | 318 | 2.422 | 1.037 | 0.071 | 0.035 |
| E.Absorptive | 3.20E−94 | 259 | 597 | 3.764 | 1.869 | 0.067 | 0.042 |
| E.Absorptive | 1.62E−20 | 371 | 1672 | 7.159 | 6.231 | 0.106 | 0.252 |
| E.Absorptive | 6.48E−38 | 78 | 3 | 2.437 | 0.683 | 0.116 | 0.001 |
| E.Absorptive | 2.00E−35 | 298 | 1066 | 4.479 | 3.742 | 0.111 | 0.238 |
| E.Absorptive | 1.02E−28 | 283 | 1390 | 2.314 | 2.850 | 0.018 | 0.131 |

TABLE 13-continued

| Inflamed vs Healthy Markers | | | | | | | |
|---|---|---|---|---|---|---|---|
| E.Absorptive | 8.49E−41 | 89 | 0 | 1.292 | 16.350 | 0.525 | 0.000 |
| E.Absorptive | 3.41E−37 | 90 | 123 | 1.233 | 0.242 | 0.030 | 0.021 |
| E.Absorptive | 3.92E−50 | 164 | 116 | 2.724 | 1.038 | 0.080 | 0.018 |
| E.Absorptive | 6.82E−77 | 282 | 511 | 3.886 | 2.445 | 0.134 | 0.089 |
| E.Absorptive | 6.35E−35 | 148 | 205 | 1.012 | 0.544 | 0.029 | 0.029 |
| E.Absorptive | 1.58E−23 | 40 | 0 | 0.468 | −16.350 | 0.127 | 0.000 |
| E.Absorptive | 3.03E−25 | 94 | 68 | 1.088 | 0.087 | 0.045 | 0.016 |
| E.Absorptive_All | 5.06E−183 | 499 | 1770 | 3.543 | 2.771 | 0.096 | 0.200 |
| E.Absorptive_All | 1.07E−103 | 1420 | 1658 | 4.318 | 3.137 | 0.192 | 0.099 |
| E.Absorptive_All | 1.07E−28 | 369 | 140 | 1.080 | 1.047 | 0.042 | 0.016 |
| E.Absorptive_All | 2.98E−40 | 196 | 11 | 0.329 | 0.516 | 0.083 | 0.005 |
| E.Absorptive_All | 8.56E−75 | 1546 | 2357 | 4.293 | 4.737 | 0.122 | 0.254 |
| E.Absorptive_All | 2.66E−88 | 344 | 23 | 3.817 | 1.783 | 0.413 | 0.007 |
| E.Absorptive_All | 6.90E−30 | 119 | 3 | 0.444 | −0.040 | 0.170 | 0.003 |
| E.Absorptive_All | 3.80E−71 | 1056 | 1138 | 2.072 | 1.589 | 0.084 | 0.065 |
| E.Absorptive_All | 3.95E−77 | 1522 | 2444 | 7.166 | 7.331 | 0.214 | 0.385 |
| E.Absorptive_All | 9.02E−37 | 856 | 1500 | 2.216 | 2.345 | 0.032 | 0.062 |
| E.Absorptive_All | 2.50E−26 | 105 | 5 | 0.881 | 0.092 | 0.090 | 0.002 |
| E.Absorptive_All | 3.01E−23 | 1735 | 2489 | 7.437 | 7.860 | 0.150 | 0.289 |
| E.Absorptive_All | 1.08E−71 | 1624 | 2409 | 4.913 | 5.477 | 0.066 | 0.146 |
| E.Absorptive_All | 3.03E−23 | 91 | 0 | 0.408 | −17.539 | 0.638 | 0.000 |
| E.Absorptive_All | 4.82E−35 | 1419 | 1960 | 3.283 | 2.913 | 0.073 | 0.078 |
| E.Absorptive_All | 3.80E−54 | 431 | 141 | 1.562 | 1.256 | 0.089 | 0.024 |
| E.Absorptive_All | 3.16E−22 | 160 | 36 | 0.933 | 1.601 | 0.042 | 0.015 |
| E.Absorptive_All | 3.42E−125 | 920 | 460 | 3.002 | 1.778 | 0.087 | 0.019 |
| E.Absorptive_All | 7.80E−22 | 69 | 0 | 2.368 | −17.539 | 0.257 | 0.000 |
| E.Absorptive_All | 6.50E−31 | 177 | 17 | 0.337 | 1.431 | 0.037 | 0.007 |
| E.Absorptive_All | 3.04E−73 | 773 | 591 | 2.612 | 1.755 | 0.084 | 0.036 |
| E.Absorptive_All | 7.60E−77 | 730 | 452 | 1.506 | 1.165 | 0.108 | 0.053 |
| E.Absorptive_All | 1.54E−46 | 843 | 1549 | 1.949 | 2.368 | 0.041 | 0.100 |
| E.Absorptive_All | 1.46E−21 | 76 | 0 | 0.542 | −17.539 | 0.169 | 0.000 |
| E.Absorptive_All | 3.29E−38 | 325 | 84 | 2.983 | 1.893 | 0.082 | 0.010 |
| E.Absorptive_All | 1.64E−23 | 93 | 0 | 3.614 | −17.539 | 0.846 | 0.000 |
| E.Absorptive_All | 1.12E−51 | 620 | 634 | 5.729 | 4.769 | 0.196 | 0.103 |
| E.Absorptive_All | 7.61E−35 | 1588 | 2402 | 4.612 | 4.908 | 0.127 | 0.236 |
| E.Absorptive_All | 1.04E−116 | 729 | 219 | 3.864 | 2.852 | 0.385 | 0.057 |
| E.Absorptive_All | 1.04E−39 | 159 | 2 | 0.058 | 1.779 | 0.118 | 0.005 |
| E.Absorptive_All | 3.45E−56 | 1691 | 2487 | 7.162 | 7.586 | 0.193 | 0.381 |
| E.Absorptive_All | 2.14E−274 | 1177 | 517 | 4.189 | 2.265 | 0.436 | 0.050 |
| E.Absorptive_All | 1.39E−28 | 1505 | 2317 | 4.054 | 4.443 | 0.135 | 0.272 |
| E.Absorptive_All | 1.83E−85 | 739 | 442 | 2.499 | 2.072 | 0.170 | 0.076 |
| E.Absorptive_All | 3.67E−46 | 155 | 3 | 2.961 | 1.219 | 0.259 | 0.002 |
| E.Absorptive_All | 1.17E−117 | 432 | 39 | 4.135 | 1.191 | 0.214 | 0.003 |
| E.Absorptive_All | 3.25E−102 | 833 | 482 | 2.349 | 1.403 | 0.161 | 0.048 |
| E.Absorptive_All | 2.68E−202 | 1159 | 957 | 3.596 | 2.147 | 0.197 | 0.060 |
| E.Absorptive_All | 1.74E−95 | 1745 | 2469 | 6.831 | 5.829 | 0.275 | 0.194 |
| E.Absorptive_All | 2.81E−65 | 259 | 3 | 2.452 | 1.956 | 0.265 | 0.002 |
| E.Absorptive_All | 0.00E+00 | 1060 | 152 | 3.259 | 1.072 | 0.406 | 0.013 |
| E.Absorptive_All | 1.13E−53 | 983 | 971 | 4.085 | 3.343 | 0.238 | 0.140 |
| E.Absorptive_All | 5.91E−55 | 1159 | 1974 | 2.878 | 3.300 | 0.078 | 0.177 |
| E.Absorptive_All | 3.95E−49 | 216 | 0 | 1.169 | −17.539 | 0.707 | 0.000 |
| E.Absorptive_All | 9.70E−52 | 255 | 89 | 1.308 | 0.390 | 0.076 | 0.014 |
| E.Absorptive_All | 2.95E−67 | 465 | 106 | 2.102 | 1.260 | 0.117 | 0.015 |
| E.Absorptive_All | 6.51E−168 | 910 | 319 | 3.398 | 2.057 | 0.183 | 0.025 |
| E.Absorptive_All | 3.72E−205 | 683 | 37 | 2.154 | 0.887 | 0.059 | 0.001 |
| E.Absorptive_All | 4.74E−59 | 213 | 2 | 2.231 | 0.680 | 0.657 | 0.002 |
| E.Absorptive_All | 1.02E−25 | 109 | 6 | 0.210 | 0.649 | 0.066 | 0.005 |
| E.Absorptive_All | 8.34E−31 | 325 | 165 | 0.971 | 0.712 | 0.056 | 0.024 |
| E.Absorptive_All | 9.55E−19 | 63 | 0 | 0.619 | −17.539 | 0.153 | 0.000 |
| E.Absorptive_All | 4.63E−21 | 82 | 0 | −0.334 | −17.539 | 0.382 | 0.000 |
| E.Absorptive_TA_1 | 6.59E−22 | 287 | 1127 | 4.349 | 4.683 | 0.038 | 0.188 |
| E.Absorptive_TA_1 | 9.35E−22 | 32 | 0 | 2.997 | −16.123 | 0.159 | 0.000 |
| E.Absorptive_TA_1 | 1.86E−32 | 48 | 0 | 4.117 | −16.123 | 0.280 | 0.000 |
| E.Absorptive_TA_1 | 2.17E−20 | 282 | 1113 | 4.277 | 4.599 | 0.032 | 0.156 |
| E.Absorptive_TA_1 | 3.94E−33 | 305 | 1175 | 4.861 | 5.329 | 0.041 | 0.218 |
| E.Absorptive_TA_1 | 5.38E−23 | 124 | 181 | 6.262 | 5.640 | 0.098 | 0.093 |
| E.Absorptive_TA_1 | 4.01E−53 | 158 | 124 | 3.474 | 2.132 | 0.107 | 0.033 |
| E.Absorptive_TA_1 | 2.90E−52 | 113 | 28 | 4.725 | 2.681 | 0.184 | 0.011 |
| E.Absorptive_TA_1 | 1.29E−49 | 89 | 10 | 5.391 | 2.272 | 0.137 | 0.002 |
| E.Absorptive_TA_1 | 1.17E−23 | 345 | 1190 | 5.632 | 6.131 | 0.028 | 0.139 |
| E.Absorptive_TA_1 | 5.40E−24 | 288 | 1114 | 4.851 | 5.283 | 0.024 | 0.127 |
| E.Absorptive_TA_1 | 1.45E−18 | 324 | 1160 | 4.973 | 5.378 | 0.034 | 0.159 |
| E.Absorptive_TA_1 | 7.17E−23 | 284 | 1135 | 4.886 | 5.183 | 0.038 | 0.186 |
| E.Absorptive_TA_1 | 1.97E−25 | 326 | 1166 | 5.373 | 5.832 | 0.030 | 0.146 |
| E.Absorptive_TA_1 | 1.05E−19 | 353 | 1201 | 6.053 | 6.492 | 0.036 | 0.167 |
| E.Absorptive_TA_1 | 2.64E−24 | 342 | 1178 | 5.895 | 6.451 | 0.032 | 0.162 |
| E.Absorptive_TA_1 | 1.39E−20 | 248 | 1066 | 4.626 | 4.803 | 0.030 | 0.147 |
| E.Absorptive_TA_1 | 2.31E−26 | 200 | 420 | 4.010 | 2.805 | 0.061 | 0.056 |

TABLE 13-continued

| Inflamed vs Healthy Markers | | | | | | | |
|---|---|---|---|---|---|---|---|
| E.Absorptive_TA_1 | 2.27E−63 | 118 | 16 | 3.177 | 2.420 | 0.090 | 0.007 |
| E.Absorptive_TA_1 | 1.88E−19 | 28 | 0 | 4.104 | −16.123 | 0.206 | 0.000 |
| E.Absorptive_TA_2 | 1.67E−49 | 108 | 978 | 2.753 | 2.209 | 0.016 | 0.099 |
| E.Absorptive_TA_2 | 5.72E−26 | 244 | 762 | 1.317 | 1.042 | 0.018 | 0.046 |
| E.Absorptive_TA_2 | 2.03E−32 | 230 | 709 | 1.100 | 0.888 | 0.020 | 0.052 |
| E.Absorptive_TA_2 | 1.04E−29 | 125 | 136 | 0.487 | 0.004 | 0.017 | 0.014 |
| E.Absorptive_TA_2 | 3.17E−27 | 80 | 33 | 3.099 | 1.067 | 0.101 | 0.010 |
| E.Absorptive_TA_2 | 3.39E−26 | 0 | 196 | 15.775 | 1.382 | 0.000 | 0.414 |
| E.Absorptive_TA_2 | 9.60E−35 | 179 | 1000 | 1.859 | 2.173 | 0.006 | 0.045 |
| E.Absorptive_TA_2 | 9.89E−63 | 285 | 1071 | 3.715 | 2.380 | 0.129 | 0.192 |
| E.Absorptive_TA_2 | 3.17E−36 | 236 | 723 | 2.088 | 1.210 | 0.021 | 0.035 |
| E.Absorptive_TA_2 | 1.48E−30 | 174 | 955 | 1.427 | 1.858 | 0.007 | 0.054 |
| E.Absorptive_TA_2 | 6.59E−27 | 286 | 1098 | 4.565 | 3.788 | 0.069 | 0.155 |
| E.Absorptive_TA_2 | 1.08E−21 | 284 | 1168 | 5.498 | 6.173 | 0.051 | 0.335 |
| E.Absorptive_TA_2 | 8.69E−134 | 260 | 393 | 2.514 | 0.418 | 0.092 | 0.033 |
| E.Absorptive_TA_2 | 4.16E−65 | 203 | 174 | 3.529 | 2.182 | 0.143 | 0.048 |
| E.Absorptive_TA_2 | 6.47E−27 | 52 | 0 | −0.858 | −15.775 | 0.028 | 0.000 |
| E.Absorptive_TA_2 | 4.48E−63 | 258 | 869 | 2.012 | 1.269 | 0.042 | 0.084 |
| E.Absorptive_TA_2 | 4.35E−74 | 181 | 98 | 4.252 | 1.520 | 0.207 | 0.017 |
| E.Absorptive_TA_2 | 2.15E−36 | 0 | 223 | −15.775 | 0.428 | 0.000 | 0.383 |
| E.Absorptive_TA_2 | 5.99E−156 | 275 | 640 | 4.217 | 1.691 | 0.176 | 0.071 |
| E.Absorptive_TA_2 | 3.72E−119 | 263 | 173 | 2.341 | 1.663 | 0.191 | 0.079 |
| E.Absorptive_TA_2 | 2.16E−31 | 194 | 453 | 1.214 | 0.782 | 0.022 | 0.037 |
| E.Absorptive_TA_2 | 5.48E−24 | 278 | 1099 | 2.848 | 2.347 | 0.047 | 0.130 |
| E.Absorptive_TA_2 | 1.17E−62 | 133 | 38 | 2.935 | 0.315 | 0.044 | 0.002 |
| E.Absorptive_TA_2 | 8.97E−33 | 217 | 469 | 1.352 | 0.707 | 0.033 | 0.046 |
| E.Absorptive_TA_2 | 1.52E−35 | 0 | 128 | −15.775 | 0.241 | 0.000 | 0.480 |
| E.Absorptive_TA_2 | 4.75E−20 | 277 | 1164 | 3.804 | 3.300 | 0.032 | 0.096 |
| E.Absorptive_TA_2 | 8.98E−21 | 287 | 1160 | 4.829 | 4.037 | 0.064 | 0.149 |
| E.Absorptive_TA_2 | 9.43E−84 | 282 | 1031 | 3.086 | 1.900 | 0.045 | 0.073 |
| E.Absorptive_TA_2 | 1.75E−23 | 288 | 1168 | 6.355 | 5.263 | 0.063 | 0.120 |
| E.Absorptive_TA_2 | 3.59E−28 | 67 | 3 | 1.502 | 1.961 | 0.049 | 0.003 |
| E.Absorptive_TA_2 | 3.81E−179 | 264 | 91 | 2.802 | 0.469 | 0.146 | 0.010 |
| E.Absorptive_TA_2 | 4.03E−27 | 162 | 295 | 0.156 | 0.557 | 0.014 | 0.033 |
| E.Absorptive_TA_2 | 7.64E−24 | 276 | 1102 | 3.102 | 2.616 | 0.024 | 0.068 |
| E.Absorptive_TA_2 | 2.21E−42 | 157 | 126 | 0.848 | 0.179 | 0.021 | 0.010 |
| E.Absorptive_TA_2 | 5.98E−24 | 280 | 1075 | 2.697 | 2.218 | 0.031 | 0.085 |
| E.Absorptive_TA_2 | 1.80E−23 | 79 | 19 | −0.213 | −0.276 | 0.035 | 0.008 |
| E.Absorptive_TA_2 | 1.86E−55 | 168 | 76 | 0.440 | 0.306 | 0.071 | 0.029 |
| E.Best4_Enterocytes | 2.05E−22 | 25 | 560 | 2.688 | 2.214 | 0.004 | 0.061 |
| E.Best4_Enterocytes | 1.82E−27 | 26 | 382 | 3.039 | 4.311 | 0.004 | 0.148 |
| E.Best4_Enterocytes | 2.45E−22 | 96 | 270 | 1.260 | 0.959 | 0.018 | 0.041 |
| E.Best4_Enterocytes | 7.78E−29 | 101 | 353 | 1.532 | 1.073 | 0.026 | 0.065 |
| E.Best4_Enterocytes | 9.26E−22 | 115 | 620 | 2.667 | 2.338 | 0.012 | 0.050 |
| E.Best4_Enterocytes | 1.81E−21 | 105 | 447 | 1.823 | 1.591 | 0.014 | 0.049 |
| E.Best4_Enterocytes | 3.05E−31 | 107 | 429 | 2.315 | 1.465 | 0.039 | 0.088 |
| E.Best4_Enterocytes | 6.68E−26 | 110 | 369 | 2.730 | 2.114 | 0.045 | 0.099 |
| E.Best4_Enterocytes | 2.87E−19 | 114 | 679 | 4.122 | 3.100 | 0.021 | 0.063 |
| E.Best4_Enterocytes | 1.99E−19 | 114 | 667 | 3.374 | 2.549 | 0.019 | 0.064 |
| E.Best4_Enterocytes | 7.59E−39 | 99 | 459 | 4.832 | 2.087 | 0.035 | 0.024 |
| E.Best4_Enterocytes | 2.80E−32 | 111 | 503 | 3.229 | 2.037 | 0.021 | 0.042 |
| E.Cycling_TA | 5.07E−54 | 192 | 73 | −0.165 | −0.156 | 0.064 | 0.024 |
| E.Cycling_TA | 3.68E−32 | 229 | 414 | 0.233 | 0.023 | 0.016 | 0.025 |
| E.Cycling_TA | 1.26E−65 | 295 | 772 | 1.373 | 0.610 | 0.023 | 0.036 |
| E.Cycling_TA | 7.50E−29 | 99 | 20 | −0.848 | −0.545 | 0.023 | 0.006 |
| E.Cycling_TA | 3.57E−43 | 290 | 712 | 0.945 | 0.435 | 0.038 | 0.066 |
| E.Cycling_TA | 2.72E−21 | 43 | 0 | 0.046 | −16.039 | 0.400 | 0.000 |
| E.Cycling_TA | 3.31E−41 | 300 | 884 | 1.345 | 0.986 | 0.019 | 0.043 |
| E.Cycling_TA | 2.46E−45 | 95 | 1 | 1.899 | −0.996 | 0.129 | 0.000 |
| E.Cycling_TA | 8.52E−60 | 335 | 1115 | 3.118 | 2.367 | 0.070 | 0.138 |
| E.Cycling_TA | 2.85E−25 | 0 | 196 | −16.039 | 1.191 | 0.000 | 0.437 |
| E.Cycling_TA | 2.76E−29 | 86 | 4 | 0.594 | −0.174 | 0.046 | 0.001 |
| E.Cycling_TA | 1.58E−26 | 331 | 1124 | 3.177 | 2.784 | 0.020 | 0.051 |
| E.Cycling_TA | 3.05E−44 | 185 | 168 | 0.709 | −0.238 | 0.027 | 0.013 |
| E.Cycling_TA | 1.83E−63 | 216 | 187 | 2.645 | 0.621 | 0.020 | 0.004 |
| E.Cycling_TA | 2.09E−63 | 300 | 721 | 1.352 | 0.729 | 0.034 | 0.053 |
| E.Cycling_TA | 2.00E−24 | 109 | 52 | −0.617 | 0.124 | 0.014 | 0.012 |
| E.Cycling_TA | 8.80E−54 | 313 | 920 | 1.986 | 0.980 | 0.026 | 0.038 |
| E.Cycling_TA | 2.28E−19 | 261 | 1008 | 1.140 | 1.931 | 0.009 | 0.062 |
| E.Cycling_TA | 2.25E−57 | 317 | 1010 | 2.274 | 1.402 | 0.041 | 0.072 |
| E.Cycling_TA | 9.20E−24 | 150 | 106 | 1.316 | 0.861 | 0.015 | 0.008 |
| E.Cycling_TA | 2.07E−20 | 59 | 0 | 1.276 | −16.039 | 0.363 | 0.000 |
| E.Cycling_TA | 2.71E−22 | 171 | 276 | 3.852 | 3.351 | 0.032 | 0.037 |
| E.Cycling_TA | 8.20E−110 | 312 | 552 | 1.899 | 0.016 | 0.077 | 0.037 |
| E.Cycling_TA | 1.01E−89 | 317 | 963 | 1.906 | 1.041 | 0.047 | 0.078 |
| E.Cycling_TA | 3.95E−49 | 166 | 87 | 3.890 | 0.168 | 0.152 | 0.006 |
| E.Cycling_TA | 4.80E−33 | 77 | 6 | −0.386 | −0.939 | 0.027 | 0.001 |
| E.Cycling_TA | 3.04E−38 | 0 | 215 | −16.039 | 0.091 | 0.000 | 0.312 |

TABLE 13-continued

Inflamed vs Healthy Markers

| | | | | | | | |
|---|---|---|---|---|---|---|---|
| E.Cycling_TA | 8.54E−128 | 327 | 766 | 3.655 | 1.479 | 0.155 | 0.080 |
| E.Cycling_TA | 4.47E−117 | 317 | 204 | 2.128 | 1.458 | 0.193 | 0.078 |
| E.Cycling_TA | 1.15E−67 | 284 | 737 | 1.509 | 0.823 | 0.037 | 0.059 |
| E.Cycling_TA | 8.16E−64 | 332 | 1109 | 3.154 | 2.406 | 0.065 | 0.130 |
| E.Cycling_TA | 1.65E−110 | 218 | 71 | 3.325 | −0.106 | 0.088 | 0.003 |
| E.Cycling_TA | 1.40E−42 | 330 | 1123 | 3.010 | 2.584 | 0.036 | 0.091 |
| E.Cycling_TA | 3.72E−25 | 326 | 1148 | 3.522 | 3.094 | 0.052 | 0.137 |
| E.Cycling_TA | 4.98E−19 | 338 | 1144 | 4.344 | 3.572 | 0.057 | 0.113 |
| E.Cycling_TA | 2.88E−110 | 330 | 1020 | 2.905 | 1.523 | 0.049 | 0.058 |
| E.Cycling_TA | 3.37E−161 | 300 | 75 | 1.995 | −0.225 | 0.102 | 0.005 |
| E.Cycling_TA | 3.06E−38 | 88 | 0 | 1.949 | −16.039 | 0.160 | 0.000 |
| E.Cycling_TA | 3.67E−41 | 329 | 1104 | 3.205 | 2.516 | 0.031 | 0.064 |
| E.Cycling_TA | 2.07E−50 | 322 | 1015 | 1.589 | 1.204 | 0.039 | 0.094 |
| E.Cycling_TA | 1.10E−44 | 175 | 44 | −0.361 | −0.773 | 0.046 | 0.009 |
| E.Cycling_TA | 3.35E−30 | 70 | 2 | 0.257 | −1.101 | 0.074 | 0.001 |
| E.Cycling_TA | 1.82E−45 | 327 | 1094 | 2.266 | 1.793 | 0.044 | 0.107 |
| E.Enterocyte_Immature_1 | 3.94E−30 | 71 | 674 | 3.489 | 2.577 | 0.018 | 0.091 |
| E.Enterocyte_Immature_1 | 1.62E−39 | 76 | 50 | 3.467 | 1.480 | 0.127 | 0.021 |
| E.Enterocyte_Immature_1 | 1.14E−34 | 59 | 29 | 2.781 | 1.184 | 0.113 | 0.018 |
| E.Enterocyte_Immature_1 | 6.80E−19 | 194 | 876 | 3.054 | 3.556 | 0.017 | 0.111 |
| E.Enterocyte_Immature_1 | 1.66E−56 | 104 | 36 | 3.813 | 1.624 | 0.065 | 0.005 |
| E.Enterocyte_Immature_1 | 1.71E−23 | 99 | 143 | 3.221 | 2.143 | 0.053 | 0.036 |
| E.Enterocyte_Immature_1 | 3.70E−52 | 80 | 13 | 3.021 | 1.017 | 0.060 | 0.002 |
| E.Enterocyte_Immature_1 | 1.08E−18 | 24 | 0 | 3.099 | −15.690 | 0.276 | 0.000 |
| E.Enterocyte_Immature_1 | 1.45E−20 | 65 | 94 | 3.071 | 1.521 | 0.090 | 0.044 |
| E.Enterocyte_Immature_2 | 1.28E−73 | 65 | 980 | 3.494 | 2.688 | 0.015 | 0.133 |
| E.Enterocyte_Immature_2 | 1.33E−57 | 237 | 900 | 3.860 | 1.992 | 0.043 | 0.045 |
| E.Enterocyte_Immature_2 | 9.38E−60 | 112 | 983 | 3.543 | 4.692 | 0.018 | 0.354 |
| E.Enterocyte_Immature_2 | 1.01E−30 | 79 | 40 | 0.025 | 0.252 | 0.027 | 0.016 |
| E.Enterocyte_Immature_2 | 2.72E−30 | 60 | 11 | 3.704 | 1.756 | 0.171 | 0.008 |
| E.Enterocyte_Immature_2 | 3.06E−48 | 246 | 967 | 3.873 | 2.885 | 0.115 | 0.228 |
| E.Enterocyte_Immature_2 | 5.41E−68 | 189 | 301 | 1.953 | 0.832 | 0.140 | 0.102 |
| E.Enterocyte_Immature_2 | 1.07E−22 | 57 | 24 | 1.056 | 0.286 | 0.074 | 0.018 |
| E.Enterocyte_Immature_2 | 5.95E−34 | 173 | 431 | 1.181 | 0.348 | 0.032 | 0.045 |
| E.Enterocyte_Immature_2 | 2.38E−39 | 78 | 4 | 0.534 | −0.290 | 0.088 | 0.003 |
| E.Enterocyte_Immature_2 | 1.08E−36 | 64 | 9 | 3.656 | 0.681 | 0.116 | 0.002 |
| E.Enterocyte_Immature_2 | 1.07E−22 | 52 | 15 | 1.809 | 0.622 | 0.050 | 0.006 |
| E.Enterocyte_Immature_2 | 5.04E−24 | 199 | 756 | 1.317 | 0.913 | 0.012 | 0.035 |
| E.Enterocyte_Immature_2 | 1.14E−34 | 120 | 99 | 0.559 | 0.331 | 0.038 | 0.027 |
| E.Enterocyte_Immature_2 | 4.30E−40 | 88 | 736 | 0.584 | 1.254 | 0.005 | 0.069 |
| E.Enterocyte_Immature_2 | 9.39E−26 | 249 | 1141 | 5.004 | 5.844 | 0.014 | 0.113 |
| E.Enterocyte_Immature_2 | 6.11E−73 | 196 | 528 | 3.327 | 1.076 | 0.088 | 0.050 |
| E.Enterocyte_Immature_2 | 1.54E−49 | 166 | 470 | 1.710 | 0.659 | 0.025 | 0.034 |
| E.Enterocyte_Immature_2 | 4.27E−24 | 230 | 1103 | 2.452 | 3.667 | 0.022 | 0.243 |
| E.Enterocyte_Immature_2 | 1.05E−37 | 169 | 330 | 0.959 | 0.556 | 0.024 | 0.035 |
| E.Enterocyte_Immature_2 | 6.48E−20 | 144 | 288 | 1.805 | 1.058 | 0.044 | 0.052 |
| E.Enterocyte_Immature_2 | 4.08E−124 | 239 | 796 | 3.756 | 1.942 | 0.168 | 0.159 |
| E.Enterocyte_Immature_2 | 6.48E−37 | 199 | 703 | 1.494 | 0.811 | 0.024 | 0.052 |
| E.Enterocyte_Immature_2 | 9.63E−37 | 0 | 266 | −15.642 | 0.429 | 0.000 | 0.428 |
| E.Enterocyte_Immature_2 | 6.71E−124 | 213 | 202 | 3.893 | 1.041 | 0.130 | 0.017 |
| E.Enterocyte_Immature_2 | 8.08E−42 | 141 | 237 | 1.227 | 0.480 | 0.021 | 0.021 |
| E.Enterocyte_Immature_2 | 3.46E−36 | 166 | 294 | 1.462 | 0.586 | 0.029 | 0.028 |
| E.Enterocyte_Immature_2 | 2.39E−115 | 216 | 455 | 3.102 | 0.909 | 0.039 | 0.018 |
| E.Enterocyte_Immature_2 | 1.71E−32 | 253 | 1145 | 7.420 | 6.162 | 0.101 | 0.190 |
| E.Enterocyte_Immature_2 | 1.09E−35 | 60 | 0 | 2.563 | −15.642 | 0.112 | 0.000 |
| E.Enterocyte_Immature_2 | 7.40E−209 | 229 | 130 | 3.547 | 0.233 | 0.202 | 0.012 |
| E.Enterocyte_Immature_2 | 2.47E−25 | 43 | 0 | 0.839 | −15.642 | 0.034 | 0.000 |
| E.Enterocyte_Immature_2 | 9.10E−37 | 152 | 319 | 0.941 | 0.464 | 0.021 | 0.031 |
| E.Enterocyte_Immature_2 | 6.64E−21 | 47 | 2 | −0.567 | −0.713 | 0.036 | 0.001 |
| E.Enterocyte_Immature_2 | 4.54E−38 | 225 | 691 | 3.275 | 2.417 | 0.053 | 0.089 |
| E.Enterocyte_Immature_2 | 2.54E−29 | 55 | 0 | −0.463 | −15.642 | 0.043 | 0.000 |
| E.Enterocyte_Immature_2 | 1.75E−25 | 53 | 0 | 0.218 | −15.642 | 0.229 | 0.000 |
| E.Enterocyte_Immature_2 | 1.94E−81 | 191 | 166 | 2.581 | 0.688 | 0.048 | 0.011 |
| E.Enterocyte_Immature_2 | 1.39E−18 | 50 | 30 | 0.011 | −0.183 | 0.022 | 0.012 |
| E.Enterocyte_Immature_2 | 2.93E−32 | 54 | 0 | 1.504 | −15.642 | 0.221 | 0.000 |
| E.Enterocyte_Immature_2 | 6.20E−34 | 184 | 486 | 1.050 | 0.498 | 0.031 | 0.056 |
| E.Enterocyte_Immature_2 | 1.12E−27 | 114 | 164 | 0.468 | 0.336 | 0.019 | 0.026 |
| E.Enterocyte_Progenitor | 6.40E−33 | 43 | 730 | 4.134 | 2.797 | 0.016 | 0.109 |
| E.Enterocyte_Progenitor | 1.04E−19 | 154 | 718 | 4.526 | 3.249 | 0.040 | 0.078 |
| E.Enterocyte_Progenitor | 1.54E−24 | 36 | 8 | 3.640 | 3.171 | 0.109 | 0.017 |
| E.Enterocyte_Progenitor | 9.54E−33 | 125 | 399 | 3.877 | 2.457 | 0.074 | 0.088 |
| E.Enterocyte_Progenitor | 9.52E−28 | 51 | 45 | 3.397 | 1.546 | 0.113 | 0.028 |
| E.Enterocyte_Progenitor | 2.55E−26 | 36 | 6 | 4.054 | 2.459 | 0.076 | 0.004 |
| E.Enterocyte_Progenitor | 5.02E−24 | 38 | 20 | 3.835 | 1.636 | 0.091 | 0.010 |
| E.Enterocyte_Progenitor | 6.59E−34 | 37 | 0 | 3.588 | −15.791 | 0.160 | 0.000 |
| E.Enterocyte_Progenitor | 2.31E−40 | 126 | 372 | 3.980 | 2.527 | 0.083 | 0.089 |
| E.Enterocyte_Progenitor | 4.70E−28 | 88 | 985 | 3.157 | 3.622 | 0.014 | 0.219 |
| E.Enterocyte_Progenitor | 1.65E−63 | 101 | 124 | 5.392 | 2.337 | 0.175 | 0.026 |

TABLE 13-continued

| Inflamed vs Healthy Markers | | | | | | | |
|---|---|---|---|---|---|---|---|
| E.Enterocyte_Progenitor | 1.61E−36 | 58 | 25 | 3.823 | 2.042 | 0.063 | 0.008 |
| E.Enterocyte_Progenitor | 4.98E−59 | 96 | 108 | 5.484 | 2.505 | 0.251 | 0.036 |
| E.Enterocyte_Progenitor | 8.16E−74 | 122 | 118 | 4.703 | 2.794 | 0.123 | 0.032 |
| E.Enterocyte_Progenitor | 1.20E−42 | 125 | 359 | 4.224 | 2.418 | 0.047 | 0.039 |
| E.Enterocyte_Progenitor | 3.89E−26 | 205 | 1181 | 7.046 | 5.789 | 0.067 | 0.161 |
| E.Enterocyte_Progenitor | 1.22E−24 | 27 | 0 | 3.071 | −15.791 | 0.059 | 0.000 |
| E.Enterocyte_Progenitor | 6.78E−108 | 128 | 33 | 3.785 | 1.938 | 0.141 | 0.010 |
| E.Enterocyte_Progenitor | 7.32E−28 | 56 | 40 | 3.942 | 1.617 | 0.030 | 0.004 |
| E.Enterocyte_Progenitor | 2.35E−19 | 21 | 0 | 2.816 | −15.791 | 0.224 | 0.000 |
| E.Enterocyte_Progenitor | 9.85E−21 | 162 | 974 | 4.744 | 3.701 | 0.022 | 0.064 |
| E.Enterocytes | 3.29E−54 | 71 | 684 | 3.154 | 2.661 | 0.014 | 0.097 |
| E.Enterocytes | 1.87E−38 | 112 | 57 | 0.696 | 0.222 | 0.053 | 0.019 |
| E.Enterocytes | 3.02E−42 | 175 | 293 | 1.501 | 0.733 | 0.030 | 0.029 |
| E.Enterocytes | 6.23E−42 | 218 | 834 | 3.330 | 4.681 | 0.032 | 0.317 |
| E.Enterocytes | 1.14E−38 | 97 | 99 | 1.409 | 0.445 | 0.024 | 0.012 |
| E.Enterocytes | 3.73E−44 | 100 | 43 | 1.540 | 0.413 | 0.045 | 0.009 |
| E.Enterocytes | 5.35E−22 | 0 | 94 | 15.546 | 0.155 | 0.000 | 0.226 |
| E.Enterocytes | 1.50E−52 | 127 | 109 | 2.084 | 0.480 | 0.093 | 0.026 |
| E.Enterocytes | 6.97E−43 | 97 | 7 | 1.678 | −0.684 | 0.234 | 0.003 |
| E.Enterocytes | 3.97E−44 | 87 | 9 | 4.272 | 1.896 | 0.211 | 0.004 |
| E.Enterocytes | 3.20E−37 | 92 | 32 | 3.499 | 1.773 | 0.173 | 0.018 |
| E.Enterocytes | 4.28E−21 | 36 | 0 | 0.182 | −15.546 | 0.021 | 0.000 |
| E.Enterocytes | 8.51E−32 | 248 | 841 | 8.636 | 9.465 | 0.060 | 0.359 |
| E.Enterocytes | 1.07E−29 | 65 | 0 | 0.184 | −15.546 | 0.301 | 0.000 |
| E.Enterocytes | 4.72E−24 | 88 | 51 | 1.237 | 0.074 | 0.021 | 0.006 |
| E.Enterocytes | 4.32E−56 | 126 | 118 | 3.658 | 0.425 | 0.078 | 0.008 |
| E.Enterocytes | 3.48E−31 | 178 | 762 | 1.690 | 2.598 | 0.018 | 0.147 |
| E.Enterocytes | 1.36E−39 | 209 | 841 | 6.294 | 6.837 | 0.080 | 0.466 |
| E.Enterocytes | 4.28E−22 | 248 | 839 | 5.747 | 5.340 | 0.044 | 0.111 |
| E.Enterocytes | 1.24E−34 | 192 | 391 | 1.815 | 1.378 | 0.071 | 0.107 |
| E.Enterocytes | 2.75E−27 | 49 | 0 | 2.465 | −15.546 | 0.268 | 0.000 |
| E.Enterocytes | 1.91E−46 | 136 | 88 | 2.979 | 1.572 | 0.022 | 0.005 |
| E.Enterocytes | 5.18E−37 | 194 | 479 | 1.779 | 1.105 | 0.047 | 0.073 |
| E.Enterocytes | 5.39E−27 | 229 | 729 | 2.790 | 2.162 | 0.024 | 0.049 |
| E.Enterocytes | 1.93E−19 | 51 | 4 | −0.021 | −0.302 | 0.043 | 0.003 |
| E.Enterocytes | 3.42E−27 | 186 | 410 | 1.667 | 1.006 | 0.022 | 0.030 |
| E.Enterocytes | 4.00E−22 | 53 | 4 | −0.068 | 0.548 | 0.061 | 0.007 |
| E.Enterocytes | 4.33E−31 | 192 | 303 | 1.701 | 1.062 | 0.038 | 0.039 |
| E.Enterocytes | 5.17E−23 | 50 | 0 | 4.122 | −15.546 | 0.762 | 0.000 |
| E.Enterocytes | 3.74E−52 | 131 | 100 | 2.405 | 0.805 | 0.115 | 0.029 |
| E.Enterocytes | 8.63E−29 | 91 | 26 | 2.903 | 0.208 | 0.055 | 0.002 |
| E.Enterocytes | 6.89E−36 | 77 | 9 | 0.446 | −0.229 | 0.082 | 0.006 |
| E.Enterocytes | 2.67E−47 | 0 | 244 | −15.546 | 0.626 | 0.000 | 0.468 |
| E.Enterocytes | 3.02E−64 | 171 | 320 | 2.578 | 0.513 | 0.039 | 0.018 |
| E.Enterocytes | 3.85E−22 | 73 | 44 | 0.926 | 0.707 | 0.042 | 0.022 |
| E.Enterocytes | 1.04E−77 | 165 | 60 | 3.837 | 0.490 | 0.099 | 0.004 |
| E.Enterocytes | 1.03E−22 | 125 | 204 | 0.722 | 0.347 | 0.013 | 0.016 |
| E.Enterocytes | 3.27E−44 | 189 | 499 | 2.170 | 1.288 | 0.040 | 0.058 |
| E.Enterocytes | 3.47E−57 | 233 | 675 | 3.182 | 1.867 | 0.054 | 0.063 |
| E.Enterocytes | 7.65E−68 | 235 | 528 | 3.016 | 2.234 | 0.096 | 0.125 |
| E.Enterocytes | 4.84E−37 | 73 | 7 | 4.233 | 1.021 | 0.059 | 0.001 |
| E.Enterocytes | 2.15E−53 | 173 | 165 | 2.644 | 1.062 | 0.061 | 0.019 |
| E.Enterocytes | 9.71E−97 | 148 | 94 | 4.066 | 0.314 | 0.051 | 0.002 |
| E.Enterocytes | 1.77E−36 | 68 | 0 | 2.542 | −15.546 | 0.102 | 0.000 |
| E.Enterocytes | 4.50E−63 | 139 | 41 | 3.038 | 0.623 | 0.104 | 0.006 |
| E.Enterocytes | 2.34E−28 | 58 | 0 | 0.669 | −15.546 | 0.088 | 0.000 |
| E.Enterocytes | 2.33E−32 | 72 | 0 | 1.442 | −15.546 | 0.466 | 0.000 |
| E.Enterocytes | 4.92E−34 | 76 | 86 | 1.177 | 0.259 | 0.027 | 0.016 |
| E.Enterocytes | 5.42E−25 | 241 | 837 | 4.131 | 4.960 | 0.057 | 0.350 |
| E.Enterocytes | 7.96E−26 | 77 | 13 | 0.155 | 1.455 | 0.041 | 0.017 |
| E.Enterocytes | 3.08E−59 | 203 | 332 | 4.155 | 2.209 | 0.138 | 0.059 |
| E.Enterocytes | 3.29E−38 | 75 | 1 | 2.458 | 0.451 | 0.473 | 0.002 |
| E.Enterocytes | 1.62E−23 | 103 | 83 | 0.758 | 0.933 | 0.025 | 0.022 |
| E.Enterocytes | 1.71E−28 | 125 | 147 | 1.130 | 0.424 | 0.025 | 0.018 |
| E.Enterocytes | 1.80E−21 | 63 | 24 | 1.327 | 0.022 | 0.037 | 0.006 |
| E.Epithelial | 2.13E−159 | 839 | 1715 | 3.231 | 2.717 | 0.119 | 0.170 |
| E.Epithelial | 6.16E−24 | 198 | 35 | 3.025 | 2.847 | 0.024 | 0.004 |
| E.Epithelial | 4.46E−35 | 338 | 14 | 0.143 | 0.148 | 0.115 | 0.005 |
| E.Epithelial | 6.55E−22 | 98 | 0 | 0.913 | −17.770 | 0.806 | 0.000 |
| E.Epithelial | 1.02E−19 | 199 | 26 | 0.696 | 0.389 | 0.079 | 0.008 |
| E.Epithelial | 4.64E−24 | 247 | 26 | 0.592 | 0.061 | 0.034 | 0.002 |
| E.Epithelial | 3.31E−70 | 497 | 46 | 3.316 | 1.590 | 0.418 | 0.012 |
| E.Epithelial | 1.08E−43 | 424 | 747 | 1.433 | 1.137 | 0.009 | 0.012 |
| E.Epithelial | 2.34E−21 | 165 | 1 | 0.116 | −0.004 | 0.175 | 0.001 |
| E.Epithelial | 5.29E−66 | 1547 | 1170 | 1.943 | 1.519 | 0.088 | 0.050 |
| E.Epithelial | 4.84E−31 | 893 | 1001 | 1.392 | 1.587 | 0.028 | 0.036 |
| E.Epithelial | 4.88E−24 | 231 | 4 | −0.302 | 1.057 | 0.061 | 0.003 |
| E.Epithelial | 4.23E−24 | 226 | 5 | 1.148 | −0.241 | 0.131 | 0.001 |

TABLE 13-continued

| Inflamed vs Healthy Markers | | | | | | | |
|---|---|---|---|---|---|---|---|
| E.Epithelial | 6.77E−34 | 1353 | 1568 | 2.315 | 2.483 | 0.045 | 0.059 |
| E.Epithelial | 2.80E−74 | 2283 | 2393 | 4.849 | 5.360 | 0.080 | 0.119 |
| E.Epithelial | 1.44E−24 | 227 | 38 | 1.658 | 2.925 | 0.060 | 0.024 |
| E.Epithelial | 2.14E−47 | 1986 | 2179 | 4.030 | 4.341 | 0.119 | 0.162 |
| E.Epithelial | 1.92E−58 | 692 | 142 | 1.358 | 1.060 | 0.093 | 0.016 |
| E.Epithelial | 2.37E−21 | 308 | 33 | 0.569 | 1.572 | 0.047 | 0.010 |
| E.Epithelial | 9.94E−27 | 448 | 147 | 1.699 | 1.108 | 0.054 | 0.012 |
| E.Epithelial | 1.41E−50 | 1618 | 1351 | 2.237 | 2.072 | 0.100 | 0.074 |
| E.Epithelial | 7.08E−25 | 178 | 0 | −0.162 | −17.770 | 0.545 | 0.000 |
| E.Epithelial | 3.12E−19 | 323 | 39 | 0.084 | 0.665 | 0.039 | 0.007 |
| E.Epithelial | 3.67E−20 | 524 | 197 | 1.037 | 1.273 | 0.024 | 0.010 |
| E.Epithelial | 5.76E−72 | 933 | 330 | 1.322 | 1.311 | 0.091 | 0.032 |
| E.Epithelial | 1.40E−55 | 1348 | 1663 | 2.104 | 2.505 | 0.063 | 0.102 |
| E.Epithelial | 9.47E−68 | 633 | 107 | 2.974 | 2.402 | 0.126 | 0.014 |
| E.Epithelial | 5.73E−32 | 176 | 0 | 2.875 | −17.770 | 0.906 | 0.000 |
| E.Epithelial | 1.50E−97 | 1019 | 596 | 5.516 | 4.447 | 0.322 | 0.090 |
| E.Epithelial | 9.97E−20 | 2291 | 2385 | 4.475 | 4.737 | 0.168 | 0.210 |
| E.Epithelial | 1.31E−20 | 92 | 0 | 0.319 | −17.770 | 0.568 | 0.000 |
| E.Epithelial | 3.64E−26 | 192 | 2 | −0.274 | −0.967 | 0.089 | 0.001 |
| E.Epithelial | 3.45E−129 | 1589 | 1154 | 2.248 | 1.581 | 0.184 | 0.084 |
| E.Epithelial | 1.41E−28 | 187 | 2 | 0.115 | 0.095 | 0.082 | 0.001 |
| E.Epithelial | 1.13E−18 | 216 | 38 | 0.980 | 1.343 | 0.073 | 0.017 |
| E.Epithelial | 1.65E−69 | 968 | 397 | 2.219 | 2.053 | 0.143 | 0.052 |
| E.Epithelial | 2.51E−24 | 211 | 2 | 2.524 | −0.295 | 0.237 | 0.000 |
| E.Epithelial | 1.18E−19 | 1912 | 2023 | 4.445 | 4.668 | 0.129 | 0.159 |
| E.Epithelial | 2.04E−33 | 2270 | 2357 | 4.877 | 5.154 | 0.120 | 0.151 |
| E.Epithelial | 1.75E−31 | 2145 | 2278 | 4.760 | 5.076 | 0.129 | 0.171 |
| E.Epithelial | 3.26E−44 | 2081 | 2208 | 4.699 | 5.094 | 0.102 | 0.142 |
| E.Epithelial | 2.18E−30 | 2207 | 2280 | 5.026 | 5.375 | 0.107 | 0.141 |
| E.Epithelial | 2.42E−44 | 2268 | 2338 | 4.878 | 5.215 | 0.143 | 0.187 |
| E.Epithelial | 2.59E−38 | 2017 | 2167 | 4.476 | 4.837 | 0.140 | 0.193 |
| E.Epithelial | 4.00E−61 | 2269 | 2369 | 5.373 | 5.725 | 0.131 | 0.175 |
| E.Epithelial | 6.38E−50 | 2242 | 2331 | 5.044 | 5.451 | 0.124 | 0.170 |
| E.Epithelial | 2.02E−34 | 2100 | 2252 | 4.871 | 5.236 | 0.104 | 0.144 |
| E.Epithelial | 3.82E−50 | 1949 | 2130 | 4.329 | 4.688 | 0.124 | 0.174 |
| E.Epithelial | 5.00E−26 | 2265 | 2315 | 5.477 | 5.857 | 0.124 | 0.165 |
| E.Epithelial | 2.41E−19 | 1964 | 2089 | 4.239 | 4.440 | 0.119 | 0.146 |
| E.Epithelial | 1.81E−18 | 2057 | 2143 | 4.702 | 4.946 | 0.131 | 0.161 |
| E.Epithelial | 3.79E−29 | 2145 | 2242 | 4.599 | 4.880 | 0.137 | 0.174 |
| E.Epithelial | 1.29E−220 | 1772 | 1196 | 3.351 | 1.969 | 0.220 | 0.057 |
| E.Epithelial | 1.21E−164 | 2476 | 2461 | 6.627 | 5.634 | 0.380 | 0.190 |
| E.Epithelial | 6.89E−51 | 347 | 5 | 2.014 | 0.112 | 0.205 | 0.001 |
| E.Epithelial | 2.19E−40 | 1204 | 795 | 3.740 | 3.222 | 0.253 | 0.117 |
| E.Epithelial | 5.15E−51 | 1773 | 2001 | 3.174 | 3.549 | 0.133 | 0.194 |
| E.Epithelial | 3.60E−45 | 258 | 0 | 0.980 | −17.770 | 0.778 | 0.000 |
| E.Epithelial | 3.58E−41 | 369 | 69 | 0.908 | 0.298 | 0.062 | 0.008 |
| E.Epithelial | 2.30E−59 | 800 | 206 | 1.653 | 0.915 | 0.134 | 0.021 |
| E.Epithelial | 2.32E−28 | 192 | 4 | 1.092 | 2.658 | 0.174 | 0.011 |
| E.Epithelial | 2.57E−24 | 208 | 7 | 0.762 | 0.119 | 0.067 | 0.001 |
| E.Epithelial | 1.26E−26 | 126 | 0 | 1.453 | −17.770 | 0.302 | 0.000 |
| E.Epithelial | 1.97E−220 | 1135 | 105 | 2.030 | 1.996 | 0.071 | 0.006 |
| E.Epithelial | 1.56E−50 | 251 | 0 | 1.818 | −17.770 | 0.505 | 0.000 |
| E.Goblet | 4.89E−19 | 65 | 49 | 1.932 | 1.652 | 0.043 | 0.027 |
| E.Goblet | 2.40E−42 | 109 | 106 | 4.608 | 2.874 | 0.104 | 0.031 |
| E.Immature_Enterocytes | 4.47E−116 | 179 | 1782 | 3.674 | 2.807 | 0.040 | 0.220 |
| E.Immature_Enterocytes | 5.85E−19 | 701 | 2422 | 5.364 | 4.770 | 0.063 | 0.144 |
| E.Immature_Enterocytes | 1.42E−64 | 531 | 1451 | 3.921 | 2.608 | 0.077 | 0.084 |
| E.Immature_Enterocytes | 1.25E−20 | 372 | 1685 | 2.473 | 2.669 | 0.028 | 0.144 |
| E.Immature_Enterocytes | 8.76E−34 | 114 | 62 | 1.042 | 0.714 | 0.073 | 0.031 |
| E.Immature_Enterocytes | 4.07E−23 | 48 | 3 | 0.678 | 0.057 | 0.032 | 0.001 |
| E.Immature_Enterocytes | 1.94E−63 | 141 | 36 | 3.999 | 2.544 | 0.338 | 0.032 |
| E.Immature_Enterocytes | 6.15E−44 | 175 | 153 | 2.143 | 1.137 | 0.129 | 0.056 |
| E.Immature_Enterocytes | 1.33E−48 | 613 | 2356 | 4.225 | 4.702 | 0.056 | 0.298 |
| E.Immature_Enterocytes | 5.39E−51 | 113 | 7 | 1.397 | 0.790 | 0.187 | 0.008 |
| E.Immature_Enterocytes | 1.17E−64 | 128 | 16 | 3.901 | 2.106 | 0.216 | 0.008 |
| E.Immature_Enterocytes | 1.97E−32 | 82 | 25 | 2.359 | 0.891 | 0.085 | 0.009 |
| E.Immature_Enterocytes | 1.53E−52 | 127 | 60 | 3.504 | 1.417 | 0.185 | 0.021 |
| E.Immature_Enterocytes | 4.29E−35 | 416 | 1093 | 2.099 | 1.521 | 0.039 | 0.069 |
| E.Immature_Enterocytes | 3.48E−19 | 698 | 2507 | 7.664 | 7.791 | 0.131 | 0.514 |
| E.Immature_Enterocytes | 1.55E−20 | 39 | 3 | 1.593 | 0.918 | 0.064 | 0.003 |
| E.Immature_Enterocytes | 3.01E−52 | 653 | 2426 | 4.807 | 5.516 | 0.027 | 0.166 |
| E.Immature_Enterocytes | 1.50E−22 | 43 | 0 | 0.817 | −17.136 | 0.587 | 0.000 |
| E.Immature_Enterocytes | 5.26E−113 | 394 | 708 | 3.566 | 1.849 | 0.155 | 0.085 |
| E.Immature_Enterocytes | 1.32E−25 | 461 | 1230 | 2.604 | 2.094 | 0.060 | 0.112 |
| E.Immature_Enterocytes | 1.18E−21 | 568 | 1904 | 3.283 | 2.760 | 0.034 | 0.079 |
| E.Immature_Enterocytes | 1.59E−19 | 112 | 113 | 1.528 | 1.469 | 0.025 | 0.024 |
| E.Immature_Enterocytes | 2.24E−45 | 331 | 525 | 2.780 | 1.677 | 0.030 | 0.022 |
| E.Immature_Enterocytes | 2.90E−39 | 205 | 280 | 2.516 | 1.519 | 0.024 | 0.016 |

TABLE 13-continued

| Inflamed vs Healthy Markers | | | | | | | |
|---|---|---|---|---|---|---|---|
| E.Immature_Enterocytes | 3.79E−38 | 315 | 511 | 1.538 | 1.289 | 0.056 | 0.077 |
| E.Immature_Enterocytes | 5.49E−133 | 306 | 311 | 4.871 | 1.766 | 0.281 | 0.033 |
| E.Immature_Enterocytes | 1.03E−221 | 578 | 1299 | 4.124 | 2.429 | 0.307 | 0.213 |
| E.Immature_Enterocytes | 1.55E−19 | 657 | 2439 | 4.816 | 5.070 | 0.068 | 0.299 |
| E.Immature_Enterocytes | 2.54E−27 | 47 | 0 | 0.482 | −17.136 | 0.070 | 0.000 |
| E.Immature_Enterocytes | 1.15E−51 | 0 | 335 | −17.136 | 1.332 | 0.070 | 0.625 |
| E.Immature_Enterocytes | 9.59E−212 | 439 | 262 | 4.152 | 1.922 | 0.235 | 0.030 |
| E.Immature_Enterocytes | 2.37E−23 | 623 | 2345 | 4.161 | 4.603 | 0.068 | 0.350 |
| E.Immature_Enterocytes | 4.96E−46 | 316 | 506 | 2.507 | 1.988 | 0.090 | 0.100 |
| E.Immature_Enterocytes | 7.12E−44 | 110 | 35 | 3.715 | 0.764 | 0.051 | 0.002 |
| E.Immature_Enterocytes | 9.35E−60 | 312 | 458 | 2.565 | 1.514 | 0.086 | 0.061 |
| E.Immature_Enterocytes | 1.71E−139 | 418 | 656 | 3.543 | 1.786 | 0.086 | 0.040 |
| E.Immature_Enterocytes | 3.42E−66 | 716 | 2486 | 7.092 | 6.015 | 0.162 | 0.267 |
| E.Immature_Enterocytes | 3.74E−55 | 95 | 0 | 2.752 | −17.136 | 0.125 | 0.000 |
| E.Immature_Enterocytes | 1.68E−293 | 437 | 130 | 3.542 | 0.830 | 0.295 | 0.013 |
| E.Immature_Enterocytes | 9.40E−35 | 257 | 450 | 1.832 | 1.332 | 0.054 | 0.067 |
| E.Immature_Enterocytes | 3.60E−28 | 69 | 5 | 0.391 | 0.133 | 0.094 | 0.006 |
| E.Immature_Enterocytes | 8.23E−58 | 533 | 1225 | 4.159 | 3.311 | 0.155 | 0.198 |
| E.Immature_Enterocytes | 8.08E−36 | 411 | 1843 | 2.260 | 2.811 | 0.023 | 0.152 |
| E.Immature_Enterocytes | 1.67E−36 | 76 | 0 | 1.232 | −17.136 | 0.475 | 0.000 |
| E.Immature_Enterocytes | 1.42E−32 | 93 | 73 | 1.567 | 0.190 | 0.040 | 0.012 |
| E.Immature_Enterocytes | 1.80E−75 | 242 | 378 | 3.974 | 1.646 | 0.168 | 0.052 |
| E.Immature_Enterocytes | 1.67E−126 | 382 | 317 | 3.326 | 1.579 | 0.116 | 0.029 |
| E.Immature_Enterocytes | 2.92E−21 | 37 | 3 | 2.374 | 0.303 | 0.214 | 0.004 |
| E.Immature_Enterocytes | 4.69E−59 | 99 | 0 | 2.355 | −17.136 | 0.465 | 0.000 |
| E.Immature_Goblet | 1.08E−20 | 52 | 536 | 2.942 | 2.472 | 0.009 | 0.069 |
| E.Immature_Goblet | 6.12E−19 | 40 | 7 | 2.868 | 2.057 | 0.077 | 0.008 |
| E.Immature_Goblet | 2.18E−26 | 224 | 1027 | 3.912 | 4.587 | 0.024 | 0.173 |
| E.Immature_Goblet | 1.47E−19 | 239 | 1063 | 6.042 | 6.699 | 0.020 | 0.144 |
| E.Immature_Goblet | 9.16E−20 | 235 | 1046 | 4.949 | 5.517 | 0.025 | 0.162 |
| E.Immature_Goblet | 2.65E−100 | 191 | 95 | 3.178 | 1.753 | 0.135 | 0.025 |
| E.Immature_Goblet | 5.94E−63 | 136 | 60 | 4.142 | 1.956 | 0.083 | 0.008 |
| E.Immature_Goblet | 3.89E−23 | 76 | 56 | 2.986 | 2.331 | 0.099 | 0.046 |
| E.Secretory | 4.32E−21 | 71 | 55 | 1.881 | 1.575 | 0.046 | 0.029 |
| E.Secretory | 4.04E−44 | 217 | 768 | 6.071 | 3.721 | 0.082 | 0.057 |
| E.Secretory_All | 5.43E−56 | 186 | 1439 | 2.490 | 2.417 | 0.020 | 0.150 |
| E.Secretory_All | 2.17E−20 | 257 | 376 | 0.761 | 1.187 | 0.025 | 0.049 |
| E.Secretory_All | 1.95E−34 | 92 | 12 | 0.381 | 0.262 | 0.053 | 0.006 |
| E.Secretory_All | 3.44E−22 | 44 | 0 | 0.224 | −17.009 | 0.715 | 0.000 |
| E.Secretory_All | 2.15E−60 | 617 | 2286 | 4.044 | 4.617 | 0.051 | 0.284 |
| E.Secretory_All | 1.29E−35 | 447 | 968 | 2.042 | 1.769 | 0.041 | 0.074 |
| E.Secretory_All | 4.55E−28 | 96 | 38 | 1.493 | 1.517 | 0.064 | 0.026 |
| E.Secretory_All | 1.86E−29 | 66 | 2 | 1.578 | −0.049 | 0.076 | 0.001 |
| E.Secretory_All | 7.64E−24 | 581 | 2105 | 4.109 | 4.548 | 0.046 | 0.226 |
| E.Secretory_All | 3.99E−28 | 566 | 1507 | 4.011 | 4.091 | 0.119 | 0.335 |
| E.Secretory_All | 2.66E−33 | 527 | 1389 | 2.622 | 2.603 | 0.058 | 0.151 |
| E.Secretory_All | 6.46E−21 | 304 | 1213 | 1.453 | 2.328 | 0.016 | 0.119 |
| E.Secretory_All | 1.58E−22 | 45 | 0 | 0.572 | −17.009 | 0.882 | 0.000 |
| E.Secretory_All | 6.42E−30 | 660 | 2383 | 5.048 | 5.494 | 0.070 | 0.344 |
| E.Secretory_All | 8.95E−72 | 256 | 122 | 3.104 | 2.914 | 0.078 | 0.032 |
| E.Secretory_All | 5.50E−26 | 262 | 526 | 5.573 | 4.918 | 0.104 | 0.133 |
| E.Secretory_All | 1.60E−25 | 43 | 0 | 2.332 | −17.009 | 0.780 | 0.000 |
| E.Secretory_All | 1.71E−19 | 665 | 2372 | 4.094 | 4.443 | 0.048 | 0.220 |
| E.Secretory_All | 9.73E−21 | 239 | 355 | 1.705 | 2.202 | 0.043 | 0.090 |
| E.Secretory_All | 2.04E−27 | 668 | 2378 | 5.856 | 6.413 | 0.042 | 0.219 |
| E.Secretory_All | 1.86E−19 | 657 | 2349 | 4.978 | 5.365 | 0.047 | 0.221 |
| E.Secretory_All | 8.54E−20 | 634 | 2261 | 5.035 | 5.410 | 0.055 | 0.254 |
| E.Secretory_All | 8.90E−27 | 679 | 2377 | 5.780 | 6.265 | 0.049 | 0.240 |
| E.Secretory_All | 2.24E−22 | 614 | 2156 | 4.810 | 5.301 | 0.042 | 0.207 |
| E.Secretory_All | 8.45E−40 | 658 | 2291 | 4.915 | 5.454 | 0.052 | 0.262 |
| E.Secretory_All | 7.52E−22 | 594 | 2062 | 4.443 | 4.892 | 0.050 | 0.236 |
| E.Secretory_All | 3.10E−27 | 654 | 2331 | 5.584 | 5.985 | 0.053 | 0.251 |
| E.Secretory_All | 5.76E−36 | 656 | 2277 | 5.725 | 6.412 | 0.045 | 0.249 |
| E.Secretory_All | 3.35E−30 | 654 | 2294 | 5.129 | 5.662 | 0.048 | 0.243 |
| E.Secretory_All | 1.46E−31 | 574 | 2063 | 4.392 | 4.898 | 0.048 | 0.243 |
| E.Secretory_All | 9.71E−22 | 671 | 2351 | 5.513 | 6.014 | 0.047 | 0.234 |
| E.Secretory_All | 3.28E−45 | 513 | 1284 | 2.627 | 2.022 | 0.055 | 0.090 |
| E.Secretory_All | 7.95E−26 | 59 | 7 | 1.212 | 3.224 | 0.101 | 0.049 |
| E.Secretory_All | 3.78E−26 | 84 | 31 | 0.817 | 1.254 | 0.037 | 0.018 |
| E.Secretory_All | 2.16E−111 | 367 | 190 | 1.991 | 2.936 | 0.029 | 0.029 |
| E.Secretory_All | 1.06E−20 | 53 | 8 | 0.507 | 0.705 | 0.043 | 0.007 |
| E.Secretory_TA | 6.93E−34 | 67 | 762 | 2.016 | 1.736 | 0.006 | 0.060 |
| E.Secretory_TA | 3.58E−31 | 205 | 948 | 5.003 | 3.805 | 0.070 | 0.141 |
| E.Secretory_TA | 7.63E−24 | 182 | 659 | 1.193 | 0.989 | 0.017 | 0.052 |
| E.Secretory_TA | 2.51E−21 | 31 | 0 | 0.852 | −15.563 | 0.481 | 0.000 |
| E.Secretory_TA | 1.39E−29 | 55 | 2 | 1.518 | −0.493 | 0.059 | 0.001 |
| E.Secretory_TA | 2.58E−19 | 93 | 112 | −0.123 | 0.144 | 0.011 | 0.017 |
| E.Secretory_TA | 1.04E−32 | 131 | 214 | 0.668 | 0.288 | 0.024 | 0.030 |

TABLE 13-continued

| Inflamed vs Healthy Markers | | | | | | | |
|---|---|---|---|---|---|---|---|
| E.Secretory_TA | 1.78E−32 | 157 | 470 | 1.308 | 0.614 | 0.018 | 0.033 |
| E.Secretory_TA | 5.29E−32 | 123 | 829 | 1.015 | 1.932 | 0.007 | 0.084 |
| E.Secretory_TA | 7.34E−29 | 178 | 699 | 1.975 | 1.026 | 0.015 | 0.030 |
| E.Secretory_TA | 3.49E−40 | 170 | 385 | 1.717 | 0.423 | 0.040 | 0.037 |
| E.Secretory_TA | 9.81E−40 | 189 | 702 | 1.694 | 1.029 | 0.026 | 0.060 |
| E.Secretory_TA | 2.86E−24 | 85 | 50 | 2.785 | 0.438 | 0.044 | 0.005 |
| E.Secretory_TA | 3.26E−22 | 0 | 145 | −15.563 | 0.302 | 0.000 | 0.258 |
| E.Secretory_TA | 1.65E−86 | 190 | 174 | 2.626 | 1.649 | 0.167 | 0.078 |
| E.Secretory_TA | 4.15E−41 | 151 | 465 | 1.456 | 0.576 | 0.020 | 0.033 |
| E.Secretory_TA | 1.04E−59 | 137 | 164 | 3.663 | 0.951 | 0.068 | 0.012 |
| E.Secretory_TA | 1.60E−31 | 196 | 820 | 2.335 | 1.556 | 0.020 | 0.050 |
| E.Secretory_TA | 6.08E−101 | 174 | 85 | 2.445 | 0.603 | 0.088 | 0.012 |
| E.Secretory_TA | 3.13E−27 | 48 | 0 | 1.467 | −15.563 | 0.092 | 0.000 |
| E.Secretory_TA | 1.96E−28 | 95 | 45 | −0.018 | −0.222 | 0.030 | 0.012 |
| E.Secretory_TA | 1.35E−32 | 175 | 597 | 1.434 | 0.739 | 0.021 | 0.045 |
| E.Secretory_TA | 7.74E−26 | 44 | 2 | 1.126 | −1.075 | 0.093 | 0.001 |
| E.Stem | 2.50E−23 | 74 | 148 | 3.162 | 1.471 | 0.031 | 0.019 |
| E.Stem | 8.44E−50 | 85 | 70 | 2.597 | 1.657 | 0.088 | 0.038 |
| E.Stem | 2.94E−23 | 74 | 179 | 2.280 | 0.755 | 0.037 | 0.031 |
| F.Crypt | 1.98E−19 | 20 | 0 | 1.954 | −16.921 | 0.283 | 0.000 |
| F.Crypt | 1.56E−18 | 327 | 2176 | 5.041 | 4.216 | 0.024 | 0.089 |
| F.Crypt | 7.18E−31 | 97 | 192 | 5.654 | 4.084 | 0.057 | 0.038 |
| F.Crypt | 2.16E−22 | 233 | 1232 | 3.855 | 2.862 | 0.051 | 0.134 |
| F.Crypt | 9.05E−43 | 113 | 147 | 3.698 | 2.610 | 0.070 | 0.043 |
| F.Crypt_hiFos | 3.60E−23 | 75 | 694 | 3.780 | 4.902 | 0.016 | 0.331 |
| F.Crypt_hiFos | 1.05E−27 | 47 | 35 | 3.524 | 2.199 | 0.034 | 0.010 |
| F.Crypt_loFos_1 | 4.61E−19 | 43 | 66 | 3.554 | 2.123 | 0.030 | 0.017 |
| F.Crypt_loFos_2 | 3.84E−29 | 110 | 615 | 6.214 | 7.384 | 0.041 | 0.519 |
| F.Crypt_loFos_2 | 5.18E−29 | 62 | 33 | 6.053 | 4.850 | 0.052 | 0.012 |
| F.Endothelial | 2.78E−21 | 47 | 1 | 0.968 | 0.308 | 0.086 | 0.001 |
| F.Endothelial | 2.27E−51 | 376 | 555 | 4.040 | 2.994 | 0.103 | 0.074 |
| F.Endothelial | 4.73E−23 | 305 | 316 | 3.545 | 3.217 | 0.062 | 0.052 |
| F.Endothelial | 8.95E−19 | 454 | 831 | 4.686 | 4.120 | 0.060 | 0.074 |
| F.Endothelial | 1.15E−28 | 472 | 972 | 5.206 | 5.921 | 0.064 | 0.218 |
| F.Endothelial | 1.54E−23 | 484 | 968 | 5.303 | 5.938 | 0.073 | 0.225 |
| F.Endothelial | 4.82E−22 | 382 | 648 | 4.926 | 4.096 | 0.106 | 0.101 |
| F.Endothelial | 1.53E−55 | 219 | 74 | 4.257 | 4.980 | 0.052 | 0.029 |
| F.Endothelial | 1.16E−30 | 434 | 739 | 4.965 | 3.807 | 0.042 | 0.032 |
| F.Endothelial | 3.80E−21 | 103 | 46 | 5.034 | 4.605 | 0.152 | 0.050 |
| F.Endothelial | 2.17E−22 | 400 | 640 | 4.404 | 3.357 | 0.129 | 0.100 |
| F.Endothelial | 7.96E−35 | 457 | 805 | 4.862 | 4.155 | 0.135 | 0.146 |
| F.Fibroblast | 1.32E−19 | 49 | 7 | 2.706 | 2.526 | 0.273 | 0.034 |
| F.Fibroblast | 5.35E−28 | 117 | 45 | 2.743 | 2.323 | 0.093 | 0.027 |
| F.Fibroblast | 1.48E−40 | 717 | 1585 | 3.721 | 3.260 | 0.162 | 0.260 |
| F.Fibroblast | 1.94E−31 | 168 | 113 | 2.089 | 2.273 | 0.099 | 0.076 |
| F.Fibroblast | 6.14E−32 | 69 | 0 | 3.069 | −17.109 | 0.919 | 0.000 |
| F.Fibroblast | 2.59E−21 | 38 | 0 | 1.956 | −17.109 | 0.315 | 0.000 |
| F.Fibroblast | 1.69E−35 | 66 | 0 | 1.718 | −17.109 | 0.440 | 0.000 |
| F.Fibroblast | 2.36E−77 | 364 | 256 | 4.988 | 4.375 | 0.110 | 0.051 |
| F.Fibroblast | 2.38E−24 | 45 | 0 | 1.883 | −17.109 | 0.439 | 0.000 |
| F.Fibroblast | 1.77E−62 | 295 | 201 | 3.026 | 2.214 | 0.157 | 0.061 |
| F.Fibroblast | 1.98E−32 | 910 | 2319 | 5.271 | 4.805 | 0.085 | 0.157 |
| F.Fibroblast | 6.46E−21 | 888 | 2397 | 4.993 | 5.369 | 0.069 | 0.243 |
| F.Fibroblast | 4.59E−28 | 657 | 1933 | 3.324 | 3.809 | 0.044 | 0.180 |
| F.Fibroblast | 8.74E−31 | 920 | 2340 | 5.419 | 4.709 | 0.093 | 0.144 |
| F.Fibroblast | 6.10E−29 | 105 | 55 | 2.990 | 2.114 | 0.148 | 0.042 |
| F.Fibroblast | 5.39E−24 | 43 | 0 | 2.835 | −17.109 | 0.727 | 0.000 |
| F.Fibroblast | 6.38E−130 | 891 | 2100 | 5.637 | 4.077 | 0.308 | 0.246 |
| F.Glia | 2.11E−30 | 47 | 207 | 6.097 | 4.677 | 0.063 | 0.104 |
| F.Glia | 4.60E−20 | 24 | 2 | 2.928 | 3.996 | 0.311 | 0.054 |
| F.Pcap_Venules | 3.97E−23 | 168 | 163 | 4.186 | 3.081 | 0.060 | 0.027 |
| F.Pcap_Venules | 1.22E−28 | 125 | 31 | 2.471 | 1.782 | 0.205 | 0.032 |
| F.Pcap_Venules | 2.80E−20 | 195 | 215 | 4.447 | 3.783 | 0.141 | 0.098 |
| F.Pcap_Venules | 1.07E−26 | 135 | 61 | 2.764 | 1.834 | 0.106 | 0.025 |
| F.Pcap_Venules | 5.94E−32 | 151 | 66 | 3.759 | 2.793 | 0.208 | 0.047 |
| F.Pcap_Venules | 3.83E−23 | 111 | 31 | 3.011 | 2.740 | 0.085 | 0.020 |
| F.Stromal | 5.18E−27 | 60 | 0 | 2.677 | −17.437 | 0.068 | 0.000 |
| F.Stromal | 1.53E−20 | 175 | 95 | 2.093 | 2.476 | 0.097 | 0.068 |
| F.Stromal | 5.21E−26 | 75 | 0 | 2.969 | −17.437 | 0.926 | 0.000 |
| F.Stromal | 1.56E−30 | 335 | 261 | 2.621 | 2.292 | 0.150 | 0.093 |
| F.Stromal | 7.34E−28 | 67 | 0 | 1.704 | −17.437 | 0.448 | 0.000 |
| F.Stromal | 5.18E−97 | 583 | 269 | 4.755 | 4.581 | 0.136 | 0.056 |
| F.Stromal | 1.14E−22 | 58 | 0 | 1.822 | −17.437 | 0.503 | 0.000 |
| F.Stromal | 1.47E−22 | 358 | 309 | 4.532 | 4.779 | 0.137 | 0.140 |
| F.Stromal | 4.36E−19 | 1344 | 2379 | 4.908 | 5.246 | 0.094 | 0.211 |
| F.Stromal | 9.19E−29 | 1033 | 1928 | 3.279 | 3.731 | 0.063 | 0.161 |
| F.Stromal | 2.30E−29 | 1041 | 1451 | 3.919 | 3.291 | 0.113 | 0.102 |
| F.Stromal | 1.22E−29 | 1354 | 2268 | 5.288 | 4.642 | 0.119 | 0.128 |

TABLE 13-continued

| Inflamed vs Healthy Markers | | | | | | | |
|---|---|---|---|---|---|---|---|
| F.Stromal | 3.48E−30 | 1409 | 2367 | 5.497 | 4.938 | 0.126 | 0.143 |
| F.Villus | 8.61E−21 | 277 | 953 | 4.656 | 4.105 | 0.131 | 0.308 |
| F.Villus | 2.80E−31 | 230 | 508 | 4.183 | 3.868 | 0.077 | 0.137 |
| F.Villus | 2.35E−20 | 297 | 1189 | 6.482 | 5.598 | 0.114 | 0.247 |
| F.Villus | 1.13E−31 | 163 | 250 | 3.229 | 2.957 | 0.172 | 0.218 |
| F.Villus | 7.92E−55 | 288 | 1065 | 6.131 | 4.367 | 0.210 | 0.229 |
| F.Villus__1 | 3.92E−22 | 102 | 210 | 4.101 | 3.592 | 0.042 | 0.061 |
| F.Villus__1 | 9.12E−23 | 79 | 104 | 4.507 | 3.997 | 0.035 | 0.033 |
| F.Villus__1 | 1.62E−34 | 116 | 440 | 6.109 | 4.030 | 0.130 | 0.117 |
| F.Villus__2 | 2.22E−19 | 96 | 133 | 3.314 | 3.091 | 0.141 | 0.167 |
| F.Villus__2 | 2.38E−21 | 172 | 625 | 6.146 | 4.565 | 0.151 | 0.183 |
| I.Immune | 1.55E−49 | 895 | 1415 | 3.606 | 3.541 | 0.155 | 0.235 |
| I.Immune | 4.26E−55 | 672 | 1082 | 7.127 | 7.775 | 0.201 | 0.507 |
| I.Lymphoid | 4.76E−42 | 891 | 1383 | 3.525 | 3.493 | 0.146 | 0.222 |
| I.Lymphoid | 1.56E−20 | 720 | 1058 | 4.300 | 4.512 | 0.141 | 0.241 |
| I.Lymphoid | 4.29E−19 | 119 | 15 | 1.892 | 2.304 | 0.121 | 0.020 |
| I.Lymphoid | 6.05E−38 | 703 | 1057 | 7.564 | 7.959 | 0.239 | 0.473 |
| M.CD69pos__Mast | 8.40E−22 | 189 | 255 | 4.288 | 4.007 | 0.221 | 0.246 |
| M.CD69pos__Mast | 8.92E−19 | 248 | 482 | 5.527 | 5.053 | 0.134 | 0.187 |
| M.Macrophages | 1.08E−21 | 405 | 1020 | 9.202 | 9.664 | 0.150 | 0.519 |
| M.Mast | 1.61E−22 | 70 | 16 | 3.561 | 3.432 | 0.083 | 0.017 |
| M.Mast | 9.61E−22 | 215 | 308 | 4.302 | 4.051 | 0.227 | 0.273 |
| M.Mast | 6.93E−23 | 276 | 538 | 5.537 | 5.010 | 0.145 | 0.196 |
| M.Monocytes | 2.42E−19 | 366 | 1237 | 3.727 | 3.459 | 0.082 | 0.230 |
| M.Monocytes | 1.27E−19 | 33 | 0 | 2.730 | −16.729 | 0.829 | 0.000 |
| M.Monocytes | 3.80E−25 | 699 | 1775 | 7.238 | 7.798 | 0.145 | 0.543 |
| M.Monocytes | 4.59E−95 | 658 | 1743 | 5.981 | 6.943 | 0.106 | 0.549 |
| M.Monocytes | 3.47E−26 | 315 | 1208 | 3.733 | 3.629 | 0.066 | 0.235 |
| M.Myeloid | 1.39E−19 | 33 | 0 | 2.730 | −17.202 | 0.831 | 0.000 |
| M.Myeloid | 2.35E−19 | 216 | 286 | 2.492 | 1.889 | 0.074 | 0.065 |
| M.Myeloid | 1.18E−18 | 708 | 2093 | 4.784 | 4.902 | 0.089 | 0.286 |
| M.Myeloid | 5.11E−31 | 816 | 1919 | 4.614 | 4.019 | 0.138 | 0.215 |
| M.Myeloid | 6.53E−22 | 538 | 967 | 4.008 | 3.606 | 0.136 | 0.185 |
| M.Neutrophils | 1.55E−28 | 139 | 101 | 5.153 | 6.964 | 0.039 | 0.100 |
| M.Neutrophils | 1.43E−23 | 130 | 78 | 6.818 | 4.463 | 0.238 | 0.028 |
| T.Activated__CD4__hiFos | 1.99E−22 | 186 | 396 | 5.084 | 4.054 | 0.072 | 0.075 |
| T.Activated__CD4__loFos | 9.55E−41 | 190 | 980 | 4.647 | 4.983 | 0.059 | 0.383 |
| T.Activated__CD4__loFos | 6.89E−24 | 175 | 459 | 5.409 | 4.321 | 0.081 | 0.099 |
| T.Activated__CD4__loFos | 5.79E−20 | 290 | 953 | 5.257 | 4.669 | 0.067 | 0.146 |
| T.CD4 | 3.46E−27 | 609 | 1150 | 3.759 | 3.661 | 0.127 | 0.224 |
| T.CD4 | 7.92E−21 | 259 | 116 | 2.939 | 3.015 | 0.134 | 0.063 |
| T.CD4 | 8.80E−149 | 626 | 1712 | 4.589 | 4.983 | 0.122 | 0.437 |
| T.CD4 | 2.96E−63 | 530 | 1299 | 5.073 | 5.153 | 0.137 | 0.354 |
| T.CD4 | 3.71E−40 | 114 | 0 | 4.953 | −17.403 | 0.824 | 0.000 |
| T.CD4 | 5.26E−44 | 928 | 616 | 4.815 | 4.116 | 0.140 | 0.057 |
| T.CD4 | 4.06E−29 | 141 | 15 | 2.266 | 3.009 | 0.098 | 0.017 |
| T.CD4 | 1.69E−40 | 2004 | 2492 | 6.946 | 7.310 | 0.175 | 0.280 |
| T.CD4 | 3.62E−22 | 2001 | 2488 | 6.447 | 6.696 | 0.171 | 0.252 |
| T.CD4 | 1.73E−31 | 1995 | 2475 | 6.126 | 6.468 | 0.177 | 0.278 |
| T.CD4 | 2.34E−22 | 1998 | 2479 | 6.362 | 6.628 | 0.162 | 0.241 |
| T.CD4 | 4.29E−24 | 2003 | 2482 | 6.476 | 6.819 | 0.170 | 0.267 |
| T.CD4 | 2.99E−38 | 1980 | 2449 | 5.861 | 6.212 | 0.173 | 0.273 |
| T.CD4 | 2.10E−23 | 1994 | 2483 | 6.313 | 6.585 | 0.175 | 0.264 |
| T.CD4 | 2.54E−24 | 1706 | 1943 | 4.685 | 4.416 | 0.284 | 0.268 |
| T.CD4 | 7.99E−42 | 842 | 1536 | 3.807 | 4.013 | 0.098 | 0.206 |
| T.CD8 | 2.23E−29 | 367 | 1396 | 3.958 | 4.457 | 0.067 | 0.359 |
| T.CD8 | 3.71E−36 | 743 | 1473 | 4.015 | 3.854 | 0.232 | 0.411 |
| T.CD8 | 1.19E−29 | 538 | 1501 | 3.494 | 3.896 | 0.040 | 0.146 |
| T.CD8 | 2.16E−19 | 526 | 1484 | 4.204 | 4.593 | 0.065 | 0.242 |
| T.CD8 | 1.42E−21 | 103 | 42 | 2.723 | 2.616 | 0.140 | 0.053 |
| T.CD8 | 1.04E−23 | 975 | 2294 | 6.012 | 5.688 | 0.138 | 0.259 |
| T.CD8 | 1.57E−21 | 973 | 2371 | 5.696 | 6.100 | 0.084 | 0.272 |
| T.CD8 | 1.08E−25 | 936 | 2301 | 4.784 | 5.147 | 0.071 | 0.225 |
| T.CD8 | 1.68E−24 | 891 | 1994 | 4.868 | 4.412 | 0.121 | 0.198 |
| T.CD8 | 7.49E−20 | 97 | 54 | 2.923 | 2.770 | 0.098 | 0.049 |
| T.CD8 | 2.30E−24 | 577 | 1701 | 3.863 | 4.309 | 0.084 | 0.338 |
| T.CD8__IELs | 3.52E−37 | 107 | 163 | 4.332 | 3.519 | 0.139 | 0.121 |
| T.CD8__LP | 2.38E−28 | 234 | 831 | 4.205 | 4.712 | 0.058 | 0.291 |
| T.CD8__LP | 4.36E−22 | 213 | 272 | 3.785 | 3.279 | 0.226 | 0.203 |
| T.CD8__LP | 1.85E−19 | 369 | 644 | 4.183 | 3.900 | 0.269 | 0.386 |
| T.CD8__LP | 4.74E−19 | 222 | 336 | 5.037 | 4.217 | 0.081 | 0.070 |
| T.Cycling__T | 2.46E−20 | 62 | 14 | 2.621 | 2.705 | 0.098 | 0.024 |
| T.Memory__CD4 | 2.79E−42 | 92 | 565 | 4.414 | 4.883 | 0.031 | 0.260 |
| T.Memory__CD4 | 1.37E−20 | 63 | 382 | 5.277 | 5.550 | 0.031 | 0.224 |
| T.Memory__CD4 | 7.19E−20 | 46 | 3 | 3.185 | 2.559 | 0.426 | 0.018 |
| T.Tcells | 5.36E−55 | 812 | 1376 | 3.860 | 3.792 | 0.162 | 0.261 |
| T.Tcells | 6.96E−51 | 876 | 1412 | 4.448 | 4.659 | 0.170 | 0.318 |
| T.Tcells | 1.93E−24 | 197 | 39 | 2.531 | 2.768 | 0.122 | 0.029 |

TABLE 13-continued

| | Inflamed vs Healthy Markers | | | | | | |
|---|---|---|---|---|---|---|---|
| T.Tcells | 3.60E−29 | 96 | 0 | 4.859 | −17.752 | 0.889 | 0.000 |
| T.Tcells | 2.08E−26 | 137 | 10 | 2.331 | 2.875 | 0.093 | 0.010 |
| T.Tcells | 1.80E−35 | 2108 | 1886 | 4.624 | 4.310 | 0.319 | 0.230 |
| T.Tcells | 3.25E−32 | 2495 | 2521 | 7.967 | 8.342 | 0.220 | 0.289 |
| T.Tcells | 7.65E−27 | 1195 | 1589 | 3.861 | 3.944 | 0.129 | 0.182 |
| T.Tregs | 1.68E−33 | 327 | 277 | 4.124 | 3.647 | 0.212 | 0.129 |
| T.Tregs | 8.45E−27 | 264 | 166 | 3.660 | 3.334 | 0.273 | 0.137 |
| T.Tregs | 7.35E−24 | 245 | 145 | 3.525 | 3.280 | 0.306 | 0.153 |

TABLE 14

Inflamed vs Non-Inflamed Markers

| ident | gene | coefD | pvalD | coefC | pvalC | mastfc | pvalH |
|---|---|---|---|---|---|---|---|
| B.Bcells | ACTG1 | 0.270 | 5.04E−02 | 7.92E−01 | 7..87E−37 | 0.683 | 1.86E−36 |
| B.Bcells | ALOX5AP | 1.113 | 2.65E−23 | 4.41E−01 | 5.15E−06 | 1.206 | 1.03E−26 |
| B.Bcells | ARHGDIB | 0.388 | 2.70E−04 | 6.71E−01 | 2.39E−31 | 0.794 | 4.64E−33 |
| B.Bcells | ARPC1B | 0.579 | 3.83E−10 | 7.39E−01 | 5.22E−31 | 0.862 | 2.35E−38 |
| B.Bcells | ARPC5 | 0.667 | 7.21E−13 | 5.39E−01 | 4.36E−19 | 0.581 | 3.26E−29 |
| B.Bcells | CD52 | 0.369 | 3.12E−05 | 7.63E−01 | 2.40E−21 | 0.733 | 4.94E−24 |
| B.Bcells | CD53 | 0.583 | 1.33E−10 | 8.15E−01 | 2.47E−42 | 0.665 | 4.66E−50 |
| B.Bcells | CFL1 | 0.234 | 1.10E−01 | 7.65E−01 | 1.27E−41 | 0.640 | 6.06E−41 |
| B.Bcells | CORO1A | 0.567 | 8.48E−10 | 7.67E−01 | 4.11E−26 | 0.952 | 3.68E−33 |
| B.Bcells | COTL1 | 0.656 | 9.48E−13 | 6.51E−01 | 1.10E−15 | 0.881 | 9.67E−26 |
| B.Bcells | DHRS9 | 2.253 | 1.67E−38 | 6.91E−01 | 2.03E−04 | 0.667 | 2.75E−40 |
| B.Bcells | EVL | 0.637 | 7.66E−11 | 5.01E−01 | 8.00E−15 | 0.598 | 5.05E−23 |
| B.Bcells | GAPDH | 0.703 | 6.02E−05 | 7.07E−01 | 2.86E−40 | 1.072 | 1.53E−42 |
| B.Bcells | HLA-DMA | 0.623 | 3.76E−12 | 5.61E−01 | 3.07E−18 | 0.742 | 1.13E−27 |
| B.Bcells | HLA-DPA1 | 0.341 | 3.29E−04 | 7.53E−01 | 2.61E−17 | 0.886 | 4.45E−19 |
| B.Bcells | HLA-DPB1 | 0.518 | 4.22E−09 | 7.06E−01 | 3.94E−12 | 1.223 | 1.12E−18 |
| B.Bcells | HLA-DQA1 | 0.464 | 1.19E−07 | 7.19E−01 | 3.46E−17 | 0.918 | 3.04E−22 |
| B.Bcells | HLA-DRB1 | 0.411 | 6.00E−06 | 9.67E−01 | 2.71E−20 | 1.120 | 1.13E−23 |
| B.Bcells | IGHA1 | −0.818 | 2.00E−13 | −1.76E+00 | 1.66E−33 | −1.536 | 4.75E−44 |
| B.Bcells | IGHA2 | −1.021 | 2.10E−29 | −4.84E−01 | 1.07E−03 | −0.548 | 1.41E−30 |
| B.Bcells | IGJ | −0.595 | 2.67E−09 | −1.53E+00 | 6.12E−33 | −0.735 | 1.89E−39 |
| B.Bcells | IRF8 | 1.119 | 1.27E−25 | 4.66E−01 | 2.46E−09 | 0.595 | 3.17E−32 |
| B.Bcells | ITGB2 | 0.919 | 5.59E−16 | 5.53E−01 | 8.84E−11 | 0.819 | 4.23E−24 |
| B.Bcells | JUN | −0.878 | 2.18E−18 | −4.02E−01 | 1.80E−10 | −0.519 | 3.57E−26 |
| B.Bcells | LAPTM5 | 0.556 | 2.49E−10 | 7.54E−01 | 1.55E−24 | 0.900 | 4.07E−32 |
| B.Bcells | LCP1 | 0.940 | 1.74E−19 | 3.73E−01 | 3.02E−07 | 0.635 | 3.99E−24 |
| B.Bcells | LMO2 | 2.231 | 1.51E−26 | 1.92E−01 | 2.88E−01 | 0.531 | 1.16E−25 |
| B.Bcells | UCP2 | 0.650 | 4.07E−13 | 5.08E−01 | 3.28E−15 | 0.592 | 1.24E−25 |
| B.Cycling | ACTB | 0.439 | 6.44E−01 | 1.99E+00 | 1.93E−21 | 2.038 | 2.09E−20 |
| B.Cycling | HMGB1 | 1.804 | 5.95E−04 | 1.28E+00 | 4.98E−17 | 2.065 | 1.46E−18 |
| B.Cycling | HMGN2 | 1.138 | 8.01E−03 | 1.45E+00 | 3.95E−21 | 1.203 | 1.40E−21 |
| B.FO | PFN1 | 0.359 | 1.82E−01 | 9.87E−01 | 1.32E−24 | 1.005 | 7.00E−24 |
| B.Plasma | IGHA1 | −0.203 | 3.71E−01 | −1.88E+00 | 3.28E−37 | −1.279 | 3.53E−36 |
| B.Plasma | IGJ | −0.360 | 1.15E−01 | −1.55E+00 | 2.98E−43 | −0.787 | 1.49E−42 |
| E.Absorptive | CXCL1 | 1.378 | 3.33E−12 | 1.76E+00 | 1.91E−09 | 0.526 | 4.37E−19 |
| E.Absorptive | GSN | 0.716 | 1.02E−03 | 8.13E−01 | 3.03E−25 | 0.533 | 1.80E−26 |
| E.Absorptive | HLA-DRB1 | 1.345 | 4.90E−18 | 9.64E−01 | 3.85E−11 | 2.221 | 1.76E−26 |
| E.Absorptive | RARRES3 | 0.801 | 1.82E−07 | 6.14E−01 | 1.42E−22 | 0.858 | 2.16E−27 |
| E.Absorptive | REG4 | 1.946 | 1.69E−19 | 4.60E−01 | 2.56E−01 | 0.505 | 1.02E−18 |
| E.Absorptive | S100A11 | 0.628 | 1.59E−04 | 9.39E−01 | 3.68E−22 | 0.966 | 3.62E−24 |
| E.Absorptive_All | CXCL1 | 1.593 | 8.90E−30 | 1.30E+00 | 1.79E−09 | 0.579 | 1.76E−36 |
| E.Absorptive_All | FOSB | −1.301 | 4.06E−32 | −6.54E−02 | 3.47E−01 | −0.603 | 3.89E−31 |
| E.Absorptive_All | HLA-DRB1 | 0.979 | 3.64E−28 | 8.31E−01 | 7.00E−14 | 1.658 | 3.38E−39 |
| E.Absorptive_All | RBPMS | 2.383 | 1.48E−22 | 2.24E−01 | 3.62E−01 | 0.951 | 1.21E−21 |
| E.Absorptive_All | S100A11 | 0.495 | 6.82E−08 | 6.73E−01 | 1.37E−27 | 0.763 | 9.01E−33 |
| E.Absorptive_All | S100A7 | 4.547 | 7.36E−19 | | 1.00E+00 | 3.200 | 7.36E−19 |
| E.Absorptive_All | S100A9 | 1.871 | 1.30E−27 | 7.36E−01 | 3.26E−06 | 0.910 | 3.54E−31 |
| E.Absorptive_All | SOCS1 | 1.163 | 9.71E−15 | 7.36E−01 | 9.29E−09 | 0.521 | 6.59E−21 |
| E.Absorptive_All | TIMP1 | 1.310 | 5.00E−36 | 4.23E−01 | 2.36E−04 | 1.458 | 9.17E−38 |
| E.Absorptive_TA_2 | FOS | −1.880 | 5.78E−18 | −3.44E−01 | 4.50E−03 | −1.292 | 1.12E−18 |
| E.Absorptive_TA_2 | MUC12 | 2.134 | 1.50E−19 | 8.02E−01 | 1.48E−17 | 0.648 | 2.77E−34 |
| E.Absorptive_TA_2 | PRAC1 | 4.156 | 3.34E−65 | −3.64E−01 | 3.07E−05 | 0.675 | 1.21E−67 |
| E.Absorptive_TA_2 | RP11-708H21.4 | −4.967 | 1.18E−22 | | 1.00E+00 | 3.217 | 1.18E−22 |
| E.Cycling_TA | MUC12 | 1.573 | 1.73E−09 | 6.38E−01 | 2.92E−13 | 0.606 | 3.64E−20 |
| E.Cycling_TA | PRAC1 | 4.651 | 9.03E−79 | −8.12E−01 | 1.67E−18 | 1.017 | 3.97E−94 |
| E.Enterocyte_Immature_2 | MUC12 | 1.674 | 7.19E−09 | 1.16E+00 | 1.13E−36 | 0.584 | 9.65E−43 |
| E.Enterocyte_Immature_2 | S100A11 | 1.180 | 9.06E−07 | 9.33E−01 | 3.01E−20 | 1.632 | 2.03E−24 |
| E.Enterocytes | C4orf3 | 0.792 | 6.34E−05 | 7.19E−01 | 6.37E−18 | 0.632 | 2.34E−20 |
| E.Enterocytes | PSME2 | 1.231 | 3.38E−05 | 7.97E−01 | 1.37E−19 | 1.177 | 2.92E−22 |
| E.Enterocytes | RARRES3 | 0.990 | 1.09E−03 | 6.33E−01 | 5.35E−18 | 0.954 | 2.83E−19 |

TABLE 14-continued

| Inflamed vs Non-Inflamed Markers | | | | | | | | |
|---|---|---|---|---|---|---|---|---|
| E.Enterocytes | S100A11 | 1.304 | 2.80E−10 | 1.59E+00 | 2.99E−21 | 2.035 | 8.12E−29 |
| E.Epithelial | CXCL1 | 1.347 | 4.30E−21 | 1.45E+00 | 5.43E−13 | 0.681 | 2.57E−31 |
| E.Epithelial | FOSB | −1.273 | 1.00E−27 | −1.49E−01 | 1.64E−02 | −0.573 | 7.74E−28 |
| E.Epithelial | MMP7 | 4.654 | 5.46E−27 | | 1.00E+00 | 2.888 | 5.46E−27 |
| E.Epithelial | RBPMS | 2.173 | 1.61E−19 | 1.78E−01 | 3.76E−01 | 0.988 | 1.25E−18 |
| E.Epithelial | S100A11 | 0.488 | 1.28E−05 | 6.56E−01 | 1.03E−29 | 0.760 | 1.07E−32 |
| E.Epithelial | S100A9 | 1.738 | 5.54E−20 | 8.89E−01 | 1.70E−03 | 0.843 | 4.67E−21 |
| E.Epithelial | SOCS1 | 1.325 | 2.37E−16 | 6.41E−01 | 1.01E−06 | 0.713 | 1.60E−20 |
| E.Epithelial | TIMP1 | 1.536 | 4.81E−41 | 3.71E−01 | 4.52E−04 | 1.705 | 1.73E−42 |
| E.Immature_Enterocytes | CXCL1 | 2.078 | 2.05E−28 | 1.48E+00 | 2.50E−06 | 1.034 | 4.41E−32 |
| E.Immature_Enterocytes | HLA-DRB1 | 0.924 | 1.72E−17 | 6.09E−01 | 1.44E−05 | 1.336 | 1.52E−20 |
| E.Immature_Enterocytes | PPP1R14A | −2.410 | 1.12E−20 | −6.04E−01 | 6.20E−02 | −0.741 | 2.31E−20 |
| E.Immature_Enterocytes | S100A11 | 0.547 | 9.26E−07 | 5.89E−01 | 1.07E−15 | 0.771 | 6.43E−20 |
| E.Immature_Enterocytes | S100A6 | 2.392 | 1.87E−02 | 5.95E−01 | 6.29E−19 | 1.944 | 4.46E−19 |
| E.Immature_Enterocytes | S100A9 | 1.532 | 3.65E−15 | 1.52E+00 | 1.20E−07 | 0.650 | 2.99E−20 |
| E.Secretory_All | TIMP1 | 1.089 | 1.83E−23 | 2.08E−01 | 4.67E−02 | 1.093 | 3.21E−23 |
| E.Secretory_TA | PRAC1 | 4.571 | 2.02E−60 | −5.40E−01 | 8.66E−07 | 0.941 | 2.32E−64 |
| E.Stem | PRAC1 | 3.706 | 7.35E−23 | −3.74E−01 | 2.63E−03 | 0.554 | 9.92E−24 |
| F.Fibroblast | TIMP1 | 0.593 | 1.59E−04 | 8.03E−01 | 8.36E−35 | 0.649 | 1.04E−36 |
| M.Monocytes | RGS1 | −1.005 | 1.10E−18 | −2.29E−01 | 1.01E−02 | −0.504 | 4.50E−19 |
| T.CD4 | TPT1 | −0.473 | 4.86E−03 | −3.97E−01 | 1.05E−18 | −0.529 | 2.23E−19 |

| ident | n | ref_n | mu | ref_mu | total | ref_total |
|---|---|---|---|---|---|---|
| B.Bcells | 1088 | 784 | 4.568 | 3.684 | 0.356 | 0.139 |
| B.Bcells | 363 | 113 | 2.490 | 2.404 | 0.267 | 0.078 |
| B.Bcells | 996 | 698 | 3.365 | 2.788 | 0.324 | 0.152 |
| B.Bcells | 830 | 483 | 3.223 | 2.507 | 0.308 | 0.109 |
| B.Bcells | 727 | 376 | 2.578 | 2.122 | 0.318 | 0.120 |
| B.Bcells | 738 | 489 | 4.554 | 4.249 | 0.454 | 0.243 |
| B.Bcells | 843 | 509 | 3.015 | 2.089 | 0.511 | 0.163 |
| B.Bcells | 1103 | 803 | 4.002 | 3.139 | 0.275 | 0.110 |
| B.Bcells | 878 | 553 | 3.954 | 3.425 | 0.459 | 0.200 |
| B.Bcells | 579 | 280 | 3.274 | 2.800 | 0.266 | 0.093 |
| B.Bcells | 251 | 22 | 2.056 | 1.627 | 0.644 | 0.042 |
| B.Bcells | 428 | 204 | 2.247 | 2.074 | 0.314 | 0.133 |
| B.Bcells | 1148 | 820 | 4.349 | 3.461 | 0.279 | 0.108 |
| B.Bcells | 777 | 433 | 2.966 | 2.496 | 0.330 | 0.133 |
| B.Bcells | 892 | 609 | 4.349 | 3.839 | 0.213 | 0.102 |
| B.Bcells | 756 | 458 | 4.753 | 4.354 | 0.218 | 0.100 |
| B.Bcells | 699 | 423 | 4.029 | 3.483 | 0.258 | 0.107 |
| B.Bcells | 824 | 526 | 5.128 | 4.513 | 0.238 | 0.099 |
| B.Bcells | 898 | 801 | 10.040 | 10.530 | 0.437 | 0.547 |
| B.Bcells | 586 | 660 | 7.980 | 8.085 | 0.447 | 0.541 |
| B.Bcells | 834 | 733 | 8.424 | 9.119 | 0.408 | 0.580 |
| B.Bcells | 427 | 131 | 2.748 | 2.460 | 0.564 | 0.142 |
| B.Bcells | 331 | 116 | 2.119 | 1.727 | 0.261 | 0.070 |
| B.Bcells | 773 | 714 | 3.640 | 4.069 | 0.271 | 0.337 |
| B.Bcells | 656 | 374 | 3.965 | 3.333 | 0.461 | 0.170 |
| B.Bcells | 416 | 150 | 2.374 | 2.251 | 0.418 | 0.138 |
| B.Bcells | 171 | 14 | 1.940 | 2.195 | 0.640 | 0.063 |
| B.Bcells | 627 | 319 | 2.674 | 2.286 | 0.385 | 0.150 |
| B.Cycling | 247 | 66 | 7.126 | 5.999 | 0.141 | 0.017 |
| B.Cycling | 244 | 56 | 4.953 | 4.301 | 0.270 | 0.040 |
| B.Cycling | 236 | 54 | 4.838 | 3.868 | 0.374 | 0.044 |
| B.FO | 331 | 301 | 5.213 | 4.171 | 0.123 | 0.054 |
| B.Plasma | 513 | 439 | 10.681 | 11.096 | 0.449 | 0.513 |
| B.Plasma | 509 | 441 | 8.796 | 9.454 | 0.403 | 0.551 |
| E.Absorptive | 98 | 41 | 4.137 | 2.399 | 0.299 | 0.037 |
| E.Absorptive | 339 | 478 | 3.011 | 2.206 | 0.150 | 0.121 |
| E.Absorptive | 294 | 279 | 2.895 | 1.786 | 0.022 | 0.010 |
| E.Absorptive | 298 | 365 | 2.781 | 2.203 | 0.173 | 0.142 |
| E.Absorptive | 100 | 25 | 3.802 | 2.852 | 0.194 | 0.025 |
| E.Absorptive | 259 | 294 | 3.764 | 2.592 | 0.098 | 0.049 |
| E.Absorptive_All | 231 | 62 | 3.762 | 2.713 | 0.414 | 0.054 |
| E.Absorptive_All | 266 | 494 | 1.325 | 1.467 | 0.038 | 0.078 |
| E.Absorptive_All | 620 | 396 | 3.145 | 1.983 | 0.048 | 0.014 |
| E.Absorptive_All | 103 | 10 | 3.442 | 2.027 | 0.438 | 0.016 |
| E.Absorptive_All | 774 | 714 | 3.645 | 3.004 | 0.201 | 0.119 |
| E.Absorptive_All | 58 | 0 | 2.227 | −16.655 | 0.974 | 0.000 |
| E.Absorptive_All | 170 | 32 | 2.499 | 0.471 | 0.090 | 0.004 |
| E.Absorptive_All | 163 | 59 | 1.370 | 0.337 | 0.098 | 0.017 |
| E.Absorptive_All | 438 | 201 | 2.289 | 2.938 | 0.049 | 0.035 |
| E.Absorptive_TA_2 | 179 | 306 | 1.859 | 2.794 | 0.012 | 0.041 |
| E.Absorptive_TA_2 | 260 | 226 | 2.514 | 1.359 | 0.226 | 0.088 |
| E.Absorptive_TA_2 | 263 | 144 | 2.341 | 2.749 | 0.310 | 0.225 |
| E.Absorptive_TA_2 | 0 | 62 | −14.615 | −0.994 | 0.000 | 0.621 |
| E.Cycling_TA | 312 | 271 | 1.899 | 0.879 | 0.102 | 0.044 |

TABLE 14-continued

| Inflamed vs Non-Inflamed Markers | | | | | | |
|---|---|---|---|---|---|---|
| E.Cycling_TA | 317 | 144 | 2.128 | 3.093 | 0.180 | 0.160 |
| E.Enterocyte_Immature_2 | 239 | 274 | 3.756 | 2.470 | 0.346 | 0.163 |
| E.Enterocyte_Immature_2 | 216 | 244 | 3.102 | 2.071 | 0.049 | 0.027 |
| E.Enterocytes | 175 | 142 | 1.501 | 0.868 | 0.050 | 0.026 |
| E.Enterocytes | 233 | 256 | 3.182 | 2.363 | 0.088 | 0.055 |
| E.Enterocytes | 235 | 270 | 3.016 | 2.530 | 0.176 | 0.144 |
| E.Enterocytes | 148 | 73 | 4.066 | 2.916 | 0.076 | 0.017 |
| E.Epithelial | 219 | 75 | 3.487 | 1.606 | 0.419 | 0.039 |
| E.Epithelial | 341 | 513 | 1.365 | 1.481 | 0.063 | 0.103 |
| E.Epithelial | 83 | 0 | 3.198 | −16.298 | 0.976 | 0.000 |
| E.Epithelial | 101 | 13 | 0.301 | 1.545 | 0.078 | 0.024 |
| E.Epithelial | 770 | 683 | 3.325 | 2.826 | 0.198 | 0.124 |
| E.Epithelial | 140 | 32 | 1.890 | −0.213 | 0.054 | 0.003 |
| E.Epithelial | 161 | 50 | 1.120 | 0.474 | 0.107 | 0.021 |
| E.Epithelial | 491 | 234 | 2.033 | 2.160 | 0.049 | 0.025 |
| E.Immature_Enterocytes | 128 | 30 | 3.901 | 2.461 | 0.218 | 0.019 |
| E.Immature_Enterocytes | 331 | 289 | 2.780 | 1.885 | 0.024 | 0.011 |
| E.Immature_Enterocytes | 8 | 123 | 1.439 | 2.462 | 0.003 | 0.108 |
| E.Immature_Enterocytes | 418 | 507 | 3.543 | 3.087 | 0.110 | 0.097 |
| E.Immature_Enterocytes | 716 | 1046 | 7.092 | 6.491 | 0.312 | 0.301 |
| E.Immature_Enterocytes | 95 | 34 | 2.752 | 0.286 | 0.064 | 0.004 |
| E.Secretory_All | 367 | 273 | 1.991 | 2.174 | 0.037 | 0.031 |
| E.Secretory_TA | 190 | 128 | 2.626 | 3.132 | 0.215 | 0.206 |
| E.Stem | 85 | 123 | 2.597 | 3.008 | 0.152 | 0.293 |
| F.Fibroblast | 891 | 857 | 5.637 | 4.449 | 0.515 | 0.218 |
| M.Monocytes | 315 | 434 | 3.733 | 3.747 | 0.206 | 0.286 |
| T.CD4 | 1003 | 1101 | 5.109 | 5.533 | 0.222 | 0.327 |

TABLE 15

Non-inflamed vs Healthy Markers

| ident | gene | coefD | pvalD | coefC | pvalC | mastfc | pvalH |
|---|---|---|---|---|---|---|---|
| B.Bcells | AC009501.4 | −0.916 | 1.55E−31 | −0.107 | 6.46E−02 | −0.937 | 4.15E−31 |
| B.Bcells | ATP5E | 0.717 | 3.01E−10 | 0.379 | 1.33E−21 | 0.759 | 3.93E−29 |
| B.Bcells | IGHA2 | −0.527 | 3.04E−09 | −2.008 | 1.75E−72 | −0.743 | 9.22E−79 |
| B.Bcells | KLF6 | 0.650 | 7.92E−16 | 0.382 | 2.87E−13 | 0.510 | 2.17E−26 |
| B.Bcells | MT-ND3 | 0.607 | 7.92E−14 | 1.195 | 1.36E−44 | 0.881 | 1.81E−55 |
| B.Bcells | PTPRC | 1.051 | 4.91E−27 | 0.155 | 2.46E−02 | 0.623 | 5.35E−27 |
| B.Bcells | RPL37 | 0.554 | 6.90E−04 | 0.717 | 1.27E−55 | 0.737 | 7.91E−57 |
| B.Bcells | RPL37A | 0.455 | 1.21E−02 | 0.588 | 2.93E−41 | 0.620 | 2.14E−41 |
| B.Bcells | RPL39 | 0.601 | 1.10E−12 | 1.357 | 4.74E−68 | 0.777 | 1.04E−77 |
| B.Bcells | RPS21 | 0.504 | 6.05E−05 | 0.538 | 3.12E−33 | 0.581 | 1.52E−35 |
| B.Bcells | RPS29 | 0.650 | 2.45E−04 | 0.760 | 2.70E−44 | 1.063 | 5.70E−46 |
| B.Bcells | TPT1 | 0.749 | 1.23E−03 | 0.468 | 5.06E−34 | 0.893 | 4.18E−35 |
| B.FO | RPL39 | 0.886 | 1.90E−10 | 1.068 | 6.35E−19 | 0.825 | 1.11E−26 |
| B.Plasma | IGHA2 | −2.624 | 3.65E−18 | −1.896 | 5.43E−59 | −1.489 | 4.45E−74 |
| E.Absorptive | AC009501.4 | −1.463 | 4.21E−49 | −0.120 | 8.47E−02 | −1.284 | 1.77E−48 |
| E.Absorptive | HLA-B | 0.270 | 4.72E−01 | 0.595 | 1.05E−24 | 0.590 | 1.06E−23 |
| E.Absorptive | MTRNR2L1 | 0.895 | 1.84E−19 | 1.658 | 4.14E−33 | 1.112 | 1.32E−49 |
| E.Absorptive | RARRES3 | 0.747 | 3.06E−14 | 0.347 | 1.38E−09 | 0.581 | 3.19E−21 |
| E.Absorptive | RPL39 | 0.677 | 2.87E−09 | 1.244 | 1.17E−39 | 0.626 | 4.26E−46 |
| E.Absorptive_All | AC009501.4 | −1.264 | 7.06E−103 | 0.123 | 1.28E−03 | −1.066 | 1.07E−103 |
| E.Absorptive_All | FTL | −0.526 | 2.31E−04 | −0.455 | 1.65E−33 | −0.900 | 2.86E−35 |
| E.Absorptive_All | HLA-B | 0.362 | 6.39E−04 | 0.449 | 2.48E−34 | 0.703 | 1.12E−35 |
| E.Absorptive_All | MTRNR2L1 | 0.785 | 2.86E−38 | 1.951 | 2.10E−98 | 0.999 | 2.59E−133 |
| E.Absorptive_All | RARRES3 | 0.675 | 2.18E−23 | 0.231 | 5.64E−06 | 0.516 | 9.20E−27 |
| E.Absorptive_All | REG4 | 1.752 | 3.37E−33 | 1.859 | 3.20E−11 | 0.815 | 1.39E−41 |
| E.Absorptive_All | S100A11 | 0.548 | 2.71E−17 | 0.545 | 1.55E−33 | 0.619 | 6.88E−48 |
| E.Absorptive_All | TIMP1 | 2.067 | 1.81E−50 | 0.866 | 5.73E−05 | 2.216 | 1.04E−52 |
| E.Absorptive_TA_1 | MTRNR2L1 | 1.146 | 8.46E−19 | 1.516 | 7.17E−15 | 1.172 | 6.75E−31 |
| E.Absorptive_TA_2 | AC009501.4 | −1.739 | 2.56E−40 | 0.117 | 1.47E−01 | −1.461 | 1.50E−39 |
| E.Absorptive_TA_2 | DDX5 | 0.525 | 1.79E−03 | 0.636 | 2.15E−21 | 0.544 | 1.98E−22 |
| E.Absorptive_TA_2 | IFITM3 | 0.720 | 2.42E−06 | 0.852 | 1.52E−22 | 0.710 | 2.80E−26 |
| E.Absorptive_TA_2 | LDHA | 1.028 | 1.02E−05 | 0.611 | 1.09E−24 | 0.761 | 8.33E−28 |
| E.Absorptive_TA_2 | MTRNR2L1 | 0.757 | 4.60E−09 | 1.727 | 1.02E−21 | 0.900 | 4.28E−28 |
| E.Absorptive_TA_2 | PDIA3 | 1.141 | 4.53E−09 | 0.697 | 4.79E−36 | 0.613 | 2.59E−42 |
| E.Absorptive_TA_2 | S100A11 | 0.607 | 6.77E−03 | 0.723 | 4.50E−28 | 0.621 | 1.60E−28 |
| E.Best4_Enterocytes | RPL39 | 0.631 | 7.34E−04 | 1.861 | 4.91E−48 | 0.792 | 3.01E−49 |
| E.Cycling_TA | FN1 | 2.929 | 2.97E−19 | 1.569 | 1.55E−03 | 0.880 | 2.26E−20 |
| E.Cycling_TA | HLA-DMA | 1.190 | 3.46E−16 | 0.628 | 1.63E−08 | 0.619 | 4.26E−22 |
| E.Cycling_TA | HLA-DRB1 | 1.763 | 2.23E−35 | 1.262 | 1.08E−13 | 2.259 | 3.56E−46 |
| E.Cycling_TA | LDHA | 0.909 | 1.46E−03 | 0.590 | 1.40E−22 | 0.699 | 1.10E−23 |
| E.Cycling_TA | MTRNR2L1 | 0.929 | 7.85E−13 | 1.225 | 8.88E−13 | 0.969 | 5.82E−23 |

TABLE 15-continued

| | Non-inflamed vs Healthy Markers | | | | | | |
|---|---|---|---|---|---|---|---|
| E.Cycling_TA | PITX1 | 3.030 | 3.58E-24 | 0.562 | 4.71E-02 | 1.405 | 6.40E-24 |
| E.Cycling_TA | REG4 | 1.963 | 4.32E-33 | 1.134 | 1.47E-06 | 0.648 | 6.04E-37 |
| E.Cycling_TA | RPL38 | -1.583 | 6.37E-05 | 0.661 | 5.53E-29 | -0.562 | 2.63E-31 |
| E.Cycling_TA | S100A11 | 0.845 | 1.29E-03 | 0.879 | 8.92E-41 | 0.946 | 8.50E-42 |
| E.Cycling_TA | S100P | 2.892 | 1.31E-66 | 1.107 | 1.75E-15 | 0.576 | 5.05E-79 |
| E.Enterocyte_Immature_1 | MTRNR2L1 | 0.847 | 1.93E-11 | 1.959 | 6.13E-27 | 0.960 | 1.38E-35 |
| E.Enterocyte_Immature_1 | MUC1 | 2.061 | 6.50E-29 | 1.062 | 3.51E-11 | 0.817 | 2.72E-37 |
| E.Enterocyte_Immature_1 | PLA2G2A | 2.363 | 1.20E-33 | 1.177 | 1.84E-05 | 0.916 | 1.90E-36 |
| E.Enterocyte_Immature_2 | AC009501.4 | -1.893 | 1.08E-44 | -0.057 | 4.96E-01 | -1.574 | 1.52E-43 |
| E.Enterocyte_Immature_2 | CYBA | 0.963 | 4.30E-04 | 0.635 | 2.64E-22 | 1.235 | 6.61E-24 |
| E.Enterocyte_Immature_2 | MTRNR2L1 | 0.546 | 2.06E-05 | 2.221 | 7.06E-35 | 0.745 | 1.27E-37 |
| E.Enterocyte_Immature_2 | S100A11 | 1.196 | 1.16E-15 | 0.792 | 5.29E-21 | 1.325 | 7.45E-34 |
| E.Enterocyte_Immature_2 | S100P | 3.046 | 4.72E-88 | 1.572 | 1.22E-42 | 0.691 | 2.49E-127 |
| E.Enterocyte_Progenitor | AC009501.4 | -0.854 | 1.06E-13 | 0.590 | 4.97E-12 | -0.577 | 4.42E-23 |
| E.Enterocyte_Progenitor | AGR2 | 1.071 | 3.71E-15 | 1.141 | 4.91E-29 | 0.796 | 2.57E-21 |
| E.Enterocyte_Progenitor | MTRNR2L1 | 0.728 | 8.62E-09 | 1.572 | 1.45E-16 | 0.795 | 9.74E-23 |
| E.Enterocyte_Progenitor | PLA2G2A | 2.281 | 3.64E-63 | 1.180 | 1.13E-13 | 0.796 | 8.26E-74 |
| E.Enterocyte_Progenitor | REG4 | 2.664 | 1.23E-24 | 3.575 | 1.27E-11 | 1.488 | 1.76E-33 |
| E.Enterocyte_Progenitor | S100A11 | 0.971 | 2.84E-15 | 0.673 | 1.71E-13 | 1.012 | 4.59E-26 |
| E.Enterocyte_Progenitor | S100P | 3.348 | 4.03E-89 | 0.786 | 1.07E-04 | 0.666 | 5.56E-91 |
| E.Enterocyte_Progenitor | TFF1 | 1.890 | 5.74E-23 | 1.734 | 2.85E-08 | 1.005 | 1.47E-28 |
| E.Enterocyte_Progenitor | TPT1 | 0.621 | 2.36E-04 | 0.665 | 1.18E-25 | 0.881 | 1.81E-27 |
| E.Enterocytes | AC009501.4 | -1.866 | 1.23E-40 | -0.142 | 1.36E-01 | -1.561 | 6.81E-40 |
| E.Enterocytes | MDK | 1.676 | 1.04E-12 | 0.471 | 5.07E-12 | 0.802 | 4.25E-22 |
| E.Enterocytes | MTRNR2L1 | 0.692 | 2.57E-07 | 2.089 | 4.41E-29 | 0.927 | 1.07E-33 |
| E.Enterocytes | MUC1 | 1.587 | 4.06E-23 | 1.250 | 4.29E-27 | 0.567 | 2.98E-47 |
| E.Enterocytes | PLA2G2A | 1.809 | 2.99E-24 | 1.895 | 3.53E-16 | 0.692 | 1.41E-37 |
| E.Epithelial | AC009501.4 | -1.108 | 9.77E-81 | 0.257 | 1.42E-11 | -0.935 | 2.86E-89 |
| E.Epithelial | CXCL14 | -0.921 | 9.13E-40 | 0.230 | 3.49E-02 | -0.614 | 1.64E-39 |
| E.Epithelial | FTL | -0.513 | 1.00E-04 | -0.458 | 4.59E-33 | -0.910 | 3.60E-35 |
| E.Epithelial | HLA-B | 0.396 | 3.47E-04 | 0.443 | 1.30E-37 | 0.774 | 3.49E-39 |
| E.Epithelial | MT-ATP6 | -1.097 | 1.66E-23 | -0.006 | 8.87E-01 | -0.895 | 2.08E-22 |
| E.Epithelial | MT-ND2 | -1.167 | 2.79E-21 | 0.202 | 8.79E-08 | -0.994 | 2.03E-26 |
| E.Epithelial | MTRNR2L1 | 0.850 | 9.20E-44 | 1.674 | 4.88E-82 | 0.679 | 1.89E-122 |
| E.Epithelial | RARRES3 | 0.620 | 4.04E-18 | 0.207 | 1.23E-04 | 0.628 | 2.79E-20 |
| E.Epithelial | S100A11 | 0.530 | 3.23E-15 | 0.618 | 1.52E-51 | 0.661 | 9.39E-64 |
| E.Epithelial | S100A6 | 0.301 | 2.31E-01 | 0.496 | 2.40E-45 | 0.516 | 2.09E-44 |
| E.Epithelial | TIMP1 | 1.540 | 5.11E-48 | 0.459 | 3.01E-04 | 1.551 | 1.36E-49 |
| E.Goblet | MT-ND3 | 0.498 | 7.33E-03 | 1.601 | 2.46E-32 | 0.739 | 1.01E-32 |
| E.Immature_Enterocytes | AC009501.4 | -1.260 | 3.04E-65 | 0.211 | 4.27E-05 | -1.018 | 1.51E-67 |
| E.Immature_Enterocytes | AGR2 | 0.728 | 3.16E-18 | 0.972 | 2.62E-53 | 0.555 | 1.76E-68 |
| E.Immature_Enterocytes | CYBA | 0.445 | 1.33E-06 | 0.395 | 3.12E-19 | 0.603 | 2.98E-23 |
| E.Immature_Enterocytes | FTL | -0.752 | 1.21E-05 | -0.465 | 1.90E-20 | -1.181 | 1.56E-23 |
| E.Immature_Enterocytes | IFITM3 | 0.915 | 9.50E-20 | 0.506 | 1.85E-06 | 0.883 | 1.26E-23 |
| E.Immature_Enterocytes | LCN2 | 1.886 | 9.90E-101 | 1.402 | 1.25E-41 | 0.625 | 5.65E-139 |
| E.Immature_Enterocytes | MTRNR2L1 | 0.695 | 7.45E-20 | 2.021 | 2.85E-66 | 0.874 | 5.30E-83 |
| E.Immature_Enterocytes | PLA2G2A | 1.989 | 4.36E-103 | 1.457 | 6.45E-42 | 0.857 | 1.30E-141 |
| E.Immature_Enterocytes | REG4 | 1.956 | 1.41E-28 | 2.398 | 1.61E-13 | 0.746 | 2.99E-39 |
| E.Immature_Enterocytes | S100A11 | 0.955 | 5.32E-30 | 0.750 | 6.89E-33 | 1.131 | 7.95E-60 |
| E.Immature_Enterocytes | S100P | 2.923 | 5.34E-176 | 1.278 | 3.65E-33 | 0.536 | 1.05E-205 |
| E.Immature_Enterocytes | SPINK1 | 1.222 | 9.55E-40 | 1.004 | 8.36E-30 | 0.632 | 1.90E-66 |
| E.Immature_Enterocytes | TPT1 | 0.539 | 2.35E-05 | 0.508 | 2.12E-42 | 0.772 | 4.75E-45 |
| E.Immature_Goblet | AGR2 | 2.345 | 6.20E-08 | 0.764 | 2.47E-16 | 1.709 | 1.12E-21 |
| E.Immature_Goblet | TPT1 | 0.754 | 3.86E-02 | 0.643 | 2.05E-24 | 0.990 | 3.11E-24 |
| E.Secretory | LCN2 | 1.855 | 5.39E-27 | 1.240 | 2.36E-07 | 0.531 | 1.16E-31 |
| E.Secretory | MT-ND3 | 0.805 | 5.85E-10 | 1.765 | 4.64E-66 | 1.050 | 4.66E-73 |
| E.Secretory_All | AC009501.4 | -1.150 | 1.41E-54 | 0.201 | 2.88E-04 | -0.968 | 3.84E-56 |
| E.Secretory_All | FN1 | 3.218 | 2.44E-21 | 0.954 | 1.61E-01 | 0.852 | 1.10E-20 |
| E.Secretory_All | HLA-B | 0.401 | 8.51E-03 | 0.538 | 1.96E-33 | 0.786 | 9.36E-34 |
| E.Secretory_All | LYZ | 1.528 | 1.69E-40 | 0.007 | 9.67E-01 | 0.735 | 2.83E-39 |
| E.Secretory_All | MTRNR2L1 | 1.057 | 1.86E-42 | 1.178 | 3.07E-26 | 1.126 | 1.31E-65 |
| E.Secretory_All | TIMP1 | 1.285 | 2.27E-36 | 0.124 | 2.82E-01 | 1.065 | 2.01E-35 |
| E.Secretory_TA | AC009501.4 | -1.585 | 8.94E-31 | 0.115 | 2.12E-01 | -1.330 | 5.97E-30 |
| E.Secretory_TA | ITLN1 | 1.063 | 3.14E-05 | 1.247 | 4.03E-28 | 0.509 | 9.65E-31 |
| E.Secretory_TA | MTRNR2L1 | 0.865 | 2.67E-10 | 1.319 | 2.47E-21 | 0.940 | 4.99E-21 |
| E.Secretory_TA | SELK | 0.530 | 8.31E-03 | 0.654 | 2.11E-28 | 0.531 | 9.05E-29 |
| E.Secretory_TA | TMEM258 | 0.859 | 7.78E-03 | 0.616 | 1.36E-32 | 0.505 | 5.93E-33 |
| E.Stem | FN1 | 2.880 | 3.19E-21 | 1.215 | 2.72E-03 | 0.920 | 4.28E-22 |
| E.Stem | MT-ND3 | 0.794 | 1.31E-54 | 2.049 | 1.10E-54 | 1.199 | 6.90E-54 |
| E.Stem | RPL38 | 0.661 | 4.33E-01 | 0.802 | 1.62E-26 | 0.721 | 1.61E-25 |
| E.Stem | RPL39 | 0.477 | 2.20E-01 | 2.093 | 3.68E-66 | 0.708 | 3.76E-65 |
| E.Stem | TPT1 | 1.665 | 1.60E-01 | 0.783 | 2.20E-24 | 2.134 | 1.06E-23 |
| F.Crypt | CAV1 | 1.146 | 6.66E-21 | 0.425 | 1.19E-03 | 0.542 | 4.16E-22 |
| F.Crypt | COX4I1 | -0.620 | 5.73E-08 | -0.433 | 1.89E-23 | -0.556 | 9.59E-29 |
| F.Crypt | FOS | 0.221 | 1.37E-02 | 0.779 | 1.66E-33 | 0.510 | 1.21E-33 |
| F.Crypt | HLA-A | -0.858 | 3.01E-08 | -0.421 | 4.76E-21 | -0.885 | 1.22E-26 |
| F.Crypt | IFI27 | -0.822 | 7.61E-24 | -0.465 | 2.33E-09 | -0.509 | 1.74E-30 |
| F.Crypt | MTRNR2L1 | 1.954 | 5.69E-89 | 1.365 | 1.03E-19 | 2.153 | 1.69E-105 |

TABLE 15-continued

| | Non-inflamed vs Healthy Markers | | | | | | |
|---|---|---|---|---|---|---|---|
| F.Crypt | TAGLN | 1.641 | 6.57E-49 | 0.424 | 3.73E-03 | 0.610 | 1.82E-49 |
| F.Crypt | ZFP36 | 0.444 | 6.98E-08 | 0.650 | 5.22E-28 | 0.708 | 3.52E-33 |
| F.Crypt_loFos_1 | COL1A1 | 1.239 | 2.41E-07 | 0.734 | 4.28E-25 | 0.705 | 9.06E-30 |
| F.Crypt_loFos_1 | PRSS23 | 1.334 | 2.62E-19 | 0.656 | 2.20E-07 | 0.605 | 4.41E-24 |
| F.Crypt_loFos_1 | TAGLN | 1.894 | 1.12E-27 | 0.488 | 3.84E-02 | 0.784 | 1.80E-27 |
| F.Crypt_loFos_2 | MTRNR2L1 | 2.286 | 6.13E-29 | 1.325 | 1.91E-04 | 2.508 | 8.21E-31 |
| F.Endothelial | MTRNR2L1 | 2.323 | 2.17E-63 | 0.404 | 7.42E-02 | 2.056 | 9.32E-63 |
| F.Fibroblast | C12orf75 | 1.496 | 7.49E-23 | 0.580 | 4.57E-05 | 0.520 | 2.30E-25 |
| F.Fibroblast | HLA-A | -0.834 | 1.16E-10 | -0.397 | 4.80E-28 | -0.798 | 6.37E-36 |
| F.Fibroblast | MT-ND3 | 0.636 | 7.87E-21 | 0.470 | 2.89E-09 | 0.618 | 1.93E-26 |
| F.Fibroblast | MTRNR2L1 | 1.675 | 2.60E-106 | 1.221 | 4.14E-25 | 1.696 | 3.88E-128 |
| F.Fibroblast | PRSS23 | 1.294 | 2.72E-50 | 0.711 | 8.47E-16 | 0.612 | 4.42E-63 |
| F.Fibroblast | RPL12 | -0.736 | 1.89E-05 | -0.282 | 3.85E-18 | -0.905 | 4.50E-21 |
| F.Fibroblast | RPL6 | -0.596 | 4.05E-05 | -0.302 | 1.03E-20 | -0.723 | 2.68E-23 |
| F.Fibroblast | ZFP36 | 0.398 | 4.12E-10 | 0.492 | 1.11E-22 | 0.574 | 4.56E-30 |
| F.Stromal | COX4I1 | -0.598 | 3.29E-14 | -0.321 | 1.36E-22 | -0.543 | 5.37E-34 |
| F.Stromal | HLA-A | -0.702 | 1.63E-08 | -0.431 | 3.40E-37 | -0.748 | 6.50E-43 |
| F.Stromal | MT-ND3 | 0.674 | 9.33E-26 | 0.462 | 7.66E-09 | 0.646 | 7.06E-32 |
| F.Stromal | MTRNR2L1 | 1.682 | 8.15E-123 | 1.017 | 4.07E-20 | 1.568 | 1.14E-139 |
| F.Stromal | RPL12 | -0.826 | 1.12E-09 | -0.241 | 3.27E-15 | -0.957 | 2.87E-22 |
| F.Stromal | RPL6 | -0.475 | 9.80E-05 | -0.296 | 5.70E-23 | -0.646 | 3.61E-25 |
| F.Villus | COL3A1 | 1.208 | 3.13E-18 | 0.428 | 5.03E-13 | 0.713 | 1.60E-28 |
| F.Villus | DCN | 1.226 | 4.58E-34 | 0.195 | 3.52E-02 | 0.911 | 7.65E-34 |
| F.Villus | LUM | 1.197 | 5.30E-33 | 0.434 | 2.30E-04 | 0.865 | 9.06E-35 |
| F.Villus | MTRNR2L1 | 1.779 | 6.24E-54 | 0.986 | 2.13E-08 | 1.789 | 1.87E-59 |
| F.Villus | PRSS23 | 2.155 | 5.51E-22 | 0.943 | 9.10E-04 | 1.436 | 2.75E-23 |
| F.Villus_1 | LUM | 1.625 | 2.01E-27 | 0.865 | 9.13E-05 | 1.631 | 1.31E-29 |
| F.Villus_1 | MTRNR2L1 | 2.150 | 5.43E-37 | 1.250 | 8.12E-06 | 2.357 | 4.13E-40 |
| I.Immune | AC009501.4 | -0.932 | 5.84E-59 | 0.028 | 5.05E-01 | -0.861 | 9.53E-58 |
| I.Immune | MT-ND3 | 0.681 | 6.43E-30 | 0.847 | 8.29E-29 | 0.764 | 1.08E-55 |
| I.Lymphoid | AC009501.4 | -0.948 | 1.16E-60 | -0.149 | 4.55E-01 | -0.988 | 5.14E-62 |
| I.Lymphoid | MT-ND3 | 0.758 | 2.23E-37 | 0.926 | 2.61E-36 | 0.923 | 1.48E-70 |
| I.Lymphoid | RPL37 | 0.524 | 5.45E-11 | 0.503 | 1.44E-51 | 0.502 | 1.25E-59 |
| I.Lymphoid | RPL37A | 0.491 | 2.75E-09 | 0.453 | 4.13E-45 | 0.530 | 1.54E-51 |
| I.Lymphoid | RPL39 | 0.827 | 8.12E-45 | 1.128 | 4.65E-71 | 0.655 | 1.50E-112 |
| I.Lymphoid | RPS29 | 0.637 | 9.51E-12 | 0.707 | 1.10E-75 | 0.781 | 2.12E-84 |
| M.CD69pos_Mast | RPL39 | 1.796 | 1.16E-28 | 0.968 | 1.14E-06 | 1.658 | 1.17E-32 |
| M.Macrophages | TPT1 | 0.714 | 8.54E-03 | 0.737 | 8.30E-33 | 0.974 | 3.94E-33 |
| M.Mast | RPL39 | 1.513 | 5.56E-24 | 0.951 | 2.55E-07 | 1.346 | 1.21E-28 |
| M.Monocytes | AC009501.4 | -1.060 | 6.57E-29 | 0.372 | 1.03E-08 | -0.841 | 7.05E-35 |
| M.Monocytes | MT-ND3 | 0.733 | 6.64E-13 | 0.813 | 1.66E-14 | 0.856 | 9.86E-25 |
| M.Monocytes | TPT1 | 0.556 | 2.12E-02 | 0.816 | 1.23E-66 | 0.828 | 1.88E-66 |
| M.Myeloid | AC009501.4 | -0.944 | 2.00E-33 | 0.305 | 2.68E-07 | -0.760 | 5.44E-38 |
| M.Myeloid | MT-ND3 | 0.917 | 2.08E-27 | 0.800 | 5.64E-18 | 0.988 | 1.77E-42 |
| M.Myeloid | RPL39 | 0.610 | 2.75E-13 | 1.381 | 1.80E-68 | 0.718 | 1.01E-78 |
| M.Myeloid | RPS29 | 0.600 | 7.49E-09 | 0.445 | 2.32E-17 | 0.811 | 1.40E-23 |
| M.Myeloid | TPT1 | 0.346 | 1.47E-02 | 0.601 | 5.47E-52 | 0.526 | 5.33E-52 |
| T.Activated_CD4_hiFos | KLRB1 | 1.024 | 1.50E-15 | 0.959 | 5.25E-20 | 0.684 | 9.27E-33 |
| T.Activated_CD4_hiFos | RPL39 | 0.774 | 2.49E-09 | 1.083 | 1.30E-16 | 0.673 | 2.62E-23 |
| T.Activated_CD4_loFos | ANXA1 | -1.580 | 2.54E-20 | -0.564 | 1.84E-10 | -1.148 | 4.46E-28 |
| T.Activated_CD4_loFos | RPL39 | 0.795 | 1.80E-09 | 1.129 | 1.06E-18 | 0.758 | 1.66E-25 |
| T.Activated_CD4_loFos | RPS29 | 0.887 | 1.46E-03 | 0.801 | 2.45E-22 | 1.237 | 1.91E-23 |
| T.CD4 | AC009501.4 | -0.753 | 4.11E-29 | -0.129 | 1.39E-02 | -0.760 | 2.82E-29 |
| T.CD4 | ANXA1 | -0.895 | 1.22E-42 | -0.535 | 1.27E-24 | -0.730 | 3.47E-64 |
| T.CD4 | CCL5 | -0.778 | 3.45E-32 | -0.105 | 1.46E-01 | -0.556 | 1.79E-31 |
| T.CD4 | MT-ND3 | 1.088 | 2.62E-57 | 0.642 | 6.53E-15 | 0.984 | 3.40E-69 |
| T.CD4 | RPL3 | -0.728 | 2.37E-03 | -0.318 | 1.54E-21 | -1.038 | 1.83E-22 |
| T.CD4 | RPL37A | 0.475 | 2.69E-07 | 0.411 | 7.65E-33 | 0.501 | 2.07E-37 |
| T.CD4 | RPL39 | 0.923 | 5.13E-44 | 1.004 | 2.72E-51 | 0.705 | 4.65E-92 |
| T.CD4 | RPS29 | 0.711 | 1.15E-10 | 0.647 | 6.11E-58 | 0.900 | 1.17E-65 |
| T.CD8 | AC009501.4 | -1.089 | 1.99E-36 | -0.001 | 9.93E-01 | -0.985 | 3.16E-35 |
| T.CD8 | KLRB1 | 1.135 | 1.12E-34 | 1.051 | 7.19E-31 | 0.531 | 1.81E-62 |
| T.CD8 | RPL23 | 0.767 | 1.27E-16 | 0.346 | 2.23E-13 | 0.538 | 2.80E-27 |
| T.CD8 | RPL37 | 0.627 | 8.81E-08 | 0.482 | 7.49E-26 | 0.634 | 6.07E-31 |
| T.CD8 | RPL37A | 0.826 | 4.47E-12 | 0.319 | 2.98E-12 | 0.847 | 1.05E-21 |
| T.CD8 | RPL38 | 0.718 | 1.08E-13 | 0.414 | 1.41E-19 | 0.667 | 1.65E-30 |
| T.CD8 | RPL39 | 1.033 | 5.50E-34 | 1.030 | 9.55E-35 | 0.907 | 1.25E-65 |
| T.CD8 | RPS29 | 0.843 | 3.90E-09 | 0.789 | 8.10E-50 | 1.202 | 4.48E-56 |
| T.CD8_IELs | KLRB1 | 1.786 | 3.21E-35 | 0.713 | 2.82E-08 | 1.362 | 1.01E-40 |
| T.CD8_IELs | RPL39 | 1.082 | 1.71E-15 | 1.055 | 1.63E-15 | 0.933 | 2.86E-28 |
| T.CD8_IELs | RPS29 | 0.856 | 1.86E-04 | 0.878 | 1.09E-24 | 1.294 | 1.31E-26 |
| T.CD8_LP | RPL39 | 0.992 | 8.30E-15 | 0.870 | 1.58E-10 | 0.842 | 1.06E-22 |
| T.Memory_CD4 | ANXA1 | -1.046 | 1.67E-16 | -0.708 | 7.68E-09 | -0.987 | 9.99E-23 |
| T.Memory_CD4 | RPL39 | 1.077 | 5.94E-17 | 1.031 | 1.19E-16 | 0.931 | 7.91E-31 |
| T.Memory_CD4 | RPS29 | 0.892 | 7.88E-05 | 0.830 | 1.78E-24 | 1.253 | 9.46E-27 |
| T.Tcells | AC009501.4 | -1.080 | 1.57E-72 | -0.199 | 7.92E-06 | -1.052 | 1.65E-75 |
| T.Tcells | MT-ND3 | 0.937 | 1.37E-53 | 0.698 | 2.96E-21 | 0.877 | 9.43E-72 |
| T.Tcells | RPL37 | 0.552 | 7.33E-12 | 0.504 | 1.21E-56 | 0.510 | 1.55E-65 |

TABLE 15-continued

| | | | Non-inflamed vs Healthy Markers | | | | |
|---|---|---|---|---|---|---|---|
| T.Tcells | RPL37A | 0.695 | 1.59E−17 | 0.424 | 2.05E−41 | 0.689 | 6.00E−56 |
| T.Tcells | RPL38 | 0.691 | 8.14E−25 | 0.410 | 3.13E−37 | 0.533 | 5.34E−59 |
| T.Tcells | RPL39 | 0.917 | 7.15E−53 | 1.091 | 1.16E−73 | 0.692 | 3.64E−123 |
| T.Tcells | RPS16 | 0.532 | 6.76E−06 | 0.345 | 1.27E−33 | 0.549 | 7.74E−37 |
| T.Tcells | RPS23 | 0.460 | 7.92E−04 | 0.307 | 4.37E−24 | 0.604 | 2.01E−25 |
| T.Tcells | RPS29 | 0.688 | 3.71E−12 | 0.717 | 7.00E−89 | 0.868 | 5.80E−98 |
| T.Tcells | TMSB4X | −0.761 | 2.25E−01 | −0.421 | 6.54E−35 | −1.006 | 4.87E−34 |
| T.Tregs | RPL39 | 1.289 | 3.69E−18 | 0.954 | 7.35E−09 | 1.110 | 2.23E−24 |

| ident | n | ref_n | mu | ref_mu | total | ref_total |
|---|---|---|---|---|---|---|
| B.Bcells | 315 | 1399 | 1.732 | 2.300 | 0.021 | 0.136 |
| B.Bcells | 818 | 847 | 2.717 | 2.347 | 0.060 | 0.105 |
| B.Bcells | 660 | 2002 | 8.085 | 9.053 | 0.126 | 0.750 |
| B.Bcells | 587 | 1098 | 2.563 | 2.360 | 0.089 | 0.144 |
| B.Bcells | 579 | 1094 | 4.387 | 3.127 | 0.075 | 0.059 |
| B.Bcells | 255 | 297 | 2.180 | 2.371 | 0.081 | 0.107 |
| B.Bcells | 885 | 2227 | 3.902 | 3.143 | 0.099 | 0.147 |
| B.Bcells | 893 | 2284 | 3.925 | 3.297 | 0.087 | 0.144 |
| B.Bcells | 670 | 378 | 4.908 | 3.627 | 0.154 | 0.131 |
| B.Bcells | 845 | 2058 | 3.313 | 2.862 | 0.092 | 0.164 |
| B.Bcells | 895 | 2273 | 4.561 | 3.910 | 0.104 | 0.168 |
| B.Bcells | 910 | 2320 | 4.586 | 3.872 | 0.085 | 0.133 |
| B.FO | 262 | 482 | 5.527 | 4.678 | 0.117 | 0.120 |
| B.Plasma | 429 | 1319 | 8.601 | 9.410 | 0.134 | 0.720 |
| E.Absorptive | 232 | 1244 | 2.454 | 2.477 | 0.027 | 0.146 |
| E.Absorptive | 582 | 1639 | 5.319 | 4.978 | 0.070 | 0.156 |
| E.Absorptive | 294 | 473 | 5.538 | 4.723 | 0.135 | 0.124 |
| E.Absorptive | 365 | 675 | 2.203 | 2.124 | 0.082 | 0.144 |
| E.Absorptive | 388 | 741 | 3.887 | 1.713 | 0.069 | 0.029 |
| E.Absorptive_All | 1006 | 1770 | 3.283 | 2.771 | 0.162 | 0.200 |
| E.Absorptive_All | 2353 | 2409 | 5.065 | 5.477 | 0.107 | 0.146 |
| E.Absorptive_All | 2292 | 2228 | 4.721 | 4.370 | 0.148 | 0.113 |
| E.Absorptive_All | 1078 | 634 | 5.863 | 4.769 | 0.375 | 0.103 |
| E.Absorptive_All | 817 | 442 | 2.047 | 2.072 | 0.137 | 0.076 |
| E.Absorptive_All | 248 | 39 | 5.078 | 1.191 | 0.236 | 0.003 |
| E.Absorptive_All | 1368 | 957 | 2.892 | 2.147 | 0.143 | 0.060 |
| E.Absorptive_All | 372 | 37 | 2.660 | 0.887 | 0.045 | 0.001 |
| E.Absorptive_TA_1 | 157 | 181 | 6.221 | 5.640 | 0.120 | 0.093 |
| E.Absorptive_TA_2 | 164 | 978 | 2.742 | 2.209 | 0.024 | 0.099 |
| E.Absorptive_TA_2 | 283 | 778 | 1.155 | 1.041 | 0.015 | 0.039 |
| E.Absorptive_TA_2 | 290 | 723 | 1.776 | 1.210 | 0.021 | 0.035 |
| E.Absorptive_TA_2 | 337 | 1020 | 2.353 | 1.774 | 0.046 | 0.093 |
| E.Absorptive_TA_2 | 153 | 277 | 4.987 | 3.981 | 0.058 | 0.052 |
| E.Absorptive_TA_2 | 315 | 869 | 2.000 | 1.269 | 0.051 | 0.084 |
| E.Absorptive_TA_2 | 337 | 1031 | 2.441 | 1.900 | 0.035 | 0.073 |
| E.Best4_Enterocytes | 211 | 459 | 4.588 | 2.087 | 0.064 | 0.024 |
| E.Cycling_TA | 60 | 4 | 0.716 | −0.174 | 0.035 | 0.001 |
| E.Cycling_TA | 175 | 168 | −0.050 | −0.238 | 0.015 | 0.013 |
| E.Cycling_TA | 225 | 187 | 1.706 | 0.621 | 0.011 | 0.004 |
| E.Cycling_TA | 329 | 1010 | 2.055 | 1.402 | 0.037 | 0.072 |
| E.Cycling_TA | 165 | 276 | 4.088 | 3.351 | 0.036 | 0.037 |
| E.Cycling_TA | 58 | 6 | 0.112 | −0.939 | 0.029 | 0.001 |
| E.Cycling_TA | 127 | 71 | 3.274 | −0.106 | 0.050 | 0.003 |
| E.Cycling_TA | 332 | 1148 | 3.594 | 3.094 | 0.056 | 0.137 |
| E.Cycling_TA | 335 | 1020 | 2.945 | 1.523 | 0.051 | 0.058 |
| E.Cycling_TA | 237 | 75 | 1.477 | −0.225 | 0.056 | 0.005 |
| E.Enterocyte_Immature_1 | 174 | 298 | 6.433 | 5.302 | 0.152 | 0.119 |
| E.Enterocyte_Immature_1 | 96 | 50 | 3.275 | 1.480 | 0.141 | 0.021 |
| E.Enterocyte_Immature_1 | 94 | 36 | 3.492 | 1.624 | 0.047 | 0.005 |
| E.Enterocyte_Immature_2 | 157 | 980 | 3.004 | 2.688 | 0.027 | 0.133 |
| E.Enterocyte_Immature_2 | 327 | 1036 | 3.316 | 2.784 | 0.036 | 0.079 |
| E.Enterocyte_Immature_2 | 152 | 337 | 5.575 | 4.159 | 0.083 | 0.069 |
| E.Enterocyte_Immature_2 | 244 | 455 | 2.071 | 0.909 | 0.021 | 0.018 |
| E.Enterocyte_Immature_2 | 254 | 130 | 2.673 | 0.233 | 0.122 | 0.012 |
| E.Enterocyte_Progenitor | 168 | 730 | 3.904 | 2.797 | 0.054 | 0.109 |
| E.Enterocyte_Progenitor | 339 | 718 | 5.063 | 3.249 | 0.129 | 0.078 |
| E.Enterocyte_Progenitor | 149 | 247 | 6.112 | 5.395 | 0.111 | 0.112 |
| E.Enterocyte_Progenitor | 222 | 118 | 4.377 | 2.794 | 0.179 | 0.032 |
| E.Enterocyte_Progenitor | 60 | 12 | 6.281 | 1.470 | 0.176 | 0.001 |
| E.Enterocyte_Progenitor | 229 | 359 | 3.665 | 2.418 | 0.059 | 0.039 |
| E.Enterocyte_Progenitor | 197 | 33 | 3.042 | 1.938 | 0.130 | 0.010 |
| E.Enterocyte_Progenitor | 86 | 40 | 4.833 | 1.617 | 0.085 | 0.004 |
| E.Enterocyte_Progenitor | 348 | 974 | 4.387 | 3.701 | 0.037 | 0.064 |
| E.Enterocytes | 127 | 684 | 2.550 | 2.661 | 0.017 | 0.097 |
| E.Enterocytes | 304 | 670 | 2.972 | 2.497 | 0.139 | 0.221 |
| E.Enterocytes | 157 | 272 | 5.572 | 4.456 | 0.087 | 0.070 |
| E.Enterocytes | 129 | 100 | 2.732 | 0.805 | 0.142 | 0.029 |

TABLE 15-continued

| Non-inflamed vs Healthy Markers | | | | | | |
|---|---|---|---|---|---|---|
| E.Enterocytes | 106 | 60 | 3.870 | 0.490 | 0.065 | 0.004 |
| E.Epithelial | 1040 | 1715 | 3.458 | 2.717 | 0.172 | 0.170 |
| E.Epithelial | 418 | 747 | 2.000 | 1.137 | 0.013 | 0.012 |
| E.Epithelial | 2313 | 2393 | 4.946 | 5.360 | 0.086 | 0.119 |
| E.Epithelial | 2303 | 2268 | 4.649 | 4.295 | 0.122 | 0.094 |
| E.Epithelial | 2165 | 2368 | 6.556 | 6.541 | 0.252 | 0.273 |
| E.Epithelial | 2214 | 2400 | 6.759 | 6.517 | 0.261 | 0.239 |
| E.Epithelial | 1065 | 596 | 5.621 | 4.447 | 0.362 | 0.090 |
| E.Epithelial | 739 | 397 | 1.841 | 2.053 | 0.084 | 0.052 |
| E.Epithelial | 1509 | 1196 | 3.018 | 1.969 | 0.149 | 0.057 |
| E.Epithelial | 2474 | 2461 | 6.133 | 5.634 | 0.269 | 0.190 |
| E.Epithelial | 569 | 105 | 2.584 | 1.996 | 0.052 | 0.006 |
| E.Goblet | 211 | 527 | 5.902 | 3.597 | 0.084 | 0.042 |
| E.Immature_Enterocytes | 459 | 1782 | 3.507 | 2.807 | 0.092 | 0.220 |
| E.Immature_Enterocytes | 817 | 1451 | 4.347 | 2.608 | 0.158 | 0.084 |
| E.Immature_Enterocytes | 852 | 1726 | 3.348 | 2.928 | 0.078 | 0.119 |
| E.Immature_Enterocytes | 1037 | 2426 | 5.064 | 5.516 | 0.052 | 0.166 |
| E.Immature_Enterocytes | 299 | 280 | 1.936 | 1.519 | 0.023 | 0.016 |
| E.Immature_Enterocytes | 529 | 311 | 3.748 | 1.766 | 0.223 | 0.033 |
| E.Immature_Enterocytes | 475 | 660 | 6.100 | 4.939 | 0.248 | 0.154 |
| E.Immature_Enterocytes | 500 | 262 | 3.949 | 1.922 | 0.233 | 0.030 |
| E.Immature_Enterocytes | 113 | 35 | 5.628 | 0.764 | 0.196 | 0.002 |
| E.Immature_Enterocytes | 530 | 656 | 3.071 | 1.786 | 0.079 | 0.040 |
| E.Immature_Enterocytes | 518 | 130 | 2.782 | 0.830 | 0.207 | 0.013 |
| E.Immature_Enterocytes | 422 | 378 | 3.014 | 1.646 | 0.150 | 0.052 |
| E.Immature_Enterocytes | 1002 | 2180 | 4.413 | 3.797 | 0.089 | 0.126 |
| E.Immature_Goblet | 344 | 969 | 6.360 | 5.245 | 0.206 | 0.268 |
| E.lmmature_Goblet | 338 | 981 | 4.883 | 4.192 | 0.048 | 0.087 |
| E.Secretory | 120 | 55 | 3.684 | 1.893 | 0.066 | 0.009 |
| E.Secretory | 398 | 768 | 6.215 | 3.721 | 0.166 | 0.057 |
| E.Secretory_All | 354 | 1439 | 2.920 | 2.417 | 0.052 | 0.150 |
| E.Secretory_All | 64 | 2 | 0.437 | −0.049 | 0.033 | 0.001 |
| E.Secretory_All | 1088 | 2284 | 4.746 | 4.429 | 0.084 | 0.141 |
| E.Secretory_All | 268 | 122 | 1.816 | 2.914 | 0.033 | 0.032 |
| E.Secretory_All | 513 | 526 | 5.467 | 4.918 | 0.189 | 0.133 |
| E.Secretory_All | 314 | 190 | 2.285 | 2.936 | 0.030 | 0.029 |
| E.Secretory_TA | 126 | 762 | 1.989 | 1.736 | 0.012 | 0.060 |
| E.Secretory_TA | 301 | 818 | 4.563 | 3.164 | 0.153 | 0.158 |
| E.Secretory_TA | 154 | 259 | 4.454 | 3.805 | 0.043 | 0.046 |
| E.Secretory_TA | 278 | 720 | 1.320 | 1.046 | 0.026 | 0.057 |
| E.Secretory_TA | 303 | 877 | 1.944 | 1.608 | 0.044 | 0.102 |
| E.Stem | 63 | 6 | 1.178 | −0.485 | 0.050 | 0.002 |
| E.Stem | 237 | 575 | 6.088 | 3.493 | 0.105 | 0.042 |
| E.Stem | 239 | 604 | 3.797 | 3.107 | 0.052 | 0.081 |
| E.Stem | 233 | 549 | 5.235 | 2.766 | 0.103 | 0.044 |
| E.Stem | 240 | 613 | 4.911 | 3.971 | 0.037 | 0.050 |
| F.Crypt | 162 | 148 | 3.001 | 2.403 | 0.101 | 0.061 |
| F.Crypt | 739 | 2049 | 3.273 | 3.686 | 0.049 | 0.180 |
| F.Crypt | 689 | 1621 | 5.550 | 4.853 | 0.183 | 0.266 |
| F.Crypt | 833 | 2285 | 4.229 | 4.750 | 0.059 | 0.231 |
| F.Crypt | 429 | 1470 | 3.041 | 3.819 | 0.027 | 0.157 |
| F.Crypt | 359 | 192 | 5.360 | 4.084 | 0.171 | 0.038 |
| F.Crypt | 238 | 147 | 3.168 | 2.610 | 0.102 | 0.043 |
| F.Crypt | 630 | 1331 | 4.625 | 4.035 | 0.163 | 0.228 |
| F.Crypt_loFos_1 | 284 | 814 | 4.116 | 3.384 | 0.183 | 0.316 |
| F.Crypt_loFos_1 | 129 | 147 | 2.980 | 1.974 | 0.106 | 0.060 |
| F.Crypt_loFos_1 | 101 | 66 | 2.784 | 2.123 | 0.042 | 0.017 |
| F.Crypt_loFos_2 | 88 | 33 | 6.193 | 4.850 | 0.081 | 0.012 |
| F.Endothelial | 226 | 74 | 4.910 | 4.980 | 0.085 | 0.029 |
| F.Fibroblast | 174 | 45 | 3.194 | 2.323 | 0.190 | 0.027 |
| F.Fibroblast | 1700 | 2351 | 4.642 | 5.131 | 0.129 | 0.249 |
| F.Fibroblast | 812 | 637 | 4.188 | 3.642 | 0.098 | 0.053 |
| F.Fibroblast | 723 | 256 | 5.408 | 4.375 | 0.293 | 0.051 |
| F.Fibroblast | 488 | 201 | 3.293 | 2.214 | 0.313 | 0.061 |
| F.Fibroblast | 1778 | 2426 | 4.932 | 5.216 | 0.137 | 0.227 |
| F.Fibroblast | 1750 | 2392 | 4.780 | 5.109 | 0.145 | 0.248 |
| F.Fibroblast | 1162 | 1237 | 4.547 | 4.098 | 0.237 | 0.185 |
| F.Stromal | 1791 | 1990 | 3.355 | 3.683 | 0.109 | 0.152 |
| F.Stromal | 2171 | 2366 | 4.816 | 5.330 | 0.167 | 0.261 |
| F.Stromal | 1025 | 630 | 4.241 | 3.673 | 0.128 | 0.053 |
| F.Stromal | 949 | 269 | 5.304 | 4.581 | 0.323 | 0.056 |
| F.Stromal | 2195 | 2397 | 4.831 | 5.095 | 0.150 | 0.197 |
| F.Stromal | 2183 | 2360 | 4.695 | 5.023 | 0.162 | 0.219 |
| F.Villus | 569 | 953 | 4.500 | 4.105 | 0.242 | 0.308 |
| F.Villus | 436 | 508 | 4.004 | 3.868 | 0.129 | 0.137 |
| F.Villus | 372 | 386 | 4.842 | 4.352 | 0.164 | 0.121 |
| F.Villus | 277 | 145 | 5.429 | 4.722 | 0.139 | 0.044 |
| F.Villus | 79 | 18 | 3.522 | 2.186 | 0.099 | 0.009 |

TABLE 15-continued

| Non-inflamed vs Healthy Markers | | | | | | |
|---|---|---|---|---|---|---|
| F.Villus_1 | 181 | 104 | 5.000 | 3.997 | 0.114 | 0.033 |
| F.Villus_1 | 157 | 50 | 5.170 | 4.481 | 0.076 | 0.015 |
| I.Immune | 848 | 1415 | 3.516 | 3.541 | 0.138 | 0.235 |
| I.Immune | 1244 | 798 | 4.731 | 3.743 | 0.152 | 0.049 |
| I.Lymphoid | 800 | 1383 | 3.317 | 3.493 | 0.114 | 0.222 |
| I.Lymphoid | 1323 | 823 | 4.803 | 3.751 | 0.172 | 0.052 |
| I.Lymphoid | 2199 | 1983 | 4.285 | 3.752 | 0.239 | 0.149 |
| I.Lymphoid | 2218 | 2021 | 4.192 | 3.728 | 0.200 | 0.132 |
| I.Lymphoid | 1537 | 987 | 5.084 | 3.996 | 0.316 | 0.096 |
| I.Lymphoid | 2314 | 2141 | 5.089 | 4.344 | 0.286 | 0.158 |
| M.CD69pos_Mast | 145 | 96 | 5.003 | 4.035 | 0.059 | 0.020 |
| M.Macrophages | 354 | 936 | 5.437 | 4.616 | 0.069 | 0.103 |
| M.Mast | 160 | 115 | 4.935 | 3.926 | 0.062 | 0.022 |
| M.Monocytes | 273 | 1237 | 3.685 | 3.459 | 0.059 | 0.230 |
| M.Monocytes | 387 | 696 | 4.540 | 3.756 | 0.060 | 0.063 |
| M.Monocytes | 601 | 1679 | 5.546 | 4.538 | 0.109 | 0.151 |
| M.Myeloid | 321 | 1396 | 3.664 | 3.488 | 0.065 | 0.250 |
| M.Myeloid | 518 | 765 | 4.488 | 3.794 | 0.078 | 0.071 |
| M.Myeloid | 566 | 1047 | 4.766 | 3.594 | 0.142 | 0.117 |
| M.Myeloid | 785 | 1787 | 4.171 | 3.829 | 0.080 | 0.144 |
| M.Myeloid | 864 | 2173 | 5.316 | 4.525 | 0.120 | 0.175 |
| T.Activated_CD4_hiFos | 199 | 381 | 4.555 | 3.648 | 0.208 | 0.212 |
| T.Activated_CD4_hiFos | 210 | 396 | 5.055 | 4.054 | 0.079 | 0.075 |
| T.Activated_CD4_loFos | 220 | 980 | 4.314 | 4.983 | 0.054 | 0.383 |
| T.Activated_CD4_loFos | 201 | 459 | 5.305 | 4.321 | 0.086 | 0.099 |
| T.Activated_CD4_loFos | 298 | 953 | 5.264 | 4.669 | 0.069 | 0.146 |
| T.CD4 | 453 | 1150 | 3.452 | 3.661 | 0.076 | 0.224 |
| T.CD4 | 739 | 1712 | 4.319 | 4.983 | 0.119 | 0.437 |
| T.CD4 | 514 | 1299 | 4.767 | 5.153 | 0.107 | 0.354 |
| T.CD4 | 851 | 616 | 4.812 | 4.116 | 0.128 | 0.057 |
| T.CD4 | 1562 | 2475 | 6.156 | 6.468 | 0.141 | 0.278 |
| T.CD4 | 1408 | 1953 | 4.371 | 4.008 | 0.152 | 0.164 |
| T.CD4 | 1009 | 918 | 5.245 | 4.426 | 0.232 | 0.120 |
| T.CD4 | 1489 | 2118 | 5.240 | 4.704 | 0.198 | 0.195 |
| T.CD8 | 213 | 1267 | 3.751 | 3.703 | 0.047 | 0.268 |
| T.CD8 | 305 | 415 | 4.826 | 3.743 | 0.299 | 0.192 |
| T.CD8 | 596 | 1318 | 3.743 | 3.374 | 0.101 | 0.174 |
| T.CD8 | 689 | 1817 | 4.275 | 3.801 | 0.099 | 0.188 |
| T.CD8 | 698 | 1775 | 4.113 | 3.818 | 0.078 | 0.162 |
| T.CD8 | 622 | 1457 | 3.891 | 3.495 | 0.104 | 0.185 |
| T.CD8 | 487 | 819 | 4.945 | 4.075 | 0.132 | 0.121 |
| T.CD8 | 730 | 1994 | 5.173 | 4.412 | 0.123 | 0.198 |
| T.CD8_IELs | 148 | 163 | 4.141 | 3.519 | 0.169 | 0.121 |
| T.CD8_IELs | 191 | 399 | 4.975 | 4.012 | 0.072 | 0.077 |
| T.CD8_IELs | 274 | 907 | 5.291 | 4.350 | 0.069 | 0.118 |
| T.CD8_LP | 195 | 336 | 4.890 | 4.217 | 0.064 | 0.070 |
| T.Memory_CD4 | 117 | 565 | 3.972 | 4.883 | 0.029 | 0.260 |
| T.Memory_CD4 | 239 | 365 | 5.688 | 4.809 | 0.121 | 0.101 |
| T.Memory_CD4 | 334 | 810 | 5.759 | 4.996 | 0.100 | 0.143 |
| T.Tcells | 652 | 1376 | 3.553 | 3.792 | 0.105 | 0.261 |
| T.Tcells | 1213 | 730 | 4.762 | 4.006 | 0.157 | 0.056 |
| T.Tcells | 1981 | 1945 | 4.445 | 3.975 | 0.228 | 0.161 |
| T.Tcells | 2000 | 1915 | 4.298 | 3.911 | 0.193 | 0.141 |
| T.Tcells | 1791 | 1560 | 3.983 | 3.609 | 0.229 | 0.154 |
| T.Tcells | 1410 | 940 | 5.156 | 4.167 | 0.290 | 0.097 |
| T.Tcells | 2149 | 2267 | 5.070 | 4.717 | 0.219 | 0.180 |
| T.Tcells | 2178 | 2344 | 5.307 | 5.022 | 0.209 | 0.185 |
| T.Tcells | 2106 | 2150 | 5.215 | 4.563 | 0.259 | 0.168 |
| T.Tcells | 2256 | 2521 | 7.939 | 8.342 | 0.195 | 0.289 |
| T.Tregs | 183 | 157 | 4.882 | 4.028 | 0.064 | 0.030 |

Example 18—STAR Methods

Computational Analyses

Processing FASTQ reads into gene-expression matrices. Cell Ranger v2.0 was used to demultiplex the FASTQ reads, align them to the hg19 human transcriptome, and extract their "cell" and "UMI" barcodes. The output of this pipeline is a digital gene-expression (DGE) matrix for each sample, which records the number of UMIs for each gene that are associated with each cell barcode. DGE matrices were filtered to remove low quality cells, defined as cells in which fewer than 250 unique genes were detected. This cutoff was determined empirically: higher cutoffs led to disproportionate filtering of mast and T cells, whereas lower cutoffs did not affect the cell type distribution, but did reduce overall data quality. To account for differences in sequencing depth across cells, UMI counts were normalized by the total number of UMIs per cell and converted to transcripts-per-10,000 (henceforth "TPM").

Cell clustering overview. To cluster single cells into distinct cell subsets, Applicants followed the general procedure outlined in with additional modifications. This workflow includes the following steps: partitioning cells into epithelial, stromal, and immune compartments; and clustering the cells within each compartment, which entails the selection of "variable" genes, batch correction, dimensionality reduction (PCA), and graph clustering. Each step of this workflow is explained in detail below.

Partitioning cells into epithelial, stromal, and immune compartments. Cells were partitioned into epithelial, stromal, and immune compartments based on the expression of known marker genes. First, Applicants clustered the cells within each sample by their gene-expression profiles (with the clustering procedure below). The clusters were scored for the following gene signatures: epithelial cells (EPCAM, KRT8, KRT18), stromal cells (COL1A1, COL1A2, COL6A1, COL6A2, VWF, PLVAP, CDH5, S100B), and immune cells (CD52, CD2, CD3D, CD3G, CD3E, CD79A, CD79B, CD14, CD16, CD68, CD83, CSF1R, FCER1G). Signature scores were calculated as the mean $\log_2$(TPM) across all genes in the signature. Each cluster was assigned to the compartment of its maximal score and all cluster assignments were manually inspected to ensure the accurate segregation of cells. Finally, the cells within each compartment were assembled into three DGE matrices, comprising all epithelial cells, all stromal cells, and all immune cells.

Variable gene selection. Applicants identified sets of variable genes, defined as genes with high variance of expression relative to their mean expression. To prevent "batch" differences between samples from unduly impacting these gene sets, Applicants performed variable gene selection separately for each sample, then merged the results to form a consensus variable gene list. To identify variable genes within a sample, Applicants first calculated the mean ($\mu$) and the coefficient of variation (CV) of expression of each gene. Genes were then grouped into 20 equal-frequency bins (ventiles) according to their mean expression levels. LOESS regression was used to fit the relationship, log(CV)~log(s), and the 1,500 genes with the highest residuals were evenly sampled across these expression bins. After this procedure was performed for each sample, genes were ranked according to the number of samples from which they were recovered. A consensus set of 1,500 variable genes was then formed by selecting the genes with the greatest recovery rates across all samples and ties were broken by random sampling. This consensus gene set was then pruned through the removal of all ribosomal, mitochondrial, immunoglobulin, and HLA genes, which were found to induce unwanted batch effects in downstream clustering steps.

Batch correction. Applicants observed substantial variability between cells that had been obtained from different human subjects, which likely reflects a combination of technical and biological differences. In some cases, these "batch effects" led to cells clustering by patient or disease phenotype, rather than by cell type or cell state. To eliminate these batch differences, Applicants ran ComBat with default parameters on the $\log_2$(TPM) expression matrix, allowing cells to be clustered by cell type or cell state. Importantly, these batch-corrected data were only used for the PCA and all steps relying on PCA (e.g. clustering, diffusion map, t-SNE visualization); all other analyses (e.g. differential expression analysis) were based on the original expression data.

Dimensionality reduction, graph clustering, and t-SNE visualization. Cells were clustered at two stages of the analysis: first, to initially partition the cells within each sample into epithelial, stromal, and immune compartments (single sample clustering), and second, to cluster cells from multiple samples into distinct subsets (multi sample clustering). For single-sample clustering, Applicants first ran PCA on the variable genes of the entire $\log_2$(TPM) expression matrix. The Infomap graph clustering algorithm was then applied to the k-nearest neighbor (k-NN) graph defined using PCs 1 to 20 and k=50 nearest neighbors. These parameters were designed to "over-cluster" the cells, ensuring that cells from distinct compartments were not grouped together. In contrast, for multi-sample clustering, Applicants ran PCA on the variable genes of the batch-corrected expression matrix. Applicants then applied Phenograph to the k-NN graph defined using PCs 1 to 20 and a varying k, which was selected through close inspection of the data: k=750 for epithelial cells, k=500 for stromal cells, and k=500 for immune cells. Although most clusters were stable over a range of k, some rare epithelial cell subsets, such as tuft cells and M cells, were not well represented because they had been merged with larger clusters, requiring a higher granularity (k=750) and merged the clusters for the tuft cells, enteroendocrine cells, M cells, and BEST4$^+$ enterocytes with the original clusters. In addition, Applicants partitioned the immune cells into myeloid, B cell, and T cell compartments, and repeated the clustering using the k-NN graph defined with PCs 1 to 15 and k=50 for myeloid cells, k=100 for B cells, and k=100 for T cells. Finally, the Barnes-Hut t-Distributed Stochastic Neighbor Embedding (t-SNE) algorithm was run on the PCs with perplexity=20 and for 10,000 iterations to produce a two-dimensional embedding of the data for visualization (FIG. 1B).

Differential expression analysis. Differential expression (DE) tests were performed using MAST, which fits a hurdle model to the expression of each gene, consisting of logistic regression for the zero process (i.e. whether the gene is expressed) and linear regression for the continuous process (i.e. the expression level). To reduce the size of the inference problem, separate models were fit for all levels of the cell tree, comparing cells within the given group to all other cells (e.g. ISCs vs. non-ISCs). The regression model includes terms to capture the effects of the cell subset and the disease state on gene expression, while controlling for cell complexity (i.e. the number of genes detected per cell).

Specifically, Applicants used the regression formula, $Y_i \sim X+D+N$, where $Y_i$ is the standardized $\log_2$(TPM) expression vector for gene i across all cells, X is a binary variable reflecting cell subset membership (e.g. ISCs vs. non-ISCs), D is the disease state associated with each cell, and N is the number of genes detected in each cell. Overall, Applicants fit three types of DE models, which varied by the encoded disease states: (1) to identify cell subset markers and DE genes in UC patients relative to healthy controls, Applicants used three disease states: Healthy, UC non-inflamed, and UC inflamed; (2) to identify DE genes between non-inflamed and inflamed patient samples, Applicants used two disease states: UC non-inflamed and UC inflamed; and (3) to identify genes that are specific to cell subsets in healthy subjects and UC patients, Applicants used two disease states: Healthy and UC. Additionally, a few heuristics were used to increase the speed of the tests: Applicants required all tested genes to be expressed by at least 1% of cells and to have a minimum fold change of 1.2 within the group of interest, and cells were evenly downsampled across groups so that a maximum of 2,500 cells were tested for each cell subset. In all cases, the discrete and continuous coefficients of the model were retrieved and p-values were calculated using the likelihood ratio test in MAST. Q-values were separately estimated for each cell subset comparison using the Benjamini-Hochberg correction. Unless otherwise indicated, all reported DE coefficients and q-values correspond to the discrete component of the model (i.e. the logistic regression).

Estimation of the droplet contamination rate and filtering of putative ambient RNA contaminants. Droplets encapsulate single cells with small portions of the extracellular environment, leading to low but persistent levels of contamination by ambient RNA [REF-Macosko]. To correct for this, Applicants explicitly modeled droplet contamination. First, Applicants partitioned individual cells into the following groups: epithelial cells, fibroblasts, endothelial cells, myeloid cells, B cells, and T cells. Applicants reasoned that each group should uniquely express a subset of genes that are not found in other cells; for example, B cells uniquely express IGHA1 and T cells uniquely express CD3D. Therefore, the off-target expression of such genes in the incorrect group (e.g. IGHA1 expression in T cells) should reflect contamination rather than intrinsic gene expression. Moreover, Applicants hypothesized that the levels of such off-target gene expression could serve as an accurate indicator of contamination rates in the entire dataset. To test this hypothesis, Applicants compared the mean expression levels of genes within each group (i.e. "within-group" expression) to their mean expression levels in all other cells (i.e. "non-group" expression), which Applicants used as a proxy for the composition of extracellular RNA (e.g. B cells vs. non-B cells, FIG. 39, see "Normalization and scaling of expression levels for contamination filtering" below for details). As expected, known markers for cell groups were enriched at the edges of the point distribution, where the difference between "within-group" and "non-group" expression was greatest. For example, known B cell markers were enriched on the left edge of the point distribution (e.g. IGHA1 and IGJ, FIG. 39), while markers for other cell types were enriched on the right edge, likely reflecting droplet contamination (e.g. CD3D and TPSAB1, FIG. 39). Furthermore, Applicants noticed two other patterns that yielded insights into droplet contamination: first, genes with sufficiently high "non-group" expression always had positive "within-group" expression, and second, there was a strong linear relationship between "within-group" and "non-group" expression levels, particularly for the potential contaminants on the right edge of the point distribution (FIG. 39). Taken together, these observations suggest that contamination uniformly affects all genes and that overall levels of contamination for each gene are proportional to its representation in the extracellular RNA pool.

Therefore, to estimate the contamination rate for each cell group, Applicants fit a robust linear model to the genes on the right edge of the point distribution, whose expression is likely driven by contamination. Surprisingly, the fitted models were nearly identical across groups (slope=1.33±0.07, intercept=−7.22±0.33) and Applicants constructed a consensus model using the mean slope and mean intercept. This model corresponds to a contamination rate between 0.5% and 5% of the total RNA pool in each sample. Applicants used this model to identify potential contaminants in all cell subsets by conservatively flagging genes with residuals <5 (i.e. 32-fold increase over the estimated contamination rate) and genes in each cell subset whose expression did not exceed 1% of its total expression across all cells. This approach filtered out nearly all known contamination throughout the full dataset.

Normalization and scaling of expression levels for contamination filtering. To estimate the contamination rate, Applicants compared the within-group and non-group expression levels of each gene (see above, FIG. 39).

To estimate the droplet contamination rate, Applicants compared for each gene its within-group and non-group expression levels (e.g. B cells vs. non-B cells, FIG. 39). However, because the composition of extracellular RNA varies across samples, contamination can have different effects within each sample. For example, cells derived from EPI samples have high levels of contaminating MUC2, while cells from LP samples have high levels of contaminating IGHA1. To account for these differences across samples, Applicants used a weighted mean to compute the non-group expression levels for each gene, where the weights were chosen to match the sample distribution of the target cell group.

Gene specificity. For each expressed gene, Applicants tested whether that gene was specific to any cell subset (e.g. $T_{regs}$) or any node of the cell hierarchy (e.g. $CD4^+$ T cells). Applicants defined a gene as specific to a cell group, if it was significantly and positively DE in all pairwise comparisons to non-overlapping cell subsets and its mean expression level within the group was at least 2-fold higher than its mean expression in all other cell subsets. Additionally, Applicants searched for cases where a gene gained, lost, or changed its cell specificity between health and disease. As such cases may reflect differences in statistical power between the two cohorts, rather than changes in gene specificity, Applicants required that another cell subset have significantly higher expression of the gene in the appropriate group of cells (i.e. healthy subjects or UC patients, depending on the hypothesis being tested).

Using receptor-ligand pairs to infer cell-cell interactions. To identify cell-cell interactions, Applicants used the FANTOM5 database of literature supported receptor-ligand interactions. These receptors and ligands were mapped onto the lists of cell subset markers and DE genes within healthy, UC non-inflamed, and UC inflamed cells. To focus on genes that were enriched within a cell subset, Applicants considered a gene to be expressed within a cell only if its adjusted p-value was less than 0.05 and its discrete coefficient was greater than 1. In addition, to examine changes in cell-cell interactions with disease state, Applicants mapped the DE genes onto this network, removing edges that were not affected by DE, or adding edges in which both genes were DE.

For DE genes, receptors and ligands require that at least one gene within the interaction is differentially expressed. Because many genes showed relatively small changes in gene expression, Applicants required that all DE genes also be found as cell subset markers in either the healthy cells or cells isolated from the corresponding health state. In this way, Applicants constructed a network of cell-cell interactions, where each node is a cell type, each edge is a receptor-ligand interaction that is expressed.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method for treating a subject suffering from inflammatory bowel disease (IBD) comprising the steps of:
   determining the presence of colitis-associated inflammatory fibroblasts (CAIFs) by:
   a. obtaining a biological sample from the subject,
   b. detecting MMP3, MMP10, PLAU, IL11, IL1R1, IL13RA2, CXCL6, CCL11, TNFSF11, TNFRSF11B, CHI3L1, WNT2 gene expression, or any combination thereof in the biological sample, and
   c. administering to the subject determined to have CAIFs, a treatment comprising modulating the activity of one or more gastrointestinal tract cell types,
   wherein the one or more gastrointestinal tract cell types is chosen from the group consisting of: plasma B cells, class switching B cells, follicular B cells, microvascular cells, post-capillary venules, vitamin metabolizing, endothelial pericytes, enterocytes, tuft cells, goblet 2, absorptive TA 1, secretory TA, absorptive TA 2, cycling TA, goblet 1, stem cells, enteroendocrine, glial cells, inflammatory fibroblasts, fibroblast pericytes, myofibroblasts, villus fibroblasts, crypt fibroblasts (hiFos), crypt fibroblasts (loFos), T cells, macrophages, dendritic cells, mast cells, cycling monocytes, tolerogenic DCs, neutrophils, activated CD4 cells loFos, activated CD4 cells hiFos, CD8 IELs, CD8 LP cells, T regs, memory T cells, NK cells and cycling CD8 cells.

2. The method of claim 1, wherein the gene expression is detected by single-cell RNA-seq.

3. The method of claim 1, wherein the treatment induces intestinal stem cells to differentiate into absorptive transit amplifying (TA) 1 cells, absorptive TA 2 cells or class switching B cells.

4. The method of claim 3, wherein the treatment comprises a CRISPR-Cas system that targets WNT2, CHI3L1, or TREM1.

5. The method of claim 3, wherein the treatment comprises a CRISPR-Cas system that targets a fibrinolytic enzyme comprising MMP3, MMP10, and PLAU.

6. The method of claim 3, wherein the treatment comprises a CRISPR-Cas system that targets a fibrinolytic enzyme chosen from MMP3, MMP10, or PLAU.

7. The method of claim 3, wherein the CRISPR-Cas system targets an immune signaling molecule comprising IL11, IL1R1, IL13RA2, CXCL6, CCL11, TNFSF11, and TNFRSF11B.

8. The method of claim 3, wherein the CRISPR-Cas system targets an immune signaling molecule chosen from IL11, IL1R1, IL13RA2, CXCL6, CCL11, TNFSF11, or TNFRSF11B.

9. The method of claim 1, wherein the treatment comprises a CRISPR-Cas system that targets a signaling molecule of the JAK-STAT signaling pathway.

10. The method of claim 9, wherein the signaling molecule is STAT3.

11. The method of claim 3, wherein the treatment comprises an RNAi that targets WNT2, CHI3L1, or TREM1.

12. The method of claim 3, wherein the treatment comprises an RNAi that targets a fibrinolytic enzyme comprising MMP3, MMP10, or PLAU.

13. The method of claim 3, wherein the treatment comprises an RNAi that targets a fibrinolytic enzyme chosen from MMP3, MMP10, or PLAU.

14. The method of claim 3, wherein the treatment comprises an RNAi that targets an immune signaling molecule comprising IL11, IL1R1, IL13RA2, CXCL6, CCL11, TNFSF11, or TNFRSF11B.

15. The method of claim 3, wherein the treatment comprises an RNAi that targets an immune signaling molecule chosen from IL11, IL1R1, IL13RA2, CXCL6, CCL11, TNFSF11, or TNFRSF11B.

16. The method of claim 1, wherein the treatment comprises an RNAi that targets a signaling molecule of the JAK-STAT signaling pathway.

17. The method of claim 16, wherein the signaling molecule is STAT3.

18. The method of claim 1, wherein the treatment targets a receptor-ligand interaction in the gut.

19. The method of claim 18, wherein the treatment comprises a CRISPR-Cas system that targets CCR7 and one or more of CCL19 and CCL21, TNFB and LTBR, LGR5 and RSPO3, IL15 and IL15RA, FGF23 and FGFR1, CCL8 and CCR1, CXCL2 and XCR1, XCL2 and XCR1 or CHI3L1 and IL13RA2.

20. The method of claim 18, wherein the treatment comprises an RNAi that targets CCR7 and one or more of CCL19 and CCL21, TNFB and LTBR, LGR5 and RSPO3, IL15 and IL15RA, FGF23 and FGFR1, CCL8 and CCR1, CXCL2 and XCR1, XCL2 and XCR1 or CHI3L1 and IL13RA2.

* * * * *

UNITED STATES PATENT AND TRADEMARK OFFICE
CERTIFICATE OF CORRECTION

PATENT NO. : 12,105,089 B2
APPLICATION NO. : 16/632018
DATED : October 1, 2024
INVENTOR(S) : Alexander K. Shalek et al.

It is certified that error appears in the above-identified patent and that said Letters Patent is hereby corrected as shown below:

On the Title Page

In item (73), in Column 1, in "Assignees", Line 2, delete "Institution" and insert -- Institute --.

In item (87), in Column 1, in "PCT Pub. No.", Line 1, delete "WO2019/018844" and insert -- WO2019/018440 --.

In the Specification

In Column 4, Line 29, delete "DHRSl1," and insert -- DHRS11, --.

In Column 5, Line 1, delete "RAPiB," and insert -- RAP1B, --.

In Column 5, Line 36, delete "Clorf54," and insert -- C1orf54, --.

In Column 5, Line 54, delete "RALGAPAl;" and insert -- RALGAPA1; --.

In Column 5, Line 62, delete "GLBIL2;" and insert -- GLB1L2; --.

In Column 5, Line 66, delete "LEFTYl," and insert -- LEFTY1, --.

In Column 6, Line 7, delete "SECllC," and insert -- SEC11C, --.

In Column 6, Line 31, delete "11D3," and insert -- ID3, --.

In Column 6, Line 34, delete "SERPINGI," and insert -- SERPING1, --.

In Column 6, Line 35, delete "ADAMDECI," and insert -- ADAMDEC1, --.

Page 1 of 4

Signed and Sealed this
Twenty-ninth Day of July, 2025

Coke Morgan Stewart
*Acting Director of the United States Patent and Trademark Office*

CERTIFICATE OF CORRECTION (continued)
U.S. Pat. No. 12,105,089 B2

In Column 6, Line 42, delete "RNASEI," and insert -- RNASE1, --.

In Column 7, Line 20, delete "SERPINBI," and insert -- SERPINB1, --.

In Column 7, Line 22, delete "ILIRL1," and insert -- IL1RL1, --.

In Column 7, Line 25, delete "AKl;" and insert -- AK1; --.

In Column 7, Line 61, delete "VPS 11," and insert -- VPS11, --.

In Column 7, Line 65, delete "SiPR1," and insert -- S1PR1, --.

In Column 8, Line 13, delete "CIQTNF1," and insert -- C1QTNF1, --.

In Column 8, Line 32, delete "SCNNIA," and insert -- SCNN1A, --.

In Column 21, Line 26, before "80%" insert -- $\geq$ --.

In Column 21, Line 26, before "90%" insert -- $\geq$ --.

In Column 21, Line 26, before "100%" insert -- $\geq$ --.

In Column 27, Line 25, delete ""me" and insert -- "The --.

In Column 35, Line 2, delete "interferon-k," and insert -- interferon-$\lambda$, --.

In Column 41, Line 17, delete "CasiB," and insert -- Cas1B, --.

In Column 44, Line 45, delete "S" and insert -- S- --.

In Column 51, Line 24, delete "IV/cm" and insert -- 1V/cm --.

In Column 54, Line 57, delete "Camobacterium" and insert -- Carnobacterium --.

In Column 59, Line 50, delete "specifcity," and insert -- specificity, --.

In Column 64, Line 12, delete "5; 353" and insert -- 5;353 --.

In Column 68, Line 48, delete "ofNS" and insert -- of NS --.

In Column 71, Line 52, delete "Krüippel" and insert -- Krüppel --.

In Column 75, Line 4, delete "45o/a," and insert -- 45%, --.

In Column 76, Line 15, delete "the" and insert -- The --.

CERTIFICATE OF CORRECTION (continued)
U.S. Pat. No. 12,105,089 B2

In Column 79, Line 66, delete "100/6," and insert -- 100%, --.

In Columns 107-108, Line 34 (Table 1c-continued), delete "TUBAlA" and insert -- TUBA1A --.

In Columns 109-110, Line 13 (Table 1c-continued), delete "TUBAlA" and insert -- TUBA1A --.

In Columns 139-140, Line 1 (Table 2d), delete "Cyding" and insert -- Cycling --.

In Column 143, Line 51, delete "a" and insert -- A --.

In Column 145, Line 33, delete "WNT2B" and insert -- WNT2B$^{+}$ --.

In Column 145, Line 43, delete "the" and insert -- The --.

In Column 146, Line 34, delete "a" and insert -- A --.

In Column 150, Line 42, delete "TGFP" and insert -- TGFβ --.

In Column 151, Line 64, delete "DCIs" and insert -- DC1s --.

In Columns 157-158, Line 54 (Table 3), delete "576122.2," and insert -- 576I22.2, --.

In Columns 159-160, Line 7 (Table 3-continued), delete "CKMTIA," and insert -- CKMT1A, --.

In Columns 159-160, Line 9 (Table 3-continued), delete "C1orG10," and insert -- C1orf210, --.

In Columns 159-160, Line 44 (Table 3-continued), delete "55802.1," and insert -- 558O2.1, --.

In Columns 159-160, Line 58 (Table 3-continued), delete "AN RD36C," and insert -- ANKRD36C, --.

In Columns 159-160, Line 59 (Table 3-continued), delete "AN RD18A," and insert -- ANKRD18A, --.

In Columns 159-160, Line 61 (Table 3-continued), delete "SCNNIA," and insert -- SCNN1A, --.

In Columns 161-162, Line 22 (Table 3-continued), delete "43505.2," and insert -- 435O5.2, --.

In Columns 161-162, Line 16 (Table 4), delete "3193013.9," and insert -- 3193O13.9, --.

In Columns 163-164, Line 30 (Table 4-continued), delete "MTIG" and insert -- MT1G --.

In Columns 163-164, Line 38 (Table 4-continued), delete "C4orD6," and insert -- C4orf36, --.

In Columns 163-164, Line 41 (Table 4-continued), delete "576122.2," and insert -- 576I22.2, --.

CERTIFICATE OF CORRECTION (continued)
U.S. Pat. No. 12,105,089 B2

In Columns 165-166, Line 14 (Table 4-continued), delete "EIFIB," and insert -- EIF1B, --.

In Columns 167-168, Line 17 (Table 5-continued), delete "MARCH 1," and insert -- MARCH1, --.

In Columns 167-168, Line 59 (Table 5-continued), delete "GAT A3," and insert -- GATA3, --.

In Columns 167-168, Line 64 (Table 5-continued), delete "DEN D2D," and insert -- DENND2D, --.

In Columns 169-170, Line 45 (Table 5-continued), delete "FCGRIA, FCGRIB," and insert -- FCGR1A, FCGR1B, --.

In Columns 169-170, Line 46 (Table 5-continued), delete "RP11-365016.3," and insert -- RP11-365O16.3, --.

In Columns 169-170, Line 48 (Table 5-continued), delete "CDIE," and insert -- CD1E, --.

In Columns 169-170, Line 65 (Table 5-continued), delete "CDIB," and insert -- CD1B, --.

In Columns 173-174, Line 42 (Table 6-continued), delete "138II8.2," and insert -- 138I18.2, --.

In Columns 173-174, Line 62 (Table 6-continued), delete "CP A3," and insert -- CPA3, --.

In Columns 173-174, Line 70 (Table 6-continued), delete "P0U2AF1," and insert -- POU2AF1, --.

In Columns 177-178, Line 9 (Table 6-continued), delete "LIP A," and insert -- LIPA, --.

In Columns 179-180, Line 23 (Table 7), delete "536018.1," and insert -- 536O18.1, --.

In Columns 179-180, Line 25 (Table 7), delete "CXorD6," and insert -- CXorf36, --.

In Columns 181-182, Line 7 (Table 7-continued), delete "CYPIBI," and insert -- CYP1B1, --.

In Columns 181-182, Line 12 (Table 7-continued), delete "MYBBPIA," and insert -- MYBBP1A, --.

In Columns 181-182, Line 63 (Table 7-continued), delete "ANRD65," and insert -- ANKRD65, --.

In Columns 183-184, Line 33 (Table 7-continued), delete "ROB04," and insert -- ROBO4, --.

In Columns 185-186, Line 18 (Table 8), delete "F.Crpt" and insert -- F.Crypt --.

In Columns 185-186, Line 55 (Table 8), delete "SFTAIP," and insert -- SFTA1P, --.

In Columns 187-188, Line 32 (Table 8-continued), delete "2319112.4," and insert -- 2319I12.4, --.

In Columns 193-194, Line 53 (Table 9A-continued), delete "AII" and insert -- AII --.